US012760084B2

(12) United States Patent
Powell et al.

(10) Patent No.: US 12,760,084 B2
(45) Date of Patent: Oct. 13, 2026

(54) COMPOSITIONS AND METHODS OF T CELL RECEPTOR VB FAMILY MEMBER TARGETING FOR THE TREATMENT OF T CELL ASSOCIATED DISEASE

(71) Applicant: THE TRUSTEES OF THE UNIVERSITY OF PENNSYLVANIA, Philadelphia, PA (US)

(72) Inventors: Daniel J. Powell, Bala Cynwyd, PA (US); Stephen J. Schuster, Springfield, PA (US); Lauren Shaw, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1013 days.

(21) Appl. No.: 17/759,679

(22) PCT Filed: Jan. 29, 2021

(86) PCT No.: PCT/US2021/015659
§ 371 (c)(1),
(2) Date: Jul. 28, 2022

(87) PCT Pub. No.: WO2021/155112
PCT Pub. Date: Aug. 5, 2021

(65) Prior Publication Data

US 2023/0108300 A1 Apr. 6, 2023

Related U.S. Application Data

(60) Provisional application No. 62/967,371, filed on Jan. 29, 2020.

(51) Int. Cl.

| | |
|---|---|
| ***C12N 15/62*** | (2006.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***C07K 14/705*** | (2006.01) |
| ***C07K 16/28*** | (2006.01) |
| *A61K 40/50* | (2025.01) |

(52) U.S. Cl.
CPC .......... *C07K 14/7051* (2013.01); *A61K 40/11* (2025.01); *A61K 40/31* (2025.01); *A61K 40/32* (2025.01); *A61K 40/4202* (2025.01); *A61K 40/4211* (2025.01); *C07K 16/2809* (2013.01); *A61K 40/50* (2025.01); *A61K 2239/31* (2023.05); *A61K 2239/38* (2023.05); *A61K 2239/48* (2023.05); *C07K 2317/622* (2013.01); *C07K 2319/03* (2013.01)

(58) Field of Classification Search
CPC ............ C07K 14/7051; C07K 16/2809; C07K 2317/622; A61K 40/11; A61K 40/31; A61K 40/32; A61K 40/50
See application file for complete search history.

(56) References Cited

U.S. PATENT DOCUMENTS

| | | | | |
|---|---|---|---|---|
| 2012/0076726 | A1 | 3/2012 | Gellerfors | |
| 2016/0304617 | A1 | 10/2016 | Damle | |
| 2018/0256716 | A1* | 9/2018 | Schendel | C07K 16/2809 |
| 2019/0135914 | A1 | 5/2019 | Unverdorben | |
| 2019/0338028 | A1 | 11/2019 | Wu | |
| 2019/0389925 | A1 | 12/2019 | Powell | |

FOREIGN PATENT DOCUMENTS

| | | | |
|---|---|---|---|
| WO | 2013044225 | A1 | 3/2013 |
| WO | 2019018525 | | 1/2019 |
| WO | 2019052562 | | 3/2019 |
| WO | 2020010250 | | 1/2020 |

OTHER PUBLICATIONS

Mclean-Tooke et al (Clin Experim Immun 151:190-198, 2007 (Year: 2007).*
Ying et al (Mole Therapy: Oncolytics 15: 60-68, Dec. 2019). (Year: 2019).*
Chen KH, Wada M, Pinz KG, Liu H, Lin KW, Jares A, et al. Preclinical targeting of aggressive T-cell malignancies using anti-CD5 chimeric antigen receptor. Leukemia. 2017, 31, 2151-2160.
Gomes-Silva et al., "CD7-edited T cells expressing a CD7-specific CAR for the therapy of T-cell malignancies", Blood, Jul. 20, 2017 x vol. 130, No. 3, 12 pages.
Hamblin et al., "Initial Experience in Treating Human Lymphoma With a Chimeric Univalent Derivative of Monoclonal Anti-idiotype Antibody", Blood, vol. 69, No. 3 Mar. 1987: pp. 790-797.
International Search Report and Written Opinion issued in App. No. PCT/US21/15659, mailing date Jun. 28, 2021, 21 pages.
Maciocia PM, Wawrzyniecka PA, Philip B, et al. Targeting the T cell receptor -chain constant region for Immunotherapy of T cell malignancies. Nat. Med. 2017;(October) pp. 1416-1423.
Mamonkin M, Rouce RH, Tashiro H, Brenner MK. A T-cell-directed chimeric antigen receptor for the selective treatment of T-cell malignancies. Blood. 2015;126(8):983-92.
Raikar SS, Fleischer LC, Moot R, Fedanov A, Paik NY, Knight KA, et al. Development of chimeric antigen receptors targeting T-cell malignancies using two structurally different anti-CD5 antigen binding domains in NK and CRISPR-edited T cell lines. Oncoimmunology. 2018;7(3):e1407898.
Schuster et al., "Vaccination With Patient-Specific Tumor-Derived Antigen in First Remission Improves Disease-Free Survival in Follicular Lymphoma", Journal of Clinical Oncology, vol. 29, 8 pages, No. 20, 2011.

(Continued)

*Primary Examiner* — Lei Yao
(74) *Attorney, Agent, or Firm* — Saul Ewing LLP; Kathryn Doyle; Alireza Behrooz

(57) ABSTRACT

Provided is a chimeric antigen receptor (CAR) comprising a domain that binds a Vβ region of a T cell receptor. Also provided is a T cell genetically modified to express the CAR, and methods for treating cancer in a subject in need thereof.

19 Claims, 31 Drawing Sheets

Specification includes a Sequence Listing.

(56) References Cited

OTHER PUBLICATIONS

Stevenson et al., “Antibodies to Shared Idiotypes as Agents for Analysis and Therapy for Human B Cell Tumors”, Blood, vol. 68, No. 2 (August), 1986, pp. 430-436.
Fleischer, L.C., et al., “Targeting T cell malignancies using CAR based immunotherapy: challenges and potential solutions”, Journal of Hermatology & Oncology, 12:141, 2019, 21 pages.
Partial Supplementary European Search Report issued Apr. 10, 2024 in European Patent Application No. 21748087.0.
Salameire, D., et al., “Accurate detection of the tumor clone in peripheral T-cell lymphoma biopsies by flow cytometric analysis of TCR-Vb repertoire”, Modern Pathology, vol. 25, pp. 1246-1257, 2012.
Walcheck, B., et al., “INK-CD64/16A cells: a promising approach for ADCC?”, Expert Opinion on Biological Therapy, 19:12, 1229-1232, 2019.
Wang, J., et al., “A Novel Approach for the Treatment of T Cell Malignancies: Targeting T Cell Receptor Vβ Families”, Vaccines, 2020, 8, 631. 13 pages.

* cited by examiner

A

B

COMPOSITIONS AND METHODS OF T CELL RECEPTOR VB FAMILY MEMBER TARGETING FOR THE TREATMENT OF T CELL ASSOCIATED DISEASE

CROSS-REFERENCE TO RELATED APPLICATIONS

The present application is a 35 U.S.C. § 371 national phase application of, and claims priority to, International Application No. PCT/US2021/015659, filed Jan. 29, 2021, which is entitled to priority under 35 U.S.C. § 119(e) to U.S. Provisional Patent Application No. 62/967,371 filed Jan. 29, 2020, all of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jan. 27, 2021, is named 046483-7217US1_SequenceListing.txt and is 419 kilobytes in size.

BACKGROUND OF THE INVENTION

Peripheral T-cell lymphomas are a deadly form of non-Hodgkin lymphoma (NHL) that accounts for approximately 10% of all NHL cases and affects both children and adults (Rudiger T, Weisenburger D D, Anderson J R, Armitage J O, Diebold J, MacLennan K A, et al. Peripheral T-cell lymphoma (excluding anaplastic large-cell lymphoma): results from the Non-Hodgkin's Lymphoma Classification Project. Ann Oncol. 2002; 13(1):140-9). Peripheral T-cell lymphoma, not otherwise specified (PTCL-NOS), Angioimmunoblastic T-cell lymphoma (AITL), and Anaplastic large-cell lymphoma (ALCL) are the most common subtypes and account for up to 74% of all T-cell lymphomas (Vose J, Armitage J, Weisenburger D, International TCLP. International peripheral T-cell and natural killer/T-cell lymphoma study: pathology findings and clinical outcomes. J Clin Oncol. 2008; 26(25):4124-30). Other less common T-cell lymphomas include enteropathy-associated T-cell lymphoma (EATL), adult T-cell leukemia/lymphoma (ATLL), hepatosplenic T-cell lymphoma (HSTL), and subcutaneous panniculitis-like T-cell lymphoma (SPTCL) (Tang T, Tay K, Quek R, Tao M, Tan S Y, Tan L, et al. Peripheral T-cell lymphoma: review and updates of current management strategies. Advances in hematology. 2010; 2010:624040). All PTCL subtypes involve the malignant transformation of T lymphocytes.

When compared to B-cell NHL, the prognosis for PTCL remains poor, mainly due to lower response rates and shorter duration of response to standard combination chemotherapy regimens. There remains no consensus on standard therapy in either the upfront setting or in relapsed/recurrent PTCL. For most subtypes of PTCL, the frontline treatment regimen is multi-agent chemotherapy, such as CHOP (cyclophosphamide, doxorubicin, vincristine, prednisone), EPOCH (etoposide, vincristine, doxorubicin, cyclophosphamide, prednisone), or other multi-drug regimens. However, long-term remissions occur in few patients, resulting in a median survival of 9 to 42 months (Huang H Q, Peng Y L, Lin X B, Sun X F, Lin T Y, Xia Z J, et al. [Clinical outcomes of 106 patients with peripheral T-cell lymphoma treated by standard CHOP regimen]. Ai zheng=Aizheng=Chinese journal of cancer. 2004; 23(11 Suppl):1443-7; Lopez-Guillermo A, Cid J, Salar A, Lopez A, Montalban C, Castrillo J M, et al. Peripheral T-cell lymphomas: initial features, natural history, and prognostic factors in a series of 174 patients diagnosed according to the R.E.A.L. Classification. Ann Oncol. 1998; 9(8):849-55). The 5-year overall survival for patients with PTCL is only 10-30% (Vose J, Armitage J, Weisenburger D, International TCLP. International peripheral T-cell and natural killer/T-cell lymphoma study: pathology findings and clinical outcomes. J Clin Oncol. 2008; 26(25):4124-30).

Given the overall poor outcomes with conventional therapy as frontline treatment for PTCL, the role of high-dose chemotherapy with autologous hematopoietic stem cell transplant (HCT) has been studied as a consolidation option after successful frontline therapy; however, the additive benefit of autologous HCT as first consolidation in PTCL is controversial, because a significant fraction of patients in prospective trials had disease that was refractory to induction therapy and did not undergo autologous HCT (Rodriguez J, Conde E, Gutierrez A, Arranz R, Leon A, Marin J, et al. Frontline autologous stem cell transplantation in high-risk peripheral T-cell lymphoma: a prospective study from The Gel-Tamo Study Group. European journal of haematology. 2007; 79(1):32-8; Corradini P, Tarella C, Zallio F, Dodero A, Zanni M, Valagussa P, et al. Long-term follow-up of patients with peripheral T-cell lymphomas treated up-front with high-dose chemotherapy followed by autologous stem cell transplantation. Leukemia. 2006; 20(9):1533-8). For relapsed/refractory PTCL, salvage combination chemotherapy followed by autologous HCT is often offered, but few patients experience a durable benefit from this approach (Kewalramani T, Zelenetz A D, Teruya-Feldstein J, Hamlin P, Yahalom J, Horwitz S, et al. Autologous transplantation for relapsed or primary refractory peripheral T-cell lymphoma. British journal of haematology. 2006; 134(2):202-7; Chen A I, McMillan A, Negrin R S, Horning S J, Laport G G. Long-term results of autologous hematopoietic cell transplantation for peripheral T cell lymphoma: the Stanford experience. Biol Blood Marrow Transplant. 2008; 14(7): 741-7). Allogeneic HCT is also being explored for relapsed/refractory PTCL, with some encouraging results reported (Feyler S, Prince H M, Pearce R, Towlson K, Nivison-Smith I, Schey S, et al. The role of high-dose therapy and stem cell rescue in the management of T-cell malignant lymphomas: a BSBMT and ABMTRR study. Bone Marrow Transplant. 2007; 40(5):443-50; Corradini P, Dodero A, Zallio F, Caracciolo D, Casini M, Bregni M, et al. Graft-versus-lymphoma effect in relapsed peripheral T-cell non-Hodgkin's lymphomas after reduced-intensity conditioning followed by allogeneic transplantation of hematopoietic cells. J Clin Oncol. 2004; 22(11):2172-6), but toxicities associated with allogeneic cell transplant, particularly graft versus host disease, are common and sometimes lethal. Even with an increased understanding of PTCL biology and pathogenesis, there currently remains no accepted single standard of care for newly diagnosed patients, and for those with relapsed or refractory disease, prognosis remains dismal (Casulo C, O'Connor O, Shustov A, Fanale M, Friedberg J W, Leonard J P, et al. T-Cell Lymphoma: Recent Advances in Characterization and New Opportunities for Treatment. J Natl Cancer Inst. 2017; 109(2)). The National Comprehensive Cancer Network (NCCN) guidelines for PTCL reflect in part this lack of conclusive data and consensus on treatment, and clinical trial participation is encouraged for all PTCL patients (Network TNCC. The NCCN Clinical Practice Guidelines in Oncology: Non-Hodgkin's Lymphomas. 2014).

There is an urgent need in the art for novel targeted strategies for treating T cell associated diseases, such as peripheral T-cell lymphomas. This invention addresses this need.

SUMMARY OF THE INVENTION

As described herein, the present invention relates to a chimeric antigen receptor (CAR) comprising a domain that binds a Vβ region of a T cell receptor. The invention also relates to methods for treating cancer in a subject, the methods comprising administering to the subject an effective amount of the T cell genetically modified to express the CAR.

In one aspect, the invention includes a nucleic acid encoding a chimeric antigen receptor (CAR), wherein the CAR comprises an extracellular domain that binds a Vβ region of a T cell receptor, a transmembrane domain, and an intracellular signaling domain, wherein the intracellular signaling domain comprises a costimulatory signaling region.

In various embodiments of the above aspect or any other aspect of the invention delineated herein, the extracellular domain that binds a Vβ region is selected from the group consisting of an antibody, a Fab, and a scFv.

In various embodiments of the above aspect or any other aspect of the invention delineated herein, the Vβ region is selected from the group consisting of Vβ1, Vβ2, Vβ4, Vβ5.1, Vβ7.1, Vβ7.2, Vβ9, Vβ11, Vβ12, Vβ13.2, Vβ13.3, and Vβ22.

In certain embodiments, the extracellular domain that binds a Vβ region of a T cell receptor comprises a complementarity determining region (CDR) comprising an amino acid sequence selected from the group consisting of SEQ ID NOs: 58-60, 62-64, 66-68, 70-72, 74-76, 78-80, 82-84, 86-88, 90-92, 94-96, 98-100, 102-104, 106-108, and 110-112.

In certain embodiments, the extracellular domain that binds a Vβ region of a T cell receptor comprises a heavy chain variable region (VH) comprising an amino acid sequence selected from the group consisting of SEQ ID NOs: 57, 65, 73, 81, 89, 97, 105, 113, 121, 129, 137, and 145.

In certain embodiments, the extracellular domain that binds a Vβ region of a T cell receptor comprises a light chain variable region (VL) comprising an amino acid sequence selected from the group consisting of SEQ ID NOs: 61, 69, 77, 85, 93, 101, 109, 117, 125, 133, 141, and 149.

In certain embodiments, the extracellular domain that binds a Vβ region of a T cell receptor comprises an scFv encoded by a nucleotide sequence selected from the group consisting of SEQ ID NOs: 33-56.

In certain embodiments, the costimulatory signaling region comprises the intracellular domain of a costimulatory molecule selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83.

In certain embodiments, the preceding claims, wherein the intracellular signaling domain comprises a CD3zeta chain.

In certain embodiments, the intracellular signaling domain comprises CD28 and CD3zeta.

In certain embodiments, the intracellular signaling domain comprises 4-1BB and CD3zeta.

In certain embodiments, the CAR is encoded by a nucleotide sequence selected from the group consisting of SEQ ID NOs: 1-32.

In certain embodiments, the CAR comprises an amino acid sequence selected from the group consisting of SEQ ID NOs: 153-184.

In another aspect, the invention includes a vector comprising the nucleic acid of any one of claims 1-13.

In another aspect, the invention includes a CAR comprising an extracellular domain that binds a Vβ region of a T cell receptor, a transmembrane domain, and an intracellular signaling domain, wherein the intracellular signaling domain comprises a costimulatory signaling region.

In various embodiments of the above aspect or any other aspect of the invention delineated herein, the extracellular domain that binds a Vβ region is selected from the group consisting of an antibody, a Fab, and an scFv.

In various embodiments of the above aspect or any other aspect of the invention delineated herein, the Vβ region is selected from the group consisting of Vβ1, Vβ2, Vβ4, Vβ5.1, Vβ7.1, Vβ7.2, Vβ9, Vβ11, Vβ12, Vβ13.2, Vβ13.3, and Vβ22.

In certain embodiments, the extracellular domain that binds a Vβ region comprises a CDR region comprising an amino acid sequence selected from the group consisting of SEQ ID NO: 58-60, 62-64, 66-68, 70-72, 74-76, 78-80, 82-84, 86-88, 90-92, 94-96, 98-100, 102-104, 106-108, and 110-112.

In certain embodiments, the extracellular domain that binds a Vβ region comprises a VH region comprising an amino acid sequence selected from the group consisting of SEQ ID NOs:

57, 65, 73, 81, 89, 97, 105, 113, 121, 129, 137, and 145.

In certain embodiments, the extracellular domain that binds a Vβ region comprises a VL region comprising an amino acid sequence selected from the group consisting of SEQ ID NOs: 61, 69, 77, 85, 93, 101, 109, 117, 125, 133, 141, and 149.

In certain embodiments, the extracellular domain that binds a Vβ region comprises an scFv encoded by a nucleotide sequence selected from the group consisting of SEQ ID NO: SEQ ID NOs: 33-56.

In certain embodiments, the costimulatory signaling region comprises the intracellular domain of a costimulatory molecule selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83.

In certain embodiments, the intracellular signaling domain comprises a CD3zeta chain.

In certain embodiments, the intracellular signaling domain comprises CD28 and CD3zeta.

In certain embodiments, the intracellular signaling domain comprises 4-1BB and CD3zeta.

In another aspect, the invention includes a modified T cell comprising the nucleic acid, the vector of claim 14, or the CAR of any one of the above aspects or any other aspect of the invention delineated herein.

In another aspect, the invention includes a T cell genetically modified to express a recombinant T cell receptor, wherein the recombinant T cell receptor comprises a domain that binds a Vβ region of a T cell receptor.

In certain embodiments, the domain that binds a Vβ region of a T cell receptor is an α/β heterodimer of the recombinant T cell receptor.

In another aspect, the invention includes a method for treating cancer in a subject, the method comprising:

administering to the subject a therapeutically effective amount of a T cell comprising a CAR, wherein the CAR comprises an extracellular domain that binds a Vβ region of a T cell receptor, a transmembrane domain, and an intracellular signaling domain, wherein the intracellular signaling domain comprises a costimulatory signaling region.

In various embodiments of the above aspect or any other aspect of the invention delineated herein, the cancer is selected from the group consisting of T-cell lymphoma, T-cell leukemia, cutaneous T-cell lymphoma, peripheral T-cell lymphoma (PTCL), not otherwise specified PTCL (PTCL-NOS), angioimmunoblastic T cell lymphoma (AITL), anaplastic large-cell lymphoma (ALCL), enteropathy-associated T-cell lymphoma (EATL), adult T-cell leukemia/lymphoma (ATLL), hepatosplenic T-cell lymphoma (HSTL), subcutaneous panniculitis-like T-cell lymphoma (SPTCL), and T cell acute lymphoblastic leukemia (T-ALL).

In another aspect, the invention includes a method for treating a T-cell-associated disease in a subject in need thereof, the method comprising:

administering to the subject a therapeutically effective amount of a T cell comprising a CAR, wherein the CAR comprises an extracellular domain that binds a Vβ region of a T cell receptor, a transmembrane domain, and an intracellular signaling domain, wherein the intracellular signaling domain comprises a costimulatory signaling region.

In certain embodiments, the T-cell-associated disease is an autoimmune disease.

In certain embodiments, the autoimmune disease is selected from the group consisting of rheumatoid arthritis, inflammatory bowel disease, multiple sclerosis, insulin dependent diabetes mellitus, and Kawasaki disease.

In certain embodiments, the Vβ region is selected from the group consisting of Vβ1, Vβ2, Vβ4, Vβ5.1, Vβ7.1, Vβ7.2, Vβ9, Vβ11, Vβ12, Vβ13.2, Vβ13.3, and Vβ22.

In certain embodiments, the extracellular domain that binds a Vβ region comprises a CDR region comprising an amino acid sequence selected from the group consisting of SEQ ID NO: 58-60, 62-64, 66-68, 70-72, 74-76, 78-80, 82-84, 86-88, 90-92, 94-96, 98-100, 102-104, 106-108, and 110-112.

In certain embodiments, the extracellular domain that binds a Vβ region comprises a VH region comprising an amino acid sequence selected from the group consisting of SEQ ID NOs: 57, 65, 73, 81, 89, 97, 105, 113, 121, 129, 137, and 145.

In certain embodiments, the extracellular domain that binds a Vβ region comprises a VL region comprising an amino acid sequence selected from the group consisting of SEQ ID NOs: 61, 69, 77, 85, 93, 101, 109, 117, 125, 133, 141, and 149.

In certain embodiments, the extracellular domain that binds a Vβ region comprises an scFv encoded by a nucleotide sequence selected from the group consisting of SEQ ID NO: SEQ ID NOs: 33-56.

In certain embodiments, the costimulatory signaling region comprises the intracellular domain of a costimulatory molecule selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83.

In certain embodiments, wherein the intracellular signaling domain comprises a CD3zeta chain.

In certain embodiments, the intracellular signaling domain comprises CD28 and CD3zeta.

In certain embodiments, the intracellular signaling domain comprises 4-1BB and CD3zeta.

In another aspect, the invention includes a method for treating cancer in a subject, the method comprising administering to the subject an effective amount of an antibody-drug conjugate (ADC), wherein the ADC binds to a Vβ region of a T cell receptor.

In certain embodiments, the cancer is selected from the group consisting of T-cell lymphoma, T-cell leukemia, cutaneous T-cell lymphoma, peripheral T-cell lymphoma (PTCL), not otherwise specified PTCL (PTCL-NOS), angioimmunoblastic T cell lymphoma (AITL), anaplastic large-cell lymphoma (ALCL), enteropathy-associated T-cell lymphoma (EATL), adult T-cell leukemia/lymphoma (ATLL), hepatosplenic T-cell lymphoma (HSTL), subcutaneous panniculitis-like T-cell lymphoma (SPTCL), and T cell acute lymphoblastic leukemia (T-ALL).

In another aspect, the invention includes a method for treating cancer in a subject, the method comprising administering to the subject an effective amount of an antibody that binds to a Vβ region of a T cell receptor and a CD64-expressing immune cell.

In certain embodiments, the cancer is selected from the group consisting of T-cell lymphoma, T-cell leukemia, cutaneous T-cell lymphoma, peripheral T-cell lymphoma (PTCL), not otherwise specified PTCL (PTCL-NOS), angioimmunoblastic T cell lymphoma (AITL), anaplastic large-cell lymphoma (ALCL), enteropathy-associated T-cell lymphoma (EATL), adult T-cell leukemia/lymphoma (ATLL), hepatosplenic T-cell lymphoma (HSTL), subcutaneous panniculitis-like T-cell lymphoma (SPTCL), and T cell acute lymphoblastic leukemia (T-ALL).

In certain embodiments, the CD64-expressing immune cell is genetically engineered.

In certain embodiments, the CD64-expressing immune cell is genetically engineered to express a fusion protein comprising CD64, a CD28 transmembrane domain, a CD3 zeta chain and a CD28 costimulatory domain.

In another aspect, the invention includes a method for treating cancer in a subject, the method comprising administering to the subject an effective amount of a labeled antibody that binds to a Vβ region of a T cell receptor and a universal immune receptor (UIR)-expressing immune cell, wherein the universal immune receptor comprises an extracellular domain that specifically binds to the label.

In certain embodiments, the labeled antibody is administered before the UIR-expressing immune cell.

In certain embodiments, the labeled antibody is administered concurrent with the UIR-expressing immune cell.

In certain embodiments, the UIR-expressing immune cell is bound to the labeled antibody prior to administration to the subject.

In certain embodiments, the labeled antibody is labeled with DOTA and the UIR-expressing immune cell comprises an scFv that specifically binds to DOTA.

In certain embodiments, the Vβ region is selected from the group consisting of Vβ1, Vβ2, Vβ4, Vβ5.1, Vβ7.1, Vβ7.2, Vβ9, Vβ11, Vβ12, Vβ13.2, Vβ13.3, and Vβ22.

In certain embodiments, the labeled antibody that binds to a Vβ region of a T cell receptor comprises a CDR region comprising an amino acid sequence selected from the group consisting of SEQ ID NO: 58-60, 62-64, 66-68, 70-72, 74-76, 78-80, 82-84, 86-88, 90-92, 94-96, 98-100, 102-104, 106-108, and 110-112.

In certain embodiments, the labeled antibody that binds to a Vβ region of a T cell receptor comprises a VH region comprising an amino acid sequence selected from the group consisting of SEQ ID NOs: 57, 65, 73, 81, 89, 97, 105, 113, 121, 129, 137, and 145.

In certain embodiments, the labeled antibody that binds to a Vβ region of a T cell receptor comprises a VL region comprising an amino acid sequence selected from the group consisting of SEQ ID NOs: 61, 69, 77, 85, 93, 101, 109, 117, 125, 133, 141, and 149.

In certain embodiments, the cancer is selected from the group consisting of T-cell lymphoma, T-cell leukemia, cutaneous T-cell lymphoma, peripheral T-cell lymphoma (PTCL), not otherwise specified PTCL (PTCL-NOS), angioimmunoblastic T cell lymphoma (AITL), anaplastic large-cell lymphoma (ALCL), enteropathy-associated T-cell lymphoma (EATL), adult T-cell leukemia/lymphoma (ATLL), hepatosplenic T-cell lymphoma (HSTL), subcutaneous panniculitis-like T-cell lymphoma (SPTCL), and T cell acute lymphoblastic leukemia (T-ALL).

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A: Vβ family usage by dominant productive clones in diagnostic specimens from 41 patients. FIG. 2B: Vβ family usage in the T cell repertoire of bone marrow from a healthy donor.

FIG. 3A: Vβ family usage by dominant productive clones in lesional skin biopsies from 24 patients. FIG. 3B: The Vβ family usage in the T cell repertoire of a representative lesional skin biopsy from a patient with a benign reactive skin condition.

FIG. 4A: Representative H&E staining (top) and T-cell antigen receptor beta-F1 antibody staining (bottom) of paraffin embedded sections of T-cell lymphomas. FIG. 4B: Vβ family expression by dominant productive clones in eight patient specimens. Vβ family usage is determined by TRB NGS, and protein expression is determined by immunohistochemistry using the beta-F1 antibody.

FIG. 5A: Schematic structure of α/β TCR. FIG. 5B: VDJ recombination at the TCR β locus. FIG. 5C: Schematic structure of CD64-IR construct. FIG. 5D: Transduction efficiency of primary activated T cells. FIG. 5E: Schematic showing CD64 IR transduced T cells being directed toward a target malignant T cell via TCRVβ family specific mAb. FIG. 5F: CD64-IR can be loaded with mouse IgG2a and IGG2b mAb, but not IgG1.

FIGS. 6A and 6B: Autologous lysis of peripheral blood Vβ8 and Vβ12 T cells at 24 hours. Vβ family specific antibodies were used to "pre-arm" effector T cells (FIG. 6A) and "pre-paint" target T cells (FIG. 6B). FIG. 6C: coculture of T cells and Jurkat T cell line (Vβ8 family) and SupT1-Vβ12 and chromium release assay was performed at 4 hours.

FIG. 9A: Insertion of an anti-TCRVβ scFv sequence into the pELNS vector for chimeric antigen receptor (CAR) formation and lentivirus production. FIG. 9B: Various CAR constructs incorporating an encoded extracellular TCRVβ-specific scFv with various intracellular signaling modules that include CD3z, CD28 and 4-1BB signaling domains. FIG. 9C: Schematic representation of TCRVβ-specific CARs containing various intracellular signaling domains.

FIG. 10A: In ADCC assays, anti-Vβ8 Ab selectively reduces the frequency of Vβ8+ T-cells in open repertoire T cell cultures. FIG. 10B: Addition of an anti-Vβ8 Ab to ADCC co-cultures of effector cells and Vβ8+ Jurkat leukemia cells, results in increased lysis of the Vβ8+ leukemia cells in vitro. 24 hr data±SEM shown (triplicate).

FIG. 11A: diagrams representing anti-Vβ specific CARs. GFP is separated by a T2A ribosomal skip site to various CAR constructs, which incorporate an extracellular TCRvb-specific scFv that is attached via CD8a hinge and transmembrane domains to various intracellular signaling modules including CD3z, CD28, and 4-1BB signaling domains. FIG. 11B: schematic representation of Vβ-specific CARs interacting with a target T cell's TCR.

FIG. 12A: schematic representation of the CAR expressed. FIG. 12B: co-expression of GFP with CAR, stained by protein L, in expanded T cells as well as the transduction efficiency when compared to untransduced cells. FIG. 12C: expansion kinetics of untransduced T cells or T cells transduced with either the Vβ12-targeting CAR or a control CAR. The kinetics do not significantly differ, indicating minimal fratricide. FIG. 12D: specific self-depletion of the target population in expanded CAR T cells. Vβ12 and Vβ13 populations are present in untransduced cells and the Vβ12 population is no longer detectable after expression of the Vβ12-targeting CAR.

FIG. 13A: clonograms of Vβ families from 3 different normal donors that were either untransduced and expanded, in red, or transduced to express CARs targeting Vβ12 (top), Vβ9

(middle), or Vβ4 (bottom) and expanded, in blue. FIG. 13B: representation of the data as relative change when compared to untransduced cells.

FIG. 14A: flow cytometry analysis of SupT1 cells engineered to express a Vβ12+ TCR, a Vβ9+ TCR, or a Vβ13.3 TCR. The cells were stained for either Vβ12 (left), Vβ9 (middle), or with the MART1 tetramer (right) to confirm expression of the engineered TCR. FIG. 14B: cytotoxicity measured after a 20-hour co-culture in which SupT1 cell lines were incubated with CAR T cells expressing various Vβ12-targeting CARs or with untransduced T cells and ran in triplicate. Specific lysis of the Vβ12+ cell line was observed for all CARs with functional signaling domains. FIG. 14C: lysis of the target cell lines at three E:T ratios. Some lysis occurs at 0.1:1 E:T ratio and by a 1:1 E:T ratio, the lysis reaches ~100%.

FIG. 15A: lysis at 1:1 E:T ratio of both cell lines. FIG. 15B: lysis at three different E:T ratios.

FIG. 16A: clonogram of the patient's PBMCs, illustrating the dominant clone representing the malignant cells. FIG. 16B: Vβ expression of the patient's PBMCs after 24-hour co-culture with either untransduced cells, Vβ12-targeting CAR T cells without effector function, or Vβ-targeting CAR T cells with effector function. The dominant Vβ12+ clone is reduced with the functional CAR T cells while the non-targeted Vβ families are maintained. Results from two independent experiments are displayed.

DETAILED DESCRIPTION

Figure 1:
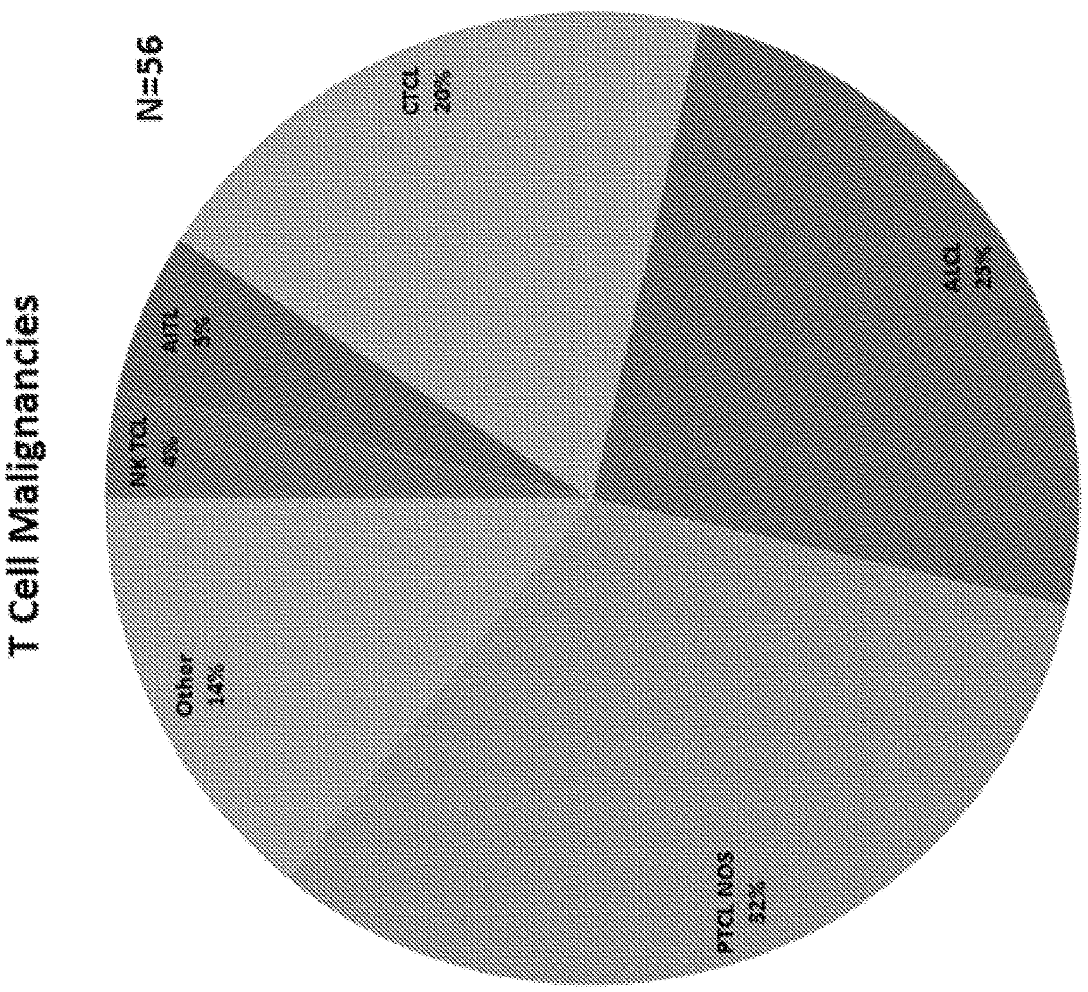
FIG. 1 illustrates the distribution of T cell malignancies in a cohort of 56 patient specimens. Other: EATL, γ/δ TCL, subcutaneous panniculitis like TCL, T-LGL, ATLL, T-ALL.
Figures 2A, 2B:
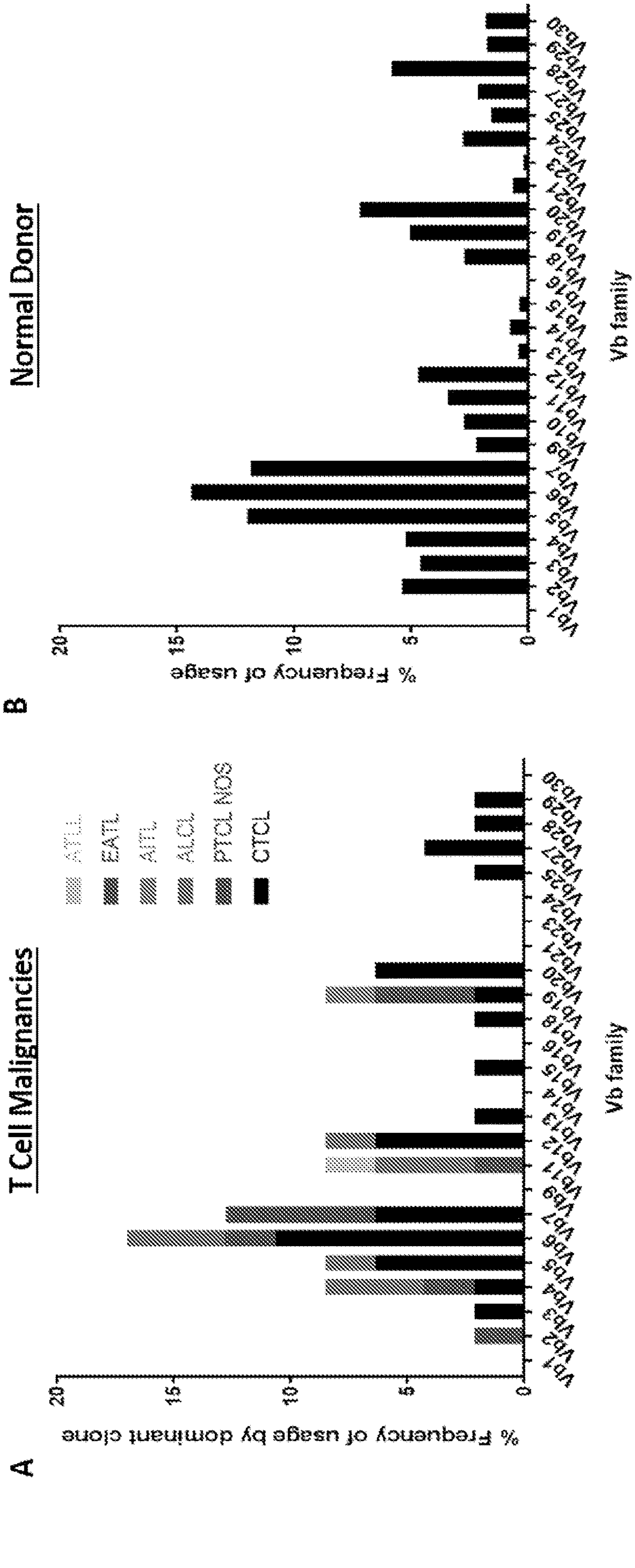
FIGS. 2A-2B illustrate the distribution of Vβ family usage by expanded clones in T cell malignancies is similar to that of the Vβ T cell repertoire in normal donor T cells. Pearson $X^2$=12.8, p=0.75. Fisher's exact test=0.76.

Provided is a T cell genetically modified to express a chimeric antigen receptor (CAR), wherein the CAR comprises a domain that binds a Vβ region of a T cell receptor, a transmembrane domain, and an intracellular signaling domain, wherein the intracellular signaling domain comprises a costimulatory signaling region.

Also provided is a T cell genetically modified to express a recombinant T cell receptor, wherein the recombinant T cell receptor comprises a domain that binds a Vβ region of a T cell receptor.

Further provided are methods for treating cancer or T cell-associated diseases (e.g. an autoimmune disease wherein T cells are the mediators of the autoimmunity) in a subject. The methods comprise: administering to the subject an effective amount of a T cell according to any one of the preceding embodiments. In some embodiments, the cancer is T-cell leukemia or lymphoma

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in some instances ±5%, in some instances ±1%, and in some instance ±0.1% from the specified value, as such variations are appropriate to perform the disclosed methods.

The term "antibody," as used herein, refers to an immunoglobulin molecule binds with an antigen. Antibodies can be intact immunoglobulins derived from natural sources or from recombinant sources and can be immunoreactive portions of intact immunoglobulins. Antibodies are typically tetramers of immunoglobulin molecules. The antibody may exist in a variety of forms where the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al, Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

The term "high affinity" as used herein refers to high specificity in binding or interacting or attraction of one molecule to a target molecule.

The term "antigen" or "Ag" as used herein is defined as a molecule that provokes an immune response. This immune response may involve either antibody production, or the activation of specific immunologically competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, "DOTA" refers to the chelating agent 1,4,7,10-tetraazacyclododecane-1,4,7,10-tetraacetic acid, also referred to as tetra-azacyclododecanetetra-acetic acid, and any salts, solvates, derivatives, or isoforms thereof. Also included are labeled forms of DOTA, for example DOTA labeled with the beta-emitting radioisotope yttrium Y90.

A "disease" is a state of health of an animal or subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

"Chimeric antigen receptor" or "CAR" refers to an engineered receptor that is expressed on a T cell or any other effector cell type capable of cell-mediated cytotoxicity. The CAR includes an antigen or fragment (e.g. extracellular domain) thereof that is specific for a ligand or receptor. The CAR optionally also includes a transmembrane domain, an intracellular domain and a signaling domain.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, for example, one or more amino acid residues within the extracellular regions of the CAR of the invention can be replaced with other amino acid residues having a similar side chain or charge and the altered CAR can be tested for the ability to bind their targets using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

The term "effector function" refers to a specialized function of a cell.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by a promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Intracellular domain" refers to a portion or region of a molecule that resides inside a cell.

The term "intracellular signaling domain" is meant to include any truncated portion of the intracellular domain sufficient to transduce the effector function signal.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

As used herein "plasma cells" refer to a type of white blood cells which can produce and secrete antibodies. Plasma cells are also referred to as plasmocytes, plasmacytes, or effector B cells.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. In some embodiments, a nucleic acid sequence is considered to have at least 95%, 96%, 97%, 98%, or 99% identity or homology to any nucleic acid sequence disclosed herein.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. In some embodiments, an amino acid sequence is considered to have at 95%, 96%, 97%, 98%, or 99% identity or homology to any amino acid sequence described herein.

The term "proinflammatory cytokine" refers to a cytokine or factor that promotes inflammation or inflammatory responses. Examples of proinflammatory cytokines include, but are not limited to, chemokines (CCL, CXCL, CX3CL, XCL), interleukins (such as, IL-1, IL-2, IL-3, IL-5, IL-6, IL-7, IL-9, IL10 and IL-15), interferons (IFNγ), and tumor necrosis factors (TNFα and TNFβ).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

"Signaling domain" refers to the portion or region of a molecule that recruits and interacts with specific proteins in response to an activating signal.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

"Transmembrane domain" refers to a portion or a region of a molecule that spans a lipid bilayer membrane.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is partly based on the discovery of a chimeric antigen receptor (CAR) comprising an extracellular domain (e.g. antigen binding domain) that binds a Vβ region of a T cell receptor, a transmembrane domain, and an intracellular signaling domain, wherein the intracellular signaling domain comprises a costimulatory signaling region.

The CAR of the invention can be engineered to comprise an extracellular domain having an antigen binding domain that targets a tumor antigen, fused to an intracellular signaling domain of the T cell antigen receptor complex zeta chain (e.g., CD3 zeta). An exemplary tumor antigen T cell antigen is TCRVβ because this antigen is expressed on malignant T cells. However, the invention is not limited to targeting TCRVβ. Rather, the invention includes any tumor antigen binding moiety. In some aspects, CARs comprise: (1) a single-chain variable fragment (scFv) targeting a clinically-relevant antigen derived from a monoclonal antibody, (2) a transmembrane domain, (3) one or more costimulatory domains, and (4) an ITAM-containing signaling domain such as CD3-zeta.

Extracellular Domain/Antigen Binding Domain

In certain embodiments, the CAR of the invention comprises an extracellular domain. The extracellular domain comprises a target-specific binding element otherwise referred to as an antigen binding domain. In some embodiments, the extracellular domain also comprises a hinge domain.

In certain embodiments, the antigen binding domain comprises an extracellular domain that is capable of binding a Vβ region of a T cell receptor. The extracellular domain that binds a Vβ region can comprise an antibody or fragment thereof, including e.g. a Fab and an scFv.

In some instances, it is beneficial that the antigen binding domain is derived from the same species in which the CAR will ultimately be used. For example, for use in humans, it may be beneficial that the antigen binding domain of the CAR comprises a human antigen receptor that binds a human antigen or a fragment thereof.

In one exemplary embodiment, a genetically engineered chimeric antigen receptor binds a Vβ region of a T cell receptor in a mammal (e.g. a human). In some embodiments, the Vβ region is from a T cell clone from a mammal having a cancer. In some embodiments, the cancer is peripheral T-cell lymphoma (PTCL).

In some embodiments, the Vβ region that the CAR is capable of binding to is selected from the group consisting of Vβ1, Vβ2, Vβ4, Vβ5.1, Vβ7.1, Vβ7.2, Vβ9, Vβ11, Vβ12, Vβ13.2, Vβ13.3, and Vβ22.

In certain embodiments, the extracellular domain/antigen binding domain comprises a heavy chain variable region that comprises three heavy chain complementarity determining regions (HCDRs), and a light chain variable region that comprises three light chain complementarity determining regions (LCDRs).

In certain embodiments, the extracellular domain comprises a complementarity determining region (CDR) comprising an amino acid sequence selected from the group consisting of SEQ ID NOs: 58-60, 62-64, 66-68, 70-72, 74-76, 78-80, 82-84, 86-88, 90-92, 94-96, 98-100, 102-104, 106-108, and 110-112.

In certain embodiments, the extracellular domain comprises a heavy chain variable region wherein HCDR1 comprises the amino acid sequence of SEQ ID NO: 58, HCDR2 comprises the amino acid sequence of SEQ ID NO: 59, and HCDR3 comprises the amino acid sequence of SEQ ID NO: 60, and/or a light chain variable region wherein LCDR1 comprises the amino acid sequence of SEQ ID NO: 62, LCDR2 comprises the amino acid sequence of SEQ ID NO: 63, and LCDR3 comprises the amino acid sequence of SEQ ID NO: 64.

In certain embodiments, the extracellular domain comprises a heavy chain variable region wherein HCDR1 comprises the amino acid sequence of SEQ ID NO: 66, HCDR2 comprises the amino acid sequence of SEQ ID NO: 67, and HCDR3 comprises the amino acid sequence of SEQ ID NO: 68, and/or a light chain variable region wherein LCDR1 comprises the amino acid sequence of SEQ ID NO: 70, LCDR2 comprises the amino acid sequence of SEQ ID NO: 71, and LCDR3 comprises the amino acid sequence of SEQ ID NO: 72.

In certain embodiments, the extracellular domain comprises a heavy chain variable region wherein HCDR1 comprises the amino acid sequence of SEQ ID NO: 74, HCDR2 comprises the amino acid sequence of SEQ ID NO: 75, and HCDR3 comprises the amino acid sequence of SEQ ID NO: 76, and/or a light chain variable region wherein LCDR1 comprises the amino acid sequence of SEQ ID NO: 78, LCDR2 comprises the amino acid sequence of SEQ ID NO: 79, and LCDR3 comprises the amino acid sequence of SEQ ID NO: 80.

In certain embodiments, the extracellular domain comprises a heavy chain variable region wherein HCDR1 comprises the amino acid sequence of SEQ ID NO: 82, HCDR2 comprises the amino acid sequence of SEQ ID NO: 83, and HCDR3 comprises the amino acid sequence of SEQ ID NO: 84, and/or a light chain variable region wherein LCDR1 comprises the amino acid sequence of SEQ ID NO: 86, LCDR2 comprises the amino acid sequence of SEQ ID NO: 87, and LCDR3 comprises the amino acid sequence of SEQ ID NO: 88.

In certain embodiments, the extracellular domain comprises a heavy chain variable region wherein HCDR1 comprises the amino acid sequence of SEQ ID NO: 90, HCDR2 comprises the amino acid sequence of SEQ ID NO: 91, and HCDR3 comprises the amino acid sequence of SEQ ID NO: 92, and/or a light chain variable region wherein LCDR1 comprises the amino acid sequence of SEQ ID NO: 94, LCDR2 comprises the amino acid sequence of SEQ ID NO: 95, and LCDR3 comprises the amino acid sequence of SEQ ID NO: 96.

In certain embodiments, the extracellular domain comprises a heavy chain variable region wherein HCDR1 comprises the amino acid sequence of SEQ ID NO: 98, HCDR2 comprises the amino acid sequence of SEQ ID NO: 99, and HCDR3 comprises the amino acid sequence of SEQ ID NO: 100, and/or a light chain variable region wherein LCDR1 comprises the amino acid sequence of SEQ ID NO: 102, LCDR2 comprises the amino acid sequence of SEQ ID NO: 103, and LCDR3 comprises the amino acid sequence of SEQ ID NO: 104.

In certain embodiments, the extracellular domain comprises a heavy chain variable region wherein HCDR1 comprises the amino acid sequence of SEQ ID NO: 106, HCDR2 comprises the amino acid sequence of SEQ ID NO: 107, and HCDR3 comprises the amino acid sequence of SEQ ID NO: 108, and/or a light chain variable region wherein LCDR1 comprises the amino acid sequence of SEQ ID NO: 110, LCDR2 comprises the amino acid sequence of SEQ ID NO: 111, and LCDR3 comprises the amino acid sequence of SEQ ID NO: 112.

In certain embodiments, the extracellular domain comprises a heavy chain variable region wherein HCDR1 comprises the amino acid sequence of SEQ ID NO: 114, HCDR2 comprises the amino acid sequence of SEQ ID NO: 115, and HCDR3 comprises the amino acid sequence of SEQ ID NO: 116, and/or a light chain variable region wherein LCDR1 comprises the amino acid sequence of SEQ ID NO: 118, LCDR2 comprises the amino acid sequence of SEQ ID NO: 119, and LCDR3 comprises the amino acid sequence of SEQ ID NO: 120.

In certain embodiments, the extracellular domain comprises a heavy chain variable region wherein HCDR1 comprises the amino acid sequence of SEQ ID NO: 122, HCDR2 comprises the amino acid sequence of SEQ ID NO: 123, and HCDR3 comprises the amino acid sequence of SEQ ID NO: 124, and/or a light chain variable region wherein LCDR1 comprises the amino acid sequence of SEQ ID NO: 126, LCDR2 comprises the amino acid sequence of SEQ ID NO: 127, and LCDR3 comprises the amino acid sequence of SEQ ID NO: 128.

In certain embodiments, the extracellular domain comprises a heavy chain variable region wherein HCDR1 comprises the amino acid sequence of SEQ ID NO: 130, HCDR2 comprises the amino acid sequence of SEQ ID NO: 131, and HCDR3 comprises the amino acid sequence of SEQ ID NO: 132, and/or a light chain variable region wherein LCDR1 comprises the amino acid sequence of SEQ ID NO: 134, LCDR2 comprises the amino acid sequence of SEQ ID NO: 135, and LCDR3 comprises the amino acid sequence of SEQ ID NO: 136.

In certain embodiments, the extracellular domain comprises a heavy chain variable region wherein HCDR1 comprises the amino acid sequence of SEQ ID NO: 138, HCDR2 comprises the amino acid sequence of SEQ ID NO: 139, and HCDR3 comprises the amino acid sequence of SEQ ID NO: 140, and/or a light chain variable region wherein LCDR1 comprises the amino acid sequence of SEQ ID NO: 142, LCDR2 comprises the amino acid sequence of SEQ ID NO: 143, and LCDR3 comprises the amino acid sequence of SEQ ID NO: 144.

In certain embodiments, the extracellular domain comprises a heavy chain variable region wherein HCDR1 comprises the amino acid sequence of SEQ ID NO: 146, HCDR2 comprises the amino acid sequence of SEQ ID NO: 147, and HCDR3 comprises the amino acid sequence of SEQ ID NO: 148, and/or a light chain variable region wherein LCDR1 comprises the amino acid sequence of SEQ ID NO: 150, LCDR2 comprises the amino acid sequence of SEQ ID NO: 151, and LCDR3 comprises the amino acid sequence of SEQ ID NO: 152.

In certain embodiments, the extracellular domain comprises a heavy chain variable region comprising an amino acid sequence selected from the group consisting of SEQ ID NOs: 57, 65, 73, 81, 89, 97, 105, 113, 121, 129, 137, and 145, and/or a light chain variable region comprising an amino acid sequence selected from the group consisting of SEQ ID NOs: 61, 69, 77, 85, 93, 101, 109, 117, 125, 133, 141, and 149.

In certain embodiments, the extracellular domain comprises a heavy chain variable region comprising the amino acid sequence of SEQ ID NO: 57 and/or a light chain variable region comprising the amino acid sequence of SEQ ID NO: 61.

In certain embodiments, the extracellular domain comprises a heavy chain variable region comprising the amino acid sequence of SEQ ID NO: 65 and/or a light chain variable region comprising the amino acid sequence of SEQ ID NO: 69.

In certain embodiments, the extracellular domain comprises a heavy chain variable region comprising the amino acid sequence of SEQ ID NO: 73 and/or a light chain variable region comprising the amino acid sequence of SEQ ID NO: 77.

In certain embodiments, the extracellular domain comprises a heavy chain variable region comprising the amino acid sequence of SEQ ID NO: 81 and/or a light chain variable region comprising the amino acid sequence of SEQ ID NO: 85.

In certain embodiments, the extracellular domain comprises a heavy chain variable region comprising the amino acid sequence of SEQ ID NO: 89 and/or a light chain variable region comprising the amino acid sequence of SEQ ID NO: 93.

In certain embodiments, the extracellular domain comprises a heavy chain variable region comprising the amino acid sequence of SEQ ID NO: 97 and/or a light chain variable region comprising the amino acid sequence of SEQ ID NO: 101.

In certain embodiments, the extracellular domain comprises a heavy chain variable region comprising the amino acid sequence of SEQ ID NO: 105 and/or a light chain variable region comprising the amino acid sequence of SEQ ID NO: 109.

In certain embodiments, the extracellular domain comprises a heavy chain variable region comprising the amino acid sequence of SEQ ID NO: 113 and/or a light chain variable region comprising the amino acid sequence of SEQ ID NO: 117.

In certain embodiments, the extracellular domain comprises a heavy chain variable region comprising the amino acid sequence of SEQ ID NO: 121 and/or a light chain variable region comprising the amino acid sequence of SEQ ID NO: 125.

In certain embodiments, the extracellular domain comprises a heavy chain variable region comprising the amino acid sequence of SEQ ID NO: 129 and/or a light chain variable region comprising the amino acid sequence of SEQ ID NO: 133.

In certain embodiments, the extracellular domain comprises a heavy chain variable region comprising the amino acid sequence of SEQ ID NO: 137 and/or a light chain variable region comprising the amino acid sequence of SEQ ID NO: 141.

In certain embodiments, the extracellular domain comprises a heavy chain variable region comprising the amino acid sequence of SEQ ID NO: 145 and/or a light chain variable region comprising the amino acid sequence of SEQ ID NO: 149.

In certain embodiments, the extracellular domain/antigen binding domain is an scFv encoded by a nucleotide sequence set forth in any one of SEQ ID NOs: 33-56.

Any of the scFvs disclosed herein can be combined with any of the transmembrane domains, any of the hinge domains, and any of the intracellular domains disclosed herein.

Tolerable variations of the extracellular domain/antigen binding domain sequences will be known to those of skill in the art. For example, in some embodiments the extracellular domain/antigen binding domain is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 33, 34, 35, 36, 37, 38, 39, 40, 41, 42, 43, 44, 45, 46, 47, 48, 49, 50, 51, 52, 53, 54, 55, or 56. In some embodiments the extracellular domain/antigen binding domain comprises an amino acid sequence that has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence set forth in any one of SEQ ID NOs: 57-152.

```
scFV Sequences:
Vb12HL scFv
                                        (SEQ ID NO: 33)
GAAGTGATGCTGGTGGAATCTGGCGGCGGACTGGTTAAGCCTGGCGGATC

TCTGAAGCTGAGCTGTGCCGCCAGCGGCTTCACCTTTAGAAGCTACGCCA

TGAGCTGGGTCCGACAGACCCCTGAGAAGAGACTGGAATGGGTCGCCACA

ATCAGCAGCGGCGGCAGCTACACAAACTACCCCGATAGCGTGAAGGGCAG

ATTCACCATCAGCCGGGACAACGCCAAGAACACCCTGAACCTGCAGATGA

ACAGCCTGCGGAGCGAGGACACCGCCATGTACTATTGTGCCAGAGGCTAC

CACGGCTACCTGGATGTTTGGGGAGCCGGCACAACCGTGACAGTTTCTTC

TGGTGGCGGAGGATCTGGCGGAGGTGGAAGCGGCGGAGGCGGATCTGATA

TTCTGCTGACTCAGAGCCCCGCCTTCCTGTCTGTTTCTCCTGGCGAGAGA

GTGTCCTTCAGCTGCAGAGCCTCTCAGAGCATCGGCACCTCCATCCACTG

GTATCAGCAGAGGACCAACGGCAGCCCCAGACTGCTGATTAAGTACGCCA

GCGAGAGCTTCAGCGGCATCCCCAGCAGATTTTCTGGCTCTGGCAGCGGC

ACCGACTTCACCCTGTCTATCAGCTCCGTGGAAAGCGAGGATATCGCCGA

CTACTACTGCCAGCAGTCCTACAGCTGGCCCTACACATTTGGCGGAGGCA

CCAAGCTGGAAATCAAG

Vb12LH scFv
                                        (SEQ ID NO: 34)
GACATCCTGCTGACTCAGAGCCCTGCCTTCCTGTCTGTGTCTCCTGGCGA

GAGAGTGTCCTTCAGCTGTAGAGCCAGCCAGAGCATCGGCACCAGCATCC

ACTGGTATCAGCAGCGGACAAACGGCAGCCCCAGACTGCTGATTAAGTAC

GCCAGCGAGAGCTTCAGCGGCATCCCCAGCAGATTTTCTGGCAGCGGCTC

TGGCACCGACTTCACCCTGTCTATCAGCTCCGTGGAAAGCGAGGATATCG

CCGACTACTACTGCCAGCAGTCCTACAGCTGGCCCTACACATTTGGCGGA

GGCACCAAGCTGGAAATCAAAGGCGGCGGAGGAAGCGGAGGCGGAGGATC

TGGTGGTGGTGGATCTGAAGTGATGCTGGTCGAGTCTGGCGGCGGACTTG

TGAAACCTGGCGGAAGCCTGAAGCTGAGCTGTGCCGCTTCCGGCTTCACC

TTTAGAAGCTACGCCATGAGCTGGGTCCGACAGACCCCTGAGAAGAGACT

GGAATGGGTCGCCACCATCTCTAGCGGCGGCAGCTACACAAACTACCCCG
```

-continued

ACTCTGTGAAGGGCAGATTCACCATCAGCCGGGACAACGCCAAGAACACC

CTGAACCTGCAGATGAACAGCCTGCGGAGCGAGGACACCGCCATGTACTA

TTGTGCCAGAGGCTACCACGGCTACCTGGATGTTTGGGGAGCCGGCACAA

CCGTGACAGTGTCATCT

Vb9HL scFv (SEQ ID NO: 35)

ATGAAGTTCAGCTGGGTCATCTTCTTTCTGATGGCCGTGGTCACCGGCGT

GAACTCTGAAGTGCAACTGCAGCAGAGCGTGGCCGAACTCGTTAGACCTG

GCGCCTCTGTGAAGCTGAGCTGTACCGCCAGCGGCTTCAACATCAAGAAC

ACCTTCATGCACTGGGTCAAGCAGCGGCCTGAGCAGGGACTCGAGTGGAT

CGGAAGAATCGACCCCACCAACGGCTACACCAAGTTCGCCCCTAAGTTCC

AGGGCAAAGCCACACTGACAGCCGTGACCAGCAGCAACACAGTGTACCTG

CAGCTGAGCAGCCTGACCTCTGAGGACACCGCCATCTACTACTGCGCCCA

CGATTACGACGCCCCTTGGTTTGCCTATTGGGGCCAGGGCACACTGGTCA

TTGTGTCTGCTGGTGGCGGAGGATCTGGCGGAGGTGGAAGCGGCGGAGGC

GGATCTATGCTTTCTCCTGCTCCTCTGCTGAGCCTGCTGCTGCTGTGCGT

GTCAGATAGCAGAGCCGAGACAACCGTGACACAGTCTCCAGCCAGTCTGT

CTGTGGCCACCGGCGAGAAAGTGACCATCAGATGCATCAGCAGCACCGAC

ATCGACGACGACATGAACTGGTATCAGCAGAAGTCCGGCGAGCCTCCTAA

GCTGCTGATCTCCGAGGGCAATACTCTGAGGCCTGGCGTGCCAAGCAGAT

TCAGCAGCTCTGGCTACGGCACCGACTTCGTGTTCACCATCGAGAACATG

CTGAGCGAGGACGTGGCCGATTACTACTGCCTGCAGAGCGACAACATGCC

CCTGACATTTGGAGCCGGCACCAAGCTGGAACTGAAG

Vb9LH scFv (SEQ ID NO: 36)

ATGCTGTCTCCAGCTCCTCTGCTGTCTCTGCTGCTGCTGTGCGTGTCCGA

TAGCAGAGCCGAGACAACCGTGACACAGTCTCCAGCCAGTCTGTCTGTGG

CCACCGGCGAGAAAGTGACCATCAGATGCATCAGCAGCACCGACATCGAC

GACGACATGAACTGGTATCAGCAGAAGTCCGGCGAGCCTCCTAAGCTGCT

GATCTCCGAGGGCAATACTCTGAGGCCTGGCGTGCCAAGCAGATTCAGCA

GCTCTGGCTACGGCACCGACTTCGTGTTCACCATCGAGAACATGCTGAGC

GAGGACGTGGCCGACTACTACTGCCTGCAGAGCGACAACATGCCCCTGAC

ATTTGGAGCCGGCACCAAGCTGGAACTGAAAGGCGGCGGAGGATCTGGCG

GAGGTGGAAGCGGAGGCGGTGGCAGCATGAAGTTCAGCTGGGTCATCTTC

TTTCTGATGGCCGTGGTCACCGGCGTGAACTCTGAAGTGCAACTGCAGCA

GAGCGTGGCCGAACTCGTTAGACCTGGCGCCTCTGTGAAGCTGAGCTGTA

CCGCCAGCGGCTTCAACATCAAGAACACCTTCATGCACTGGGTCAAGCAG

CGGCCTGAGCAGGGACTCGAGTGGATCGGAAGAATCGACCCCACCAACGG

CTACACCAAGTTCGCCCCTAAGTTCCAGGGCAAAGCCACACTGACAGCCG

TGACCAGCAGCAACACAGTGTACCTGCAGCTGAGCAGCCTGACCTCTGAG

GACACCGCCATCTACTACTGTGCCCACGACTACGACGCCCCTTGGTTTGC

CTATTGGGGCCAGGGCACACTGGTCATCGTTTCTGCT

-continued

Vb1HL scFv (SEQ ID NO: 37)

ATGGACTGGGTCTGGAACCTGCTGTTCCTGATGGCCGTTGCTCAGACAGG

TGCTCAGGCTCAGCTGCAACTGGTGCAGTCTGGACCTGAGCTGAGAGAAC

CTGGCGAGAGCGTGAAGATCTCCTGCAAGGCCAGCGGCTACACCTTCACC

GACTACATCGTGCACTGGGTCAAGCAGGCCCCTGGCAAGGGACTGAAATG

GATGGGCTGGATCAACACCTACACCGGCACACCCACCTACGCCGACGATT

TCGAGGGCAGATTCGTGTTCAGCCTGGAAGCCTCTGCCAGCACCGCCAAC

CTGCAGATCAGCAACCTGAAGAACGAGGACACCGCCACCTACTTTTGCGC

CAGATCTTGGCGGAGAGGCATCCGCGGCATCGGCTTTGATTATTGGGGAC

AGGGCGTGATGGTCACCGTGTCTAGCGGAGGCGGAGGATCTGGTGGCGGA

GGAAGTGGCGGAGGCGGTTCTATGAGAGTGCAGATCCAGTTCTGGGGACT

GCTGCTGCTGTGGACAAGCGGCATCCAGTGTGACGTGCAGATGACACAGA

GCCCCTACAACCTGGCTGCCTCTCCTGGCGAGTCCGTGTCCATCAATTGC

AAGGCCTCCAAGAGCATCAACAAGTACCTGGCCTGGTATCAGCAGAAGCC

CGGCAAGCCTAACAAGCTGCTGATCTACGATGGCAGCACCCTGCAGAGCG

GAATCCCCAGCAGATTTTCTGGCAGCGGCTCCGGCACCGATTTCACCCTG

ACAATCAGAGGCCTGGAACCAGAGGACTTCGGCCTGTACTACTGCCAGCA

GCACAACGAGTACCCTCCAACCTTTGGAGCCGGCACCAAGCTGGAACTGA

AG

Vb1LH scFv (SEQ ID NO: 38)

ATGAGAGTGCAGATCCAGTTCTGGGGCCTGCTGCTGCTGTGGACATCTGG

CATCCAGTGCGACGTGCAGATGACACAGAGCCCCTACAACCTGGCTGCCT

CTCCTGGCGAGAGCGTGTCCATCAATTGCAAGGCCAGCAAGAGCATCAAC

AAGTACCTGGCCTGGTATCAGCAGAAGCCCGGCAAGCCTAACAAGCTGCT

GATCTACGATGGCAGCACCCTGCAGAGCGGCATCCCTAGCAGATTTTCTG

GCAGCGGCTCCGGCACCGATTTCACCCTGACAATCAGAGGCCTGGAACCT

GAGGACTTCGGCCTGTACTACTGCCAGCAGCACAACGAGTACCCTCCAAC

CTTTGGAGCCGGCACCAAGCTGGAACTTAAAGGCGGCGGAGGATCTGGCG

GAGGTGGAAGCGGAGGCGGTGGATCTATGGACTGGGTCTGGAATCTGCTG

TTCCTGATGGCCGTGGCTCAGACAGGTGCTCAGGCTCAGCTGCAACTGGT

GCAGTCTGGACCTGAGCTGAGAGAACCTGGCGAGTCCGTGAAGATCTCCT

GCAAGGCCTCCGGCTACACCTTCACCGACTACATCGTGCACTGGGTCAAA

CAGGCCCCTGGCAAGGGACTGAAGTGGATGGGCTGGATCAACACCTACAC

CGGCACACCCACCTACGCCGACGATTTCGAGGGCAGATTCGTGTTCAGCC

TGGAAGCCTCTGCCAGCACCGCCAACCTGCAGATCAGCAACCTGAAGAAC

GAGGACACCGCCACCTACTTTTGCGCCAGATCTTGGAGGCGGGGCATCAG

AGGCATCGGCTTTGATTATTGGGGCCAGGGCGTGATGGTCACCGTGTCCT

CT

Vb2HL scFv (SEQ ID NO: 39)

ATGAAGTTCAGCTGGGTCATCTTCTTTCTGATGGCCGTGGTCACCGGCGT

GAACTCTGAAGTGCAACTGCAGCAGAGCGTGGCCGATCTCGTTAGACCTG

-continued

GCGCCTCTCTGAAGCTGAGCTGTACCGCCAGCGGCTTCAACATCAAGAGC
GCCTACATGCACTGGGTTATCCAGCGGCCAGATCAGGGCCCAGAGTGTCT
GGGAAGAATCGATCCTGCCACCGGCAAGACCAAATACGCCCCTAAGTTTC
AGGCCAAGGCCACCATCACCGCCGACACCTCTAGCAATACCGCCTACCTG
CAGCTGAGCAGCCTGACCTCTGAGGACACCGCCATCTACTACTGCACCAG
AAGCCTGAACTGGGACTACGGCCTGGATTATTGGGGCCAGGGCACAAGCG
TGACAGTGTCTAGCGGAGGCGGAGGATCTGGTGGCGGAGGAAGTGGCGGA
GGCGGTAGCATGGAAACCGATACACTGCTGCTGTGGGTGCTGCTCCTTTG
GGTGCCCGGATCTACAGGCGACATCGTGCTGACACAGTCTCCCGCTTCTC
TGGCCGTGTCTCTGGGACAGAGAGCCACCATCTCTTGCAGAGCCAGCAAG
AGCGTGTCCATCCTGGGCACACACCTGATCCACTGGTATCAGCAGAAGCC
CGGCCAGCCTCCTAAGCTGCTGATCTACGCCGCCAGCAATCTGGAAAGCG
GAGTGCCTGCCAGATTTTCCGGCAGCGGAAGCGAAACCGTGTTCACCCTG
AACATTCACCCCGTGGAAGAAGAGGACGCCGCCACCTATTTCTGCCAGCA
GTCTATCGAGGACCCCTGGACATTTGGAGGCGGCACAAAGCTGGGCATCA
AG

Vb2LH scFv (SEQ ID NO: 40)

ATGGAAACCGACACACTGCTGCTGTGGGTGCTGCTTCTTTGGGTGCCCGG
AAGCACAGGCGACATCGTGCTGACACAGAGCCCTGCTTCTCTGGCCGTGT
CTCTGGGACAGAGAGCCACCATCAGCTGCAGAGCCAGCAAGAGCGTGTCC
ATCCTGGGCACACACCTGATCCACTGGTATCAGCAGAAGCCCGGCCAGCC
TCCTAAGCTGCTGATCTACGCCGCCAGCAATCTGGAAAGCGGAGTGCCTG
CCAGATTTTCCGGCAGCGGAAGCGAGACAGTGTTCACCCTGAACATTCAC
CCCGTGGAAGAAGAGGACGCCGCCACCTACTTTTGCCAGCAGTCTATCGA
GGACCCCTGGACCTTTGGCGGCGGAACAAAGCTGGGAATCAAAGGCGGCG
GAGGATCTGGCGGAGGTGGAAGCGGAGGCGGTGGCAGCATGAAGTTCAGC
TGGGTCATCTTCTTTCTGATGGCCGTGGTCACCGGCGTGAACTCTGAAGT
GCAACTGCAGCAGAGCGTGGCCGATCTCGTTAGACCTGGCGCCTCTCTGA
AGCTGAGCTGTACCGCCAGCGGCTTCAACATCAAGAGCGCCTACATGCAC
TGGGTTATCCAGCGGCCAGATCAGGGCCCAGAGTGTCTGGGAAGAATCGA
TCCTGCCACCGGCAAGACCAAATACGCCCCTAAGTTTCAGGCCAAGGCCA
CAATCACCGCCGACACCTCTAGCAACACAGCCTACCTGCAGCTGTCCAGC
CTGACCTCTGAGGATACCGCCATCTACTACTGCACCAGAAGCCTGAACTG
GGACTACGGCCTGGATTATTGGGGCCAGGGCACAAGCGTGACCGTGTCAT
CT

Vb4HL scFv (SEQ ID NO: 41)

ATGGAATGGTCCTGGATCTTCCTGTTCCTGCTGAGCGTGACAGCCGTGGT
GCATTCTCAGGTTCAGCTGCAGCAGTCTGGCGCCGAACTGGCCAAACCTG
GCACAAGCGTGAAGCTGAGCTGTAAAGCCAGCGGCTACACCTTCACCAGC
TACTACATCTACTGGGTCAAGCAGCGGCCTGGACAGGGACTTGAGTGGCT

-continued

GGGCTATATCTACCCTGGCAACGGCGGCACCTACTACAGCGAGAAGTTCA
AGGGCAAAGCCACCTTTACCGCCGACACCAGCAGCAACACAGCCTACATG
CTGCTGGGCAGCCTGACACCTGAGGACAGCGCCTACTACTTCTGTGCCAG
AGGCAGCGGCGACCGGTACAATTCTCTGGCCTATTGGGGCCAGGGCACCC
TGGTTACAGTTTCTTCTGGTGGCGGAGGATCTGGCGGAGGTGGAAGCGGC
GGAGGCGGATCTATGGCTATTCCTACACAGCTGCTGGGACTGCTGCTGCT
CTGGATCACCGATGCCATCTGCGACATCCAGATGACACAGAGCCCTCACA
GCCTGTCTGCCAGCCTGGGAGAGACAGTGTCCATTGAGTGTCTGGCCAGC
GAGGGCATCAGCAACTTTCTGGCCTGGTATCAGCAGAAGCCCGGCAAGTC
TCCTCAGCTGCTGATCTACTACACAAGCAGCCTGCAGGATGGCGTGCCCT
CTAGATTTTCTGGCTCTGGCAGCGGCACCCAGTACAGCCTGAAGATCAGC
AACATGCAGCCCGAGGACGAGGGCGTGTACTATTGTCAGCAGGGCTACAA
GTTCCCCAGAACCTTTGGCGGAGGCACCAAGCTGGAACTGAAG

Vb4LH scFv (SEQ ID NO: 42)

ATGGCTATCCCCACACAACTGCTGGGACTGCTGCTGCTGTGGATCACCGA
TGCCATCTGCGACATCCAGATGACACAGAGCCCTCACAGCCTGTCTGCCA
GCCTGGGAGAGACAGTGTCCATTGAGTGTCTGGCCAGCGAGGGCATCAGC
AACTTTCTGGCCTGGTATCAGCAGAAGCCCGGCAAGTCTCCTCAGCTGCT
GATCTACTACACCAGCAGCCTGCAGGATGGCGTGCCCAGCAGATTTTCTG
GCAGCGGCTCTGGCACACAGTACAGCCTGAAGATCAGCAACATGCAGCCC
GAGGACGAGGGCGTGTACTATTGTCAGCAGGGCTACAAGTTCCCCAGAAC
CTTTGGCGGAGGCACCAAGCTGGAACTGAAAGGCGGCGGAGGAAGCGGAG
GCGGAGGATCTGGTGGTGGTGGATCTATGGAATGGTCCTGGATCTTCCTG
TTCCTGCTGAGCGTGACAGCCGTGGTGCATTCTCAGGTTCAGCTGCAGCA
GAGCGGAGCCGAACTGGCCAAACCTGGCACAAGCGTGAAGCTGAGCTGTA
AAGCCAGCGGCTACACCTTCACCAGCTACTACATCTACTGGGTCAAGCAG
CGGCCTGGACAGGGACTTGAGTGGCTGGGCTATATCTACCCTGGCAACGG
CGGCACCTACTACAGCGAGAAGTTCAAGGGCAAAGCCACCTTTACCGCCG
ACACCAGCTCCAACACAGCCTACATGCTGCTCGGCAGCCTGACACCTGAG
GACAGCGCCTACTACTTTTGCGCTAGAGGCAGCGGCGACCGGTACAATTC
TCTGGCCTATTGGGGCCAGGGCACCCTGGTTACAGTCAGCTCT

Vb5.1HL scFv (SEQ ID NO: 43)

ATGGGCTGGTCCTGGATCTTCCTGTTCCTGCTGTCTGAGACTGCCGGCGT
GCTGAGTGAAGTTCAGCTGCAGCAGTCTGGCCCCGTGCTTGTGAAACCTG
GCGCCTCTGTCAGAATGAGCTGCAAGGCCAGCGGCTACACCTTCACCGAC
TACAACATCCACTGGGTCAAGCAGAGCCACGGCAGATCCCTTGAGTGGGT
CGGATATATCAACCCCTACAACGGCCGGACCGGCTACAACCAGAAGTTCA
AGGCCAAGGCCACACTGACCGTGAACAAGAGCAGCAGCACCGCCTACATG
GACCTGAGAAGCCTGACCAGCGAGGACAGCGCCGTGTACTATTGCGCCAG
ATGGGATGGCAGCAGCTACTTCGATTATTGGGGCCAGGGCACAACCCTGA
CCGTTTCTTCTGGTGGCGGAGGATCTGGCGGAGGTGGAAGCGGCGGAGGC

-continued

GGATCTATGGATTTCCGGGTGCAGATCTTCAGCTTCCTGCTGATCTCCGT
GACCGTGTCCAGAGGCGAGATCGTGCTGACACAGAGCCCTGCCATTACAG
CCGCTTCTCTGGGCCAGAAAGTGACCATCACATGCAGCGCCAGCAGCAGC
GTGTCCTACATGCACTGGTATCAGCAGAAGTCCGGCACAAGCCCCAAGCC
TTGGATCTACGAGATCTCCAAGCTGGCCTCTGGCGTGCCAGCCAGATTTT
CTGGCTCTGGCAGCGGCACCAGCTACTCCCTGACAATCAGCAGCATGGAA
GCCGAGGACGCCGCCATCTACTACTGCCAGCAGTGGAACTACCCTCTGAT
CACCTTTGGAGCCGGCACCAAGCTGGAACTGAAG

Vb5.1LH (SEQ ID NO: 44)
ATGGACTTCCGGGTGCAGATCTTCAGCTTCCTGCTGATCTCCGTGACCGT
GTCCAGAGGCGAGATCGTGCTGACACAGAGCCCTGCCATTACAGCCGCTT
CTCTGGGCCAGAAAGTGACCATCACATGCAGCGCCAGCAGCAGCGTGTCC
TACATGCACTGGTATCAGCAGAAGTCCGGCACAAGCCCCAAGCCTTGGAT
CTACGAGATCTCCAAGCTGGCCTCTGGCGTGCCAGCCAGATTTTCTGGCT
CTGGCAGCGGCACCAGCTACAGCCTGACAATCAGCAGCATGGAAGCCGAG
GACGCCGCCATCTACTACTGCCAGCAGTGGAACTACCCTCTGATCACCTT
TGGAGCCGGCACCAAGCTGGAACTGAAAGGCGGCGGAGGATCTGGCGGAG
GTGGAAGCGGAGGCGGTGGATCTATGGGATGGTCCTGGATCTTCCTGTTC
CTGCTGTCCGAAACAGCCGGCGTGCTGTCTGAAGTTCAGCTGCAGCAGTC
TGGCCCCGTGCTTGTGAAACCTGGCGCCTCTGTCAGAATGAGCTGCAAGG
CCAGCGGCTACACCTTCACCGACTACAACATCCACTGGGTCAAGCAGAGC
CACGGCAGATCCCTTGAGTGGGTCGGATATATCAACCCCTACAACGGCCG
GACCGGCTACAACCAGAAGTTCAAGGCCAAGGCCACACTGACCGTGAACA
AGAGCAGCAGCACCGCCTACATGGACCTGAGAAGCCTGACCAGCGAGGAC
AGCGCCGTGTACTATTGCGCCAGATGGGATGGCAGCAGCTACTTCGATTA
TTGGGGCCAGGGCACAACCCTGACAGTGTCCTCT

Vb7.1HL (SEQ ID NO: 45)
ATGAACTTCGGCCTGAGCCTGATCTTCCTGGTGCTGTTCCTGAAGGGCGT
GCAGTGCGAAGTGCAGCTGGTTGAATCTGGCGGCGGACTGGTTAAGCCTG
GCGGATCTCTGAAGCTGAGCTGTGCCGCCAGCGGCTTCACCTTCAGCGAC
TACTACATGTACTGGGTCCGACAGACCCCTGAGAAGCGGCTGGAATGGGT
CGCCACAATTTCTGGCGGAGGCAGCTACACATACAGCCCCGATTCTGTGA
AGGGCAGATTCACCATCAGCCGGGACAACGCCAAGAACAACCTGTACCTG
CAGATGAGCAGCCTGCGGAGCGAGGACACCGCCATGTACTTTTGCGCCAG
AGAGCGGGACATCTACTACGGCAACTTCAACGCCATGGTGTACTGGGGCA
GAGGCACCAGCGTGACAGTTAGTAGCGGAGGCGGAGGATCAGGTGGCGGT
GGAAGTGGTGGTGGCGGCAGCATGGAAACCGATACACTGCTGCTGTGGGT
GCTGCTCCTTTGGGTGCCCGGATCTACAGGCGACATCGTGCTGACACAGA
GCCCCGTGTCTCTGACAGTGTCCCTGGGACAGAGAGCCACAATCAGCTGC
AGAGCCAGCAAGAGCGTGTCCACAAGCGGCTACAGCTACATGCACTGGTA

-continued

TCAGCAGAAGCCCGGCCAGCCTCCTAAGCTGCTGATCTACCTGGCCAGCA
ACCTGGAAAGCGGAGTGCCTGCCAGATTTTCTGGCAGCGGCTCTGGCACC
GACTTCACCCTGAATATCCATCCTGTGGAAGAAGAGGACGCCGCCACCTA
CTACTGTCAGCACAGCAGAGATCTGCCCTGGACCTTTGGAGGCGGCACCA
AGCTGGAAATCAAG

Vb7.1LH scFv (SEQ ID NO: 46)
ATGGAAACCGACACACTGCTGCTGTGGGTGCTGCTTCTTTGGGTGCCCGG
AAGCACAGGCGACATCGTGCTTACACAGAGCCCCGTGTCTCTGACAGTGT
CCCTGGGACAGAGAGCCACCATCAGCTGTAGAGCCAGCAAGAGCGTGTCC
ACCAGCGGCTACAGCTACATGCACTGGTATCAGCAGAAGCCCGGCCAGCC
TCCTAAGCTGCTGATCTACCTGGCCAGCAACCTGGAAAGCGGAGTGCCTG
CCAGATTTTCTGGCAGCGGCTCTGGCACCGACTTCACCCTGAATATCCAT
CCTGTGGAAGAAGAGGACGCCGCCACCTACTACTGTCAGCACAGCAGAGA
TCTGCCCTGGACCTTTGGCGGCGGAACAAAGCTGGAAATCAAAGGCGGCG
GAGGATCTGGCGGAGGTGGAAGCGGAGGCGGTGGCTCTATGAATTTTGGC
CTGAGCCTGATCTTCCTGGTGCTGTTCCTGAAGGGCGTGCAGTGCGAAGT
GCAGCTGGTTGAAAGTGGCGGAGGCCTGGTTAAGCCTGGCGGATCTCTGA
AGCTGAGCTGTGCCGCCAGCGGCTTCACCTTCAGCGACTACTACATGTAC
TGGGTCCGACAGACCCCTGAGAAGCGGCTGGAATGGGTCGCCACAATTTC
AGGCGGAGGCAGCTACACATACAGCCCCGATTCTGTGAAGGGCCGCTTTA
CCATCAGCCGGGACAACGCCAAGAACAACCTGTACCTGCAGATGAGCAGC
CTGCGGAGCGAGGACACCGCCATGTACTTTTGCGCCAGAGAGCGGGACAT
CTACTACGGCAACTTCAACGCCATGGTGTACTGGGGCAGAGGCACCTCTG
TGACCGTTAGCTCT

Vb7.2HL scFv (SEQ ID NO: 47)
ATGGAACGGCACTGGATCTTTCTGCTGCTGCTGAGCGTTACAGCCGGCGC
TCACTCTCAAGTGCATCTGCAGCAATCTGGCGCCGAGCTTGCTAGACCTG
GCGCCTCTGTGAAGATGAGCTGTAAAGCCAGCGGCTACATCTTCACCGAC
TACACCATGCACTGGGTCAAGCAGAGGCCTGGACAGGGACTCGAGTGGAT
CGGCCACATCAATCCTAGCTCCGGCTACAGCACCTACAACCAGAAGTTCA
AGGACAAGGCCACACTGACCGCCGACAAGAGCAGCTCTACAGCCTACATG
CAGCTGAGCAGCCTGACCAGCGAAGATAGCGCCGTGTACTACTGCGCCAG
AAGCCTGCAGCTGGGCAGAGATTATTGGGGCCAGGGCACAACCCTGACCG
TTTCTTCTGGTGGCGGAGGATCTGGCGGAGGTGGAAGCGGCGGAGGCGGA
TCTATGGAATCTCAGATCCAGGTGTTCGTGTTTGTGTTCCTGTGGCTGTC
TGGCGTGGACGGCGATATCGTGATGACCCAGAGCCACAAGTTCATGAGCA
CCAGCGTGGGCGACAGAGTGTCCATCACATGCAAGGCCAGCCAGGACGTG
TACACAGCCGTGGCTTGGTATCAGCAGAAGCCCGGCCAGTCTCCTAAGCT
GCTGATCTACAGCGCCAGCAACAGATACACCGGCGTGCCCGATAGATTCA
CAGGCTCTGGCAGCGGCACCGACTTCACCTTTACAATCAGCAGCGTGCAG
GCCGAGGACCTGGCCGTGTATTATTGCCAGCAGCACTACACCACACCTCG

-continued

GACCTTTGGCGGCGGAACAAAGCTGGAAATCAAG

Vb7.2LH scFv (SEQ ID NO: 48)

ATGGAAAGCCAGATCCAGGTGTTCGTGTTTGTGTTCCTGTGGCTGTCTGG
CGTGGACGGCGATATCGTGATGACCCAGAGCCACAAGTTCATGAGCACCA
GCGTGGGCGACAGAGTGTCCATCACCTGTAAAGCCAGCCAGGACGTGTAC
ACAGCCGTGGCCTGGTATCAGCAGAAGCCTGGCCAGTCTCCTAAGCTGCT
GATCTACAGCGCCAGCAACAGATACACCGGCGTGCCCGATAGATTCACAG
GCTCTGGCAGCGGCACCGACTTCACCTTTACAATCAGCAGCGTGCAGGCC
GAGGACCTGGCCGTGTATTATTGCCAGCAGCACTACACCACACCTCGGAC
CTTTGGCGGCGGAACAAAGCTGGAAATCAAAGGCGGCGGAGGATCTGGCG
GAGGTGGAAGCGGAGGCGGTGGTTCTATGGAACGGCACTGGATCTTTCTG
CTGCTGCTGAGCGTTACAGCCGGCGCTCACTCTCAAGTGCATCTGCAGCA
ATCTGGCGCCGAGCTTGCTAGACCTGGCGCCTCTGTGAAGATGAGCTGCA
AGGCCAGCGGCTACATCTTCACCGACTACACCATGCACTGGGTCAAGCAG
AGGCCTGGACAGGGACTCGAGTGGATCGGCCACATCAATCCTAGCTCCGG
CTACAGCACCTACAACCAGAAGTTCAAGGACAAGGCCACACTGACCGCCG
ACAAGAGCAGCTCTACAGCCTACATGCAGCTGAGCAGCCTGACCAGCGAA
GATAGCGCCGTGTACTACTGCGCTAGAAGCCTGCAGCTGGGCAGAGATTA
TTGGGGCCAGGGCACAACCCTGACCGTGTCATCT

Vb11HL scFv (SEQ ID NO: 49)

ATGGGCTGGTCCTGCATCATCTTTTTTCTGGTGGCCACTGCCACCGGCGT
GCACTCTCAAGTTCAGCTGCAGCAGTCTGGCCCCGAAGTCGTTAGACCTG
GCGTGTCCGTGAAGATCAGCTGCAAAGGCAGCGGCTACCGGTTCACCGAT
TCTGCCATGCACTGGGTCAAGCAGAGCCACGCCAAGAGCCTGGAATGGAT
CGGCGTGATCAGCAGCTACAACGGCAACACCAACTACAACCAGAAGTTCA
AGGGCAAAGCCACCATGACCGTGGACAAGAGCAGCAGCACCGCCTACATG
GAACTGGCCAGAATGACCAGCGAGGACAGCGCCATCTACTACTGCGCCAG
ATCCAGAGATGCCATGGACTATTGGGGCCAGGGCACCAGCGTGACAGTTT
CTTCTGGCGGCGGAGGAAGCGGAGGCGGAGGTTCTGGTGGTGGTGGCTCT
ATGAGAACCCCTGCTCAGTTCCTGGGCATCCTGCTGCTTTGGTTCCCCGG
CATCAAGTGCGACATCAAGATGACACAGAGCCCCAGCTCTATGTACGCCA
GCCTGGGAGAGAGAGTGACCATTACCTGCAAGGCCAGCCAGGACATCAAC
AGCTACCTGAGCTGGTTCCAGCAGAAGGCCGGCAAGAGCCCCAAGACACT
GATCTACAGAGCCAACAGACTGGTGGACGGCGTGCCCAGCAGATTTTCTG
GAAGCGGCAGCGGCCAGGACTACAGCCTGACAATCAGCTCCCTGGAATAC
GAGGACATGGGGATCTACTATTGCCTGCAGTACGACGAGTTCCCATTCAC
CTTTGGCGGAGGCACCCGGCTGGAAATCAAA

Vb11LH scFv (SEQ ID NO: 50)

ATGAGAACCCCTGCTCAGTTCCTGGGCATCCTGCTGCTTTGGTTCCCCGG
CATCAAGTGCGACATCAAGATGACACAGAGCCCCAGCTCTATGTACGCCA

-continued

GCCTGGGAGAGAGAGTGACCATTACCTGCAAGGCCAGCCAGGACATCAAC
AGCTACCTGAGCTGGTTCCAGCAGAAGGCCGGCAAGAGCCCCAAGACACT
GATCTACAGAGCCAACAGACTGGTGGACGGCGTGCCCAGCAGATTTTCTG
GCTCTGGAAGCGGCCAGGACTACAGCCTGACAATCAGCAGCCTGGAATAC
GAGGACATGGGCATCTACTACTGCCTGCAGTACGACGAGTTCCCATTCAC
CTTTGGCGGCGGAACCCGGCTGGAAATCAAAGGTGGCGGAGGATCTGGCG
GAGGCGGATCAGGCGGCGGTGGATCTATGGGCTGGTCCTGCATCATCTTT
TTTCTGGTGGCCACTGCCACCGGCGTGCACTCTCAAGTTCAGCTGCAGCA
GTCTGGCCCCGAAGTCGTTAGACCTGGCGTGTCCGTGAAGATCAGCTGCA
AAGGCAGCGGCTACCGGTTCACCGATTCTGCCATGCACTGGGTCAAGCAG
AGCCACGCCAAGTCTCTGGAATGGATCGGCGTGATCAGCAGCTACAACGG
CAACACCAACTACAACCAGAAGTTCAAGGGCAAAGCCACCATGACCGTGG
ACAAGAGCAGCAGCACCGCCTACATGGAACTGGCCAGAATGACCAGCGAG
GACAGCGCCATCTATTACTGTGCCAGATCCAGGGACGCCATGGACTATTG
GGGCCAGGGAACAAGCGTGACCGTGTCCTCT

Vb13.2HL scFv (SEQ ID NO: 51)

ATGGGCTGGTCCTGGATCTTCCTGTTTCTGCTGTCTGGCACAGCCGGCGT
GCACTCTGAAGTTCAGCTGCAGCAGTCTGGCCCCGAGCTTGTGAAACCTG
GCGCCTCTGTGAAGATGAGCTGCAACGCCAGCGGCTACACCTTCACCGAC
TACTACATCCACTGGCTGAAGCAGCGGCACGGCAAAGGCCTGGAATGGAT
CGGCATCGTGAACACCAACAACGGCGACACCAACTACAACCAGCGGTTCA
AGGGCAAAGCCAGCCTGACCGTGGATAAGAGCAGCAGCACCGCCTACATG
GAACTGAACTCCCTGACCAGCGAGGACAGCGCCGTGTTCTATTGTGCCAG
GGCTCTGTACACCGGCAGCTATTGGTTCGCCTATTGGGGCCAGGGCACCC
TGGTTACAGTTTCTGCAGGCGGCGGAGGATCTGGCGGAGGTGGAAGCGGA
GGCGGTGGCTCTATGGATTTCCACGTGCAGATCTTCAGCTTCATGCTGAT
CTCCGTGACCGTGATGCTGTCCAGCGGAGAGATCGTGCTGACACAGTCTC
CAGCCGTGATGGCTGCTTCCCCTGGCGAGAAAGTGACCATCACATGTAGC
GCCAGCAGCTCCATCAGCTCCACCAACCTGCACTGGTATCAGCAGAAGTC
CGAGACAAGCCCCAAGCCTTGGATCTACGGCACCAGCAATCTGGCCAGCG
GAGTGCCTGTCAGATTTTCTGGCAGCGGCTCTGGCACCAGCTACAGCCTG
ACAATCAGCAGCATCGAGGCCGAAGATGCCGCCACCTACTACTGCCAGCA
GTGGTCCAGATATCCCCTGACATTTGGCTCCGGCACCAAGCTGGAAATCA
TT

Vb13.2LH scFv (SEQ ID NO: 52)

ATGGACTTCCACGTGCAGATCTTCAGCTTCATGCTGATCTCCGTGACCGT
GATGCTGAGCAGCGGAGAGATCGTGCTGACACAGTCTCCAGCCGTGATGG
CTGCTTCCCCTGGCGAGAAAGTGACCATCACATGTAGCGCCAGCAGCAGC
ATCAGCAGCACCAACCTGCACTGGTATCAGCAGAAGTCCGAGACAAGCCC
CAAGCCTTGGATCTACGGCACCAGCAATCTGGCCAGCGGAGTGCCTGTCA
GATTTTCTGGCAGCGGCTCTGGCACCAGCTACAGCCTGACAATCAGCTCC

ATCGAGGCCGAAGATGCCGCCACCTACTACTGCCAGCAGTGGTCCAGATA
TCCCCTGACATTCGGCAGCGGCACCAAGCTGGAAATCATCGGAGGCGGAG
GATCTGGTGGCGGAGGAAGCGGTGGCGGCGGATCTATGGGATGGTCCTGG
ATCTTCCTGTTCCTGCTGTCTGGAACAGCCGGCGTGCACTCTGAAGTTCA
GCTGCAGCAGTCTGGCCCCGAGCTTGTGAAACCTGGCGCCTCTGTGAAGA
TGAGCTGCAACGCCAGCGGCTACACCTTCACCGACTACTACATCCACTGG
CTGAAGCAGAGACACGGCAAAGGCCTGGAATGGATCGGCATCGTGAACAC
CAACAACGGCGACACCAACTACAACCAGCGGTTCAAGGGCAAAGCCAGCC
TGACCGTGGATAAGAGCAGCTCCACCGCCTACATGGAACTGAACTCCCTG
ACCAGCGAGGACAGCGCCGTGTTCTATTGTGCCAGGGCTCTGTACACCGG
CAGCTATTGGTTCGCCTATTGGGGCCAGGGCACCCTGGTTACAGTTTCTG
CT

Vb13.3HL scFv (SEQ ID NO: 53)
ATGGGCTGGTCCTGCATCATCCTGATTCTGGTGGCTGCCGCTACAGGCGT
GCACTCTCAGGTTCAGCTTCAGCAGCCTGGCGCCGAGCTTGTGAAACCTG
GCGCCTCTGTGAAGATGAGCTGCAAGGCCAGCGGCTACACCTTCACCAGC
TACTGGATCACCTGGGTCAAGCAGAGGCCTGGACAGGGACTCGAGTGGAT
CGGCGATATCTATCCTGGCAGCGGCAGCATCAACTACAACGAGAAGTTCA
ACAACAAGGCCACACTGACCGTGGACACCAGCAGCAGCACAGCCTACATG
CAGCTGAGCAGCCTGACCAGCGAAGATAGCGCCGTGTACTACTGCGCCAG
ACGGGACTACTACAGCCTGTACTACTATGCCCTGGACTACTGGGGCCAGG
GCACAAGCGTGACAGTTTCTTCTGGCGGCGGAGGATCTGGCGGAGGTGGA
AGCGGAGGCGGTGGATCTATGTCTGTGCCTACACAGGTGCTGGGCCTGCT
GCTTCTGTGGTTGACAGGCGCCAGATGCGACATCCAGATGACACAGAGCC
CTGCCAGCCTGAGTGCCTCTGTGGGAGAGACAGTGACCATGACCTGTCGG
GCCAGCGAGAACATCTACAGCAACCTGGCCTGGTATCAGCAGAAGCAGGG
CAAGTCTCCTCAGCTGCTGGTCTACGCCGCCACCAATCTTGCTGATGGCG
TGCCCAGCAGATTCAGCGTGTCCGGATCTGGCACCCACTTCAGCCTGAAG
ATCAACAGCCTGCAGCCAGAGGACTTCGGCAGCTACTACTGCCAGCACTT
CTACGGCACCCCTTACACCTTTGGCGGAGGCACCAAGCTGGAAATCAAG

Vb13.3LH scFv (SEQ ID NO: 54)
ATGAGCGTGCCAACACAGGTTCTGGGACTGCTGCTGCTGTGGCTGACAGG
CGCCAGATGCGACATCCAGATGACACAGAGCCCTGCCAGCCTGTCTGCCT
CTGTGGGAGAGACAGTGACCATGACCTGTCGGGCCAGCGAGAACATCTAC
AGCAACCTGGCCTGGTATCAGCAGAAGCAGGGCAAGTCTCCTCAGCTGCT
GGTGTACGCCGCCACCAATCTTGCTGATGGCGTGCCCAGCAGATTCAGCG
TGTCCGGATCTGGCACCCACTTCAGCCTGAAGATCAACAGCCTGCAGCCT
GAGGACTTCGGCAGCTACTACTGCCAGCACTTCTACGGCACCCCTTACAC
CTTTGGCGGAGGCACCAAGCTGGAAATCAAAGGCGGCGGAGGAAGCGGAG
GCGGAGGATCTGGTGGTGGTGGATCTATGGGCTGGTCCTGCATCATCCTG
ATCCTGGTGGCTGCTGCTACAGGCGTGCACTCTCAGGTTCAGCTGCAACA
GCCAGGCGCCGAGCTTGTGAAACCTGGCGCCTCTGTGAAGATGAGCTGCA
AGGCCAGCGGCTACACCTTCACCAGCTACTGGATCACCTGGGTCAAGCAG
AGGCCTGGACAGGGACTCGAGTGGATCGGCGATATCTATCCTGGCAGCGG
CAGCATCAACTACAACGAGAAGTTCAACAACAAGGCCACACTGACCGTGG
ACACCAGCTCTAGCACAGCCTACATGCAGCTGAGCAGCCTGACCAGCGAA
GATAGCGCCGTGTACTACTGCGCCAGACGGGACTACTACAGCCTGTACTA
CTATGCCCTGGACTACTGGGGCCAGGGCACAAGCGTGACAGTCTCTTCT

Vb22HL scFv (SEQ ID NO: 55)
ATGGACTTCGGCCTGATCTTCTTCATCGTGGCCCTGCTGAAAGGCGTGCA
GTGCGAAGTGAAGCTGCTGGAATCTGGCGGAGGACTGGTTCAGCCTGGCG
GATCTCTGAAGCTGTCTTGTGCCGCCAGCGGCTTCGACTTCAGCCGGTAC
TGGATGAACTGGGTCCGACAGGCCCCTGGCAAAGGCCTGGAATGGATCGG
CGAGATCAACAGCGACAGCAACACCATCAACTACACCCCTAGCCTGAAGG
ACAAGTTCATCATCAGCCGGGACAACGCCAAGAACACCCTGTACCTGCAG
ATGAACAAAGTGCGGAGCGAGGACACAGCCCTGTACTACTGTGCTAGAGG
CGGCCTGCTGAGAGATGTGTGGGGAGCTGGAACCACCGTGACAGTTTCTA
GCGGAGGCGGAGGTTCTGGCGGCGGAGGAAGTGGTGGCGGAGGCTCTATG
GCTTGGATCTCCCTGATCCTGTCTCTGCTGGCCCTTAGCTCTGGCGCCAT
TTCTCAGGCCGTGGTCACACAAGAGAGCGCCCTGACAACAAGCCCTGGCG
AGACAGTGACCCTGACCTGTAGATCTTCTACAGGCGCCGTGACCACCAGC
AACTACGCCAATTGGGTGCAAGAGAAGCCCGACCACCTGTTCACAGGACT
GATCGGCGGCACCAACAATAGAGCACCTGGCGTGCCAGCCAGATTCAGCG
GTTCTCTGATCGGAGACAGAGCCGCACTGACAATCACAGGCGCCCAGACA
GAGGACGAGGCCATCTACTTTTGCGCCCTGTGGTACAGCAACCACTGGGT
TTTCGGCGGAGGCACCAAGCTGACAGTTCTG

Vb22LH scFv (SEQ ID NO: 56)
ATGGCCTGGATTAGCCTGATCCTGTCTCTGCTGGCCCTGTCTAGCGGAGC
CATTTCTCAGGCCGTGGTCACACAAGAGAGCGCCCTGACAACAAGCCCTG
GCGAGACAGTGACCCTGACCTGCAGATCTTCTACAGGCGCCGTGACCACC
AGCAACTACGCCAATTGGGTGCAAGAGAAGCCCGACCACCTGTTCACAGG
ACTGATCGGCGGCACCAACAATAGAGCACCTGGCGTGCCAGCCAGATTCA
GCGGATCTCTGATCGGAGACAGAGCCGCACTGACAATCACAGGCGCCCAG
ACAGAGGACGAGGCCATCTACTTTTGCGCCCTGTGGTACAGCAACCACTG
GGTTTTCGGCGGAGGCACCAAGCTGACAGTTCTTGGAGGCGGAGGATCTG
GCGGAGGTGGAAGTGGCGGAGGCGGCTCTATGGATTTCGGCCTGATCTTC
TTCATCGTGGCCCTGCTGAAAGGCGTGCAGTGCGAAGTGAAGCTGCTGGA
ATCTGGTGGCGGACTGGTTCAGCCTGGCGGCTCTCTGAAACTGTCTTGTG
CCGCCAGCGGCTTCGACTTCAGCCGGTACTGGATGAACTGGGTCCGACAG
GCCCCTGGCAAAGGCCTGGAATGGATCGGCGAGATCAACAGCGACAGCAA
CACCATCAACTACACCCCTAGCCTGAAGGACAAGTTCATCATCAGCCGGG

-continued

ACAACGCCAAGAACACACTGTACCTCCAGATGAACAAAGTGCGGAGCGAG

GACACAGCCCTGTACTACTGTGCTAGAGGCGGCCTGCTGAGAGATGTGTG

GGGAGCTGGAACCACCGTGACCGTTAGTTCT

Heavy Chain Variable Region (VH) and Light Chain Variable Region (VL) Sequences:

(CDRs are in bold)

Vb12 VH (SEQ ID NO: 57)

EVMLVESGGGLVKPGGSLKLSCAASGFTFRSYAMSWVRQTPEKRLEWVA

TISSGGSYTNYPDSVKGRFTISRDNAKNTLNLQMNSLRSEDTAMYYCAR

*GYHGYLDV*WGAGTTVTVSS

Bold - HCDR1 (SEQ ID NO: 58)

Bold underline - HCDR2 (SEQ ID NO: 59)

Bold italics - HCDR3 (SEQ ID NO: 60)

Vb12 VL (SEQ ID NO: 61)

DILLTQSPAFLSVSPGERVSFSCRASQSIGTSIHWYQQRTNGSPRLLIK

YASEFSGIPSRFSGSGSGTDFTLSISSVESEDIADYYC*QQSYSWPYT*F

GGGTKLEIK

Bold - LCDR1 (SEQ ID NO: 62)

Bold underline - LCDR2 (SEQ ID NO: 63)

Bold italics - LCDR3 (SEQ ID NO: 64)

Vb9 VH (SEQ ID NO: 65)

MKFSWVIFFLMAVVTGVNSEVQLQQSVAELVRPGASVKLSCTASGFNIK

NTFMHWVKQRPEQGLEWIGRIDPTNGYTKFAPKFQGKATLTAVTSSNTV

YLQLSSLTSEDTAIYYCAH*DYDAPWFAY*WGQGTLVIVSA

Bold - HCDR1 (SEQ ID NO: 66)

Bold underline - HCDR2 (SEQ ID NO: 67)

Bold italics - HCDR3 (SEQ ID NO: 68)

Vb9 VL (SEQ ID NO: 69)

MLSPAPLLSLLLLCVSDSRAETTVTQSPASLSVATGEKVTIRCISSTDI

DDDMNWYQQKSGEPPKLLISEGNTLRPGVPSRFSSSGYGTDFVFTIENM

LSEDVADYYC*LQSDNMPLT*FGAGTKLELK

Bold - LCDR1 (SEQ ID NO: 70)

Bold underline - LCDR2 (SEQ ID NO: 71)

Bold italics - LCDR3 (SEQ ID NO: 72)

Vb1 VH (SEQ ID NO: 73)

MDWVWNLLFLMAVAQTGAQAQLQLVQSGPELREPGESVKISCKASGYTF

TDYIVHWVKQAPGKGLKWMGWINTYTGTPTYADDFEGRFVFSLEASAST

ANLQISNLKNEDTATYFCAR*SWRRGIRGIGFDY*WGQGVMVTVSS

-continued

Bold - HCDR1 (SEQ ID NO: 74)

Bold underline - HCDR2 (SEQ ID NO: 75)

Bold italics - HCDR3 (SEQ ID NO: 76)

Vb1 VL (SEQ ID NO: 77)

MRVQIQFWGLLLLWTSGIQCDVQMTQSPYNLAASPGESVSINCKASKSI

NKYLAWYQQKPGKPNKLLIYDGSTLQSGIPSRFSGSGSGTDFTLTIRGL

EPEDFGLYYC*QQHNEYPPT*FGAGTKLELK

Bold - LCDR1 (SEQ ID NO: 78)

Bold underline - LCDR2 (SEQ ID NO: 79)

Bold italics - LCDR3 (SEQ ID NO: 80)

Vb2 VH (SEQ ID NO: 81)

MKFSWVIFFLMAVVTGVNSEVQLQQSVADLVRPGASLKLSCTASGFNIK

SAYMHWVIQRPDQGPECLGRIDPATGKTKYAPKFQAKATITADTSSNTA

YLQLSSLTSEDTAIYYCTR*SLNWDYGLDY*WGQGTSVTVSS

Bold - HCDR1 (SEQ ID NO: 82)

Bold underline - HCDR2 (SEQ ID NO: 83)

Bold italics - HCDR3 (SEQ ID NO: 84)

Vb2 VL (SEQ ID NO: 85)

METDTLLLWVLLLWVPGSTGDIVLTQSPASLAVSLGQRATISCRASKSV

SILGTHLIHWYQQKPGQPPKLLIYAASNLESGVPARFSGSGSETVFTLN

IHPVEEEDAATYFC*QQSIEDPWT*FGGGTKLGIK

Bold - LCDR1 (SEQ ID NO: 86)

Bold underline - LCDR2 (SEQ ID NO: 87)

Bold italics - LCDR3 (SEQ ID NO: 88)

Vb4 VH (SEQ ID NO: 89)

MEWSWIFLFLLSVTAVVHSQVQLQQSGAELAKPGTSVKLSCKASGYTFT

SYYIYWVKQRPGQGLEWLGYIYPGNGGTYYSEKFKGKATFTADTSSNTA

YMLLGSLTPEDSAYYFCAR*GSGDRYNSLAY*WGQGTLVTVSS

Bold - HCDR1 (SEQ ID NO: 90)

Bold underline - HCDR2 (SEQ ID NO: 91)

Bold italics - HCDR3 (SEQ ID NO: 92)

Vb4 VL (SEQ ID NO: 93)

MAIPTQLLGLLLLWITDAICDIQMTQSPHSLSASLGETVSIECLASEGI

SNFLAWYQQKPGKSPQLLIYYTSSLQDGVPSRFSGSGSGTQYSLKISNM

QPEDEGVYYC *QQGYKFPRT*FGGGTKLELK

Bold - LCDR1 (SEQ ID NO: 94)

Bold underline - LCDR2 (SEQ ID NO: 95)

Bold italics - LCDR3 (SEQ ID NO: 96)

Vb5.1 VH (SEQ ID NO: 97)

MGWSWIFLFLLSETAGVLSEVQLQQSGPVLVKPGASVRMSCKASGYTFTDYNIHWVKQSHGRSLEWVG<u>YINPYNGRTGYNQKFKA</u>KATLTVNKSSSTAYMDLRSLTSEDSAVYYCAR*WDGSSYFDY*WGQGTTLTVSS

Bold - HCDR1 (SEQ ID NO: 98)

Bold underline - HCDR2 (SEQ ID NO: 99)

Bold italics - HCDR3 (SEQ ID NO: 100)

Vb5.1 VL (SEQ ID NO: 101)

MDFRVQIFSFLLISVTVSRGEIVLTQSPAITAASLGQKVTITCSASSSVSYMHWYQQKSGTSPKPWIY<u>EISKLAS</u>GVPARFSGSGSGTSYSLTISSMEAEDAAIYYC*QQWNYPLIT*FGAGTKLELK

Bold - LCDR1 (SEQ ID NO: 102)

Bold underline - LCDR2 (SEQ ID NO: 103)

Bold italics - LCDR3 (SEQ ID NO: 104)

Vb7.1 VH (SEQ ID NO: 105)

MNFGLSLIFLVLFLKGVQCEVQLVESGGGLVKPGGSLKLSCAASGFTFSDYYMYWVRQTPEKRLEWVA<u>TISGGGSYTYSPDSVKG</u>RFTISRDNAKNNLYLQMSSLRSEDTAMYFCAR*ERDIYYGNFNAMVY*WGRGISVTVSS

Bold - HCDR1 (SEQ ID NO: 106)

Bold underline - HCDR2 (SEQ ID NO: 107)

Bold italics - HCDR3 (SEQ ID NO: 108)

Vb7.1 VL (SEQ ID NO: 109)

METDTLLLWVLLLWVPGSTGDIVLTQSPVSLTVSLGQRATISCRASKSVSTSGYSYMHWYQQKPGQPPKLLIY<u>LASNLES</u>GVPARFSGSGSGTDFTLNIHPVEEEDAATYYC*QHSRDLPWT*FGGGTKLEIK

Bold - LCDR1 (SEQ ID NO: 110)

Bold underline - LCDR2 (SEQ ID NO: 111)

Bold italics - LCDR3 (SEQ ID NO: 112)

Vb7.2 VH (SEQ ID NO: 113)

MERHWIFLLLLSVTAGAHSQVHLQQSGAELARPGASVKMSCKASGYIFTDYTMHWVKQRPGQGLEWIG<u>HINPSSGYSTYNQKFKD</u>DKATLTADKSSSTAYMQLSSLTSEDSAVYYCARS*LQLGRDY*WGQGTTLTVSS

Bold - HCDR1 (SEQ ID NO: 114)

Bold underline - HCDR2 (SEQ ID NO: 115)

Bold italics - HCDR3 (SEQ ID NO: 116)

Vb7.2 VL (SEQ ID NO: 117)

MESQIQVFVFVFLWLSGVDGDIVMTQSHKFMSTSVGDRVSITCKASQDVYTAVAWYQQKPGQSPKLLIYS<u>ASNRYT</u>GVPDRFTGSGSGTDFTFTISSVQAEDLAVYYC*QQHYTTPRT*FGGGTKLEIK

Bold - LCDR1 (SEQ ID NO: 118)

Bold underline - LCDR2 (SEQ ID NO: 119)

Bold italics - LCDR3 (SEQ ID NO: 120)

Vb11 VH (SEQ ID NO: 121)

MGWSCIIFFLVATATGVHSQVQLQQSGPEVVRPGVSVKISCKGSGYRFTDSAMHWVKQSHAKSLEWIG<u>VISSYNGNTNYNQKFKG</u>KATMTVDKSSSTAYMELARMTSEDSAIYYCARS*RDAMDY*WGQGTSVTVSS

Bold - HCDR1 (SEQ ID NO: 122)

Bold underline - HCDR2 (SEQ ID NO: 123)

Bold italics - HCDR3 (SEQ ID NO: 124)

Vb11 VL (SEQ ID NO: 125)

MRTPAQFLGILLLWFPGIKCDIKMTQSPSSMYASLGERVTITCKASQDINSYLSWFQQKAGKSPKTLIY<u>RANRLVD</u>GVPSRFSGSGSGQDYSLTISSLEYEDMGIYYC*LQYDEFPFT*FGGGTRLEIK

Bold - LCDR1 (SEQ ID NO: 126)

Bold underline - LCDR2 (SEQ ID NO: 127)

Bold italics - LCDR3 (SEQ ID NO: 128)

Vb13.2 VH (SEQ ID NO: 129)

MGWSWIFLFLLSGTAGVHSEVQLQQSGPELVKPGASVKMSCNASGYTFTDYYIHWLKQRHGKGLEWIG<u>IVNTNNGDTNYNQRFKG</u>KASLTVDKSSSTAYMELNSLTSEDSAVFYCAR*ALYTGSYWFAY*WGQGTLVTVSA

Bold - HCDR1 (SEQ ID NO: 130)

Bold underline - HCDR2 (SEQ ID NQ : 131)

Bold italics - HCDR3 (SEQ ID NO: 132)

Vb13.2 VL (SEQ ID NO: 133)

MDFHVQIFSFMLISVTVMLSSGEIVLTQSPAVMAASPGEKVTITCSASSSISSTNLHWYQQKSETSPKPWIY<u>GTSNLAS</u>GVPVRFSGSGSGTSYSLTISSIEAEDAATYYC*QQWSRYPLT*FGSGTKLEII

Bold - LCDR1 (SEQ ID NO: 134)

Bold underline - LCDR2 (SEQ ID NO: 135)

Bold italics - LCDR3 (SEQ ID NO: 136)

Vb13.3 VH (SEQ ID NO: 137)

MGWSCIILILVAAATGVHSQVQLQQPGAELVKPGASVKMSCKASGYTFTSYWITWVKQRPGQGLEWIG<u>DIYPGSGSINYNEKF</u>NNKATLTVDTSSSTAYMQLSSLTSEDSAVYYCAR*RDYYSLYYYALDY*WGQGTSVTVSS

Bold - HCDR1 (SEQ ID NO: 138)

Bold underline - HCDR2 (SEQ ID NO: 139)

Bold italics - HCDR3 (SEQ ID NO: 140)

Vb13.3 VL

-continued (SEQ ID NO: 141)

MSVPTQVLGLLLLWLTGARCDIQMTQSPASLSASVGETVTMTCRASENI

YSNLAWYQQKQGKSPQLLVYAATNLADGVPSRFSVSGSGTHFSLKINSL

QPEDFGSYYC*QHFYGTPYT*FGGGTKLEIK

Bold - LCDR1 (SEQ ID NO: 142)

Bold underline - LCDR2 (SEQ ID NO: 143)

Bold italics - LCDR3 (SEQ ID NO: 144)

Vb22 VH (SEQ ID NO: 145)

MDFGLIFFIVALLKGVQCEVKLLESGGGLVQPGGSLKLSCAASGFDFSR

YWMNWVRQAPGKGLEWIGEINSDSNTINYTPSLKDKFIISRDNAKNTLY

LQMNKVRSEDTALYYCAR*GGLLRDV*WGAGTTVTVSS

Bold - HCDR1 (SEQ ID NO: 146)

Bold underline - HCDR2 (SEQ ID NO: 147)

Bold italics - HCDR3 (SEQ ID NO: 148)

Vb22 VL (SEQ ID NO: 149)

MAWISLILSLLALSSGAISQAVVTQESALTTSPGETVTLTCRSSTGAVT

TSNYANWVQEKPDHLFTGLIGGTNNRAPGVPARESGSLIGDRAALTITG

AQTEDEAIYFC*ALWYSNHWV*FGGGTKLTVL

Bold - LCDR1 (SEQ ID NO: 150)

Bold underline - LCDR2 (SEQ ID NO: 151)

Bold italics - LCDR3 (SEQ ID NO: 152)

Any of the extracellular domains/antigen binding domains disclosed herein can be combined with any of the transmembrane domains, any of the hinge domains, and any of the intracellular domains disclosed herein.

Transmembrane Domain and/or Hinge Domain

With respect to the transmembrane domain, in various embodiments, the CAR comprises a transmembrane domain that is fused to the extracellular domain of the CAR. In one embodiment, the CAR comprises a transmembrane domain that naturally is associated with one of the domains in the CAR. In some instances, the transmembrane domain is selected or modified by amino acid substitution to avoid binding to the transmembrane domains of the same or different surface membrane proteins in order to minimize interactions with other members of the receptor complex.

The transmembrane domain may be derived either from a natural or from a synthetic source. When the source is natural, the domain may be derived from any membrane-bound or transmembrane protein. In one embodiment, the transmembrane domain may be synthetic, in which case it will comprise predominantly hydrophobic residues such as leucine and valine. In one aspect a triplet of phenylalanine, tryptophan and valine will be found at each end of a synthetic transmembrane domain. Optionally, a short oligo- or polypeptide linker, between 2 and 10 amino acids in length may form the linkage between the transmembrane domain and the cytoplasmic signaling domain of the CAR. A glycine-serine (GS) doublet provides a particularly suitable linker.

In some instances, a variety of human hinges can be employed as well including, but not limited to, the human Ig (immunoglobulin) hinge domain and the CD8 alpha hinge domain.

Examples of the hinge and/or transmembrane domain include, but are not limited to, a hinge and/or transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIR, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

Intracellular Signaling Domain

A subject CAR of the present invention also includes an intracellular signaling domain. In certain embodiments, the intracellular signaling domain comprises a costimulatory signaling region. The intracellular signaling domain of the CAR is responsible for activation of at least one of the effector functions of the cell in which the CAR is expressed (e.g., immune cell). The intracellular domain transduces the effector function signal and directs the cell (e.g., immune cell) to perform its specialized function, e.g., harming and/or destroying a target cell.

Examples of an intracellular signaling domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular signaling domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In certain embodiments, the intracellular signaling domain of the CAR includes any portion of one or more co-stimulatory molecules, such as at least one signaling domain from CD2, CD3, CD8, CD27, CD28, ICOS (CD278), 4-1BB, PD-1, any derivative or variant thereof, any synthetic sequence thereof that has the same functional capability, and any combination thereof. In certain embodiments, the intracellular domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3 (CD276), or a variant thereof, or an intracellular domain derived from a killer immunoglobulin-like receptor (KIR).

In one embodiment, the CAR of the invention comprises a CD137 (4-1BB) signaling domain. For example, inclusion of the CD137 (4-1BB) signaling domain significantly increased CAR mediated activity and in vivo persistence of CAR T cells compared to an otherwise identical CAR T cell not engineered to express CD137 (4-1BB). However, the invention is not limited to a specific CAR. Rather, any CAR that targets a Vβ region of a T cell receptor, can be used in the present invention. Compositions and methods of making and using CARs have been described in PCT/US11/64191, which is incorporated by reference in its entirety herein.

The present invention provides a T cell genetically modified to express a chimeric antigen receptor (CAR) comprising an extracellular and intracellular domain. Compositions and methods of making CARs have been described in PCT/US11/64191, which is incorporated in its entirety by reference herein.

In one embodiment, the intracellular domain comprises a costimulatory signaling domain and a CD3 zeta chain portion. The costimulatory signaling domain refers to a portion of the CAR comprising the intracellular domain of a costimulatory molecule. Costimulatory molecules are cell surface molecules other than antigen receptors or their ligands that are required for an efficient response of lymphocytes to antigen.

In some embodiments, the costimulatory signaling region comprises the intracellular domain of a costimulatory molecule selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83.

In some embodiments, the intracellular signaling domain comprises a CD3zeta chain.

In certain embodiments, the CAR is encoded by the nucleotide sequence set forth in any one of SEQ ID NOs: 1-32. In certain embodiments, the CAR comprises the amino acid sequence set forth in any one of SEQ ID NOs: 153-184.

Tolerable variations of the CAR sequences will be known to those of skill in the art. For example, in some embodiments the CAR comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, and 184. In some embodiments the CAR is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32.

Recombinant T Cell Receptors

Provided is a T cell genetically modified to express a recombinant T cell receptor, wherein the recombinant T cell receptor comprises a domain that binds a Vβ region of a T cell receptor. In some embodiments, the domain that binds a Vβ region of a T cell receptor is an α/β heterodimer of the recombinant T cell receptor.

Vectors

The present invention also provides a vector in which a nucleic acid molecule encoding the CAR or the recombinant T cell receptor (TCR) of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

In brief summary, the expression of natural or synthetic nucleic acid molecule encoding CARs or recombinant TCRs is typically achieved by operably linking a nucleic acid encoding the CAR polypeptide or the TCR polypeptide(s) or portions thereof to a promoter (e.g. EF1alpha promoter), and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid molecule can be cloned into any number of different types of vectors. For example, the nucleic acid molecule can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1α promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence, which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or a TCR or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Biological methods for introducing a polynucleotide of interest into a host cell include the use of DNA and RNA vectors. RNA vectors include vectors having a RNA promoter and/other relevant domains for production of a RNA transcript. Viral vectors, and especially retroviral vectors, have become the most widely used method for inserting genes into mammalian, e.g., human cells. Other viral vectors may be derived from lentivirus, poxviruses, herpes simplex virus, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances, which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Any domains and/or fragments of the CAR or recombinant TCR, vector, and the promoter may be synthesized gene fragments amplified by PCR or any other means known in the art.

A self-inactivating lentiviral vector plasmid can be used in which the expression of the CAR or recombinant TCR is regulated by the human elongation factor 1 alpha promoter. This results in stable (permanent) expression of the CAR or recombinant TCR in the host T cell. As an alternative approach, the encoding mRNA can be electroporated into the host cell, which would achieve the same therapeutic effect as the virally transduced T cells, but would not be permanent because the mRNA would dilute out with cell division.

Cells Comprising the CAR

Also provided is a genetically modified T cell comprising the Vβ chimeric antigen receptor (CAR) disclosed herein.

In some embodiments, the genetically modified cell expresses the Vβ CAR. In further embodiments, the cell has high affinity for cells expressing Vβ ligands.

In some embodiments, the genetically modified cell is a T cell, such as a helper T cell, a cytotoxic T cell, a memory T cell, regulatory T cell, gamma delta T cell, a natural killer cell, cytokine induced killer cell, a cell line thereof, a T memory stem cell, or other T effector cell. It is also useful for the T cell to have limited toxicity toward healthy cells and to have specificity to cells expressing the Vβ region of a T cell receptor. In some embodiments, the genetically modified T cell is specific for the Vβ region of a T cell receptor from a specific T cell clone. Such specificity prevents or reduces off-target toxicity that is prevalent in current therapies that are not specific. In one embodiment, the T cell has limited toxicity toward healthy cells. In one embodiment the T cell is an autologous cell. In another embodiment, the T cell is an allogeneic cell.

In some embodiments, the invention includes genetically modified immune cells derived from pluripotent stem cells that were differentiated in vitro. In other embodiments, the invention includes T cells, such as primary cells, expanded T cells derived from primary T cells, T cells derived from stem cells differentiated in vitro, T cell lines such as Jurkat cells, other sources of T cells, combinations thereof, and other effector cells.

Cells Comprising the Genetically Modified TCR

Also provided is a genetically modified T cell comprising the recombinant TCR disclosed herein, wherein the recombinant TCR comprises a domain that binds a Vβ region of a T cell receptor.

In some embodiments, the genetically modified cell expresses the Vβ CAR. In further embodiments, the cell has high affinity for cells expressing Vβ ligands.

In some embodiments, the genetically modified cell is a T cell, such as a helper T cell, a cytotoxic T cell, a memory T cell, regulatory T cell, gamma delta T cell, a natural killer cell, cytokine induced killer cell, a cell line thereof, a T memory stem cell, or other T effector cell. It is also useful for the T cell to have limited toxicity toward healthy cells and to have specificity to cells expressing the Vβ region of a T cell receptor. In some embodiments, the T genetically modified T cell is specific for the Vβ region of a T cell receptor from a specific clone. Such specificity prevents or reduces off-target toxicity that is prevalent in current therapies that are not specific. In one embodiment, the T cell has limited toxicity toward healthy cells. In one embodiment the T cell is an autologous cell. In another embodiment, the T cell is an allogeneic cell.

In some embodiments, the invention includes genetically modified immune cells derived from pluripotent stem cells that were differentiated in vitro. In other embodiments, the invention includes T cells, such as primary cells, expanded T cells derived from primary T cells, T cells derived from stem cells differentiated in vitro, T cell lines such as Jurkat cells, other sources of T cells, combinations thereof, and other effector cells.

Diseases

The present invention also provides methods for preventing, treating and/or managing a cancer or T-cell-associated disease (e.g. an autoimmune disease). The methods comprise administering to a subject in need thereof a genetically modified T cell comprising a CAR, wherein the CAR comprises a domain that binds a Vβ region of a T cell receptor, a transmembrane domain, and an intracellular signaling domain, wherein the intracellular signaling domain comprises a costimulatory signaling region. In one aspect, the subject is a human.

In some aspects, the invention provides a method of treating cancer in a subject in need thereof. Any type of T-cell-associated cancer or T-cell malignancy can be treated with the methods disclosed herein, including but not limited to T-cell lymphoma, T-cell leukemia, cutaneous T-cell lymphoma, peripheral T-cell lymphoma (PTCL), not otherwise specified PTCL (PTCL-NOS), angioimmunoblastic T-cell lymphoma (AITL), anaplastic large-cell lymphoma (ALCL), enteropathy-associated T-cell lymphoma (EATL), adult T-cell leukemia/lymphoma (ATLL), hepatosplenic T-cell lymphoma (HSTL), subcutaneous panniculitis-like T-cell lymphoma (SPTCL), and T-cell acute lymphoblastic leukemia (T-ALL).

The methods of treatment disclosed herein also extend beyond the treatment of T-cell malignancies, as the concept of refined targeting of specific subsets of T-cells can be applied to any disease in which expansions of certain clonal T-cell subsets contribute to the disease process. Thus, certain aspects of the invention provide a method of treating a T cell-associated disease in a subject in need thereof. In certain embodiments, the T cell-associated disease is an autoimmune disease wherein T cells are the mediators of the autoimmunity. In certain embodiments, the CAR T cells disclosed herein can be used to target a pathogenic T cell population responsible for an autoimmune disease. Autoimmune diseases that can be treated with the methods disclosed herein include, but are not limited to, rheumatoid arthritis, inflammatory bowel disease, multiple sclerosis, insulin dependent diabetes mellitus and Kawasaki disease.

The cells of the invention to be administered may be autologous, allogeneic or xenogeneic with respect to the subject undergoing therapy. In the methods of treatment, T cells isolated from a subject can be modified to express the appropriate CAR, expanded ex vivo and then reinfused into the same subject (e.g., the T cells are autologous T cells). In some embodiments the T cells are reinfused into a different subject than the original T cells' donor (e.g., the T cells are allogeneic T cells). The modified T cells recognize target cells, such as cells expressing a Vβ region of a T cell receptor, and become activated, resulting in killing of the target cells.

Sources of T Cells

Prior to expansion and genetic modification, T cells (e.g., autologous or allogeneic T cells) can be obtained from a subject. Examples of subjects include humans, dogs, cats, mice, rats, and transgenic species thereof. T cells can be obtained from a number of sources, including skin, peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^+$, $GITR^+$, and $FoxP3^+$. Alternatively, in certain embodiments, T regulatory cells are depleted by anti-CD25 conjugated beads or other similar method of selection. In other embodiments, subpopulation of T cells, such as, but not limited to, cells positive or expressing high levels of one or more surface markers e.g. CD28+, CD8+, CCR7+, CD27+, CD127+, CD45RA+, and/or CD45RO+ T cells, can be isolated by positive or negative selection techniques.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as, but not limited to, rituximab or other anti-CD20 or anti-CD19 agents, anti-FcRn agents, Btk inhibitors, plasmapheresis, corticosteroids, mycophenolate, azathioprine, methotrexate, cyclosporine, cyclophosphamide. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before or simultaneous ablative therapy such as fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD8^+$ T cell expansion and T cell growth is used. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, $CD4^+$) that is greater than the cytotoxic or suppressor T cell population ($T_C$, $CD8^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_C$ cells or $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Applications—CARs

In one aspect, the invention includes a method for treating cancer in a subject, the method comprising: administering to the subject an effective amount of a T cell genetically modified to express a CAR, wherein the CAR comprises a domain that binds a Vβ region of a T cell receptor, a transmembrane domain, and an intracellular signaling domain, wherein the intracellular signaling domain comprises a costimulatory signaling region. In some embodiments, the costimulatory signaling region comprises the intracellular domain of a costimulatory molecule selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83. In some embodiments, the intracellular signaling domain comprises a CD3zeta chain.

In another aspect, the invention includes a method for preventing or reducing cancer progression in a subject. The method comprises: administering to the subject an effective amount of a T cell genetically modified to express a CAR, wherein the CAR comprises a domain that binds a Vβ region of a T cell receptor, a transmembrane domain, and an intracellular signaling domain, wherein the intracellular signaling domain comprises a costimulatory signaling region, thereby preventing or reducing cancer progression in the subject.

In one embodiment, the cancer is T-cell lymphoma. In one embodiment, the cancer is T-cell leukemia. In certain embodiments, the cancer is selected from the group consisting of cutaneous T-cell lymphoma, peripheral T-cell lymphoma (PTCL), not otherwise specified PTCL (PTCL-NOS), angioimmunoblastic T-cell lymphoma (AITL), anaplastic large-cell lymphoma (ALCL), enteropathy-associated T-cell lymphoma (EATL), adult T-cell leukemia/lymphoma (ATLL), hepatosplenic T-cell lymphoma (HSTL), subcutaneous panniculitis-like T-cell lymphoma (SPTCL), and T-cell acute lymphoblastic leukemia (T-ALL).

In another aspect, the invention includes a method for treating a T-cell-associated disease in a subject in need thereof. In some embodiments, the T-cell-associated disease is an autoimmune disease. In some embodiments, the autoimmune disease is selected from the group consisting of rheumatoid arthritis, inflammatory bowel disease, multiple sclerosis, insulin dependent diabetes mellitus and Kawasaki disease.

Without wishing to be bound by any particular theory, the immune response elicited by the CAR-modified T cells may be an active or a passive immune response. In one embodiment, the genetically modified T cells of the invention are modified by a fully-human CAR. In one embodiment, the fully-human CAR-genetically modified T cells may be a type of vaccine for ex vivo immunization and/or in vivo therapy in a mammal. In one embodiment, the mammal is a human.

With respect to ex vivo immunization, at least one of the following occurs in vitro prior to administering the cell into a mammal: i) expansion of the cells, ii) introducing to the cells a nucleic acid molecule encoding a CAR iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also includes compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the Vβ CAR-modified T cells of the invention are used in the treatment of cancer. In certain embodiments, the cells of the invention are used in the treatment of patients at risk for developing a cancer. Thus, the present invention provides methods for the treatment or prevention of α/β T cell receptor-related cancers comprising administering to a subject in need thereof, a therapeutically effective amount of the Vβ CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," or "a therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, activated T cells are administered to a subject. Subsequent to administration, blood is redrawn or apheresis is performed, and T cells are activated and expanded therefrom using the methods described here, and are then reinfused back into the patient. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The cells of the invention to be administered may be autologous, allogeneic or xenogeneic with respect to the subject undergoing therapy.

Administration of the cells of the invention may be carried out using any convenient means, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir, interleukin-2, Cytarabine (also known as ARA-C), rituximab (or any other generalized B cell depleting agent such as Btk inhibitors or other anti-CD20/CD19 or B cell targeting agents) and/or Soliris® (eculizumab, a terminal complement inhibitor). In further embodiments, the T cells of the invention may be used in combination with an antibody anti-FcRn, IVIg, or plasmapheresis in order to reduce the anti-NKG2D antibody concentration before therapy. In yet other embodiments, a mild lymphodepletion regimen (e.g. Low-dose fludarabine or Cytoxan) might precede treatment with the T cells of the invention.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances smaller or larger doses of up to 40 mg per day may be used (described in U.S. Pat. No. 6,120,766).

In certain embodiments, the subject is provided a secondary treatment. Secondary treatments include but are not limited to chemotherapy, radiation, surgery, and medications.

In some embodiments, the subject can be administered a conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant, doi.org/*10.1016/j.bbmt.2018.12.758; Neelapu et al. (2018) *Nat Rev Clin Oncology,* 15:47; Teachey et al. (2016) *Cancer Discov,* 6(6):664-679).

Therapeutic Applications—ADCs

In one aspect, the invention includes a method for treating cancer in a subject, the method comprising administering to the subject an effective amount of an antibody-drug conjugate (ADC), wherein the antibody portion of the ADC binds to a Vβ region of a T cell receptor. In some embodiments, the cancer is PTCL. In some embodiments, the drug used to make the ADC is MMAE (monomethyl auristatin E), a calichaemicin, or a cytotoxic maytansinoid, for example DM1.

Therapeutic Applications—ADCC

In one aspect, the invention includes a method for treating cancer in a subject, the method comprising administering to the subject an effective amount of an antibody that binds to a Vβ region of a T cell receptor and a CD64-expressing immune cell.

In some embodiments, the cancer is PTCL.

In some embodiments, the CD64-expressing immune cell is genetically engineered. In further embodiments, the CD64-expressing immune cell is genetically engineered to express a fusion protein comprising CD64, a CD28 transmembrane domain, a CD3 zeta chain and a CD28 costimulatory domain.

Therapeutic Applications—Universal Immune Receptor Systems

In one aspect, the invention includes a method for treating cancer in a subject, the method comprising administering to the subject an effective amount of a labeled antibody that binds to a Vβ region of a T cell receptor and a universal immune receptor (UIR)-expressing immune cell, wherein the universal immune receptor comprises an extracellular domain that specifically binds to the label.

In some embodiments, the labeled antibody is administered before the UIR-expressing immune cell. In some embodiments, the labeled antibody is administered concurrent with the UIR-expressing immune cell. In some embodiments, the UIR-expressing immune cell is bound to the labeled antibody prior to administration to the subject.

Universal immune receptor (UIR or UnivIR) systems are a rapidly emerging form of CAR T cell therapy. Like typical CAR T cell constructs, UIR receptors contain transmembrane and intracellular signaling domains adapted from other immune receptors. However instead of antibody-based antigen-binding extracellular domains, UIRs contain an extracellular binding domain that can be covalently or non-covalently bound to a complementary tag domain that can be engineered onto any number of ligand-binding molecules including but not limited to an oligonucleotide, an antibody, an antibody fragment, a scFv, a protein scaffold, a peptide, a ligand, an aptamer, a labelling agent, a tumor antigen, a self-antigen, a viral antigen, among others, and any combination thereof. In certain embodiments, the labelling agent is selected from the group consisting of myc-tag, FLAG-tag, His-tag, HA-tag, a fluorescent protein (e.g. green fluorescent protein (GFP)), a fluorophore (e.g. tetramethylrhodamine (TRITC), fluorescein isothiocyanate (FITC)), dinitrophenol, peridinin chlorophyll protein complex, green fluorescent protein, phycoerythrin (PE), histidine, biotin, streptavidin, avidin, horse radish peroxidase, palmitoylation, nitrosylation, alkalanine phosphatase, glucose oxidase, Glutathione S-transferase (GST), maltose binding protein, a radioisotope, and any types of compounds used for radioisotope labeling including, 1,4,7,10-tetraazacyclododecane-1,4,7,10-tetraacetic acid (DOTA), diethylene triamine pentaacetic acid (DTPA), and 1,4,7-triazacyclononane-1,4,7-triacetic acid (NOTA). By decoupling antigen recognition and T-cell signaling, universal immune receptors can regulate T-cell effector function and target multiple antigens with a single receptor while also possessing the potential to overcome safety and antigen escape challenges faced by conventional chimeric antigen receptor (CAR) T-cell therapy.

In certain embodiments, the universal immune receptor (UIR) comprises an extracellular binding domain bound to an extracellular hinge region, which is in turn bound to a transmembrane domain which is in turn bound to a T cell receptor intracellular signaling domain. In certain embodiments, the extracellular binding domain is bound to the extracellular hinge domain. In certain embodiments, the extracellular binding domain is bound to the extracellular hinge domain. In certain embodiments, the T cell receptor intracellular signaling domain further comprises a costimulatory molecule. In certain embodiments, the intracellular domain of the costimulatory molecule is selected from the group consisting of CD27, CD28, CD2, CD3, 4-1BB, OX40, CD30, CD40, PD-1, ICOS, lymphocyte function-associated antigen-1 (LFA-1), CD7, LIGHT, NKG2C, B7-H3, a ligand that specifically binds with CD83, and any combination thereof. In certain embodiments, the labeled molecule comprises at least one selected from the group consisting of an oligonucleotide, an antibody, an antibody fragment, a scFv, a protein scaffold, a peptide, a ligand, an aptamer, a labelling agent, a tumor antigen, a self-antigen, a viral antigen, and any combination thereof. In some embodiments, the label is selected from the group consisting of myc-tag, FLAG-tag, His-tag, HA-tag, a fluorescent protein (e.g. green fluorescent protein (GFP)), a fluorophore (e.g. tetramethylrhodamine (TRITC), fluorescein isothiocyanate (FITC)), dinitrophenol, peridinin chlorophyll protein complex, phycoerythrin (PE), histidine, biotin, streptavidin, avidin, horse radish peroxidase, palmitoylation, nitrosylation, alkalanine phosphatase, glucose oxidase, Glutathione S-transferase (GST), maltose binding protein, a radioisotope, and any types of compounds used for radioisotope labeling including, 1,4,7,10-tetraazacyclododecane-1,4,7,10-tetraacetic acid (DOTA), diethylene triamine pentaacetic acid (DTPA), and 1,4,7-triazacyclononane-1,4,7-triacetic acid (NOTA).

In certain embodiments, the antibodies of the current invention are conjugated with Y-DOTA as previously described (Orcutt et al., Nucl Med Biol 38, 223-233 (2011)). In certain embodiments, T cells are transduced to express UIR constructs comprising anti-DOTA scFv linked to hinge and transmembrane domains. These UIR constructs further comprised either CD28 and CD3 intracellular signaling domains (28z), 4-1BB and CD3 intracellular signaling domains (BBz), or, as a control, no intracellular signaling domains (Delta z or Dz). DOTA-based labeling and UIR systems are described in PCT/US2020/02957. In certain embodiments, the antibodies of the invention are labeled with other tags which are able to be bound by complementary ligand-binding domains linked to universal immune receptors. A non-exclusive example of such a ligand/ligand-binding system is SpyCatcher/SpyTag which is described in PCT/US2016/068055 and U.S. Ser. No. 16/064,875.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention.

Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The results of the experiments are now described.

Example 1: T Cell Receptor Repertoire in T Cell Malignancies: Evaluating Antigenic Drive and Shared Environmental Exposures

Materials and Methods

Subjects and Tissues. The University of Pennsylvania Hospital Pathology database was searched for cases indexed as a T cell malignancy from the period 2000-2017. After excluding all outside cases and bone marrow only cases, 140 tissue blocks and accompanying slides were retrieved and reviewed. Cases with controversial diagnoses or inadequate biopsy material were excluded from the study. The remaining 34 formalin fixed paraffin embedded (FFPE) blocks were cut into 5×5-micron scrolls for DNA extraction. The specimens were derived from biopsies of lymph nodes, skin, bone marrow, and other tissue sites. In addition, 22 DNA samples were identified and acquired from the molecular laboratory at the University of Pennsylvania, providing a total number of 56 T cell malignancy patient samples. One patient had two histologically distinct diagnoses of T cell malignancies on two separate biopsies. As controls, fresh peripheral blood total T cells were obtained from nine normal donors were obtained through the Human Immunology Core Facility at the University of Pennsylvania. Basic demographic data and clinical diagnostic information regarding the patient cases were obtained from chart review. This retrospective study was conducted with institutional review board approval and in accordance with the Declaration of Helsinki.

TCR library sequencing. TCR Vβ sequencing was performed by the Human Immunology Core Facility at the University of Pennsylvania. DNA was extracted from FFPE T cell malignancy patient samples or fresh peripheral blood T cells from normal donor subjects using Qiagen Gentra Puregene cell kit and following manufacturer directions (Qiagen, Valencia, CA, Cat. No. 158388). TCR family-specific PCR was performed on all 56 genomic DNA samples. The libraries for sequencing of the Illumina MiSeq platform were prepared using a cocktail of 23 Vβ families from framework region (FR)2 forward primers, and 13 Jβ region reverse primers modified from the BIOMED2 primer series (van Dongen J J M, Langerak A W, Bruggemann M, et al. Design and standardization of PCR primers and protocols for detection of clonal immunoglobulin and T-cell receptor gene recombinations in suspect lymphoproliferations: Report of the BIOMED-2 concerted action BMH4-CT98-3936. *Leukemia.* 2003; 17(12):2257-2317). Library quality was evaluated using Bioanalyzer 2100 (Agilent Technologies, Santa Clara, CA) and quantified by Qubit Fluorometric Quantitation (Thermo Fisher Scientific, Grand Island, NY). A sharp single band from Bioanalyzer analysis indicated a good quality library and was used for sequencing. The reading from Qubit using dsDNA HS (high sensitivity) assay kit (Cat. No. Q32851) was used to calculate the molarity of the library. Libraries were then loaded onto an Illumina MiSeq in the Human Immunology Core Facility at the University of Pennsylvania. 2×300 bp paired end kits were used for all experiments (Illumina MiSeq Reagent Kit v3, 600 cycle, Illumina Inc., San Diego, Cat. No. MS-102-3003).

Raw sequence analysis. Raw sequence data (fastq files) were filtered as previously described (Meng W, Zhang B, Schwartz G W, et al. An atlas of B-cell clonal distribution in the human body. *Nat. Biotechnol.* 2017; 35(9):879-886). Filtered sequence alignment and clone assembly were processed by MiXCR (version 2.1) (Bolotin D A, Poslaysky S, Mitrophanov I, et al. MiXCR: Software for comprehensive adaptive immunity profiling. *Nat. Methods.* 2015; 12(5): 380-381) and MiXCR (version 1.1.5) (Shugay M, Bagaev D V, Turchaninova M A, et al. VDJtools: Unifying Post-analysis of T Cell Receptor Repertoires. *PLOS Comput. Biol.* 2015; 11(11):e1004503). Subsequent bioinformatic analyses of the CDR3 sequence data and predicted amino acid strings were performed by the Human Immunology Core using R.

TCR clones were identified by their CDR3 nucleotide sequence. Dominant clones were defined as those that represent at least 3% of the T cell repertoire, and which are at least three times as frequent as the next most frequent clone. Productive rearrangements are CDR3 nucleotide sequences that are in frame and do not have stop codons.

Normal control dataset. In addition to the nine normal donor peripheral blood samples sequenced by the HIC as described above, a publicly available TCRVβ sequencing dataset from 666 normal bone marrow donors was downloaded from Adaptive Biotech, and a random sampling of this dataset was included in the final analysis (https://clients.adaptivebiotech.com/pub/emerson-2017-natgen).

Identification of public clonotypes. The published literature was searched for public (or shared) CDR3 sequences with disease associations or known antigenic specificity. Over 1000 public CDR3 sequences were identified from the literature, including ~200 published EBV reactive TCR CDR3 sequences, 1000 CMV reactive TCR CDR3 sequences, and 164 CMV associated sequences (Emerson R O, DeWitt W S, Vignali M, et al. Immunosequencing identifies signatures of cytomegalovirus exposure history and HLA-mediated effects on the T cell repertoire. *Nat. Genet.* 2017; 49(5):659-665). In addition, a publicly available curated database of >17, 000 TCR CDR3 sequences with known antigen specificity was downloaded (https://vdjdb.cdr3.net) (Shugay M, Bagaev D V., Zvyagin I V., et al. VDJdb: A curated database of T-cell receptor sequences with known antigen specificity. *Nucleic Acids Res.* 2018; 46(D1): D419-D427). Dominant CDR3 amino acid sequences in the T cell malignancy samples, and the total T cell repertoire in control and patient samples were compared to the published public clones.

Results

Clinical Features. The median age of the patients at the time of biopsy was 61, ranging from 19 to 87 years. The majority (69%, 38/55) of the patients were men, and the specimen analyzed was taken from the time of initial diagnosis in 64% (35/55) of the cases. Treatment history was unavailable for four patients, and in the remainder of the cases, the sequenced specimen was from time of disease progression or relapse. The patient specimens represented a wide range of T cell malignancies; the breakdown of histologic diagnoses is shown (FIG. 1). Peripheral T cell lymphoma (PTCL) NOS and anaplastic large cell lymphoma represented the most common histologies which is consistent with the reported epidemiology of mature T cell malignancies.

Sequence analysis for common antigenic driver. For each of the 56 T cell malignancy patient samples, TCRβ NGS was performed, identifying each unique clone and its abundance in the sample. In our dataset, we found 23 samples with a dominant clone. Seven samples had two dominant rearrangements, but only two of these samples had two productive dominant rearrangements.

The productive dominant rearrangements were compared to a list of >1500 published clones associated with a diverse array of infectious, autoimmune, and neoplastic conditions. None of the dominant clones in the T cell malignancy dataset was identical to a previously published TCR CDR3 sequence, although the sequence CASAGYEQYF was a close match to the published CMV reactive sequence CASAGETQYF.

Identification of recurrent T cell clones in T cell malignancies. The T cell repertoire based on TCR Vβ CDR3 sequences from the patient samples was analyzed for recurrent clonotypes. In total, 57 sequences occurred in three samples or more (range 3-17 samples), with some clones occurring in very low frequency ($<5\times10^{-6}$). Analyzing the 10 most frequent clones for each sample, we identified 13 T cell CDR3 amino acid sequences that occurred in two or more patients. Shared clonotypes frequently occurred in more than one histology. Four CDR3 amino acid strings occurred in a dominant clone, but none occurred in more than one dominant clone (table 1). The most frequently recurrent CDR3 sequence (CASSIRRGNQPQHF) could be found amongst the top 10 clones in eight patient specimens and was found in the total T cell repertoire in 17 different samples. The sequences CASAGYEQYF, CASSRAGPISY-NEQFF, CSVEEYNEQFF, and CASSITSSSYNEQFF occurred in the top 10 sequences of three patient samples. Thus, a total of five CDR3 sequences were found to recur in at least three patients in the top 10 clones of the T cell malignancy samples. These sequences are referred to herein as "high frequency recurrent lymphoma sequences." In addition, three sequences were identified that occurred in the total T cell repertoires of 6 or more samples, but which do not occur in the top 10 sequences of each sample. These sequences were termed "low frequency recurrent lymphoma sequences."

Determining common environmental exposures. After identifying these eight recurrent lymphoma associated sequences in the T cell malignancy samples, it was examined whether the same recurrent sequences occurred in normal control subjects. Finding recurrent sequences in patient samples but not in normal donor samples may suggest a common environmental exposure for the patients. Fifty-six normal donor total T cell repertoires were randomly selected from Adaptive Biotechnologies' publicly available dataset and examined for the occurrence of these recurrent lymphoma sequences. Seven of the eight sequences were statistically significantly more likely to occur in patient samples compared to control samples (Table 2).

In case the differences were found due to sequencing platform or to the source of normal donor T cells, the occurrence of these sequences in the nine normal donor peripheral blood samples was also independently evaluated. Only two of the sequences, CSVEEYNEQFF and CASSHGGGRETQYF, occurred once in the set of nine peripheral blood normal donor total T cell repertoires. Statistical significance was not reached in any of the comparisons due to small sample size of the normal controls. The most highly recurrent lymphoma associated clone CAS-SIRRGNQPQHF which recurred in 17 of the 56 T cell malignancy samples was not found in any of the nine normal donor samples, with p-value trending toward statistical significance (p=0.054).

Identifying public clonotypes in the recurrent lymphoma clones. To understand what potential environmental exposures may be in T cell malignancies, the recurrent lymphoma associated clones was compared to the list of ~18,000 public TCR CDR3 sequences. No matches were found however this comparison is grossly underpowered.

TABLE 1

Identification of recurrent T cell clones in T cell malignancies. All productive recurrent sequences in the top 10 clones of each sample are shown.

| TCRP CDR3 amino acid sequence | Subject ID | | | | Frequency | Dominant? |
|---|---|---|---|---|---|---|
| CASAGYEQYF | 23 | PTCL NOS | Spleen | Top sequence | 0.887687 | Yes |
| | 11 | PTCL NOS | Buccal mucosa | Top sequence | 0.243332 | No |
| | 56 | T-ALL | Pleural mass | 8th sequence | 0.000813 | |
| CASSLESGTGTFF | 31 | ALK− ALCL | Lung | Top sequence | 0.932 | Yes |
| | 32 | ALK+ ALCL | Omental nodule | 2nd sequence | 0.167 | |
| CASSLEGQGAGGYTF | 54 | ALK− ALCL | Lymph node | Top sequence | 0.29118 | Yes |
| | 48 | Cutaneous γ δ T cell lymphoma | Skin | Top sequence | 0.039804 | No |
| CASSIRRGNQPQHF | 12 | CTCL | Skin | Top sequence | 0.744838 | Yes |
| | 21 | CTCL | Skin | Top sequence | 0.226456 | No |
| | 19 | PTCL NOS | Tissue | Top sequence | 0.09619 | No |
| | 11 | PTCL NOS | Buccal mucosa | 2nd sequence | 0.138827 | |
| | 15 | PTCL NOS (CD30+) | Tongue | 3rd sequence | 0.089187 | |

TABLE 1-continued

Identification of recurrent T cell clones in T cell malignancies. All productive recurrent sequences in the top 10 clones of each sample are shown.

| TCRP CDR3 amino acid sequence | Subject ID | | | | Frequency | Dominant? |
|---|---|---|---|---|---|---|
| | 34 | ALK+ ALCL | Lymph node | 2nd sequence | 0.081538 | |
| | 9 | PTCL NOS | Omentum | 5th sequence | 0.04937 | |
| | 1 | AITL | Lymph node | 9th sequence | 0.018157 | |
| CATGRSYNEQFF | 34 | ALK+ ALCL | Lymph node | 10th sequence | 0.030 | |
| | 12 | CTCL | Skin | 7th sequence | 0.0018 | |
| CASSYSGNTEAFF | 47 | PTCL NOS | Bone marrow | Top sequence | 0.142 | No |
| | 3 | EATL | Intra abdominal mass | 5th sequence | 0.0058 | |
| CASSRRGSTDTQYF | 7 | PTCL NOS | Lymph node | 9th sequence | 0.0126 | |
| | 38 | CTCL | Skin | 10th sequence | 0.00547 | |
| CASSRAGPISYNEQFF | 17 | T-LGL | Lymph node | 3rd sequence | 0.0526 | |
| | 3 | EATL | Intra abdominal mass | 3rd sequence | 0.0066 | |
| | 31 | ALK- ALCL | Lung | 5th sequence | 0.006 | |
| CSVEEYNEQFF | 9 | PTCL NOS | Omentum | Top sequence | 0.128483 | No |
| | 17 | T-LGL | Lymph node | Top sequence | 0.090198 | No |
| | 3 | EATL | Intra abdominal mass | 6th sequence | 0.005272 | |
| CASSITSSSYNEQFF | 2 | SP TCL | Skin | 8th sequence | 0.037 | |
| | 4 | NK TCL | Nasal mass | 5th sequence | 0.056 | |
| | 15 | PTCL NOS (CD30+) | Tongue | 8th sequence | 0.0499 | |
| CASSHGGGRETQYF | 6 | CTCL | Lymph node | 2nd sequence | 0.333 | |
| | 1 | AITL | Lymph node | 4th sequence | 0.0717 | |
| CASSELAGGPDTQYF | 17 | T-LGL | Lymph node | 2nd sequence | 0.057 | |
| | 32 | ALK+ ALCL | Omental nodule | 3rd sequence | 0.00955 | |

TABLE 1-continued

Identification of recurrent T cell clones in T cell malignancies. All productive recurrent sequences in the top 10 clones of each sample are shown.

| TCRP CDR3 amino acid sequence | Subject ID | | | | Frequency | Dominant? |
|---|---|---|---|---|---|---|
| CAGLTAQDGYTF | 19 | PTCL NOS | Tissue | 9th sequence | 0.0227 | |
| | 10 | AITL | Lymph node | 4th sequence | 0.0551 | |

TABLE 2

Comparison of recurrent T cell clones in T cell malignancies to normal controls. A) Comparison is made between the proportion of patient samples that have a highly recurrent sequence in the T cell repertoire to the proportion of normal donor samples that have the same sequence in the repertoire. Only recurrent sequences that occurred in the top 10 clones of 3 or more patient samples are included. Statistical analysis is performed using the two-sample test of proportions. B) Similar to table 2A, except recurrent sequences occurring in the total T cell repertoire of at least 6 patient samples are included.

A

| "High frequency recurrent" TCRβ CDR3 amino acid sequence | Number of patient samples with the sequence in top 10 clones | Proportion of patient samples with the sequence in T cell repertoire | Proportion of normal donor bone marrow samples with the sequence in T cell repertoire | P value |
|---|---|---|---|---|
| **CASSIRRGNQPQHF** | 8 | 17/56 | 0/56 | <0.00001 |
| **CASAGYEQYF** | 3 | 12/56 | 0/56 | 0.0002 |
| CSVEEYNEQFF | 3 | 7/56 | 0/56 | 0.0063 |
| CASSRAGPISYNEQFF | 3 | 5/56 | 0/56 | 0.022 |
| CASSITSSSYNEQFF | 3 | 5/56 | 0/56 | 0.022 |

B

| "Low frequency recurrent" TCRβ CDR3 amino acid sequence | Proportion of patient samples with sequence in T cell repertoire | Proportion of normal donor bone marrow samples with sequence in T cell repertoire | P value |
|---|---|---|---|
| **CASSLESGTGTFF** | 11/56 | 0/56 | 0.0005 |
| CASSHGGGRETQYF | 8/56 | 0/56 | 0.0033 |
| CASSISGGVTDTQYF | 6/56 | 3/56 | 0.297 |

Although there is substantial evidence for the role of antigenic drivers in the development of some B cell malignancies, the causes of the development of T cell malignancies are much less clear. Wide geographic variation in the prevalence of T cell malignancies raises the prospect that both genetic and environmental factors play etiologic roles. Indeed, viral oncogenesis by EBV or HTLV has been identified as mechanisms of lymphomagenesis in specific subtypes of T cell lymphoma, but alternatively, antigenic stimulation may contribute to T cell lymphomagenesis by activation of the TCR/CD3 complex and downstream signal transduction. (Wilcox R A. A three-signal model of T-cell lymphoma pathogenesis. Am. J. Hematol. 2016; 91(1):113-122) One aim of this study was to characterize the TCR repertoire in 56 T cell malignancy specimens, and to identify possible antigenic drivers of T cell lymphomagenesis, putative recurrent T cell malignancy associated clones, and possible common environmental exposures shared amongst T cell malignancy patients.

In a cohort of 56 pathologic samples which included only 23 dominant clones, dominant clones that were shared between patient samples were not found; nor were any sequence identities found between the dominant clones with published public TCR CDR3 sequences. Since this study is limited by sample size, the results do not preclude the possibility that antigenic drivers may play a role in the development of some T cell malignancies. For example, chronic viral stimulation has long been suspected to be associated with cutaneous T cell lymphoma, (Mirvish E D, Pomerantz R G, Geskin L J. Infectious agents in cutaneous T-cell lymphoma. *J. Am. Acad. Dermatol.* 2011; 64(2):423-431) and superantigenic stimulation by bacterial toxins causing overexpansion of TCR Vβ families has also been suggested as a possible etiologic cause of CTCL. (Jackow C, Cather J, Hearne V, et al. Association of Erythrodermic Cutaneous T Cell Lymphoma, Superantigen-Positive *Staphylococcus aureus*, and Oligoclonal T Cell Receptor Vbeta Gene Expansion. *Blood.* 1997; 89(1):32-40; Tokura Y, Heald P W, Yan S L, Edelson R L. Stimulation of Cutaneous T cell Lymphoma Cells with Superantigenic Staphylococcal Toxins.pdf. *J. Invest. Dermatol.* 1992). One dominant T cell clone with a CDR3 sequence (CASAGYEQYF) was identified that has remarkable sequence similarity with a published public CDR3 sequence with known reactivity to CMV (CASAGETQYF). Unfortunately, since the tissue from this specimen was formalin fixed and paraffin embedded, it was not possible to investigate the reactivity of the T cell clone to CMV epitopes, and so CMV reactivity could not be confirmed. In addition to this putative case of a CMV reactive dominant clone, subject 47 had a top clone, not quite meeting criteria for clonal dominance in the study, that was an exact match with a public CMV reactive sequence.

Although the study is underpowered for CDR3 sequence identity analysis in the dominant clones, the statistically significant sharing of three TCRβ CDR3 sequences amongst the lymphoma samples that were not shared amongst normal controls was observed. These may be considered "disease associated" CDR3 sequences and could suggest common environmental exposures. One of the shared clones is again CASAGYEQYF. Again, none of the three lymphoma associated sequences yielded any matches with our list of >1600 public TCR CDR3 sequences.

Given the diversity of the possible TCR rearrangements, it is not surprising that in a study with limited sample size, no sequence identities between the recurrent lymphoma associated clones and known public pathogen-reactive CDR3 sequences were found. It is well recognized that TCR repertoire is markedly diverse for a variety of chronic viral infections. (Cose S C, Kelly J M, Carbone F R. Characterization of diverse primary herpes simplex virus type 1 gB-specific cytotoxic T-cell response showing a preferential V beta bias. *J. Virol.* 1995; 69(9):5849-52; Cohen G B, Islam S A, Noble M S, et al. Clonotype tracking of TCR repertoires during chronic virus infections. Virology. 2002; 304(2):474-84; Horwitz M S, Yanagi Y, Oldstone M B. T-cell receptors from virus-specific cytotoxic T lymphocytes recognizing a single immunodominant nine-amino-acid viral epitope show marked diversity. *J. Virol.* 1994; 68(1):352-7; Cole G A, Hogg T L, Woodland D L. The MHC class I-restricted T cell response to Sendai virus infection in C57BL/6 mice: a single immunodominant epitope elicits an extremely diverse repertoire of T cells. *Int. Immunol.* 1994; 6(11):1767-75). There are many reasons for a high diversity of TCR sequences against the same pathogen. First, TCR responses may be generated against different epitopes of the same pathogen, yielding different CDR3 sequences. Second, since T cell receptors interact with antigen presented in the context of MHC, TCR CDR3 sequences differ between individuals of different HLA subtypes. With three MHC class I antigens and 6 MHC class II antigens, and multiple isoforms of each, humans have significant inter-individual variation in HLA type that in turn influences the TCR sequences in everyone. Third, VDJ recombination in TCR development creates a vast diversity of TCR sequences enabling the adaptive immune system to respond to myriad antigens. Therefore, given all the possibilities of CDR3 sequences generated, it is entirely possible T cell malignancy patients have common antigenic drivers or common environmental exposures that are not recognized through CDR3 sequencing of a few patient samples.

Another consideration is that since the tissue samples studied in this Example encompass many different T cell malignancy subtypes, we cannot expect to find the same etiological factors or environmental exposures for this diverse group of diseases. To better address our study aims, we would need to amass a large number of pathologic specimens in any one subtype of T cell malignancy. For comparison, in the CLL studies that carefully examined B cell receptor rearrangements and stereotypy, almost 7500 patients were included. Since T cell malignancies are a rare disease, with even rarer morphologic subtypes, it is difficult to procure enough samples at a single institution to conduct a more ideal analysis.

Example 2: Defining the TCR Vb Family Usage of T Cell Malignancies

The β chain of human α/β T cell receptors (TCRs) can be grouped into >20 different functional Vβ families which can be differentially identified by monoclonal antibodies. Since the majority of T cell malignancies arise from α/β T cells, TCR Vβ family targeting may be feasible for this group of diseases. However, TCR Vβ family usage by T cell malignancies is currently undefined, with some prior reports suggesting skewed usage. In developing novel therapies, it is important to know if there is skewed TCR Vβ family usage in T cell malignancies because development of a few products targeting the prevalent families may cover the majority of patients. Here TCRβ next generation sequencing was used to definitively determine the TCR family usage in a pooled dataset of 93 T cell malignancy samples and the usage was compared to that of a normal and reactive T cell repertoire. No skewed usage was found. Further analysis for protein expression by immunohistochemistry (IHC) showed that 50% of the T cell malignancy cases evaluated had α/β TCR expression suggesting that therapeutic approaches targeting Vβ families may be feasible in a subset of patients.

Materials and Methods

Sample identification. 56 T cell malignancy samples were identified and acquired from the period 2000-2017 from the University of Pennsylvania Pathology Department and Molecular Laboratory as described previously in Example 1.

Adaptive CTCL and control datasets. A dataset of another 37 cases of CTCL and 25 cases of reactive skin disease previously sequenced using Adaptive Biotechnologies' Immunoseq platform were identified. A publicly available dataset of normal donor T cell repertoires sequenced also using Immunoseq was downloaded (clients.adaptivebiotech.com/pub/emerson-2017-natgen).

TCRβ next generation sequencing. All 56 samples were sequenced for the TCR β gene using next generation sequencing through the Human Immunology Core as previously described in Example 1.

TCR Vβ family determination. TCR Vβ family usage was determined for all dominant and productive rearrangements in the T cell malignancies samples and Adaptive CTCL dataset. As previously described, dominant clones were defined as those whose frequency in the sample is greater than 3% and at least three times as frequent as the next most frequent clone. Productive rearrangements are those that do not have stop codons and are in frame. Vβ family assignment was made according to the IMGT nomenclature for T cell receptors.

Data Analysis. To determine if there is preferential usage of certain Vβ families by the dominant productive clones in T cell malignancies, the usage of TCR Vβ families in the T cell repertoire of a randomly selected normal donor from Adaptive's publicly available dataset was first determined. The frequencies of all productive rearrangements that were unequivocally assigned to a Vβ family were summed to determine the frequency of each Vβ family in that sample. Supposing that T cell malignancies developed without preference for certain Vβ families, we determined the expected frequencies of Vβ family usage by malignant T cell clones as the calculated frequency of each family in a normal donor. Pearson $\chi^2$ statistic and Fisher's exact test were performed to compare the observed frequencies of TCR Vβ family usage by dominant productive rearrangements in T cell malignancy cases and the calculated expected frequencies. Comparison was likewise made between the dominant productive clones in the CTCL cases and a randomly selected reactive skin sample.

Immunohistochemistry. Tissue blocks from 34 T cell malignancy cases were available for immunohistochemistry. Slides were prepared and stained for αβ TCR expression using T cell antigen receptor β-F1 (Clone 8A3) mouse monoclonal antibody (Zeta Corporation, catalog #Z2230) which binds to an epitope on the human TCR b chain constant region. Slides were evaluated by a hematopathologist who was blinded to any diagnostic information. The degree of staining of the neoplastic T cells was graded as "negative" if no, or very few neoplastic cells show staining, "2+" for moderate or variable staining, and "3+" for strong uniform staining of neoplastic T cells. Two cases were unevaluable due to lack of overtly positive neoplastic T cells in the absence of infiltrating T cells to serve as a positive internal control. Histopathology reports were reviewed in the medical chart (EPIC) for CD3 staining.

Results

TCR Vβ usage in T cell malignancies compared to normal donor control. Using TCR β NGS, only 41 of 93 samples (44%), demonstrated clonal dominance with a productive rearrangement. This represented 7/18 (39%) PTCL NOS, 7/14 (50%) nodal ALCL, 24/47 CTCL (51%), 1/3 AITL (33%), 1/2 EATL (50%). In addition, the single case of cutaneous ALCL was not clonal, and the single case of ATLL was clonal. The Vβ family usage by dominant productive clones was wide ranging and did not exhibit any preferential usage in our samples of T cell malignancies compared to the expected frequencies calculated from the T cell repertoire from a bone marrow specimen from a normal donor (FIG. 1). Evaluation of TCR Vβ usage by the various histologic subtypes of PTCL is limited by small sample size.

Figures 3A, 3B:
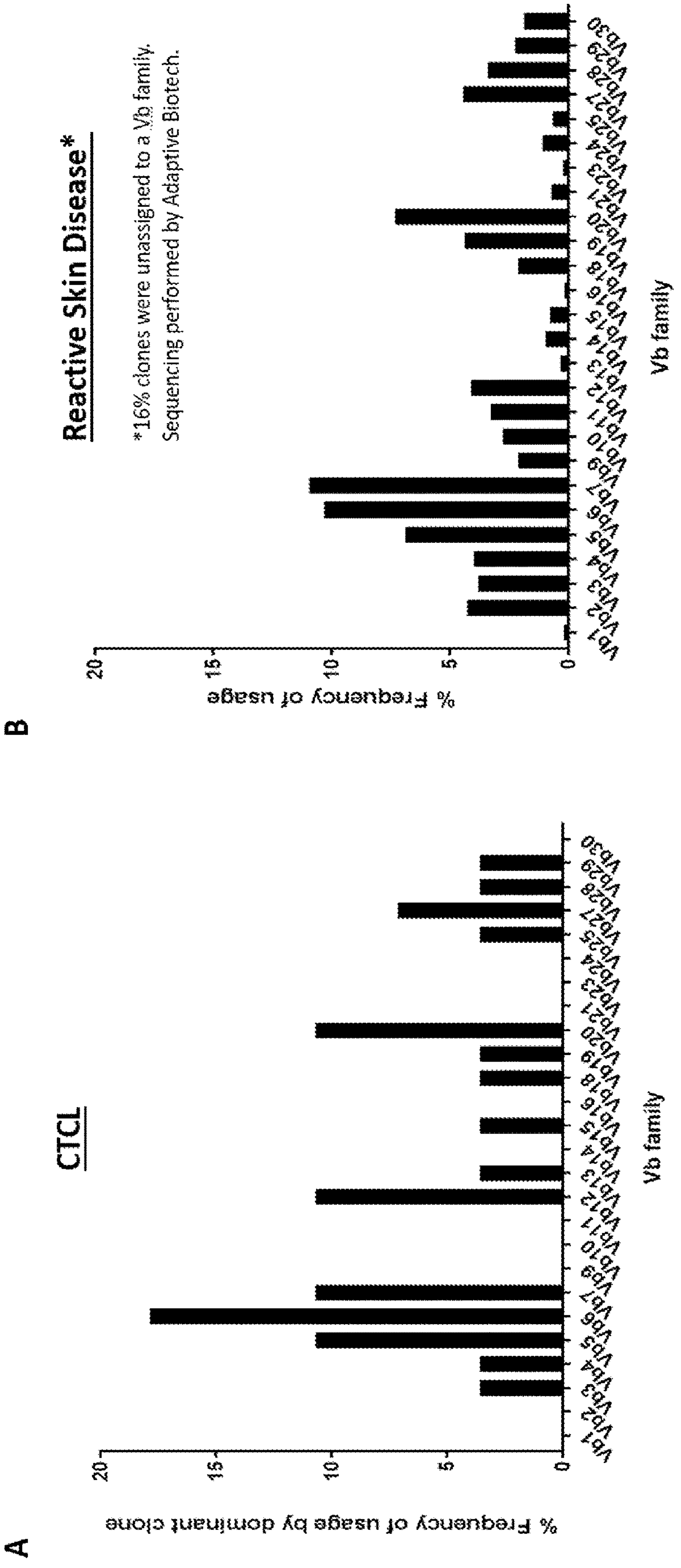
FIGS. 3A-3B illustrate the distribution of Vβ family usage by expanded clones in CTCL is similar to that of the Vβ T cell repertoire in reactive skin disease. Pearson $X^2$=10.67, p=0.776. Fisher's exact test=0.81.
Figure 4A:
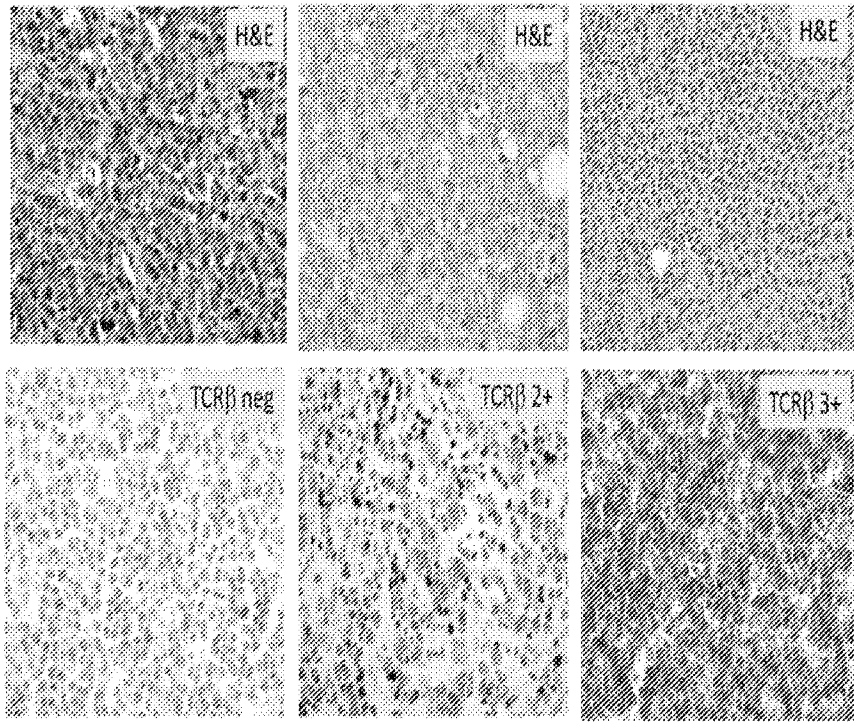
FIGS. 4A-4B illustrates α/β TCR expression by T cell malignancies.
Figure 4B:
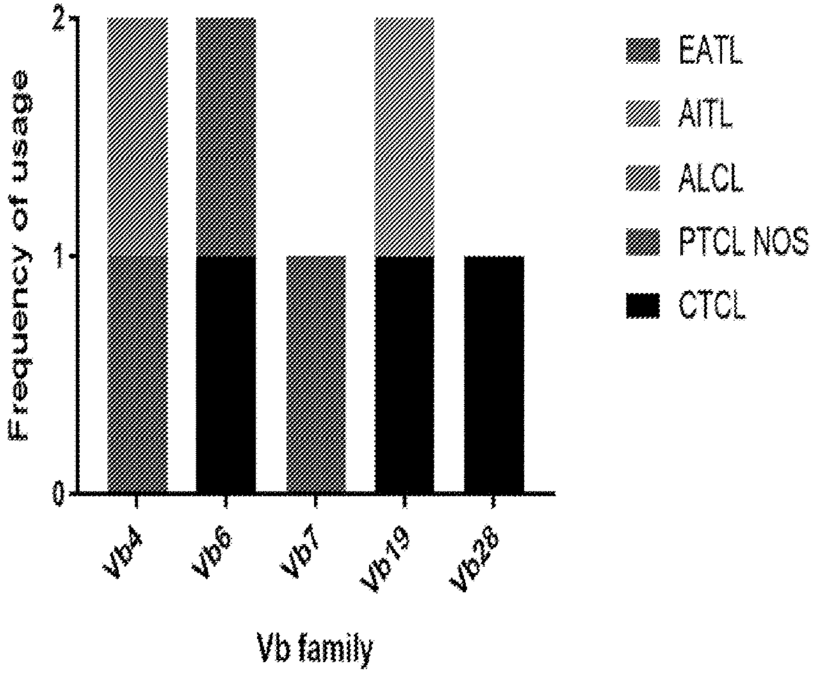

TCR Vβ usage in CTCL compared to benign reactive skin lesion. Considering that the TCR Vβ family usage by T cells may differ in different tissues, Vβ family usage by dominant productive clones in lesional skin in 24 evaluable CTCL specimens were compared to the expected frequencies calculated from the T cell repertoire in a benign reactive skin lesion. No preferential Vβ family usage was found by the dominant productive clones in CTCL in this measure (FIG. 3).

α/β TCR protein expression in T cell malignancies. To develop novel immunotherapies targeting TCR Vβ families, it was determined if malignant T cells express the TCR, and what Vβ families of the TCR are expressed by T cell malignancies. Of the evaluable cases for which tissue blocks were available for IHC, 100% of CTCL cases, 63% of PTCL NOS, 44% of nodal ALCL, and 33% of AITL expressed α/β TCR (Table 3). Since CD3 must associate with the TCR heterodimer before the TCR can be expressed at the cell surface membrane, CD3 expression was evaluated in the cases that did not express TCR. In all 4 cases of nodal ALCL that did not express α/β TCR, the neoplastic cells lacked CD3 expression. This contrasts with all other cases of T cell malignancies evaluated that did not express α/β TCR despite positive CD3 staining.

TABLE 3

Expression of α/β TCR and CD3 by malignant cells

| Diagnosis | Expression of αβ TCR by malignant cells (%) | Degree of expression of the positive samples | CD3 expression by neoplastic cells that are negative for αβ TCR |
|---|---|---|---|
| PTCL NOS | 5/8 (63) | 2+, 3+ | 3/3 positive |
| AITL | 1/3 (33) | 3+ (1/1) | 2/2 positive |
| Nodal ALCL | 4/9 (44) | 2+ (4/4) | 5/5 negative |
| Cutaneous ALCL | 0/1 | n/a | 1/1 positive |
| CTCL | 5/5 (100) | 2+, 3+ | n/a |
| EATL | 1/2 (50) | 3+ (1/1) | 1/1 positive |
| NK TCL | 0/2 | n/a | 2/2 positive |
| T LGL | 0/1 | n/a | unknown |
| SP TCL | 0/1 | n/a | 1/1 positive |
| Total | 16/32 (50%) | | |

Novel therapies are greatly needed for the treatment of T cell malignancies. Immunotherapy approaches such as CAR T cells directed toward TCR Vβ families represent an attractive therapeutic approach because it would spare the majority of healthy T cells, avoiding clinically significant immunocompromise. If there is preferential usage of TCR Vβ families in T cell malignancies, then production of a few CARs with specificities toward the most highly involved TCR Vβ families may cover most patients. However, TCR Vβ family usage in T cell malignancies remains largely unexplored. Despite efforts in determining TCR Vβ family usage in CTCL using monoclonal antibodies, and RT PCR, there is controversy regarding TCR family usage in this disease.

With the ability to perform TCR Vβ next generation sequencing (NGS) and the availability of bioinformatic pipelines, we sought to definitively define the TCR Vβ family usage in our cohort of T cell malignancy specimens, determine if there is preferential usage, and to determine TCR expression in these specimens which is important for immunotherapeutic targeting.

Prior studies examining Vβ usage in T cell malignancies are mostly in CTCL, and there is dearth of information regarding Vβ usage in other T cell malignancies. A couple of studies which relied on monoclonal antibody determination of Vβ usage in CTCL showed preferential TCR vβ family usage, including TCR Vβ8 and Vβ5 in tissue and leukemic phase disease respectively. (Jack A S, Boylston A W, Carrel S, Grigor I. Cutaneous T-Cell Lymphoma Cells Employ a Restricted Range of T-Cell Antigen Receptor Variable Region Genes. *Am J Pathol.* 1990; 136(1):17-21;

Vonderheid E C, Boselli C M, Conroy M, et al. Evidence for Restricted Vβ Usage in the Leukemic Phase of Cutaneous T Cell Lymphoma. *J Investig Dermatol.* 2005; 124(3):651-661) In these studies, a large fraction of the studied cases exhibited reactivity to a Vβ antibody specific to a single family. Other studies which similarly used Vβ monoclonal antibodies for family determination did not show predominant usage of any single Vβ family. (Boehncke W, Krettek S, Parwaresch M, Sterry W. Demonstration of clonal disease in early mycosis fungoides. *Am. J. Dermatopathol.* 1992; 14:95-99; Bahler D W, Berry G, Oksenberg J, Warnke R A, Levy R. Diversity of T-cell antigen receptor variable genes used by mycosis fungoides cells. *Am. J. Pathol.* 1992; 140(1):1-8) Studies that examined this question using molecular techniques like PCR amplification also did not show marked skewing in TCR usage in CTCL, but results suggested that usage is largely limited to Vβ5, Vβ6, Vβ8, Vβ13, and Vβ18. (Bahler D W, Berry G, Oksenberg J, Warnke R A, Levy R. Diversity of T-cell antigen receptor variable genes used by mycosis fungoides cells. *Am. J. Pathol.* 1992; 140(1):1-8; Gorochov G, Bachelez H, Cayuela J M, et al. Expression of Vβ Gene Segments by Sezary Cells. *J. Invest. Dermatol.* 1995; 105(1):56-61; Kono D H, Baccala R, Balderas R S, et al. Application of a multiprobe RNase protection assay and junctional sequences to define V beta gene diversity in Sezary syndrome. *Am. J. Pathol.* 1992; 140(4):823-30) Our study examining Vβ family usage in CTCL and other T cell malignancies using TCR NGS showed highly diverse TCRVβ family usage without preferential usage in any disease subtype. The distribution of Vβ family usage by the dominant clones in T cell malignancies is similar to the distribution of Vβ family usage seen in the T cell repertoire of control specimens.

The differences in results between our study and prior published work in CTCL is most likely due to differences in methodology. Interpretation of monoclonal antibody staining TCR Vβ families is complicated by uncertainty of antibody specificity and poor antibody reactivity (Hunt S J, Charley M R, Jegasothy B V. Cutaneous T-cell lymphoma: Utility of antibodies to the variable regions of the human T-cell antigen receptor. *J. Am. Acad. Dermatol.* 1992; 26(4): 552-558; Gilks C, Ho V, Gascoyne R, Ellison D. T-cell receptor variable region gene expression in cutaneous T-cell lymphomas. *J. Cutan. Pathol.* 1992; 19(1):21-26; Finn D T, Jaworsky C, Chooback L, Jensen P J, Lessin S R. Correlation between clonotypic T-cell receptor beta chain variable region (TCR-V beta) gene expression and aberrant T-cell antigen expression in cutaneous T-cell lymphoma. *J. Cutan. Pathol.* 1996; 23(0303-6987 (Print)):306-311; Bagot M, Wechsler J, Lescs M C, et al. Intraepidermal localization of the clone in cutaneous T-cell lymphoma. *J. Am. Acad. Dermatol.* 1992; 27(4):589-593; Bigler R D, Boselli C M, Foley B, Vonderheid E C. Failure of anti-T-cell receptor V beta antibodies to consistently identify a malignant T-cell clone in Sezary syndrome. *Am. J. Pathol.* 1996; 149(5): 1477-1483). The antibodies used in the studies which showed skewed usage of TCR Vβ families may have been much less specific than the authors originally thought. Poor TCR Vβ antibody reactivity was frequently encountered (Ralfkiaer E, Wollf-Sneedorff A, Vejlsgaard G L. Use of antibodies against the variable regions of the T-cell receptor α/β heterodimer for the study of cutaneous T-cell lymphomas. *Br. J Dermatol.* 1991; 125(5):409-412); in 11 series reported in the literature in CTCL, a Vβ positive clone was detected in <20% of patients with mycosis fungoides (Vonderheid E C, Boselli C M, Conroy M, et al. Evidence for Restricted Vβ Usage in the Leukemic Phase of Cutaneous T Cell Lymphoma. *J Investig Dermatol.* 2005; 124(3):651-661). This may be due to a variety of reasons, including poor sensitivity of the antibody, non-recognition of some Vβ gene segments which are not covered by the available Vβ antibodies, (Langerak A, van Den Beemd R, Wolvers-Tettero I L, et al. Molecular and flow cytometric analysis of the Vbeta repertoire for clonality assessment in mature TCRalphabeta T-cell proliferations. Blood. 2001; 98(1):165-173) lack of a clonal T cell population in the specimen especially in early stage lesions (Boehncke W, Krettek S, Parwaresch M, Sterry W. Demonstration of clonal disease in early mycosis fungoides. *Am. J Dermatopathol.* 1992; 14:95-99), and lack of surface expression of the TCR by neoplastic T cells. (Vonderheid E C, Boselli C M, Conroy M, et al. Evidence for Restricted Vβ Usage in the Leukemic Phase of Cutaneous T Cell Lymphoma. *J Investig Dermatol.* 2005; 124(3):651-661) DNA based molecular testing circumvents problems of antibody specificity and reactivity, as DNA primers can be designed to amplify each of the specific Vβ families; however, the clonal Vβ population corresponding to the tumor cells can be challenging to identify on an agarose gel. (Tissier F, Martinon F, Camilleri-Broet S, et al. T-cell receptor V beta P repertoire in nodal non-anaplastic peripheral T-cell lymphomas. *Pathol. Res. Pract.* 2002; 198(6): 389-395) In our study, although not all tumor specimens had a dominant clone, we could clearly identify the dominant clones using the clone frequency count of the top clone compared to that of adjacent clones. Furthermore, sequencing reads of at least 36 nucleotides into the V gene beyond the CDR3 region allowed for accurate assignment of the dominant clone into Vβ families. Therefore, these data in CTCL obtained using TCRβ NGS were greatly more reliable than other previously used techniques for Vβ family usage determination.

Data regarding TCR Vβ family usage in the nodal T cell lymphomas also do not show predilection for usage of a few TCR Vβ families. Limitations include having relatively few samples in nodal T cell lymphomas which had a dominant clone by the criteria herein, and given and the rarity of some subtypes, it is difficult to draw definitive conclusions regarding TCRVβ usage in specific subtypes of the PTCLs. Very few studies look at TCR Vβ usage by any method in the T cell malignancies other than CTCL, with most series including very few numbers of patients. (Tissier F, Martinon F, Camilleri-Broet S, et al. T-cell receptor V beta P repertoire in nodal non-anaplastic peripheral T-cell lymphomas. *Pathol. Res. Pract.* 2002; 198(6):389-395; Preesman A H, Hu H-Z, Tilanus M G J, et al. T-Cell Receptor Vbeta]-Family Usage in Primary Cutaneous and Primary Nodal T-Cell Non-Hodgkin's Lymphomas. *J Investig Dermatol.* 1992; 99(5):587-593; Salameire D, Solly F, Fabre B, et al. Accurate detection of the tumor clone in peripheral T-cell lymphoma biopsies by flow cytometric analysis of TCR-VB repertoire. *Mod. Pathol.* 2012; 25(9):1246-1257; Smith J L, Lane A C, Hodges E, et al. T-Cell receptor variable (V) gene usage by lymphoid populations in T-cell lymphoma. *J Pathol.* 1992; 166(2):109-112) Tissier et al. examined the TCR Vβ usage in PTCL NOS and AITL using an antibody panel for the different families and highlighted the challenges of this method. They noted that reactive T cell infiltrates were common in these diseases, and they could only identify a dominant T cell population in two of the eight PTCL NOS specimens. In two cases of AITL, the malignant clone in AITL could not be identified using monoclonal antibodies despite positive clonality using TCRγ gene rearrangement PCR studies. (Tissier F, Martinon F, Camilleri-Broet S, et al. T-cell receptor V beta P repertoire in nodal non-anaplastic peripheral T-cell lymphomas. *Pathol. Res. Pract.* 2002; 198(6):389-395) In another study, an expanded TCR Vβ population was found in a nodal T cell lymphoma specimen in the absence of clonality by TCR gene rearrangement, suggesting possible cross reactivity of Vβ antibody with other clones. (Smith J L, Lane A C, Hodges E, et al. T-Cell receptor variable (V) gene usage by lymphoid populations in T-cell lymphoma. *J. Pathol.* 1992; 166(2): 109-112) Our data from TCRβ NGS in the nodal lymphomas comprehensively and quantitatively determine the TCR Vβ usage in the entire T cell repertoire of each specimen and do not suggest skewed usage by the dominant productive clones, but future studies may be necessary to expand the number of samples in the different histological subtypes.

To inform the development of CAR T cells and other TCR Vβ family directed immunotherapies for T cell malignancies, knowledge of expression of the TCR in T cell neoplasms is important. It is possible that skewed TCR Vβ family usage may be seen in T cell neoplasms that express the TCR, compared to those that may aberrantly downregulate its expression. Therefore, in parallel to TCR sequencing, immunohistochemical staining of all available tissue blocks was performed using the TCRβ F1 antibody. This antibody recognizes a conserved region of the TCR chain constant region and is used in clinical applications to distinguish α/β TCR from γ/δ TCR. Obvious skewed Vβ family usage was not found amongst the samples that had TCR expression, although the final sample size was very small as there were limited samples for which tissue blocks were available and which met criteria for having a dominant clone and α/β TCR expression.

It has been reported that over 90% of peripheral T cell lymphomas, excluding ALCL, express α/β TCR. (Tissier F, Martinon F, Camilleri-Broet S, et al. T-cell receptor V beta P repertoire in nodal non-anaplastic peripheral T-cell lymphomas. Pathol. Res. Pract. 2002; 198(6):389-395; Salameire D, Solly F, Fabre B, et al. Accurate detection of the tumor clone in peripheral T-cell lymphoma biopsies by flow cytometric analysis of TCR-VB repertoire. *Mod. Pathol.* 2012; 25(9):1246-1257) In the present study, only about half of non-ALCL T cell malignancies had α/β TCR expression by the neoplastic T cells. Of the subtypes of T cell malignancies, CTCL cases most consistently expressed α/β TCR, although unfortunately, no tissue block was available in most cases of CTCL included in this study. It is unclear why the data show a lower than expected frequency of α/β TCR expression. In reviewing the slides, positive categorization was very carefully avoided if only the reactive T cells stained positively.

In ALCL, aberrant loss of CD3 by the neoplastic T cells occurs in the majority of cases, with loss of TCR surface expression. (Bonzheim I, Geissinger E, Roth S, et al. Anaplastic large cell lymphomas lack the expression of T-cell receptor molecules or molecules of proximal T-cell receptor signaling Brief report Anaplastic large cell lymphomas lack the expression of T-cell receptor molecules or molecules of proximal T-cell. 2012; 104(10):3358-3360; Chott A, Kaserer K, Augustin I, et al. Ki-1-positive large cell lymphoma. A clinicopathologic study of 41 cases. *Am. J. Surg. Pathol.* 1990; 14(5):439-48). Data herein are congruent with this finding, and all nodal ALCL cases which lacked α/β TCR expression also lacked CD3. Interestingly, in all the non-ALCL samples without α/β TCR expression for which CD3 staining was available, CD3 expression was preserved. While the case of enteropathy associated T cell lymphoma (EATL) may have been negative for β F1 staining because this entity likely expresses the γ/δ T cell receptor, the remaining cases of β F-1 negative T cell malignancies have lost TCR expression for reasons other than CD3 loss. Further studies would be needed to determine if this loss of TCR expression arises as a feature of relapsed/refractory disease possibly due to clonal evolution versus if loss of TCR expression is present at onset of disease.

Example 3: CD64-Immune Receptor (IR) Modified T Cells: A Flexible Approach for Targeting T Cell Receptor Vβ Families in T Cell Malignancies

Materials and Methods

CD64 immune receptor construction (CD64 IR). Human CD64 DNA sequence was amplified from primary human monocytes using primers. After amplification and the insertion of 3'-Bam-H1 and 5'-Nhe-1 restriction sites, the PCR product was digested with Bam-H1 and NheI enzymes and ligated into pELNS, a third-generation self-inactivating lentiviral expression vector, containing human CD28-CD3z signaling endodomains, under an EF-1a promoter. The resulting construct was designated pELNS CD64-IR-28z.

Recombinant lentivirus production. High-titer replication-defective lentiviral vectors were produced and concentrated as previously described (Perez E, Riley J, Carroll R, Vonlaer D, June C. Suppression of HIV-1 infection in primary CD4 T cells transduced with a self-inactivating lentiviral vector encoding a membrane expressed gp41-derived fusion inhibitor. *Clin. Immunol.* 2005; 115(1):26-32; Song D-G, Ye Q, Carpenito C, et al. In Vivo Persistence, Tumor Localization, and Antitumor Activity of CAR-Engineered T Cells Is Enhanced by Costimulatory Signaling through CD137 (4-1BB). *Cancer Res.* 2011; 71(13):4617-4627). Briefly, 293T cells were transfected with pVSV-G (VSV glycoprotein expression plasmid), pRSV.REV (Rev expression plasmid), pMDLg/p.RRE (Gag/Pol expression plasmid), and pELNS transfer plasmid using Lipofectamine 2000 (Invitrogen). The viral supernatant was harvested at 24 and 48 h post-transfection, sterile filtered using a 0.45 uM filter, and concentrated by ultracentrifugation at 26000 rpm for 2 hours at 4° C. Aliquots of high titer lentivirus were stored at −80° C. until use.

Generation of Vβ12 TCR transduced SupT1 cell line. Generation of PG13 MART 1 DMF4 TCR packaging cell line was performed as previously described. Retroviral supernatant was collected 24 hours after seeding the PG-13 producer clone at 70% of confluence. Non-tissue culture treated 6-well plates were coated with retronectin and blocked with 2% BSA per manufacturer's protocol (Takara, Cat #T100A/B). 2.3 mL retroviral supernatant was added per well and centrifuged at 2000 g for 2 hours, and supernatant aspirated. Target cell line SupT1 was plated at a density $4\times10^5$ cells/mL and centrifuged for 10 minutes at 1000 g. Retronectin retroviral transduction was repeated the following day, and the transduced cell line was stained with MART1 tetramer and evaluated by flow cytometry. Vβ family usage was verified using Vβ12-FITC antibody (clone S511, Thermo Scientific Cat #TCR2654). The transduced cells were enriched using MACS magnetic bead cell separation (Miltenyi Biotec).

Primary T cell activation, transduction, and expansion. Primary human total T-cells were isolated from healthy volunteer donors following leukapheresis by negative selection, and purchased from the Human Immunology Core at University of Pennsylvania. All specimens were collected under a University Institutional Review Board-approved protocol, and written informed consent was obtained from each donor. T-cells were cultured in complete media (RPMI 1640 supplemented with 10% heat inactivated low IgG fetal bovine serum (FBS), 100 U/ml penicillin, 100 ug/ml streptomycin sulfate), and stimulated with anti-CD3 and anti-CD28 monoclonal antibody coated beads (Invitrogen) on day 0 as described. 24 hours after activation, T-cells were transduced with lentiviral vectors at MOI of ~5. Human recombinant interleukin-2 (IL-2; Novartis) was added every other day to 100 IU/ml final concentration and a 0.5-1×10$^6$ cells/ml cell density was maintained. Starting at day 11-12 of culture, no more IL-2 was added to allow the T cells to rest. Rested T cells were used in subsequent coculture assays (adapted from "Targeted cancer immunotherapy via combination of designer bispecific antibody and novel gene-engineered T cells").

Cytotoxicity Assays. $^{51}$Cr release assays were performed as described. Target cells were labeled with 100mCi $^{51}$Cr at 37° C. and TCR Vβ family specific monoclonal antibody (1 ug per million target cells) for 1.5 hours in low IgG R10 media. Target cells were washed three times in PBS, resuspended in phenol red free RPMI with 5% low IgG FBS (CM) at 10$^5$ cells/mL and 100 uL added per well of a 96-well U-bottom plate. Effector cells were washed twice in CM and added to wells at the given ratios. Plates were centrifuged to settle cells, and incubated at 37° C. in a 5% CO2 incubator for 4 hours. The supernatants were harvested, transferred to a luminex-plate (Packard) and counted using a 1450 Microbeta Liquid Scintillation Counter (Perkin-Elmer). Spontaneous $^{51}$Cr release was evaluated in target cells incubated with medium alone. Maximal $^{51}$Cr release was measured in target cells incubated with SDS at a final concentration of 5% (v/v). Percent specific lysis was calculated as (experimental−spontaneous lysis/maximal−spontaneous lysis)×100.

Results

Figures 5A, 5B, 5C, 5D, 5E, 5F:
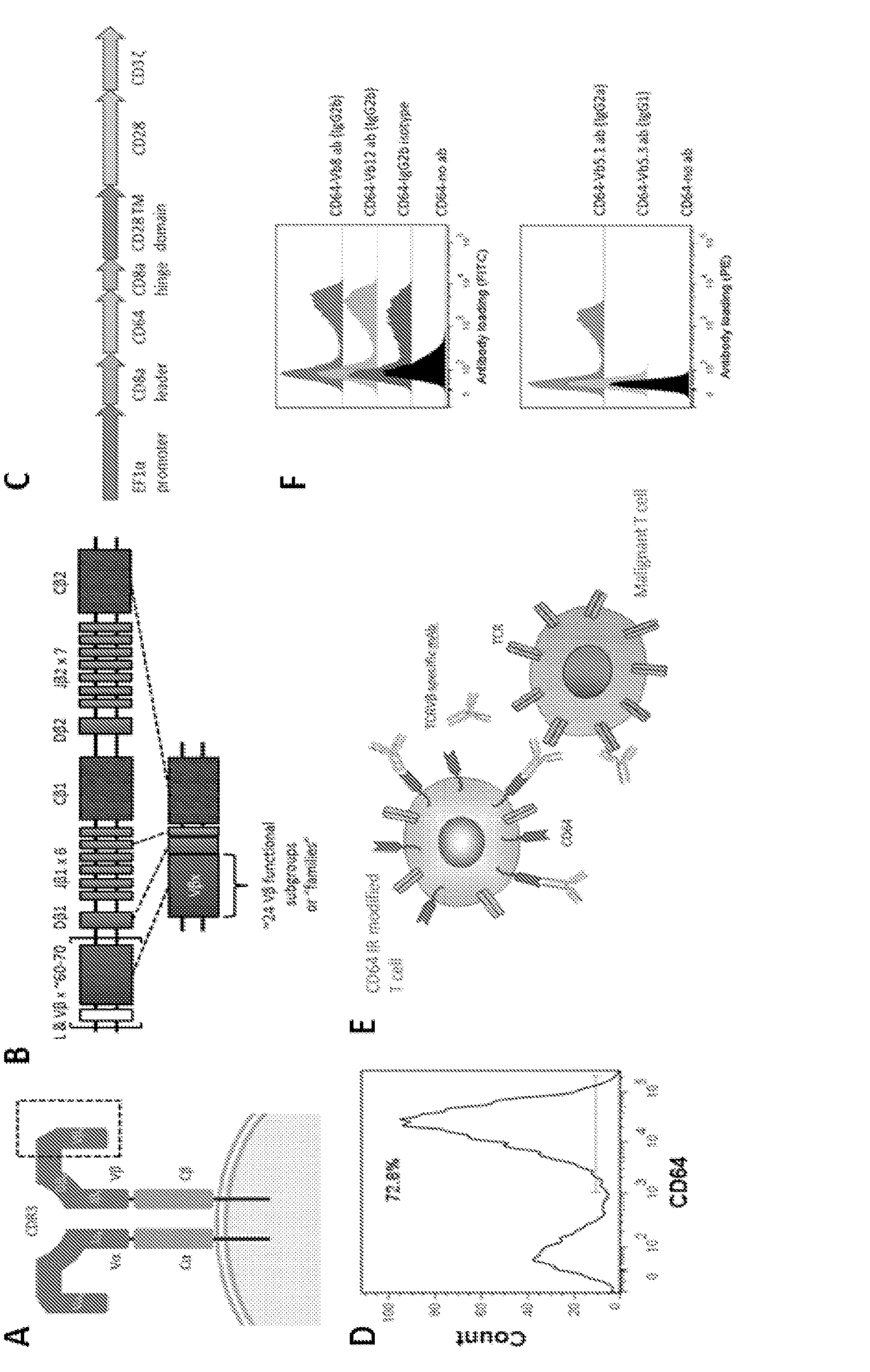
FIGS. 5A-5F illustrate that CD64 IR modified T cells can be directed toward target T cells via TCRVβ specific antibodies.

CD64 IR construction. One goal of the study was to create a flexible platform for redirecting T cells toward different antigenic targets through antibody specific binding in order to validate the suitability of targeting specific Vβ families. Therefore, a DNA construct was generated that comprises the extracellular immune receptor, CD64 (FcγRIII), a CD28 transmembrane domain, and T cell signaling domain CD3, in tandem with a CD28 costimulatory domain. The transgene CD64 immune receptor was called (CD64 IR). CD64 IR expression is driven by the EF1α promoter in the pELNs expression plasmid (FIG. 5C). When a T cell, expressing CD64 IR, binds the Fc portion of a monoclonal antibody directed toward the desired antigen, T cell costimulation and activation occur (FIG. 5D). Primary T cells were successfully transduced with the CD64 IR construct using high titer lentivirus, and CD64 surface expression was confirmed by flow cytometry. In a typical experiment, up to 70% transduction of T cells was achieved. In this way, the CD64 IR modified T cells are designed to serve as a platform for binding to antibodies specific for Vβ families, thereby lysing their target in an MEW independent manner.

CD64 IR is a flexible platform for antibody loading. After generating the CD64 IR modified T cells, the ability of different monoclonal antibodies to load onto the CD64 IR was ascertained. Murine monoclonal antibodies of IgG1, IgG2a and IgG2b subclasses were used to load CD64 IR modified T cells. Successful antibody loading was observed with murine IgG2a and IgG2b subclasses, but not murine IgG1 (FIG. 5E).

CD64 IR modified T cells display effective and specific cytolytic function against TCR Vβ families. The CD64 IR flexible platform was used for testing antibody directed cellular cytotoxicity (ADCC) using T cell receptor Vβ family directed monoclonal antibodies. For clonal T cell diseases such as in T cell malignancies, it would be advantageous to selectively target the deleterious T cell clone, as identified by their TCR Vβ family.

Figures 6A, 6B, 6C:
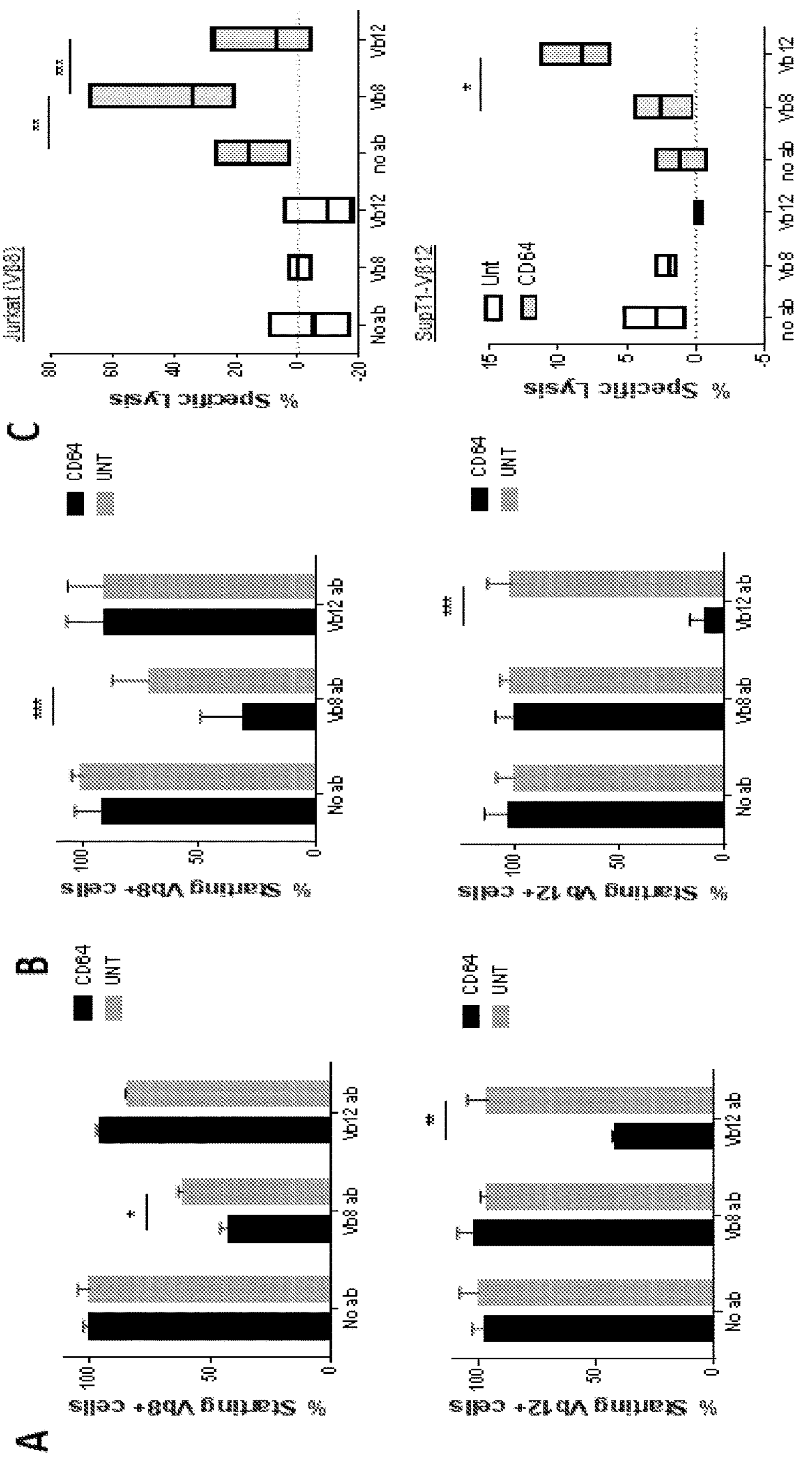
FIGS. 6A-6C illustrate CD64 IR modified T cells display specific cytolytic function against TCR Vβ families.
Figure 7:
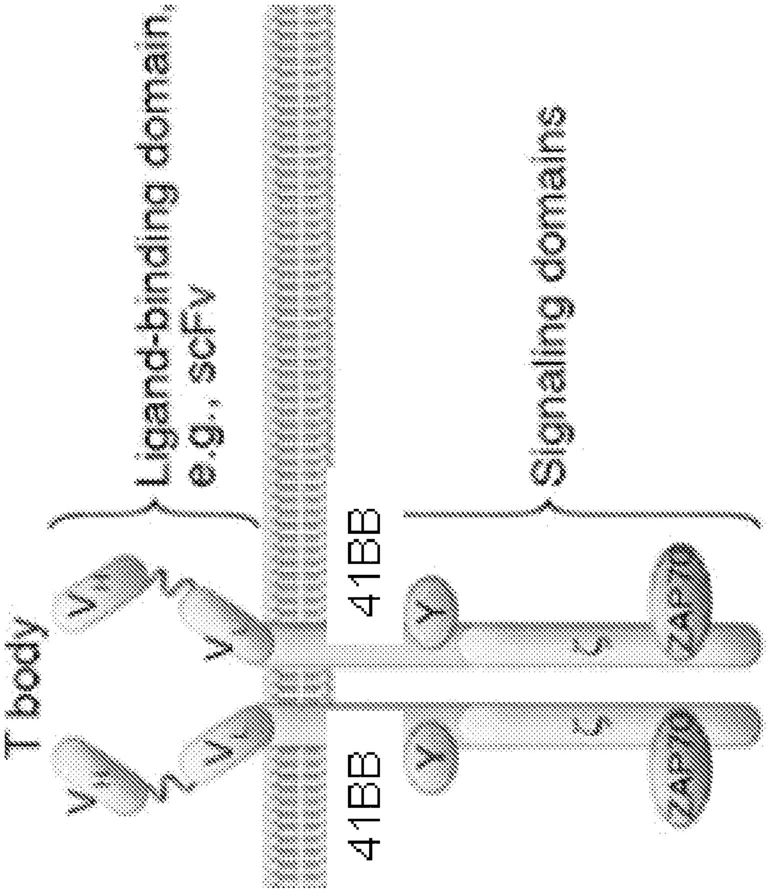
FIG. 7 illustrates a chimeric antigen receptor (CAR) design.
Figure 8:
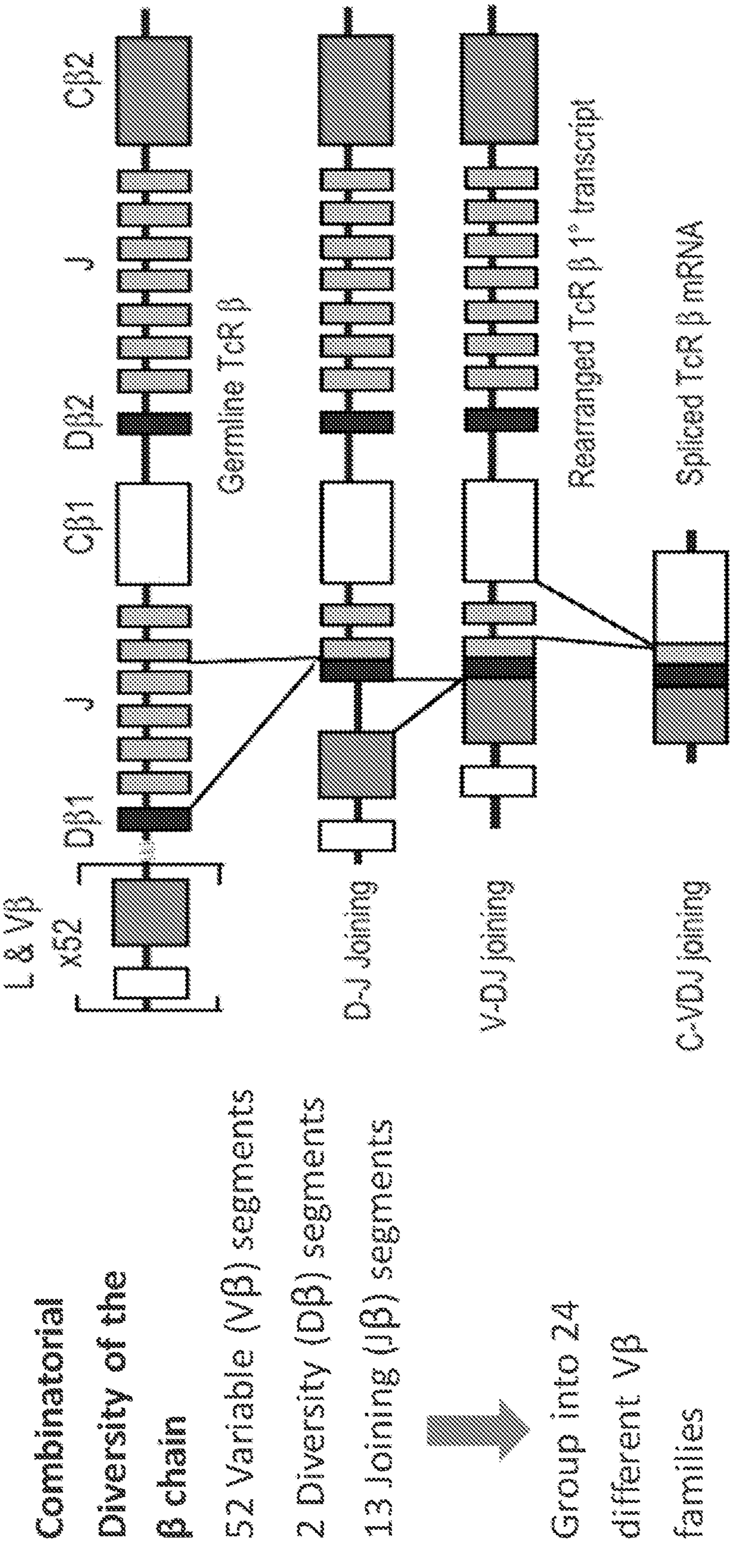
FIG. 8 illustrates the diversity in α/β TCR is generated by variable (V), joining (J), and diversity (D) gene assembly (in the β chain) to form a complete Vβ gene, resulting in the formation of 24 distinct Vβ families.

Coculture assays were performed using CD64 IR T cells and the target T cell lymphoblastic cell lines, Jurkat and engineered line SupT1-Vβ12, which express Vβ8 TCR and Vβ12 TCR respectively. In these in vitro assays, effectors and targets were cocultured in a 1:1 ratio, and target T cells were either "pre-targeted" with Vβ specific monoclonal antibody, or the CD64 IR modified T cells were "pre-armed" with antibody. At 24 hours, Vβ family specific depletion was assayed by flow cytometry. Results show Vβ family specific cytolysis of target T cells when cocultured with CD64 IR T cells in the presence of the relevant Vβ specific monoclonal antibody. Both "pre-arming" of effectors and "pre-targeting" of targets resulted in Vβ family specific depletion when assayed by flow cytometry (FIG. 6A, 6B). Even though the targeting antibody used in each case was fluorochrome labeled, and samples were re-stained prior to flow analysis, the possibility of epitope masking remains.

Four-hour chromium release assays were performed to determine Vβ family target specificity. At an effector to target ratio of 5:1, specific cytolysis of both Jurkats and SupT1-Vβ12 was achieved when the target specific Vβ directed monoclonal antibody was used. Significantly less cytolysis was seen when a control antibody, directly toward a different Vβ family was used (FIG. 6C).

That the β chain of human T cell receptors (TCRs) can be grouped into >20 different functional Vβ families has been established for over 30 years, but this knowledge has not been used for therapeutic purposes. In this study, we have shown proof of concept using a flexible platform of CD64 immune receptor (IR) modified T cells in combination with Vβ specific monoclonal antibodies that it is possible to differentially target T cells based on their TCR Vβ family. This will inform the development of novel immunotherapies for the treatment of PTCLs and other T cell malignancies.

There has been recent interest in developing cellular immunotherapies to target malignant T cells. Others have already demonstrated that it is possible to induce T cell killing using chimeric antigen receptor (CAR) modified T cells targeting a variety of T cell targets like CD5, CD7, and CD3. (Mamonkin M, Rouce R H, Tashiro H, Brenner M K. A T-cell-directed chimeric antigen receptor for the selective treatment of T-cell malignancies. *Blood.* 2015; 126(8):983-92; Gomes-Silva D, Srinivasan M, Sharma S, et al. CD7-edited T cells expressing a CD7-specific CAR for the therapy of T-cell malignancies. Blood. 2017; 130(3):285-296; Chen K H, Wada M, Firor A E, et al. Novel anti-CD3 chimeric antigen receptor targeting of aggressive T cell malignancies. *Oncotarget.* 2016; 5(35)) While it is possible to address T cell "fratricide" by using gene editing techniques to abrogate expression of the antigenic target on the CAR T cells themselves, (Gomes-Silva D, Srinivasan M, Sharma S, et al. CD7-edited T cells expressing a CD7-specific CAR for the therapy of T-cell malignancies. *Blood.* 2017; 130(3):285-296) normal healthy T cells also expressing the antigenic target are inevitably killed, which may lead to pan T cell depletion and significant immunocompromise.

To achieve ultimate specificity to the clonal population of malignant T cells, personalized anti-idiotype directed immunotherapies would be required. This approach has been used successfully in the treatment of some B cell lymphomas, (Stevenson F K, Wrightham M, Glennie M J, et al. Antibodies to Shared Idiotypes as Agents for Analysis and Therapy for Human B Cell Tumors. *Blood.* 1986; 68(2): 430-436; Schuster S J, Neelapu S S, Gause B L, et al. Vaccination With Patient-Specific Tumor-Derived Antigen in First Remission Improves Disease-Free Survival in Follicular Lymphoma. *J. Clin. Oncol.* 2011; 29(20):2787-2794; Hamblin T J, Cattan A R, Glennie M J, et al. Initial Experience in Treating Human Lymphoma With a Chimeric Univalent Derivative of Monoclonal Anti-idiotype Antibody. *Blood.* 1987; 69(3):790-797) but would require manufacturing of a different product for each patient. Pule and colleagues recognized that since TCRs utilize one of only two β chain constant domains, they targeted a specific TCR β constant region which would be more practical than the anti-idiotype approaches, while providing improved specificity compared to targeting a pan T cell antigen. Importantly, they demonstrated that targeting the TCR is feasible, and that virus specific T cells use both constant domains, so cytolysis of T cells bearing one constant domain is predicted to preserve some viral immunity. (Maciocia P M, Wawrzyniecka P A, Philip B, et al. Targeting the T cell receptor β-chain constant region for immunotherapy of T cell malignancies. *Nat. Med.* 2017; (October)) We note however, that targeting one of two constant domains of the TCR would still result in the cytolysis of approximately half of the T cell population, substantially decreasing the TCR repertoire in the patient. Furthermore, the abundance of target cells is believed to contribute to the severity of cytokine release syndrome, a known and potentially serious complication of CAR T cell therapy. (Maude S L, Barrett D, Teachey D T, Grupp S A. Managing cytokine release syndrome associated with novel T cell-engaging therapies. *Cancer J.* 2014; 20(2):119-22) Our approach of targeting each of the TCR Vβ families allows for family specific killing that would include the malignant clone in a given patient with very limited cytolysis of healthy T cells likely reducing cytokine mediated toxicities associated with therapy compared to less targeted approaches. As demonstrated in Example 2, even the most highly represented Vβ family only encompasses ~15% of the entire normal T cell repertoire, and so cytolysis of one Vβ family in an individual would not be predicted to significantly affect immunity or contribute to toxicity as much as the less specific approaches.

Developing CAR T cells specific to all 24 functional Vβ families represents a significant challenge. Herein, proof of concept that TCR Vβ specific cytolysis is possible was demonstrated using the flexible CD64 IR platform. While the platform itself is likely unsuitable for clinical application since CD64 would bind to circulating immunoglobulins in the patient, diminishing the desired target specific effect, the concept of targeting Vβ families will inform the development of other efficacious Vβ family directed immunotherapies for the treatment of T cell malignancies.

Example 4: Development of CAR Constructs Against Specific TCRVβ Families

The most common TCRVβ family used in PTCL is not well defined. However, the targeting of Vβ5 and Vβ8 was chosen.

Figures 9A, 9B, 9C:
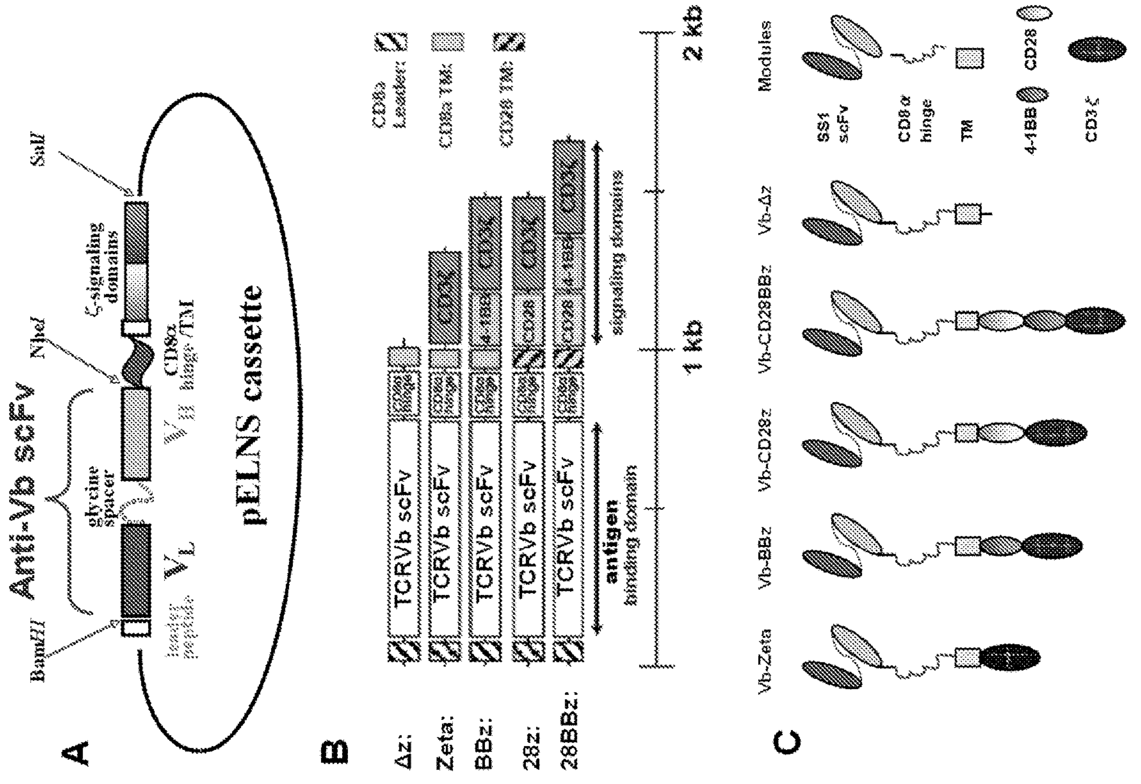
FIGS. 9A-9C are series of diagrams illustrating the construction of anti-TCRVβ specific CAR T-cells.

Anti-TCRVβ TCR CAR constructs are generated, comprised of an extracellular scFv and intracellular CD3-zeta and costimulatory signaling modules as shown in FIGS. 9A-9C. Gene sequences that encode for Vβ5 and Vβ8 specific scFvs in both $V_H$-$V_L$ and $V_L$-$V_H$ formations are synthesized (FIG. 9A). Vβ5 and Vβ8 are targeted initially, and then targets are expanded to other TCRVβ families. Lentiviral vectors encoding the Vβ5 or Vβ8 scFvs coupled with a cytosolic tail comprised of modular combinations of CD3 zeta plus 4-1BB and/or CD28 costimulatory domains are engineered.

Using CAR constructs designed for clinical application (Porter D L, Hwang W T, Frey N V, Lacey S F, Shaw P A, Loren A W, et al. Chimeric antigen receptor T cells persist and induce sustained remissions in relapsed refractory chronic lymphocytic leukemia. Sci Transl Med. 2015; 7(303):303ra139), Vβ5, Vβ8 and other scFvs are "swapped" with the scFv region of the pELNS vector using novel BamHI and NheI digestion sites between the CD8a leader peptide and the hinge regions (FIG. 9A). Cloning these scFv sequences into five established vectors allows for the creation of CARs that contain either (1) CD3zeta; (2) CD3zeta/CD28; (3) CD3zeta/4-1BB; (4) CD3zeta/CD28/4-1BB; or (5) a CD3zeta signaling deficient module; Δzeta (FIG. 9C). Vβ5 and Vβ8 scFvs sequences are tested in $V_H$-$V_L$ and $V_L$-$V_H$ formations. High titer lentivirus is produced using standardized lab procedures. In all assays, lentiviral transduction of T-cells is performed under conditions of optimal transduction efficiency. Control green fluorescent protein (GFP) lentiviral transduction as well as anti-CD5 (as positive control (Mamonkin M, Rouce R H, Tashiro H, Brenner M K. A T-cell-directed chimeric antigen receptor for the selective treatment of T-cell malignancies. Blood. 2015; 126(8):983-92; Chen K H, Wada M, Pinz K G, Liu H, Lin K W, Jares A, et al. Preclinical targeting of aggressive T-cell malignancies using anti-CD5 chimeric antigen receptor. Leukemia. 2017; Raikar S S, Fleischer L C, Moot R, Fedanov A, Paik N Y, Knight K A, et al. Development of chimeric antigen receptors targeting T-cell malignancies using two structurally different anti-CD5 antigen binding domains in NK and CRISPR-edited T cell lines. Oncoimmunology. 2018; 7(3):e1407898) and anti-CD19 CAR (as negative control (Milone M C, Fish J D, Carpenito C, Carroll R G, Binder G K, Teachey D, et al. Chimeric receptors containing CD137 signal transduction domains mediate enhanced survival of T cells and increased antileukemic efficacy in vivo. Mol Ther. 2009; 17(8):1453-64)) transduction is performed in parallel cultures. Prior to functional assays, transduction efficiencies are equilibrated for all experimental T-cell groups.

Flow cytometric analysis using goat anti-rat antibody or protein-L as detection agent is used to validate and to quantify scFv surface expression on T-cells after transduction. In some embodiments, a myc tag is inserted followed by a GGG linker between the scFv and CD8α hinge sequences, and expression is stained for using anti-myc antibody. Untransduced T cells are expected to lack detectable scFv expression, or GFP expression.

A primary objective in the development of the TCRVβ CAR platform is to express anti-TCRVβ scFvs on transduced T-cells to endow them with the capacity for Vβ-specific PTCL tumor recognition (FIG. 9C), however, transduction of human T-cells containing the wide array of Vβ subfamilies with an anti-Vβ CAR induces low level fratricide limited to only that specific Vβ family in the final CAR T-cell product, and preserving about 95% of non-targeted T-cells. For instance, transduction of healthy donor T-cells comprised of a normally distributed Vβ repertoire with a CAR specific for Vβ8 leaves the non-Vβ8 repertoire intact, but results in selective and specific elimination of the small fraction of Vβ8+ T-cells.

In addition to measurements for cell-surface scFv expression, TCRVβ8 CAR transduced T-cells are measured longitudinally for selective elimination of the minor Vβ8+ subpopulation of normal T-cells and the maintenance of all other Vβ subfamilies. To do so, flow cytometry is performed using Beckman Coutler's IOTest® Beta Mark TCR V beta Repertoire Kit, in order to quantitatively determine the distribution of the 24 family TCR Vβ repertoire of human T lymphocytes (Wu D, Anderson M M, Othus M, Wood B L. Clinical Experience With Modified, Single-Tube T-Cell Receptor Vbeta Flow Cytometry Analysis for T-Cell Clonality. Am J Clin Pathol. 2016; 145(4):467-85). Confirmation of specific TCRVβ family depletion is performed at the genetic level using Adaptive Biotechnologies' TCRVβ immunoSeq technology (Tumeh P C, Harview C L, Yearley J H, Shintaku I P, Taylor E J, Robert L, et al. PD-1 blockade induces responses by inhibiting adaptive immune resistance. Nature. 2014; 515(7528):568-71; Tsankova N M, Bevan C, Jobanputra V, Ko Y C, Mayer E W, Lefkowitch J H, et al. Peripheral T-cell lymphoma emerging in a patient with aggressive polymyositis: molecular evidence for neoplastic transformation of an oligoclonal T-cell infiltrate. Acta neuropathologica. 2013; 126(4):595-601). For rigor, CAR mediated Vβ8-family specific depletion (compared to control CARs) is tested using 10 independent healthy donor T-cell samples purchased from Penn's Human Immunology Core. Although healthy T-cell cultures will not contain PTCL cells, results stemming from these phenotypic analyses will serve as indirect measurements to define the specificity and functional activity of TCRVβ CAR T-cells.

TCRVβ8 CAR constructs are tested for Vβ8-family-specific depletion using several de-identified T-cell lymphoma samples of defined TCRVβ clonality. The viability and clonality of the specimens is validated, and their suitability for these studies is determined. More so, these samples are characterized by their TCRVβ family usage using standard flow cytometry techniques and commercially available Vβ family specific antibodies (Vonderheid E C, Boselli C M, Conroy M, Casaus L, Espinoza L C, Venkataramani P, et al. Evidence for restricted Vbeta usage in the leukemic phase of cutaneous T cell lymphoma. J Invest Dermatol. 2005; 124(3):651-61), and specimens are identified that screen positive for Vβ5 or Vβ8 PTCL expansions. Using patient donor samples with known Vβ8 clonality, T-cells are transduced and measurements are taken for depletion of both normal and malignant T-cells using TCRVβ immunoSeq technology (Tumeh P C, Harview C L, Yearley J H, Shintaku I P, Taylor E J, Robert L, et al. PD-1 blockade induces responses by inhibiting adaptive immune resistance. Nature. 2014; 515(7528):568-71; Tsankova N M, Bevan C, Jobanputra V, Ko Y C, Mayer E W, Lefkowitch J H, et al. Peripheral T-cell lymphoma emerging in a patient with aggressive polymyositis: molecular evidence for neoplastic transformation of an oligoclonal T-cell infiltrate. Acta neuropathologica. 2013; 126(4):595-601). In these assays, differences in the prevalence of the CAR targeted- and the non-targeted-TCRVβ families are analyzed for statistical significance. Paired comparisons in TCRVβ distribution between TCRVβ8 CAR transduced and untreated (and control CAR) conditions are made.

It is possible that some antibodies may not easily convert to scFv format with retained antigen specificity and activity. Should this occur, new antibodies/scFvs that confer Vβ-family-specificity are isolated. Antigen specific scFvs are isolated based upon known binding specificity and are assembled into functional CAR constructs. CAR expression and/or function may be influenced by $V_H$-$V_L$ or $V_L$-$V_H$ orientation, and therefore various formations are evaluated. CAR constructs exhibiting both high expression and antigen-specific functional activity are prioritized for additional evaluation in direct functional assays in vitro and in vivo. All transduced T-cells are equilibrated to similar transduction efficiency before use in latter assays of antigen specific response.

Peripheral blood T-cells activated and engineered to express a given TCRVβ CAR will be evaluated as to the diversity of their TCRVβ repertoire. Levels of the targeted Vβ family are measured by the end of culture at day 14 post-transduction. The targeted Vβ family are expected to be eliminated within days of CAR transduction, while all other Vβ families remain intact. If CAR constructs exhibit a weak elimination of the targeted Vβ family, new scFvs are isolated and tested, the impact of scFv affinity is explored by fine-tuning the CAR, hinge length, cytokine exposure and costimulatory domain.

Example 5: Antibody-Dependent Cell-Mediated Cytotoxicity (ADCC)

Figures 10A, 10B:
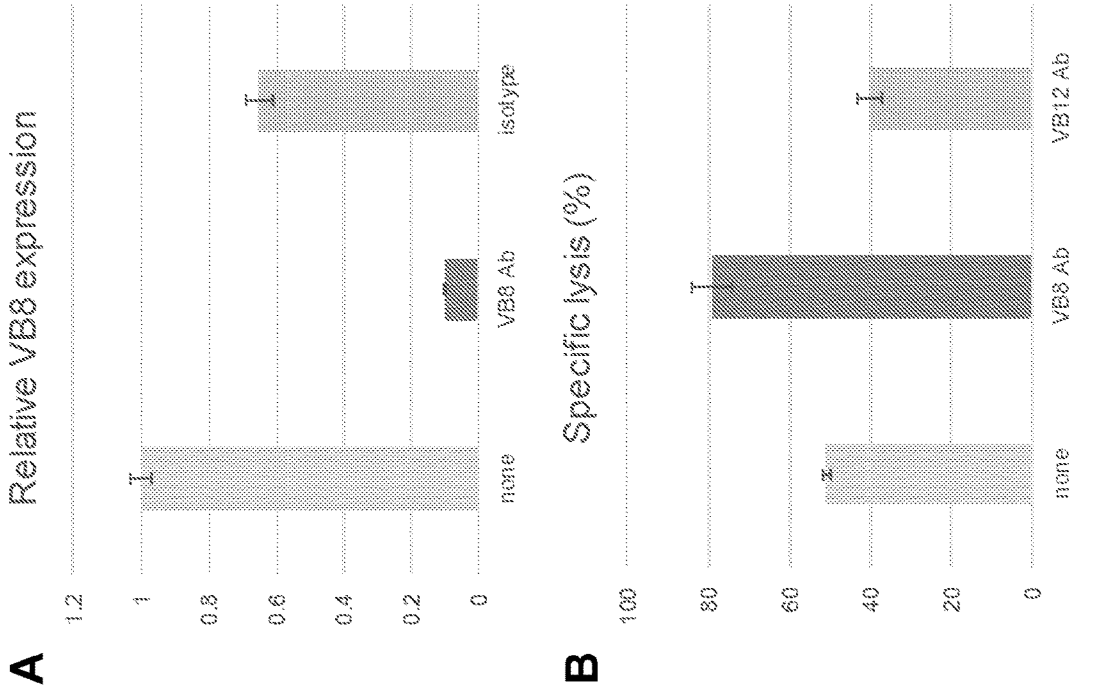
FIGS. 10A-10B are series of graphs showing antibody-dependent cell-mediated cytolysis of clonotypic TCRVβ on T-cell leukemia.

Central to this application is the hypothesis that TCRVβ-specific CAR T-cells recognize and exert robust effector functions in response to TCRVβ family expressing cancer cells. To establish proof of principle for Vβ8-specific targeting, preliminary studies were conducted using an antibody-dependent cell-mediated cytotoxicity (ADCC) assay, wherein Vβ8-specific antibody was added to co-cultures of open repertoire human T cells and CD64-expressing immune cells. ADCC redirected against Vβ8 resulted in a specific reduction in the Vβ8-expressing T cell subset (FIG. 10A). All other Vβ families were preserved (not shown). The capacity of Vβ8-specific ADCC to lyse Jurkat human leukemic T-cell lymphoblasts, which naturally express TCRVβ8 (Hu H Z, de Weger R A, Bosboom-Kalsbeek K, Tilanus M G, Rozing J, Schuurman H J. T cell receptor V beta variable gene family expression in human peripheral blood lymphocytes at the mRNA and membrane protein level. Clin Exp Immunol. 1992; 88(2):335-40) was evaluated. After 24 hrs, ADCC cultures that received a Vβ8 antibody exhibited specific ADCC of Jurkat cells (FIG. 10B) which was superior to parallel cultures receiving control isotype or Vβ12 antibody. ADCC activity is known to be substantially weaker than that of CAR T cells (Clemenceau B, Guillaume T, Robillard N, Vivien R, Peterlin P, Gamier A, et al. In Vitro Comparison of ADCC and CAR Sensitivity of Adult HER-2+B-ALL Using the NK-92 Human Cell Line Transduced with a Human CD16 (ADCC) or an Anti-HER2 Chimeric Antigen Receptor (CAR)), however, these preliminary results lend confidence to the notion that a conventional TCRVβ CAR T-cell approach will facilitate robust and specific cytolytic activity against T-cell lymphomas.

Example 6: Test for Vβ-Specific Recognition and Tumor Cell Killing by CAR T-Cells In Vitro Using Vβ8 as a model target tumor antigen in PTCL, CAR-expressing T cells specific for either Vβ8 or Vβ5.3 are co-cultured with the Vβ8+ Jurkat cell line, or control established human leukemia cancer lines that do not express Vβ8 (HSB; Vβ5.3 and Molt-3; Vβ2/12) (Hu H Z, de Weger R A, Bosboom-Kalsbeek K, Tilanus M G, Rozing J, Schuurman H J. T cell receptor V beta variable gene family expression in human peripheral blood lymphocytes at the mRNA and membrane protein level. Clin Exp Immunol. 1992; 88(2): 335-40) or non-T-cell lines that lack TCR. TCRVβ8 CAR T-cells (and controls) are tested in triplicate for the capacity to respond to Vβ8 antigen expressing tumor cells in co-culture assays, through measurement of cytokine secretion (ELISA, Luminex assay), T cell proliferation (CFSE dilution) and specific lysis ($Cr^{51}$ release and Xcelligence real time lysis assays) at various effector to target cell ratios and after various times in culture. CAR constructs are tested for relative activity in whole CD3+ T cells as well as sorted CD4+ and CD8+ T cell subsets. Cytokine secretion assays evaluate relative Th1 (e.g. IFNgamma, TNFalpha, IL-2) and Th2 (e.g. IL-4, IL-5, IL-13) production. For all assays, TCRVβ-specific CAR T cells are tested in parallel with CD5 CAR (positive control), CD19 CAR, GFP or non-transduced T-cells (negative controls). Immune recognition by TCRVβ8 CAR T-cells is detected in response to Vβ8-expressing cell lines but absent in response to target cells lacking Vβ8 expression.

The impact of Vβ8 antigen expression level by target tumor cells on the magnitude of response is assessed using Vβ8-negative HSB and Molt-3 cells engineered for cell-surface Vβ8 expression at high, intermediate or low levels. TCRVβ8 CAR T-cells are co-cultured with parental or Vβ8-engineered HSB and Molt-3 cells and assessed for antigen dependent immune recognition using measurements of cytokine secretion and target cell killing. All assays and results are evaluated for reproducibility.

T-cell lymphomas are a group of cancers of growing interest in the CAR T cell field that, unlike most solid tumors, can express various costimulatory ligands and T-cells have antigen-presentation capacity (Zhang Q, Wang H Y, Wei F, Liu X, Paterson J C, Roy D, et al. Cutaneous T cell lymphoma expresses immunosuppressive CD80 (B7-1) cell surface protein in a STAT5-dependent manner. J Immunol. 2014; 192(6):2913-9; Lanzavecchia A, Roosnek E, Gregory T, Berman P, Abrignani S. T cells can present antigens such as HIV gp120 targeted to their own surface molecules. Nature. 1988; 334(6182):530-2). The optimal CAR design for T-cell lymphoma is not defined. The impact of various costimulatory module selection in TCRVβ8 CAR design on antigen-stimulated CAR T cell proliferation, cytokine secretion and killing, is determined. CAR backbones containing 4-1BB, CD28, ICOS and CD27 are generated for interrogation in the context of TCRVβ targeting. Impact of costimulatory domain selection on CAR T-cell cytokine secretion, proliferation and specific lysis is assessed in vitro and in vivo. Secondary to these efforts, the impact of hinge length on CAR function is assessed.

Without wishing to be bound by theory, addition of costimulatory modules may increase antigen-driven T cell division and the diversity and quantity of cytokines produced by TCRVβ8 CAR T-cells. In reciprocal experiments, TCRVβ5.3 CAR T-cells are evaluated for specific recognition and killing of the Vβ5.3+ cell line, HSB. All functional assays are performed in triplicate and assessed for reproducibility and statistical significance in independent assays.

Following proof of concept assays using established T-cell leukemia lines, studies are extended to de-identified primary T-cell lymphoma samples. These samples are characterized for TCRVβ family usage by standard flow cytometry techniques. Before performing functional assays, Vβ family usage is validated using Adaptive Biotechnologies' TCRVβ ImmunoSeq technology. Allogeneic donor T cells are transduced with TCRVβ8 CAR (or control) constructs, exposed to primary T-cell lymphoma samples with confirmed Vβ8 clonality, and longitudinally monitored for changes in the TCRVβ repertoire over 14 days by flow cytometry using Beckman Coutler's IOTest® Beta Mark TCR V beta Repertoire Kit, and by TCRVβ immunoSeq technology and/or RT-PCR. In parallel assays, cytolysis of the malignant PTCL samples is measured by standard chromium release assay and cytokine secretion assays are performed on resultant supernatants using Luminex technology.

Healthy autologous T-cells from patients with PTCL can be outfitted with a TCRVβ-specific CAR and used to attack autologous lymphoma cells. "Healthy" T-cells are enriched by the removal of the dominant PTCL clone using Vβ-specific antibodies and paramagnetic bead separation systems for positive-selection/depletion. Further assays use non-enriched T-cells from PTCL patients to determine whether self-Vβ-depletion results in a cell product free of the targeted TCRVβ family (both healthy and malignant TCRVβ+ T-cells), and to draw functional comparisons with enriched healthy T-cells described above. The influence of pre-enrichment of the healthy T-cell subset on CAR T-cell expansion, effector function and differentiation status of TCRVβ CAR T-cells throughout 14 days of cell cultivation is examined. In co-cultures assays, enriched "healthy" or non-enriched "whole" TCRVβ CAR T cells from PTCL patients are exposed to autologous PTCL cells and measured for their capacity to proliferate, secrete various cytokines and mediate the cytolysis of the autologous cancer cells using functional assays described above.

Additionally, because both CAR T-cells and PTCL cells themselves have the capacity for effector function, whether reciprocal cytolysis of TCRVβ CAR T cells occurs when they are exposed to autologous T-cell lymphoma cells is evaluated using a selective chromium labeling technique. TCRVβ CAR T cells are labeled with chromium, exposed to autologous PTCL cells and then measured for their specific lysis. Non-specific TCRVβ CAR T cells are used as a control for antigen specificity. In parallel, autologous PTCL cells are labeled with chromium, exposed to TCRVβ CAR T cells and then measured for their specific lysis to compare and contrast their susceptibility to T-cell mediated lysis. The impact of effector to target T-cell ratio is evaluated at a wide range in order to identify optimal effector to target ratios for efficient cancer cell killing.

Finally, targeted deletion of a single TCRVβ family is expected to allow for maintenance of the majority of virus-specific T cells, and leave TCRVβ CAR treated patients largely immune competent. However, T-cell responses to a particular virus could be skewed toward one of the various TCR Vβ subpopulations and depletion of that one subset might then result in loss of cellular immunity. To address this possibility, oligoclonal influenza (FLU), cytomegalovirus (CMV) and Epstein-Barr virus (EBV)-specific cytotoxic T cell lines are generated using cells from 5-10 healthy donors, using established in vitro stimulation methods (Powell D J, Jr., Dudley M E, Hogan K A, Wunderlich J R, Rosenberg S A. Adoptive transfer of vaccine-induced peripheral blood mononuclear cells to patients with metastatic melanoma following lymphodepletion. J Immunol. 2006; 177(9):6527-39; Bollard C M, Savoldo B, Rooney C M, Heslop H E. Adoptive T-cell therapy for EBV-associated post-transplant lymphoproliferative disease. Acta Haematol. 2003; 110(2-3):139-48). Using Beckman Coutler's IOTest® Beta Mark TCR V beta Repertoire Kit and virus-specific peptide/MHC dextramers (Immudex), the distribution of virus specific T-cells is evaluated across the TCRVβ repertoire to determine whether skewing toward a TCR subpopulation exists at baseline. Similarly, retained presence of virus-specific T cells is measured following TCRVβ CAR transduction and specific elimination of a given TCR subpopulation. In addition, following TCRVβ CAR transduction, virus-specific T cell responses are measured to test for retained function, as identified by interferon (IFN)-γ expression across the TCRVβ repertoire following virus-specific peptide stimulation. All assays are performed using triplicate cultures and performed twice to test for reproducibility in and across experiments. The statistical significance of TCRVβ CAR transduction on virus-specific T cell responses, compared to irrelevant CAR control transduction, is assessed using standard paired sample t-test.

Example 7: Evaluate the Potency and Persistence of Biobody-Loaded Engineered T Cells In Vivo To model and test the clinical efficacy and safety of TCRVβ-specific CAR T-cell therapy, the Vβ8+ Jurkat human acute lymphoblastic T-cell leukemia line (Hu H Z, de Weger R A, Bosboom-Kalsbeek K, Tilanus M G, Rozing J, Schuurman H J. T cell receptor V beta variable gene family expression in human peripheral blood lymphocytes at the mRNA and membrane protein level. Clin Exp Immunol. 1992; 88(2):335-40) are genetically tagged with firefly luciferase (fLuc) and 5e6 cells are inoculated by s.c. injection into NOD/SCID IL2γc−/− (NSG) mice (10 mice/grp). After tumor establishment (~5 wks), TCRVβ8 CAR T-cells derived from healthy donors are infused by single tail vein injection at cell doses ranging from $1\times10^6$ to $40\times10^6$, and tumor progression are temporally monitored using caliper measurement and bioluminescence imaging by IVIS Xenogen. All in vivo experiments include control cohorts that receive untransduced T-cells, GFP transduced T-cells, or positive control CD5 CAR T-cells, irrelevant control TCRVβ5.3 CAR T-cells or CD19 CAR transduced T-cells. In follow up studies, fLuc+ lymphoma cells are infused by i.v. injection followed by i.v. injection of CAR T-cells to better model the treatment of disseminated disease. Retro-orbital blood are drawn at multiple times over the course of the study to i) measure for levels of serum cytokines that are prevalent in patients experiencing cytokine release syndrome (CRS), including IFNgamma, IL-6, IL-8, IL-10 and TNFalpha, and ii) evaluate the persistence of the transferred TCRVβ8 CAR T-cells, relative to controls. Therapy is tested in both male and female NSG mice in independent cohorts to assess comparability.

To more closely model the treatment of T-cell lymphoma patients using autologous TCRVβ CAR T-cells, NSG mice are engrafted, through i.v. infusion, with donor T-cell lymphoma cells, and an autologous TCRVβ CAR T-cell product is generated using T-cells from the same patient donor. In preparation for future studies, a sample with TCRVβ8 clonality has already been identified that has the capacity for in vivo engraftment.

To monitor for specific TCRVβ family depletion in treated mice, peripheral blood is collected prior to CAR T-cell infusion and at weekly intervals following adoptive transfer, and measured for circulating human T-cell counts using Tru-Count beads as well as Vβ distribution using the Beckman Coutler's IOTest® Beta Mark TCR V beta Repertoire Kit, and Adaptive Biotechnologies' TCRVβ immunoSeq technology and/or RT-PCR. The TCRVβ immunoSeq and RT-PCR method provide a distinct advantage over flow cytometric analyses given their sensitivity and ability to quantify using smaller number of cells for analysis. Comparisons are drawn against a cohort of mice receiving CD5-specific CAR T-cells, which are anticipated to have considerably less precision for selective cancer cell killing, and thus more killing of healthy T-cells, than TCRVβ CAR T-cells.

Treated mice are monitored for disease progression with continued follow up until mice show signs of morbidity or discomfort. Infused TCRVβ CAR T-cells are evaluated for their persistence in the blood, relative to controls. Further, in this model, where primary donor lymphoma cells may contribute to CRS sequela, peripheral blood is drawn at multiple time point over the course of the study and measured for levels of serum cytokines associated with CRS (described above). In order to determine if the T-cell lymphoma, as a target, fosters increased risk of CRS, the C30 ovarian cancer cell line (a non-T-cell target cell) is engineered to express firefly luciferase and TCRVβ at similar levels to those on Jurkat cells and primary donor lymphoma cells. NSG mice are inoculated with fLuc+ TCRVβ8+C30 cancer cells and treated with TCRVβ CAR T-cells to assess serum cytokines levels. These serum cytokines levels are compared to those detected in mice bearing TCRVβ+ T-cell lymphoma cells and treated with TCRVβ CAR T-cells. This is assessed for reproducibility using several primary donor lymphoma cells and other non-T-cell lines, such as SKOV3, that engraft well in immunodeficient mice.

Lymphoma-bearing mice treated with TCRVβ CAR T-cells containing CD28, 4-1BB or a tandem CD28/4-1BB costimulatory domain (or other costimulatory domains, as rationalized by in vitro results of Example 3) will be longitudinally assayed for relative level of CRS induction, CAR T-cell persistence and antitumor activity.

At the end of study, immunohistochemistry is performed to ascertain CAR T-cell tissue distribution and determine whether antigen escape occurs following treatment. Median survival times are determined using Kaplan-Meier survival curves and compared between CAR T cell groups by log rank analysis, with Bonferroni adjustment for multiple comparisons.

TCRVβ CAR T-cells will mediate antigen-specific anti-tumor responses in NSG mice bearing either Jurkat leukemia cells or autologous T-cell lymphoma xenografts from donors. Moreover, TCRVβ CAR T-cells will carve a hole in the T-cell repertoire, in effect eliminating the clonotypic malignant T-cell population and leaving nearly 95% of the diverse TCRVβ repertoire intact. In contrast, CD5 CAR T cells will have broader activity, inducing pan T-cell depletion and some level of fratricide of CAR T-cells in vivo. Efficacy is CAR T-cell dose dependent with higher doses achieving higher effective E:T ratios in vivo, and being associated with improved anti-tumor response. Cell dose are optimized to achieve maximal CAR T-cell persistence and cancer cell killing with minimal toxicity.

If generation of autologous CAR T-cell products becomes a challenge, one may resort to allogeneic T-cell products, as described in Example 6. Without wishing to be bound by theory, TCRVβ CAR T cells undergo antigen-driven expansion and persistence following infusion to levels exceeding that of T-cell controls, and that expansion/persistence will be both CAR T-cell dose- and antigen-dependent. Without wishing to be bound by theory, CAR T-cells bearing 4-1BB endodomain may persist better than similar CARs outfitted with CD28, but that CD28 may promote increased early anti-tumor activity and be accompanied by greater production of serum CRS-associated cytokines. This is an interesting and relatively poorly explored area of research that has obvious clinical importance.

Emerging preclinical studies suggest a role for macrophages in the development of CAR-associated CRS through an IL-1 associated mechanism (Giavridis T, van der Stegen S J C, Eyquem J, Hamieh M, Piersigilli A, Sadelain M. CAR T cell-induced cytokine release syndrome is mediated by macrophages and abated by IL-1 blockade. Nat Med. 2018). Whether T-cell lymphomas as target cells also contribute to enhanced CRS effects after CAR T-cell infusion is unknown.

T-cell lymphoma cells do have the capacity to produce proflammatory cytokines and chemokines, such as IL-2 and the chemokines, IL-8, MIP-1α, MIP-1β and MCP-1 being produced in detectable quantities (Bartelt R R, Cruz-Orcutt N, Collins M, Houtman J C. Comparison of T cell receptor-induced proximal signaling and downstream functions in immortalized and primary T cells. PLoS One. 2009; 4(5): e5430). Higher levels of serum cytokines may be detected from T-cell lymphoma bearing NSG mice treated with TCRVβ8 CAR T-cells, compared to mice bearing non-T-cell cancers expressing TCRVβ8. Knowledge in this area will help guide treatment and management strategies for future first-in-man clinical trials.

If TCRVβ T-cells mediate unexpected immunopathology, treated mice undergo extensive full body autopsy to explore biodistribution of CAR T-cells, degree of organ specific pathology, signs of cerebral edema and levels of serum enzymes associated with organ toxicity. If toxicity is a challenge, an RNA transfer system of transient CAR expression may be employed (Schutsky K, Song D G, Lynn R, Smith J B, Poussin M, Figini M, et al. Rigorous optimization and validation of potent RNA CAR T cell therapy for the treatment of common epithelial cancers expressing folate receptor. Oncotarget. 2015; 6(30):28911-28) to control CAR T cell persistence and toxicity, and to allow for recovery of the healthy TCRVβ subset after treatment. Alternatively, suicide-gene approaches may be incorporated to eliminate the TCRVβ CAR T-cells in vivo after tumor clearance, allowing for recovery of health. These approaches may be central to future first in man trials for advanced T-cell lymphoma.

Figures 11A, 11B:
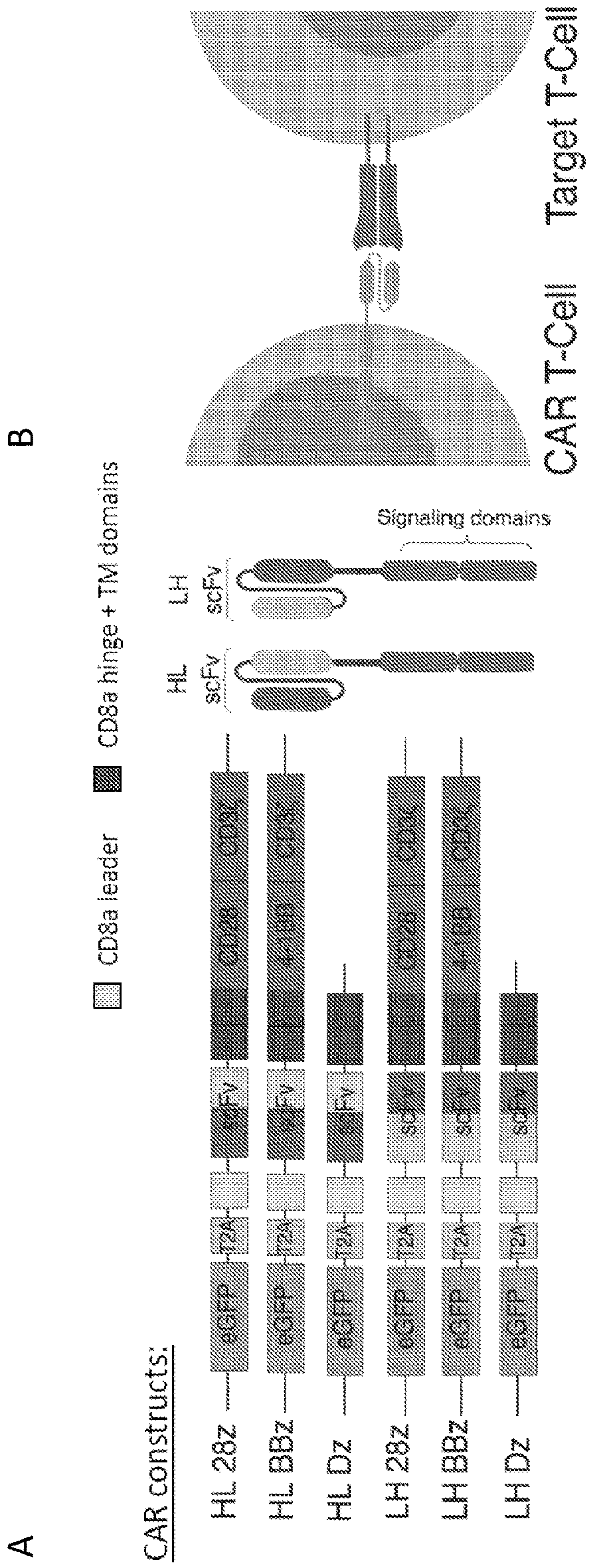
FIGS. 11A-11B illustrate the design of the anti-TCRVβ specific CARs.

Example 8: TCRVβ CAR T Cell Therapy for Precision Targeting of T Cell Malignant Clones Developing a CAR T cell platform to treat T cell malignancies is challenging because there are no tumor-associated antigens (TAAs) to distinguish cancerous T cells from healthy T cells, which make up the immune repertoire of the patient as well as the CAR T cells themselves. A CAR T cell platform for PTCLs that avoids self-depletion, is effective, and avoids immunosuppression in the patient must therefore target a TAA with ubiquitous expression by malignant cells and limited expression by healthy T cells. PTCLs consist of mature, clonally expanded T cells so the malignant population will be derived from one of 24 T cell receptor beta chain variable region (TCRvβ) families. It was proposed herein that CAR T cells specific for a TCRvβ family mediates TCRvβ family-specific lysis of malignant T cells while preserving the majority of the healthy T cell population. To demonstrate this, CAR constructs specific for individual TCRvβ family members were designed and generated (FIGS. 11A-11B). Each CAR sequence contained a CD8a leader, the scFv in either heavy chain-GGGS(3×)-light chain (HL) or light chain-GGGS(3×)-heavy chain orientation (LH), CD8a hinge domain, transmembrane domain, and CD28/CD3z or 4-1BB/CD3z signaling domains, if present (SEQ ID NOs: 1-32 and 153-184).

Figures 12A, 12B:
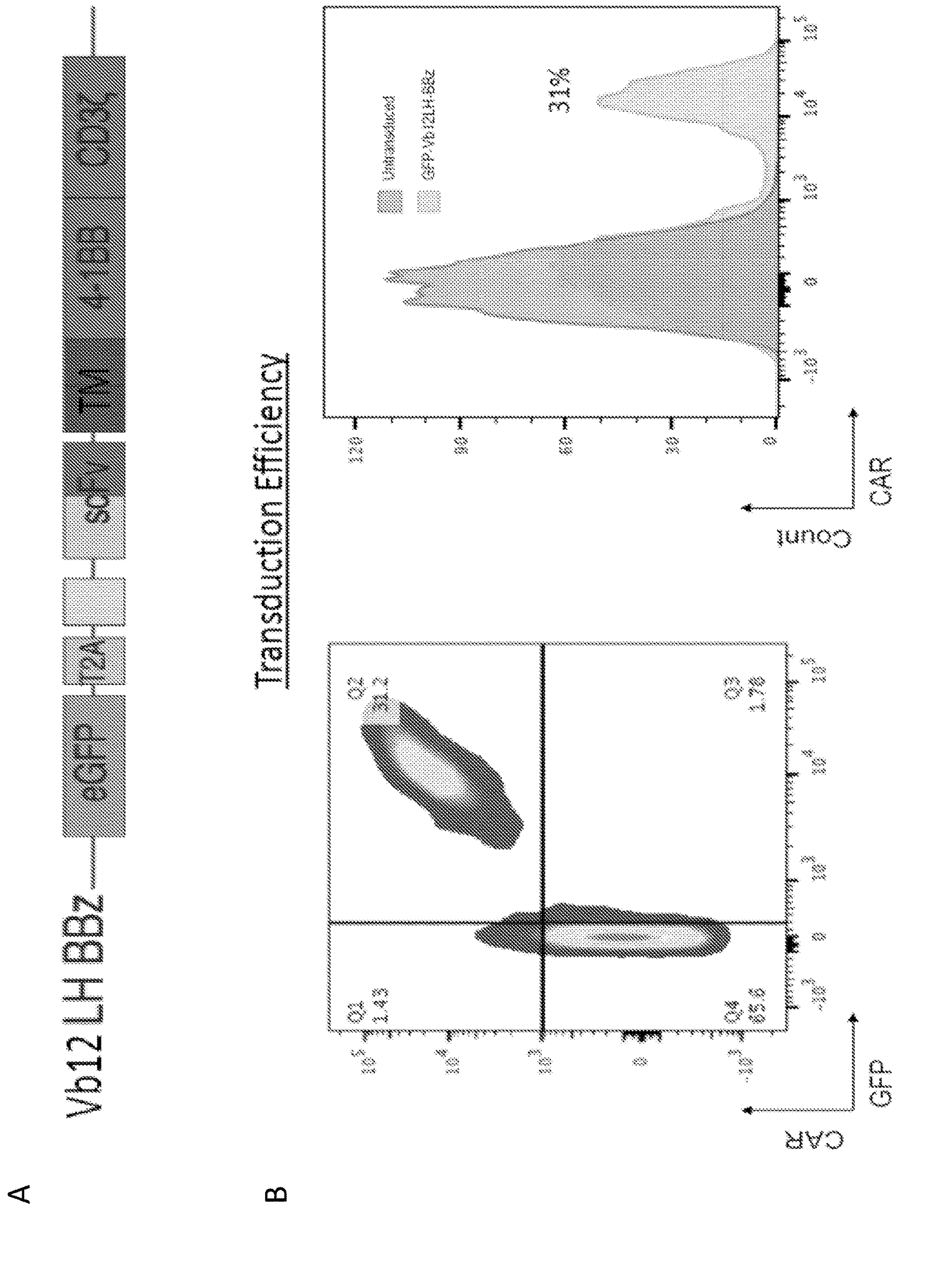
FIGS. 12A-12D illustrate the expansion of T cells transduced to express a Vβ12-targeting CAR.
Figure 21:
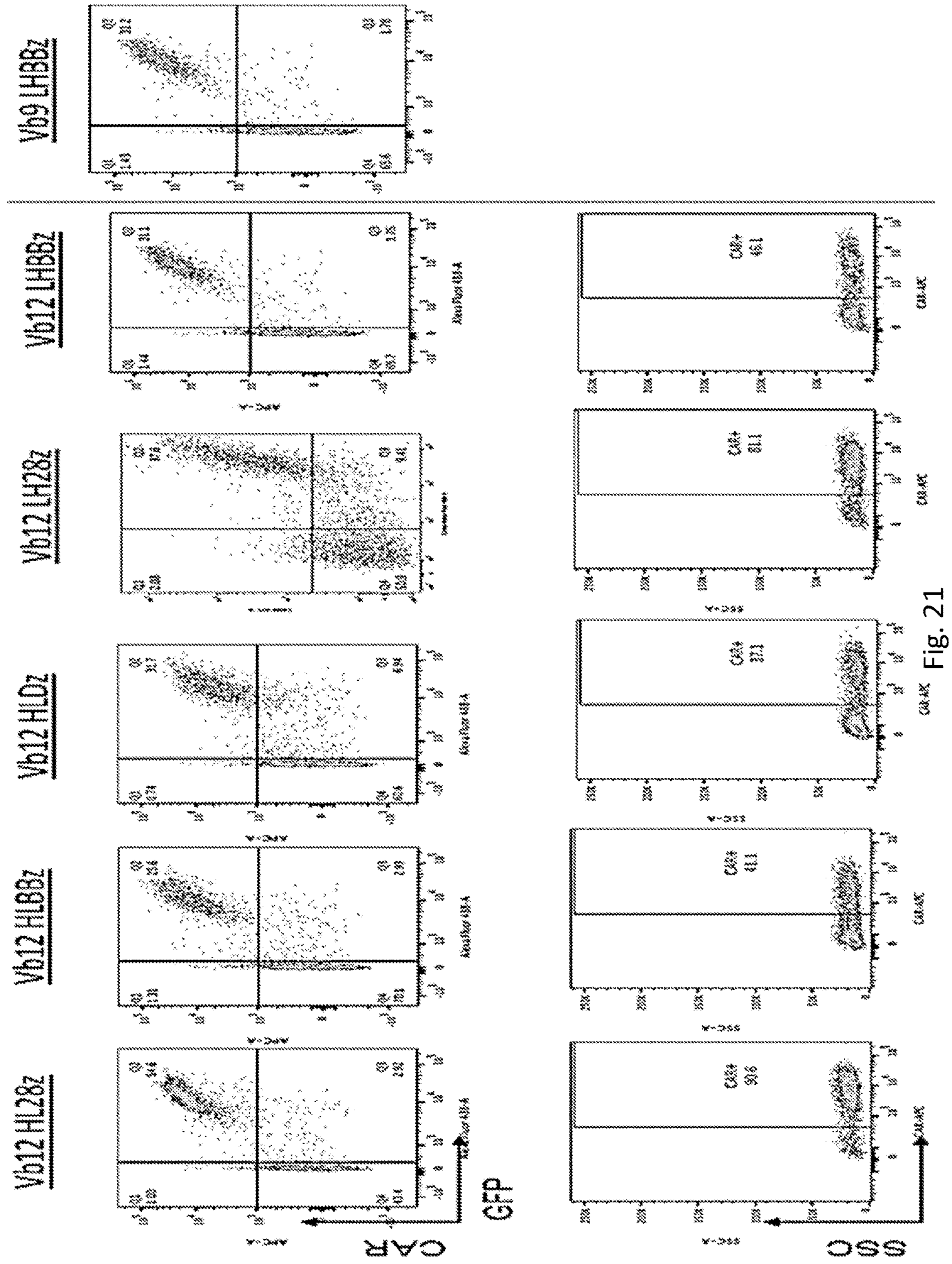
FIG. 21 is a series of dot plots showing the transduction efficiencies of various Vβ12 CAR constructs.

(a) Creating CARs specific for TCRvβ family members. CAR constructs were generated that encode for an antibody-derived extracellular single-chain variable fragment (scFv) specific for a single TCRvβ family member linked to intracellular stimulatory and co-stimulatory domains using standard cloning techniques. Possible scFvs were derived from the sequences of the variable regions of antibodies against 12 TCRvβ segments, obtained via collaboration with Beckman Coulter, and designed in two orientations: heavy chain-linker-light chain (HL) and light chain-linker-heavy chain (LH). Constructs without signaling domains were used as negative controls (Δz CARs). Both GFP and non-GFP containing vectors were made. A schematic of the complete CAR designs can be seen in FIG. 11A. An exemplary CAR construct was made to target TCRvβ12 (FIG. 12A). Lentivirus was produced and added to a 1:1 mixture of CD4+ and CD8+ T cells that were expanded for 14 days. Flow cytometry was used to determine surface expression by staining with protein L, which binds to the kappa light chain of scFvs, and monitored for co-expression with GFP (FIG. 12B). Similar studies to examine the transduction efficiencies of the other TCRvβ12 and TCRvβ9 constructs were also conducted (FIG. 21).

Figure 12C:
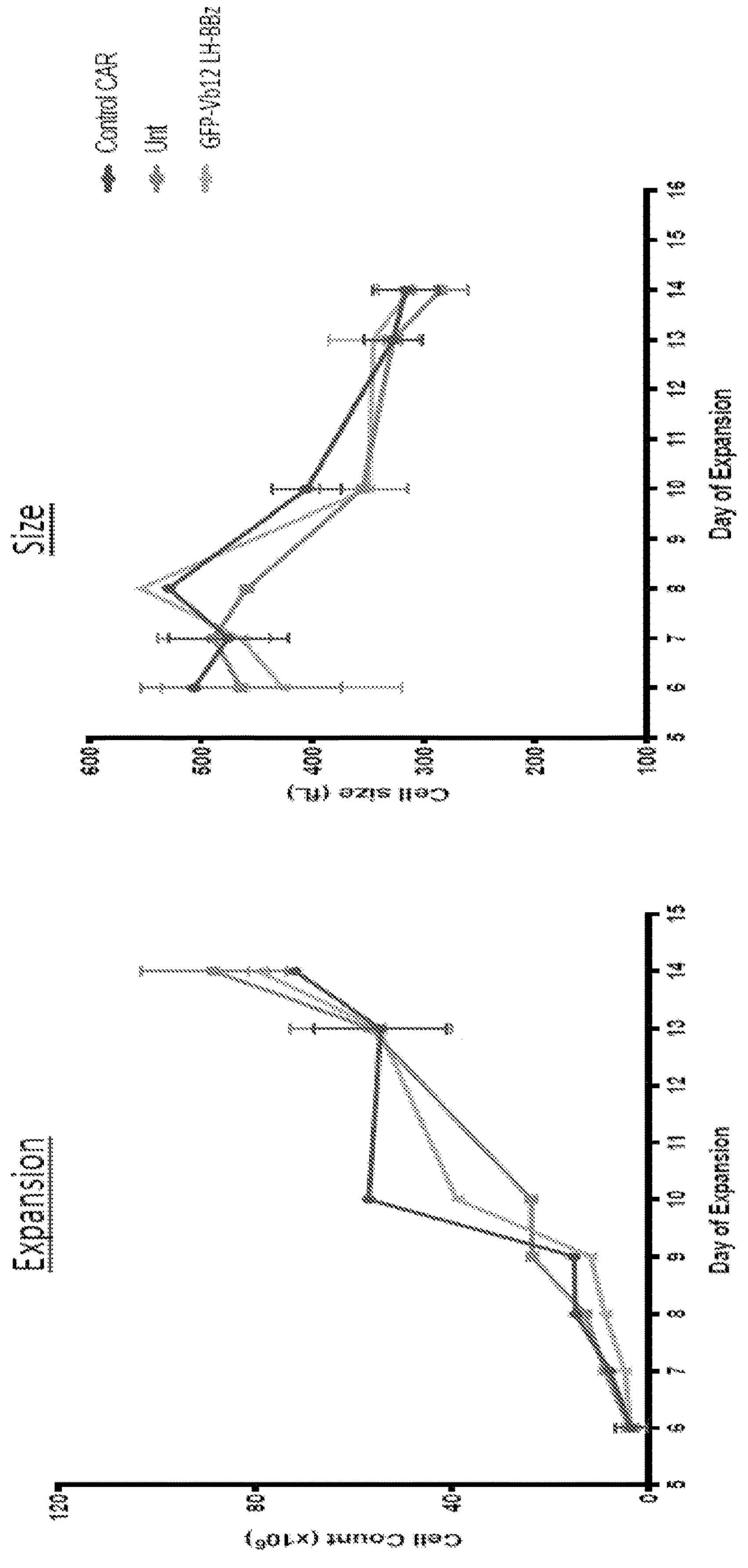
Figure 12D:
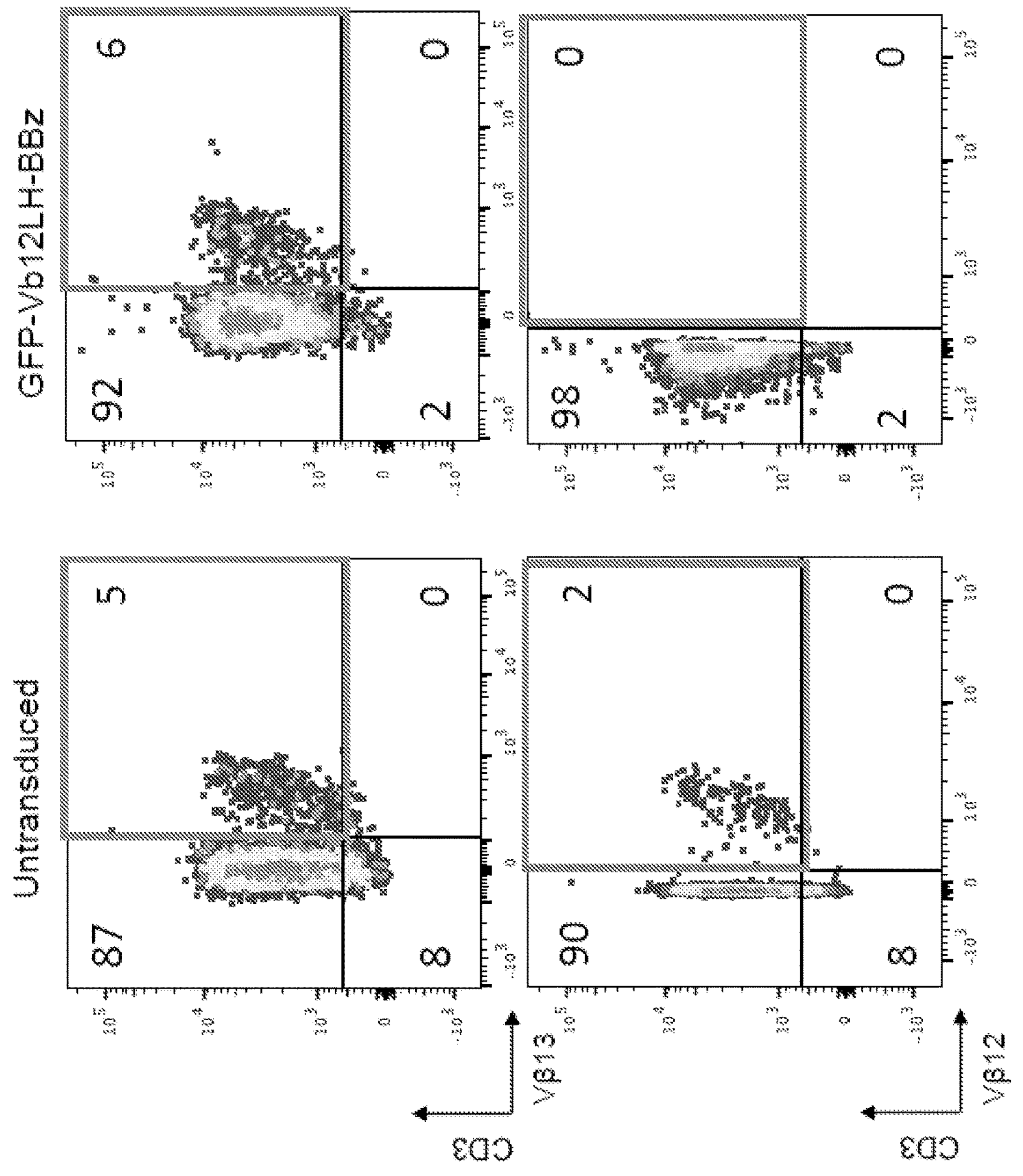
Figure 13A:
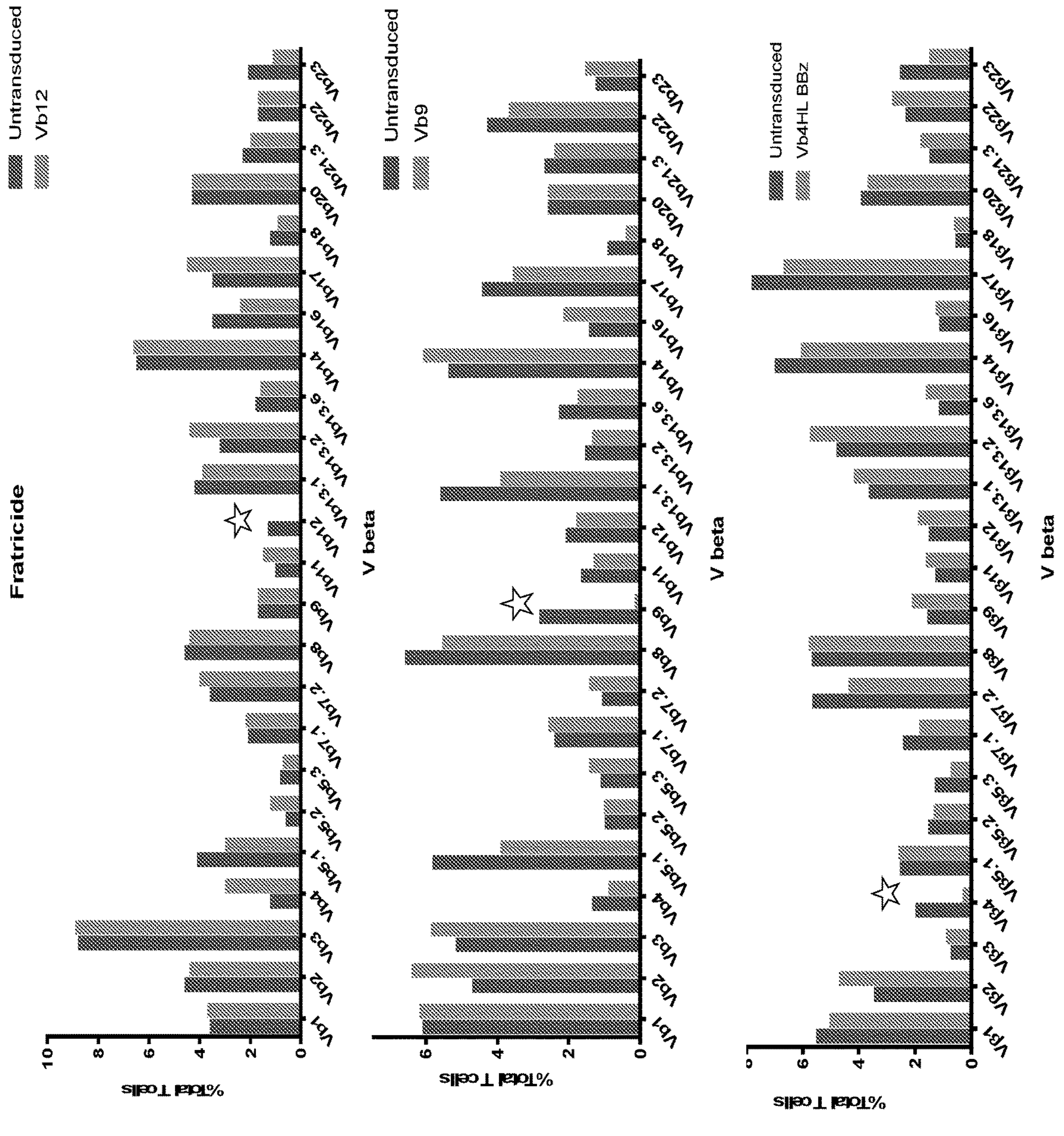
FIGS. 13A-13B illustrate specific depletion of target populations after expansion of normal donor T cells transduced to express Vβ-family specific CAR T cells.
Figure 13B:
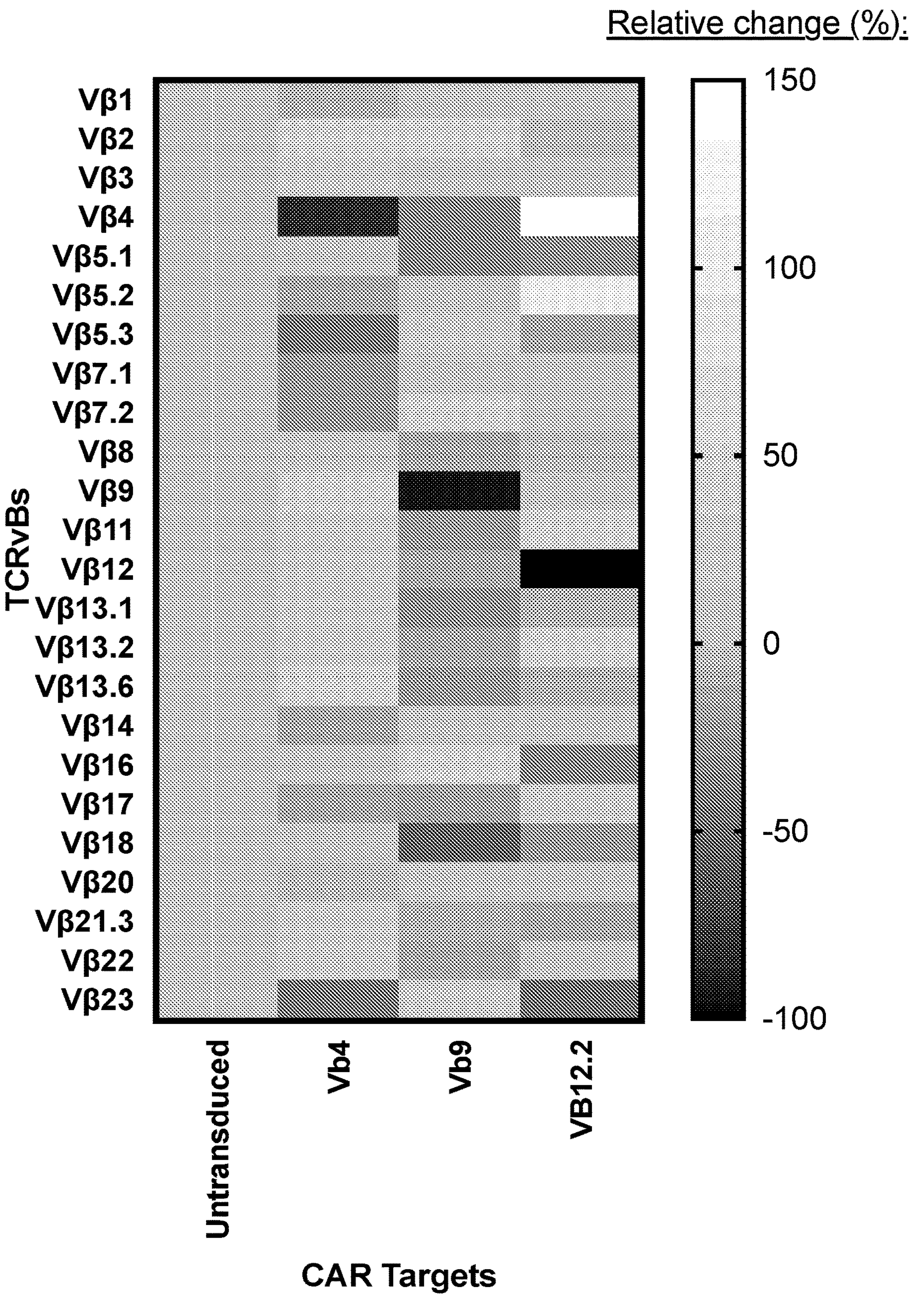
Figures 14A, 14B:
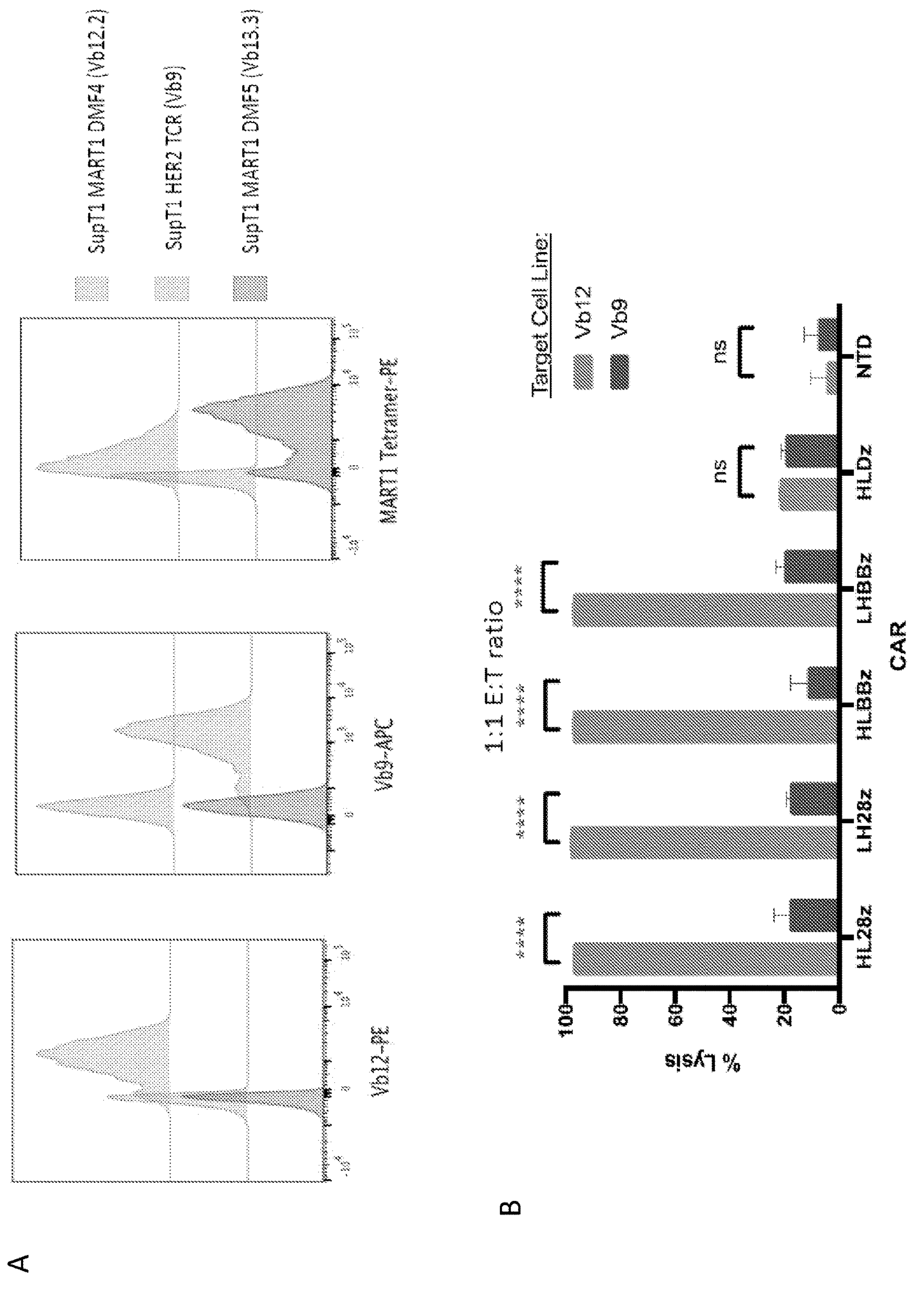
FIGS. 14A-14C illustrate specific lysis of SupT1 cells engineered to express three different TCRs.
Figure 14C:
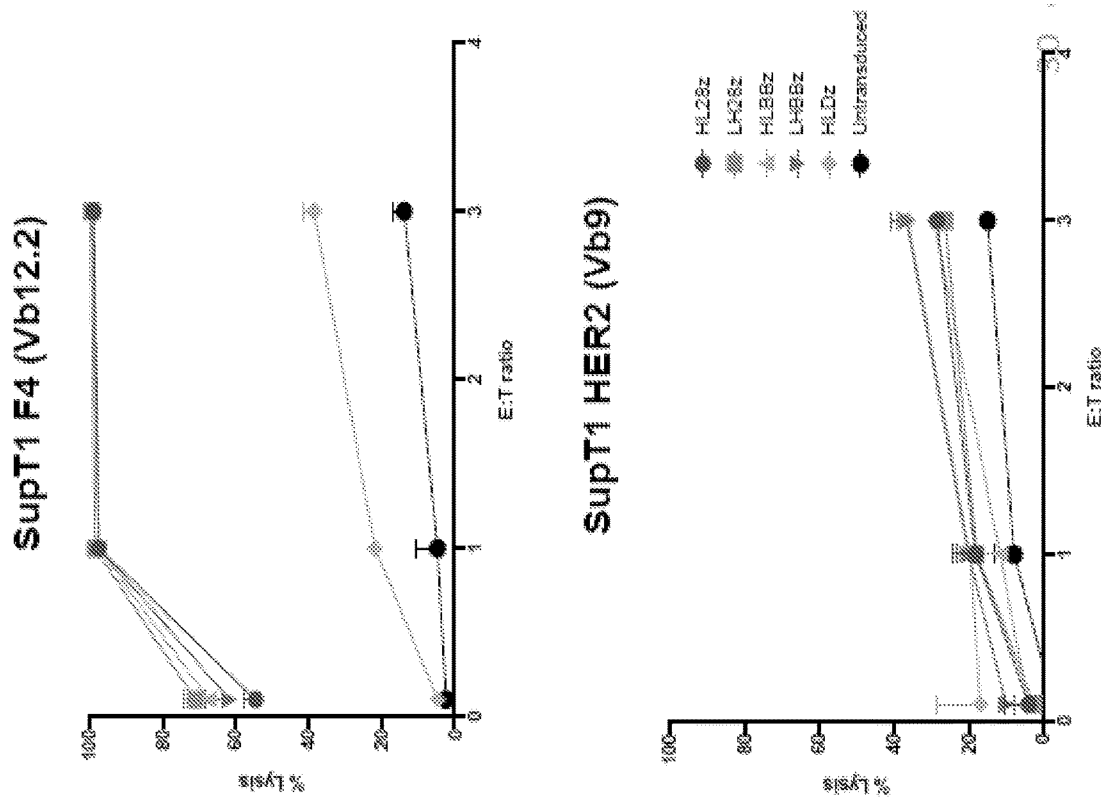
Figures 15A, 15B:
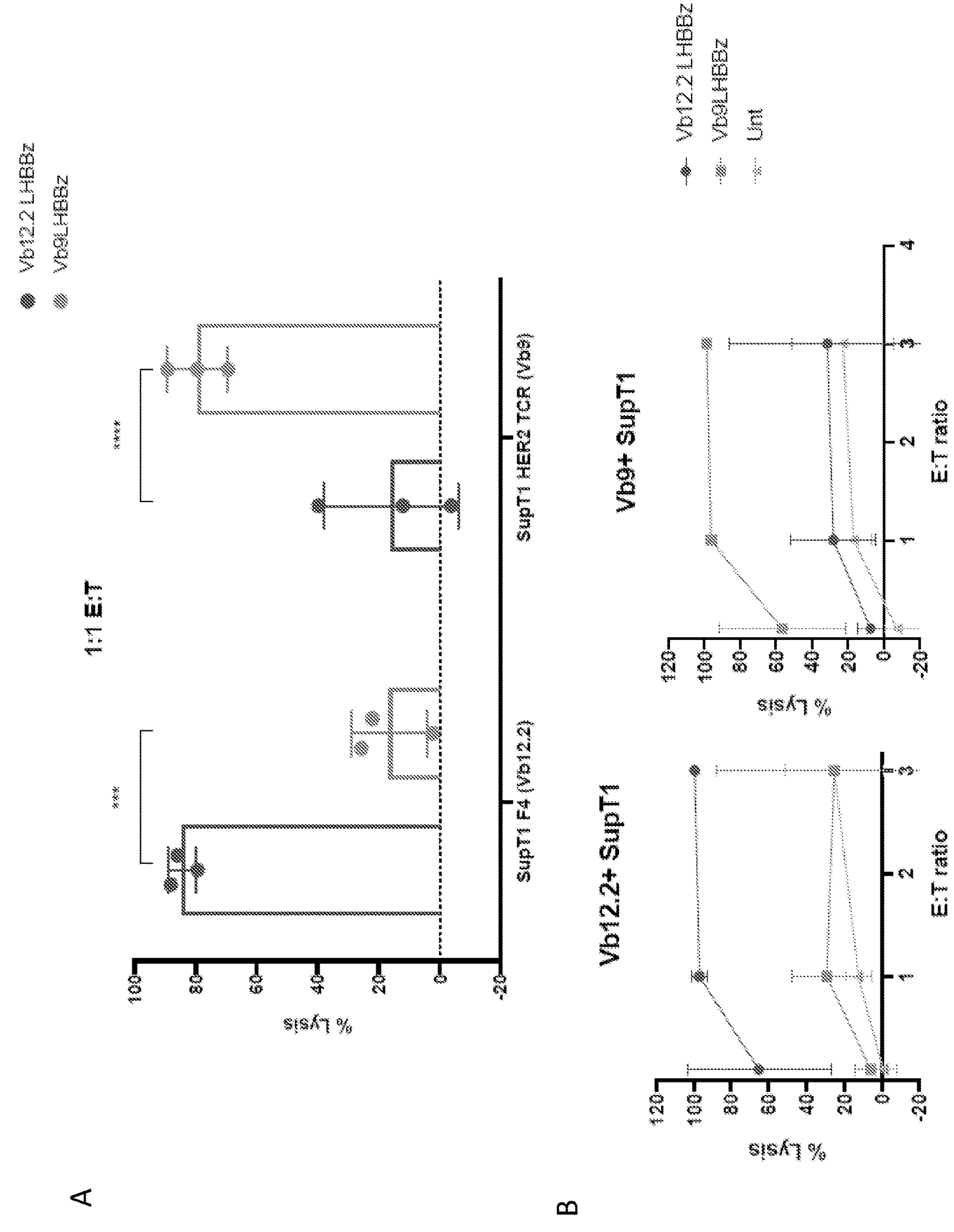
FIGS. 15A-15B show the specific lysis of SupT1 cell lines incubated with CAR T cells expressing either a Vβ12-targeting CAR or a Vβ9-targeting CAR across 3 different technical replicates.

(b) Monitoring T cell fratricide in expanded CAR T cells. Healthy donor T cells used in (Example 8 (a)) have a regular distribution of TCRvβs. During expansion of these cells, the CAR-expressing T cells deplete the subset that expresses the target TCRvβ. However, the targeted population represents only 2-5% of total cells and therefore should not significantly affect the growth kinetics. Growth and size were measured over the expansion period and TCRvβ expression was analyzed by flow cytometry (FIGS. 12C-12D). To determine TCRvβ expression, the IO Test Beta Mark TCRvβ repertoire kit (TO Test) from Beckman Coulter was used to stain for 24 TCRvβ segments, covering 70% of the TCRvβ repertoire. Cells transduced to express CARs targeting either TCRvβ12, TCRvβ9, or TCRvβ 4 and were analyzed by flow cytometry to show specific depletion of the targeting population (FIGS. 13A-13B). As each CAR is developed against the 12 TCRvβ members, the TO Test is used to confirm specific depletion of each target population.

(c): Measuring specific lysis of target cells. The immortalized lymphoblastic lymphoma line, SupT1, was engineered to express known TCRs. The TCRs were specific for melanoma antigen recognized by T cells 1 (MART1) clone DMF4, MART1 clone DMF5, or human epidermal growth factor receptor 2 (HER2). Sequence alignments indicated that the MART1 DMF4 TCR included the TCRvβ12 segment, the MART1 DMF5 TCR included the TCRvβ13.3/5 segment, and the HER2-specific TCR included the TCRvβ9 segment. Heavy chain and light chain variable region sequences from antibodies specific for all three of these TCRvβ members were used for CAR design in (Example 8 (a)). These cell lines were transduced with a GFP/firefly luciferase (fLuc) lentiviral vector and analyzed by flow cytometry to confirm surface expression of GFP, CD3c, and TCRvβ families. SupT1 cells were co-cultured with targeting or non-targeting CAR T cells for 24 hours and cell death was measured, indicated by bioluminescence. A range of effector to target (E:T) ratios was used and total number of T cells added was normalized based on transduction efficiency. Each condition was run in triplicate and CAR T cells from multiple donors were tested. Both TCRvβ12 and TCRvβ9 CAR T cells specifically lysed antigen-positive cells (FIGS. 14A-14C and 15A-15B).

Figure 16A:
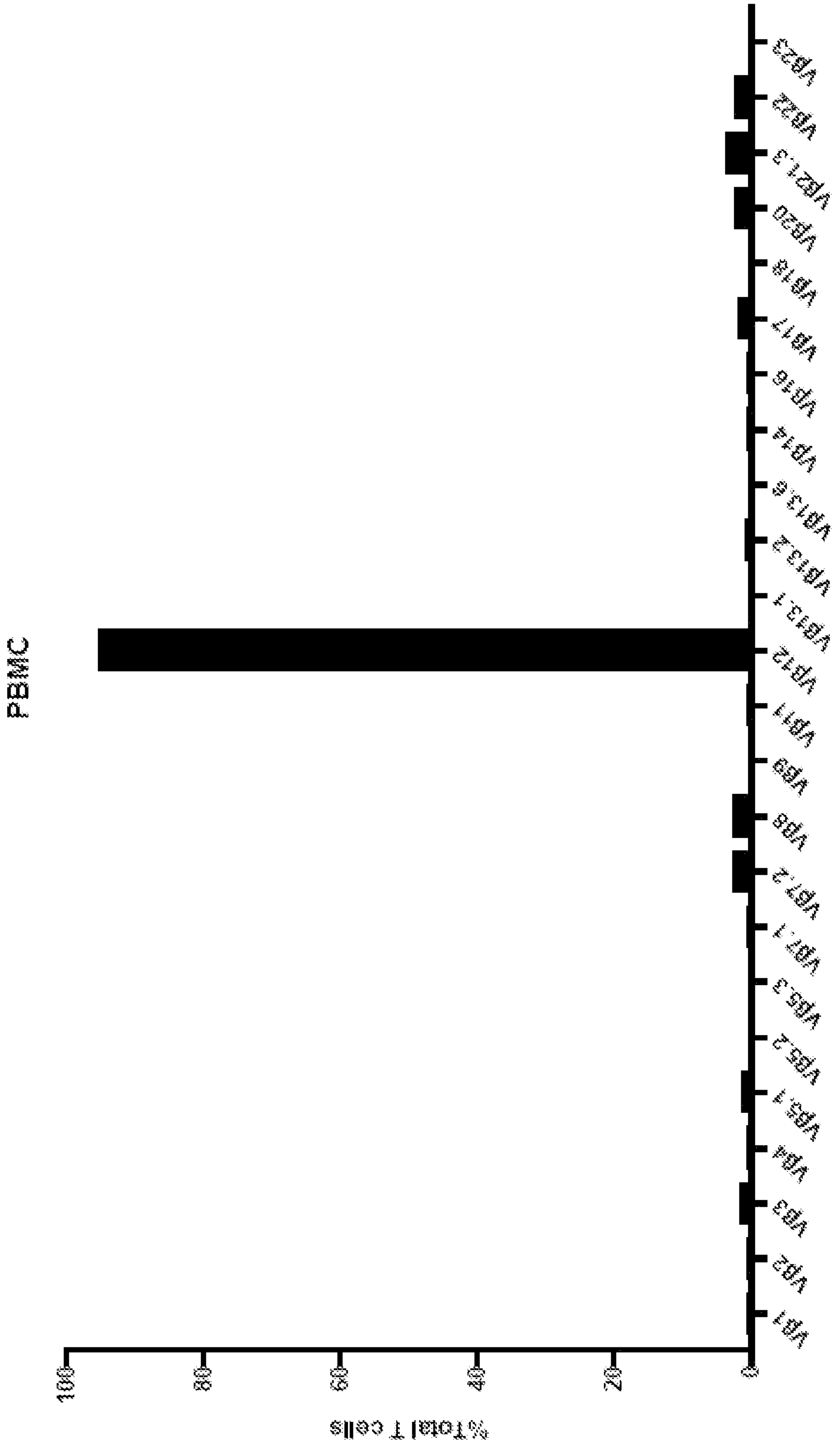
FIGS. 16A-16B illustrate the Vβ repertoire of PBMCs derived from a patient with Sezary syndrome before and after a 24-hour co-culture.
Figure 16B:
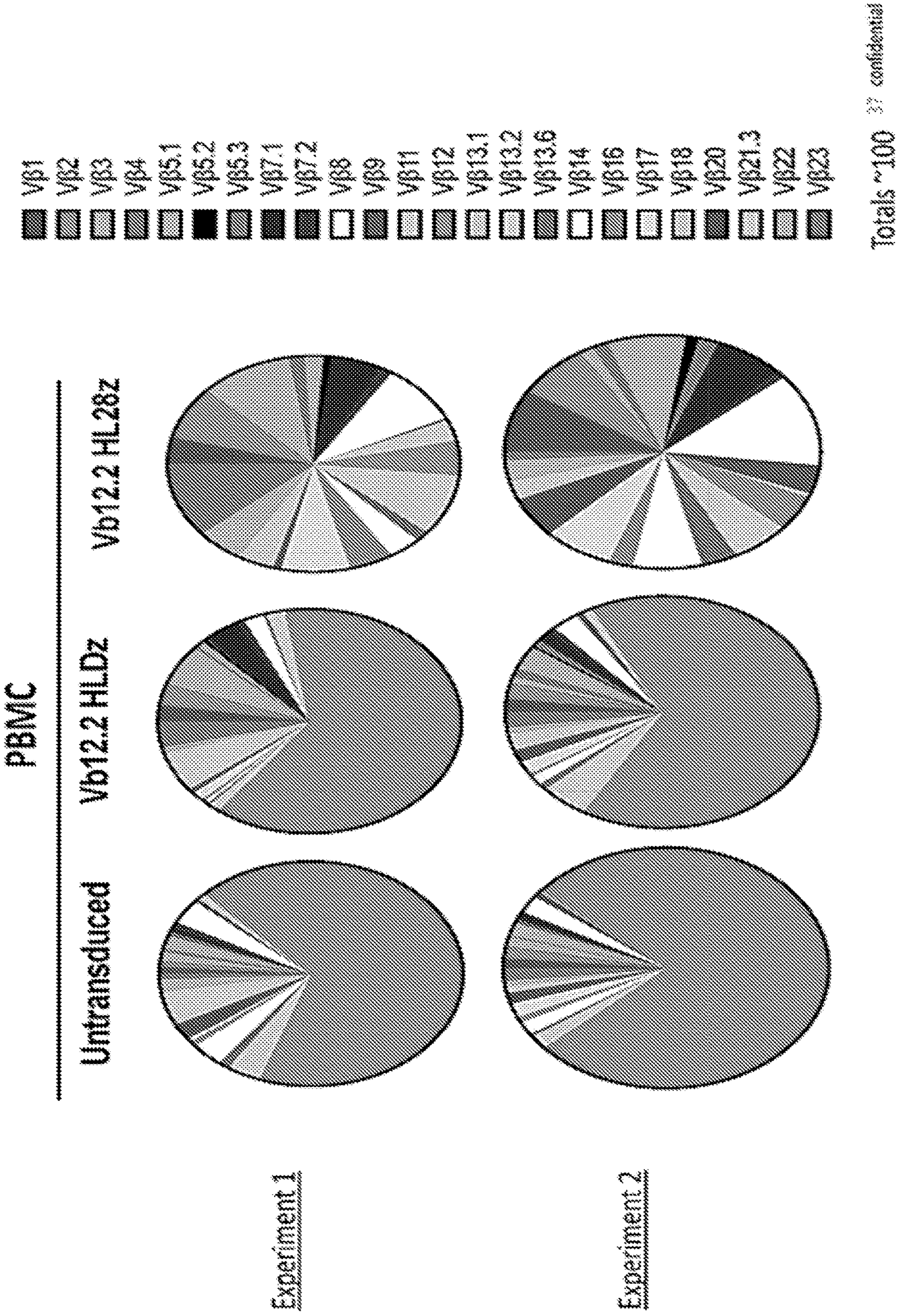

For a more clinically relevant model, PTCL patient PBMCs were obtained to use as targets. Patient-derived PBMCs were characterized by flow cytometry using the TO Test and the dominant clone that was identified in the clinic was confirmed (FIG. 16A). For lysis experiments, a flow cytometric setup with analysis combining cell-tracking dye and the TO Test was used. The TCRvβ repertoire of live PBMCs was measured after 24 hour co-culture with either untransduced cells, CAR T cells targeting TCRvβ12 without signaling domains, or CAR T cells targeting TCRvβ12 with signaling domains. CART cells were added at a 1:1 E:T ratio and the total number of T cells added was normalized based on transduction efficiency. A significant reduction in the TCRvβ12+ population was observed after co-culture with the functional CAR T cells (FIG. 16B).

Figure 17:
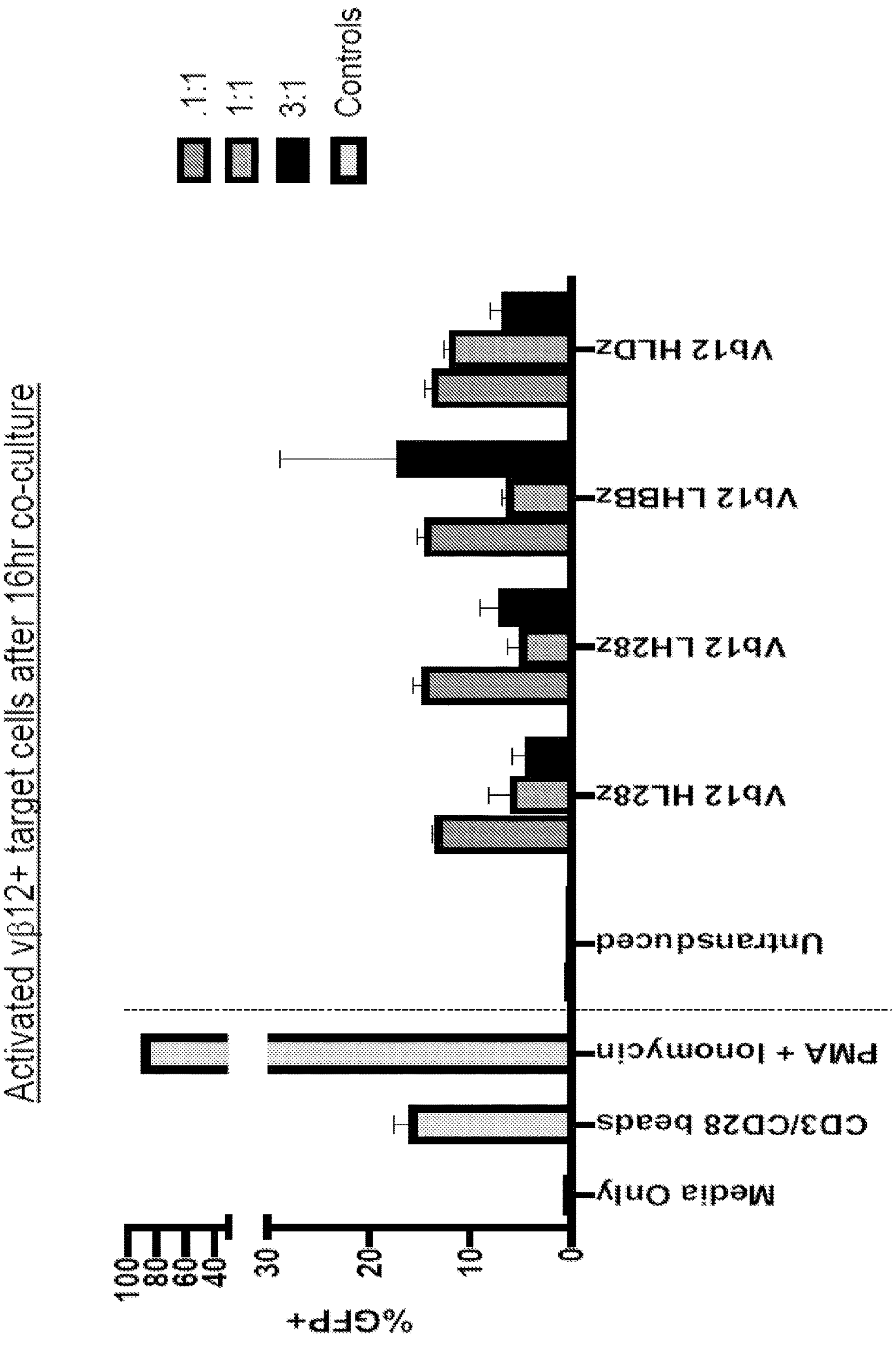
FIG. 17 shows the level of activation of SupT1 cells after co-culture with Vβ12-targeting CAR T cells. SupT1 cells were engineered to express both a Vβ12+ TCR and a reporter system in which GFP expression is induced after cells are activated via the TCR. As controls, SupT1s were incubated with either media, CD3/CD28 stimulating beads, or a cell stimulation cocktail containing PMA and ionomycin. Co-cultures were performed at three E:T ratios. After 20-hour co-culture with CAR T cells, a percentage of target cells were activated as indicated by % GFP+.

(d): Determining activation of target cells via TCR engagement. Targeting a component of the TCR risks activating the TCR pathway in target cells, which could result in proliferation of malignant cells or reciprocal killing of CAR T cells. To study this, a reporter system was used that capitalizes on the convergence of the TCR pathway to the nuclear factor of activated T cells (NFAT) family of transcription factors. SupT1 cells were transduced to constitutively express mCherry as a transduction marker and to induce expression of GFP when NFAT is shuttled to the nucleus downstream of TCR engagement. Co-culture experiments were set up as in ((Example 8 (c) and GFP was measured as an indication of TCR-mediated activation of the malignant cells. Stimulation with CD3/CD28 beads or a cocktail containing ionomycin and PMA, which activates the pathway downstream of the TCR, were used as a positive control for T cell activation mediated GFP upregulation in target cells. Some activation was seen in target cells when they were co-cultured with CAR T cells that engage their TCR (FIG. 17).

Figure 18:
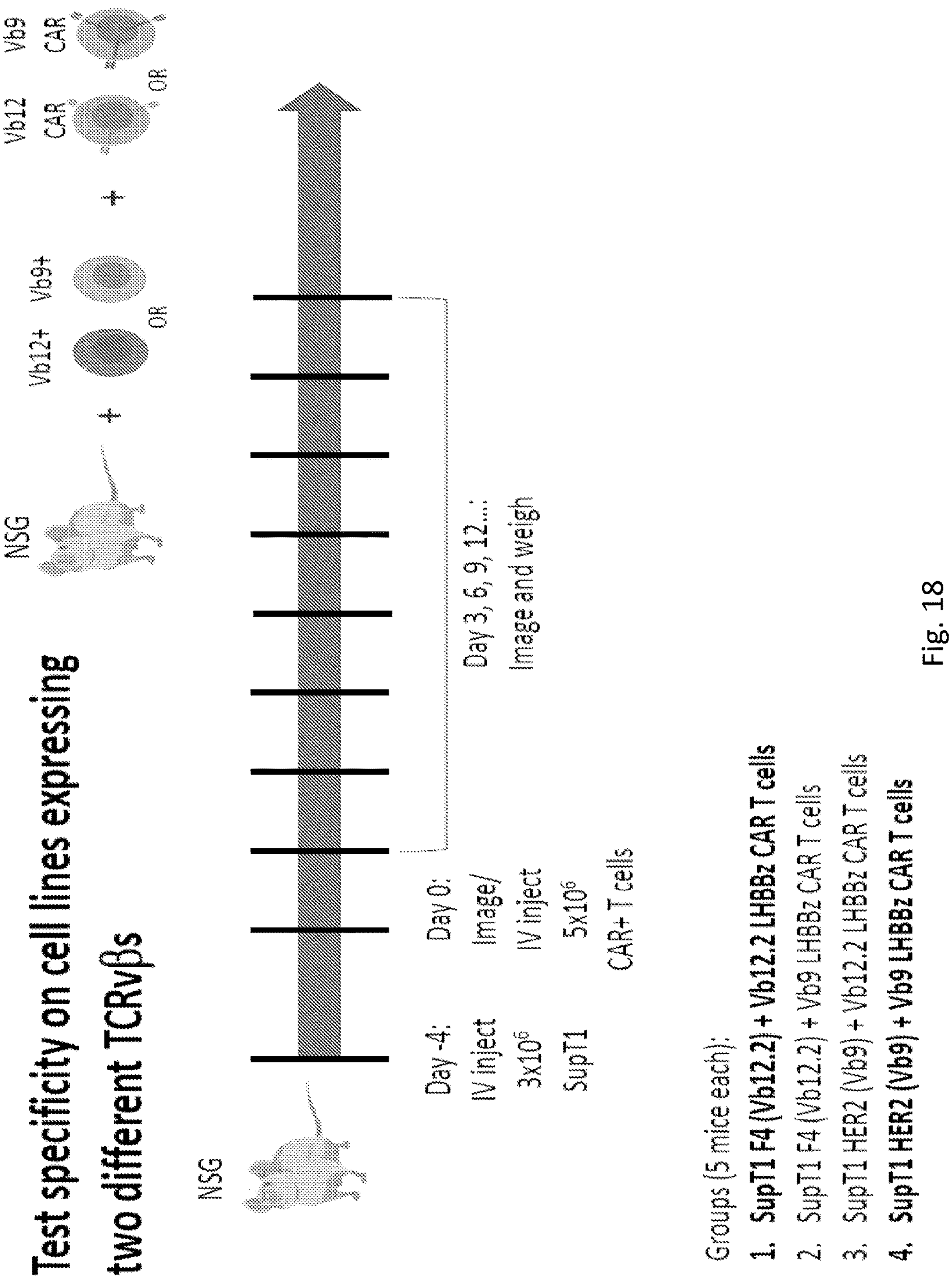
FIG. 18 illustrates the experimental set up of an in vivo experiment designed to test the specificity of the CAR T cells against cell lines expressing either Vβ12 or Vβ9. NOD/SCID IL2γc−/− (NSG) mice were intravenously injected with 3×106 SupT1 cells. After 4 days to allow for tumor establishment, 5×106 CAR+ T cells were intravenously injected into the mice. Tumor progression was monitored via bioluminescence imaging and weighing every 3 days. The treatment groups received either Vβ12+ SupT1s and Vβ12-targeting CAR T cells or Vβ9+ SupT1s and Vβ9-targeting CAR T cells. The control groups included mice received non-targeting CAR T cells.
Figure 19:
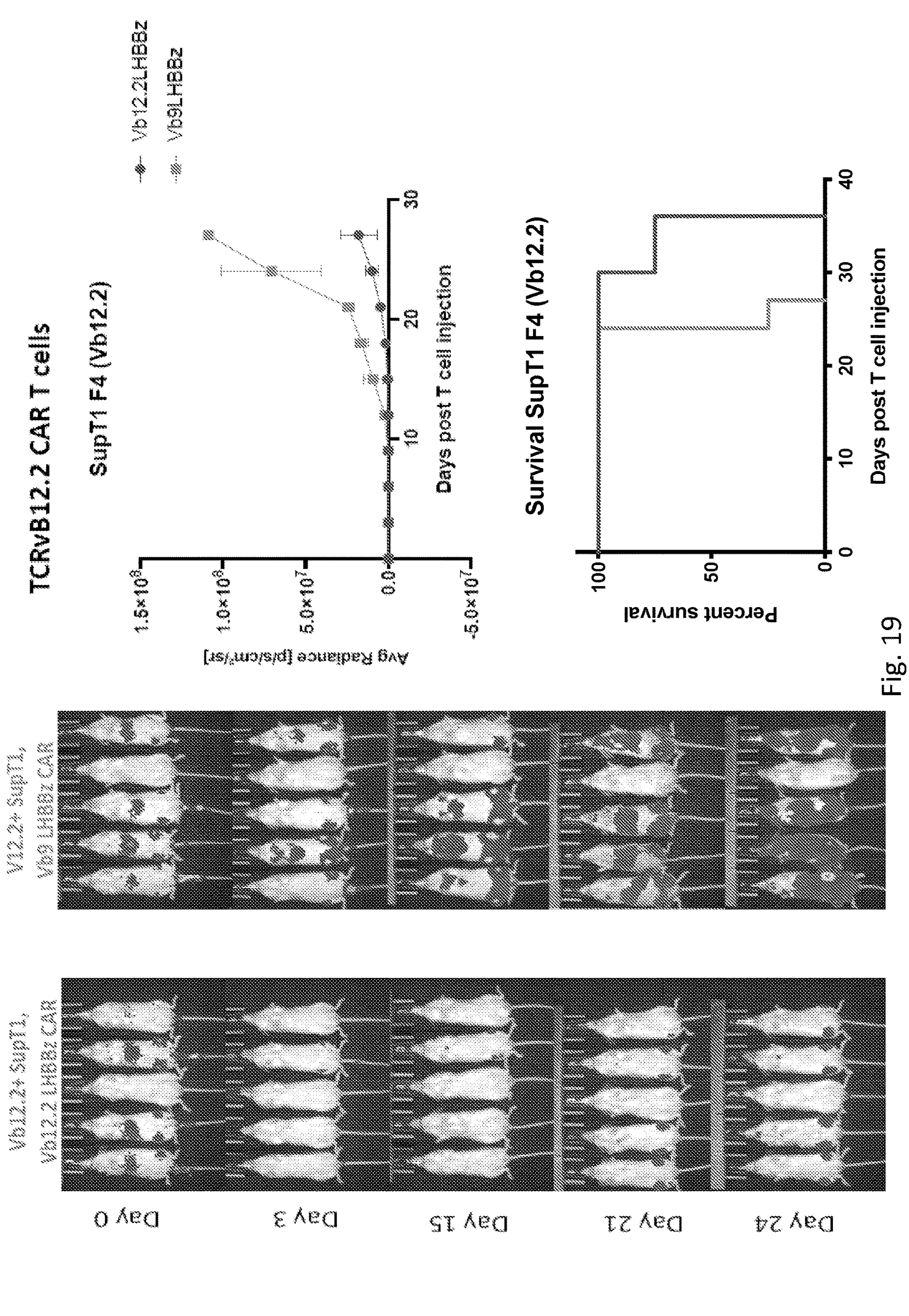
FIG. 19 shows data obtained from groups receiving Vβ12+ target cells. By day 3 after CAR T cell injection, tumor reduction was observed in the treatment group. The tumor burden remained lower in the treatment group for the remainder of the experiment and survival was significantly improved.
Figure 20:
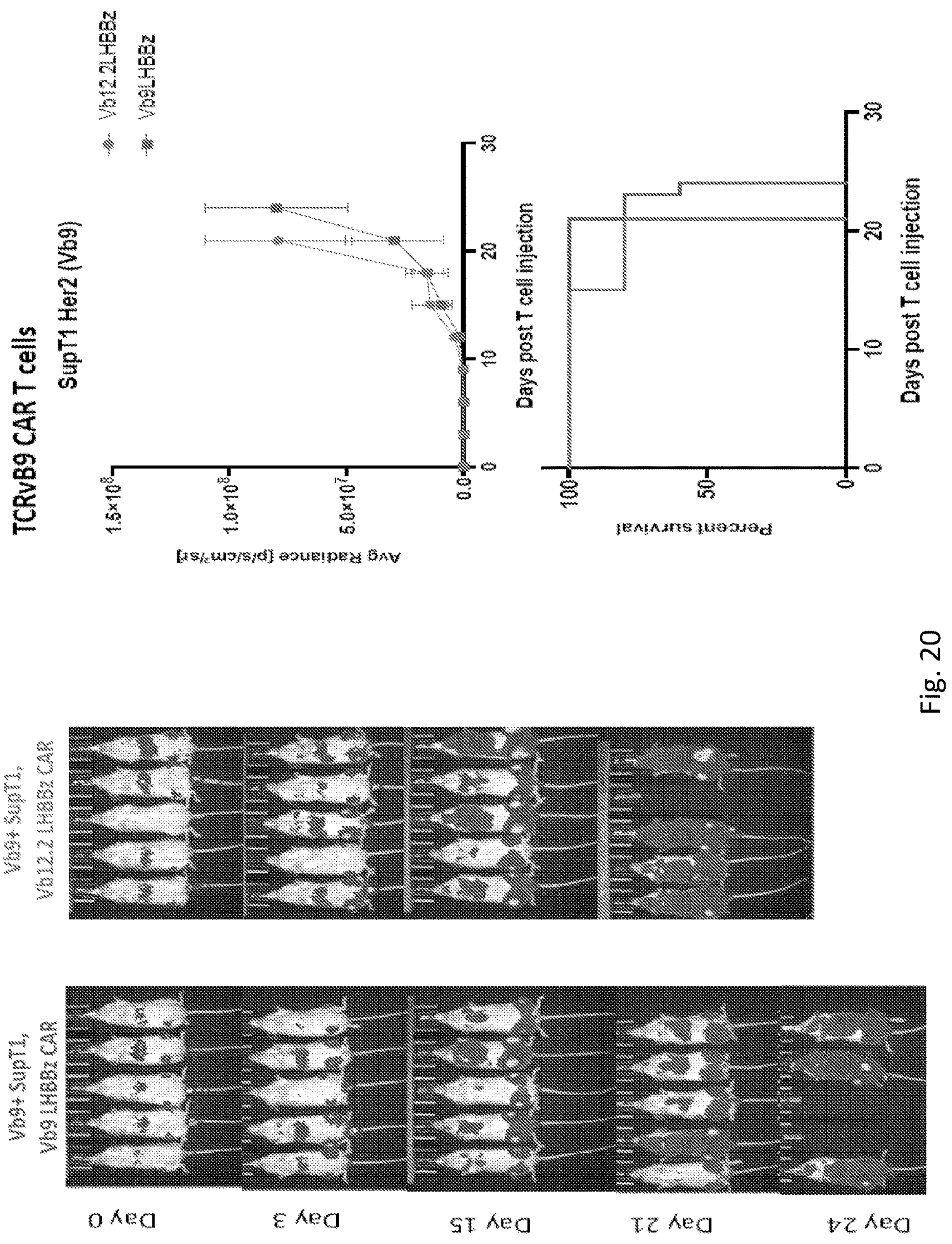
FIG. 20 shows data obtained from groups receiving Vβ9+ target cells. The treatment group had a minimal impact when compared to the non-treatment group, potentially due to the increased kinetics of tumor growth as compared to the Vβ12+ tumors.
Figure 22:
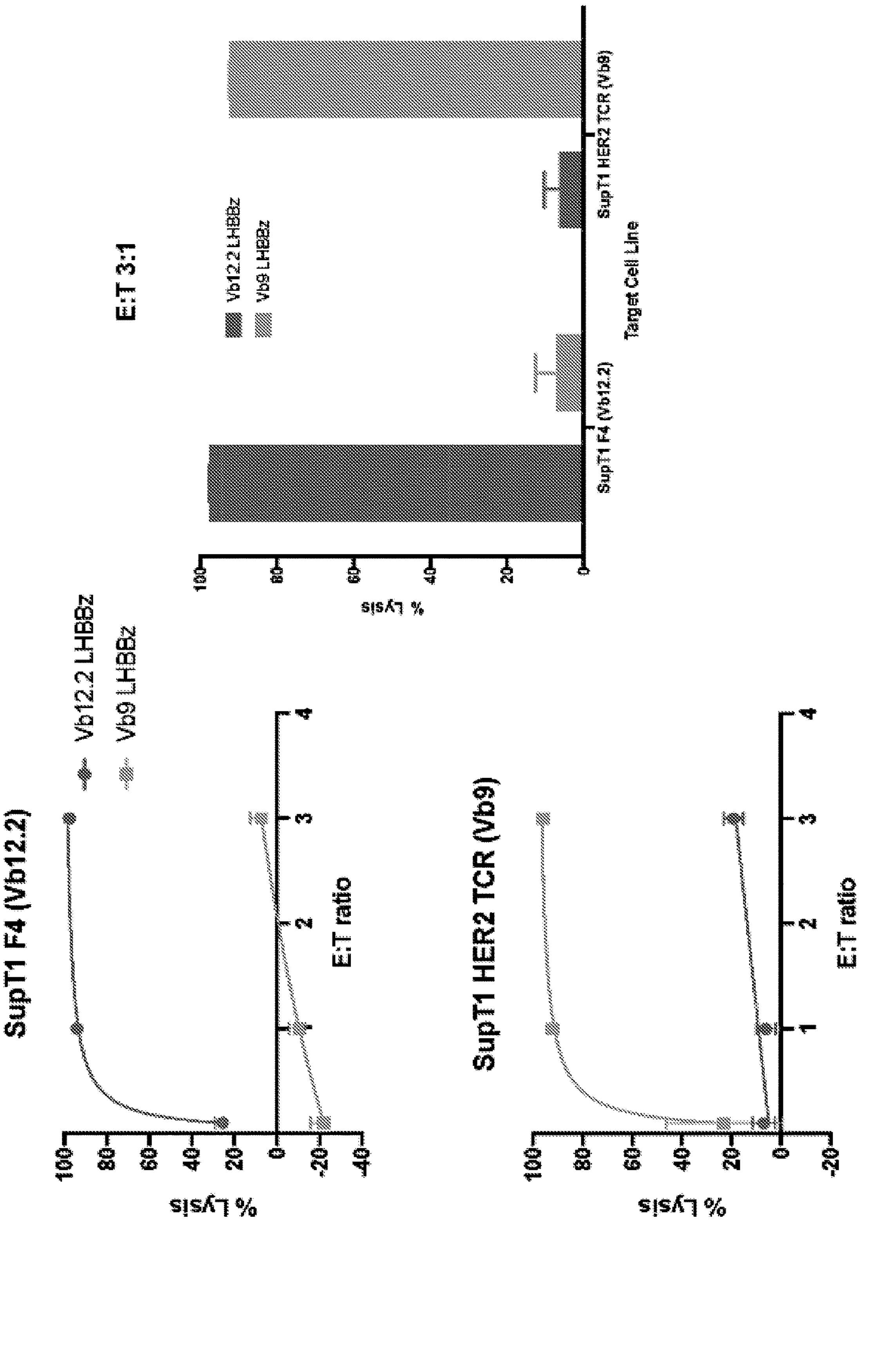
FIG. 22 shows the ability of cryopreserved Vβ12 and Vβ9 CAR transduced T cells to maintain antigen-specific functionality after thawing.
Figure 23:
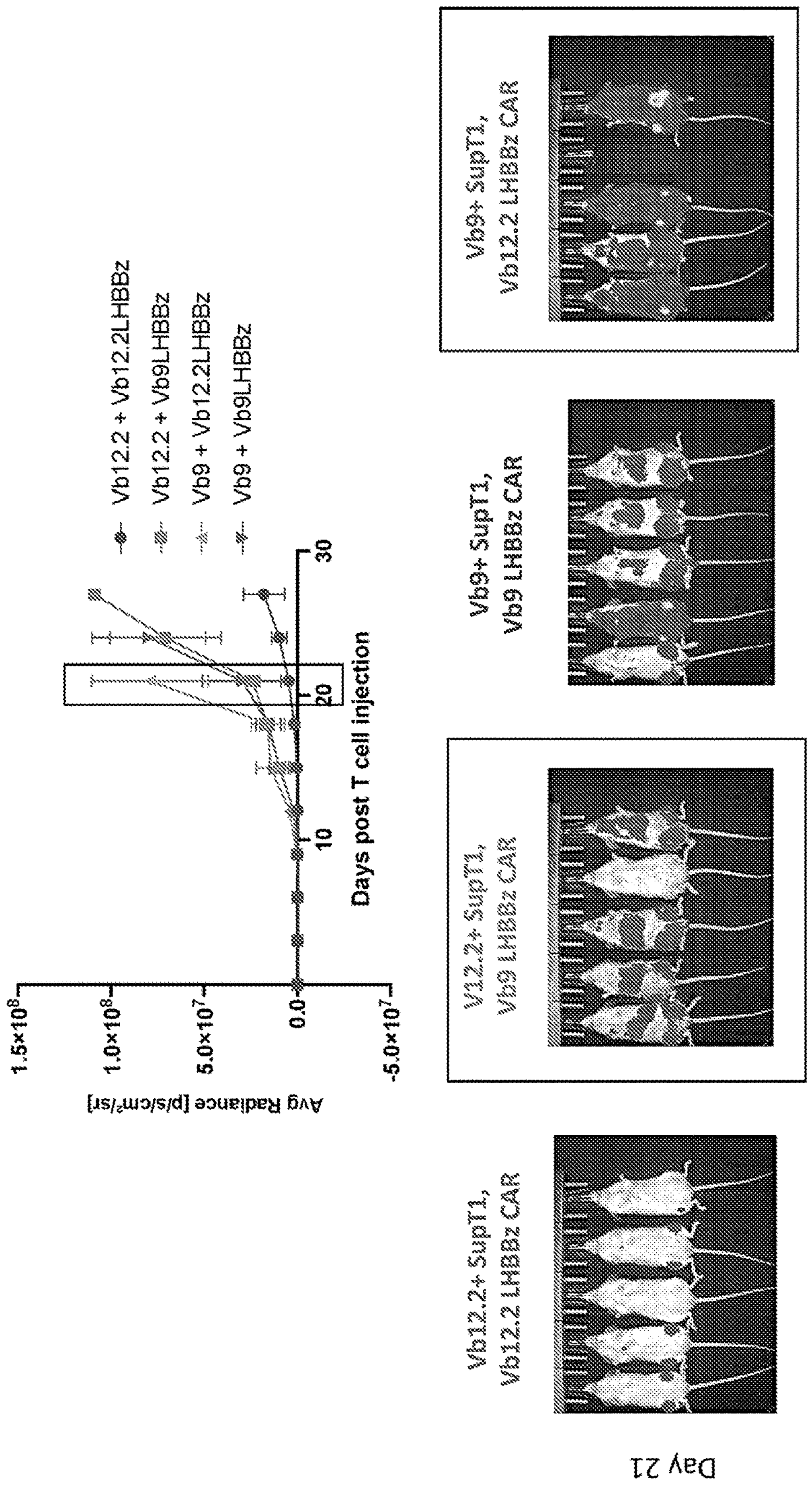
FIG. 23 shows data from FIGS. 18 and 19 overlaid for comparison.

(e): Testing specificity on cell lines expressing two TCRvβ families in vivo. The ability of expanded and cryopreserved CAR T cells was first assessed using in vitro lysis assays (FIG. 22). CART cells transduced with either TCRvβ12- or TCRvβ9-targeting CARs displayed robust target-specific cytotoxic function. T cell function and persistence were then assessed in vivo. NOD.Cg-Prkdc$^{scid}$ Il2rg$^{tm1Wjl}$/SzJ (NSG) mice were engrafted with tumor cells expressing either TCRvβ12 or TCRvβ9 and treated with CAR T cell therapy. The study was set up with 4 experimental groups of 5 mice each. These included (1) TCRvβ12+ tumor and TCRvβ12-targeting CAR T cells, (2) TCRvβ9+ tumor and TCRvβ9-targeting CAR T cells, (3) TCRvβ9+ tumor and TCRvβ12-targeting CAR T cells, and (4) TCRvβ12+ tumor and TCRvβ9-targeting CAR T cells (FIG. 18). SupT1 cells were injected IV and, following engraftment, CART cells were infused IV. Bioluminescence imaging was used to monitor tumor growth. Significant decrease in tumor burden and increased survival was observed in mice engrafted with a TCRvβ12+ tumor and treated with TCRvβ12-targeting CAR T cells (FIG. 19). A non-significant effect was observed in mice engrafted with a TCRvβ9+ tumor and treated with TCRvβ9-targeting CAR T cells (FIG. 20). Without wishing to be bound by theory, the reduced effect of CAR T cell treatment in these mice could be potentially due to the increased kinetics of tumor growth as compared to the Vβ12+ tumors, as illustrated by the overlay of the growth curves from these studies in FIG. 23.

Example 9: Use of a Universal Immune Receptor (UIR) System with TCRVβ CAR T Cell Therapy Universal immune receptor (UIR or UnivIR) systems are a rapidly emerging form of CAR T cell therapy. Like typical CAR T cell constructs, UIR receptors contain transmembrane and intracellular signaling domains adapted from other immune receptors. However instead of antibody-based antigen-binding extracellular domains, UIRs contain an extracellular binding domain that can be covalently or non-covalently bound to a complementary tag domain that can be engineered onto any number of ligand-binding molecules including but not limited to antibodies, antibody fragments, scFvs, protein scaffolds, and peptides among others. By decoupling antigen recognition and T-cell signaling, universal immune receptors can regulate T-cell effector function and target multiple antigens with a single receptor while also possessing the potential to overcome safety and antigen escape challenges faced by conventional chimeric antigen receptor (CAR) T-cell therapy.

Figure 24:
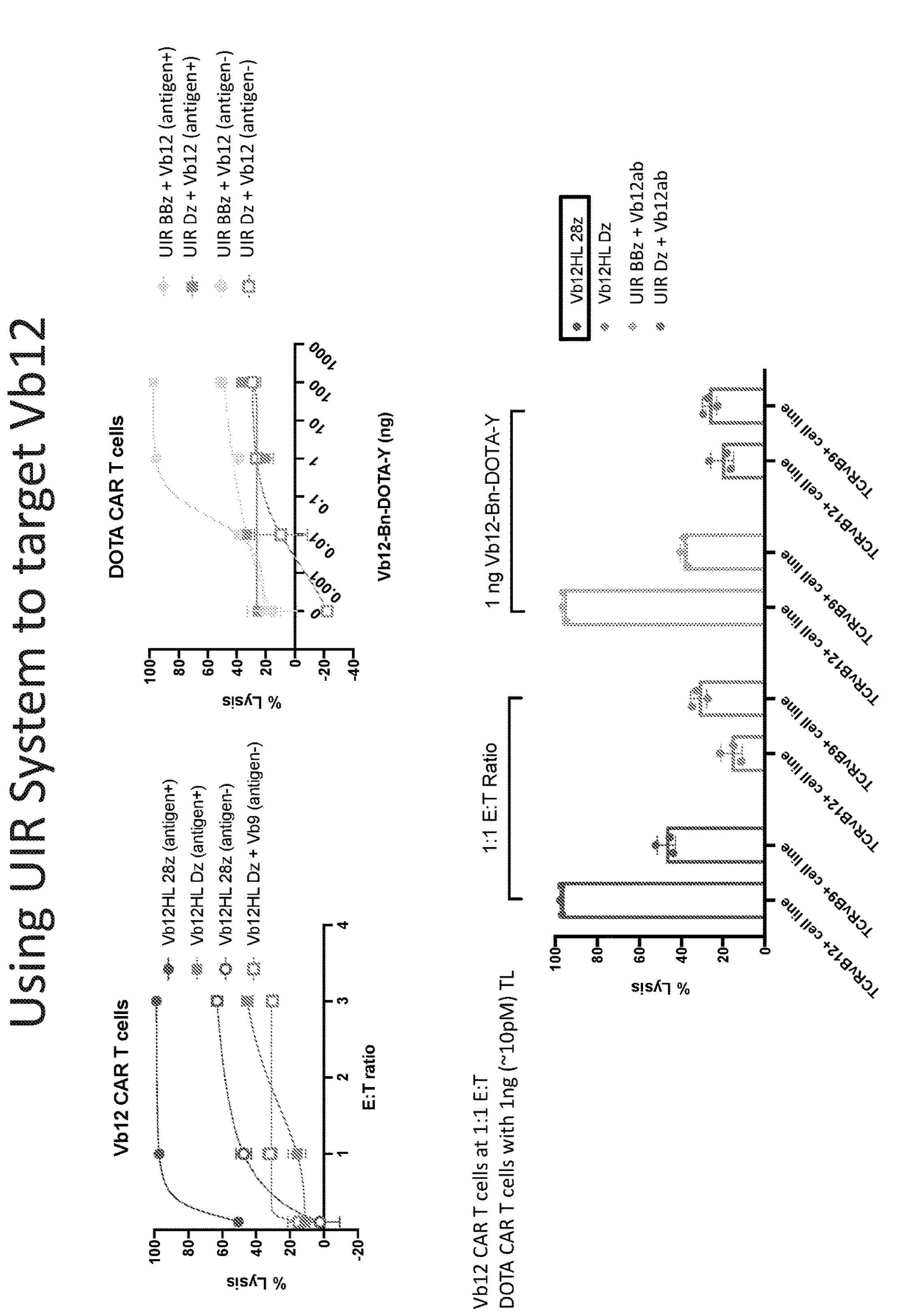
FIG. 24 shows a comparison of Vβ12 CAR T cells and universal immune receptor (UIR) expressing CAR T cells conjugated to tagged Vβ12 antibody. CAR T cells express receptors comprising either CD28/CD3 intracellular signaling domains (28z) or no intracellular signaling domains (Dz)
Figure 25:
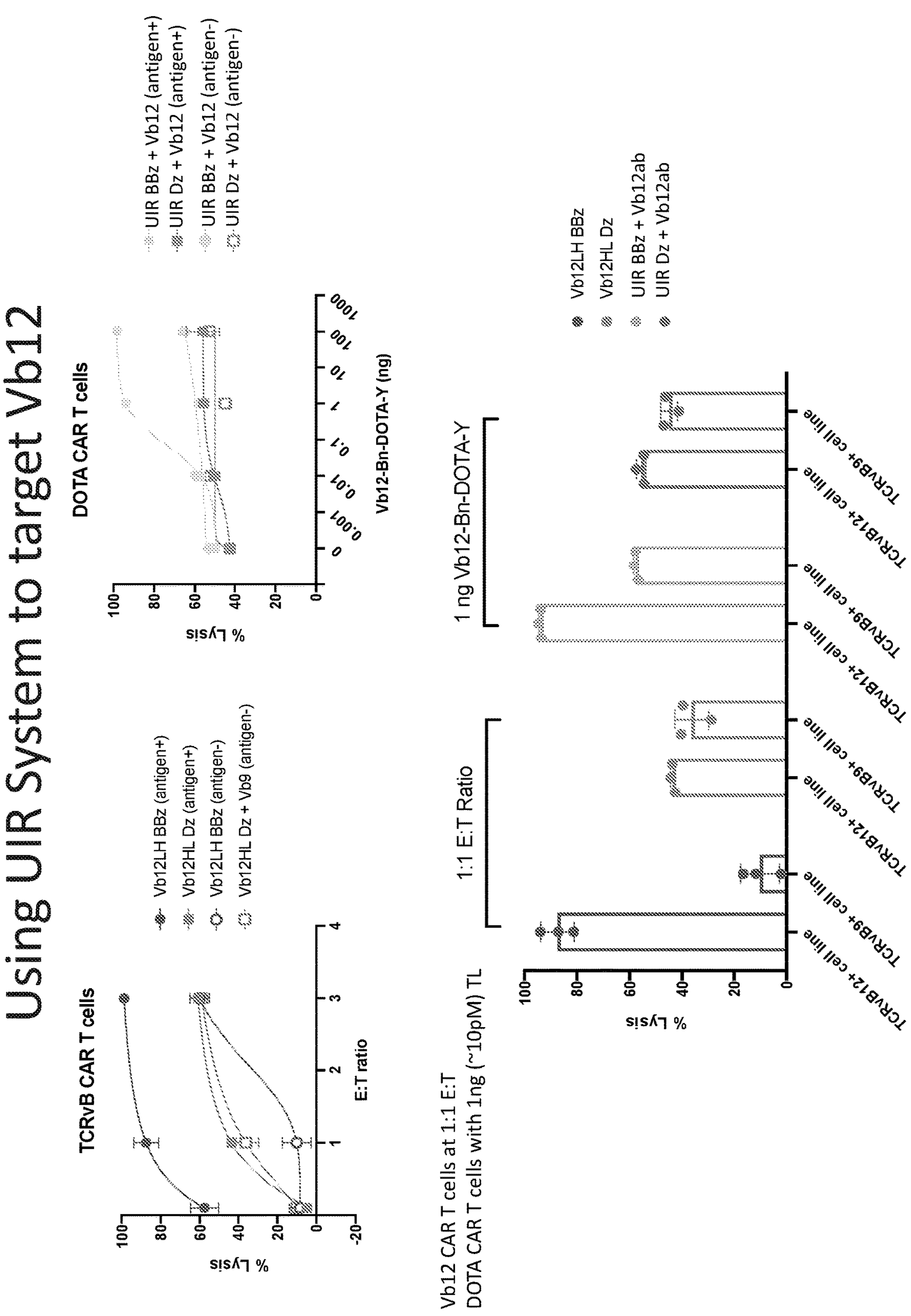
FIG. 25 shows a comparison of Vβ12 CART cells and universal immune receptor (UIR) expressing CAR T cells conjugated to tagged Vβ12 antibody. Both CAR T cells and UIR cells express CAR or UIR constructs comprising either 4-1BB/CD3ζ (BBz) intracellular signaling domains or lacking intracellular signaling domains.
Figure 26:
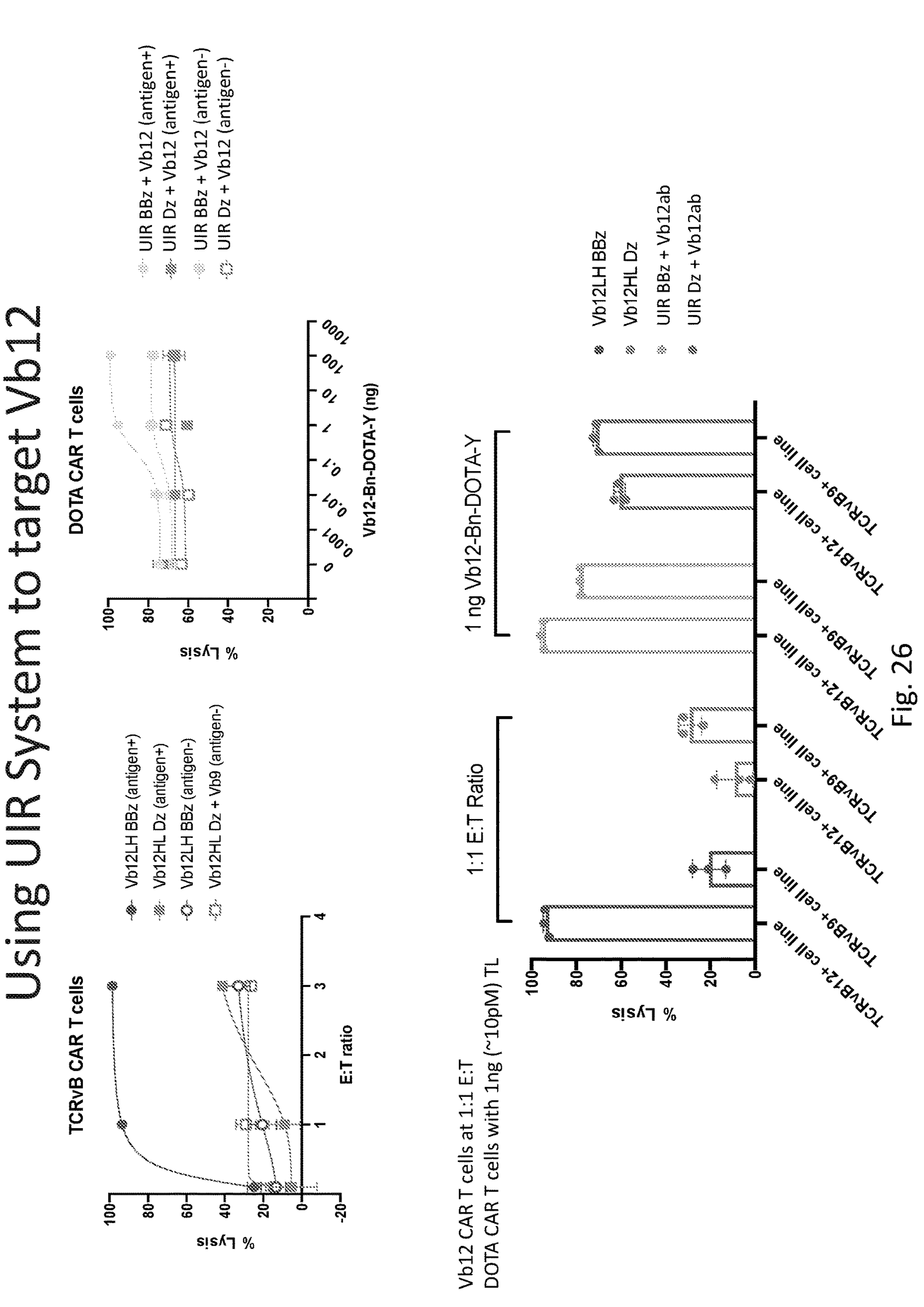
FIG. 26 shows a similar study to FIG. 25.

In vitro assays were conducted to demonstrate the effective function of UIR expressing T cells labeled with anti-Vβ12 antibody. Here, function of these cells as compared to anti-Vβ12 CAR expressing T cells described previously in the present disclosure. For these studies, anti-Vβ12 and anti-Vβ20 antibodies of the current invention were first conjugated with Y-DOTA (Orcutt et al., Nucl Med Biol 38, 223-233 (2011)). These antibodies were then used to label Vβ12-expressing target cells at various concentrations. T cells were then transduced to express UIR constructs comprising anti-DOTA scFv linked to hinge and transmembrane domains. These UIR constructs further comprised either CD28 and CD3 intracellular signaling domains (28z), 4-1BB and CD3ζ intracellular signaling domains (BBz), or, as a control, no intracellular signaling domains (Delta z or Dz). This DOTA-based labeling and UIR system is described in PCT/US2020/02957. In vitro cytotoxicity assays were then performed comparing UIR-expressing CAR T cells incubated with anti-Vβ12-Y-DOTA labeled target cells with Vβ12 CAR T cells expressing either Vβ12HL 28z or Vβ12HL Dz CAR constructs incubated with Vβ12 expressing target cells (FIG. 24). These studies demonstrated equivalent cytotoxic abilities between the two types of CAR T cells. Follow-up studies were then conducted comparing UIR-expressing CAR T cells with Vβ12LH and Vβ12HL CAR T cells expressing BBz intracellular signaling domains (FIG. 25 and FIG. 26). These studies also demonstrated the ability of UIR CAR T cells to lyse target cells. Without wishing to be bound by theory, these data demonstrate the ability of the Vβ-directed antibodies and scFv of the present disclosure to be combined with DOTA-based UIR systems to achieve TCRVβ-targeted immunotherapy.

Sequences of CARs generated herein:

Vb12HL-28z (SEQ ID NO: 1)

```
atggccttaccagtgaccgccttgctcctgccgctggccttgctgctccacgccgccaggccgg

GATCCGAAGTGATGCTGGTGGAATCTGGCGGCGGACTGGTTAAGCCTGGCGGATCTCTGAAGCT

GAGCTGTGCCGCCAGCGGCTTCACCTTTAGAAGCTACGCCATGAGCTGGGTCCGACAGACCCCT
```

-continued

GAGAAGAGACTGGAATGGGTCGCCACAATCAGCAGCGGCGGCAGCTACACAAACTACCCCGATA
GCGTGAAGGGCAGATTCACCATCAGCCGGGACAACGCCAAGAACACCCTGAACCTGCAGATGAA
CAGCCTGCGGAGCGAGGACACCGCCATGTACTATTGTGCCAGAGGCTACCACGGCTACCTGGAT
GTTTGGGGAGCCGGCACAACCGTGACAGTTTCTTCTGGTGGCGGAGGATCTGGCGGAGGTGGAA
GCGGCGGAGGCGGATCTGATATTCTGCTGACTCAGAGCCCCGCCTTCCTGTCTGTTTCTCCTGG
CGAGAGAGTGTCCTTCAGCTGCAGAGCCTCTCAGAGCATCGGCACCTCCATCCACTGGTATCAG
CAGAGGACCAACGGCAGCCCCAGACTGCTGATTAAGTACGCCAGCGAGAGCTTCAGCGGCATCC
CCAGCAGATTTTCTGGCTCTGGCAGCGGCACCGACTTCACCCTGTCTATCAGCTCCGTGGAAAG
CGAGGATATCGCCGACTACTACTGCCAGCAGTCCTACAGCTGGCCCTACACATTTGGCGGAGGC
ACCAAGCTGGAAATCAAGGctagcaccacgacgccagcgccgcgaccaccaacaccggcgccca
ccatcgcgtcgcagcccctgtccctgcgcccagaggcgtgccggccagcggcggggggcgcagt
gcacacgagggggctggacttcgcctgtgatttttgggtgctggtggtggttggtggagtcctg
gcttgctatagcttgctagtaacagtggcctttattattttctgggtgaggagtaagaggagca
ggctcctgcacagtgactacatgaacatgactccccgccgccccgggcccacccgcaagcatta
ccagccctatgccccaccacgcgacttcgcagcctatcgctccatcgatagagtgaagttcagc
aggagcgcagacgcccccgcgtaccagcagggccagaaccagctctataacgagctcaatctag
gacgaagagaggagtacgatgttttggacaagagacgtggccgggaccctgagatggggggaaa
gccgagaaggaagaaccctcaggaaggcctgtacaatgaactgcagaaagataagatggcggag
gcctacagtgagattgggatgaaaggcgagcgccggaggggcaaggggcacgatggcctttacc
agggtctcagtacagccaccaaggacacctacgacgcccttcacatgcaggccctgccccctcg
ctaa Vb12HL-BBz (SEQ ID NO: 2)

atggccttaccagtgaccgccttgctcctgccgctggccttgctgctccacgccgccaggccgg
GATCCGAAGTGATGCTGGTGGAATCTGGCGGCGGACTGGTTAAGCCTGGCGGATCTCTGAAGCT
GAGCTGTGCCGCCAGCGGCTTCACCTTTAGAAGCTACGCCATGAGCTGGGTCCGACAGACCCCT
GAGAAGAGACTGGAATGGGTCGCCACAATCAGCAGCGGCGGCAGCTACACAAACTACCCCGATA
GCGTGAAGGGCAGATTCACCATCAGCCGGGACAACGCCAAGAACACCCTGAACCTGCAGATGAA
CAGCCTGCGGAGCGAGGACACCGCCATGTACTATTGTGCCAGAGGCTACCACGGCTACCTGGAT
GTTTGGGGAGCCGGCACAACCGTGACAGTTTCTTCTGGTGGCGGAGGATCTGGCGGAGGTGGAA
GCGGCGGAGGCGGATCTGATATTCTGCTGACTCAGAGCCCCGCCTTCCTGTCTGTTTCTCCTGG
CGAGAGAGTGTCCTTCAGCTGCAGAGCCTCTCAGAGCATCGGCACCTCCATCCACTGGTATCAG
CAGAGGACCAACGGCAGCCCCAGACTGCTGATTAAGTACGCCAGCGAGAGCTTCAGCGGCATCC
CCAGCAGATTTTCTGGCTCTGGCAGCGGCACCGACTTCACCCTGTCTATCAGCTCCGTGGAAAG
CGAGGATATCGCCGACTACTACTGCCAGCAGTCCTACAGCTGGCCCTACACATTTGGCGGAGGC
ACCAAGCTGGAAATCAAGGctagcaccacgacgccagcgccgcgaccaccaacaccggcgccca
ccatcgcgtcgcagcccctgtccctgcgcccagaggcgtgccggccagcggcggggggcgcagt
gcacacgagggggctggacttcgcctgtgatatctacatctgggcgcccttggccgggacttgt
ggggtccttctcctgtcactggttatcaccctttactgcaaacggggcagaaagaaactcctgt
atatattcaaacaaccatttatgagaccagtacaaactactcaagaggaagatggctgtagctg
ccgatttccagaagaagaagaaggaggatgtgaactgagagtgaagttcagcaggagcgcagac -continued gcccccgcgtacaagcagggccagaaccagctctataacgagctcaatctaggacgaagagagg agtacgatgttttggacaagagacgtggccgggaccctgagatggggggaaagccgagaaggaa gaaccctcaggaaggcctgtacaatgaactgcagaaagataagatggcggaggcctacagtgag attgggatgaaaggcgagcgccggaggggcaaggggcacgatggcctttaccagggtctcagta cagccaccaaggacacctacgacgcccttcacatgcaggccctgccccctcgctaa Vb12HL-Dz (SEQ ID NO: 3)

atggccttaccagtgaccgccttgctcctgccgctggccttgctgctccacgccgccaggccgg

GATCCGAAGTGATGCTGGTGGAATCTGGCGGCGGACTGGTTAAGCCTGGCGGATCTCTGAAGCT

GAGCTGTGCCGCCAGCGGCTTCACCTTTAGAAGCTACGCCATGAGCTGGGTCCGACAGACCCCT

GAGAAGAGACTGGAATGGGTCGCCACAATCAGCAGCGGCGGCAGCTACACAAACTACCCCGATA

GCGTGAAGGGCAGATTCACCATCAGCCGGGACAACGCCAAGAACACCCTGAACCTGCAGATGAA

CAGCCTGCGGAGCGAGGACACCGCCATGTACTATTGTGCCAGAGGCTACCACGGCTACCTGGAT

GTTTGGGGAGCCGGCACAACCGTGACAGTTTCTTCTGGTGGCGGAGGATCTGGCGGAGGTGGAA

GCGGCGGAGGCGGATCTGATATTCTGCTGACTCAGAGCCCCGCCTTCCTGTCTGTTTCTCCTGG

CGAGAGAGTGTCCTTCAGCTGCAGAGCCTCTCAGAGCATCGGCACCTCCATCCACTGGTATCAG

CAGAGGACCAACGGCAGCCCCAGACTGCTGATTAAGTACGCCAGCGAGAGCTTCAGCGGCATCC

CCAGCAGATTTTCTGGCTCTGGCAGCGGCACCGACTTCACCCTGTCTATCAGCTCCGTGGAAAG

CGAGGATATCGCCGACTACTACTGCCAGCAGTCCTACAGCTGGCCCTACACATTTGGCGGAGGC

ACCAAGCTGGAAATCAAGGctagcaccacgacgccagcgccgcgaccaccaacaccggcgccca ccatcgcgtcgcagcccctgtccctgcgcccagaggcgtgccggccagcggcggggggcgcagt gcacacgagggggctggacttcgcctgtgatttttgggtgctggtggtggttggtggagtcctg gcttgctatagcttgctagtaacagtggcctttattattttctgggtgaggagtaagaggagct aa Vb12LH-28z (SEQ ID NO: 4)

atggccttaccagtgaccgccttgctcctgccgctggccttgctgctccacgccgccaggccgg

GATCCGACATCCTGCTGACTCAGAGCCCTGCCTTCCTGTCTGTGTCTCCTGGCGAGAGAGTGTC

CTTCAGCTGTAGAGCCAGCCAGAGCATCGGCACCAGCATCCACTGGTATCAGCAGCGGACAAAC

GGCAGCCCCAGACTGCTGATTAAGTACGCCAGCGAGAGCTTCAGCGGCATCCCCAGCAGATTTT

CTGGCAGCGGCTCTGGCACCGACTTCACCCTGTCTATCAGCTCCGTGGAAAGCGAGGATATCGC

CGACTACTACTGCCAGCAGTCCTACAGCTGGCCCTACACATTTGGCGGAGGCACCAAGCTGGAA

ATCAAAGGCGGCGGAGGAAGCGGAGGCGGAGGATCTGGTGGTGGTGGATCTGAAGTGATGCTGG

TCGAGTCTGGCGGCGGACTTGTGAAACCTGGCGGAAGCCTGAAGCTGAGCTGTGCCGCTTCCGG

CTTCACCTTTAGAAGCTACGCCATGAGCTGGGTCCGACAGACCCCTGAGAAGAGACTGGAATGG

GTCGCCACCATCTCTAGCGGCGGCAGCTACACAAACTACCCCGACTCTGTGAAGGGCAGATTCA

CCATCAGCCGGGACAACGCCAAGAACACCCTGAACCTGCAGATGAACAGCCTGCGGAGCGAGGA

CACCGCCATGTACTATTGTGCCAGAGGCTACCACGGCTACCTGGATGTTTGGGGAGCCGGCACA

ACCGTGACAGTGTCATCTGCtagcaccacgacgccagcgccgcgaccaccaacaccggcgccca ccatcgcgtcgcagcccctgtccctgcgcccagaggcgtgccggccagcggcggggggcgcagt gcacacgagggggctggacttcgcctgtgatttttgggtgctggtggtggttggtggagtcctg gcttgctatagcttgctagtaacagtggcctttattattttctgggtgaggagtaagaggagca ggctcctgcacagtgactacatgaacatgactccccgccgccccgggcccacccgcaagcatta -continued ccagccctatgccccaccacgcgacttcgcagcctatcgctccatcgatagagtgaagttcagc
aggagcgcagacgcccccgcgtaccagcagggccagaaccagctctataacgagctcaatctag
gacgaagagaggagtacgatgttttggacaagagacgtggccgggaccctgagatggggggaaa
gccgagaaggaagaaccctcaggaaggcctgtacaatgaactgcagaaagataagatggcggag
gcctacagtgagattgggatgaaaggcgagcgccggaggggcaaggggcacgatggcctttacc
agggtctcagtacagccaccaaggacacctacgacgcccttcacatgcaggccctgccccctcg
ctaa Vb12LH-BBz (SEQ ID NO: 5)

atggccttaccagtgaccgccttgctcctgccgctggccttgctgctccacgccgccaggccgg
GATCCGACATCCTGCTGACTCAGAGCCCTGCCTTCCTGTCTGTGTCTCCTGGCGAGAGAGTGTC
CTTCAGCTGTAGAGCCAGCCAGAGCATCGGCACCAGCATCCACTGGTATCAGCAGCGGACAAAC
GGCAGCCCCAGACTGCTGATTAAGTACGCCAGCGAGAGCTTCAGCGGCATCCCCAGCAGATTTT
CTGGCAGCGGCTCTGGCACCGACTTCACCCTGTCTATCAGCTCCGTGGAAAGCGAGGATATCGC
CGACTACTACTGCCAGCAGTCCTACAGCTGGCCCTACACATTTGGCGGAGGCACCAAGCTGGAA
ATCAAAGGCGGCGGAGGAAGCGGAGGCGGAGGATCTGGTGGTGGTGGATCTGAAGTGATGCTGG
TCGAGTCTGGCGGCGGACTTGTGAAACCTGGCGGAAGCCTGAAGCTGAGCTGTGCCGCTTCCGG
CTTCACCTTTAGAAGCTACGCCATGAGCTGGGTCCGACAGACCCCTGAGAAGAGACTGGAATGG
GTCGCCACCATCTCTAGCGGCGGCAGCTACACAAACTACCCCGACTCTGTGAAGGGCAGATTCA
CCATCAGCCGGGACAACGCCAAGAACACCCTGAACCTGCAGATGAACAGCCTGCGGAGCGAGGA
CACCGCCATGTACTATTGTGCCAGAGGCTACCACGGCTACCTGGATGTTTGGGGAGCCGGCACA
ACCGTGACAGTGTCATCTGctagcaccacgacgccagcgccgcgaccaccaacaccggcgccca
ccatcgcgtcgcagcccctgtccctgcgcccagaggcgtgccggccagcggcggggggcgcagt
gcacacgagggggctggacttcgcctgtgatatctacatctgggcgcccttggccgggacttgt
ggggtccttctcctgtcactggttatcaccctttactgcaaacggggcagaaagaaactcctgt
atatattcaaacaaccatttatgagaccagtacaaactactcaagaggaagatggctgtagctg
ccgatttccagaagaagaagaaggaggatgtgaactgagagtgaagttcagcaggagcgcagac
gcccccgcgtacaagcagggccagaaccagctctataacgagctcaatctaggacgaagagagg
agtacgatgttttggacaagagacgtggccgggaccctgagatggggggaaagccgagaaggaa
gaaccctcaggaaggcctgtacaatgaactgcagaaagataagatggcggaggcctacagtgag
attgggatgaaaggcgagcgccggaggggcaaggggcacgatggcctttaccagggtctcagta
cagccaccaaggacacctacgacgcccttcacatgcaggccctgccccctcgctaa Vb12LH-Dz (SEQ ID NO: 6)

atggccttaccagtgaccgccttgctcctgccgctggccttgctgctccacgccgccaggccgg
GATCCGACATCCTGCTGACTCAGAGCCCTGCCTTCCTGTCTGTGTCTCCTGGCGAGAGAGTGTC
CTTCAGCTGTAGAGCCAGCCAGAGCATCGGCACCAGCATCCACTGGTATCAGCAGCGGACAAAC
GGCAGCCCCAGACTGCTGATTAAGTACGCCAGCGAGAGCTTCAGCGGCATCCCCAGCAGATTTT
CTGGCAGCGGCTCTGGCACCGACTTCACCCTGTCTATCAGCTCCGTGGAAAGCGAGGATATCGC
CGACTACTACTGCCAGCAGTCCTACAGCTGGCCCTACACATTTGGCGGAGGCACCAAGCTGGAA
ATCAAAGGCGGCGGAGGAAGCGGAGGCGGAGGATCTGGTGGTGGTGGATCTGAAGTGATGCTGG
TCGAGTCTGGCGGCGGACTTGTGAAACCTGGCGGAAGCCTGAAGCTGAGCTGTGCCGCTTCCGG -continued CTTCACCTTTAGAAGCTACGCCATGAGCTGGGTCCGACAGACCCCTGAGAAGAGACTGGAATGG
GTCGCCACCATCTCTAGCGGCGGCAGCTACACAAACTACCCCGACTCTGTGAAGGGCAGATTCA
CCATCAGCCGGGACAACGCCAAGAACACCCTGAACCTGCAGATGAACAGCCTGCGGAGCGAGGA
CACCGCCATGTACTATTGTGCCAGAGGCTACCACGGCTACCTGGATGTTTGGGGAGCCGGCACA
ACCGTGACAGTGTCATCTGctagcaccacgacgccagcgccgcgaccaccaacaccggcgccca
ccatcgcgtcgcagcccctgtccctgcgcccagaggcgtgccggccagcggcggggggcgcagt
gcacacgagggggctggacttcgcctgtgatttttgggtgctggtggtggttggtggagtcctg
gcttgctatagcttgctagtaacagtggcctttattattttctgggtgaggagtaagaggagct
aa Vb9HL-28z (SEQ ID NO: 7)

atggccttaccagtgaccgccttgctcctgccgctggccttgctgctccacgccgccaggccgg
GATCCATGAAGTTCAGCTGGGTCATCTTCTTTCTGATGGCCGTGGTCACCGGCGTGAACTCTGA
AGTGCAACTGCAGCAGAGCGTGGCCGAACTCGTTAGACCTGGCGCCTCTGTGAAGCTGAGCTGT
ACCGCCAGCGGCTTCAACATCAAGAACACCTTCATGCACTGGGTCAAGCAGCGGCCTGAGCAGG
GACTCGAGTGGATCGGAAGAATCGACCCCACCAACGGCTACACCAAGTTCGCCCCTAAGTTCCA
GGGCAAAGCCACACTGACAGCCGTGACCAGCAGCAACACAGTGTACCTGCAGCTGAGCAGCCTG
ACCTCTGAGGACACCGCCATCTACTACTGCGCCCACGATTACGACGCCCCTTGGTTTGCCTATT
GGGGCCAGGGCACACTGGTCATTGTGTCTGCTGGTGGCGGAGGATCTGGCGGAGGTGGAAGCGG
CGGAGGCGGATCTATGCTTTCTCCTGCTCCTCTGCTGAGCCTGCTGCTGCTGTGCGTGTCAGAT
AGCAGAGCCGAGACAACCGTGACACAGTCTCCAGCCAGTCTGTCTGTGGCCACCGGCGAGAAAG
TGACCATCAGATGCATCAGCAGCACCGACATCGACGACGACATGAACTGGTATCAGCAGAAGTC
CGGCGAGCCTCCTAAGCTGCTGATCTCCGAGGGCAATACTCTGAGGCCTGGCGTGCCAAGCAGA
TTCAGCAGCTCTGGCTACGGCACCGACTTCGTGTTCACCATCGAGAACATGCTGAGCGAGGACG
TGGCCGATTACTACTGCCTGCAGAGCGACAACATGCCCCTGACATTTGGAGCCGGCACCAAGCT
GGAACTGAAGGctagcaccacgacgccagcgccgcgaccaccaacaccggcgcccaccatcgcg
tcgcagcccctgtccctgcgcccagaggcgtgccggccagcggcggggggcgcagtgcacacga
gggggctggacttcgcctgtgatttttgggtgctggtggtggttggtggagtcctggcttgcta
tagcttgctagtaacagtggcctttattattttctgggtgaggagtaagaggagcaggctcctg
cacagtgactacatgaacatgactccccgccgccccgggcccacccgcaagcattaccagccct
atgccccaccacgcgacttcgcagcctatcgctccatcgatagagtgaagttcagcaggagcgc
agacgcccccgcgtaccagcagggccagaaccagctctataacgagctcaatctaggacgaaga
gaggagtacgatgttttggacaagagacgtggccgggaccctgagatggggggaaagccgagaa
ggaagaaccctcaggaaggcctgtacaatgaactgcagaaagataagatggcggaggcctacag
tgagattgggatgaaaggcgagcgccggaggggcaaggggcacgatggcctttaccagggtctc
agtacagccaccaaggacacctacgacgcccttcacatgcaggccctgccccctcgctaa Vb9HL-BBz (SEQ ID NO: 8)

atggccttaccagtgaccgccttgctcctgccgctggccttgctgctccacgccgccaggccgg
GATCCATGAAGTTCAGCTGGGTCATCTTCTTTCTGATGGCCGTGGTCACCGGCGTGAACTCTGA
AGTGCAACTGCAGCAGAGCGTGGCCGAACTCGTTAGACCTGGCGCCTCTGTGAAGCTGAGCTGT
ACCGCCAGCGGCTTCAACATCAAGAACACCTTCATGCACTGGGTCAAGCAGCGGCCTGAGCAGG
GACTCGAGTGGATCGGAAGAATCGACCCCACCAACGGCTACACCAAGTTCGCCCCTAAGTTCCA -continued

GGGCAAAGCCACACTGACAGCCGTGACCAGCAGCAACACAGTGTACCTGCAGCTGAGCAGCCTG

ACCTCTGAGGACACCGCCATCTACTACTGCGCCCACGATTACGACGCCCCTTGGTTTGCCTATT

GGGGCCAGGGCACACTGGTCATTGTGTCTGCTGGTGGCGGAGGATCTGGCGGAGGTGGAAGCGG

CGGAGGCGGATCTATGCTTTCTCCTGCTCCTCTGCTGAGCCTGCTGCTGCTGTGCGTGTCAGAT

AGCAGAGCCGAGACAACCGTGACACAGTCTCCAGCCAGTCTGTCTGTGGCCACCGGCGAGAAAG

TGACCATCAGATGCATCAGCAGCACCGACATCGACGACGACATGAACTGGTATCAGCAGAAGTC

CGGCGAGCCTCCTAAGCTGCTGATCTCCGAGGGCAATACTCTGAGGCCTGGCGTGCCAAGCAGA

TTCAGCAGCTCTGGCTACGGCACCGACTTCGTGTTCACCATCGAGAACATGCTGAGCGAGGACG

TGGCCGATTACTACTGCCTGCAGAGCGACAACATGCCCCTGACATTTGGAGCCGGCACCAAGCT

GGAACTGAAGGctagcaccacgacgccagcgccgcgaccaccaacaccggcgcccaccatcgcg tcgcagcccctgtccctgcgcccagaggcgtgccggccagcggcggggggcgcagtgcacacga gggggctggacttcgcctgtgatatctacatctgggcgcccttggccgggacttgtggggtcct tctcctgtcactggttatcaccctttactgcaaacggggcagaaagaaactcctgtatatattc aaacaaccatttatgagaccagtacaaactactcaagaggaagatggctgtagctgccgatttc cagaagaagaagaaggaggatgtgaactgagagtgaagttcagcaggagcgcagacgcccccgc gtaccagcagggccagaaccagctctataacgagctcaatctaggacgaagagaggagtacgat gttttggacaagagacgtggccgggaccctgagatggggggaaagccgagaaggaagaaccctc aggaaggcctgtacaatgaactgcagaaagataagatggcggaggcctacagtgagattgggat gaaaggcgagcgccggaggggcaaggggcacgatggcctttaccagggtctcagtacagccacc aaggacacctacgacgcccttcacatgcaggccctgccccctcgctaa Vb9HL-Dz (SEQ ID NO: 9)

atggccttaccagtgaccgccttgctcctgccgctggccttgctgctccacgccgccaggccgg

GATCCATGAAGTTCAGCTGGGTCATCTTCTTTCTGATGGCCGTGGTCACCGGCGTGAACTCTGA

AGTGCAACTGCAGCAGAGCGTGGCCGAACTCGTTAGACCTGGCGCCTCTGTGAAGCTGAGCTGT

ACCGCCAGCGGCTTCAACATCAAGAACACCTTCATGCACTGGGTCAAGCAGCGGCCTGAGCAGG

GACTCGAGTGGATCGGAAGAATCGACCCCACCAACGGCTACACCAAGTTCGCCCCTAAGTTCCA

GGGCAAAGCCACACTGACAGCCGTGACCAGCAGCAACACAGTGTACCTGCAGCTGAGCAGCCTG

ACCTCTGAGGACACCGCCATCTACTACTGCGCCCACGATTACGACGCCCCTTGGTTTGCCTATT

GGGGCCAGGGCACACTGGTCATTGTGTCTGCTGGTGGCGGAGGATCTGGCGGAGGTGGAAGCGG

CGGAGGCGGATCTATGCTTTCTCCTGCTCCTCTGCTGAGCCTGCTGCTGCTGTGCGTGTCAGAT

AGCAGAGCCGAGACAACCGTGACACAGTCTCCAGCCAGTCTGTCTGTGGCCACCGGCGAGAAAG

TGACCATCAGATGCATCAGCAGCACCGACATCGACGACGACATGAACTGGTATCAGCAGAAGTC

CGGCGAGCCTCCTAAGCTGCTGATCTCCGAGGGCAATACTCTGAGGCCTGGCGTGCCAAGCAGA

TTCAGCAGCTCTGGCTACGGCACCGACTTCGTGTTCACCATCGAGAACATGCTGAGCGAGGACG

TGGCCGATTACTACTGCCTGCAGAGCGACAACATGCCCCTGACATTTGGAGCCGGCACCAAGCT

GGAACTGAAGGctagcaccacgacgccagcgccgcgaccaccaacaccggcgcccaccatcgcg tcgcagcccctgtccctgcgcccagaggcgtgccggccagcggcggggggcgcagtgcacacga gggggctggacttcgcctgtgattttgggtgctggtggtggttggtggagtcctggcttgcta tagcttgctagtaacagtggcctttattattttctgggtgaggagtaagaggagctaa -continued Vb9LH-28z (SEQ ID NO: 10)

atggccttaccagtgaccgccttgctcctgccgctggccttgctgctccacgccgccaggccgg

GATCCATGCTGTCTCCAGCTCCTCTGCTGTCTCTGCTGCTGCTGTGCGTGTCCGATAGCAGAGC

CGAGACAACCGTGACACAGTCTCCAGCCAGTCTGTCTGTGGCCACCGGCGAGAAAGTGACCATC

AGATGCATCAGCAGCACCGACATCGACGACGACATGAACTGGTATCAGCAGAAGTCCGGCGAGC

CTCCTAAGCTGCTGATCTCCGAGGGCAATACTCTGAGGCCTGGCGTGCCAAGCAGATTCAGCAG

CTCTGGCTACGGCACCGACTTCGTGTTCACCATCGAGAACATGCTGAGCGAGGACGTGGCCGAC

TACTACTGCCTGCAGAGCGACAACATGCCCCTGACATTTGGAGCCGGCACCAAGCTGGAACTGA

AAGGCGGCGGAGGATCTGGCGGAGGTGGAAGCGGAGGCGGTGGCAGCATGAAGTTCAGCTGGGT

CATCTTCTTTCTGATGGCCGTGGTCACCGGCGTGAACTCTGAAGTGCAACTGCAGCAGAGCGTG

GCCGAACTCGTTAGACCTGGCGCCTCTGTGAAGCTGAGCTGTACCGCCAGCGGCTTCAACATCA

AGAACACCTTCATGCACTGGGTCAAGCAGCGGCCTGAGCAGGGACTCGAGTGGATCGGAAGAAT

CGACCCCACCAACGGCTACACCAAGTTCGCCCCTAAGTTCCAGGGCAAAGCCACACTGACAGCC

GTGACCAGCAGCAACACAGTGTACCTGCAGCTGAGCAGCCTGACCTCTGAGGACACCGCCATCT

ACTACTGTGCCCACGACTACGACGCCCCTTGGTTTGCCTATTGGGGCCAGGGCACACTGGTCAT

CGTTTCTGCTGctagcaccacgacgccagcgccgcgaccaccaacaccggcgcccaccatcgcg tcgcagcccctgtccctgcgcccagaggcgtgccggccagcggcggggggcgcagtgcacacga gggggctggacttcgcctgtgatttttgggtgctggtggtggttggtggagtcctggcttgcta tagcttgctagtaacagtggcctttattattttctgggtgaggagtaagaggagcaggctcctg cacagtgactacatgaacatgactccccgccgccccgggcccacccgcaagcattaccagccct atgccccaccacgcgacttcgcagcctatcgctccatcgatagagtgaagttcagcaggagcgc agacgcccccgcgtaccagcagggccagaaccagctctataacgagctcaatctaggacgaaga gaggagtacgatgttttggacaagagacgtggccgggaccctgagatggggggaaagccgagaa ggaagaaccctcaggaaggcctgtacaatgaactgcagaaagataagatggcggaggcctacag tgagattgggatgaaaggcgagcgccggaggggcaaggggcacgatggcctttaccagggtctc agtacagccaccaaggacacctacgacgcccttcacatgcaggccctgccccctcgctaa Vb9LH-BBz (SEQ ID NO: 11)

atggccttaccagtgaccgccttgctcctgccgctggccttgctgctccacgccgccaggccgg

GATCCATGCTGTCTCCAGCTCCTCTGCTGTCTCTGCTGCTGCTGTGCGTGTCCGATAGCAGAGC

CGAGACAACCGTGACACAGTCTCCAGCCAGTCTGTCTGTGGCCACCGGCGAGAAAGTGACCATC

AGATGCATCAGCAGCACCGACATCGACGACGACATGAACTGGTATCAGCAGAAGTCCGGCGAGC

CTCCTAAGCTGCTGATCTCCGAGGGCAATACTCTGAGGCCTGGCGTGCCAAGCAGATTCAGCAG

CTCTGGCTACGGCACCGACTTCGTGTTCACCATCGAGAACATGCTGAGCGAGGACGTGGCCGAC

TACTACTGCCTGCAGAGCGACAACATGCCCCTGACATTTGGAGCCGGCACCAAGCTGGAACTGA

AAGGCGGCGGAGGATCTGGCGGAGGTGGAAGCGGAGGCGGTGGCAGCATGAAGTTCAGCTGGGT

CATCTTCTTTCTGATGGCCGTGGTCACCGGCGTGAACTCTGAAGTGCAACTGCAGCAGAGCGTG

GCCGAACTCGTTAGACCTGGCGCCTCTGTGAAGCTGAGCTGTACCGCCAGCGGCTTCAACATCA

AGAACACCTTCATGCACTGGGTCAAGCAGCGGCCTGAGCAGGGACTCGAGTGGATCGGAAGAAT

CGACCCCACCAACGGCTACACCAAGTTCGCCCCTAAGTTCCAGGGCAAAGCCACACTGACAGCC

GTGACCAGCAGCAACACAGTGTACCTGCAGCTGAGCAGCCTGACCTCTGAGGACACCGCCATCT

-continued

ACTACTGTGCCCACGACTACGACGCCCCTTGGTTTGCCTATTGGGGCCAGGGCACACTGGTCAT

CGTTTCTGCTGctagcaccacgacgccagcgccgcgaccaccaacaccggcgcccaccatcgcg tcgcagcccctgtccctgcgcccagaggcgtgccggccagcggcggggggcgcagtgcacacga gggggctggacttcgcctgtgatatctacatctgggcgcccttggccgggacttgtggggtcct tctcctgtcactggttatcaccctttactgcaaacggggcagaaagaaactcctgtatatattc aaacaaccatttatgagaccagtacaaactactcaagaggaagatggctgtagctgccgatttc cagaagaagaagaaggaggatgtgaactgagagtgaagttcagcaggagcgcagacgcccccgc gtaccagcagggccagaaccagctctataacgagctcaatctaggacgaagagaggagtacgat gttttggacaagagacgtggccgggaccctgagatggggggaaagccgagaaggaagaaccctc aggaaggcctgtacaatgaactgcagaaagataagatggcggaggcctacagtgagattgggat gaaaggcgagcgccggaggggcaaggggcacgatggcctttaccagggtctcagtacagccacc aaggacacctacgacgcccttcacatgcaggccctgccccctcgctaa Vb9LH-Dz (SEQ ID NO: 12)

atggccttaccagtgaccgccttgctcctgccgctggccttgctgctccacgccgccaggccgg

GATCCATGCTGTCTCCAGCTCCTCTGCTGTCTCTGCTGCTGCTGTGCGTGTCCGATAGCAGAGC

CGAGACAACCGTGACACAGTCTCCAGCCAGTCTGTCTGTGGCCACCGGCGAGAAAGTGACCATC

AGATGCATCAGCAGCACCGACATCGACGACGACATGAACTGGTATCAGCAGAAGTCCGGCGAGC

CTCCTAAGCTGCTGATCTCCGAGGGCAATACTCTGAGGCCTGGCGTGCCAAGCAGATTCAGCAG

CTCTGGCTACGGCACCGACTTCGTGTTCACCATCGAGAACATGCTGAGCGAGGACGTGGCCGAC

TACTACTGCCTGCAGAGCGACAACATGCCCCTGACATTTGGAGCCGGCACCAAGCTGGAACTGA

AAGGCGGCGGAGGATCTGGCGGAGGTGGAAGCGGAGGCGGTGGCAGCATGAAGTTCAGCTGGGT

CATCTTCTTTCTGATGGCCGTGGTCACCGGCGTGAACTCTGAAGTGCAACTGCAGCAGAGCGTG

GCCGAACTCGTTAGACCTGGCGCCTCTGTGAAGCTGAGCTGTACCGCCAGCGGCTTCAACATCA

AGAACACCTTCATGCACTGGGTCAAGCAGCGGCCTGAGCAGGGACTCGAGTGGATCGGAAGAAT

CGACCCCACCAACGGCTACACCAAGTTCGCCCCTAAGTTCCAGGGCAAAGCCACACTGACAGCC

GTGACCAGCAGCAACACAGTGTACCTGCAGCTGAGCAGCCTGACCTCTGAGGACACCGCCATCT

ACTACTGTGCCCACGACTACGACGCCCCTTGGTTTGCCTATTGGGGCCAGGGCACACTGGTCAT

CGTTTCTGCTGctagcaccacgacgccagcgccgcgaccaccaacaccggcgcccaccatcgcg tcgcagcccctgtccctgcgcccagaggcgtgccggccagcggcggggggcgcagtgcacacga gggggctggacttcgcctgtgatttttgggtgctggtggtggttggtggagtcctggcttgcta tagcttgctagtaacagtggcctttattattttctgggtgaggagtaagaggagctaa Vb1HL-BBz (SEQ ID NO: 13)

atggccttaccagtgaccgccttgctcctgccgctggccttgctgctccacgccgccaggccgg

GATCCATGGACTGGGTCTGGAACCTGCTGTTCCTGATGGCCGTTGCTCAGACAGGTGCTCAGGC

TCAGCTGCAACTGGTGCAGTCTGGACCTGAGCTGAGAGAACCTGGCGAGAGCGTGAAGATCTCC

TGCAAGGCCAGCGGCTACACCTTCACCGACTACATCGTGCACTGGGTCAAGCAGGCCCCTGGCA

AGGGACTGAAATGGATGGGCTGGATCAACACCTACACCGGCACACCCACCTACGCCGACGATTT

CGAGGGCAGATTCGTGTTCAGCCTGGAAGCCTCTGCCAGCACCGCCAACCTGCAGATCAGCAAC

CTGAAGAACGAGGACACCGCCACCTACTTTTGCGCCAGATCTTGGCGGAGAGGCATCCGCGGCA

TCGGCTTTGATTATTGGGGACAGGGCGTGATGGTCACCGTGTCTAGCGGAGGCGGAGGATCTGG

TGGCGGAGGAAGTGGCGGAGGCGGTTCTATGAGAGTGCAGATCCAGTTCTGGGGACTGCTGCTG

-continued

CTGTGGACAAGCGGCATCCAGTGTGACGTGCAGATGACACAGAGCCCCTACAACCTGGCTGCCT
CTCCTGGCGAGTCCGTGTCCATCAATTGCAAGGCCTCCAAGAGCATCAACAAGTACCTGGCCTG
GTATCAGCAGAAGCCCGGCAAGCCTAACAAGCTGCTGATCTACGATGGCAGCACCCTGCAGAGC
GGAATCCCCAGCAGATTTTCTGGCAGCGGCTCCGGCACCGATTTCACCCTGACAATCAGAGGCC
TGGAACCAGAGGACTTCGGCCTGTACTACTGCCAGCAGCACAACGAGTACCCTCCAACCTTTGG
AGCCGGCACCAAGCTGGAACTGAAGGctagcaccacgacgccagcgccgcgaccaccaacaccg
gcgcccaccatcgcgtcgcagcccctgtccctgcgcccagaggcgtgccggccagcggcggggg
gcgcagtgcacacgagggggctggacttcgcctgtgatatctacatctgggcgcccttggccgg
gacttgtggggtccttctcctgtcactggttatcaccctttactgcaaacggggcagaaagaaa
ctcctgtatatattcaaacaaccatttatgagaccagtacaaactactcaagaggaagatggct
gtagctgccgatttccagaagaagaagaaggaggatgtgaactgagagtgaagttcagcaggag
cgcagacgcccccgcgtaccagcagggccagaaccagctctataacgagctcaatctaggacga
agagaggagtacgatgttttggacaagagacgtggccgggaccctgagatggggggaaagccga
gaaggaagaaccctcaggaaggcctgtacaatgaactgcagaaagataagatggcggaggccta
cagtgagattgggatgaaaggcgagcgccggaggggcaaggggcacgatggcctttaccagggt
ctcagtacagccaccaaggacacctacgacgcccttcacatgcaggccctgccccctcgctaa Vb1LH-BBz (SEQ ID NO: 14)

atggccttaccagtgaccgccttgctcctgccgctggccttgctgctccacgccgccaggccgg
GATCCATGAGAGTGCAGATCCAGTTCTGGGGCCTGCTGCTGCTGTGGACATCTGGCATCCAGTG
CGACGTGCAGATGACACAGAGCCCCTACAACCTGGCTGCCTCTCCTGGCGAGAGCGTGTCCATC
AATTGCAAGGCCAGCAAGAGCATCAACAAGTACCTGGCCTGGTATCAGCAGAAGCCCGGCAAGC
CTAACAAGCTGCTGATCTACGATGGCAGCACCCTGCAGAGCGGCATCCCTAGCAGATTTTCTGG
CAGCGGCTCCGGCACCGATTTCACCCTGACAATCAGAGGCCTGGAACCTGAGGACTTCGGCCTG
TACTACTGCCAGCAGCACAACGAGTACCCTCCAACCTTTGGAGCCGGCACCAAGCTGGAACTTA
AAGGCGGCGGAGGATCTGGCGGAGGTGGAAGCGGAGGCGGTGGATCTATGGACTGGGTCTGGAA
TCTGCTGTTCCTGATGGCCGTGGCTCAGACAGGTGCTCAGGCTCAGCTGCAACTGGTGCAGTCT
GGACCTGAGCTGAGAGAACCTGGCGAGTCCGTGAAGATCTCCTGCAAGGCCTCCGGCTACACCT
TCACCGACTACATCGTGCACTGGGTCAAACAGGCCCCTGGCAAGGGACTGAAGTGGATGGGCTG
GATCAACACCTACACCGGCACACCCACCTACGCCGACGATTTCGAGGGCAGATTCGTGTTCAGC
CTGGAAGCCTCTGCCAGCACCGCCAACCTGCAGATCAGCAACCTGAAGAACGAGGACACCGCCA
CCTACTTTTGCGCCAGATCTTGGAGGCGGGGCATCAGAGGCATCGGCTTTGATTATTGGGGCCA
GGGCGTGATGGTCACCGTGTCCTCTGctagcaccacgacgccagcgccgcgaccaccaacaccg
gcgcccaccatcgcgtcgcagcccctgtccctgcgcccagaggcgtgccggccagcggcggggg
gcgcagtgcacacgagggggctggacttcgcctgtgatatctacatctgggcgcccttggccgg
gacttgtggggtccttctcctgtcactggttatcaccctttactgcaaacggggcagaaagaaa
ctcctgtatatattcaaacaaccatttatgagaccagtacaaactactcaagaggaagatggct
gtagctgccgatttccagaagaagaagaaggaggatgtgaactgagagtgaagttcagcaggag
cgcagacgcccccgcgtaccagcagggccagaaccagctctataacgagctcaatctaggacga
agagaggagtacgatgttttggacaagagacgtggccgggaccctgagatggggggaaagccga
gaaggaagaaccctcaggaaggcctgtacaatgaactgcagaaagataagatggcggaggccta -continued cagtgagattgggatgaaaggcgagcgccggaggggcaaggggcacgatggcctttaccagggt ctcagtacagccaccaaggacacctacgacgcccttcacatgcaggccctgccccctcgctaa Vb2HL-BBz (SEQ ID NO: 15)

atggccttaccagtgaccgccttgctcctgccgctggccttgctgctccacgccgccaggccgg

GATCCATGAAGTTCAGCTGGGTCATCTTCTTTCTGATGGCCGTGGTCACCGGCGTGAACTCTGA

AGTGCAACTGCAGCAGAGCGTGGCCGATCTCGTTAGACCTGGCGCCTCTCTGAAGCTGAGCTGT

ACCGCCAGCGGCTTCAACATCAAGAGCGCCTACATGCACTGGGTTATCCAGCGGCCAGATCAGG

GCCCAGAGTGTCTGGGAAGAATCGATCCTGCCACCGGCAAGACCAAATACGCCCCTAAGTTTCA

GGCCAAGGCCACCATCACCGCCGACACCTCTAGCAATACCGCCTACCTGCAGCTGAGCAGCCTG

ACCTCTGAGGACACCGCCATCTACTACTGCACCAGAAGCCTGAACTGGGACTACGGCCTGGATT

ATTGGGGCCAGGGCACAAGCGTGACAGTGTCTAGCGGAGGCGGAGGATCTGGTGGCGGAGGAAG

TGGCGGAGGCGGTAGCATGGAAACCGATACACTGCTGCTGTGGGTGCTGCTCCTTTGGGTGCCC

GGATCTACAGGCGACATCGTGCTGACACAGTCTCCCGCTTCTCTGGCCGTGTCTCTGGGACAGA

GAGCCACCATCTCTTGCAGAGCCAGCAAGAGCGTGTCCATCCTGGGCACACACCTGATCCACTG

GTATCAGCAGAAGCCCGGCCAGCCTCCTAAGCTGCTGATCTACGCCGCCAGCAATCTGGAAAGC

GGAGTGCCTGCCAGATTTTCCGGCAGCGGAAGCGAAACCGTGTTCACCCTGAACATTCACCCCG

TGGAAGAAGAGGACGCCGCCACCTATTTCTGCCAGCAGTCTATCGAGGACCCCTGGACATTTGG

AGGCGGCACAAAGCTGGGCATCAAGGctagcaccacgacgccagcgccgcgaccaccaacaccg gcgcccaccatcgcgtcgcagcccctgtccctgcgcccagaggcgtgccggccagcggcggggg gcgcagtgcacacgagggggctggacttcgcctgtgatatctacatctgggcgcccttggccgg gacttgtggggtccttctcctgtcactggttatcaccctttactgcaaacggggcagaaagaaa ctcctgtatatattcaaacaaccatttatgagaccagtacaaactactcaagaggaagatggct gtagctgccgatttccagaagaagaagaaggaggatgtgaactgagagtgaagttcagcaggag cgcagacgcccccgcgtaccagcagggccagaaccagctctataacgagctcaatctaggacga agagaggagtacgatgttttggacaagagacgtggccgggaccctgagatggggggaaagccga gaaggaagaaccctcaggaaggcctgtacaatgaactgcagaaagataagatggcggaggccta cagtgagattgggatgaaaggcgagcgccggaggggcaaggggcacgatggcctttaccagggt ctcagtacagccaccaaggacacctacgacgcccttcacatgcaggccctgccccctcgctaa Vb2LH-BBz (SEQ ID NO: 16)

atggccttaccagtgaccgccttgctcctgccgctggccttgctgctccacgccgccaggccgg

GATCCATGGAAACCGACACACTGCTGCTGTGGGTGCTGCTTCTTTGGGTGCCCGGAAGCACAGG

CGACATCGTGCTGACACAGAGCCCTGCTTCTCTGGCCGTGTCTCTGGGACAGAGAGCCACCATC

AGCTGCAGAGCCAGCAAGAGCGTGTCCATCCTGGGCACACACCTGATCCACTGGTATCAGCAGA

AGCCCGGCCAGCCTCCTAAGCTGCTGATCTACGCCGCCAGCAATCTGGAAAGCGGAGTGCCTGC

CAGATTTTCCGGCAGCGGAAGCGAGACAGTGTTCACCCTGAACATTCACCCCGTGGAAGAAGAG

GACGCCGCCACCTACTTTTGCCAGCAGTCTATCGAGGACCCCTGGACCTTTGGCGGCGGAACAA

AGCTGGGAATCAAAGGCGGCGGAGGATCTGGCGGAGGTGGAAGCGGAGGCGGTGGCAGCATGAA

GTTCAGCTGGGTCATCTTCTTTCTGATGGCCGTGGTCACCGGCGTGAACTCTGAAGTGCAACTG

CAGCAGAGCGTGGCCGATCTCGTTAGACCTGGCGCCTCTCTGAAGCTGAGCTGTACCGCCAGCG

GCTTCAACATCAAGAGCGCCTACATGCACTGGGTTATCCAGCGGCCAGATCAGGGCCCAGAGTG

TCTGGGAAGAATCGATCCTGCCACCGGCAAGACCAAATACGCCCCTAAGTTTCAGGCCAAGGCC

-continued

ACAATCACCGCCGACACCTCTAGCAACACAGCCTACCTGCAGCTGTCCAGCCTGACCTCTGAGG

ATACCGCCATCTACTACTGCACCAGAAGCCTGAACTGGGACTACGGCCTGGATTATTGGGGCCA

GGGCACAAGCGTGACCGTGTCATCTGctagcaccacgacgccagcgccgcgaccaccaacaccg gcgcccaccatcgcgtcgcagcccctgtccctgcgcccagaggcgtgccggccagcggcggggg gcgcagtgcacacgagggggctggacttcgcctgtgatatctacatctgggcgcccttggccgg gacttgtggggtccttctcctgtcactggttatcaccctttactgcaaacggggcagaaagaaa ctcctgtatatattcaaacaaccatttatgagaccagtacaaactactcaagaggaagatggct gtagctgccgatttccagaagaagaagaaggaggatgtgaactgagagtgaagttcagcaggag cgcagacgcccccgcgtaccagcagggccagaaccagctctataacgagctcaatctaggacga agagaggagtacgatgttttggacaagagacgtggccgggaccctgagatggggggaaagccga gaaggaagaaccctcaggaaggcctgtacaatgaactgcagaaagataagatggcggaggccta cagtgagattgggatgaaaggcgagcgccggaggggcaaggggcacgatggcctttaccagggt ctcagtacagccaccaaggacacctacgacgcccttcacatgcaggccctgccccctcgctaa Vb4HLBBz (SEQ ID NO: 17)

atggccttaccagtgaccgccttgctcctgccgctggccttgctgctccacgccgccaggccgg

GATCCATGGAATGGTCCTGGATCTTCCTGTTCCTGCTGAGCGTGACAGCCGTGGTGCATTCTCA

GGTTCAGCTGCAGCAGTCTGGCGCCGAACTGGCCAAACCTGGCACAAGCGTGAAGCTGAGCTGT

AAAGCCAGCGGCTACACCTTCACCAGCTACTACATCTACTGGGTCAAGCAGCGGCCTGGACAGG

GACTTGAGTGGCTGGGCTATATCTACCCTGGCAACGGCGGCACCTACTACAGCGAGAAGTTCAA

GGGCAAAGCCACCTTTACCGCCGACACCAGCAGCAACACAGCCTACATGCTGCTGGGCAGCCTG

ACACCTGAGGACAGCGCCTACTACTTCTGTGCCAGAGGCAGCGGCGACCGGTACAATTCTCTGG

CCTATTGGGGCCAGGGCACCCTGGTTACAGTTTCTTCTGGTGGCGGAGGATCTGGCGGAGGTGG

AAGCGGCGGAGGCGGATCTATGGCTATTCCTACACAGCTGCTGGGACTGCTGCTGCTCTGGATC

ACCGATGCCATCTGCGACATCCAGATGACACAGAGCCCTCACAGCCTGTCTGCCAGCCTGGGAG

AGACAGTGTCCATTGAGTGTCTGGCCAGCGAGGGCATCAGCAACTTTCTGGCCTGGTATCAGCA

GAAGCCCGGCAAGTCTCCTCAGCTGCTGATCTACTACACAAGCAGCCTGCAGGATGGCGTGCCC

TCTAGATTTTCTGGCTCTGGCAGCGGCACCCAGTACAGCCTGAAGATCAGCAACATGCAGCCCG

AGGACGAGGGCGTGTACTATTGTCAGCAGGGCTACAAGTTCCCCAGAACCTTTGGCGGAGGCAC

CAAGCTGGAACTGAAGGctagcaccacgacgccagcgccgcgaccaccaacaccggcgcccacc atcgcgtcgcagcccctgtccctgcgcccagaggcgtgccggccagcggcggggggcgcagtgc acacgagggggctggacttcgcctgtgatatctacatctgggcgcccttggccgggacttgtgg ggtccttctcctgtcactggttatcaccctttactgcaaacggggcagaaagaaactcctgtat atattcaaacaaccatttatgagaccagtacaaactactcaagaggaagatggctgtagctgcc gatttccagaagaagaagaaggaggatgtgaactgagagtgaagttcagcaggagcgcagacgc ccccgcgtaccagcagggccagaaccagctctataacgagctcaatctaggacgaagagaggag tacgatgttttggacaagagacgtggccgggaccctgagatggggggaaagccgagaaggaaga accctcaggaaggcctgtacaatgaactgcagaaagataagatggcggaggcctacagtgagat tgggatgaaaggcgagcgccggaggggcaaggggcacgatggcctttaccagggtctcagtaca gccaccaaggacacctacgacgcccttcacatgcaggccctgccccctcgctaa -continued Vb4LH-BBz (SEQ ID NO: 18)

atggccttaccagtgaccgccttgctcctgccgctggccttgctgctccacgccgccaggccgg

GATCCATGGCTATCCCCACACAACTGCTGGGACTGCTGCTGCTGTGGATCACCGATGCCATCTG

CGACATCCAGATGACACAGAGCCCTCACAGCCTGTCTGCCAGCCTGGGAGAGACAGTGTCCATT

GAGTGTCTGGCCAGCGAGGGCATCAGCAACTTTCTGGCCTGGTATCAGCAGAAGCCCGGCAAGT

CTCCTCAGCTGCTGATCTACTACACCAGCAGCCTGCAGGATGGCGTGCCCAGCAGATTTTCTGG

CAGCGGCTCTGGCACACAGTACAGCCTGAAGATCAGCAACATGCAGCCCGAGGACGAGGGCGTG

TACTATTGTCAGCAGGGCTACAAGTTCCCCAGAACCTTTGGCGGAGGCACCAAGCTGGAACTGA

AAGGCGGCGGAGGAAGCGGAGGCGGAGGATCTGGTGGTGGTGGATCTATGGAATGGTCCTGGAT

CTTCCTGTTCCTGCTGAGCGTGACAGCCGTGGTGCATTCTCAGGTTCAGCTGCAGCAGAGCGGA

GCCGAACTGGCCAAACCTGGCACAAGCGTGAAGCTGAGCTGTAAAGCCAGCGGCTACACCTTCA

CCAGCTACTACATCTACTGGGTCAAGCAGCGGCCTGGACAGGGACTTGAGTGGCTGGGCTATAT

CTACCCTGGCAACGGCGGCACCTACTACAGCGAGAAGTTCAAGGGCAAAGCCACCTTTACCGCC

GACACCAGCTCCAACACAGCCTACATGCTGCTCGGCAGCCTGACACCTGAGGACAGCGCCTACT

ACTTTTGCGCTAGAGGCAGCGGCGACCGGTACAATTCTCTGGCCTATTGGGGCCAGGGCACCCT

GGTTACAGTCAGCTCTGctagcaccacgacgccagcgccgcgaccaccaacaccggcgcccacc atcgcgtcgcagcccctgtccctgcgcccagaggcgtgccggccagcggcggggggcgcagtgc acacgagggggctggacttcgcctgtgatatctacatctgggcgcccttggccgggacttgtgg ggtccttctcctgtcactggttatcaccctttactgcaaacggggcagaaagaaactcctgtat atattcaaacaaccatttatgagaccagtacaaactactcaagaggaagatggctgtagctgcc gatttccagaagaagaagaaggaggatgtgaactgagagtgaagttcagcaggagcgcagacgc cccgcgtaccagcagggccagaaccagctctataacgagctcaatctaggacgaagagaggag tacgatgttttggacaagagacgtggccgggaccctgagatgggggggaaagccgagaaggaaga accctcaggaaggcctgtacaatgaactgcagaaagataagatggcggaggcctacagtgagat tgggatgaaaggcgagcgccggaggggcaaggggcacgatggcctttaccagggtctcagtaca gccaccaaggacacctacgacgcccttcacatgcaggccctgccccctcgctaa Vb5.1HL-BBz (SEQ ID NO: 19)

atggccttaccagtgaccgccttgctcctgccgctggccttgctgctccacgccgccaggccgg

GATCCATGGGCTGGTCCTGGATCTTCCTGTTCCTGCTGTCTGAGACTGCCGGCGTGCTGAGTGA

AGTTCAGCTGCAGCAGTCTGGCCCCGTGCTTGTGAAACCTGGCGCCTCTGTCAGAATGAGCTGC

AAGGCCAGCGGCTACACCTTCACCGACTACAACATCCACTGGGTCAAGCAGAGCCACGGCAGAT

CCCTTGAGTGGGTCGGATATATCAACCCCTACAACGGCCGGACCGGCTACAACCAGAAGTTCAA

GGCCAAGGCCACACTGACCGTGAACAAGAGCAGCAGCACCGCCTACATGGACCTGAGAAGCCTG

ACCAGCGAGGACAGCGCCGTGTACTATTGCGCCAGATGGGATGGCAGCAGCTACTTCGATTATT

GGGGCCAGGGCACAACCCTGACCGTTTCTTCTGGTGGCGGAGGATCTGGCGGAGGTGGAAGCGG

CGGAGGCGGATCTATGGATTTCCGGGTGCAGATCTTCAGCTTCCTGCTGATCTCCGTGACCGTG

TCCAGAGGCGAGATCGTGCTGACACAGAGCCCTGCCATTACAGCCGCTTCTCTGGGCCAGAAAG

TGACCATCACATGCAGCGCCAGCAGCAGCGTGTCCTACATGCACTGGTATCAGCAGAAGTCCGG

CACAAGCCCCAAGCCTTGGATCTACGAGATCTCCAAGCTGGCCTCTGGCGTGCCAGCCAGATTT

TCTGGCTCTGGCAGCGGCACCAGCTACTCCCTGACAATCAGCAGCATGGAAGCCGAGGACGCCG

-continued

CCATCTACTACTGCCAGCAGTGGAACTACCCTCTGATCACCTTTGGAGCCGGCACCAAGCTGGA

ACTGAAGGctagcaccacgacgccagcgccgcgaccaccaacaccggcgcccaccatcgcgtcg cagcccctgtccctgcgcccagaggcgtgccggccagcggcggggggcgcagtgcacacgaggg ggctggacttcgcctgtgatatctacatctgggcgcccttggccgggacttgtggggtccttct cctgtcactggttatcaccctttactgcaaacggggcagaaagaaactcctgtatatattcaaa caaccatttatgagaccagtacaaactactcaagaggaagatggctgtagctgccgatttccag aagaagaagaaggaggatgtgaactgagagtgaagttcagcaggagcgcagacgcccccgcgta ccagcagggccagaaccagctctataacgagctcaatctaggacgaagagaggagtacgatgtt ttggacaagagacgtggccgggaccctgagatggggggaaagccgagaaggaagaaccctcagg aaggcctgtacaatgaactgcagaaagataagatggcggaggcctacagtgagattgggatgaa aggcgagcgccggaggggcaaggggcacgatggcctttaccagggtctcagtacagccaccaag gacacctacgacgcccttcacatgcaggccctgccccctcgctaa Vb5.1LH-BBz (SEQ ID NO: 20)

atggccttaccagtgaccgccttgctcctgccgctggccttgctgctccacgccgccaggccgg

GATCCATGGACTTCCGGGTGCAGATCTTCAGCTTCCTGCTGATCTCCGTGACCGTGTCCAGAGG

CGAGATCGTGCTGACACAGAGCCCTGCCATTACAGCCGCTTCTCTGGGCCAGAAAGTGACCATC

ACATGCAGCGCCAGCAGCAGCGTGTCCTACATGCACTGGTATCAGCAGAAGTCCGGCACAAGCC

CCAAGCCTTGGATCTACGAGATCTCCAAGCTGGCCTCTGGCGTGCCAGCCAGATTTTCTGGCTC

TGGCAGCGGCACCAGCTACAGCCTGACAATCAGCAGCATGGAAGCCGAGGACGCCGCCATCTAC

TACTGCCAGCAGTGGAACTACCCTCTGATCACCTTTGGAGCCGGCACCAAGCTGGAACTGAAAG

GCGGCGGAGGATCTGGCGGAGGTGGAAGCGGAGGCGGTGGATCTATGGGATGGTCCTGGATCTT

CCTGTTCCTGCTGTCCGAAACAGCCGGCGTGCTGTCTGAAGTTCAGCTGCAGCAGTCTGGCCCC

GTGCTTGTGAAACCTGGCGCCTCTGTCAGAATGAGCTGCAAGGCCAGCGGCTACACCTTCACCG

ACTACAACATCCACTGGGTCAAGCAGAGCCACGGCAGATCCCTTGAGTGGGTCGGATATATCAA

CCCCTACAACGGCCGGACCGGCTACAACCAGAAGTTCAAGGCCAAGGCCACACTGACCGTGAAC

AAGAGCAGCAGCACCGCCTACATGGACCTGAGAAGCCTGACCAGCGAGGACAGCGCCGTGTACT

ATTGCGCCAGATGGGATGGCAGCAGCTACTTCGATTATTGGGGCCAGGGCACAACCCTGACAGT

GTCCTCTGctagcaccacgacgccagcgccgcgaccaccaacaccggcgcccaccatcgcgtcg cagcccctgtccctgcgcccagaggcgtgccggccagcggcggggggcgcagtgcacacgaggg ggctggacttcgcctgtgatatctacatctgggcgcccttggccgggacttgtggggtccttct cctgtcactggttatcaccctttactgcaaacggggcagaaagaaactcctgtatatattcaaa caaccatttatgagaccagtacaaactactcaagaggaagatggctgtagctgccgatttccag aagaagaagaaggaggatgtgaactgagagtgaagttcagcaggagcgcagacgcccccgcgta ccagcagggccagaaccagctctataacgagctcaatctaggacgaagagaggagtacgatgtt ttggacaagagacgtggccgggaccctgagatggggggaaagccgagaaggaagaaccctcagg aaggcctgtacaatgaactgcagaaagataagatggcggaggcctacagtgagattgggatgaa aggcgagcgccggaggggcaaggggcacgatggcctttaccagggtctcagtacagccaccaag gacacctacgacgcccttcacatgcaggccctgccccctcgctaa Vb7.1HL-BBz (SEQ ID NO: 21)

atggccttaccagtgaccgccttgctcctgccgctggccttgctgctccacgccgccaggccgg

GATCCATGAACTTCGGCCTGAGCCTGATCTTCCTGGTGCTGTTCCTGAAGGGCGTGCAGTGCGA

-continued

AGTGCAGCTGGTTGAATCTGGCGGCGGACTGGTTAAGCCTGGCGGATCTCTGAAGCTGAGCTGT
GCCGCCAGCGGCTTCACCTTCAGCGACTACTACATGTACTGGGTCCGACAGACCCCTGAGAAGC
GGCTGGAATGGGTCGCCACAATTTCTGGCGGAGGCAGCTACACATACAGCCCCGATTCTGTGAA
GGGCAGATTCACCATCAGCCGGGACAACGCCAAGAACAACCTGTACCTGCAGATGAGCAGCCTG
CGGAGCGAGGACACCGCCATGTACTTTTGCGCCAGAGAGCGGGACATCTACTACGGCAACTTCA
ACGCCATGGTGTACTGGGGCAGAGGCACCAGCGTGACAGTTAGTAGCGGAGGCGGAGGATCAGG
TGGCGGTGGAAGTGGTGGTGGCGGCAGCATGGAAACCGATACACTGCTGCTGTGGGTGCTGCTC
CTTTGGGTGCCCGGATCTACAGGCGACATCGTGCTGACACAGAGCCCCGTGTCTCTGACAGTGT
CCCTGGGACAGAGAGCCACAATCAGCTGCAGAGCCAGCAAGAGCGTGTCCACAAGCGGCTACAG
CTACATGCACTGGTATCAGCAGAAGCCCGGCCAGCCTCCTAAGCTGCTGATCTACCTGGCCAGC
AACCTGGAAAGCGGAGTGCCTGCCAGATTTTCTGGCAGCGGCTCTGGCACCGACTTCACCCTGA
ATATCCATCCTGTGGAAGAAGAGGACGCCGCCACCTACTACTGTCAGCACAGCAGAGATCTGCC
CTGGACCTTTGGAGGCGGCACCAAGCTGGAAATCAAGGctagcaccacgacgccagcgccgcga
ccaccaacaccggcgcccaccatcgcgtcgcagcccctgtccctgcgcccagaggcgtgccggc
cagcggcggggggcgcagtgcacacgagggggctggacttcgcctgtgatatctacatctgggc
gcccttggccgggacttgtggggtccttctcctgtcactggttatcaccctttactgcaaacgg
ggcagaaagaaactcctgtatatattcaaacaaccatttatgagaccagtacaaactactcaag
aggaagatggctgtagctgccgatttccagaagaagaagaaggaggatgtgaactgagagtgaa
gttcagcaggagcgcagacgcccccgcgtaccagcagggccagaaccagctctataacgagctc
aatctaggacgaagagaggagtacgatgttttggacaagagacgtggccgggaccctgagatgg
ggggaaagccgagaaggaagaaccctcaggaaggcctgtacaatgaactgcagaaagataagat
ggcggaggcctacagtgagattgggatgaaaggcgagcgccggaggggcaaggggcacgatggc
ctttaccagggtctcagtacagccaccaaggacacctacgacgcccttcacatgcaggccctgc
cccctcgctaa Vb7.1LH-BBz (SEQ ID NO: 22)

atggccttaccagtgaccgccttgctcctgccgctggccttgctgctccacgccgccaggccgg
GATCCATGGAAACCGACACACTGCTGCTGTGGGTGCTGCTTCTTTGGGTGCCCGGAAGCACAGG
CGACATCGTGCTTACACAGAGCCCCGTGTCTCTGACAGTGTCCCTGGGACAGAGAGCCACCATC
AGCTGTAGAGCCAGCAAGAGCGTGTCCACCAGCGGCTACAGCTACATGCACTGGTATCAGCAGA
AGCCCGGCCAGCCTCCTAAGCTGCTGATCTACCTGGCCAGCAACCTGGAAAGCGGAGTGCCTGC
CAGATTTTCTGGCAGCGGCTCTGGCACCGACTTCACCCTGAATATCCATCCTGTGGAAGAAGAG
GACGCCGCCACCTACTACTGTCAGCACAGCAGAGATCTGCCCTGGACCTTTGGCGGCGGAACAA
AGCTGGAAATCAAAGGCGGCGGAGGATCTGGCGGAGGTGGAAGCGGAGGCGGTGGCTCTATGAA
TTTTGGCCTGAGCCTGATCTTCCTGGTGCTGTTCCTGAAGGGCGTGCAGTGCGAAGTGCAGCTG
GTTGAAAGTGGCGGAGGCCTGGTTAAGCCTGGCGGATCTCTGAAGCTGAGCTGTGCCGCCAGCG
GCTTCACCTTCAGCGACTACTACATGTACTGGGTCCGACAGACCCCTGAGAAGCGGCTGGAATG
GGTCGCCACAATTTCAGGCGGAGGCAGCTACACATACAGCCCCGATTCTGTGAAGGGCCGCTTT
ACCATCAGCCGGGACAACGCCAAGAACAACCTGTACCTGCAGATGAGCAGCCTGCGGAGCGAGG
ACACCGCCATGTACTTTTGCGCCAGAGAGCGGGACATCTACTACGGCAACTTCAACGCCATGGT
GTACTGGGGCAGAGGCACCTCTGTGACCGTTAGCTCTGctagcaccacgacgccagcgccgcga -continued ccaccaacaccggcgcccaccatcgcgtcgcagcccctgtccctgcgcccagaggcgtgccggc cagcggcggggggcgcagtgcacacgagggggctggacttcgcctgtgatatctacatctgggc gcccttggccgggacttgtggggtccttctcctgtcactggttatcaccctttactgcaaacgg ggcagaaagaaactcctgtatatattcaaacaaccatttatgagaccagtacaaactactcaag aggaagatggctgtagctgccgatttccagaagaagaagaaggaggatgtgaactgagagtgaa gttcagcaggagcgcagacgcccccgcgtaccagcagggccagaaccagctctataacgagctc aatctaggacgaagagaggagtacgatgttttggacaagagacgtggccgggaccctgagatgg ggggaaagccgagaaggaagaaccctcaggaaggcctgtacaatgaactgcagaaagataagat ggcggaggcctacagtgagattgggatgaaaggcgagcgccggaggggcaaggggcacgatggc ctttaccagggtctcagtacagccaccaaggacacctacgacgcccttcacatgcaggccctgc cccctcgctaa Vb7.2HL-BBz (SEQ ID NO: 23)

atggccttaccagtgaccgccttgctcctgccgctggccttgctgctccacgccgccaggccgg

GATCCATGGAACGGCACTGGATCTTTCTGCTGCTGCTGAGCGTTACAGCCGGCGCTCACTCTCA

AGTGCATCTGCAGCAATCTGGCGCCGAGCTTGCTAGACCTGGCGCCTCTGTGAAGATGAGCTGT

AAAGCCAGCGGCTACATCTTCACCGACTACACCATGCACTGGGTCAAGCAGAGGCCTGGACAGG

GACTCGAGTGGATCGGCCACATCAATCCTAGCTCCGGCTACAGCACCTACAACCAGAAGTTCAA

GGACAAGGCCACACTGACCGCCGACAAGAGCAGCTCTACAGCCTACATGCAGCTGAGCAGCCTG

ACCAGCGAAGATAGCGCCGTGTACTACTGCGCCAGAAGCCTGCAGCTGGGCAGAGATTATTGGG

GCCAGGGCACAACCCTGACCGTTTCTTCTGGTGGCGGAGGATCTGGCGGAGGTGGAAGCGGCGG

AGGCGGATCTATGGAATCTCAGATCCAGGTGTTCGTGTTTGTGTTCCTGTGGCTGTCTGGCGTG

GACGGCGATATCGTGATGACCCAGAGCCACAAGTTCATGAGCACCAGCGTGGGCGACAGAGTGT

CCATCACATGCAAGGCCAGCCAGGACGTGTACACAGCCGTGGCTTGGTATCAGCAGAAGCCCGG

CCAGTCTCCTAAGCTGCTGATCTACAGCGCCAGCAACAGATACACCGGCGTGCCCGATAGATTC

ACAGGCTCTGGCAGCGGCACCGACTTCACCTTTACAATCAGCAGCGTGCAGGCCGAGGACCTGG

CCGTGTATTATTGCCAGCAGCACTACACCACACCTCGGACCTTTGGCGGCGGAACAAAGCTGGA

AATCAAGGctagcaccacgacgccagcgccgcgaccaccaacaccggcgcccaccatcgcgtcg cagcccctgtccctgcgcccagaggcgtgccggccagcggcggggggcgcagtgcacacgaggg ggctggacttcgcctgtgatatctacatctgggcgcccttggccgggacttgtggggtccttct cctgtcactggttatcaccctttactgcaaacggggcagaaagaaactcctgtatatattcaaa caaccatttatgagaccagtacaaactactcaagaggaagatggctgtagctgccgatttccag aagaagaagaaggaggatgtgaactgagagtgaagttcagcaggagcgcagacgcccccgcgta ccagcagggccagaaccagctctataacgagctcaatctaggacgaagagaggagtacgatgtt ttggacaagagacgtggccgggaccctgagatggggggaaagccgagaaggaagaaccctcagg aaggcctgtacaatgaactgcagaaagataagatggcggaggcctacagtgagattgggatgaa aggcgagcgccggaggggcaaggggcacgatggcctttaccagggtctcagtacagccaccaag gacacctacgacgcccttcacatgcaggccctgccccctcgctaa Vb7.2LH-BBz (SEQ ID NO: 24)

atggccttaccagtgaccgccttgctcctgccgctggccttgctgctccacgccgccaggccgg

GATCCATGGAAAGCCAGATCCAGGTGTTCGTGTTTGTGTTCCTGTGGCTGTCTGGCGTGGACGG

CGATATCGTGATGACCCAGAGCCACAAGTTCATGAGCACCAGCGTGGGCGACAGAGTGTCCATC

-continued

ACCTGTAAAGCCAGCCAGGACGTGTACACAGCCGTGGCCTGGTATCAGCAGAAGCCTGGCCAGT

CTCCTAAGCTGCTGATCTACAGCGCCAGCAACAGATACACCGGCGTGCCCGATAGATTCACAGG

CTCTGGCAGCGGCACCGACTTCACCTTTACAATCAGCAGCGTGCAGGCCGAGGACCTGGCCGTG

TATTATTGCCAGCAGCACTACACCACACCTCGGACCTTTGGCGGCGGAACAAAGCTGGAAATCA

AAGGCGGCGGAGGATCTGGCGGAGGTGGAAGCGGAGGCGGTGGTTCTATGGAACGGCACTGGAT

CTTTCTGCTGCTGCTGAGCGTTACAGCCGGCGCTCACTCTCAAGTGCATCTGCAGCAATCTGGC

GCCGAGCTTGCTAGACCTGGCGCCTCTGTGAAGATGAGCTGCAAGGCCAGCGGCTACATCTTCA

CCGACTACACCATGCACTGGGTCAAGCAGAGGCCTGGACAGGGACTCGAGTGGATCGGCCACAT

CAATCCTAGCTCCGGCTACAGCACCTACAACCAGAAGTTCAAGGACAAGGCCACACTGACCGCC

GACAAGAGCAGCTCTACAGCCTACATGCAGCTGAGCAGCCTGACCAGCGAAGATAGCGCCGTGT

ACTACTGCGCTAGAAGCCTGCAGCTGGGCAGAGATTATTGGGGCCAGGGCACAACCCTGACCGT

GTCATCTGctagcaccacgacgccagcgccgcgaccaccaacaccggcgcccaccatcgcgtcg cagcccctgtccctgcgcccagaggcgtgccggccagcggcggggggcgcagtgcacacgaggg ggctggacttcgcctgtgatatctacatctgggcgcccttggccgggacttgtggggtccttct cctgtcactggttatcaccctttactgcaaacggggcagaaagaaactcctgtatatattcaaa caaccatttatgagaccagtacaaactactcaagaggaagatggctgtagctgccgatttccag aagaagaagaaggaggatgtgaactgagagtgaagttcagcaggagcgcagacgcccccgcgta ccagcagggccagaaccagctctataacgagctcaatctaggacgaagagaggagtacgatgtt ttggacaagagacgtggccgggaccctgagatggggggaaagccgagaaggaagaaccctcagg aaggcctgtacaatgaactgcagaaagataagatggcggaggcctacagtgagattgggatgaa aggcgagcgccggaggggcaaggggcacgatggcctttaccagggtctcagtacagccaccaag gacacctacgacgcccttcacatgcaggccctgccccctcgctaa Vb11HL-BBz (SEQ ID NO: 25)

atggccttaccagtgaccgccttgctcctgccgctggccttgctgctccacgccgccaggccgg

GATCCATGGGCTGGTCCTGCATCATCTTTTTCTGGTGGCCACTGCCACCGGCGTGCACTCTCA

AGTTCAGCTGCAGCAGTCTGGCCCCGAAGTCGTTAGACCTGGCGTGTCCGTGAAGATCAGCTGC

AAAGGCAGCGGCTACCGGTTCACCGATTCTGCCATGCACTGGGTCAAGCAGAGCCACGCCAAGA

GCCTGGAATGGATCGGCGTGATCAGCAGCTACAACGGCAACACCAACTACAACCAGAAGTTCAA

GGGCAAAGCCACCATGACCGTGGACAAGAGCAGCAGCACCGCCTACATGGAACTGGCCAGAATG

ACCAGCGAGGACAGCGCCATCTACTACTGCGCCAGATCCAGAGATGCCATGGACTATTGGGGCC

AGGGCACCAGCGTGACAGTTTCTTCTGGCGGCGGAGGAAGCGGAGGCGGAGGTTCTGGTGGTGG

TGGCTCTATGAGAACCCCTGCTCAGTTCCTGGGCATCCTGCTGCTTTGGTTCCCCGGCATCAAG

TGCGACATCAAGATGACACAGAGCCCCAGCTCTATGTACGCCAGCCTGGGAGAGAGAGTGACCA

TTACCTGCAAGGCCAGCCAGGACATCAACAGCTACCTGAGCTGGTTCCAGCAGAAGGCCGGCAA

GAGCCCCAAGACACTGATCTACAGAGCCAACAGACTGGTGGACGGCGTGCCCAGCAGATTTTCT

GGAAGCGGCAGCGGCCAGGACTACAGCCTGACAATCAGCTCCCTGGAATACGAGGACATGGGGA

TCTACTATTGCCTGCAGTACGACGAGTTCCCATTCACCTTTGGCGGAGGCACCCGGCTGGAAAT

CAAAGctagcaccacgacgccagcgccgcgaccaccaacaccggcgcccaccatcgcgtcgcag cccctgtccctgcgcccagaggcgtgccggccagcggcggggggcgcagtgcacacgagggggc tggacttcgcctgtgatatctacatctgggcgcccttggccgggacttgtggggtccttctcct -continued gtcactggttatcacccctttactgcaaacggggcagaaagaaactcctgtatatattcaaacaa ccatttatgagaccagtacaaactactcaagaggaagatggctgtagctgccgatttccagaag aagaagaaggaggatgtgaactgagagtgaagttcagcaggagcgcagacgcccccgcgtacca gcagggccagaaccagctctataacgagctcaatctaggacgaagagaggagtacgatgttttg gacaagagacgtggccgggaccctgagatggggggaaagccgagaaggaagaaccctcaggaag gcctgtacaatgaactgcagaaagataagatggcggaggcctacagtgagattgggatgaaagg cgagcgccggaggggcaaggggcacgatggcctttaccagggtctcagtacagccaccaaggac acctacgacgcccttcacatgcaggccctgccccctcgctaa Vb11LH-BBz (SEQ ID NO: 26)

atggccttaccagtgaccgccttgctcctgccgctggccttgctgctccacgccgccaggccgg

GATCCATGAGAACCCCTGCTCAGTTCCTGGGCATCCTGCTGCTTTGGTTCCCCGGCATCAAGTG

CGACATCAAGATGACACAGAGCCCCAGCTCTATGTACGCCAGCCTGGGAGAGAGAGTGACCATT

ACCTGCAAGGCCAGCCAGGACATCAACAGCTACCTGAGCTGGTTCCAGCAGAAGGCCGGCAAGA

GCCCCAAGACACTGATCTACAGAGCCAACAGACTGGTGGACGGCGTGCCCAGCAGATTTTCTGG

CTCTGGAAGCGGCCAGGACTACAGCCTGACAATCAGCAGCCTGGAATACGAGGACATGGGCATC

TACTACTGCCTGCAGTACGACGAGTTCCCATTCACCTTTGGCGGCGGAACCCGGCTGGAAATCA

AAGGTGGCGGAGGATCTGGCGGAGGCGGATCAGGCGGCGGTGGATCTATGGGCTGGTCCTGCAT

CATCTTTTTTCTGGTGGCCACTGCCACCGGCGTGCACTCTCAAGTTCAGCTGCAGCAGTCTGGC

CCCGAAGTCGTTAGACCTGGCGTGTCCGTGAAGATCAGCTGCAAAGGCAGCGGCTACCGGTTCA

CCGATTCTGCCATGCACTGGGTCAAGCAGAGCCACGCCAAGTCTCTGGAATGGATCGGCGTGAT

CAGCAGCTACAACGGCAACACCAACTACAACCAGAAGTTCAAGGGCAAAGCCACCATGACCGTG

GACAAGAGCAGCAGCACCGCCTACATGGAACTGGCCAGAATGACCAGCGAGGACAGCGCCATCT

ATTACTGTGCCAGATCCAGGGACGCCATGGACTATTGGGGCCAGGGAACAAGCGTGACCGTGTC

CTCTGctagcaccacgacgccagcgccgcgaccaccaacaccggcgcccaccatcgcgtcgcag cccctgtccctgcgcccagaggcgtgccggccagcggcggggggcgcagtgcacacgagggggc tggacttcgcctgtgatatctacatctgggcgcccttggccgggacttgtggggtccttctcct gtcactggttatcacccctttactgcaaacggggcagaaagaaactcctgtatatattcaaacaa ccatttatgagaccagtacaaactactcaagaggaagatggctgtagctgccgatttccagaag aagaagaaggaggatgtgaactgagagtgaagttcagcaggagcgcagacgcccccgcgtacca gcagggccagaaccagctctataacgagctcaatctaggacgaagagaggagtacgatgttttg gacaagagacgtggccgggaccctgagatggggggaaagccgagaaggaagaaccctcaggaag gcctgtacaatgaactgcagaaagataagatggcggaggcctacagtgagattgggatgaaagg cgagcgccggaggggcaaggggcacgatggcctttaccagggtctcagtacagccaccaaggac acctacgacgcccttcacatgcaggccctgccccctcgctaa Vb13.2HL-BBz (SEQ ID NO: 27)

atggccttaccagtgaccgccttgctcctgccgctggccttgctgctccacgccgccaggccgg

GATCCATGGGCTGGTCCTGGATCTTCCTGTTTCTGCTGTCTGGCACAGCCGGCGTGCACTCTGA

AGTTCAGCTGCAGCAGTCTGGCCCCGAGCTTGTGAAACCTGGCGCCTCTGTGAAGATGAGCTGC

AACGCCAGCGGCTACACCTTCACCGACTACTACATCCACTGGCTGAAGCAGCGGCACGGCAAAG

GCCTGGAATGGATCGGCATCGTGAACACCAACAACGGCGACACCAACTACAACCAGCGGTTCAA

GGGCAAAGCCAGCCTGACCGTGGATAAGAGCAGCAGCACCGCCTACATGGAACTGAACTCCCTG

-continued

ACCAGCGAGGACAGCGCCGTGTTCTATTGTGCCAGGGCTCTGTACACCGGCAGCTATTGGTTCG
CCTATTGGGGCCAGGGCACCCTGGTTACAGTTTCTGCAGGCGGCGGAGGATCTGGCGGAGGTGG
AAGCGGAGGCGGTGGCTCTATGGATTTCCACGTGCAGATCTTCAGCTTCATGCTGATCTCCGTG
ACCGTGATGCTGTCCAGCGGAGAGATCGTGCTGACACAGTCTCCAGCCGTGATGGCTGCTTCCC
CTGGCGAGAAAGTGACCATCACATGTAGCGCCAGCAGCTCCATCAGCTCCACCAACCTGCACTG
GTATCAGCAGAAGTCCGAGACAAGCCCCAAGCCTTGGATCTACGGCACCAGCAATCTGGCCAGC
GGAGTGCCTGTCAGATTTTCTGGCAGCGGCTCTGGCACCAGCTACAGCCTGACAATCAGCAGCA
TCGAGGCCGAAGATGCCGCCACCTACTACTGCCAGCAGTGGTCCAGATATCCCCTGACATTTGG
CTCCGGCACCAAGCTGGAAATCATTGctagcaccacgacgccagcgccgcgaccaccaacaccg
gcgcccaccatcgcgtcgcagcccctgtccctgcgcccagaggcgtgccggccagcggcggggg
gcgcagtgcacacgagggggctggacttcgcctgtgatatctacatctgggcgcccttggccgg
gacttgtggggtccttctcctgtcactggttatcaccctttactgcaaacggggcagaaagaaa
ctcctgtatatattcaaacaaccatttatgagaccagtacaaactactcaagaggaagatggct
gtagctgccgatttccagaagaagaagaaggaggatgtgaactgagagtgaagttcagcaggag
cgcagacgcccccgcgtaccagcagggccagaaccagctctataacgagctcaatctaggacga
agagaggagtacgatgttttggacaagagacgtggccgggaccctgagatgggggaaagccga
gaaggaagaaccctcaggaaggcctgtacaatgaactgcagaaagataagatggcggaggccta
cagtgagattgggatgaaaggcgagcgccggaggggcaaggggcacgatggcctttaccagggt
ctcagtacagccaccaaggacacctacgacgcccttcacatgcaggccctgccccctcgctaa Vb13.2LH-BBz (SEQ ID NO: 28)

atggccttaccagtgaccgccttgctcctgccgctggccttgctgctccacgccgccaggccgg
GATCCATGGACTTCCACGTGCAGATCTTCAGCTTCATGCTGATCTCCGTGACCGTGATGCTGAG
CAGCGGAGAGATCGTGCTGACACAGTCTCCAGCCGTGATGGCTGCTTCCCCTGGCGAGAAAGTG
ACCATCACATGTAGCGCCAGCAGCAGCATCAGCAGCACCAACCTGCACTGGTATCAGCAGAAGT
CCGAGACAAGCCCCAAGCCTTGGATCTACGGCACCAGCAATCTGGCCAGCGGAGTGCCTGTCAG
ATTTTCTGGCAGCGGCTCTGGCACCAGCTACAGCCTGACAATCAGCTCCATCGAGGCCGAAGAT
GCCGCCACCTACTACTGCCAGCAGTGGTCCAGATATCCCCTGACATTCGGCAGCGGCACCAAGC
TGGAAATCATCGGAGGCGGAGGATCTGGTGGCGGAGGAAGCGGTGGCGGCGGATCTATGGGATG
GTCCTGGATCTTCCTGTTCCTGCTGTCTGGAACAGCCGGCGTGCACTCTGAAGTTCAGCTGCAG
CAGTCTGGCCCCGAGCTTGTGAAACCTGGCGCCTCTGTGAAGATGAGCTGCAACGCCAGCGGCT
ACACCTTCACCGACTACTACATCCACTGGCTGAAGCAGAGACACGGCAAAGGCCTGGAATGGAT
CGGCATCGTGAACACCAACAACGGCGACACCAACTACAACCAGCGGTTCAAGGGCAAAGCCAGC
CTGACCGTGGATAAGAGCAGCTCCACCGCCTACATGGAACTGAACTCCCTGACCAGCGAGGACA
GCGCCGTGTTCTATTGTGCCAGGGCTCTGTACACCGGCAGCTATTGGTTCGCCTATTGGGGCCA
GGGCACCCTGGTTACAGTTTCTGCTGctagcaccacgacgccagcgccgcgaccaccaacaccg
gcgcccaccatcgcgtcgcagcccctgtccctgcgcccagaggcgtgccggccagcggcggggg
gcgcagtgcacacgagggggctggacttcgcctgtgatatctacatctgggcgcccttggccgg
gacttgtggggtccttctcctgtcactggttatcaccctttactgcaaacggggcagaaagaaa
ctcctgtatatattcaaacaaccatttatgagaccagtacaaactactcaagaggaagatggct
gtagctgccgatttccagaagaagaagaaggaggatgtgaactgagagtgaagttcagcaggag -continued cgcagacgcccccgcgtaccagcagggccagaaccagctctataacgagctcaatctaggacga agagaggagtacgatgttttggacaagagacgtggccgggaccctgagatgggggggaaagccgaa gaaggaagaaccctcaggaaggcctgtacaatgaactgcagaaagataagatggcggaggccta cagtgagattgggatgaaaggcgagcgccggaggggcaaggggcacgatggcctttaccagggt ctcagtacagccaccaaggacacctacgacgcccttcacatgcaggccctgccccctcgctaa Vb13.3HL-BBz (SEQ ID NO: 29)

atggccttaccagtgaccgccttgctcctgccgctggccttgctgctccacgccgccaggccgg

GATCCATGGGCTGGTCCTGCATCATCCTGATTCTGGTGGCTGCCGCTACAGGCGTGCACTCTCA

GGTTCAGCTTCAGCAGCCTGGCGCCGAGCTTGTGAAACCTGGCGCCTCTGTGAAGATGAGCTGC

AAGGCCAGCGGCTACACCTTCACCAGCTACTGGATCACCTGGGTCAAGCAGAGGCCTGGACAGG

GACTCGAGTGGATCGGCGATATCTATCCTGGCAGCGGCAGCATCAACTACAACGAGAAGTTCAA

CAACAAGGCCACACTGACCGTGGACACCAGCAGCAGCACAGCCTACATGCAGCTGAGCAGCCTG

ACCAGCGAAGATAGCGCCGTGTACTACTGCGCCAGACGGGACTACTACAGCCTGTACTACTATG

CCCTGGACTACTGGGGCCAGGGCACAAGCGTGACAGTTTCTTCTGGCGGCGGAGGATCTGGCGG

AGGTGGAAGCGGAGGCGGTGGATCTATGTCTGTGCCTACACAGGTGCTGGGCCTGCTGCTTCTG

TGGTTGACAGGCGCCAGATGCGACATCCAGATGACACAGAGCCCTGCCAGCCTGAGTGCCTCTG

TGGGAGAGACAGTGACCATGACCTGTCGGGCCAGCGAGAACATCTACAGCAACCTGGCCTGGTA

TCAGCAGAAGCAGGGCAAGTCTCCTCAGCTGCTGGTCTACGCCGCCACCAATCTTGCTGATGGC

GTGCCCAGCAGATTCAGCGTGTCCGGATCTGGCACCCACTTCAGCCTGAAGATCAACAGCCTGC

AGCCAGAGGACTTCGGCAGCTACTACTGCCAGCACTTCTACGGCACCCCTTACACCTTTGGCGG

AGGCACCAAGCTGGAAATCAAGGctagcaccacgacgccagcgccgcgaccaccaacaccggcg cccaccatcgcgtcgcagcccctgtccctgcgcccagaggcgtgccggccagcggcggggggcg cagtgcacacgagggggctggacttcgcctgtgatatctacatctgggcgcccttggccgggac ttgtggggtccttctcctgtcactggttatcaccctttactgcaaacggggcagaaagaaactc ctgtatatattcaaacaaccatttatgagaccagtacaaactactcaagaggaagatggctgta gctgccgatttccagaagaagaagaaggaggatgtgaactgagagtgaagttcagcaggagcgc agacgcccccgcgtaccagcagggccagaaccagctctataacgagctcaatctaggacgaaga gaggagtacgatgttttggacaagagacgtggccgggaccctgagatgggggggaaagccgagaa ggaagaaccctcaggaaggcctgtacaatgaactgcagaaagataagatggcggaggcctacag tgagattgggatgaaaggcgagcgccggaggggcaaggggcacgatggcctttaccagggtctc agtacagccaccaaggacacctacgacgcccttcacatgcaggccctgccccctcgctaa Vb13.3LH-BBz (SEQ ID NO: 30)

atggccttaccagtgaccgccttgctcctgccgctggccttgctgctccacgccgccaggccgg

GATCCATGAGCGTGCCAACACAGGTTCTGGGACTGCTGCTGCTGTGGCTGACAGGCGCCAGATG

CGACATCCAGATGACACAGAGCCCTGCCAGCCTGTCTGCCTCTGTGGGAGAGACAGTGACCATG

ACCTGTCGGGCCAGCGAGAACATCTACAGCAACCTGGCCTGGTATCAGCAGAAGCAGGGCAAGT

CTCCTCAGCTGCTGGTGTACGCCGCCACCAATCTTGCTGATGGCGTGCCCAGCAGATTCAGCGT

GTCCGGATCTGGCACCCACTTCAGCCTGAAGATCAACAGCCTGCAGCCTGAGGACTTCGGCAGC

TACTACTGCCAGCACTTCTACGGCACCCCTTACACCTTTGGCGGAGGCACCAAGCTGGAAATCA

AAGGCGGCGGAGGAAGCGGAGGCGGAGGATCTGGTGGTGGTGGATCTATGGGCTGGTCCTGCAT

CATCCTGATCCTGGTGGCTGCTGCTACAGGCGTGCACTCTCAGGTTCAGCTGCAACAGCCAGGC

-continued

GCCGAGCTTGTGAAACCTGGCGCCTCTGTGAAGATGAGCTGCAAGGCCAGCGGCTACACCTTCA

CCAGCTACTGGATCACCTGGGTCAAGCAGAGGCCTGGACAGGGACTCGAGTGGATCGGCGATAT

CTATCCTGGCAGCGGCAGCATCAACTACAACGAGAAGTTCAACAACAAGGCCACACTGACCGTG

GACACCAGCTCTAGCACAGCCTACATGCAGCTGAGCAGCCTGACCAGCGAAGATAGCGCCGTGT

ACTACTGCGCCAGACGGGACTACTACAGCCTGTACTACTATGCCCTGGACTACTGGGGCCAGGG

CACAAGCGTGACAGTCTCTTCTGctagcaccacgacgccagcgccgcgaccaccaacaccggcg cccaccatcgcgtcgcagcccctgtccctgcgcccagaggcgtgccggccagcggcgggggggcg cagtgcacacgagggggctggacttcgcctgtgatatctacatctgggcgcccttggccgggac ttgtggggtccttctcctgtcactggttatcaccctttactgcaaacggggcagaaagaaactc ctgtatatattcaaacaaccatttatgagaccagtacaaactactcaagaggaagatggctgta gctgccgatttccagaagaagaagaaggaggatgtgaactgagagtgaagttcagcaggagcgc agacgcccccgcgtaccagcagggccagaaccagctctataacgagctcaatctaggacgaaga gaggagtacgatgttttggacaagagacgtggccgggaccctgagatggggggaaagccgagaa ggaagaaccctcaggaaggcctgtacaatgaactgcagaaagataagatggcggaggcctacag tgagattgggatgaaaggcgagcgccggaggggcaaggggcacgatggcctttaccagggtctc agtacagccaccaaggacacctacgacgcccttcacatgcaggccctgccccctcgctaa Vb22HL-BBz (SEQ ID NO: 31)

atggccttaccagtgaccgccttgctcctgccgctggccttgctgctccacgccgccaggccgg

GATCCATGGACTTCGGCCTGATCTTCTTCATCGTGGCCCTGCTGAAAGGCGTGCAGTGCGAAGT

GAAGCTGCTGGAATCTGGCGGAGGACTGGTTCAGCCTGGCGGATCTCTGAAGCTGTCTTGTGCC

GCCAGCGGCTTCGACTTCAGCCGGTACTGGATGAACTGGGTCCGACAGGCCCCTGGCAAAGGCC

TGGAATGGATCGGCGAGATCAACAGCGACAGCAACACCATCAACTACACCCCTAGCCTGAAGGA

CAAGTTCATCATCAGCCGGGACAACGCCAAGAACACCCTGTACCTGCAGATGAACAAAGTGCGG

AGCGAGGACACAGCCCTGTACTACTGTGCTAGAGGCGGCCTGCTGAGAGATGTGTGGGGAGCTG

GAACCACCGTGACAGTTTCTAGCGGAGGCGGAGGTTCTGGCGGCGGAGGAAGTGGTGGCGGAGG

CTCTATGGCTTGGATCTCCCTGATCCTGTCTCTGCTGGCCCTTAGCTCTGGCGCCATTTCTCAG

GCCGTGGTCACACAAGAGAGCGCCCTGACAACAAGCCCTGGCGAGACAGTGACCCTGACCTGTA

GATCTTCTACAGGCGCCGTGACCACCAGCAACTACGCCAATTGGGTGCAAGAGAAGCCCGACCA

CCTGTTCACAGGACTGATCGGCGGCACCAACAATAGAGCACCTGGCGTGCCAGCCAGATTCAGC

GGTTCTCTGATCGGAGACAGAGCCGCACTGACAATCACAGGCGCCCAGACAGAGGACGAGGCCA

TCTACTTTTGCGCCCTGTGGTACAGCAACCACTGGGTTTTCGGCGGAGGCACCAAGCTGACAGT

TCTGGctagcaccacgacgccagcgccgcgaccaccaacaccggcgcccaccatcgcgtcgcag cccctgtccctgcgcccagaggcgtgccggccagcggcggggggcgcagtgcacacgagggggc tggacttcgcctgtgatatctacatctgggcgcccttggccgggacttgtggggtccttctcct gtcactggttatcaccctttactgcaaacggggcagaaagaaactcctgtatatattcaaacaa ccatttatgagaccagtacaaactactcaagaggaagatggctgtagctgccgatttccagaag aagaagaaggaggatgtgaactgagagtgaagttcagcaggagcgcagacgcccccgcgtacca gcagggccagaaccagctctataacgagctcaatctaggacgaagagaggagtacgatgttttg gacaagagacgtggccgggaccctgagatggggggaaagccgagaaggaagaaccctcaggaag gcctgtacaatgaactgcagaaagataagatggcggaggcctacagtgagattgggatgaaagg -continued cgagcgccggaggggcaaggggcacgatggcctttaccagggtctcagtacagccaccaaggac acctacgacgcccttcacatgcaggccctgccccctcgctaa Vb22LH-BBz (SEQ ID NO: 32)

atggccttaccagtgaccgccttgctcctgccgctggccttgctgctccacgccgccaggccgg

GATCCATGGCCTGGATTAGCCTGATCCTGTCTCTGCTGGCCCTGTCTAGCGGAGCCATTTCTCA

GGCCGTGGTCACACAAGAGAGCGCCCTGACAACAAGCCCTGGCGAGACAGTGACCCTGACCTGC

AGATCTTCTACAGGCGCCGTGACCACCAGCAACTACGCCAATTGGGTGCAAGAGAAGCCCGACC

ACCTGTTCACAGGACTGATCGGCGGCACCAACAATAGAGCACCTGGCGTGCCAGCCAGATTCAG

CGGATCTCTGATCGGAGACAGAGCCGCACTGACAATCACAGGCGCCCAGACAGAGGACGAGGCC

ATCTACTTTTGCGCCCTGTGGTACAGCAACCACTGGGTTTTCGGCGGAGGCACCAAGCTGACAG

TTCTTGGAGGCGGAGGATCTGGCGGAGGTGGAAGTGGCGGAGGCGGCTCTATGGATTTCGGCCT

GATCTTCTTCATCGTGGCCCTGCTGAAAGGCGTGCAGTGCGAAGTGAAGCTGCTGGAATCTGGT

GGCGGACTGGTTCAGCCTGGCGGCTCTCTGAAACTGTCTTGTGCCGCCAGCGGCTTCGACTTCA

GCCGGTACTGGATGAACTGGGTCCGACAGGCCCCTGGCAAAGGCCTGGAATGGATCGGCGAGAT

CAACAGCGACAGCAACACCATCAACTACACCCCTAGCCTGAAGGACAAGTTCATCATCAGCCGG

GACAACGCCAAGAACACACTGTACCTCCAGATGAACAAAGTGCGGAGCGAGGACACAGCCCTGT

ACTACTGTGCTAGAGGCGGCCTGCTGAGAGATGTGTGGGGAGCTGGAACCACCGTGACCGTTAG

TTCTGctagcaccacgacgccagcgccgcgaccaccaacaccggcgcccaccatcgcgtcgcag cccctgtccctgcgcccagaggcgtgccggccagcggcggggggcgcagtgcacacgagggggc tggacttcgcctgtgatatctacatctgggcgcccttggccgggacttgtggggtccttctcct gtcactggttatcaccctttactgcaaacggggcagaaagaaactcctgtatatattcaaacaa ccatttatgagaccagtacaaactactcaagaggaagatggctgtagctgccgatttccagaag aagaagaaggaggatgtgaactgagagtgaagttcagcaggagcgcagacgcccccgcgtacca gcagggccagaaccagctctataacgagctcaatctaggacgaagagaggagtacgatgttttg gacaagagacgtggccgggaccctgagatggggggaaagccgagaaggaagaaccctcaggaag gcctgtacaatgaactgcagaaagataagatggcggaggcctacagtgagattgggatgaaagg cgagcgccggaggggcaaggggcacgatggcctttaccagggtctcagtacagccaccaaggac acctacgacgcccttcacatgcaggccctgccccctcgctaa Amino acid sequences of CARs:

Vb12HL-28z (SEQ ID NO: 153)

EVMLVESGGGLVKPGGSLKLSCAASGFTFRSYAMSWVRQTPEKRLEWVATISSGGSYTNYPDSV

KGRFTISRDNAKNTLNLQMNSLRSEDTAMYYCARGYHGYLDVWGAGTTVTVSSGGGGSGGGGSG

GGGSDILLTQSPAFLSVSPGERVSFSCRASQSIGTSIHWYQQRTNGSPRLLIKYASESFSGIPS

RFSGSGSGTDFTLSISSVESEDIADYYCQQSYSWPYTFGGGTKLEIKASTTTPAPRPPTPAPTI

ASQPLSLRPEACRPAAGGAVHTRGLDFACDFWVLVVVGGVLACYSLLVTVAFIIFWVRSKRSRL

LHSDYMNMTPRRPGPTRKHYQPYAPPRDFAAYRSIDRVKFSRSADAPAYQQGQNQLYNELNLGR

REEYDVLDKRRGRDPEMGGKPRRKNPQEGLYNELQKDKMAEAYSEIGMKGERRRGKGHDGLYQG

LSTATKDTYDALHMQALPPR

Vb12HL-BBz (SEQ ID NO: 154)

EVMLVESGGGLVKPGGSLKLSCAASGFTFRSYAMSWVRQTPEKRLEWVATISSGGSYTNYPDSV

KGRFTISRDNAKNTLNLQMNSLRSEDTAMYYCARGYHGYLDVWGAGTTVTVSSGGGGSGGGGSG

-continued

GGGSDILLTQSPAFLSVSPGERVSFSCRASQSIGTSIHWYQQRTNGSPRLLIKYASESFSGIPS

RFSGSGSGTDFTLSISSVESEDIADYYCQQSYSWPYTFGGGTKLEIKASTTTPAPRPPTPAPTI

ASQPLSLRPEACRPAAGGAVHTRGLDFACDIYIWAPLAGTCGVLLLSLVITLYCKRGRKKLLYI

FKQPFMRPVQTTQEEDGCSCRFPEEEEGGCELRVKFSRSADAPAYKQGQNQLYNELNLGRREEY

DVLDKRRGRDPEMGGKPRRKNPQEGLYNELQKDKMAEAYSEIGMKGERRRGKGHDGLYQGLSTA

TKDTYDALHMQALPPR

Vb12HL-Dz (SEQ ID NO: 155)

EVMLVESGGGLVKPGGSLKLSCAASGFTFRSYAMSWVRQTPEKRLEWVATISSGGSYTNYPDSV

KGRFTISRDNAKNTLNLQMNSLRSEDTAMYYCARGYHGYLDVWGAGTTVTVSSGGGGSGGGGSG

GGGSDILLTQSPAFLSVSPGERVSFSCRASQSIGTSIHWYQQRTNGSPRLLIKYASESFSGIPS

RFSGSGSGTDFTLSISSVESEDIADYYCQQSYSWPYTFGGGTKLEIKASTTTPAPRPPTPAPTI

ASQPLSLRPEACRPAAGGAVHTRGLDFACDFWVLVVVGGVLACYSLLVTVAFIIFWVRSKRS

Vb12LH-28z (SEQ ID NO: 156)

DILLTQSPAFLSVSPGERVSFSCRASQSIGTSIHWYQQRTNGSPRLLIKYASESFSGIPSRFSG

SGSGTDFTLSISSVESEDIADYYCQQSYSWPYTFGGGTKLEIKGGGGSGGGGSGGGGSEVMLVE

SGGGLVKPGGSLKLSCAASGFTFRSYAMSWVRQTPEKRLEWVATISSGGSYTNYPDSVKGRFTI

SRDNAKNTLNLQMNSLRSEDTAMYYCARGYHGYLDVWGAGTTVTVSSASTTTPAPRPPTPAPTI

ASQPLSLRPEACRPAAGGAVHTRGLDFACDFWVLVVVGGVLACYSLLVTVAFIIFWVRSKRSRL

LHSDYMNMTPRRPGPTRKHYQPYAPPRDFAAYRSIDRVKFSRSADAPAYQQGQNQLYNELNLGR

REEYDVLDKRRGRDPEMGGKPRRKNPQEGLYNELQKDKMAEAYSEIGMKGERRRGKGHDGLYQG

LSTATKDTYDALHMQALPPR

Vb12LH-BBz (SEQ ID NO: 157)

DILLTQSPAFLSVSPGERVSFSCRASQSIGTSIHWYQQRTNGSPRLLIKYASESFSGIPSRFSG

SGSGTDFTLSISSVESEDIADYYCQQSYSWPYTFGGGTKLEIKGGGGSGGGGSGGGGSEVMLVE

SGGGLVKPGGSLKLSCAASGFTFRSYAMSWVRQTPEKRLEWVATISSGGSYTNYPDSVKGRFTI

SRDNAKNTLNLQMNSLRSEDTAMYYCARGYHGYLDVWGAGTTVTVSSASTTTPAPRPPTPAPTI

ASQPLSLRPEACRPAAGGAVHTRGLDFACDIYIWAPLAGTCGVLLLSLVITLYCKRGRKKLLYI

FKQPFMRPVQTTQEEDGCSCRFPEEEEGGCELRVKFSRSADAPAYKQGQNQLYNELNLGRREEY

DVLDKRRGRDPEMGGKPRRKNPQEGLYNELQKDKMAEAYSEIGMKGERRRGKGHDGLYQGLSTA

TKDTYDALHMQALPPR

Vb12LH-Dz (SEQ ID NO: 158)

DILLTQSPAFLSVSPGERVSFSCRASQSIGTSIHWYQQRTNGSPRLLIKYASESFSGIPSRFSG

SGSGTDFTLSISSVESEDIADYYCQQSYSWPYTFGGGTKLEIKGGGGSGGGGSGGGGSEVMLVE

SGGGLVKPGGSLKLSCAASGFTFRSYAMSWVRQTPEKRLEWVATISSGGSYTNYPDSVKGRFTI

SRDNAKNTLNLQMNSLRSEDTAMYYCARGYHGYLDVWGAGTTVTVSSASTTTPAPRPPTPAPTI

ASQPLSLRPEACRPAAGGAVHTRGLDFACDFWVLVVVGGVLACYSLLVTVAFIIFWVRSKRS*

Vb9HL-28z (SEQ ID NO: 159)

MKFSWVIFFLMAVVTGVNSEVQLQQSVAELVRPGASVKLSCTASGFNIKNTFMHWVKQRPEQGL

EWIGRIDPTNGYTKFAPKFQGKATLTAVTSSNTVYLQLSSLTSEDTAIYYCAHDYDAPWFAYWG

QGTLVIVSAGGGGSGGGGSGGGGSMLSPAPLLSLLLLCVSDSRAETTVTQSPASLSVATGEKVT

IRCISSTDIDDDMNWYQQKSGEPPKLLISEGNTLRPGVPSRFSSSGYGTDFVFTIENMLSEDVA

-continued

DYYCLQSDNMPLTFGAGTKLELKASTTTPAPRPPTPAPTIASQPLSLRPEACRPAAGGAVHTRG

LDFACDFWVLVVVGGVLACYSLLVTVAFIIFWVRSKRSRLLHSDYMNMTPRRPGPTRKHYQPYA

PPRDFAAYRSIDRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR

Vb9HL-BBz (SEQ ID NO: 160)

MKFSWVIFFLMAVVTGVNSEVQLQQSVAELVRPGASVKLSCTASGFNIKNTFMHWVKQRPEQGL

EWIGRIDPTNGYTKFAPKFQGKATLTAVTSSNTVYLQLSSLTSEDTAIYYCAHDYDAPWFAYWG

QGTLVIVSAGGGGSGGGGSGGGGSMLSPAPLLSLLLLCVSDSRAETTVTQSPASLSVATGEKVT

IRCISSTDIDDDMNWYQQKSGEPPKLLISEGNTLRPGVPSRFSSSGYGTDFVFTIENMLSEDVA

DYYCLQSDNMPLTFGAGTKLELKASTTTPAPRPPTPAPTIASQPLSLRPEACRPAAGGAVHTRG

LDFACDIYIWAPLAGTCGVLLLSLVITLYCKRGRKKLLYIFKQPFMRPVQTTQEEDGCSCRFPE

EEEGGCELRVKFSRSADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHMQALPPR

VB9HL-Dz (SEQ ID NO: 161)

DILLTQSPAFLSVSPGERVSFSCRASQSIGTSIHWYQQRTNGSPRLLIKYASESFSGIPSRFSG

SGSGTDFTLSISSVESEDIADYYCQQSYSWPYTFGGGTKLEIKGGGGSGGGGSGGGGSEVMLVE

SGGGLVKPGGSLKLSCAASGFTFRSYAMSWVRQTPEKRLEWVATISSGGSYTNYPDSVKGRFTI

SRDNAKNTLNLQMNSLRSEDTAMYYCARGYHGYLDVWGAGTTVTVSSASTTTPAPRPPTPAPTI

ASQPLSLRPEACRPAAGGAVHTRGLDFACDFWVLVVVGGVLACYSLLVTVAFIIFWVRSKRSRL

LHSDYMNMTPRRPGPTRKHYQPYAPPRDFAAYRSIDRVKFSRSADAPAYQQGQNQLYNELNLGR

REEYDVLDKRRGRDPEMGGKPRRKNPQEGLYNELQKDKMAEAYSEIGMKGERRRGKGHDGLYQG

LSTATKDTYDALHMQALPPR

Vb9LH-28z (SEQ ID NO: 162)

MLSPAPLLSLLLLCVSDSRAETTVTPSPASLSVATGEKVTIRCISSTDIDDDMNWYPPKSGEPP

KLLISEGNTLRPGVPSRFSSSGYGTDFVFTIENMLSEDVADYYCLPSDNMPLTFGAGTKLELKG

GGGSGGGGSGGGGSMKFSWVIFFLMAVVTGVNSEVPLPPSVAELVRPGASVKLSCTASGFNIKN

TFMHWVKPRPEPGLEWIGRIDPTNGYTKFAPKFPGKATLTAVTSSNTVYLPLSSLTSEDTAIYY

CAHDYDAPWFAYWGPGTLVIVSAASTTTPAPRPPTPAPTIASPPLSLRPEACRPAAGGAVHTRG

LDFACDFWVLVVVGGVLACYSLLVTVAFIIFWVRSKRSRLLHSDYMNMTPRRPGPTRKHYPPYA

PPRDFAAYRSIDRVKFSRSADAPAYPPGPNPLYNELNLGRREEYDVLDKRRGRDPEMGGKPRRK

NPPEGLYNELPKDKMAEAYSEIGMKGERRRGKGHDGLYPGLSTATKDTYDALHMPALPPR

Vb9LH-BBz (SEQ ID NO: 163)

MLSPAPLLSLLLLCVSDSRAETTVTPSPASLSVATGEKVTIRCISSTDIDDDMNWYPPKSGEPP

KLLISEGNTLRPGVPSRFSSSGYGTDFVFTIENMLSEDVADYYCLPSDNMPLTFGAGTKLELKG

GGGSGGGGSGGGGSMKFSWVIFFLMAVVTGVNSEVPLPPSVAELVRPGASVKLSCTASGFNIKN

TFMHWVKPRPEPGLEWIGRIDPTNGYTKFAPKFPGKATLTAVTSSNTVYLPLSSLTSEDTAIYY

CAHDYDAPWFAYWGPGTLVIVSAASTTTPAPRPPTPAPTIASPPLSLRPEACRPAAGGAVHTRG

LDFACDIYIWAPLAGTCGVLLLSLVITLYCKRGRKKLLYIFKPPFMRPVPTTPEEDGCSCRFPE

EEEGGCELRVKFSRSADAPAYPPGPNPLYNELNLGRREEYDVLDKRRGRDPEMGGKPRRKNPPE

GLYNELPKDKMAEAYSEIGMKGERRRGKGHDGLYPGLSTATKDTYDALHMPALPPR

-continued

Vb9LH-Dz (SEQ ID NO: 164)

MLSPAPLLSLLLLCVSDSRAETTVTQSPASLSVATGEKVTIRCISSTDIDDDMNWYQQKSGEPP

KLLISEGNTLRPGVPSRFSSSGYGTDFVFTIENMLSEDVADYYCLQSDNMPLTFGAGTKLELKG

GGGSGGGGSGGGGSMKFSWVIFFLMAVVTGVNSEVQLQQSVAELVRPGASVKLSCTASGFNIKN

TFMHWVKQRPEQGLEWIGRIDPTNGYTKFAPKFQGKATLTAVTSSNTVYLQLSSLTSEDTAIYY

CAHDYDAPWFAYWGQGTLVIVSAASTTTPAPRPPTPAPTIASQPLSLRPEACRPAAGGAVHTRG

LDFACDFWVLVVVGGVLACYSLLVTVAFIIFWVRSKRS

Vb1HL-BBz (SEQ ID NO: 165)

MDWVWNLLFLMAVAQTGAQAQLQLVQSGPELREPGESVKISCKASGYTFTDYIVHWVKQAPGKG

LKWMGWINTYTGTPTYADDFEGRFVFSLEASASTANLQISNLKNEDTATYFCARSWRRGIRGIG

FDYWGQGVMVTVSSGGGGSGGGGSGGGGSMRVQIQFWGLLLLWTSGIQCDVQMTQSPYNLAASP

GESVSINCKASKSINKYLAWYQQKPGKPNKLLIYDGSTLQSGIPSRFSGSGSGTDFTLTIRGLE

PEDFGLYYCQQHNEYPPTFGAGTKLELKASTTTPAPRPPTPAPTIASQPLSLRPEACRPAAGGA

VHTRGLDFACDIYIWAPLAGTCGVLLLSLVITLYCKRGRKKLLYIFKQPFMRPVQTTQEEDGCS

CRFPEEEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPPR f (SEQ ID NO: 166)

MRVQIQFWGLLLLWTSGIQCDVQMTQSPYNLAASPGESVSINCKASKSINKYLAWYQQKPGKPN

KLLIYDGSTLQSGIPSRFSGSGSGTDFTLTIRGLEPEDFGLYYCQQHNEYPPTFGAGTKLELKG

GGGSGGGGSGGGGSMDWVWNLLFLMAVAQTGAQAQLQLVQSGPELREPGESVKISCKASGYTFT

DYIVHWVKQAPGKGLKWMGWINTYTGTPTYADDFEGRFVFSLEASASTANLQISNLKNEDTATY

FCARSWRRGIRGIGFDYWGQGVMVTVSSASTTTPAPRPPTPAPTIASQPLSLRPEACRPAAGGA

VHTRGLDFACDIYIWAPLAGTCGVLLLSLVITLYCKRGRKKLLYIFKQPFMRPVQTTQEEDGCS

CRFPEEEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPPR

Vb2HL-BBz (SEQ ID NO: 167)

MKFSWVIFFLMAVVTGVNSEVQLQQSVADLVRPGASLKLSCTASGFNIKSAYMHWVIQRPDQGP

ECLGRIDPATGKTKYAPKFQAKATITADTSSNTAYLQLSSLTSEDTAIYYCTRSLNWDYGLDYW

GQGTSVTVSSGGGGSGGGGSGGGGSMETDTLLLWVLLLWVPGSTGDIVLTQSPASLAVSLGQRA

TISCRASKSVSILGTHLIHWYQQKPGQPPKLLIYAASNLESGVPARFSGSGSETVFTLNIHPVE

EEDAATYFCQQSIEDPWTFGGGTKLGIKASTTTPAPRPPTPAPTIASQPLSLRPEACRPAAGGA

VHTRGLDFACDIYIWAPLAGTCGVLLLSLVITLYCKRGRKKLLYIFKQPFMRPVQTTQEEDGCS

CRFPEEEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPPR

Vb2LH-BBz (SEQ ID NO: 168)

METDTLLLWVLLLWVPGSTGDIVLTQSPASLAVSLGQRATISCRASKSVSILGTHLIHWYQQKP

GQPPKLLIYAASNLESGVPARFSGSGSETVFTLNIHPVEEEDAATYFCQQSIEDPWTFGGGTKL

GIKGGGGSGGGGSGGGGSMKFSWVIFFLMAVVTGVNSEVQLQQSVADLVRPGASLKLSCTASGF

NIKSAYMHWVIQRPDQGPECLGRIDPATGKTKYAPKFQAKATITADTSSNTAYLQLSSLTSEDT

AIYYCTRSLNWDYGLDYWGQGTSVTVSSASTTTPAPRPPTPAPTIASQPLSLRPEACRPAAGGA

VHTRGLDFACDIYIWAPLAGTCGVLLLSLVITLYCKRGRKKLLYIFKQPFMRPVQTTQEEDGCS

-continued

CRFPEEEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPPR

Vb4HL-BBz (SEQ ID NO: 169)

MEWSWIFLFLLSVTAVVHSQVQLQQSGAELAKPGTSVKLSCKASGYTFTSYYIYWVKQRPGQGL

EWLGYIYPGNGGTYYSEKFKGKATFTADTSSNTAYMLLGSLTPEDSAYYFCARGSGDRYNSLAY

WGQGTLVTVSSGGGGSGGGGSGGGGSMAIPTQLLGLLLLWITDAICDIQMTQSPHSLSASLGET

VSIECLASEGISNFLAWYQQKPGKSPQLLIYYTSSLQDGVPSRFSGSGSGTQYSLKISNMQPED

EGVYYCQQGYKFPRTFGGGTKLELKASTTTPAPRPPTPAPTIASQPLSLRPEACRPAAGGAVHT

RGLDFACDIYIWAPLAGTCGVLLLSLVITLYCKRGRKKLLYIFKQPFMRPVQTTQEEDGCSCRF

PEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

Vb4LH-BBz (SEQ ID NO: 170)

MAIPTQLLGLLLLWITDAICDIQMTQSPHSLSASLGETVSIECLASEGISNFLAWYQQKPGKSP

QLLIYYTSSLQDGVPSRFSGSGSGTQYSLKISNMQPEDEGVYYCQQGYKFPRTFGGGTKLELKG

GGGSGGGGSGGGGSMEWSWIFLFLLSVTAVVHSQVQLQQSGAELAKPGTSVKLSCKASGYTFTS

YYIYWVKQRPGQGLEWLGYIYPGNGGTYYSEKFKGKATFTADTSSNTAYMLLGSLTPEDSAYYF

CARGSGDRYNSLAYWGQGTLVTVSSASTTTPAPRPPTPAPTIASQPLSLRPEACRPAAGGAVHT

RGLDFACDIYIWAPLAGTCGVLLLSLVITLYCKRGRKKLLYIFKQPFMRPVQTTQEEDGCSCRF

PEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

Vb5.1HL-BBz (SEQ ID NO: 171)

MGWSWIFLFLLSETAGVLSEVQLQQSGPVLVKPGASVRMSCKASGYTFTDYNIHWVKQSHGRSL

EWVGYINPYNGRTGYNQKFKAKATLTVNKSSSTAYMDLRSLTSEDSAVYYCARWDGSSYFDYWG

QGTTLTVSSGGGGSGGGGSGGGGSMDFRVQIFSFLLISVTVSRGEIVLTQSPAITAASLGQKVT

ITCSASSSVSYMHWYQQKSGTSPKPWIYEISKLASGVPARFSGSGSGTSYSLTISSMEAEDAAI

YYCQQWNYPLITFGAGTKLELKASTTTPAPRPPTPAPTIASQPLSLRPEACRPAAGGAVHTRGL

DFACDIYIWAPLAGTCGVLLLSLVITLYCKRGRKKLLYIFKQPFMRPVQTTQEEDGCSCRFPEE

EEGGCELRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

Vb5.1LH-BBz (SEQ ID NO: 172)

MDFRVQIFSFLLISVTVSRGEIVLTQSPAITAASLGQKVTITCSASSSVSYMHWYQQKSGTSPK

PWIYEISKLASGVPARFSGSGSGTSYSLTISSMEAEDAAIYYCQQWNYPLITFGAGTKLELKGG

GGSGGGGSGGGGSMGWSWIFLFLLSETAGVLSEVQLQQSGPVLVKPGASVRMSCKASGYTFTDY

NIHWVKQSHGRSLEWVGYINPYNGRTGYNQKFKAKATLTVNKSSSTAYMDLRSLTSEDSAVYYC

ARWDGSSYFDYWGQGTTLTVSSASTTTPAPRPPTPAPTIASQPLSLRPEACRPAAGGAVHTRGL

DFACDIYIWAPLAGTCGVLLLSLVITLYCKRGRKKLLYIFKQPFMRPVQTTQEEDGCSCRFPEE

EEGGCELRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

-continued

Vb7.1HL-BBz (SEQ ID NO: 173)

MNFGLSLIFLVLFLKGVQCEVQLVESGGGLVKPGGSLKLSCAASGFTFSDYYMYWVRQTPEKRL

EWVATISGGGSYTYSPDSVKGRFTISRDNAKNNLYLQMSSLRSEDTAMYFCARERDIYYGNFNA

MVYWGRGTSVTVSSGGGGSGGGGSGGGGSMETDTLLLWVLLLWVPGSTGDIVLTQSPVSLTVSL

GQRATISCRASKSVSTSGYSYMHWYQQKPGQPPKLLIYLASNLESGVPARFSGSGSGTDFTLNI

HPVEEEDAATYYCQHSRDLPWTFGGGTKLEIKASTTTPAPRPPTPAPTIASQPLSLRPEACRPA

AGGAVHTRGLDFACDIYIWAPLAGTCGVLLLSLVITLYCKRGRKKLLYIFKQPFMRPVQTTQEE

DGCSCRFPEEEEGGCELRVKFSRSADAPAYQQGQNQLYNELNLGRREEYDVLDKRRGRDPEMGG

KPRRKNPQEGLYNELQKDKMAEAYSEIGMKGERRRGKGHDGLYQGLSTATKDTYDALHMQALPP

R

Vb7.1LH-BBz (SEQ ID NO: 174)

METDTLLLWVLLLWVPGSTGDIVLTQSPVSLTVSLGQRATISCRASKSVSTSGYSYMHWYQQKP

GQPPKLLIYLASNLESGVPARFSGSGSGTDFTLNIHPVEEEDAATYYCQHSRDLPWTFGGGTKL

EIKGGGGSGGGGSGGGGSMNFGLSLIFLVLFLKGVQCEVQLVESGGGLVKPGGSLKLSCAASGF

TFSDYYMYWVRQTPEKRLEWVATISGGGSYTYSPDSVKGRFTISRDNAKNNLYLQMSSLRSEDT

AMYFCARERDIYYGNFNAMVYWGRGTSVTVSSASTTTPAPRPPTPAPTIASQPLSLRPEACRPA

AGGAVHTRGLDFACDIYIWAPLAGTCGVLLLSLVITLYCKRGRKKLLYIFKQPFMRPVQTTQEE

DGCSCRFPEEEEGGCELRVKFSRSADAPAYQQGQNQLYNELNLGRREEYDVLDKRRGRDPEMGG

KPRRKNPQEGLYNELQKDKMAEAYSEIGMKGERRRGKGHDGLYQGLSTATKDTYDALHMQALPP

R

Vb7.2HL-BBz (SEQ ID NO: 175)

MERHWIFLLLLSVTAGAHSQVHLQQSGAELARPGASVKMSCKASGYIFTDYTMHWVKQRPGQGL

EWIGHINPSSGYSTYNQKFKDKATLTADKSSSTAYMQLSSLTSEDSAVYYCARSLQLGRDYWGQ

GTTLTVSSGGGGSGGGGSGGGGSMESQIQVFVFVFLWLSGVDGDIVMTQSHKFMSTSVGDRVSI

TCKASQDVYTAVAWYQQKPGQSPKLLIYSASNRYTGVPDRFTGSGSGTDFTFTISSVQAEDLAV

YYCQQHYTTPRTFGGGTKLEIKASTTTPAPRPPTPAPTIASQPLSLRPEACRPAAGGAVHTRGL

DFACDIYIWAPLAGTCGVLLLSLVITLYCKRGRKKLLYIFKQPFMRPVQTTQEEDGCSCRFPEE

EEGGCELRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

Vb7.2LH-BBz (SEQ ID NO: 176)

MESQIQVFVFVFLWLSGVDGDIVMTQSHKFMSTSVGDRVSITCKASQDVYTAVAWYQQKPGQSP

KLLIYSASNRYTGVPDRFTGSGSGTDFTFTISSVQAEDLAVYYCQQHYTTPRTFGGGTKLEIKG

GGGSGGGGSGGGGSMERHWIFLLLLSVTAGAHSQVHLQQSGAELARPGASVKMSCKASGYIFTD

YTMHWVKQRPGQGLEWIGHINPSSGYSTYNQKFKDKATLTADKSSSTAYMQLSSLTSEDSAVYY

CARSLQLGRDYWGQGTTLTVSSASTTTPAPRPPTPAPTIASQPLSLRPEACRPAAGGAVHTRGL

DFACDIYIWAPLAGTCGVLLLSLVITLYCKRGRKKLLYIFKQPFMRPVQTTQEEDGCSCRFPEE

EEGGCELRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

-continued

Vb11HL-BBz (SEQ ID NO: 177)
MGWSCIIFFLVATATGVHSQVQLQQSGPEVVRPGVSVKISCKGSGYRFTDSAMHWVKQSHAKSL
EWIGVISSYNGNTNYNQKFKGKATMTVDKSSSTAYMELARMTSEDSAIYYCARSRDAMDYWGQG
TSVTVSSGGGGSGGGGSGGGGSMRTPAQFLGILLLWFPGIKCDIKMTQSPSSMYASLGERVTIT
CKASQDINSYLSWFQQKAGKSPKTLIYRANRLVDGVPSRFSGSGSGQDYSLTISSLEYEDMGIY
YCLQYDEFPFTFGGGTRLEIKASTTTPAPRPPTPAPTIASQPLSLRPEACRPAAGGAVHTRGLD
FACDIYIWAPLAGTCGVLLLSLVITLYCKRGRKKLLYIFKQPFMRPVQTTQEEDGCSCRFPEEE
EGGCELRVKFSRSADAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR

Vb11LH-BBz (SEQ ID NO: 178)
MRTPAQFLGILLLWFPGIKCDIKMTQSPSSMYASLGERVTITCKASQDINSYLSWFQQKAGKSP
KTLIYRANRLVDGVPSRFSGSGSGQDYSLTISSLEYEDMGIYYCLQYDEFPFTFGGGTRLEIKG
GGGSGGGGSGGGGSMGWSCIIFFLVATATGVHSQVQLQQSGPEVVRPGVSVKISCKGSGYRFTD
SAMHWVKQSHAKSLEWIGVISSYNGNTNYNQKFKGKATMTVDKSSSTAYMELARMTSEDSAIYY
CARSRDAMDYWGQGTSVTVSSASTTTPAPRPPTPAPTIASQPLSLRPEACRPAAGGAVHTRGLD
FACDIYIWAPLAGTCGVLLLSLVITLYCKRGRKKLLYIFKQPFMRPVQTTQEEDGCSCRFPEEE
EGGCELRVKFSRSADAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR

Vb13.2HL-BBz (SEQ ID NO: 179)
MGWSWIFLFLLSGTAGVHSEVQLQQSGPELVKPGASVKMSCNASGYTFTDYYIHWLKQRHGKGL
EWIGIVNTNNGDTNYNQRFKGKASLTVDKSSSTAYMELNSLTSEDSAVFYCARALYTGSYWFAY
WGQGTLVTVSAGGGGSGGGGSGGGGSMDFHVQIFSFMLISVTVMLSSGEIVLTQSPAVMAASPG
EKVTITCSASSSISSTNLHWYQQKSETSPKPWIYGTSNLASGVPVRFSGSGSGTSYSLTISSIE
AEDAATYYCQQWSRYPLTFGSGTKLEIIASTTTPAPRPPTPAPTIASQPLSLRPEACRPAAGGA
VHTRGLDFACDIYIWAPLAGTCGVLLLSLVITLYCKRGRKKLLYIFKQPFMRPVQTTQEEDGCS
CRFPEEEEGGCELRVKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTYDALHMQALPPR

Vb13.2LH-BBz (SEQ ID NO: 180)
MDFHVQIFSFMLISVTVMLSSGEIVLTQSPAVMAASPGEKVTITCSASSSISSTNLHWYQQKSE
TSPKPWIYGTSNLASGVPVRFSGSGSGTSYSLTISSIEAEDAATYYCQQWSRYPLTFGSGTKLE
IIGGGGSGGGGSGGGGSMGWSWIFLFLLSGTAGVHSEVQLQQSGPELVKPGASVKMSCNASGYT
FTDYYIHWLKQRHGKGLEWIGIVNTNNGDTNYNQRFKGKASLTVDKSSSTAYMELNSLTSEDSA
VFYCARALYTGSYWFAYWGQGTLVTVSAASTTTPAPRPPTPAPTIASQPLSLRPEACRPAAGGA
VHTRGLDFACDIYIWAPLAGTCGVLLLSLVITLYCKRGRKKLLYIFKQPFMRPVQTTQEEDGCS
CRFPEEEEGGCELRVKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTYDALHMQALPPR

Vb13.3HL-BBz (SEQ ID NO: 181)
MGWSCIILILVAAATGVHSQVQLQQPGAELVKPGASVKMSCKASGYTFTSYWITWVKQRPGQGL
EWIGDIYPGSGSINYNEKFNNKATLTVDTSSSTAYMQLSSLTSEDSAVYYCARRDYYSLYYYAL
DYWGQGTSVTVSSGGGGSGGGGSGGGGSMSVPTQVLGLLLLWLTGARCDIQMTQSPASLSASVG

-continued

ETVTMTCRASENIYSNLAWYQQKQGKSPQLLVYAATNLADGVPSRFSVSGSGTHFSLKINSLQP

EDFGSYYCQHFYGTPYTFGGGTKLEIKASTTTPAPRPPTPAPTIASQPLSLRPEACRPAAGGAV

HTRGLDFACDIYIWAPLAGTCGVLLLSLVITLYCKRGRKKLLYIFKQPFMRPVQTTQEEDGCSC

RFPEEEEGGCELRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR

Vb13.3LH-BBz (SEQ ID NO: 182)

MSVPTQVLGLLLLWLTGARCDIQMTQSPASLSASVGETVTMTCRASENIYSNLAWYQQKQGKSP

QLLVYAATNLADGVPSRFSVSGSGTHFSLKINSLQPEDFGSYYCQHFYGTPYTFGGGTKLEIKG

GGGSGGGGSGGGGSMGWSCIILILVAAATGVHSQVQLQQPGAELVKPGASVKMSCKASGYTFTS

YWITWVKQRPGQGLEWIGDIYPGSGSINYNEKFNNKATLTVDTSSSTAYMQLSSLTSEDSAVYY

CARRDYYSLYYYALDYWGQGTSVTVSSASTTTPAPRPPTPAPTIASQPLSLRPEACRPAAGGAV

HTRGLDFACDIYIWAPLAGTCGVLLLSLVITLYCKRGRKKLLYIFKQPFMRPVQTTQEEDGCSC

RFPEEEEGGCELRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR

Vb22HL-BBz (SEQ ID NO: 183)

MDFGLIFFIVALLKGVQCEVKLLESGGGLVQPGGSLKLSCAASGFDFSRYWMNWVRQAPGKGLE

WIGEINSDSNTINYTPSLKDKFIISRDNAKNTLYLQMNKVRSEDTALYYCARGGLLRDVWGAGT

TVTVSSGGGGSGGGGSGGGGSMAWISLILSLLALSSGAISQAVVTQESALTTSPGETVTLTCRS

STGAVTTSNYANWVQEKPDHLFTGLIGGTNNRAPGVPARFSGSLIGDRAALTITGAQTEDEAIY

FCALWYSNHWVFGGGTKLTVLASTTTPAPRPPTPAPTIASQPLSLRPEACRPAAGGAVHTRGLD

FACDIYIWAPLAGTCGVLLLSLVITLYCKRGRKKLLYIFKQPFMRPVQTTQEEDGCSCRFPEEE

EGGCELRVKFSRSADAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR

Vb22LH-BBz (SEQ ID NO: 184)

MAWISLILSLLALSSGAISQAVVTQESALTTSPGETVTLTCRSSTGAVTTSNYANWVQEKPDHL

FTGLIGGTNNRAPGVPARFSGSLIGDRAALTITGAQTEDEAIYFCALWYSNHWVFGGGTKLTVL

GGGGSGGGGSGGGGSMDFGLIFFIVALLKGVQCEVKLLESGGGLVQPGGSLKLSCAASGFDFSR

YWMNWVRQAPGKGLEWIGEINSDSNTINYTPSLKDKFIISRDNAKNTLYLQMNKVRSEDTALYY

CARGGLLRDVWGAGTTVTVSSASTTTPAPRPPTPAPTIASQPLSLRPEACRPAAGGAVHTRGLD

FACDIYIWAPLAGTCGVLLLSLVITLYCKRGRKKLLYIFKQPFMRPVQTTQEEDGCSCRFPEEE

EGGCELRVKFSRSADAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Enumerated Embodiments

The following enumerated embodiments are provided, the numbering of which is not to be construed as designating levels of importance.

Embodiment 1 provides a nucleic acid encoding a chimeric antigen receptor (CAR), wherein the CAR comprises an extracellular domain that binds a Vβ region of a T cell receptor, a transmembrane domain, and an intracellular signaling domain, wherein the intracellular signaling domain comprises a costimulatory signaling region.

Embodiment 2 provides the nucleic acid of embodiment 1, wherein the extracellular domain that binds a Vβ region is selected from the group consisting of an antibody, a Fab, and a scFv.

Embodiment 3 provides the nucleic acid of embodiment 1, wherein the Vβ region is selected from the group consisting of Vβ1, Vβ2, Vβ4, Vβ5.1, Vβ7.1, Vβ7.2, Vβ9, Vβ11, Vβ12, Vβ13.2, Vβ13.3, and Vβ22.

Embodiment 4 provides the nucleic acid of embodiment 1, wherein the extracellular domain that binds a Vβ region of a T cell receptor comprises a complementarity determining region (CDR) comprising an amino acid sequence selected from the group consisting of SEQ ID NOs: 58-60, 62-64, 66-68, 70-72, 74-76, 78-80, 82-84, 86-88, 90-92, 94-96, 98-100, 102-104, 106-108, and 110-112.

Embodiment 5 provides the nucleic acid of embodiment 1, wherein the extracellular domain that binds a Vβ region of a T cell receptor comprises a heavy chain variable region (VH) comprising an amino acid sequence selected from the group consisting of SEQ ID NOs: 57, 65, 73, 81, 89, 97, 105, 113, 121, 129, 137, and 145.

Embodiment 6 provides the nucleic acid of embodiment 1, wherein the extracellular domain that binds a Vβ region of a T cell receptor comprises a light chain variable region (VL) comprising an amino acid sequence selected from the group consisting of SEQ ID NOs: 61, 69, 77, 85, 93, 101, 109, 117, 125, 133, 141, and 149.

Embodiment 7 provides the nucleic acid of embodiment 1, wherein the extracellular domain that binds a Vβ region of a T cell receptor comprises an scFv encoded by a nucleotide sequence selected from the group consisting of SEQ ID NOs: 33-56.

Embodiment 8 provides the nucleic acid of any of the preceding embodiments, wherein the costimulatory signaling region comprises the intracellular domain of a costimulatory molecule selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83.

Embodiment 9 provides the nucleic acid of any of the preceding embodiments, wherein the intracellular signaling domain comprises a CD3zeta chain.

Embodiment 10 provides the nucleic acid of any of the preceding embodiments, wherein the intracellular signaling domain comprises CD28 and CD3zeta.

Embodiment 11 provides the nucleic acid of any one of embodiments 1-7, wherein the intracellular signaling domain comprises 4-1BB and CD3zeta.

Embodiment 12 provides the nucleic acid of embodiment 1, wherein the CAR is encoded by a nucleotide sequence selected from the group consisting of SEQ ID NOs: 1-32.

Embodiment 13 provides the nucleic acid of embodiment 1, wherein the CAR comprises an amino acid sequence selected from the group consisting of SEQ ID NOs: 153-184.

Embodiment 14 provides a vector comprising the nucleic acid of any one of embodiments 1-13.

Embodiment 15 provides a CAR comprising an extracellular domain that binds a Vβ region of a T cell receptor, a transmembrane domain, and an intracellular signaling domain, wherein the intracellular signaling domain comprises a costimulatory signaling region.

Embodiment 16 provides the CAR of embodiment 15, wherein the extracellular domain that binds a Vβ region is selected from the group consisting of an antibody, a Fab, and an scFv.

Embodiment 17 provides the CAR of embodiment 15, wherein the Vβ region is selected from the group consisting of Vβ1, Vβ2, Vβ4, Vβ5.1, Vβ7.1, Vβ7.2, Vβ9, Vβ11, Vβ12, Vβ13.2, Vβ13.3, and Vβ22.

Embodiment 18 provides the CAR of embodiment 15, wherein the extracellular domain that binds a Vβ region comprises a CDR region comprising an amino acid sequence selected from the group consisting of SEQ ID NO: 58-60, 62-64, 66-68, 70-72, 74-76, 78-80, 82-84, 86-88, 90-92, 94-96, 98-100, 102-104, 106-108, and 110-112.

Embodiment 19 provides the CAR of embodiment 15, wherein the extracellular domain that binds a Vβ region comprises a VH region comprising an amino acid sequence selected from the group consisting of SEQ ID NOs: 57, 65, 73, 81, 89, 97, 105, 113, 121, 129, 137, and 145.

Embodiment 20 provides the CAR of embodiment 15, wherein the extracellular domain that binds a Vβ region comprises a VL region comprising an amino acid sequence selected from the group consisting of SEQ ID NOs: 61, 69, 77, 85, 93, 101, 109, 117, 125, 133, 141, and 149.

Embodiment 21 provides the CAR of embodiment 15, wherein the extracellular domain that binds a Vβ region comprises an scFv encoded by a nucleotide sequence selected from the group consisting of SEQ ID NO: SEQ ID NOs: 33-56.

Embodiment 22 provides the CAR of embodiment 15, wherein the costimulatory signaling region comprises the intracellular domain of a costimulatory molecule selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83.

Embodiment 23 provides the CAR of embodiment 15, wherein the intracellular signaling domain comprises a CD3zeta chain.

Embodiment 24 provides the CAR of embodiment 15, wherein the intracellular signaling domain comprises CD28 and CD3zeta.

Embodiment 25 provides the CAR of embodiment 15, wherein the intracellular signaling domain comprises 4-1BB and CD3zeta.

Embodiment 26 provides a modified T cell comprising the nucleic acid of any one of embodiments 1-14, the vector of embodiment 14, or the CAR of any one of embodiments 15-25.

Embodiment 27 provides a T cell genetically modified to express a recombinant T cell receptor, wherein the recombinant T cell receptor comprises a domain that binds a Vβ region of a T cell receptor.

Embodiment 28 provides the T cell of embodiment 27, wherein the domain that binds a Vβ region of a T cell receptor is an α/β heterodimer of the recombinant T cell receptor.

Embodiment 29 provides a method for treating cancer in a subject, the method comprising:

administering to the subject a therapeutically effective amount of a T cell comprising a CAR, wherein the CAR comprises an extracellular domain that binds a Vβ region of a T cell receptor, a transmembrane domain, and an intracellular signaling domain, wherein the intracellular signaling domain comprises a costimulatory signaling region.

Embodiment 30 provides the method of embodiment 29, wherein the cancer is selected from the group consisting of T-cell lymphoma, T-cell leukemia, cutaneous T-cell lymphoma, peripheral T-cell lymphoma (PTCL), not otherwise specified PTCL (PTCL-NOS), angioimmunoblastic T cell lymphoma (AITL), anaplastic large-cell lymphoma (ALCL), enteropathy-associated T-cell lymphoma (EATL), adult T-cell leukemia/lymphoma (ATLL), hepatosplenic T-cell lymphoma (HSTL), subcutaneous panniculitis-like T-cell lymphoma (SPTCL), and T cell acute lymphoblastic leukemia (T-ALL).

Embodiment 31 provides a method for treating a T-cell-associated disease in a subject in need thereof, the method comprising:

administering to the subject a therapeutically effective amount of a T cell comprising a CAR, wherein the CAR comprises an extracellular domain that binds a Vβ region of a T cell receptor, a transmembrane domain, and an intracellular signaling domain, wherein the intracellular signaling domain comprises a costimulatory signaling region.

Embodiment 32 provides the method of embodiment 31, wherein the T-cell-associated disease is an autoimmune disease.

Embodiment 33 provides the method of embodiment 32, wherein the autoimmune disease is selected from the group consisting of rheumatoid arthritis, inflammatory bowel disease, multiple sclerosis, insulin dependent diabetes mellitus, and Kawasaki disease.

Embodiment 34 provides the method of any one of embodiments 29-33, wherein the Vβ region is selected from the group consisting of Vβ1, Vβ2, Vβ4, Vβ5.1, Vβ7.1, Vβ7.2, Vβ9, Vβ11, Vβ12, Vβ13.2, Vβ13.3, and Vβ22.

Embodiment 35 provides the method of any one of claims 29-33, wherein the extracellular domain that binds a Vβ region comprises a CDR region comprising an amino acid sequence selected from the group consisting of SEQ ID NO: 58-60, 62-64, 66-68, 70-72, 74-76, 78-80, 82-84, 86-88, 90-92, 94-96, 98-100, 102-104, 106-108, and 110-112.

Embodiment 36 provides the method of any one of embodiments 29-33, wherein the extracellular domain that binds a Vβ region comprises a VH region comprising an amino acid sequence selected from the group consisting of SEQ ID NOs: 57, 65, 73, 81, 89, 97, 105, 113, 121, 129, 137, and 145.

Embodiment 37 provides the method of any one of embodiments 29-33, wherein the extracellular domain that binds a Vβ region comprises a VL region comprising an amino acid sequence selected from the group consisting of SEQ ID NOs: 61, 69, 77, 85, 93, 101, 109, 117, 125, 133, 141, and 149.

Embodiment 38 provides the method of any one of embodiments 29-33, wherein the extracellular domain that binds a Vβ region comprises an scFv encoded by a nucleotide sequence selected from the group consisting of SEQ ID NO: SEQ ID NOs: 33-56.

Embodiment 39 provides the method of any one of embodiments 29-33, wherein the costimulatory signaling region comprises the intracellular domain of a costimulatory molecule selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83.

Embodiment 40 provides the method of any one of embodiments 29-33, wherein the intracellular signaling domain comprises a CD3zeta chain.

Embodiment 41 provides the method of any one of embodiments 29-33, wherein the intracellular signaling domain comprises CD28 and CD3zeta.

Embodiment 42 provides the method of any one of embodiments 29-33, wherein the intracellular signaling domain comprises 4-1BB and CD3zeta.

Embodiment 43 provides a method for treating cancer in a subject, the method comprising administering to the subject an effective amount of an antibody-drug conjugate (ADC), wherein the ADC binds to a Vβ region of a T cell receptor.

Embodiment 44 provides the method of embodiment 43, wherein the cancer is selected from the group consisting of T-cell lymphoma, T-cell leukemia, cutaneous T-cell lymphoma, peripheral T-cell lymphoma (PTCL), not otherwise specified PTCL (PTCL-NOS), angioimmunoblastic T cell lymphoma (AITL), anaplastic large-cell lymphoma (ALCL), enteropathy-associated T-cell lymphoma (EATL), adult T-cell leukemia/lymphoma (ATLL), hepatosplenic T-cell lymphoma (HSTL), subcutaneous panniculitis-like T-cell lymphoma (SPTCL), and T cell acute lymphoblastic leukemia (T-ALL).

Embodiment 45 provides a method for treating cancer in a subject, the method comprising administering to the subject an effective amount of an antibody that binds to a Vβ region of a T cell receptor and a CD64-expressing immune cell.

Embodiment 46 provides the method of embodiment 45, wherein the cancer is selected from the group consisting of T-cell lymphoma, T-cell leukemia, cutaneous T-cell lymphoma, peripheral T-cell lymphoma (PTCL), not otherwise specified PTCL (PTCL-NOS), angioimmunoblastic T cell lymphoma (AITL), anaplastic large-cell lymphoma (ALCL), enteropathy-associated T-cell lymphoma (EATL), adult T-cell leukemia/lymphoma (ATLL), hepatosplenic T-cell lymphoma (HSTL), subcutaneous panniculitis-like T-cell lymphoma (SPTCL), and T cell acute lymphoblastic leukemia (T-ALL).

Embodiment 47 provides the method of embodiment 45, wherein the CD64-expressing immune cell is genetically engineered.

Embodiment 48 provides the method of embodiment 45, wherein the CD64-expressing immune cell is genetically engineered to express a fusion protein comprising CD64, a CD28 transmembrane domain, a CD3 zeta chain and a CD28 costimulatory domain.

Embodiment 49 provides a method for treating cancer in a subject, the method comprising administering to the subject an effective amount of a labeled antibody that binds to a Vβ region of a T cell receptor and a universal immune receptor (UIR)-expressing immune cell, wherein the universal immune receptor comprises an extracellular domain that specifically binds to the label.

Embodiment 50 provides the method of embodiment 49, wherein the labeled antibody is administered before the UIR-expressing immune cell.

Embodiment 51 provides the method of embodiment 49, wherein the labeled antibody is administered concurrent with the UIR-expressing immune cell.

Embodiment 52 provides the method of embodiment 49, wherein the UIR-expressing immune cell is bound to the labeled antibody prior to administration to the subject.

Embodiment 53 provides the method of embodiment 49, wherein the antibody is labeled with DOTA and the UIR-expressing immune cell comprises an scFv that specifically binds to DOTA.

Embodiment 54 provides the method of embodiment 49, wherein the Vβ region is selected from the group consisting of Vβ1, Vβ2, Vβ4, Vβ5.1, Vβ7.1, Vβ7.2, Vβ9, Vβ11, Vβ12, Vβ13.2, Vβ13.3, and Vβ22.

Embodiment 55 provides the method of embodiment 49, wherein the labeled antibody that binds to a Vβ region of a T cell receptor comprises a CDR region comprising an amino acid sequence selected from the group consisting of SEQ ID NO: 58-60, 62-64, 66-68, 70-72, 74-76, 78-80, 82-84, 86-88, 90-92, 94-96, 98-100, 102-104, 106-108, and 110-112.

Embodiment 56 provides the method of embodiment 49, wherein the labeled antibody that binds to a Vβ region of a T cell receptor comprises a VH region comprising an amino acid sequence selected from the group consisting of SEQ ID NOs: 57, 65, 73, 81, 89, 97, 105, 113, 121, 129, 137, and 145.

Embodiment 57 provides the method of embodiment 49, wherein the labeled antibody that binds to a Vβ region of a T cell receptor comprises a VL region comprising an amino acid sequence selected from the group consisting of SEQ ID NOs: 61, 69, 77, 85, 93, 101, 109, 117, 125, 133, 141, and 149.

Embodiment 58 provides the method of embodiment 49, wherein the cancer is selected from the group consisting of T-cell lymphoma, T-cell leukemia, cutaneous T-cell lymphoma, peripheral T-cell lymphoma (PTCL), not otherwise specified PTCL (PTCL-NOS), angioimmunoblastic T cell lymphoma (AITL), anaplastic large-cell lymphoma (ALCL), enteropathy-associated T-cell lymphoma (EATL), adult T-cell leukemia/lymphoma (ATLL), hepatosplenic T-cell lymphoma (HSTL), subcutaneous panniculitis-like T-cell lymphoma (SPTCL), and T cell acute lymphoblastic leukemia (T-ALL).

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention 5 has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A CAR comprising an extracellular domain that binds a Vβ region of a T cell receptor, a transmembrane domain, and an intracellular signaling domain, wherein the intracellular signaling domain comprises a costimulatory signaling region;
   - wherein the extracellular domain that binds a Vβ region is selected from the group consisting of an antibody, a Fab, and an scFv; and
   - wherein the extracellular domain comprises a light chain variable region (VL) comprising three light chain complementarity determining regions 1-3 (LCDR1-3) and a heavy chain variable region (VH) comprising three heavy chain complementarity determining regions 1-3 (HCDR1-3), and wherein the Vβ region is:
   - (a) Vβ12, wherein the LCDRs 1-3 comprise the sequences of SEQ ID NOs: 62-64, respectively, and the HCDRs 1-3 comprise the sequences of SEQ ID NOs: 58-60, respectively;
   - (b) Vβ5.1, wherein the LCDRs 1-3 comprise the sequences of SEQ ID NOs: 102-104, respectively, and the HCDRs 1-3 comprise the sequences of SEQ ID NOs: 98-100, respectively; or
   - (c) Vβ4, wherein the LCDRs 1-3 comprise the sequences of SEQ ID NOs: 94-96, respectively, and the HCDRs 1-3 comprise the sequences of SEQ ID NOs: 90-92, respectively.

2. The CAR of claim 1, wherein the Vβ region is Vβ12, wherein the LCDRs 1-3 comprise the sequences of SEQ ID NOs: 62-64, respectively, and the HCDRs 1-3 comprise the sequences of SEQ ID NOs: 58-60, respectively.

3. The CAR of claim 1, wherein the Vβ region is:
   - (a) Vβ12, wherein the VH and VL comprise the sequence of SEQ ID NO: 57 and 61, respectively;
   - (b) Vβ5.1, wherein the VH and VL comprise the sequence of SEQ ID NO: 97 and 101, respectively; or
   - (c) Vβ4, wherein the VH and VL comprise the sequence of SEQ ID NO: 89 and 93, respectively.

4. The CAR of claim 1, wherein the extracellular domain comprises an scFv encoded by a nucleotide sequence, wherein the Vβ region is
   - (a) Vβ12, wherein the nucleotide sequence comprises the sequence of SEQ ID NO: 33 or 34;
   - (b) Vβ5.1, wherein the nucleotide sequence comprises the sequence of SEQ ID NO: 43 or 44; or
   - (c) Vβ4, wherein the nucleotide sequence comprises the sequence of SEQ ID NO: 41 or 42.

5. The CAR of claim 1, wherein the costimulatory signaling region comprises the intracellular domain of a costimulatory molecule selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83.

6. The CAR of claim 1, wherein the intracellular signaling domain comprises a CD3zeta chain.

7. The CAR of claim 1, wherein the intracellular signaling domain comprises CD28 and CD3zeta.

8. The CAR of claim 1, wherein the intracellular signaling domain comprises 4-1BB and CD3zeta.

9. A nucleic acid encoding a chimeric antigen receptor (CAR), wherein the CAR comprises an extracellular domain that binds a Vβ region of a T cell receptor, a transmembrane domain, and an intracellular signaling domain, wherein the intracellular signaling domain comprises a costimulatory signaling region;
   - wherein the extracellular domain that binds a Vβ region is selected from the group consisting of an antibody, a Fab, and a scFv; and
   - wherein the extracellular domain comprises a light chain variable region (VL) comprising three light chain complementarity determining regions 1-3 (LCDR1-3) and a heavy chain variable region (VH) comprising three heavy chain complementarity determining regions 1-3 (HCDR1-3), and wherein the Vβ region is:

(a) Vβ12, wherein the LCDRs 1-3 comprise the sequences of SEQ ID NOs: 62-64, respectively, and the HCDRs 1-3 comprise the sequences of SEQ ID NOs: 58-60, respectively;

(b) Vβ5.1, wherein the LCDRs 1-3 comprise the sequences of SEQ ID NOs: 102-104, respectively, and the HCDRs 1-3 comprise the sequences of SEQ ID NOs: 98-100, respectively; or (c) Vβ4, wherein the LCDRs 1-3 comprise the sequences of SEQ ID NOs: 94-96, respectively, and the HCDRs 1-3 comprise the sequences of SEQ ID NOs: 90-92, respectively.

10. The nucleic acid of claim 9, wherein the Vβ region is Vβ12, wherein the LCDRs 1-3 comprise the sequences of SEQ ID NOs: 62-64, respectively, and the HCDRs 1-3 comprise the sequences of SEQ ID NOs: 58-60, respectively.

11. The nucleic acid of claim 9, wherein the Vβ region is:

(a) Vβ12, wherein the VH and VL comprise the sequence of SEQ ID NO: 57 and 61, respectively;

(b) Vβ5.1, wherein the VH and VL comprise the sequence of SEQ ID NO: 97 and 101, respectively; or (c) Vβ4, wherein the VH and VL comprise the sequence of SEQ ID NO: 89 and 93, respectively.

12. The nucleic acid of claim 9, wherein the extracellular domain comprises an scFv encoded by a nucleotide sequence, wherein the Vβ region is:

(a) Vβ12, wherein the nucleotide sequence comprises the sequence of SEQ ID NO: 33 or 34;

(b) Vβ5.1, wherein the nucleotide sequence comprises the sequence of SEQ ID NO: 43 or 44; or (c) Vβ4, wherein the nucleotide sequence comprises the sequence of SEQ ID NO: 41 or 42.

13. The nucleic acid of claim 9, wherein the costimulatory signaling region comprises the intracellular domain of a costimulatory molecule selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83.

14. The nucleic acid of claim 9, wherein the intracellular signaling domain comprises a CD3zeta chain.

15. The nucleic acid of claim 9, wherein the intracellular signaling domain comprises CD28 and CD3zeta.

16. The nucleic acid of claim 9, wherein the intracellular signaling domain comprises 4-1BB and CD3zeta.

17. The nucleic acid of claim 9, wherein the CAR:

(a) comprises an antigen binding domain that binds Vβ12 and comprises an amino acid sequence selected from the group consisting of SEQ ID NOs: 153-158;

(b) comprises an antigen binding domain that binds Vβ4 and comprises and amino acid sequence selected from the group consisting of SEQ ID NOs: 169-170; or (c) comprises and antigen binding domain that binds Vβ5.1 and comprises an amino acid sequence selected from the group consisting of SEQ ID NOs: 171-172.

18. The nucleic acid of claim 17, comprising a nucleotide sequence selected from the group consisting of SEQ ID NOs: 1-6 and 17-20.

19. A vector comprising the nucleic acid of claim 18.

* * * * *

SEQUENCE LISTING

```
<160> NUMBER OF SEQ ID NOS: 184

<210> SEQ ID NO 1
<211> LENGTH: 1476
<212> TYPE: DNA
<213> ORGANISM: Artificial Sequence
<220> FEATURE:
<223> OTHER INFORMATION: Vb12HL-28z

<400> SEQUENCE: 1

atggccttac cagtgaccgc cttgctcctg ccgctggcct tgctgctcca cgccgccagg      60

ccgggatccg aagtgatgct ggtggaatct ggcggcggac tggttaagcc tggcggatct     120

ctgaagctga gctgtgccgc cagcggcttc acctttagaa gctacgccat gagctgggtc     180

cgacagaccc ctgagaagag actggaatgg gtcgccacaa tcagcagcgg cggcagctac     240

acaaactacc ccgatagcgt gaagggcaga ttcaccatca gccgggacaa cgccaagaac     300

accctgaacc tgcagatgaa cagcctgcgg agcgaggaca ccgccatgta ctattgtgcc     360

agaggctacc acggctacct ggatgtttgg ggagccggca caaccgtgac agtttcttct     420

ggtggcggag gatctggcgg aggtggaagc ggcggaggcg gatctgatat tctgctgact     480

cagagccccg ccttcctgtc tgtttctcct ggcgagagag tgtccttcag ctgcagagcc     540

tctcagagca tcggcacctc catccactgg tatcagcaga ggaccaacgg cagccccaga     600

ctgctgatta agtacgccag cgagagcttc agcggcatcc ccagcagatt ttctggctct     660

ggcagcggca ccgacttcac cctgtctatc agctccgtgg aaagcgagga tatcgccgac     720

tactactgcc agcagtccta cagctggccc tacacatttg gcggaggcac caagctggaa     780

atcaaggcta gcaccacgac gccagcgccg cgaccaccaa caccggcgcc caccatcgcg     840

tcgcagcccc tgtccctgcg cccagaggcg tgccggccag cggcgggggg cgcagtgcac     900

acgagggggc tggacttcgc ctgtgatttt tgggtgctgg tggtggttgg tggagtcctg     960

gcttgctata gcttgctagt aacagtggcc tttattattt tctgggtgag gagtaagagg    1020

agcaggctcc tgcacagtga ctacatgaac atgactcccc gccgccccgg gcccacccgc    1080

aagcattacc agccctatgc cccaccacgc gacttcgcag cctatcgctc catcgataga    1140

gtgaagttca gcaggagcgc agacgccccc gcgtaccagc agggccagaa ccagctctat    1200
```

aacgagctca atctaggacg aagagaggag tacgatgttt tggacaagag acgtggccgg 1260
gaccctgaga tggggggaaa gccgagaagg aagaaccctc aggaaggcct gtacaatgaa 1320
ctgcagaaag ataagatggc ggaggcctac agtgagattg ggatgaaagg cgagcgccgg 1380
aggggcaagg ggcacgatgg cctttaccag ggtctcagta cagccaccaa ggacacctac 1440
gacgcccttc acatgcaggc cctgcccccct cgctaa 1476

<210> SEQ ID NO 2
<211> LENGTH: 1464
<212> TYPE: DNA
<213> ORGANISM: Artificial Sequence
<220> FEATURE:
<223> OTHER INFORMATION: Vb12HL-BBz

<400> SEQUENCE: 2
atggccttac cagtgaccgc cttgctcctg ccgctggcct tgctgctcca cgccgccagg 60
ccgggatccg aagtgatgct ggtggaatct ggcggcggac tggttaagcc tggcggatct 120
ctgaagctga gctgtgccgc cagcggcttc acctttagaa gctacgccat gagctgggtc 180
cgacagaccc ctgagaagag actggaatgg gtcgccacaa tcagcagcgg cggcagctac 240
acaaactacc ccgatagcgt gaagggcaga ttcaccatca gccgggacaa cgccaagaac 300
accctgaacc tgcagatgaa cagcctgcgg agcgaggaca ccgccatgta ctattgtgcc 360
agaggctacc acggctacct ggatgtttgg ggagccggca caaccgtgac agtttcttct 420
ggtggcggag gatctggcgg aggtggaagc ggcggaggcg gatctgatat tctgctgact 480
cagagccccg ccttcctgtc tgtttctcct ggcgagagag tgtccttcag ctgcagagcc 540
tctcagagca tcggcacctc catccactgg tatcagcaga ggaccaacgg cagccccaga 600
ctgctgatta agtacgccag cgagagcttc agcggcatcc ccagcagatt ttctggctct 660
ggcagcggca ccgacttcac cctgtctatc agctccgtgg aaagcgagga tatcgccgac 720
tactactgcc agcagtccta cagctggccc tacacatttg gcggaggcac caagctggaa 780
atcaaggcta gcaccacgac gccagcgccg cgaccaccaa caccggcgcc caccatcgcg 840
tcgcagcccc tgtccctgcg cccagaggcg tgccggccag cggcgggggg cgcagtgcac 900
acgagggggc tggacttcgc ctgtgatatc tacatctggg cgcccttggc cgggacttgt 960
ggggtccttc tcctgtcact ggttatcacc ctttactgca aacggggcag aaagaaactc 1020
ctgtatatat tcaaacaacc atttatgaga ccagtacaaa ctactcaaga ggaagatggc 1080
tgtagctgcc gatttccaga agaagaagaa ggaggatgtg aactgagagt gaagttcagc 1140
aggagcgcag acgcccccgc gtacaagcag ggccagaacc agctctataa cgagctcaat 1200
ctaggacgaa gagaggagta cgatgttttg gacaagagac gtggccggga ccctgagatg 1260
gggggaaagc cgagaaggaa gaaccctcag gaaggcctgt acaatgaact gcagaaagat 1320
aagatggcgg aggcctacag tgagattggg atgaaaggcg agcgccggag gggcaagggg 1380
cacgatggcc tttaccaggg tctcagtaca gccaccaagg acacctacga cgcccttcac 1440
atgcaggccc tgccccctcg ctaa 1464

<210> SEQ ID NO 3
<211> LENGTH: 1026
<212> TYPE: DNA
<213> ORGANISM: Artificial Sequence
<220> FEATURE:
<223> OTHER INFORMATION: Vb12HL-Dz

<400> SEQUENCE: 3
atggccttac cagtgaccgc cttgctcctg ccgctggcct tgctgctcca cgccgccagg 60
ccgggatccg aagtgatgct ggtggaatct ggcggcggac tggttaagcc tggcggatct 120
ctgaagctga gctgtgccgc cagcggcttc acctttagaa gctacgccat gagctgggtc 180
cgacagaccc ctgagaagag actggaatgg gtcgccacaa tcagcagcgg cggcagctac 240
acaaactacc ccgatagcgt gaagggcaga ttcaccatca gccgggacaa cgccaagaac 300
accctgaacc tgcagatgaa cagcctgcgg agcgaggaca ccgccatgta ctattgtgcc 360
agaggctacc acggctacct ggatgtttgg ggagccggca caaccgtgac agtttcttct 420
ggtggcggag gatctggcgg aggtggaagc ggcggaggcg gatctgatat tctgctgact 480
cagagccccg ccttcctgtc tgtttctcct ggcgagagag tgtccttcag ctgcagagcc 540
tctcagagca tcggcacctc catccactgg tatcagcaga ggaccaacgg cagccccaga 600
ctgctgatta agtacgccag cgagagcttc agcggcatcc ccagcagatt ttctggctct 660
ggcagcggca ccgacttcac cctgtctatc agctccgtgg aaagcgagga tatcgccgac 720
tactactgcc agcagtccta cagctggccc tacacatttg gcggaggcac caagctggaa 780
atcaaggcta gcaccacgac gccagcgccg cgaccaccaa caccggcgcc caccatcgcg 840
tcgcagcccc tgtccctgcg cccagaggcg tgccggccag cggcgggggg cgcagtgcac 900
acgagggggc tggacttcgc ctgtgatttt tgggtgctgg tggtggttgg tggagtcctg 960
gcttgctata gcttgctagt aacagtggcc tttattattt tctgggtgag gagtaagagg 1020
agctaa 1026

<210> SEQ ID NO 4
<211> LENGTH: 1476
<212> TYPE: DNA
<213> ORGANISM: Artificial Sequence
<220> FEATURE:
<223> OTHER INFORMATION: Vb12LH-28z

<400> SEQUENCE: 4
atggccttac cagtgaccgc cttgctcctg ccgctggcct tgctgctcca cgccgccagg 60
ccgggatccg acatcctgct gactcagagc cctgccttcc tgtctgtgtc tcctggcgag 120
agagtgtcct tcagctgtag agccagccag agcatcggca ccagcatcca ctggtatcag 180
cagcggacaa acggcagccc cagactgctg attaagtacg ccagcgagag cttcagcggc 240
atccccagca gattttctgg cagcggctct ggcaccgact tcaccctgtc tatcagctcc 300
gtggaaagcg aggatatcgc cgactactac tgccagcagt cctacagctg gccctacaca 360
tttggcggag gcaccaagct ggaaatcaaa ggcggcggag gaagcggagg cggaggatct 420
ggtggtggtg gatctgaagt gatgctggtc gagtctggcg gcggacttgt gaaacctggc 480
ggaagcctga agctgagctg tgccgcttcc ggcttcacct ttagaagcta cgccatgagc 540
tgggtccgac agacccctga gaagagactg gaatgggtcg ccaccatctc tagcggcggc 600
agctacacaa actaccccga ctctgtgaag ggcagattca ccatcagccg ggacaacgcc 660
aagaacaccc tgaacctgca gatgaacagc ctgcggagcg aggacaccgc catgtactat 720
tgtgccagag gctaccacgg ctacctggat gtttggggag ccggcacaac cgtgacagtg 780
tcatctgcta gcaccacgac gccagcgccg cgaccaccaa caccggcgcc caccatcgcg 840
tcgcagcccc tgtccctgcg cccagaggcg tgccggccag cggcgggggg cgcagtgcac 900
acgagggggc tggacttcgc ctgtgatttt tgggtgctgg tggtggttgg tggagtcctg 960

```
gcttgctata gcttgctagt aacagtggcc tttattattt tctgggtgag gagtaagagg   1020
agcaggctcc tgcacagtga ctacatgaac atgactcccc gccgccccgg gcccacccgc   1080
aagcattacc agccctatgc cccaccacgc gacttcgcag cctatcgctc catcgataga   1140
gtgaagttca gcaggagcgc agacgccccc gcgtaccagc agggccagaa ccagctctat   1200
aacgagctca atctaggacg aagagaggag tacgatgttt tggacaagag acgtggccgg   1260
gaccctgaga tggggggaaa gccgagaagg aagaaccctc aggaaggcct gtacaatgaa   1320
ctgcagaaag ataagatggc ggaggcctac agtgagattg ggatgaaagg cgagcgccgg   1380
aggggcaagg ggcacgatgg cctttaccag ggtctcagta cagccaccaa ggacacctac   1440
gacgcccttc acatgcaggc cctgcccccct cgctaa                             1476
```

```
<210> SEQ ID NO 5
<211> LENGTH: 1464
<212> TYPE: DNA
<213> ORGANISM: Artificial Sequence
<220> FEATURE:
<223> OTHER INFORMATION: Vb12LH-BBz

<400> SEQUENCE: 5

atggccttac cagtgaccgc cttgctcctg ccgctggcct tgctgctcca cgccgccagg     60
ccgggatccg acatcctgct gactcagagc cctgccttcc tgtctgtgtc tcctggcgag    120
agagtgtcct tcagctgtag agccagccag agcatcggca ccagcatcca ctggtatcag    180
cagcggacaa acggcagccc cagactgctg attaagtacg ccagcgagag cttcagcggc    240
atccccagca gattttctgg cagcggctct ggcaccgact tcaccctgtc tatcagctcc    300
gtggaaagcg aggatatcgc cgactactac tgccagcagt cctacagctg gccctacaca    360
tttggcggag gcaccaagct ggaaatcaaa ggcggcggag gaagcggagg cggaggatct    420
ggtggtggtg gatctgaagt gatgctggtc gagtctggcg gcggacttgt gaaacctggc    480
ggaagcctga agctgagctg tgccgcttcc ggcttcacct ttagaagcta cgccatgagc    540
tgggtccgac agacccctga gaagagactg gaatgggtcg ccaccatctc tagcggcggc    600
agctacacaa actaccccga ctctgtgaag ggcagattca ccatcagccg ggacaacgcc    660
aagaacaccc tgaacctgca gatgaacagc ctgcggagcg aggacaccgc catgtactat    720
tgtgccagag gctaccacgg ctacctggat gtttggggag ccggcacaac cgtgacagtg    780
tcatctgcta gcaccacgac gccagcgccg cgaccaccaa caccggcgcc caccatcgcg    840
tcgcagcccc tgtccctgcg cccagaggcg tgccggccag cggcgggggg cgcagtgcac    900
acgagggggc tggacttcgc ctgtgatatc tacatctggg cgcccttggc cgggacttgt    960
ggggtccttc tcctgtcact ggttatcacc ctttactgca aacggggcag aaagaaactc   1020
ctgtatatat tcaaacaacc atttatgaga ccagtacaaa ctactcaaga ggaagatggc   1080
tgtagctgcc gatttccaga agaagaagaa ggaggatgtg aactgagagt gaagttcagc   1140
aggagcgcag acgcccccgc gtacaagcag ggccagaacc agctctataa cgagctcaat   1200
ctaggacgaa gagaggagta cgatgttttg gacaagagac gtggccggga ccctgagatg   1260
gggggaaagc cgagaaggaa gaaccctcag gaaggcctgt acaatgaact gcagaaagat   1320
aagatggcgg aggcctacag tgagattggg atgaaaggcg agcgccggag gggcaagggg   1380
cacgatggcc tttaccaggg tctcagtaca gccaccaagg acacctacga cgcccttcac   1440
atgcaggccc tgccccctcg ctaa                                           1464
```

<210> SEQ ID NO 6
<211> LENGTH: 1026
<212> TYPE: DNA
<213> ORGANISM: Artificial Sequence
<220> FEATURE:
<223> OTHER INFORMATION: Vb12LH-Dz

<400> SEQUENCE: 6
atggccttac cagtgaccgc cttgctcctg ccgctggcct tgctgctcca cgccgccagg 60
ccgggatccg acatcctgct gactcagagc cctgccttcc tgtctgtgtc tcctggcgag 120
agagtgtcct tcagctgtag agccagccag agcatcggca ccagcatcca ctggtatcag 180
cagcggacaa acggcagccc cagactgctg attaagtacg ccagcgagag cttcagcggc 240
atccccagca gattttctgg cagcggctct ggcaccgact tcaccctgtc tatcagctcc 300
gtggaaagcg aggatatcgc cgactactac tgccagcagt cctacagctg gccctacaca 360
tttggcggag gcaccaagct ggaaatcaaa ggcggcggag gaagcggagg cggaggatct 420
ggtggtggtg gatctgaagt gatgctggtc gagtctggcg gcggacttgt gaaacctggc 480
ggaagcctga agctgagctg tgccgcttcc ggcttcacct ttagaagcta cgccatgagc 540
tgggtccgac agacccctga gaagagactg gaatgggtcg ccaccatctc tagcggcggc 600
agctacacaa actaccccga ctctgtgaag ggcagattca ccatcagccg ggacaacgcc 660
aagaacaccc tgaacctgca gatgaacagc ctgcggagcg aggacaccgc catgtactat 720
tgtgccagag gctaccacgg ctacctggat gtttggggag ccggcacaac cgtgacagtg 780
tcatctgcta gcaccacgac gccagcgccg cgaccaccaa caccggcgcc caccatcgcg 840
tcgcagcccc tgtccctgcg cccagaggcg tgccggccag cggcgggggg cgcagtgcac 900
acgagggggc tggacttcgc ctgtgatttt tgggtgctgg tggtggttgg tggagtcctg 960
gcttgctata gcttgctagt aacagtggcc tttattattt tctgggtgag gagtaagagg 1020
agctaa 1026

<210> SEQ ID NO 7
<211> LENGTH: 1596
<212> TYPE: DNA
<213> ORGANISM: Artificial Sequence
<220> FEATURE:
<223> OTHER INFORMATION: Vb9HL-28z

<400> SEQUENCE: 7
atggccttac cagtgaccgc cttgctcctg ccgctggcct tgctgctcca cgccgccagg 60
ccgggatcca tgaagttcag ctgggtcatc ttctttctga tggccgtggt caccggcgtg 120
aactctgaag tgcaactgca gcagagcgtg gccgaactcg ttagacctgg cgcctctgtg 180
aagctgagct gtaccgccag cggcttcaac atcaagaaca ccttcatgca ctgggtcaag 240
cagcggcctg agcagggact cgagtggatc ggaagaatcg accccaccaa cggctacacc 300
aagttcgccc ctaagttcca gggcaaagcc acactgacag ccgtgaccag cagcaacaca 360
gtgtacctgc agctgagcag cctgacctct gaggacaccg ccatctacta ctgcgcccac 420
gattacgacg ccccttggtt tgcctattgg ggccagggca cactggtcat tgtgtctgct 480
ggtggcggag gatctggcgg aggtggaagc ggcggaggcg gatctatgct ttctcctgct 540
cctctgctga gcctgctgct gctgtgcgtg tcagatagca gagccgagac aaccgtgaca 600
cagtctccag ccagtctgtc tgtggccacc ggcgagaaag tgaccatcag atgcatcagc 660
agcaccgaca tcgacgacga catgaactgg tatcagcaga agtccggcga gcctcctaag 720

```
ctgctgatct ccgagggcaa tactctgagg cctggcgtgc caagcagatt cagcagctct     780

ggctacggca ccgacttcgt gttcaccatc gagaacatgc tgagcgagga cgtggccgat     840

tactactgcc tgcagagcga caacatgccc ctgacatttg gagccggcac caagctggaa     900

ctgaaggcta gcaccacgac gccagcgccg cgaccaccaa caccggcgcc caccatcgcg     960

tcgcagcccc tgtccctgcg cccagaggcg tgccggccag cggcgggggg cgcagtgcac    1020

acgagggggc tggacttcgc ctgtgatttt tgggtgctgg tggtggttgg tggagtcctg    1080

gcttgctata gcttgctagt aacagtggcc tttattattt tctgggtgag gagtaagagg    1140

agcaggctcc tgcacagtga ctacatgaac atgactcccc gccgccccgg gcccacccgc    1200

aagcattacc agccctatgc cccaccacgc gacttcgcag cctatcgctc catcgataga    1260

gtgaagttca gcaggagcgc agacgccccc gcgtaccagc agggccagaa ccagctctat    1320

aacgagctca atctaggacg aagagaggag tacgatgttt tggacaagag acgtggccgg    1380

gaccctgaga tgggggggaaa gccgagaagg aagaaccctc aggaaggcct gtacaatgaa    1440

ctgcagaaag ataagatggc ggaggcctac agtgagattg ggatgaaagg cgagcgccgg    1500

aggggcaagg ggcacgatgg cctttaccag ggtctcagta cagccaccaa ggacacctac    1560

gacgcccttc acatgcaggc cctgccccct cgctaa                              1596
```

<210> SEQ ID NO 8
<211> LENGTH: 1584
<212> TYPE: DNA
<213> ORGANISM: Artificial Sequence
<220> FEATURE:
<223> OTHER INFORMATION: Vb9HL-BBz

<400> SEQUENCE: 8

```
atggccttac cagtgaccgc cttgctcctg ccgctggcct tgctgctcca cgccgccagg      60

ccgggatcca tgaagttcag ctgggtcatc ttctttctga tggccgtggt caccggcgtg     120

aactctgaag tgcaactgca gcagagcgtg gccgaactcg ttagacctgg cgcctctgtg     180

aagctgagct gtaccgccag cggcttcaac atcaagaaca ccttcatgca ctgggtcaag     240

cagcggcctg agcagggact cgagtggatc ggaagaatcg accccaccaa cggctacacc     300

aagttcgccc ctaagttcca gggcaaagcc acactgacag ccgtgaccag cagcaacaca     360

gtgtacctgc agctgagcag cctgacctct gaggacaccg ccatctacta ctgcgcccac     420

gattacgacg ccccttggtt tgcctattgg ggccagggca cactggtcat tgtgtctgct     480

ggtggcggag gatctggcgg aggtggaagc ggcggaggcg gatctatgct ttctcctgct     540

cctctgctga gcctgctgct gctgtgcgtg tcagatagca gagccgagac aaccgtgaca     600

cagtctccag ccagtctgtc tgtggccacc ggcgagaaag tgaccatcag atgcatcagc     660

agcaccgaca tcgacgacga catgaactgg tatcagcaga agtccggcga gcctcctaag     720

ctgctgatct ccgagggcaa tactctgagg cctggcgtgc caagcagatt cagcagctct     780

ggctacggca ccgacttcgt gttcaccatc gagaacatgc tgagcgagga cgtggccgat     840

tactactgcc tgcagagcga caacatgccc ctgacatttg gagccggcac caagctggaa     900

ctgaaggcta gcaccacgac gccagcgccg cgaccaccaa caccggcgcc caccatcgcg     960

tcgcagcccc tgtccctgcg cccagaggcg tgccggccag cggcgggggg cgcagtgcac    1020

acgagggggc tggacttcgc ctgtgatatc tacatctggg cgcccttggc cgggacttgt    1080

ggggtccttc tcctgtcact ggttatcacc ctttactgca aacggggcag aaagaaactc    1140

ctgtatatat tcaaacaacc atttatgaga ccagtacaaa ctactcaaga ggaagatggc    1200
```

```
tgtagctgcc gatttccaga agaagaagaa ggaggatgtg aactgagagt gaagttcagc   1260

aggagcgcag acgcccccgc gtaccagcag ggccagaacc agctctataa cgagctcaat   1320

ctaggacgaa gagaggagta cgatgttttg gacaagagac gtggccggga ccctgagatg   1380

gggggaaagc cgagaaggaa gaaccctcag gaaggcctgt acaatgaact gcagaaagat   1440

aagatggcgg aggcctacag tgagattggg atgaaaggcg agcgccggag gggcaagggg   1500

cacgatggcc tttaccaggg tctcagtaca gccaccaagg acacctacga cgcccttcac   1560

atgcaggccc tgccccctcg ctaa                                          1584
```

```
<210> SEQ ID NO 9
<211> LENGTH: 1146
<212> TYPE: DNA
<213> ORGANISM: Artificial Sequence
<220> FEATURE:
<223> OTHER INFORMATION: Vb9HL-Dz

<400> SEQUENCE: 9

atggccttac cagtgaccgc cttgctcctg ccgctggcct tgctgctcca cgccgccagg     60

ccgggatcca tgaagttcag ctgggtcatc ttctttctga tggccgtggt caccggcgtg    120

aactctgaag tgcaactgca gcagagcgtg gccgaactcg ttagacctgg cgcctctgtg    180

aagctgagct gtaccgccag cggcttcaac atcaagaaca ccttcatgca ctgggtcaag    240

cagcggcctg agcagggact cgagtggatc ggaagaatcg accccaccaa cggctacacc    300

aagttcgccc ctaagttcca gggcaaagcc acactgacag ccgtgaccag cagcaacaca    360

gtgtacctgc agctgagcag cctgacctct gaggacaccg ccatctacta ctgcgcccac    420

gattacgacg ccccttggtt tgcctattgg ggccagggca cactggtcat tgtgtctgct    480

ggtggcggag gatctggcgg aggtggaagc ggcggaggcg gatctatgct ttctcctgct    540

cctctgctga gcctgctgct gctgtgcgtg tcagatagca gagccgagac aaccgtgaca    600

cagtctccag ccagtctgtc tgtggccacc ggcgagaaag tgaccatcag atgcatcagc    660

agcaccgaca tcgacgacga catgaactgg tatcagcaga agtccggcga gcctcctaag    720

ctgctgatct ccgagggcaa tactctgagg cctggcgtgc caagcagatt cagcagctct    780

ggctacggca ccgacttcgt gttcaccatc gagaacatgc tgagcgagga cgtggccgat    840

tactactgcc tgcagagcga caacatgccc ctgacatttg gagccggcac caagctggaa    900

ctgaaggcta gcaccacgac gccagcgccg cgaccaccaa caccggcgcc caccatcgcg    960

tcgcagcccc tgtccctgcg cccagaggcg tgccggccag cggcgggggg cgcagtgcac   1020

acgagggggc tggacttcgc ctgtgatttt tgggtgctgg tggtggttgg tggagtcctg   1080

gcttgctata gcttgctagt aacagtggcc tttattattt tctgggtgag gagtaagagg   1140

agctaa                                                              1146
```

```
<210> SEQ ID NO 10
<211> LENGTH: 1596
<212> TYPE: DNA
<213> ORGANISM: Artificial Sequence
<220> FEATURE:
<223> OTHER INFORMATION: Vb9LH-28z

<400> SEQUENCE: 10

atggccttac cagtgaccgc cttgctcctg ccgctggcct tgctgctcca cgccgccagg     60

ccgggatcca tgctgtctcc agctcctctg ctgtctctgc tgctgctgtg cgtgtccgat    120
```

```
agcagagccg agacaaccgt gacacagtct ccagccagtc tgtctgtggc caccggcgag    180

aaagtgacca tcagatgcat cagcagcacc gacatcgacg acgacatgaa ctggtatcag    240

cagaagtccg gcgagcctcc taagctgctg atctccgagg gcaatactct gaggcctggc    300

gtgccaagca gattcagcag ctctggctac ggcaccgact tcgtgttcac catcgagaac    360

atgctgagcg aggacgtggc cgactactac tgcctgcaga gcgacaacat gcccctgaca    420

tttggagccg gcaccaagct ggaactgaaa ggcggcggag gatctggcgg aggtggaagc    480

ggaggcggtg gcagcatgaa gttcagctgg gtcatcttct ttctgatggc cgtggtcacc    540

ggcgtgaact ctgaagtgca actgcagcag agcgtggccg aactcgttag acctggcgcc    600

tctgtgaagc tgagctgtac cgccagcggc ttcaacatca agaacacctt catgcactgg    660

gtcaagcagc ggcctgagca gggactcgag tggatcggaa gaatcgaccc caccaacggc    720

tacaccaagt tcgcccctaa gttccagggc aaagccacac tgacagccgt gaccagcagc    780

aacacagtgt acctgcagct gagcagcctg acctctgagg acaccgccat ctactactgt    840

gcccacgact acgacgcccc ttggtttgcc tattggggcc agggcacact ggtcatcgtt    900

tctgctgcta gcaccacgac gccagcgccg cgaccaccaa caccggcgcc caccatcgcg    960

tcgcagcccc tgtccctgcg cccagaggcg tgccggccag cggcgggggg cgcagtgcac   1020

acgagggggc tggacttcgc ctgtgatttt tgggtgctgg tggtggttgg tggagtcctg   1080

gcttgctata gcttgctagt aacagtggcc tttattattt tctgggtgag gagtaagagg   1140

agcaggctcc tgcacagtga ctacatgaac atgactcccc gccgccccgg gcccacccgc   1200

aagcattacc agccctatgc cccaccacgc gacttcgcag cctatcgctc catcgataga   1260

gtgaagttca gcaggagcgc agacgccccc gcgtaccagc agggccagaa ccagctctat   1320

aacgagctca atctaggacg aagagaggag tacgatgttt tggacaagag acgtggccgg   1380

gaccctgaga tgggggggaaa gccgagaagg aagaaccctc aggaaggcct gtacaatgaa   1440

ctgcagaaag ataagatggc ggaggcctac agtgagattg ggatgaaagg cgagcgccgg   1500

aggggcaagg ggcacgatgg cctttaccag ggtctcagta cagccaccaa ggacacctac   1560

gacgcccttc acatgcaggc cctgcccccct cgctaa                            1596
```

<210> SEQ ID NO 11
<211> LENGTH: 1584
<212> TYPE: DNA
<213> ORGANISM: Artificial Sequence
<220> FEATURE:
<223> OTHER INFORMATION: Vb9LH-BBz

<400> SEQUENCE: 11

```
atggccttac cagtgaccgc cttgctcctg ccgctggcct tgctgctcca cgccgccagg     60

ccgggatcca tgctgtctcc agctcctctg ctgtctctgc tgctgctgtg cgtgtccgat    120

agcagagccg agacaaccgt gacacagtct ccagccagtc tgtctgtggc caccggcgag    180

aaagtgacca tcagatgcat cagcagcacc gacatcgacg acgacatgaa ctggtatcag    240

cagaagtccg gcgagcctcc taagctgctg atctccgagg gcaatactct gaggcctggc    300

gtgccaagca gattcagcag ctctggctac ggcaccgact tcgtgttcac catcgagaac    360

atgctgagcg aggacgtggc cgactactac tgcctgcaga gcgacaacat gcccctgaca    420

tttggagccg gcaccaagct ggaactgaaa ggcggcggag gatctggcgg aggtggaagc    480

ggaggcggtg gcagcatgaa gttcagctgg gtcatcttct ttctgatggc cgtggtcacc    540

ggcgtgaact ctgaagtgca actgcagcag agcgtggccg aactcgttag acctggcgcc    600
```

```
tctgtgaagc tgagctgtac cgccagcggc ttcaacatca agaacacctt catgcactgg     660

gtcaagcagc ggcctgagca gggactcgag tggatcggaa gaatcgaccc caccaacggc     720

tacaccaagt tcgcccctaa gttccagggc aaagccacac tgacagccgt gaccagcagc     780

aacacagtgt acctgcagct gagcagcctg acctctgagg acaccgccat ctactactgt     840

gcccacgact acgacgcccc ttggtttgcc tattggggcc agggcacact ggtcatcgtt     900

tctgctgcta gcaccacgac gccagcgccg cgaccaccaa caccggcgcc caccatcgcg     960

tcgcagcccc tgtccctgcg cccagaggcg tgccggccag cggcgggggg cgcagtgcac    1020

acgagggggc tggacttcgc ctgtgatatc tacatctggg cgcccttggc cgggacttgt    1080

ggggtccttc tcctgtcact ggttatcacc ctttactgca aacggggcag aaagaaactc    1140

ctgtatatat tcaaacaacc atttatgaga ccagtacaaa ctactcaaga ggaagatggc    1200

tgtagctgcc gatttccaga agaagaagaa ggaggatgtg aactgagagt gaagttcagc    1260

aggagcgcag acgcccccgc gtaccagcag ggccagaacc agctctataa cgagctcaat    1320

ctaggacgaa gagaggagta cgatgttttg gacaagagac gtggccggga ccctgagatg    1380

gggggaaagc cgagaaggaa gaaccctcag gaaggcctgt acaatgaact gcagaaagat    1440

aagatggcgg aggcctacag tgagattggg atgaaaggcg agcgccggag gggcaagggg    1500

cacgatggcc tttaccaggg tctcagtaca gccaccaagg acacctacga cgcccttcac    1560

atgcaggccc tgccccctcg ctaa                                           1584
```

<210> SEQ ID NO 12
<211> LENGTH: 1146
<212> TYPE: DNA
<213> ORGANISM: Artificial Sequence
<220> FEATURE:
<223> OTHER INFORMATION: Vb9LH-Dz

<400> SEQUENCE: 12

```
atggccttac cagtgaccgc cttgctcctg ccgctggcct tgctgctcca cgccgccagg      60

ccgggatcca tgctgtctcc agctcctctg ctgtctctgc tgctgctgtg cgtgtccgat     120

agcagagccg agacaaccgt gacacagtct ccagccagtc tgtctgtggc caccggcgag     180

aaagtgacca tcagatgcat cagcagcacc gacatcgacg acgacatgaa ctggtatcag     240

cagaagtccg gcgagcctcc taagctgctg atctccgagg gcaatactct gaggcctggc     300

gtgccaagca gattcagcag ctctggctac ggcaccgact tcgtgttcac catcgagaac     360

atgctgagcg aggacgtggc cgactactac tgcctgcaga gcgacaacat gcccctgaca     420

tttggagccg gcaccaagct ggaactgaaa ggcggcggag gatctggcgg aggtggaagc     480

ggaggcggtg gcagcatgaa gttcagctgg gtcatcttct ttctgatggc cgtggtcacc     540

ggcgtgaact ctgaagtgca actgcagcag agcgtggccg aactcgttag acctggcgcc     600

tctgtgaagc tgagctgtac cgccagcggc ttcaacatca agaacacctt catgcactgg     660

gtcaagcagc ggcctgagca gggactcgag tggatcggaa gaatcgaccc caccaacggc     720

tacaccaagt tcgcccctaa gttccagggc aaagccacac tgacagccgt gaccagcagc     780

aacacagtgt acctgcagct gagcagcctg acctctgagg acaccgccat ctactactgt     840

gcccacgact acgacgcccc ttggtttgcc tattggggcc agggcacact ggtcatcgtt     900

tctgctgcta gcaccacgac gccagcgccg cgaccaccaa caccggcgcc caccatcgcg     960

tcgcagcccc tgtccctgcg cccagaggcg tgccggccag cggcgggggg cgcagtgcac    1020
```

```
acgagggggc tggacttcgc ctgtgatttt tgggtgctgg tggtggttgg tggagtcctg   1080

gcttgctata gcttgctagt aacagtggcc tttattattt tctgggtgag gagtaagagg   1140

agctaa                                                              1146
```

<210> SEQ ID NO 13
<211> LENGTH: 1599
<212> TYPE: DNA
<213> ORGANISM: Artificial Sequence
<220> FEATURE:
<223> OTHER INFORMATION: Vb1HL-BBz

<400> SEQUENCE: 13

```
atggccttac cagtgaccgc cttgctcctg ccgctggcct tgctgctcca cgccgccagg     60

ccgggatcca tggactgggt ctggaacctg ctgttcctga tggccgttgc tcagacaggt    120

gctcaggctc agctgcaact ggtgcagtct ggacctgagc tgagagaacc tggcgagagc    180

gtgaagatct cctgcaaggc cagcggctac accttcaccg actacatcgt gcactgggtc    240

aagcaggccc ctggcaaggg actgaaatgg atgggctgga tcaacaccta caccggcaca    300

cccacctacg ccgacgattt cgagggcaga ttcgtgttca gcctggaagc ctctgccagc    360

accgccaacc tgcagatcag caacctgaag aacgaggaca ccgccaccta cttttgcgcc    420

agatcttggc ggagaggcat ccgcggcatc ggctttgatt attggggaca gggcgtgatg    480

gtcaccgtgt ctagcggagg cggaggatct ggtggcggag gaagtggcgg aggcggttct    540

atgagagtgc agatccagtt ctggggactg ctgctgctgt ggacaagcgg catccagtgt    600

gacgtgcaga tgacacagag cccctacaac ctggctgcct ctcctggcga gtccgtgtcc    660

atcaattgca aggcctccaa gagcatcaac aagtacctgg cctggtatca gcagaagccc    720

ggcaagccta acaagctgct gatctacgat ggcagcaccc tgcagagcgg aatccccagc    780

agattttctg gcagcggctc cggcaccgat ttcaccctga caatcagagg cctggaacca    840

gaggacttcg gcctgtacta ctgccagcag cacaacgagt accctccaac ctttggagcc    900

ggcaccaagc tggaactgaa ggctagcacc acgacgccag cgccgcgacc accaacaccg    960

gcgcccacca tcgcgtcgca gcccctgtcc ctgcgcccag aggcgtgccg gccagcggcg   1020

gggggcgcag tgcacacgag ggggctggac ttcgcctgtg atatctacat ctgggcgccc   1080

ttggccggga cttgtggggt ccttctcctg tcactggtta tcacccttta ctgcaaacgg   1140

ggcagaaaga aactcctgta tatattcaaa caaccattta tgagaccagt acaaactact   1200

caagaggaag atggctgtag ctgccgattt ccagaagaag aagaaggagg atgtgaactg   1260

agagtgaagt tcagcaggag cgcagacgcc cccgcgtacc agcagggcca gaaccagctc   1320

tataacgagc tcaatctagg acgaagagag gagtacgatg ttttggacaa gagacgtggc   1380

cgggaccctg agatgggggg aaagccgaga aggaagaacc ctcaggaagg cctgtacaat   1440

gaactgcaga aagataagat ggcggaggcc tacagtgaga ttgggatgaa aggcgagcgc   1500

cggaggggca aggggcacga tggcctttac cagggtctca gtacagccac caaggacacc   1560

tacgacgccc ttcacatgca ggccctgccc cctcgctaa                          1599
```

<210> SEQ ID NO 14
<211> LENGTH: 1599
<212> TYPE: DNA
<213> ORGANISM: Artificial Sequence
<220> FEATURE:
<223> OTHER INFORMATION: Vb1LH-BBz

<400> SEQUENCE: 14

```
atggccttac cagtgaccgc cttgctcctg ccgctggcct tgctgctcca cgccgccagg     60
ccgggatcca tgagagtgca gatccagttc tggggcctgc tgctgctgtg gacatctggc    120
atccagtgcg acgtgcagat gacacagagc ccctacaacc tggctgcctc tcctggcgag    180
agcgtgtcca tcaattgcaa ggccagcaag agcatcaaca agtacctggc ctggtatcag    240
cagaagcccg gcaagcctaa caagctgctg atctacgatg gcagcaccct gcagagcggc    300
atccctagca gattttctgg cagcggctcc ggcaccgatt tcaccctgac aatcagaggc    360
ctggaacctg aggacttcgg cctgtactac tgccagcagc acaacgagta ccctccaacc    420
tttggagccg gcaccaagct ggaacttaaa ggcggcggag gatctggcgg aggtggaagc    480
ggaggcggtg gatctatgga ctgggtctgg aatctgctgt tcctgatggc cgtggctcag    540
acaggtgctc aggctcagct gcaactggtg cagtctggac ctgagctgag agaacctggc    600
gagtccgtga agatctcctg caaggcctcc ggctacacct tcaccgacta catcgtgcac    660
tgggtcaaac aggcccctgg caagggactg aagtggatgg gctggatcaa cacctacacc    720
ggcacaccca cctacgccga cgatttcgag ggcagattcg tgttcagcct ggaagcctct    780
gccagcaccg ccaacctgca gatcagcaac ctgaagaacg aggacaccgc cacctacttt    840
tgcgccagat cttggaggcg gggcatcaga ggcatcggct ttgattattg gggccagggc    900
gtgatggtca ccgtgtcctc tgctagcacc acgacgccag cgccgcgacc accaacaccg    960
gcgcccacca tcgcgtcgca gcccctgtcc ctgcgcccag aggcgtgccg gccagcggcg   1020
gggggcgcag tgcacacgag ggggctggac ttcgcctgtg atatctacat ctgggcgccc   1080
ttggccggga cttgtggggt ccttctcctg tcactggtta tcacccttta ctgcaaacgg   1140
ggcagaaaga aactcctgta tatattcaaa caaccattta tgagaccagt acaaactact   1200
caagaggaag atggctgtag ctgccgattt ccagaagaag aagaaggagg atgtgaactg   1260
agagtgaagt tcagcaggag cgcagacgcc cccgcgtacc agcagggcca gaaccagctc   1320
tataacgagc tcaatctagg acgaagagag gagtacgatg ttttggacaa gagacgtggc   1380
cgggaccctg agatgggggg aaagccgaga aggaagaacc ctcaggaagg cctgtacaat   1440
gaactgcaga aagataagat ggcggaggcc tacagtgaga ttgggatgaa aggcgagcgc   1500
cggaggggca aggggcacga tggcctttac cagggtctca gtacagccac caaggacacc   1560
tacgacgccc ttcacatgca ggccctgccc cctcgctaa                          1599
```

<210> SEQ ID NO 15
<211> LENGTH: 1599
<212> TYPE: DNA
<213> ORGANISM: Artificial Sequence
<220> FEATURE:
<223> OTHER INFORMATION: Vb2HL-BBz

<400> SEQUENCE: 15

```
atggccttac cagtgaccgc cttgctcctg ccgctggcct tgctgctcca cgccgccagg     60
ccgggatcca tgaagttcag ctgggtcatc ttctttctga tggccgtggt caccggcgtg    120
aactctgaag tgcaactgca gcagagcgtg gccgatctcg ttagacctgg cgcctctctg    180
aagctgagct gtaccgccag cggcttcaac atcaagagcg cctacatgca ctgggttatc    240
cagcggccag atcagggccc agagtgtctg ggaagaatcg atcctgccac cggcaagacc    300
aaatacgccc ctaagtttca ggccaaggcc accatcaccg ccgacacctc tagcaatacc    360
gcctacctgc agctgagcag cctgacctct gaggacaccg ccatctacta ctgcaccaga    420
```

```
agcctgaact gggactacgg cctggattat tggggccagg gcacaagcgt gacagtgtct    480

agcggaggcg gaggatctgg tggcggagga agtggcggag gcggtagcat ggaaaccgat    540

acactgctgc tgtgggtgct gctcctttgg gtgcccggat ctacaggcga catcgtgctg    600

acacagtctc ccgcttctct ggccgtgtct ctgggacaga gagccaccat ctcttgcaga    660

gccagcaaga gcgtgtccat cctgggcaca cacctgatcc actggtatca gcagaagccc    720

ggccagcctc ctaagctgct gatctacgcc gccagcaatc tggaaagcgg agtgcctgcc    780

agattttccg gcagcggaag cgaaaccgtg ttcaccctga acattcaccc cgtggaagaa    840

gaggacgccg ccacctattt ctgccagcag tctatcgagg acccctggac atttggaggc    900

ggcacaaagc tgggcatcaa ggctagcacc acgacgccag cgccgcgacc accaacaccg    960

gcgcccacca tcgcgtcgca gcccctgtcc ctgcgcccag aggcgtgccg gccagcggcg   1020

gggggcgcag tgcacacgag ggggctggac ttcgcctgtg atatctacat ctgggcgccc   1080

ttggccggga cttgtggggt ccttctcctg tcactggtta tcacccttta ctgcaaacgg   1140

ggcagaaaga aactcctgta tatattcaaa caaccattta tgagaccagt acaaactact   1200

caagaggaag atggctgtag ctgccgattt ccagaagaag aagaaggagg atgtgaactg   1260

agagtgaagt tcagcaggag cgcagacgcc cccgcgtacc agcagggcca gaaccagctc   1320

tataacgagc tcaatctagg acgaagagag gagtacgatg ttttggacaa gagacgtggc   1380

cgggaccctg agatgggggg aaagccgaga aggaagaacc ctcaggaagg cctgtacaat   1440

gaactgcaga aagataagat ggcggaggcc tacagtgaga ttgggatgaa aggcgagcgc   1500

cggaggggca aggggcacga tggcctttac cagggtctca gtacagccac caaggacacc   1560

tacgacgccc ttcacatgca ggccctgccc cctcgctaa                          1599
```

```
<210> SEQ ID NO 16
<211> LENGTH: 1599
<212> TYPE: DNA
<213> ORGANISM: Artificial Sequence
<220> FEATURE:
<223> OTHER INFORMATION: Vb2LH-BBz

<400> SEQUENCE: 16

atggccttac cagtgaccgc cttgctcctg ccgctggcct tgctgctcca cgccgccagg     60

ccgggatcca tggaaaccga cacactgctg ctgtgggtgc tgcttctttg ggtgcccgga    120

agcacaggcg acatcgtgct gacacagagc cctgcttctc tggccgtgtc tctgggacag    180

agagccacca tcagctgcag agccagcaag agcgtgtcca tcctgggcac acacctgatc    240

cactggtatc agcagaagcc cggccagcct cctaagctgc tgatctacgc cgccagcaat    300

ctggaaagcg gagtgcctgc cagattttcc ggcagcggaa gcgagacagt gttcaccctg    360

aacattcacc ccgtggaaga agaggacgcc gccacctact tttgccagca gtctatcgag    420

gacccctgga cctttggcgg cggaacaaag ctgggaatca aaggcggcgg aggatctggc    480

ggaggtggaa gcggaggcgg tggcagcatg aagttcagct gggtcatctt ctttctgatg    540

gccgtggtca ccggcgtgaa ctctgaagtg caactgcagc agagcgtggc cgatctcgtt    600

agacctggcg cctctctgaa gctgagctgt accgccagcg gcttcaacat caagagcgcc    660

tacatgcact gggttatcca gcggccagat cagggcccag agtgtctggg aagaatcgat    720

cctgccaccg gcaagaccaa atacgcccct aagtttcagg ccaaggccac aatcaccgcc    780

gacacctcta gcaacacagc ctacctgcag ctgtccagcc tgacctctga ggataccgcc    840

atctactact gcaccagaag cctgaactgg gactacggcc tggattattg gggccagggc    900
```

```
acaagcgtga ccgtgtcatc tgctagcacc acgacgccag cgccgcgacc accaacaccg    960
gcgcccacca tcgcgtcgca gcccctgtcc ctgcgcccag aggcgtgccg gccagcggcg   1020
gggggcgcag tgcacacgag gggctggac ttcgcctgtg atatctacat ctgggcgccc    1080
ttggccggga cttgtggggt ccttctcctg tcactggtta tcacccttta ctgcaaacgg   1140
ggcagaaaga aactcctgta tatattcaaa caaccattta tgagaccagt acaaactact   1200
caagaggaag atggctgtag ctgccgattt ccagaagaag aagaaggagg atgtgaactg   1260
agagtgaagt tcagcaggag cgcagacgcc cccgcgtacc agcagggcca gaaccagctc   1320
tataacgagc tcaatctagg acgaagagag gagtacgatg ttttggacaa gagacgtggc   1380
cgggaccctg agatgggggg aaagccgaga aggaagaacc ctcaggaagg cctgtacaat   1440
gaactgcaga aagataagat ggcggaggcc tacagtgaga ttgggatgaa aggcgagcgc   1500
cggaggggca aggggcacga tggcctttac cagggtctca gtacagccac caaggacacc   1560
tacgacgccc ttcacatgca ggccctgccc cctcgctaa                          1599
```

<210> SEQ ID NO 17
<211> LENGTH: 1590
<212> TYPE: DNA
<213> ORGANISM: Artificial Sequence
<220> FEATURE:
<223> OTHER INFORMATION: Vb4HL-BBz

<400> SEQUENCE: 17

```
atggccttac cagtgaccgc cttgctcctg ccgctggcct tgctgctcca cgccgccagg     60
ccgggatcca tggaatggtc ctggatcttc ctgttcctgc tgagcgtgac agccgtggtg    120
cattctcagg ttcagctgca gcagtctggc gccgaactgg ccaaacctgg cacaagcgtg    180
aagctgagct gtaaagccag cggctacacc ttcaccagct actacatcta ctgggtcaag    240
cagcggcctg gacagggact tgagtggctg ggctatatct accctggcaa cggcggcacc    300
tactacagcg agaagttcaa gggcaaagcc acctttaccg ccgacaccag cagcaacaca    360
gcctacatgc tgctgggcag cctgacacct gaggacagcg cctactactt ctgtgccaga    420
ggcagcggcg accggtacaa ttctctggcc tattggggcc agggcaccct ggttacagtt    480
tcttctggtg gcggaggatc tggcggaggt ggaagcggcg gaggcggatc tatggctatt    540
cctacacagc tgctgggact gctgctgctc tggatcaccg atgccatctg cgacatccag    600
atgacacaga gccctcacag cctgtctgcc agcctgggag agacagtgtc cattgagtgt    660
ctggccagcg agggcatcag caactttctg gcctggtatc agcagaagcc cggcaagtct    720
cctcagctgc tgatctacta cacaagcagc ctgcaggatg gcgtgccctc tagattttct    780
ggctctggca gcggcaccca gtacagcctg aagatcagca acatgcagcc cgaggacgag    840
ggcgtgtact attgtcagca gggctacaag ttccccagaa cctttggcgg aggcaccaag    900
ctggaactga aggctagcac cacgacgcca gcgccgcgac caccaacacc ggcgcccacc    960
atcgcgtcgc agcccctgtc cctgcgccca gaggcgtgcc ggccagcggc ggggggcgca   1020
gtgcacacga gggggctgga cttcgcctgt gatatctaca tctgggcgcc cttggccggg   1080
acttgtgggg tccttctcct gtcactggtt atcacccttt actgcaaacg gggcagaaag   1140
aaactcctgt atatattcaa acaaccattt atgagaccag tacaaactac tcaagaggaa   1200
gatggctgta gctgccgatt tccagaagaa gaagaaggag gatgtgaact gagagtgaag   1260
ttcagcagga gcgcagacgc ccccgcgtac cagcagggcc agaaccagct ctataacgag   1320
```

ctcaatctag gacgaagaga ggagtacgat gttttggaca agagacgtgg ccgggaccct 1380
gagatggggg gaaagccgag aaggaagaac cctcaggaag gcctgtacaa tgaactgcag 1440
aaagataaga tggcggaggc ctacagtgag attgggatga aaggcgagcg ccggaggggc 1500
aaggggcacg atggccttta ccagggtctc agtacagcca ccaaggacac ctacgacgcc 1560
cttcacatgc aggccctgcc ccctcgctaa 1590

<210> SEQ ID NO 18
<211> LENGTH: 1590
<212> TYPE: DNA
<213> ORGANISM: Artificial Sequence
<220> FEATURE:
<223> OTHER INFORMATION: Vb4LH-BBz

<400> SEQUENCE: 18
atggccttac cagtgaccgc cttgctcctg ccgctggcct tgctgctcca cgccgccagg 60
ccgggatcca tggctatccc cacacaactg ctgggactgc tgctgctgtg gatcaccgat 120
gccatctgcg acatccagat gacacagagc cctcacagcc tgtctgccag cctgggagag 180
acagtgtcca ttgagtgtct ggccagcgag ggcatcagca actttctggc ctggtatcag 240
cagaagcccg gcaagtctcc tcagctgctg atctactaca ccagcagcct gcaggatggc 300
gtgcccagca gattttctgg cagcggctct ggcacacagt acagcctgaa gatcagcaac 360
atgcagcccg aggacgaggg cgtgtactat tgtcagcagg gctacaagtt ccccagaacc 420
tttggcggag gcaccaagct ggaactgaaa ggcggcggag gaagcggagg cggaggatct 480
ggtggtggtg gatctatgga atggtcctgg atcttcctgt tcctgctgag cgtgacagcc 540
gtggtgcatt ctcaggttca gctgcagcag agcggagccg aactggccaa acctggcaca 600
agcgtgaagc tgagctgtaa agccagcggc tacaccttca ccagctacta catctactgg 660
gtcaagcagc ggcctggaca gggacttgag tggctgggct atatctaccc tggcaacggc 720
ggcacctact acagcgagaa gttcaagggc aaagccacct ttaccgccga caccagctcc 780
aacacagcct acatgctgct cggcagcctg acacctgagg acagcgccta ctacttttgc 840
gctagaggca gcggcgaccg gtacaattct ctggcctatt ggggccaggg caccctggtt 900
acagtcagct ctgctagcac cacgacgcca gcgccgcgac caccaacacc ggcgcccacc 960
atcgcgtcgc agcccctgtc cctgcgccca gaggcgtgcc ggccagcggc ggggggcgca 1020
gtgcacacga gggggctgga cttcgcctgt gatatctaca tctgggcgcc cttggccggg 1080
acttgtgggg tccttctcct gtcactggtt atcacccttt actgcaaacg gggcagaaag 1140
aaactcctgt atatattcaa acaaccattt atgagaccag tacaaactac tcaagaggaa 1200
gatggctgta gctgccgatt tccagaagaa gaagaaggag gatgtgaact gagagtgaag 1260
ttcagcagga gcgcagacgc ccccgcgtac cagcagggcc agaaccagct ctataacgag 1320
ctcaatctag gacgaagaga ggagtacgat gttttggaca agagacgtgg ccgggaccct 1380
gagatggggg gaaagccgag aaggaagaac cctcaggaag gcctgtacaa tgaactgcag 1440
aaagataaga tggcggaggc ctacagtgag attgggatga aaggcgagcg ccggaggggc 1500
aaggggcacg atggccttta ccagggtctc agtacagcca ccaaggacac ctacgacgcc 1560
cttcacatgc aggccctgcc ccctcgctaa 1590

<210> SEQ ID NO 19
<211> LENGTH: 1581
<212> TYPE: DNA
<213> ORGANISM: Artificial Sequence
<220> FEATURE:
<223> OTHER INFORMATION: Vb5.1HL-BBz

<400> SEQUENCE: 19

```
atggccttac cagtgaccgc cttgctcctg ccgctggcct tgctgctcca cgccgccagg     60
ccgggatcca tgggctggtc ctggatcttc ctgttcctgc tgtctgagac tgccggcgtg    120
ctgagtgaag ttcagctgca gcagtctggc cccgtgcttg tgaaacctgg cgcctctgtc    180
agaatgagct gcaaggccag cggctacacc ttcaccgact acaacatcca ctgggtcaag    240
cagagccacg gcagatccct tgagtgggtc ggatatatca acccctacaa cggccggacc    300
ggctacaacc agaagttcaa ggccaaggcc acactgaccg tgaacaagag cagcagcacc    360
gcctacatgg acctgagaag cctgaccagc gaggacagcg ccgtgtacta ttgcgccaga    420
tgggatggca gcagctactt cgattattgg ggccagggca caaccctgac cgtttcttct    480
ggtggcggag gatctggcgg aggtggaagc ggcggaggcg gatctatgga tttccgggtg    540
cagatcttca gcttcctgct gatctccgtg accgtgtcca gaggcgagat cgtgctgaca    600
cagagccctg ccattacagc cgcttctctg ggccagaaag tgaccatcac atgcagcgcc    660
agcagcagcg tgtcctacat gcactggtat cagcagaagt ccggcacaag ccccaagcct    720
tggatctacg agatctccaa gctggcctct ggcgtgccag ccagattttc tggctctggc    780
agcggcacca gctactccct gacaatcagc agcatggaag ccgaggacgc cgccatctac    840
tactgccagc agtggaacta ccctctgatc acctttggag ccggcaccaa gctggaactg    900
aaggctagca ccacgacgcc agcgccgcga ccaccaacac cggcgcccac catcgcgtcg    960
cagcccctgt ccctgcgccc agaggcgtgc cggccagcgg cggggggcgc agtgcacacg   1020
agggggctgg acttcgcctg tgatatctac atctgggcgc ccttggccgg gacttgtggg   1080
gtccttctcc tgtcactggt tatcaccctt tactgcaaac ggggcagaaa gaaactcctg   1140
tatatattca aacaaccatt tatgagacca gtacaaacta ctcaagagga agatggctgt   1200
agctgccgat ttccagaaga agaagaagga ggatgtgaac tgagagtgaa gttcagcagg   1260
agcgcagacg cccccgcgta ccagcagggc cagaaccagc tctataacga gctcaatcta   1320
ggacgaagag aggagtacga tgttttggac aagagacgtg gccgggaccc tgagatgggg   1380
ggaaagccga gaaggaagaa ccctcaggaa ggcctgtaca atgaactgca gaaagataag   1440
atggcggagg cctacagtga gattgggatg aaaggcgagc gccggagggg caaggggcac   1500
gatggccttt accagggtct cagtacagcc accaaggaca cctacgacgc ccttcacatg   1560
caggccctgc cccctcgcta a                                             1581
```

<210> SEQ ID NO 20
<211> LENGTH: 1581
<212> TYPE: DNA
<213> ORGANISM: Artificial Sequence
<220> FEATURE:
<223> OTHER INFORMATION: Vb5.1LH-BBz

<400> SEQUENCE: 20

```
atggccttac cagtgaccgc cttgctcctg ccgctggcct tgctgctcca cgccgccagg     60
ccgggatcca tggacttccg ggtgcagatc ttcagcttcc tgctgatctc cgtgaccgtg    120
tccagaggcg agatcgtgct gacacagagc cctgccatta cagccgcttc tctgggccag    180
aaagtgacca tcacatgcag cgccagcagc agcgtgtcct acatgcactg gtatcagcag    240
aagtccggca caagccccaa gccttggatc tacgagatct ccaagctggc ctctggcgtg    300
```

```
ccagccagat tttctggctc tggcagcggc accagctaca gcctgacaat cagcagcatg    360

gaagccgagg acgccgccat ctactactgc cagcagtgga actaccctct gatcaccttt    420

ggagccggca ccaagctgga actgaaaggc ggcggaggat ctggcggagg tggaagcgga    480

ggcggtggat ctatgggatg gtcctggatc ttcctgttcc tgctgtccga aacagccggc    540

gtgctgtctg aagttcagct gcagcagtct ggccccgtgc ttgtgaaacc tggcgcctct    600

gtcagaatga gctgcaaggc cagcggctac accttcaccg actacaacat ccactgggtc    660

aagcagagcc acggcagatc ccttgagtgg gtcggatata tcaacccccta caacggccgg    720

accggctaca accagaagtt caaggccaag gccacactga ccgtgaacaa gagcagcagc    780

accgcctaca tggacctgag aagcctgacc agcgaggaca gcgccgtgta ctattgcgcc    840

agatgggatg gcagcagcta cttcgattat tggggccagg gcacaaccct gacagtgtcc    900

tctgctagca ccacgacgcc agcgccgcga ccaccaacac cggcgcccac catcgcgtcg    960

cagcccctgt ccctgcgccc agaggcgtgc cggccagcgg cggggggcgc agtgcacacg   1020

agggggctgg acttcgcctg tgatatctac atctgggcgc ccttggccgg gacttgtggg   1080

gtccttctcc tgtcactggt tatcaccctt tactgcaaac ggggcagaaa gaaactcctg   1140

tatatattca aacaaccatt tatgagacca gtacaaacta ctcaagagga agatggctgt   1200

agctgccgat ttccagaaga agaagaagga ggatgtgaac tgagagtgaa gttcagcagg   1260

agcgcagacg cccccgcgta ccagcagggc cagaaccagc tctataacga gctcaatcta   1320

ggacgaagag aggagtacga tgttttggac aagagacgtg gccgggaccc tgagatgggg   1380

ggaaagccga gaaggaagaa ccctcaggaa ggcctgtaca atgaactgca gaaagataag   1440

atggcggagg cctacagtga gattgggatg aaaggcgagc gccggagggg caaggggcac   1500

gatggccttt accagggtct cagtacagcc accaaggaca cctacgacgc ccttcacatg   1560

caggccctgc cccctcgcta a                                             1581
```

<210> SEQ ID NO 21
<211> LENGTH: 1611
<212> TYPE: DNA
<213> ORGANISM: Artificial Sequence
<220> FEATURE:
<223> OTHER INFORMATION: Vb7.1HL-BBz

<400> SEQUENCE: 21

```
atggccttac cagtgaccgc cttgctcctg ccgctggcct tgctgctcca cgccgccagg     60

ccgggatcca tgaacttcgg cctgagcctg atcttcctgg tgctgttcct gaagggcgtg    120

cagtgcgaag tgcagctggt tgaatctggc ggcggactgg ttaagcctgg cggatctctg    180

aagctgagct gtgccgccag cggcttcacc ttcagcgact actacatgta ctgggtccga    240

cagacccctg agaagcggct ggaatgggtc gccacaattt ctggcggagg cagctacaca    300

tacagccccg attctgtgaa gggcagattc accatcagcc gggacaacgc caagaacaac    360

ctgtacctgc agatgagcag cctgcggagc gaggacaccg ccatgtactt ttgcgccaga    420

gagcgggaca tctactacgg caacttcaac gccatggtgt actggggcag aggcaccagc    480

gtgacagtta gtagcggagg cggaggatca ggtggcggtg gaagtggtgg tggcggcagc    540

atggaaaccg atacactgct gctgtgggtg ctgctccttt gggtgcccgg atctacaggc    600

gacatcgtgc tgacacagag ccccgtgtct ctgacagtgt ccctgggaca gagagccaca    660

atcagctgca gagccagcaa gagcgtgtcc acaagcggct acagctacat gcactggtat    720

cagcagaagc ccggccagcc tcctaagctg ctgatctacc tggccagcaa cctggaaagc    780
```

```
ggagtgcctg ccagattttc tggcagcggc tctggcaccg acttcaccct gaatatccat    840

cctgtggaag aagaggacgc cgccacctac tactgtcagc acagcagaga tctgccctgg    900

acctttggag gcggcaccaa gctggaaatc aaggctagca ccacgacgcc agcgccgcga    960

ccaccaacac cggcgcccac catcgcgtcg cagcccctgt ccctgcgccc agaggcgtgc   1020

cggccagcgg cggggggcgc agtgcacacg agggggctgg acttcgcctg tgatatctac   1080

atctgggcgc ccttggccgg gacttgtggg gtccttctcc tgtcactggt tatcaccctt   1140

tactgcaaac ggggcagaaa gaaactcctg tatatattca aacaaccatt tatgagacca   1200

gtacaaacta ctcaagagga agatggctgt agctgccgat ttccagaaga agaagaagga   1260

ggatgtgaac tgagagtgaa gttcagcagg agcgcagacg cccccgcgta ccagcagggc   1320

cagaaccagc tctataacga gctcaatcta ggacgaagag aggagtacga tgttttggac   1380

aagagacgtg gccgggaccc tgagatgggg ggaaagccga gaaggaagaa ccctcaggaa   1440

ggcctgtaca atgaactgca gaaagataag atggcggagg cctacagtga gattgggatg   1500

aaaggcgagc gccggagggg caaggggcac gatggccttt accagggtct cagtacagcc   1560

accaaggaca cctacgacgc ccttcacatg caggccctgc cccctcgcta a            1611
```

<210> SEQ ID NO 22
<211> LENGTH: 1611
<212> TYPE: DNA
<213> ORGANISM: Artificial Sequence
<220> FEATURE:
<223> OTHER INFORMATION: Vb7.1LH-BBz

<400> SEQUENCE: 22

```
atggccttac cagtgaccgc cttgctcctg ccgctggcct tgctgctcca cgccgccagg     60

ccgggatcca tggaaaccga cacactgctg ctgtgggtgc tgcttctttg ggtgcccgga    120

agcacaggcg acatcgtgct tacacagagc cccgtgtctc tgacagtgtc cctgggacag    180

agagccacca tcagctgtag agccagcaag agcgtgtcca ccagcggcta cagctacatg    240

cactggtatc agcagaagcc cggccagcct cctaagctgc tgatctacct ggccagcaac    300

ctggaaagcg gagtgcctgc cagattttct ggcagcggct ctggcaccga cttcaccctg    360

aatatccatc ctgtggaaga agaggacgcc gccacctact actgtcagca cagcagagat    420

ctgccctgga cctttggcgg cggaacaaag ctggaaatca aaggcggcgg aggatctggc    480

ggaggtggaa gcggaggcgg tggctctatg aattttggcc tgagcctgat cttcctggtg    540

ctgttcctga agggcgtgca gtgcgaagtg cagctggttg aaagtggcgg aggcctggtt    600

aagcctggcg gatctctgaa gctgagctgt gccgccagcg gcttcacctt cagcgactac    660

tacatgtact gggtccgaca gacccctgag aagcggctgg aatgggtcgc cacaatttca    720

ggcggaggca gctacacata cagccccgat tctgtgaagg gccgctttac catcagccgg    780

gacaacgcca agaacaacct gtacctgcag atgagcagcc tgcggagcga ggacaccgcc    840

atgtactttt gcgccagaga gcgggacatc tactacggca acttcaacgc catggtgtac    900

tggggcagag gcacctctgt gaccgttagc tctgctagca ccacgacgcc agcgccgcga    960

ccaccaacac cggcgcccac catcgcgtcg cagcccctgt ccctgcgccc agaggcgtgc   1020

cggccagcgg cggggggcgc agtgcacacg agggggctgg acttcgcctg tgatatctac   1080

atctgggcgc ccttggccgg gacttgtggg gtccttctcc tgtcactggt tatcaccctt   1140

tactgcaaac ggggcagaaa gaaactcctg tatatattca aacaaccatt tatgagacca   1200
```

gtacaaacta ctcaagagga agatggctgt agctgccgat ttccagaaga agaagaagga 1260
ggatgtgaac tgagagtgaa gttcagcagg agcgcagacg cccccgcgta ccagcagggc 1320
cagaaccagc tctataacga gctcaatcta ggacgaagag aggagtacga tgttttggac 1380
aagagacgtg gccgggaccc tgagatgggg ggaaagccga gaaggaagaa ccctcaggaa 1440
ggcctgtaca atgaactgca gaaagataag atggcggagg cctacagtga gattgggatg 1500
aaaggcgagc gccggagggg caaggggcac gatggccttt accagggtct cagtacagcc 1560
accaaggaca cctacgacgc ccttcacatg caggccctgc cccctcgcta a 1611

<210> SEQ ID NO 23
<211> LENGTH: 1581
<212> TYPE: DNA
<213> ORGANISM: Artificial Sequence
<220> FEATURE:
<223> OTHER INFORMATION: Vb7.2HL-BBz

<400> SEQUENCE: 23
atggccttac cagtgaccgc cttgctcctg ccgctggcct tgctgctcca cgccgccagg 60
ccgggatcca tggaacggca ctggatcttt ctgctgctgc tgagcgttac agccggcgct 120
cactctcaag tgcatctgca gcaatctggc gccgagcttg ctagacctgg cgcctctgtg 180
aagatgagct gtaaagccag cggctacatc ttcaccgact acaccatgca ctgggtcaag 240
cagaggcctg gacagggact cgagtggatc ggccacatca atcctagctc cggctacagc 300
acctacaacc agaagttcaa ggacaaggcc acactgaccg ccgacaagag cagctctaca 360
gcctacatgc agctgagcag cctgaccagc gaagatagcg ccgtgtacta ctgcgccaga 420
agcctgcagc tgggcagaga ttattggggc cagggcacaa ccctgaccgt ttcttctggt 480
ggcggaggat ctggcggagg tggaagcggc ggaggcggat ctatggaatc tcagatccag 540
gtgttcgtgt ttgtgttcct gtggctgtct ggcgtggacg gcgatatcgt gatgacccag 600
agccacaagt tcatgagcac cagcgtgggc gacagagtgt ccatcacatg caaggccagc 660
caggacgtgt acacagccgt ggcttggtat cagcagaagc ccggccagtc tcctaagctg 720
ctgatctaca gcgccagcaa cagatacacc ggcgtgcccg atagattcac aggctctggc 780
agcggcaccg acttcacctt tacaatcagc agcgtgcagg ccgaggacct ggccgtgtat 840
tattgccagc agcactacac cacacctcgg acctttggcg gcggaacaaa gctggaaatc 900
aaggctagca ccacgacgcc agcgccgcga ccaccaacac cggcgcccac catcgcgtcg 960
cagcccctgt ccctgcgccc agaggcgtgc cggccagcgg cggggggcgc agtgcacacg 1020
agggggctgg acttcgcctg tgatatctac atctgggcgc ccttggccgg gacttgtggg 1080
gtccttctcc tgtcactggt tatcaccctt tactgcaaac ggggcagaaa gaaactcctg 1140
tatatattca aacaaccatt tatgagacca gtacaaacta ctcaagagga agatggctgt 1200
agctgccgat ttccagaaga agaagaagga ggatgtgaac tgagagtgaa gttcagcagg 1260
agcgcagacg cccccgcgta ccagcagggc cagaaccagc tctataacga gctcaatcta 1320
ggacgaagag aggagtacga tgttttggac aagagacgtg gccgggaccc tgagatgggg 1380
ggaaagccga gaaggaagaa ccctcaggaa ggcctgtaca atgaactgca gaaagataag 1440
atggcggagg cctacagtga gattgggatg aaaggcgagc gccggagggg caaggggcac 1500
gatggccttt accagggtct cagtacagcc accaaggaca cctacgacgc ccttcacatg 1560
caggccctgc cccctcgcta a 1581

<210> SEQ ID NO 24
<211> LENGTH: 1581
<212> TYPE: DNA
<213> ORGANISM: Artificial Sequence
<220> FEATURE:
<223> OTHER INFORMATION: Vb7.2LH-BBz

<400> SEQUENCE: 24
atggccttac cagtgaccgc cttgctcctg ccgctggcct tgctgctcca cgccgccagg 60
ccgggatcca tggaaagcca gatccaggtg ttcgtgtttg tgttcctgtg gctgtctggc 120
gtggacggcg atatcgtgat gacccagagc cacaagttca tgagcaccag cgtgggcgac 180
agagtgtcca tcacctgtaa agccagccag gacgtgtaca cagccgtggc ctggtatcag 240
cagaagcctg gccagtctcc taagctgctg atctacagcg ccagcaacag atacaccggc 300
gtgcccgata gattcacagg ctctggcagc ggcaccgact tcacctttac aatcagcagc 360
gtgcaggccg aggacctggc cgtgtattat tgccagcagc actacaccac acctcggacc 420
tttggcggcg gaacaaagct ggaaatcaaa ggcggcggag gatctggcgg aggtggaagc 480
ggaggcggtg gttctatgga acggcactgg atctttctgc tgctgctgag cgttacagcc 540
ggcgctcact ctcaagtgca tctgcagcaa tctggcgccg agcttgctag acctggcgcc 600
tctgtgaaga tgagctgcaa ggccagcggc tacatcttca ccgactacac catgcactgg 660
gtcaagcaga ggcctggaca gggactcgag tggatcggcc acatcaatcc tagctccggc 720
tacagcacct acaaccagaa gttcaaggac aaggccacac tgaccgccga caagagcagc 780
tctacagcct acatgcagct gagcagcctg accagcgaag atagcgccgt gtactactgc 840
gctagaagcc tgcagctggg cagagattat tggggccagg gcacaaccct gaccgtgtca 900
tctgctagca ccacgacgcc agcgccgcga ccaccaacac cggcgcccac catcgcgtcg 960
cagcccctgt ccctgcgccc agaggcgtgc cggccagcgg cggggggcgc agtgcacacg 1020
agggggctgg acttcgcctg tgatatctac atctgggcgc ccttggccgg gacttgtggg 1080
gtccttctcc tgtcactggt tatcaccctt tactgcaaac ggggcagaaa gaaactcctg 1140
tatatattca aacaaccatt tatgagacca gtacaaacta ctcaagagga agatggctgt 1200
agctgccgat ttccagaaga agaagaagga ggatgtgaac tgagagtgaa gttcagcagg 1260
agcgcagacg cccccgcgta ccagcagggc cagaaccagc tctataacga gctcaatcta 1320
ggacgaagag aggagtacga tgttttggac aagagacgtg gccgggaccc tgagatgggg 1380
ggaaagccga gaaggaagaa ccctcaggaa ggcctgtaca atgaactgca gaaagataag 1440
atggcggagg cctacagtga gattgggatg aaaggcgagc gccggagggg caaggggcac 1500
gatggccttt accagggtct cagtacagcc accaaggaca cctacgacgc ccttcacatg 1560
caggccctgc cccctcgcta a 1581

<210> SEQ ID NO 25
<211> LENGTH: 1578
<212> TYPE: DNA
<213> ORGANISM: Artificial Sequence
<220> FEATURE:
<223> OTHER INFORMATION: Vb11HL-BBz

<400> SEQUENCE: 25
atggccttac cagtgaccgc cttgctcctg ccgctggcct tgctgctcca cgccgccagg 60
ccgggatcca tgggctggtc ctgcatcatc tttttctgg tggccactgc caccggcgtg 120
cactctcaag ttcagctgca gcagtctggc cccgaagtcg ttagacctgg cgtgtccgtg 180

```
aagatcagct gcaaaggcag cggctaccgg ttcaccgatt ctgccatgca ctgggtcaag    240

cagagccacg ccaagagcct ggaatggatc ggcgtgatca gcagctacaa cggcaacacc    300

aactacaacc agaagttcaa gggcaaagcc accatgaccg tggacaagag cagcagcacc    360

gcctacatgg aactggccag aatgaccagc gaggacagcg ccatctacta ctgcgccaga    420

tccagagatg ccatggacta ttggggccag ggcaccagcg tgacagtttc ttctggcggc    480

ggaggaagcg gaggcggagg ttctggtggt ggtggctcta tgagaacccc tgctcagttc    540

ctgggcatcc tgctgctttg gttccccggc atcaagtgcg acatcaagat gacacagagc    600

cccagctcta tgtacgccag cctgggagag agagtgacca ttacctgcaa ggccagccag    660

gacatcaaca gctacctgag ctggttccag cagaaggccg gcaagagccc caagacactg    720

atctacagag ccaacagact ggtggacggc gtgcccagca gattttctgg aagcggcagc    780

ggccaggact acagcctgac aatcagctcc ctggaatacg aggacatggg gatctactat    840

tgcctgcagt acgacgagtt cccattcacc tttggcggag gcacccggct ggaaatcaaa    900

gctagcacca cgacgccagc gccgcgacca ccaacaccgg cgcccaccat cgcgtcgcag    960

cccctgtccc tgcgcccaga ggcgtgccgg ccagcggcgg ggggcgcagt gcacacgagg   1020

gggctggact tcgcctgtga tatctacatc tgggcgccct tggccgggac ttgtggggtc   1080

cttctcctgt cactggttat caccctttac tgcaaacggg gcagaaagaa actcctgtat   1140

atattcaaac aaccatttat gagaccagta caaactactc aagaggaaga tggctgtagc   1200

tgccgatttc cagaagaaga agaaggagga tgtgaactga gagtgaagtt cagcaggagc   1260

gcagacgccc ccgcgtacca gcagggccag aaccagctct ataacgagct caatctagga   1320

cgaagagagg agtacgatgt tttggacaag agacgtggcc gggaccctga gatgggggga   1380

aagccgagaa ggaagaaccc tcaggaaggc ctgtacaatg aactgcagaa agataagatg   1440

gcggaggcct acagtgagat tgggatgaaa ggcgagcgcc ggaggggcaa ggggcacgat   1500

ggcctttacc agggtctcag tacagccacc aaggacacct acgacgccct tcacatgcag   1560

gccctgcccc ctcgctaa                                                 1578
```

<210> SEQ ID NO 26
<211> LENGTH: 1578
<212> TYPE: DNA
<213> ORGANISM: Artificial Sequence
<220> FEATURE:
<223> OTHER INFORMATION: Vb11LH-BBz

<400> SEQUENCE: 26

```
atggccttac cagtgaccgc cttgctcctg ccgctggcct tgctgctcca cgccgccagg     60

ccgggatcca tgagaacccc tgctcagttc ctgggcatcc tgctgctttg gttccccggc    120

atcaagtgcg acatcaagat gacacagagc cccagctcta tgtacgccag cctgggagag    180

agagtgacca ttacctgcaa ggccagccag gacatcaaca gctacctgag ctggttccag    240

cagaaggccg gcaagagccc caagacactg atctacagag ccaacagact ggtggacggc    300

gtgcccagca gattttctgg ctctggaagc ggccaggact acagcctgac aatcagcagc    360

ctggaatacg aggacatggg catctactac tgcctgcagt acgacgagtt cccattcacc    420

tttggcggcg gaacccggct ggaaatcaaa ggtggcggag gatctggcgg aggcggatca    480

ggcggcggtg gatctatggg ctggtcctgc atcatctttt ttctggtggc cactgccacc    540

ggcgtgcact ctcaagttca gctgcagcag tctggccccg aagtcgttag acctggcgtg    600

tccgtgaaga tcagctgcaa aggcagcggc taccggttca ccgattctgc catgcactgg    660
```

gtcaagcaga gccacgccaa gtctctggaa tggatcggcg tgatcagcag ctacaacggc 720
aacaccaact acaaccagaa gttcaagggc aaagccacca tgaccgtgga caagagcagc 780
agcaccgcct acatggaact ggccagaatg accagcgagg acagcgccat ctattactgt 840
gccagatcca gggacgccat ggactattgg ggccagggaa caagcgtgac cgtgtcctct 900
gctagcacca cgacgccagc gccgcgacca ccaacaccgg cgcccaccat cgcgtcgcag 960
cccctgtccc tgcgcccaga ggcgtgccgg ccagcggcgg ggggcgcagt gcacacgagg 1020
gggctggact tcgcctgtga tatctacatc tgggcgccct tggccgggac ttgtggggtc 1080
cttctcctgt cactggttat caccctttac tgcaaacggg gcagaaagaa actcctgtat 1140
atattcaaac aaccatttat gagaccagta caaactactc aagaggaaga tggctgtagc 1200
tgccgatttc cagaagaaga agaaggagga tgtgaactga gagtgaagtt cagcaggagc 1260
gcagacgccc ccgcgtacca gcagggccag aaccagctct ataacgagct caatctagga 1320
cgaagagagg agtacgatgt tttggacaag agacgtggcc gggaccctga gatgggggga 1380
aagccgagaa ggaagaaccc tcaggaaggc ctgtacaatg aactgcagaa agataagatg 1440
gcggaggcct acagtgagat tgggatgaaa ggcgagcgcc ggaggggcaa ggggcacgat 1500
ggcctttacc agggtctcag tacagccacc aaggacacct acgacgccct tcacatgcag 1560
gccctgcccc ctcgctaa 1578

<210> SEQ ID NO 27
<211> LENGTH: 1599
<212> TYPE: DNA
<213> ORGANISM: Artificial Sequence
<220> FEATURE:
<223> OTHER INFORMATION: Vb13.2HL-BBz

<400> SEQUENCE: 27
atggccttac cagtgaccgc cttgctcctg ccgctggcct tgctgctcca cgccgccagg 60
ccgggatcca tgggctggtc ctggatcttc ctgtttctgc tgtctggcac agccggcgtg 120
cactctgaag ttcagctgca gcagtctggc cccgagcttg tgaaacctgg cgcctctgtg 180
aagatgagct gcaacgccag cggctacacc ttcaccgact actacatcca ctggctgaag 240
cagcggcacg gcaaaggcct ggaatggatc ggcatcgtga acaccaacaa cggcgacacc 300
aactacaacc agcggttcaa gggcaaagcc agcctgaccg tggataagag cagcagcacc 360
gcctacatgg aactgaactc cctgaccagc gaggacagcg ccgtgttcta ttgtgccagg 420
gctctgtaca ccggcagcta ttggttcgcc tattggggcc agggcaccct ggttacagtt 480
tctgcaggcg gcggaggatc tggcggaggt ggaagcggag gcggtggctc tatggatttc 540
cacgtgcaga tcttcagctt catgctgatc tccgtgaccg tgatgctgtc cagcggagag 600
atcgtgctga cacagtctcc agccgtgatg gctgcttccc ctggcgagaa agtgaccatc 660
acatgtagcg ccagcagctc catcagctcc accaacctgc actggtatca gcagaagtcc 720
gagacaagcc ccaagccttg gatctacggc accagcaatc tggccagcgg agtgcctgtc 780
agattttctg gcagcggctc tggcaccagc tacagcctga caatcagcag catcgaggcc 840
gaagatgccg ccacctacta ctgccagcag tggtccagat atcccctgac atttggctcc 900
ggcaccaagc tggaaatcat tgctagcacc acgacgccag cgccgcgacc accaacaccg 960
gcgcccacca tcgcgtcgca gcccctgtcc ctgcgcccag aggcgtgccg gccagcggcg 1020
gggggcgcag tgcacacgag ggggctggac ttcgcctgtg atatctacat ctgggcgccc 1080
ttggccggga cttgtggggt ccttctcctg tcactggtta tcacccttta ctgcaaacgg 1140
ggcagaaaga aactcctgta tatattcaaa caaccattta tgagaccagt acaaactact 1200
caagaggaag atggctgtag ctgccgattt ccagaagaag aagaaggagg atgtgaactg 1260
agagtgaagt tcagcaggag cgcagacgcc cccgcgtacc agcagggcca gaaccagctc 1320
tataacgagc tcaatctagg acgaagagag gagtacgatg ttttggacaa gagacgtggc 1380
cgggaccctg agatgggggg aaagccgaga aggaagaacc ctcaggaagg cctgtacaat 1440
gaactgcaga aagataagat ggcggaggcc tacagtgaga ttgggatgaa aggcgagcgc 1500
cggaggggca aggggcacga tggcctttac cagggtctca gtacagccac caaggacacc 1560
tacgacgccc ttcacatgca ggccctgccc cctcgctaa 1599

<210> SEQ ID NO 28
<211> LENGTH: 1599
<212> TYPE: DNA
<213> ORGANISM: Artificial Sequence
<220> FEATURE:
<223> OTHER INFORMATION: Vb13.2LH-BBz

<400> SEQUENCE: 28
atggccttac cagtgaccgc cttgctcctg ccgctggcct tgctgctcca cgccgccagg 60
ccgggatcca tggacttcca cgtgcagatc ttcagcttca tgctgatctc cgtgaccgtg 120
atgctgagca gcggagagat cgtgctgaca cagtctccag ccgtgatggc tgcttcccct 180
ggcgagaaag tgaccatcac atgtagcgcc agcagcagca tcagcagcac caacctgcac 240
tggtatcagc agaagtccga gacaagcccc aagccttgga tctacggcac cagcaatctg 300
gccagcggag tgcctgtcag attttctggc agcggctctg gcaccagcta cagcctgaca 360
atcagctcca tcgaggccga agatgccgcc acctactact gccagcagtg gtccagatat 420
cccctgacat tcggcagcgg caccaagctg gaaatcatcg gaggcggagg atctggtggc 480
ggaggaagcg gtggcggcgg atctatggga tggtcctgga tcttcctgtt cctgctgtct 540
ggaacagccg gcgtgcactc tgaagttcag ctgcagcagt ctggccccga gcttgtgaaa 600
cctggcgcct ctgtgaagat gagctgcaac gccagcggct acaccttcac cgactactac 660
atccactggc tgaagcagag acacggcaaa ggcctggaat ggatcggcat cgtgaacacc 720
aacaacggcg acaccaacta caaccagcgg ttcaagggca aagccagcct gaccgtggat 780
aagagcagct ccaccgccta catggaactg aactccctga ccagcgagga cagcgccgtg 840
ttctattgtg ccagggctct gtacaccggc agctattggt tcgcctattg gggccagggc 900
accctggtta cagtttctgc tgctagcacc acgacgccag cgccgcgacc accaacaccg 960
gcgcccacca tcgcgtcgca gcccctgtcc ctgcgcccag aggcgtgccg gccagcggcg 1020
gggggcgcag tgcacacgag ggggctggac ttcgcctgtg atatctacat ctgggcgccc 1080
ttggccggga cttgtggggt ccttctcctg tcactggtta tcacccttta ctgcaaacgg 1140
ggcagaaaga aactcctgta tatattcaaa caaccattta tgagaccagt acaaactact 1200
caagaggaag atggctgtag ctgccgattt ccagaagaag aagaaggagg atgtgaactg 1260
agagtgaagt tcagcaggag cgcagacgcc cccgcgtacc agcagggcca gaaccagctc 1320
tataacgagc tcaatctagg acgaagagag gagtacgatg ttttggacaa gagacgtggc 1380
cgggaccctg agatgggggg aaagccgaga aggaagaacc ctcaggaagg cctgtacaat 1440
gaactgcaga aagataagat ggcggaggcc tacagtgaga ttgggatgaa aggcgagcgc 1500
cggaggggca aggggcacga tggcctttac cagggtctca gtacagccac caaggacacc 1560
tacgacgccc ttcacatgca ggccctgccc cctcgctaa 1599

<210> SEQ ID NO 29
<211> LENGTH: 1596
<212> TYPE: DNA
<213> ORGANISM: Artificial Sequence
<220> FEATURE:
<223> OTHER INFORMATION: Vb13.3HL-BBz

<400> SEQUENCE: 29
atggccttac cagtgaccgc cttgctcctg ccgctggcct tgctgctcca cgccgccagg 60
ccgggatcca tgggctggtc ctgcatcatc ctgattctgg tggctgccgc tacaggcgtg 120
cactctcagg ttcagcttca gcagcctggc gccgagcttg tgaaacctgg cgcctctgtg 180
aagatgagct gcaaggccag cggctacacc ttcaccagct actggatcac ctgggtcaag 240
cagaggcctg gacagggact cgagtggatc ggcgatatct atcctggcag cggcagcatc 300
aactacaacg agaagttcaa caacaaggcc acactgaccg tggacaccag cagcagcaca 360
gcctacatgc agctgagcag cctgaccagc gaagatagcg ccgtgtacta ctgcgccaga 420
cgggactact acagcctgta ctactatgcc ctggactact ggggccaggg cacaagcgtg 480
acagtttctt ctggcggcgg aggatctggc ggaggtggaa gcggaggcgg tggatctatg 540
tctgtgccta cacaggtgct gggcctgctg cttctgtggt tgacaggcgc cagatgcgac 600
atccagatga cacagagccc tgccagcctg agtgcctctg tgggagagac agtgaccatg 660
acctgtcggg ccagcgagaa catctacagc aacctggcct ggtatcagca gaagcagggc 720
aagtctcctc agctgctggt ctacgccgcc accaatcttg ctgatggcgt gcccagcaga 780
ttcagcgtgt ccggatctgg cacccacttc agcctgaaga tcaacagcct gcagccagag 840
gacttcggca gctactactg ccagcacttc tacggcaccc cttacacctt tggcggaggc 900
accaagctgg aaatcaaggc tagcaccacg acgccagcgc cgcgaccacc aacaccggcg 960
cccaccatcg cgtcgcagcc cctgtccctg cgcccagagg cgtgccggcc agcggcgggg 1020
ggcgcagtgc acacgagggg gctggacttc gcctgtgata tctacatctg ggcgcccttg 1080
gccgggactt gtggggtcct tctcctgtca ctggttatca ccctttactg caaacggggc 1140
agaaagaaac tcctgtatat attcaaacaa ccatttatga gaccagtaca aactactcaa 1200
gaggaagatg gctgtagctg ccgatttcca gaagaagaag aaggaggatg tgaactgaga 1260
gtgaagttca gcaggagcgc agacgccccc gcgtaccagc agggccagaa ccagctctat 1320
aacgagctca atctaggacg aagagaggag tacgatgttt tggacaagag acgtggccgg 1380
gaccctgaga tgggggggaaa gccgagaagg aagaaccctc aggaaggcct gtacaatgaa 1440
ctgcagaaag ataagatggc ggaggcctac agtgagattg ggatgaaagg cgagcgccgg 1500
aggggcaagg ggcacgatgg cctttaccag ggtctcagta cagccaccaa ggacacctac 1560
gacgcccttc acatgcaggc cctgcccccct cgctaa 1596

<210> SEQ ID NO 30
<211> LENGTH: 1596
<212> TYPE: DNA
<213> ORGANISM: Artificial Sequence
<220> FEATURE:
<223> OTHER INFORMATION: Vb13.3LH-BBz

<400> SEQUENCE: 30
atggccttac cagtgaccgc cttgctcctg ccgctggcct tgctgctcca cgccgccagg 60
ccgggatcca tgagcgtgcc aacacaggtt ctgggactgc tgctgctgtg gctgacaggc 120
gccagatgcg acatccagat gacacagagc cctgccagcc tgtctgcctc tgtgggagag 180
acagtgacca tgacctgtcg ggccagcgag aacatctaca gcaacctggc ctggtatcag 240
cagaagcagg gcaagtctcc tcagctgctg gtgtacgccg ccaccaatct tgctgatggc 300
gtgcccagca gattcagcgt gtccggatct ggcacccact tcagcctgaa gatcaacagc 360
ctgcagcctg aggacttcgg cagctactac tgccagcact tctacggcac cccttacacc 420
tttggcggag gcaccaagct ggaaatcaaa ggcggcggag gaagcggagg cggaggatct 480
ggtggtggtg gatctatggg ctggtcctgc atcatcctga tcctggtggc tgctgctaca 540
ggcgtgcact ctcaggttca gctgcaacag ccaggcgccg agcttgtgaa acctggcgcc 600
tctgtgaaga tgagctgcaa ggccagcggc tacaccttca ccagctactg gatcacctgg 660
gtcaagcaga ggcctggaca gggactcgag tggatcggcg atatctatcc tggcagcggc 720
agcatcaact acaacgagaa gttcaacaac aaggccacac tgaccgtgga caccagctct 780
agcacagcct acatgcagct gagcagcctg accagcgaag atagcgccgt gtactactgc 840
gccagacggg actactacag cctgtactac tatgccctgg actactgggg ccagggcaca 900
agcgtgacag tctcttctgc tagcaccacg acgccagcgc cgcgaccacc aacaccggcg 960
cccaccatcg cgtcgcagcc cctgtccctg cgcccagagg cgtgccggcc agcggcgggg 1020
ggcgcagtgc acacgagggg gctggacttc gcctgtgata tctacatctg ggcgcccttg 1080
gccgggactt gtggggtcct tctcctgtca ctggttatca ccctttactg caaacggggc 1140
agaaagaaac tcctgtatat attcaaacaa ccatttatga gaccagtaca aactactcaa 1200
gaggaagatg gctgtagctg ccgatttcca gaagaagaag aaggaggatg tgaactgaga 1260
gtgaagttca gcaggagcgc agacgccccc gcgtaccagc agggccagaa ccagctctat 1320
aacgagctca atctaggacg aagagaggag tacgatgttt tggacaagag acgtggccgg 1380
gaccctgaga tgggggggaaa gccgagaagg aagaaccctc aggaaggcct gtacaatgaa 1440
ctgcagaaag ataagatggc ggaggcctac agtgagattg ggatgaaagg cgagcgccgg 1500
aggggcaagg ggcacgatgg cctttaccag ggtctcagta cagccaccaa ggacacctac 1560
gacgcccttc acatgcaggc cctgcccccct cgctaa 1596

<210> SEQ ID NO 31
<211> LENGTH: 1578
<212> TYPE: DNA
<213> ORGANISM: Artificial Sequence
<220> FEATURE:
<223> OTHER INFORMATION: Vb22HL-BBz

<400> SEQUENCE: 31
atggccttac cagtgaccgc cttgctcctg ccgctggcct tgctgctcca cgccgccagg 60
ccgggatcca tggacttcgg cctgatcttc ttcatcgtgg ccctgctgaa aggcgtgcag 120
tgcgaagtga agctgctgga atctggcgga ggactggttc agcctggcgg atctctgaag 180
ctgtcttgtg ccgccagcgg cttcgacttc agccggtact ggatgaactg ggtccgacag 240
gcccctggca aaggcctgga atggatcggc gagatcaaca gcgacagcaa caccatcaac 300
tacaccccta gcctgaagga caagttcatc atcagccggg acaacgccaa gaacaccctg 360
tacctgcaga tgaacaaagt gcggagcgag gacacagccc tgtactactg tgctagaggc 420
ggcctgctga gagatgtgtg gggagctgga accaccgtga cagtttctag cggaggcgga 480
ggttctggcg gcggaggaag tggtggcgga ggctctatgg cttggatctc cctgatcctg 540
tctctgctgg cccttagctc tggcgccatt tctcaggccg tggtcacaca agagagcgcc 600
ctgacaacaa gccctggcga gacagtgacc ctgacctgta gatcttctac aggcgccgtg 660
accaccagca actacgccaa ttgggtgcaa gagaagcccg accacctgtt cacaggactg 720
atcggcggca ccaacaatag agcacctggc gtgccagcca gattcagcgg ttctctgatc 780
ggagacagag ccgcactgac aatcacaggc gcccagacag aggacgaggc catctacttt 840
tgcgccctgt ggtacagcaa ccactgggtt ttcggcggag gcaccaagct gacagttctg 900
gctagcacca cgacgccagc gccgcgacca ccaacaccgg cgcccaccat cgcgtcgcag 960
cccctgtccc tgcgcccaga ggcgtgccgg ccagcggcgg ggggcgcagt gcacacgagg 1020
gggctggact tcgcctgtga tatctacatc tgggcgccct tggccgggac ttgtggggtc 1080
cttctcctgt cactggttat caccctttac tgcaaacggg gcagaaagaa actcctgtat 1140
atattcaaac aaccatttat gagaccagta caaactactc aagaggaaga tggctgtagc 1200
tgccgatttc cagaagaaga agaaggagga tgtgaactga gagtgaagtt cagcaggagc 1260
gcagacgccc ccgcgtacca gcagggccag aaccagctct ataacgagct caatctagga 1320
cgaagagagg agtacgatgt tttggacaag agacgtggcc gggaccctga gatgggggga 1380
aagccgagaa ggaagaaccc tcaggaaggc ctgtacaatg aactgcagaa agataagatg 1440
gcggaggcct acagtgagat tgggatgaaa ggcgagcgcc ggaggggcaa ggggcacgat 1500
ggcctttacc agggtctcag tacagccacc aaggacacct acgacgccct tcacatgcag 1560
gccctgcccc ctcgctaa 1578

<210> SEQ ID NO 32
<211> LENGTH: 1578
<212> TYPE: DNA
<213> ORGANISM: Artificial Sequence
<220> FEATURE:
<223> OTHER INFORMATION: Vb22LH-BBz

<400> SEQUENCE: 32
atggccttac cagtgaccgc cttgctcctg ccgctggcct tgctgctcca cgccgccagg 60
ccgggatcca tggcctggat tagcctgatc ctgtctctgc tggccctgtc tagcggagcc 120
atttctcagg ccgtggtcac acaagagagc gccctgacaa caagccctgg cgagacagtg 180
accctgacct gcagatcttc tacaggcgcc gtgaccacca gcaactacgc caattgggtg 240
caagagaagc ccgaccacct gttcacagga ctgatcggcg gcaccaacaa tagagcacct 300
ggcgtgccag ccagattcag cggatctctg atcggagaca gagccgcact gacaatcaca 360
ggcgcccaga cagaggacga ggccatctac ttttgcgccc tgtggtacag caaccactgg 420
gttttcggcg gaggcaccaa gctgacagtt cttggaggcg gaggatctgg cggaggtgga 480
agtggcggag gcggctctat ggatttcggc ctgatcttct tcatcgtggc cctgctgaaa 540
ggcgtgcagt gcgaagtgaa gctgctggaa tctggtggcg gactggttca gcctggcggc 600
tctctgaaac tgtcttgtgc cgccagcggc ttcgacttca gccggtactg gatgaactgg 660
gtccgacagg cccctggcaa aggcctggaa tggatcggcg agatcaacag cgacagcaac 720
accatcaact acacccctag cctgaaggac aagttcatca tcagccggga caacgccaag 780
aacacactgt acctccagat gaacaaagtg cggagcgagg acacagccct gtactactgt 840
gctagaggcg gcctgctgag agatgtgtgg ggagctggaa ccaccgtgac cgttagttct 900
gctagcacca cgacgccagc gccgcgacca ccaacaccgg cgcccaccat cgcgtcgcag 960

```
cccctgtccc tgcgcccaga ggcgtgccgg ccagcggcgg ggggcgcagt gcacacgagg   1020

gggctggact tcgcctgtga tatctacatc tgggcgccct tggccgggac ttgtggggtc   1080

cttctcctgt cactggttat caccctttac tgcaaacggg gcagaaagaa actcctgtat   1140

atattcaaac aaccatttat gagaccagta caaactactc aagaggaaga tggctgtagc   1200

tgccgatttc cagaagaaga agaaggagga tgtgaactga gagtgaagtt cagcaggagc   1260

gcagacgccc ccgcgtacca gcagggccag aaccagctct ataacgagct caatctagga   1320

cgaagagagg agtacgatgt tttggacaag agacgtggcc gggaccctga gatgggggga   1380

aagccgagaa ggaagaaccc tcaggaaggc ctgtacaatg aactgcagaa agataagatg   1440

gcggaggcct acagtgagat tgggatgaaa ggcgagcgcc ggaggggcaa ggggcacgat   1500

ggcctttacc agggtctcag tacagccacc aaggacacct acgacgccct tcacatgcag   1560

gccctgcccc ctcgctaa                                                 1578


<210> SEQ ID NO 33
<211> LENGTH: 717
<212> TYPE: PRT
<213> ORGANISM: Artificial Sequence
<220> FEATURE:
<223> OTHER INFORMATION: Vb12HL scFv

<400> SEQUENCE: 33

Gly Ala Ala Gly Thr Gly Ala Thr Gly Cys Thr Gly Gly Thr Gly Gly
1               5                   10                  15

Ala Ala Thr Cys Thr Gly Gly Cys Gly Gly Cys Gly Gly Ala Cys Thr
            20                  25                  30

Gly Gly Thr Thr Ala Ala Gly Cys Cys Thr Gly Gly Cys Gly Gly Ala
        35                  40                  45

Thr Cys Thr Cys Thr Gly Ala Ala Gly Cys Thr Gly Ala Gly Cys Thr
    50                  55                  60

Gly Thr Gly Cys Cys Gly Cys Cys Ala Gly Cys Gly Gly Cys Thr Thr
65                  70                  75                  80

Cys Ala Cys Cys Thr Thr Thr Ala Gly Ala Ala Gly Cys Thr Ala Cys
                85                  90                  95

Gly Cys Cys Ala Thr Gly Ala Gly Cys Thr Gly Gly Gly Thr Cys Cys
            100                 105                 110

Gly Ala Cys Ala Gly Ala Cys Cys Cys Cys Thr Gly Ala Gly Ala Ala
        115                 120                 125

Gly Ala Gly Ala Cys Thr Gly Gly Ala Ala Thr Gly Gly Gly Thr Cys
    130                 135                 140

Gly Cys Cys Ala Cys Ala Ala Thr Cys Ala Gly Cys Ala Gly Cys Gly
145                 150                 155                 160

Gly Cys Gly Gly Cys Ala Gly Cys Thr Ala Cys Ala Cys Ala Ala Ala
                165                 170                 175

Cys Thr Ala Cys Cys Cys Cys Gly Ala Thr Ala Gly Cys Gly Thr Gly
            180                 185                 190

Ala Ala Gly Gly Gly Cys Ala Gly Ala Thr Thr Cys Ala Cys Cys Ala
        195                 200                 205

Thr Cys Ala Gly Cys Cys Gly Gly Gly Ala Cys Ala Ala Cys Gly Cys
    210                 215                 220

Cys Ala Ala Gly Ala Ala Cys Ala Cys Cys Thr Gly Ala Ala Cys
225                 230                 235                 240

Cys Thr Gly Cys Ala Gly Ala Thr Gly Ala Ala Cys Ala Gly Cys Cys
                245                 250                 255
```

```
Thr Gly Cys Gly Gly Ala Gly Cys Gly Ala Gly Gly Ala Cys Ala Cys
            260                 265                 270

Cys Gly Cys Cys Ala Thr Gly Thr Ala Cys Thr Ala Thr Thr Gly Thr
        275                 280                 285

Gly Cys Cys Ala Gly Ala Gly Gly Cys Thr Ala Cys Cys Ala Cys Gly
    290                 295                 300

Gly Cys Thr Ala Cys Cys Thr Gly Gly Ala Thr Gly Thr Thr Thr Gly
305                 310                 315                 320

Gly Gly Gly Ala Gly Cys Cys Gly Gly Cys Ala Cys Ala Ala Cys Cys
                325                 330                 335

Gly Thr Gly Ala Cys Ala Gly Thr Thr Thr Cys Thr Thr Cys Thr Gly
            340                 345                 350

Gly Thr Gly Gly Cys Gly Gly Ala Gly Gly Ala Thr Cys Thr Gly Gly
        355                 360                 365

Cys Gly Gly Ala Gly Gly Thr Gly Gly Ala Ala Gly Cys Gly Gly Cys
    370                 375                 380

Gly Gly Ala Gly Gly Cys Gly Gly Ala Thr Cys Thr Gly Ala Thr Ala
385                 390                 395                 400

Thr Thr Cys Thr Gly Cys Thr Gly Ala Cys Thr Cys Ala Gly Ala Gly
                405                 410                 415

Cys Cys Cys Cys Gly Cys Cys Thr Thr Cys Cys Thr Gly Thr Cys Thr
            420                 425                 430

Gly Thr Thr Thr Cys Thr Cys Cys Thr Gly Gly Cys Gly Ala Gly Ala
        435                 440                 445

Gly Ala Gly Thr Gly Thr Cys Cys Thr Thr Cys Ala Gly Cys Thr Gly
    450                 455                 460

Cys Ala Gly Ala Gly Cys Cys Thr Cys Thr Cys Ala Gly Ala Gly Cys
465                 470                 475                 480

Ala Thr Cys Gly Gly Cys Ala Cys Cys Thr Cys Cys Ala Thr Cys Cys
                485                 490                 495

Ala Cys Thr Gly Gly Thr Ala Thr Cys Ala Gly Cys Ala Gly Ala Gly
            500                 505                 510

Gly Ala Cys Cys Ala Ala Cys Gly Gly Cys Ala Gly Cys Cys Cys Cys
        515                 520                 525

Ala Gly Ala Cys Thr Gly Cys Thr Gly Ala Thr Thr Ala Ala Gly Thr
    530                 535                 540

Ala Cys Gly Cys Cys Ala Gly Cys Gly Ala Gly Ala Gly Cys Thr Thr
545                 550                 555                 560

Cys Ala Gly Cys Gly Gly Cys Ala Thr Cys Cys Cys Ala Gly Cys
                565                 570                 575

Ala Gly Ala Thr Thr Thr Thr Cys Thr Gly Gly Cys Thr Cys Thr Gly
            580                 585                 590

Gly Cys Ala Gly Cys Gly Gly Cys Ala Cys Cys Gly Ala Cys Thr Thr
        595                 600                 605

Cys Ala Cys Cys Cys Thr Gly Thr Cys Thr Ala Thr Cys Ala Gly Cys
    610                 615                 620

Thr Cys Cys Gly Thr Gly Gly Ala Ala Ala Gly Cys Gly Ala Gly Gly
625                 630                 635                 640

Ala Thr Ala Thr Cys Gly Cys Cys Gly Ala Cys Thr Ala Cys Thr Ala
                645                 650                 655

Cys Thr Gly Cys Cys Ala Gly Cys Ala Gly Thr Cys Cys Thr Ala Cys
            660                 665                 670
```

Ala Gly Cys Thr Gly Gly Cys Cys Cys Thr Ala Cys Ala Cys Ala Thr
675 680 685

Thr Thr Gly Gly Cys Gly Gly Ala Gly Gly Cys Ala Cys Cys Ala Ala
690 695 700

Gly Cys Thr Gly Gly Ala Ala Ala Thr Cys Ala Ala Gly
705 710 715

<210> SEQ ID NO 34
<211> LENGTH: 717
<212> TYPE: PRT
<213> ORGANISM: Artificial Sequence
<220> FEATURE:
<223> OTHER INFORMATION: Vb12LH scFv

<400> SEQUENCE: 34

Gly Ala Cys Ala Thr Cys Cys Thr Gly Cys Thr Gly Ala Cys Thr Cys
1 5 10 15

Ala Gly Ala Gly Cys Cys Cys Thr Gly Cys Cys Thr Thr Cys Cys Thr
20 25 30

Gly Thr Cys Thr Gly Thr Gly Thr Cys Thr Cys Cys Thr Gly Gly Cys
35 40 45

Gly Ala Gly Ala Gly Ala Gly Thr Gly Thr Cys Cys Thr Thr Cys Ala
50 55 60

Gly Cys Thr Gly Thr Ala Gly Ala Gly Cys Cys Ala Gly Cys Cys Ala
65 70 75 80

Gly Ala Gly Cys Ala Thr Cys Gly Gly Cys Ala Cys Cys Ala Gly Cys
85 90 95

Ala Thr Cys Cys Ala Cys Thr Gly Gly Thr Ala Thr Cys Ala Gly Cys
100 105 110

Ala Gly Cys Gly Gly Ala Cys Ala Ala Ala Cys Gly Gly Cys Ala Gly
115 120 125

Cys Cys Cys Cys Ala Gly Ala Cys Thr Gly Cys Thr Gly Ala Thr Thr
130 135 140

Ala Ala Gly Thr Ala Cys Gly Cys Cys Ala Gly Cys Gly Ala Gly Ala
145 150 155 160

Gly Cys Thr Thr Cys Ala Gly Cys Gly Gly Cys Ala Thr Cys Cys Cys
165 170 175

Cys Ala Gly Cys Ala Gly Ala Thr Thr Thr Thr Cys Thr Gly Gly Cys
180 185 190

Ala Gly Cys Gly Gly Cys Thr Cys Thr Gly Gly Cys Ala Cys Cys Gly
195 200 205

Ala Cys Thr Thr Cys Ala Cys Cys Cys Thr Gly Thr Cys Thr Ala Thr
210 215 220

Cys Ala Gly Cys Thr Cys Cys Gly Thr Gly Gly Ala Ala Ala Gly Cys
225 230 235 240

Gly Ala Gly Gly Ala Thr Ala Thr Cys Gly Cys Cys Gly Ala Cys Thr
245 250 255

Ala Cys Thr Ala Cys Thr Gly Cys Cys Ala Gly Cys Ala Gly Thr Cys
260 265 270

Cys Thr Ala Cys Ala Gly Cys Thr Gly Gly Cys Cys Cys Thr Ala Cys
275 280 285

Ala Cys Ala Thr Thr Thr Gly Gly Cys Gly Gly Ala Gly Gly Cys Ala
290 295 300

Cys Cys Ala Ala Gly Cys Thr Gly Gly Ala Ala Ala Thr Cys Ala Ala
305 310 315 320

```
Ala Gly Gly Cys Gly Gly Cys Gly Gly Ala Gly Gly Ala Ala Gly Cys
                325                 330                 335

Gly Gly Ala Gly Gly Cys Gly Gly Ala Gly Gly Ala Thr Cys Thr Gly
            340                 345                 350

Gly Thr Gly Gly Thr Gly Gly Thr Gly Gly Ala Thr Cys Thr Gly Ala
        355                 360                 365

Ala Gly Thr Gly Ala Thr Gly Cys Thr Gly Gly Thr Cys Gly Ala Gly
    370                 375                 380

Thr Cys Thr Gly Gly Cys Gly Gly Cys Gly Gly Ala Cys Thr Thr Gly
385                 390                 395                 400

Thr Gly Ala Ala Ala Cys Cys Thr Gly Gly Cys Gly Gly Ala Ala Gly
                405                 410                 415

Cys Cys Thr Gly Ala Ala Gly Cys Thr Gly Ala Gly Cys Thr Gly Thr
            420                 425                 430

Gly Cys Cys Gly Cys Thr Thr Cys Cys Gly Gly Cys Thr Thr Cys Ala
        435                 440                 445

Cys Cys Thr Thr Thr Ala Gly Ala Ala Gly Cys Thr Ala Cys Gly Cys
    450                 455                 460

Cys Ala Thr Gly Ala Gly Cys Thr Gly Gly Gly Thr Cys Cys Gly Ala
465                 470                 475                 480

Cys Ala Gly Ala Cys Cys Cys Cys Thr Gly Ala Gly Ala Ala Gly Ala
                485                 490                 495

Gly Ala Cys Thr Gly Gly Ala Ala Thr Gly Gly Gly Thr Cys Gly Cys
            500                 505                 510

Cys Ala Cys Cys Ala Thr Cys Thr Cys Thr Ala Gly Cys Gly Gly Cys
        515                 520                 525

Gly Gly Cys Ala Gly Cys Thr Ala Cys Ala Cys Ala Ala Ala Cys Thr
    530                 535                 540

Ala Cys Cys Cys Cys Gly Ala Cys Thr Cys Thr Gly Thr Gly Ala Ala
545                 550                 555                 560

Gly Gly Gly Cys Ala Gly Ala Thr Thr Cys Ala Cys Cys Ala Thr Cys
                565                 570                 575

Ala Gly Cys Cys Gly Gly Gly Ala Cys Ala Ala Cys Gly Cys Cys Ala
            580                 585                 590

Ala Gly Ala Ala Cys Ala Cys Cys Cys Thr Gly Ala Ala Cys Cys Thr
        595                 600                 605

Gly Cys Ala Gly Ala Thr Gly Ala Ala Cys Ala Gly Cys Cys Thr Gly
    610                 615                 620

Cys Gly Gly Ala Gly Cys Gly Ala Gly Gly Ala Cys Ala Cys Cys Gly
625                 630                 635                 640

Cys Cys Ala Thr Gly Thr Ala Cys Thr Ala Thr Thr Gly Thr Gly Cys
                645                 650                 655

Cys Ala Gly Ala Gly Gly Cys Thr Ala Cys Cys Ala Cys Gly Gly Cys
            660                 665                 670

Thr Ala Cys Cys Thr Gly Gly Ala Thr Gly Thr Thr Thr Gly Gly Gly
        675                 680                 685

Gly Ala Gly Cys Cys Gly Gly Cys Ala Cys Ala Ala Cys Cys Gly Thr
    690                 695                 700

Gly Ala Cys Ala Gly Thr Gly Thr Cys Ala Thr Cys Thr
705                 710                 715
```

<210> SEQ ID NO 35
<211> LENGTH: 837
<212> TYPE: PRT

<213> ORGANISM: Artificial Sequence
<220> FEATURE:
<223> OTHER INFORMATION: Vb9HL scFv

<400> SEQUENCE: 35

Ala Thr Gly Ala Ala Gly Thr Thr Cys Ala Gly Cys Thr Gly Gly Gly
1 5 10 15

Thr Cys Ala Thr Cys Thr Thr Cys Thr Thr Thr Cys Thr Gly Ala Thr
20 25 30

Gly Gly Cys Cys Gly Thr Gly Gly Thr Cys Ala Cys Cys Gly Gly Cys
35 40 45

Gly Thr Gly Ala Ala Cys Thr Cys Thr Gly Ala Ala Gly Thr Gly Cys
50 55 60

Ala Ala Cys Thr Gly Cys Ala Gly Cys Ala Gly Ala Gly Cys Gly Thr
65 70 75 80

Gly Gly Cys Cys Gly Ala Ala Cys Thr Cys Gly Thr Thr Ala Gly Ala
85 90 95

Cys Cys Thr Gly Gly Cys Gly Cys Cys Thr Cys Thr Gly Thr Gly Ala
100 105 110

Ala Gly Cys Thr Gly Ala Gly Cys Thr Gly Thr Ala Cys Cys Gly Cys
115 120 125

Cys Ala Gly Cys Gly Gly Cys Thr Thr Cys Ala Ala Cys Ala Thr Cys
130 135 140

Ala Ala Gly Ala Ala Cys Ala Cys Cys Thr Thr Cys Ala Thr Gly Cys
145 150 155 160

Ala Cys Thr Gly Gly Gly Thr Cys Ala Ala Gly Cys Ala Gly Cys Gly
165 170 175

Gly Cys Cys Thr Gly Ala Gly Cys Ala Gly Gly Gly Ala Cys Thr Cys
180 185 190

Gly Ala Gly Thr Gly Gly Ala Thr Cys Gly Gly Ala Ala Gly Ala Ala
195 200 205

Thr Cys Gly Ala Cys Cys Cys Cys Ala Cys Cys Ala Ala Cys Gly Gly
210 215 220

Cys Thr Ala Cys Ala Cys Cys Ala Ala Gly Thr Thr Cys Gly Cys Cys
225 230 235 240

Cys Cys Thr Ala Ala Gly Thr Thr Cys Cys Ala Gly Gly Gly Cys Ala
245 250 255

Ala Ala Gly Cys Cys Ala Cys Ala Cys Thr Gly Ala Cys Ala Gly Cys
260 265 270

Cys Gly Thr Gly Ala Cys Cys Ala Gly Cys Ala Gly Cys Ala Ala Cys
275 280 285

Ala Cys Ala Gly Thr Gly Thr Ala Cys Cys Thr Gly Cys Ala Gly Cys
290 295 300

Thr Gly Ala Gly Cys Ala Gly Cys Cys Thr Gly Ala Cys Cys Thr Cys
305 310 315 320

Thr Gly Ala Gly Gly Ala Cys Ala Cys Cys Gly Cys Cys Ala Thr Cys
325 330 335

Thr Ala Cys Thr Ala Cys Thr Gly Cys Gly Cys Cys Cys Ala Cys Gly
340 345 350

Ala Thr Thr Ala Cys Gly Ala Cys Gly Cys Cys Cys Cys Thr Thr Gly
355 360 365

Gly Thr Thr Thr Gly Cys Cys Thr Ala Thr Thr Gly Gly Gly Gly Cys
370 375 380

Cys Ala Gly Gly Gly Cys Ala Cys Ala Cys Thr Gly Gly Thr Cys Ala 385 390 395 400

Thr Thr Gly Thr Gly Thr Cys Thr Gly Cys Thr Gly Gly Thr Gly Gly
405 410 415

Cys Gly Gly Ala Gly Gly Ala Thr Cys Thr Gly Gly Cys Gly Gly Ala
420 425 430

Gly Gly Thr Gly Gly Ala Ala Gly Cys Gly Gly Cys Gly Gly Ala Gly
435 440 445

Gly Cys Gly Gly Ala Thr Cys Thr Ala Thr Gly Cys Thr Thr Thr Cys
450 455 460

Thr Cys Cys Thr Gly Cys Thr Cys Cys Thr Cys Thr Gly Cys Thr Gly
465 470 475 480

Ala Gly Cys Cys Thr Gly Cys Thr Gly Cys Thr Gly Cys Thr Gly Thr
485 490 495

Gly Cys Gly Thr Gly Thr Cys Ala Gly Ala Thr Ala Gly Cys Ala Gly
500 505 510

Ala Gly Cys Cys Gly Ala Gly Ala Cys Ala Ala Cys Cys Gly Thr Gly
515 520 525

Ala Cys Ala Cys Ala Gly Thr Cys Thr Cys Cys Ala Gly Cys Cys Ala
530 535 540

Gly Thr Cys Thr Gly Thr Cys Thr Gly Thr Gly Gly Cys Cys Ala Cys
545 550 555 560

Cys Gly Gly Cys Gly Ala Gly Ala Ala Ala Gly Thr Gly Ala Cys Cys
565 570 575

Ala Thr Cys Ala Gly Ala Thr Gly Cys Ala Thr Cys Ala Gly Cys Ala
580 585 590

Gly Cys Ala Cys Cys Gly Ala Cys Ala Thr Cys Gly Ala Cys Gly Ala
595 600 605

Cys Gly Ala Cys Ala Thr Gly Ala Ala Cys Thr Gly Gly Thr Ala Thr
610 615 620

Cys Ala Gly Cys Ala Gly Ala Ala Gly Thr Cys Cys Gly Gly Cys Gly
625 630 635 640

Ala Gly Cys Cys Thr Cys Cys Thr Ala Ala Gly Cys Thr Gly Cys Thr
645 650 655

Gly Ala Thr Cys Thr Cys Cys Gly Ala Gly Gly Gly Cys Ala Ala Thr
660 665 670

Ala Cys Thr Cys Thr Gly Ala Gly Gly Cys Cys Thr Gly Gly Cys Gly
675 680 685

Thr Gly Cys Cys Ala Ala Gly Cys Ala Gly Ala Thr Thr Cys Ala Gly
690 695 700

Cys Ala Gly Cys Thr Cys Thr Gly Gly Cys Thr Ala Cys Gly Gly Cys
705 710 715 720

Ala Cys Cys Gly Ala Cys Thr Thr Cys Gly Thr Gly Thr Thr Cys Ala
725 730 735

Cys Cys Ala Thr Cys Gly Ala Gly Ala Ala Cys Ala Thr Gly Cys Thr
740 745 750

Gly Ala Gly Cys Gly Ala Gly Gly Ala Cys Gly Thr Gly Gly Cys Cys
755 760 765

Gly Ala Thr Thr Ala Cys Thr Ala Cys Thr Gly Cys Cys Thr Gly Cys
770 775 780

Ala Gly Ala Gly Cys Gly Ala Cys Ala Ala Cys Ala Thr Gly Cys Cys
785 790 795 800

Cys Cys Thr Gly Ala Cys Ala Thr Thr Thr Gly Gly Ala Gly Cys Cys
805 810 815

Gly Gly Cys Ala Cys Cys Ala Ala Gly Cys Thr Gly Gly Ala Ala Cys
820 825 830

Thr Gly Ala Ala Gly
835

<210> SEQ ID NO 36
<211> LENGTH: 837
<212> TYPE: PRT
<213> ORGANISM: Artificial Sequence
<220> FEATURE:
<223> OTHER INFORMATION: Vb9LH scFv

<400> SEQUENCE: 36

Ala Thr Gly Cys Thr Gly Thr Cys Thr Cys Cys Ala Gly Cys Thr Cys
1 5 10 15

Cys Thr Cys Thr Gly Cys Thr Gly Thr Cys Thr Cys Thr Gly Cys Thr
20 25 30

Gly Cys Thr Gly Cys Thr Gly Thr Gly Cys Gly Thr Gly Thr Cys Cys
35 40 45

Gly Ala Thr Ala Gly Cys Ala Gly Ala Gly Cys Cys Gly Ala Gly Ala
50 55 60

Cys Ala Ala Cys Cys Gly Thr Gly Ala Cys Ala Cys Ala Gly Thr Cys
65 70 75 80

Thr Cys Cys Ala Gly Cys Cys Ala Gly Thr Cys Thr Gly Thr Cys Thr
85 90 95

Gly Thr Gly Gly Cys Cys Ala Cys Cys Gly Gly Cys Gly Ala Gly Ala
100 105 110

Ala Ala Gly Thr Gly Ala Cys Cys Ala Thr Cys Ala Gly Ala Thr Gly
115 120 125

Cys Ala Thr Cys Ala Gly Cys Ala Gly Cys Ala Cys Cys Gly Ala Cys
130 135 140

Ala Thr Cys Gly Ala Cys Gly Ala Cys Gly Ala Cys Ala Thr Gly Ala
145 150 155 160

Ala Cys Thr Gly Gly Thr Ala Thr Cys Ala Gly Cys Ala Gly Ala Ala
165 170 175

Gly Thr Cys Cys Gly Gly Cys Gly Ala Gly Cys Cys Thr Cys Cys Thr
180 185 190

Ala Ala Gly Cys Thr Gly Cys Thr Gly Ala Thr Cys Thr Cys Cys Gly
195 200 205

Ala Gly Gly Gly Cys Ala Ala Thr Ala Cys Thr Cys Thr Gly Ala Gly
210 215 220

Gly Cys Cys Thr Gly Gly Cys Gly Thr Gly Cys Cys Ala Ala Gly Cys
225 230 235 240

Ala Gly Ala Thr Thr Cys Ala Gly Cys Ala Gly Cys Thr Cys Thr Gly
245 250 255

Gly Cys Thr Ala Cys Gly Gly Cys Ala Cys Cys Gly Ala Cys Thr Thr
260 265 270

Cys Gly Thr Gly Thr Thr Cys Ala Cys Cys Ala Thr Cys Gly Ala Gly
275 280 285

Ala Ala Cys Ala Thr Gly Cys Thr Gly Ala Gly Cys Gly Ala Gly Gly
290 295 300

Ala Cys Gly Thr Gly Gly Cys Cys Gly Ala Cys Thr Ala Cys Thr Ala
305 310 315 320

Cys Thr Gly Cys Cys Thr Gly Cys Ala Gly Ala Gly Cys Gly Ala Cys
325 330 335

```
Ala Ala Cys Ala Thr Gly Cys Cys Cys Cys Thr Gly Ala Cys Ala Thr
            340                 345                 350

Thr Thr Gly Gly Ala Gly Cys Cys Gly Gly Cys Ala Cys Cys Ala Ala
        355                 360                 365

Gly Cys Thr Gly Gly Ala Ala Cys Thr Gly Ala Ala Ala Gly Gly Cys
    370                 375                 380

Gly Gly Cys Gly Gly Ala Gly Gly Ala Thr Cys Thr Gly Gly Cys Gly
385                 390                 395                 400

Gly Ala Gly Gly Thr Gly Gly Ala Ala Gly Cys Gly Gly Ala Gly Gly
                405                 410                 415

Cys Gly Gly Thr Gly Gly Cys Ala Gly Cys Ala Thr Gly Ala Ala Gly
            420                 425                 430

Thr Thr Cys Ala Gly Cys Thr Gly Gly Gly Thr Cys Ala Thr Cys Thr
        435                 440                 445

Thr Cys Thr Thr Thr Cys Thr Gly Ala Thr Gly Gly Cys Cys Gly Thr
    450                 455                 460

Gly Gly Thr Cys Ala Cys Cys Gly Gly Cys Gly Thr Gly Ala Ala Cys
465                 470                 475                 480

Thr Cys Thr Gly Ala Ala Gly Thr Gly Cys Ala Ala Cys Thr Gly Cys
                485                 490                 495

Ala Gly Cys Ala Gly Ala Gly Cys Gly Thr Gly Gly Cys Cys Gly Ala
            500                 505                 510

Ala Cys Thr Cys Gly Thr Thr Ala Gly Ala Cys Cys Thr Gly Gly Cys
        515                 520                 525

Gly Cys Cys Thr Cys Thr Gly Thr Gly Ala Ala Gly Cys Thr Gly Ala
    530                 535                 540

Gly Cys Thr Gly Thr Ala Cys Cys Gly Cys Cys Ala Gly Cys Gly Gly
545                 550                 555                 560

Cys Thr Thr Cys Ala Ala Cys Ala Thr Cys Ala Ala Gly Ala Ala Cys
                565                 570                 575

Ala Cys Cys Thr Thr Cys Ala Thr Gly Cys Ala Cys Thr Gly Gly Gly
            580                 585                 590

Thr Cys Ala Ala Gly Cys Ala Gly Cys Gly Gly Cys Cys Thr Gly Ala
        595                 600                 605

Gly Cys Ala Gly Gly Gly Ala Cys Thr Cys Gly Ala Gly Thr Gly Gly
    610                 615                 620

Ala Thr Cys Gly Gly Ala Ala Gly Ala Ala Thr Cys Gly Ala Cys Cys
625                 630                 635                 640

Cys Cys Ala Cys Cys Ala Ala Cys Gly Gly Cys Thr Ala Cys Ala Cys
                645                 650                 655

Cys Ala Ala Gly Thr Thr Cys Gly Cys Cys Cys Cys Thr Ala Ala Gly
            660                 665                 670

Thr Thr Cys Cys Ala Gly Gly Gly Cys Ala Ala Ala Gly Cys Cys Ala
        675                 680                 685

Cys Ala Cys Thr Gly Ala Cys Ala Gly Cys Cys Gly Thr Gly Ala Cys
    690                 695                 700

Cys Ala Gly Cys Ala Gly Cys Ala Ala Cys Ala Cys Ala Gly Thr Gly
705                 710                 715                 720

Thr Ala Cys Cys Thr Gly Cys Ala Gly Cys Thr Gly Ala Gly Cys Ala
                725                 730                 735

Gly Cys Cys Thr Gly Ala Cys Cys Thr Cys Thr Gly Ala Gly Gly Ala
            740                 745                 750
```

Cys Ala Cys Cys Gly Cys Cys Ala Thr Cys Thr Ala Cys Thr Ala Cys
755 760 765

Thr Gly Thr Gly Cys Cys Cys Ala Cys Gly Ala Cys Thr Ala Cys Gly
770 775 780

Ala Cys Gly Cys Cys Cys Cys Thr Thr Gly Gly Thr Thr Thr Gly Cys
785 790 795 800

Cys Thr Ala Thr Thr Gly Gly Gly Gly Cys Cys Ala Gly Gly Gly Cys
805 810 815

Ala Cys Ala Cys Thr Gly Gly Thr Cys Ala Thr Cys Gly Thr Thr Thr
820 825 830

Cys Thr Gly Cys Thr
835

<210> SEQ ID NO 37
<211> LENGTH: 852
<212> TYPE: PRT
<213> ORGANISM: Artificial Sequence
<220> FEATURE:
<223> OTHER INFORMATION: Vb1HL scFv

<400> SEQUENCE: 37

Ala Thr Gly Gly Ala Cys Thr Gly Gly Gly Thr Cys Thr Gly Gly Ala
1 5 10 15

Ala Cys Cys Thr Gly Cys Thr Gly Thr Thr Cys Cys Thr Gly Ala Thr
20 25 30

Gly Gly Cys Cys Gly Thr Thr Gly Cys Thr Cys Ala Gly Ala Cys Ala
35 40 45

Gly Gly Thr Gly Cys Thr Cys Ala Gly Gly Cys Thr Cys Ala Gly Cys
50 55 60

Thr Gly Cys Ala Ala Cys Thr Gly Gly Thr Gly Cys Ala Gly Thr Cys
65 70 75 80

Thr Gly Gly Ala Cys Cys Thr Gly Ala Gly Cys Thr Gly Ala Gly Ala
85 90 95

Gly Ala Ala Cys Cys Thr Gly Gly Cys Gly Ala Gly Ala Gly Cys Gly
100 105 110

Thr Gly Ala Ala Gly Ala Thr Cys Thr Cys Cys Thr Gly Cys Ala Ala
115 120 125

Gly Gly Cys Cys Ala Gly Cys Gly Gly Cys Thr Ala Cys Ala Cys Cys
130 135 140

Thr Thr Cys Ala Cys Cys Gly Ala Cys Thr Ala Cys Ala Thr Cys Gly
145 150 155 160

Thr Gly Cys Ala Cys Thr Gly Gly Gly Thr Cys Ala Ala Gly Cys Ala
165 170 175

Gly Gly Cys Cys Cys Cys Thr Gly Gly Cys Ala Ala Gly Gly Gly Ala
180 185 190

Cys Thr Gly Ala Ala Ala Thr Gly Gly Ala Thr Gly Gly Gly Cys Thr
195 200 205

Gly Gly Ala Thr Cys Ala Ala Cys Ala Cys Cys Thr Ala Cys Ala Cys
210 215 220

Cys Gly Gly Cys Ala Cys Ala Cys Cys Cys Ala Cys Cys Thr Ala Cys
225 230 235 240

Gly Cys Cys Gly Ala Cys Gly Ala Thr Thr Thr Cys Gly Ala Gly Gly
245 250 255

Gly Cys Ala Gly Ala Thr Thr Cys Gly Thr Gly Thr Thr Cys Ala Gly
260 265 270

-continued

```
Cys Cys Thr Gly Gly Ala Ala Gly Cys Cys Thr Cys Thr Gly Cys Cys
        275                 280                 285

Ala Gly Cys Ala Cys Cys Gly Cys Cys Ala Ala Cys Cys Thr Gly Cys
    290                 295                 300

Ala Gly Ala Thr Cys Ala Gly Cys Ala Ala Cys Cys Thr Gly Ala Ala
305                 310                 315                 320

Gly Ala Ala Cys Gly Ala Gly Gly Ala Cys Ala Cys Cys Gly Cys Cys
                325                 330                 335

Ala Cys Cys Thr Ala Cys Thr Thr Thr Thr Gly Cys Gly Cys Cys Ala
            340                 345                 350

Gly Ala Thr Cys Thr Thr Gly Gly Cys Gly Gly Ala Gly Ala Gly Gly
        355                 360                 365

Cys Ala Thr Cys Cys Gly Cys Gly Gly Cys Ala Thr Cys Gly Gly Cys
    370                 375                 380

Thr Thr Thr Gly Ala Thr Thr Ala Thr Thr Gly Gly Gly Gly Ala Cys
385                 390                 395                 400

Ala Gly Gly Gly Cys Gly Thr Gly Ala Thr Gly Gly Thr Cys Ala Cys
                405                 410                 415

Cys Gly Thr Gly Thr Cys Thr Ala Gly Cys Gly Gly Ala Gly Gly Cys
            420                 425                 430

Gly Gly Ala Gly Gly Ala Thr Cys Thr Gly Gly Thr Gly Gly Cys Gly
        435                 440                 445

Gly Ala Gly Gly Ala Ala Gly Thr Gly Gly Cys Gly Gly Ala Gly Gly
    450                 455                 460

Cys Gly Gly Thr Thr Cys Thr Ala Thr Gly Ala Gly Ala Gly Thr Gly
465                 470                 475                 480

Cys Ala Gly Ala Thr Cys Cys Ala Gly Thr Thr Cys Thr Gly Gly Gly
                485                 490                 495

Gly Ala Cys Thr Gly Cys Thr Gly Cys Thr Gly Cys Thr Gly Thr Gly
            500                 505                 510

Gly Ala Cys Ala Ala Gly Cys Gly Gly Cys Ala Thr Cys Cys Ala Gly
        515                 520                 525

Thr Gly Thr Gly Ala Cys Gly Thr Gly Cys Ala Gly Ala Thr Gly Ala
    530                 535                 540

Cys Ala Cys Ala Gly Ala Gly Cys Cys Cys Cys Thr Ala Cys Ala Ala
545                 550                 555                 560

Cys Cys Thr Gly Gly Cys Thr Gly Cys Cys Thr Cys Thr Cys Cys Thr
                565                 570                 575

Gly Gly Cys Gly Ala Gly Thr Cys Cys Gly Thr Gly Thr Cys Cys Ala
            580                 585                 590

Thr Cys Ala Ala Thr Thr Gly Cys Ala Ala Gly Gly Cys Cys Thr Cys
        595                 600                 605

Cys Ala Ala Gly Ala Gly Cys Ala Thr Cys Ala Ala Cys Ala Ala Gly
    610                 615                 620

Thr Ala Cys Cys Thr Gly Gly Cys Cys Thr Gly Gly Thr Ala Thr Cys
625                 630                 635                 640

Ala Gly Cys Ala Gly Ala Ala Gly Cys Cys Cys Gly Gly Cys Ala Ala
                645                 650                 655

Gly Cys Cys Thr Ala Ala Cys Ala Ala Gly Cys Thr Gly Cys Thr Gly
            660                 665                 670

Ala Thr Cys Thr Ala Cys Gly Ala Thr Gly Gly Cys Ala Gly Cys Ala
        675                 680                 685

Cys Cys Cys Thr Gly Cys Ala Gly Ala Gly Cys Gly Gly Ala Ala Thr
```

690 695 700

Cys Cys Cys Cys Ala Gly Cys Ala Gly Ala Thr Thr Thr Thr Cys Thr
705 710 715 720

Gly Gly Cys Ala Gly Cys Gly Gly Cys Thr Cys Cys Gly Gly Cys Ala
725 730 735

Cys Cys Gly Ala Thr Thr Thr Cys Ala Cys Cys Cys Thr Gly Ala Cys
740 745 750

Ala Ala Thr Cys Ala Gly Ala Gly Gly Cys Cys Thr Gly Gly Ala Ala
755 760 765

Cys Cys Ala Gly Ala Gly Gly Ala Cys Thr Thr Cys Gly Gly Cys Cys
770 775 780

Thr Gly Thr Ala Cys Thr Ala Cys Thr Gly Cys Cys Ala Gly Cys Ala
785 790 795 800

Gly Cys Ala Cys Ala Ala Cys Gly Ala Gly Thr Ala Cys Cys Cys Thr
805 810 815

Cys Cys Ala Ala Cys Cys Thr Thr Thr Gly Gly Ala Gly Cys Cys Gly
820 825 830

Gly Cys Ala Cys Cys Ala Ala Gly Cys Thr Gly Gly Ala Ala Cys Thr
835 840 845

Gly Ala Ala Gly
850

<210> SEQ ID NO 38
<211> LENGTH: 852
<212> TYPE: PRT
<213> ORGANISM: Artificial Sequence
<220> FEATURE:
<223> OTHER INFORMATION: Vb1LH scFv

<400> SEQUENCE: 38

Ala Thr Gly Ala Gly Ala Gly Thr Gly Cys Ala Gly Ala Thr Cys Cys
1 5 10 15

Ala Gly Thr Thr Cys Thr Gly Gly Gly Gly Cys Cys Thr Gly Cys Thr
20 25 30

Gly Cys Thr Gly Cys Thr Gly Thr Gly Gly Ala Cys Ala Thr Cys Thr
35 40 45

Gly Gly Cys Ala Thr Cys Cys Ala Gly Thr Gly Cys Gly Ala Cys Gly
50 55 60

Thr Gly Cys Ala Gly Ala Thr Gly Ala Cys Ala Cys Ala Gly Ala Gly
65 70 75 80

Cys Cys Cys Cys Thr Ala Cys Ala Ala Cys Cys Thr Gly Gly Cys Thr
85 90 95

Gly Cys Cys Thr Cys Thr Cys Cys Thr Gly Gly Cys Gly Ala Gly Ala
100 105 110

Gly Cys Gly Thr Gly Thr Cys Cys Ala Thr Cys Ala Ala Thr Thr Gly
115 120 125

Cys Ala Ala Gly Gly Cys Cys Ala Gly Cys Ala Ala Gly Ala Gly Cys
130 135 140

Ala Thr Cys Ala Ala Cys Ala Ala Gly Thr Ala Cys Cys Thr Gly Gly
145 150 155 160

Cys Cys Thr Gly Gly Thr Ala Thr Cys Ala Gly Cys Ala Gly Ala Ala
165 170 175

Gly Cys Cys Cys Gly Gly Cys Ala Ala Gly Cys Cys Thr Ala Ala Cys
180 185 190

Ala Ala Gly Cys Thr Gly Cys Thr Gly Ala Thr Cys Thr Ala Cys Gly

-continued

```
        195                 200                 205

Ala Thr Gly Gly Cys Ala Gly Cys Ala Cys Cys Cys Thr Gly Cys Ala
    210                 215                 220

Gly Ala Gly Cys Gly Gly Cys Ala Thr Cys Cys Cys Thr Ala Gly Cys
225                 230                 235                 240

Ala Gly Ala Thr Thr Thr Thr Cys Thr Gly Gly Cys Ala Gly Cys Gly
                245                 250                 255

Gly Cys Thr Cys Cys Gly Gly Cys Ala Cys Cys Gly Ala Thr Thr Thr
            260                 265                 270

Cys Ala Cys Cys Cys Thr Gly Ala Cys Ala Ala Thr Cys Ala Gly Ala
        275                 280                 285

Gly Gly Cys Cys Thr Gly Gly Ala Ala Cys Cys Thr Gly Ala Gly Gly
    290                 295                 300

Ala Cys Thr Thr Cys Gly Gly Cys Cys Thr Gly Thr Ala Cys Thr Ala
305                 310                 315                 320

Cys Thr Gly Cys Cys Ala Gly Cys Ala Gly Cys Ala Cys Ala Ala Cys
                325                 330                 335

Gly Ala Gly Thr Ala Cys Cys Cys Thr Cys Cys Ala Ala Cys Cys Thr
            340                 345                 350

Thr Thr Gly Gly Ala Gly Cys Cys Gly Gly Cys Ala Cys Cys Ala Ala
        355                 360                 365

Gly Cys Thr Gly Gly Ala Ala Cys Thr Thr Ala Ala Ala Gly Gly Cys
    370                 375                 380

Gly Gly Cys Gly Gly Ala Gly Gly Ala Thr Cys Thr Gly Gly Cys Gly
385                 390                 395                 400

Gly Ala Gly Gly Thr Gly Gly Ala Ala Gly Cys Gly Gly Ala Gly Gly
                405                 410                 415

Cys Gly Gly Thr Gly Gly Ala Thr Cys Thr Ala Thr Gly Gly Ala Cys
            420                 425                 430

Thr Gly Gly Gly Thr Cys Thr Gly Gly Ala Ala Thr Cys Thr Gly Cys
        435                 440                 445

Thr Gly Thr Thr Cys Cys Thr Gly Ala Thr Gly Gly Cys Cys Gly Thr
    450                 455                 460

Gly Gly Cys Thr Cys Ala Gly Ala Cys Ala Gly Gly Thr Gly Cys Thr
465                 470                 475                 480

Cys Ala Gly Gly Cys Thr Cys Ala Gly Cys Thr Gly Cys Ala Ala Cys
                485                 490                 495

Thr Gly Gly Thr Gly Cys Ala Gly Thr Cys Thr Gly Gly Ala Cys Cys
            500                 505                 510

Thr Gly Ala Gly Cys Thr Gly Ala Gly Ala Gly Ala Ala Cys Cys Thr
        515                 520                 525

Gly Gly Cys Gly Ala Gly Thr Cys Cys Gly Thr Gly Ala Ala Gly Ala
    530                 535                 540

Thr Cys Thr Cys Cys Thr Gly Cys Ala Ala Gly Gly Cys Cys Thr Cys
545                 550                 555                 560

Cys Gly Gly Cys Thr Ala Cys Ala Cys Cys Thr Thr Cys Ala Cys Cys
                565                 570                 575

Gly Ala Cys Thr Ala Cys Ala Thr Cys Gly Thr Gly Cys Ala Cys Thr
            580                 585                 590

Gly Gly Gly Thr Cys Ala Ala Ala Cys Ala Gly Gly Cys Cys Cys Cys
        595                 600                 605

Thr Gly Gly Cys Ala Ala Gly Gly Gly Ala Cys Thr Gly Ala Ala Gly
    610                 615                 620
```

Thr Gly Gly Ala Thr Gly Gly Gly Cys Thr Gly Gly Ala Thr Cys Ala
625 630 635 640

Ala Cys Ala Cys Cys Thr Ala Cys Ala Cys Cys Gly Gly Cys Ala Cys
645 650 655

Ala Cys Cys Cys Ala Cys Cys Thr Ala Cys Gly Cys Cys Gly Ala Cys
660 665 670

Gly Ala Thr Thr Thr Cys Gly Ala Gly Gly Gly Cys Ala Gly Ala Thr
675 680 685

Thr Cys Gly Thr Gly Thr Thr Cys Ala Gly Cys Cys Thr Gly Gly Ala
690 695 700

Ala Gly Cys Cys Thr Cys Thr Gly Cys Cys Ala Gly Cys Ala Cys Cys
705 710 715 720

Gly Cys Cys Ala Ala Cys Cys Thr Gly Cys Ala Gly Ala Thr Cys Ala
725 730 735

Gly Cys Ala Ala Cys Cys Thr Gly Ala Ala Gly Ala Ala Cys Gly Ala
740 745 750

Gly Gly Ala Cys Ala Cys Cys Gly Cys Cys Ala Cys Cys Thr Ala Cys
755 760 765

Thr Thr Thr Thr Gly Cys Gly Cys Cys Ala Gly Ala Thr Cys Thr Thr
770 775 780

Gly Gly Ala Gly Gly Cys Gly Gly Gly Gly Cys Ala Thr Cys Ala Gly
785 790 795 800

Ala Gly Gly Cys Ala Thr Cys Gly Gly Cys Thr Thr Thr Gly Ala Thr
805 810 815

Thr Ala Thr Thr Gly Gly Gly Gly Cys Cys Ala Gly Gly Gly Cys Gly
820 825 830

Thr Gly Ala Thr Gly Gly Thr Cys Ala Cys Cys Gly Thr Gly Thr Cys
835 840 845

Cys Thr Cys Thr
850

<210> SEQ ID NO 39
<211> LENGTH: 852
<212> TYPE: PRT
<213> ORGANISM: Artificial Sequence
<220> FEATURE:
<223> OTHER INFORMATION: Vb2HL scFv

<400> SEQUENCE: 39

Ala Thr Gly Ala Ala Gly Thr Thr Cys Ala Gly Cys Thr Gly Gly Gly
1 5 10 15

Thr Cys Ala Thr Cys Thr Thr Cys Thr Thr Thr Cys Thr Gly Ala Thr
20 25 30

Gly Gly Cys Cys Gly Thr Gly Gly Thr Cys Ala Cys Cys Gly Gly Cys
35 40 45

Gly Thr Gly Ala Ala Cys Thr Cys Thr Gly Ala Ala Gly Thr Gly Cys
50 55 60

Ala Ala Cys Thr Gly Cys Ala Gly Cys Ala Gly Ala Gly Cys Gly Thr
65 70 75 80

Gly Gly Cys Cys Gly Ala Thr Cys Thr Cys Gly Thr Thr Ala Gly Ala
85 90 95

Cys Cys Thr Gly Gly Cys Gly Cys Cys Thr Cys Thr Cys Thr Gly Ala
100 105 110

Ala Gly Cys Thr Gly Ala Gly Cys Thr Gly Thr Ala Cys Cys Gly Cys
115 120 125

```
Cys Ala Gly Cys Gly Gly Cys Thr Thr Cys Ala Ala Cys Ala Thr Cys
    130                 135                 140

Ala Ala Gly Ala Gly Cys Gly Cys Cys Thr Ala Cys Ala Thr Gly Cys
145                 150                 155                 160

Ala Cys Thr Gly Gly Gly Thr Thr Ala Thr Cys Cys Ala Gly Cys Gly
                165                 170                 175

Gly Cys Cys Ala Gly Ala Thr Cys Ala Gly Gly Gly Cys Cys Cys Ala
            180                 185                 190

Gly Ala Gly Thr Gly Thr Cys Thr Gly Gly Gly Ala Ala Gly Ala Ala
        195                 200                 205

Thr Cys Gly Ala Thr Cys Cys Thr Gly Cys Cys Ala Cys Cys Gly Gly
    210                 215                 220

Cys Ala Ala Gly Ala Cys Cys Ala Ala Ala Thr Ala Cys Gly Cys Cys
225                 230                 235                 240

Cys Cys Thr Ala Ala Gly Thr Thr Thr Cys Ala Gly Gly Cys Cys Ala
                245                 250                 255

Ala Gly Gly Cys Cys Ala Cys Cys Ala Thr Cys Ala Cys Cys Gly Cys
            260                 265                 270

Cys Gly Ala Cys Ala Cys Cys Thr Cys Thr Ala Gly Cys Ala Ala Thr
        275                 280                 285

Ala Cys Cys Gly Cys Cys Thr Ala Cys Cys Thr Gly Cys Ala Gly Cys
    290                 295                 300

Thr Gly Ala Gly Cys Ala Gly Cys Cys Thr Gly Ala Cys Cys Thr Cys
305                 310                 315                 320

Thr Gly Ala Gly Gly Ala Cys Ala Cys Cys Gly Cys Cys Ala Thr Cys
                325                 330                 335

Thr Ala Cys Thr Ala Cys Thr Gly Cys Ala Cys Cys Ala Gly Ala Ala
            340                 345                 350

Gly Cys Cys Thr Gly Ala Ala Cys Thr Gly Gly Gly Ala Cys Thr Ala
        355                 360                 365

Cys Gly Gly Cys Cys Thr Gly Gly Ala Thr Thr Ala Thr Thr Gly Gly
    370                 375                 380

Gly Gly Cys Cys Ala Gly Gly Gly Cys Ala Cys Ala Ala Gly Cys Gly
385                 390                 395                 400

Thr Gly Ala Cys Ala Gly Thr Gly Thr Cys Thr Ala Gly Cys Gly Gly
                405                 410                 415

Ala Gly Gly Cys Gly Gly Ala Gly Gly Ala Thr Cys Thr Gly Gly Thr
            420                 425                 430

Gly Gly Cys Gly Gly Ala Gly Gly Ala Ala Gly Thr Gly Gly Cys Gly
        435                 440                 445

Gly Ala Gly Gly Cys Gly Gly Thr Ala Gly Cys Ala Thr Gly Gly Ala
    450                 455                 460

Ala Ala Cys Cys Gly Ala Thr Ala Cys Ala Cys Thr Gly Cys Thr Gly
465                 470                 475                 480

Cys Thr Gly Thr Gly Gly Gly Thr Gly Cys Thr Gly Cys Thr Cys Cys
                485                 490                 495

Thr Thr Thr Gly Gly Gly Thr Gly Cys Cys Cys Gly Gly Ala Thr Cys
            500                 505                 510

Thr Ala Cys Ala Gly Gly Cys Gly Ala Cys Ala Thr Cys Gly Thr Gly
        515                 520                 525

Cys Thr Gly Ala Cys Ala Cys Ala Gly Thr Cys Thr Cys Cys Cys Gly
    530                 535                 540
```

Cys Thr Thr Cys Thr Cys Thr Gly Gly Cys Cys Gly Thr Gly Thr Cys
545 550 555 560

Thr Cys Thr Gly Gly Gly Ala Cys Ala Gly Ala Gly Ala Gly Cys Cys
565 570 575

Ala Cys Cys Ala Thr Cys Thr Cys Thr Thr Gly Cys Ala Gly Ala Gly
580 585 590

Cys Cys Ala Gly Cys Ala Ala Gly Ala Gly Cys Gly Thr Gly Thr Cys
595 600 605

Cys Ala Thr Cys Cys Thr Gly Gly Gly Cys Ala Cys Ala Cys Ala Cys
610 615 620

Cys Thr Gly Ala Thr Cys Cys Ala Cys Thr Gly Gly Thr Ala Thr Cys
625 630 635 640

Ala Gly Cys Ala Gly Ala Ala Gly Cys Cys Cys Gly Gly Cys Cys Ala
645 650 655

Gly Cys Cys Thr Cys Cys Thr Ala Ala Gly Cys Thr Gly Cys Thr Gly
660 665 670

Ala Thr Cys Thr Ala Cys Gly Cys Cys Gly Cys Cys Ala Gly Cys Ala
675 680 685

Ala Thr Cys Thr Gly Gly Ala Ala Ala Gly Cys Gly Gly Ala Gly Thr
690 695 700

Gly Cys Cys Thr Gly Cys Cys Ala Gly Ala Thr Thr Thr Thr Cys Cys
705 710 715 720

Gly Gly Cys Ala Gly Cys Gly Gly Ala Ala Gly Cys Gly Ala Ala Ala
725 730 735

Cys Cys Gly Thr Gly Thr Thr Cys Ala Cys Cys Cys Thr Gly Ala Ala
740 745 750

Cys Ala Thr Thr Cys Ala Cys Cys Cys Cys Gly Thr Gly Gly Ala Ala
755 760 765

Gly Ala Ala Gly Ala Gly Gly Ala Cys Gly Cys Cys Gly Cys Cys Ala
770 775 780

Cys Cys Thr Ala Thr Thr Thr Cys Thr Gly Cys Cys Ala Gly Cys Ala
785 790 795 800

Gly Thr Cys Thr Ala Thr Cys Gly Ala Gly Gly Ala Cys Cys Cys Cys
805 810 815

Thr Gly Gly Ala Cys Ala Thr Thr Thr Gly Gly Ala Gly Gly Cys Gly
820 825 830

Gly Cys Ala Cys Ala Ala Ala Gly Cys Thr Gly Gly Gly Cys Ala Thr
835 840 845

Cys Ala Ala Gly
850

<210> SEQ ID NO 40
<211> LENGTH: 852
<212> TYPE: PRT
<213> ORGANISM: Artificial Sequence
<220> FEATURE:
<223> OTHER INFORMATION: Vb2LH scFv

<400> SEQUENCE: 40

Ala Thr Gly Gly Ala Ala Ala Cys Cys Gly Ala Cys Ala Cys Ala Cys
1 5 10 15

Thr Gly Cys Thr Gly Cys Thr Gly Thr Gly Gly Gly Thr Gly Cys Thr
20 25 30

Gly Cys Thr Thr Cys Thr Thr Thr Gly Gly Gly Thr Gly Cys Cys Cys
35 40 45

```
Gly Gly Ala Ala Gly Cys Ala Cys Ala Gly Gly Cys Gly Ala Cys Ala
    50                  55                  60

Thr Cys Gly Thr Gly Cys Thr Gly Ala Cys Ala Cys Ala Gly Ala Gly
65                  70                  75                  80

Cys Cys Cys Thr Gly Cys Thr Thr Cys Thr Cys Thr Gly Gly Cys Cys
                85                  90                  95

Gly Thr Gly Thr Cys Thr Cys Thr Gly Gly Gly Ala Cys Ala Gly Ala
            100                 105                 110

Gly Ala Gly Cys Cys Ala Cys Cys Ala Thr Cys Ala Gly Cys Thr Gly
        115                 120                 125

Cys Ala Gly Ala Gly Cys Cys Ala Gly Cys Ala Ala Gly Ala Gly Cys
    130                 135                 140

Gly Thr Gly Thr Cys Cys Ala Thr Cys Cys Thr Gly Gly Gly Cys Ala
145                 150                 155                 160

Cys Ala Cys Ala Cys Cys Thr Gly Ala Thr Cys Cys Ala Cys Thr Gly
                165                 170                 175

Gly Thr Ala Thr Cys Ala Gly Cys Ala Gly Ala Ala Gly Cys Cys Cys
            180                 185                 190

Gly Gly Cys Cys Ala Gly Cys Cys Thr Cys Cys Thr Ala Ala Gly Cys
        195                 200                 205

Thr Gly Cys Thr Gly Ala Thr Cys Thr Ala Cys Gly Cys Cys Gly Cys
    210                 215                 220

Cys Ala Gly Cys Ala Ala Thr Cys Thr Gly Gly Ala Ala Ala Gly Cys
225                 230                 235                 240

Gly Gly Ala Gly Thr Gly Cys Cys Thr Gly Cys Cys Ala Gly Ala Thr
                245                 250                 255

Thr Thr Thr Cys Cys Gly Gly Cys Ala Gly Cys Gly Gly Ala Ala Gly
            260                 265                 270

Cys Gly Ala Gly Ala Cys Ala Gly Thr Gly Thr Thr Cys Ala Cys Cys
        275                 280                 285

Cys Thr Gly Ala Ala Cys Ala Thr Thr Cys Ala Cys Cys Cys Cys Gly
    290                 295                 300

Thr Gly Gly Ala Ala Gly Ala Ala Gly Ala Gly Gly Ala Cys Gly Cys
305                 310                 315                 320

Cys Gly Cys Cys Ala Cys Cys Thr Ala Cys Thr Thr Thr Thr Gly Cys
                325                 330                 335

Cys Ala Gly Cys Ala Gly Thr Cys Thr Ala Thr Cys Gly Ala Gly Gly
            340                 345                 350

Ala Cys Cys Cys Cys Thr Gly Gly Ala Cys Cys Thr Thr Thr Gly Gly
        355                 360                 365

Cys Gly Gly Cys Gly Gly Ala Ala Cys Ala Ala Ala Gly Cys Thr Gly
    370                 375                 380

Gly Gly Ala Ala Thr Cys Ala Ala Ala Gly Gly Cys Gly Gly Cys Gly
385                 390                 395                 400

Gly Ala Gly Gly Ala Thr Cys Thr Gly Gly Cys Gly Gly Ala Gly Gly
                405                 410                 415

Thr Gly Gly Ala Ala Gly Cys Gly Gly Ala Gly Gly Cys Gly Gly Thr
            420                 425                 430

Gly Gly Cys Ala Gly Cys Ala Thr Gly Ala Ala Gly Thr Thr Cys Ala
        435                 440                 445

Gly Cys Thr Gly Gly Gly Thr Cys Ala Thr Cys Thr Thr Cys Thr Thr
    450                 455                 460

Thr Cys Thr Gly Ala Thr Gly Gly Cys Cys Gly Thr Gly Gly Thr Cys
```

465 470 475 480

Ala Cys Cys Gly Gly Cys Gly Thr Gly Ala Ala Cys Thr Cys Thr Gly
485 490 495

Ala Ala Gly Thr Gly Cys Ala Ala Cys Thr Gly Cys Ala Gly Cys Ala
500 505 510

Gly Ala Gly Cys Gly Thr Gly Gly Cys Cys Gly Ala Thr Cys Thr Cys
515 520 525

Gly Thr Thr Ala Gly Ala Cys Cys Thr Gly Gly Cys Gly Cys Cys Thr
530 535 540

Cys Thr Cys Thr Gly Ala Ala Gly Cys Thr Gly Ala Gly Cys Thr Gly
545 550 555 560

Thr Ala Cys Cys Gly Cys Cys Ala Gly Cys Gly Gly Cys Thr Thr Cys
565 570 575

Ala Ala Cys Ala Thr Cys Ala Ala Gly Ala Gly Cys Gly Cys Cys Thr
580 585 590

Ala Cys Ala Thr Gly Cys Ala Cys Thr Gly Gly Gly Thr Thr Ala Thr
595 600 605

Cys Cys Ala Gly Cys Gly Gly Cys Cys Ala Gly Ala Thr Cys Ala Gly
610 615 620

Gly Gly Cys Cys Cys Ala Gly Ala Gly Thr Gly Thr Cys Thr Gly Gly
625 630 635 640

Gly Ala Ala Gly Ala Ala Thr Cys Gly Ala Thr Cys Cys Thr Gly Cys
645 650 655

Cys Ala Cys Cys Gly Gly Cys Ala Ala Gly Ala Cys Cys Ala Ala Ala
660 665 670

Thr Ala Cys Gly Cys Cys Cys Cys Thr Ala Ala Gly Thr Thr Thr Cys
675 680 685

Ala Gly Gly Cys Cys Ala Ala Gly Gly Cys Cys Ala Cys Ala Ala Thr
690 695 700

Cys Ala Cys Cys Gly Cys Cys Gly Ala Cys Ala Cys Cys Thr Cys Thr
705 710 715 720

Ala Gly Cys Ala Ala Cys Ala Cys Ala Gly Cys Cys Thr Ala Cys Cys
725 730 735

Thr Gly Cys Ala Gly Cys Thr Gly Thr Cys Cys Ala Gly Cys Cys Thr
740 745 750

Gly Ala Cys Cys Thr Cys Thr Gly Ala Gly Gly Ala Thr Ala Cys Cys
755 760 765

Gly Cys Cys Ala Thr Cys Thr Ala Cys Thr Ala Cys Thr Gly Cys Ala
770 775 780

Cys Cys Ala Gly Ala Ala Gly Cys Cys Thr Gly Ala Ala Cys Thr Gly
785 790 795 800

Gly Gly Ala Cys Thr Ala Cys Gly Gly Cys Cys Thr Gly Gly Ala Thr
805 810 815

Thr Ala Thr Thr Gly Gly Gly Gly Cys Cys Ala Gly Gly Gly Cys Ala
820 825 830

Cys Ala Ala Gly Cys Gly Thr Gly Ala Cys Cys Gly Thr Gly Thr Cys
835 840 845

Ala Thr Cys Thr
850

<210> SEQ ID NO 41
<211> LENGTH: 843
<212> TYPE: PRT
<213> ORGANISM: Artificial Sequence
<220> FEATURE:
<223> OTHER INFORMATION: Vb4HL scFv

<400> SEQUENCE: 41

```
Ala Thr Gly Gly Ala Ala Thr Gly Gly Thr Cys Cys Thr Gly Gly Ala
1               5                   10                  15

Thr Cys Thr Thr Cys Cys Thr Gly Thr Thr Cys Cys Thr Gly Cys Thr
            20                  25                  30

Gly Ala Gly Cys Gly Thr Gly Ala Cys Ala Gly Cys Cys Gly Thr Gly
        35                  40                  45

Gly Thr Gly Cys Ala Thr Thr Cys Thr Cys Ala Gly Gly Thr Thr Cys
    50                  55                  60

Ala Gly Cys Thr Gly Cys Ala Gly Cys Ala Gly Thr Cys Thr Gly Gly
65                  70                  75                  80

Cys Gly Cys Cys Gly Ala Ala Cys Thr Gly Gly Cys Cys Ala Ala Ala
                85                  90                  95

Cys Cys Thr Gly Gly Cys Ala Cys Ala Ala Gly Cys Gly Thr Gly Ala
            100                 105                 110

Ala Gly Cys Thr Gly Ala Gly Cys Thr Gly Thr Ala Ala Ala Gly Cys
        115                 120                 125

Cys Ala Gly Cys Gly Gly Cys Thr Ala Cys Ala Cys Cys Thr Thr Cys
    130                 135                 140

Ala Cys Cys Ala Gly Cys Thr Ala Cys Thr Ala Cys Ala Thr Cys Thr
145                 150                 155                 160

Ala Cys Thr Gly Gly Gly Thr Cys Ala Ala Gly Cys Ala Gly Cys Gly
                165                 170                 175

Gly Cys Cys Thr Gly Gly Ala Cys Ala Gly Gly Gly Ala Cys Thr Thr
            180                 185                 190

Gly Ala Gly Thr Gly Gly Cys Thr Gly Gly Gly Cys Thr Ala Thr Ala
        195                 200                 205

Thr Cys Thr Ala Cys Cys Cys Thr Gly Gly Cys Ala Ala Cys Gly Gly
    210                 215                 220

Cys Gly Gly Cys Ala Cys Cys Thr Ala Cys Thr Ala Cys Ala Gly Cys
225                 230                 235                 240

Gly Ala Gly Ala Ala Gly Thr Thr Cys Ala Ala Gly Gly Gly Cys Ala
                245                 250                 255

Ala Ala Gly Cys Cys Ala Cys Cys Thr Thr Thr Ala Cys Cys Gly Cys
            260                 265                 270

Cys Gly Ala Cys Ala Cys Cys Ala Gly Cys Ala Gly Cys Ala Ala Cys
        275                 280                 285

Ala Cys Ala Gly Cys Cys Thr Ala Cys Ala Thr Gly Cys Thr Gly Cys
    290                 295                 300

Thr Gly Gly Gly Cys Ala Gly Cys Cys Thr Gly Ala Cys Ala Cys Cys
305                 310                 315                 320

Thr Gly Ala Gly Gly Ala Cys Ala Gly Cys Gly Cys Cys Thr Ala Cys
                325                 330                 335

Thr Ala Cys Thr Thr Cys Thr Gly Thr Gly Cys Cys Ala Gly Ala Gly
            340                 345                 350

Gly Cys Ala Gly Cys Gly Gly Cys Gly Ala Cys Cys Gly Gly Thr Ala
        355                 360                 365

Cys Ala Ala Thr Thr Cys Thr Cys Thr Gly Gly Cys Cys Thr Ala Thr
    370                 375                 380

Thr Gly Gly Gly Gly Cys Cys Ala Gly Gly Gly Cys Ala Cys Cys Cys
385                 390                 395                 400
```

```
Thr Gly Gly Thr Thr Ala Cys Ala Gly Thr Thr Thr Cys Thr Thr Cys
                405                 410                 415

Thr Gly Gly Thr Gly Gly Cys Gly Gly Ala Gly Gly Ala Thr Cys Thr
            420                 425                 430

Gly Gly Cys Gly Gly Ala Gly Gly Thr Gly Gly Ala Ala Gly Cys Gly
        435                 440                 445

Gly Cys Gly Gly Ala Gly Gly Cys Gly Gly Ala Thr Cys Thr Ala Thr
    450                 455                 460

Gly Gly Cys Thr Ala Thr Thr Cys Cys Thr Ala Cys Ala Cys Ala Gly
465                 470                 475                 480

Cys Thr Gly Cys Thr Gly Gly Gly Ala Cys Thr Gly Cys Thr Gly Cys
                485                 490                 495

Thr Gly Cys Thr Cys Thr Gly Gly Ala Thr Cys Ala Cys Cys Gly Ala
            500                 505                 510

Thr Gly Cys Cys Ala Thr Cys Thr Gly Cys Gly Ala Cys Ala Thr Cys
        515                 520                 525

Cys Ala Gly Ala Thr Gly Ala Cys Ala Cys Ala Gly Ala Gly Cys Cys
    530                 535                 540

Cys Thr Cys Ala Cys Ala Gly Cys Cys Thr Gly Thr Cys Thr Gly Cys
545                 550                 555                 560

Cys Ala Gly Cys Cys Thr Gly Gly Gly Ala Gly Ala Gly Ala Cys Ala
                565                 570                 575

Gly Thr Gly Thr Cys Cys Ala Thr Thr Gly Ala Gly Thr Gly Thr Cys
            580                 585                 590

Thr Gly Gly Cys Cys Ala Gly Cys Gly Ala Gly Gly Gly Cys Ala Thr
        595                 600                 605

Cys Ala Gly Cys Ala Ala Cys Thr Thr Thr Cys Thr Gly Gly Cys Cys
    610                 615                 620

Thr Gly Gly Thr Ala Thr Cys Ala Gly Cys Ala Gly Ala Ala Gly Cys
625                 630                 635                 640

Cys Cys Gly Gly Cys Ala Ala Gly Thr Cys Thr Cys Cys Thr Cys Ala
                645                 650                 655

Gly Cys Thr Gly Cys Thr Gly Ala Thr Cys Thr Ala Cys Thr Ala Cys
            660                 665                 670

Ala Cys Ala Ala Gly Cys Ala Gly Cys Cys Thr Gly Cys Ala Gly Gly
        675                 680                 685

Ala Thr Gly Gly Cys Gly Thr Gly Cys Cys Cys Thr Cys Thr Ala Gly
    690                 695                 700

Ala Thr Thr Thr Thr Cys Thr Gly Gly Cys Thr Cys Thr Gly Gly Cys
705                 710                 715                 720

Ala Gly Cys Gly Gly Cys Ala Cys Cys Cys Ala Gly Thr Ala Cys Ala
                725                 730                 735

Gly Cys Cys Thr Gly Ala Ala Gly Ala Thr Cys Ala Gly Cys Ala Ala
            740                 745                 750

Cys Ala Thr Gly Cys Ala Gly Cys Cys Cys Gly Ala Gly Gly Ala Cys
        755                 760                 765

Gly Ala Gly Gly Gly Cys Gly Thr Gly Thr Ala Cys Thr Ala Thr Thr
    770                 775                 780

Gly Thr Cys Ala Gly Cys Ala Gly Gly Gly Cys Thr Ala Cys Ala Ala
785                 790                 795                 800

Gly Thr Thr Cys Cys Cys Cys Ala Gly Ala Ala Cys Cys Thr Thr Thr
                805                 810                 815
```

Gly Gly Cys Gly Gly Ala Gly Gly Cys Ala Cys Cys Ala Ala Gly Cys
820 825 830

Thr Gly Gly Ala Ala Cys Thr Gly Ala Ala Gly
835 840

<210> SEQ ID NO 42
<211> LENGTH: 843
<212> TYPE: PRT
<213> ORGANISM: Artificial Sequence
<220> FEATURE:
<223> OTHER INFORMATION: Vb4LH scFv

<400> SEQUENCE: 42

Ala Thr Gly Gly Cys Thr Ala Thr Cys Cys Cys Cys Ala Cys Ala Cys
1 5 10 15

Ala Ala Cys Thr Gly Cys Thr Gly Gly Gly Ala Cys Thr Gly Cys Thr
20 25 30

Gly Cys Thr Gly Cys Thr Gly Thr Gly Gly Ala Thr Cys Ala Cys Cys
35 40 45

Gly Ala Thr Gly Cys Cys Ala Thr Cys Thr Gly Cys Gly Ala Cys Ala
50 55 60

Thr Cys Cys Ala Gly Ala Thr Gly Ala Cys Ala Cys Ala Gly Ala Gly
65 70 75 80

Cys Cys Cys Thr Cys Ala Cys Ala Gly Cys Cys Thr Gly Thr Cys Thr
85 90 95

Gly Cys Cys Ala Gly Cys Cys Thr Gly Gly Gly Ala Gly Ala Gly Ala
100 105 110

Cys Ala Gly Thr Gly Thr Cys Cys Ala Thr Thr Gly Ala Gly Thr Gly
115 120 125

Thr Cys Thr Gly Gly Cys Cys Ala Gly Cys Gly Ala Gly Gly Gly Cys
130 135 140

Ala Thr Cys Ala Gly Cys Ala Ala Cys Thr Thr Thr Cys Thr Gly Gly
145 150 155 160

Cys Cys Thr Gly Gly Thr Ala Thr Cys Ala Gly Cys Ala Gly Ala Ala
165 170 175

Gly Cys Cys Cys Gly Gly Cys Ala Ala Gly Thr Cys Thr Cys Cys Thr
180 185 190

Cys Ala Gly Cys Thr Gly Cys Thr Gly Ala Thr Cys Thr Ala Cys Thr
195 200 205

Ala Cys Ala Cys Cys Ala Gly Cys Ala Gly Cys Cys Thr Gly Cys Ala
210 215 220

Gly Gly Ala Thr Gly Gly Cys Gly Thr Gly Cys Cys Cys Ala Gly Cys
225 230 235 240

Ala Gly Ala Thr Thr Thr Thr Cys Thr Gly Gly Cys Ala Gly Cys Gly
245 250 255

Gly Cys Thr Cys Thr Gly Gly Cys Ala Cys Ala Cys Ala Gly Thr Ala
260 265 270

Cys Ala Gly Cys Cys Thr Gly Ala Ala Gly Ala Thr Cys Ala Gly Cys
275 280 285

Ala Ala Cys Ala Thr Gly Cys Ala Gly Cys Cys Cys Gly Ala Gly Gly
290 295 300

Ala Cys Gly Ala Gly Gly Gly Cys Gly Thr Gly Thr Ala Cys Thr Ala
305 310 315 320

Thr Thr Gly Thr Cys Ala Gly Cys Ala Gly Gly Gly Cys Thr Ala Cys
325 330 335

-continued

```
Ala Ala Gly Thr Thr Cys Cys Cys Cys Ala Gly Ala Ala Cys Cys Thr
            340                 345                 350

Thr Thr Gly Gly Cys Gly Gly Ala Gly Gly Cys Ala Cys Cys Ala Ala
        355                 360                 365

Gly Cys Thr Gly Gly Ala Ala Cys Thr Gly Ala Ala Ala Gly Gly Cys
    370                 375                 380

Gly Gly Cys Gly Gly Ala Gly Gly Ala Ala Gly Cys Gly Gly Ala Gly
385                 390                 395                 400

Gly Cys Gly Gly Ala Gly Gly Ala Thr Cys Thr Gly Gly Thr Gly Gly
                405                 410                 415

Thr Gly Gly Thr Gly Gly Ala Thr Cys Thr Ala Thr Gly Gly Ala Ala
            420                 425                 430

Thr Gly Gly Thr Cys Cys Thr Gly Gly Ala Thr Cys Thr Thr Cys Cys
        435                 440                 445

Thr Gly Thr Thr Cys Cys Thr Gly Cys Thr Gly Ala Gly Cys Gly Thr
    450                 455                 460

Gly Ala Cys Ala Gly Cys Cys Gly Thr Gly Gly Thr Gly Cys Ala Thr
465                 470                 475                 480

Thr Cys Thr Cys Ala Gly Gly Thr Thr Cys Ala Gly Cys Thr Gly Cys
                485                 490                 495

Ala Gly Cys Ala Gly Ala Gly Cys Gly Gly Ala Gly Cys Cys Gly Ala
            500                 505                 510

Ala Cys Thr Gly Gly Cys Cys Ala Ala Ala Cys Cys Thr Gly Gly Cys
        515                 520                 525

Ala Cys Ala Ala Gly Cys Gly Thr Gly Ala Ala Gly Cys Thr Gly Ala
    530                 535                 540

Gly Cys Thr Gly Thr Ala Ala Ala Gly Cys Cys Ala Gly Cys Gly Gly
545                 550                 555                 560

Cys Thr Ala Cys Ala Cys Cys Thr Thr Cys Ala Cys Cys Ala Gly Cys
                565                 570                 575

Thr Ala Cys Thr Ala Cys Ala Thr Cys Thr Ala Cys Thr Gly Gly Gly
            580                 585                 590

Thr Cys Ala Ala Gly Cys Ala Gly Cys Gly Gly Cys Cys Thr Gly Gly
        595                 600                 605

Ala Cys Ala Gly Gly Gly Ala Cys Thr Thr Gly Ala Gly Thr Gly Gly
    610                 615                 620

Cys Thr Gly Gly Gly Cys Thr Ala Thr Ala Thr Cys Thr Ala Cys Cys
625                 630                 635                 640

Cys Thr Gly Gly Cys Ala Ala Cys Gly Gly Cys Gly Gly Cys Ala Cys
                645                 650                 655

Cys Thr Ala Cys Thr Ala Cys Ala Gly Cys Gly Ala Gly Ala Ala Gly
            660                 665                 670

Thr Thr Cys Ala Ala Gly Gly Gly Cys Ala Ala Ala Gly Cys Cys Ala
        675                 680                 685

Cys Cys Thr Thr Thr Ala Cys Cys Gly Cys Cys Gly Ala Cys Ala Cys
    690                 695                 700

Cys Ala Gly Cys Thr Cys Cys Ala Ala Cys Ala Cys Ala Gly Cys Cys
705                 710                 715                 720

Thr Ala Cys Ala Thr Gly Cys Thr Gly Cys Thr Cys Gly Gly Cys Ala
                725                 730                 735

Gly Cys Cys Thr Gly Ala Cys Ala Cys Cys Thr Gly Ala Gly Gly Ala
            740                 745                 750

Cys Ala Gly Cys Gly Cys Cys Thr Ala Cys Thr Ala Cys Thr Thr Thr
```

755 760 765

Thr Gly Cys Gly Cys Thr Ala Gly Ala Gly Gly Cys Ala Gly Cys Gly
770 775 780

Gly Cys Gly Ala Cys Cys Gly Gly Thr Ala Cys Ala Ala Thr Thr Cys
785 790 795 800

Thr Cys Thr Gly Gly Cys Cys Thr Ala Thr Thr Gly Gly Gly Gly Cys
805 810 815

Cys Ala Gly Gly Gly Cys Ala Cys Cys Cys Thr Gly Gly Thr Thr Ala
820 825 830

Cys Ala Gly Thr Cys Ala Gly Cys Thr Cys Thr
835 840

<210> SEQ ID NO 43
<211> LENGTH: 834
<212> TYPE: PRT
<213> ORGANISM: Artificial Sequence
<220> FEATURE:
<223> OTHER INFORMATION: Vb5.1HL scFv

<400> SEQUENCE: 43

Ala Thr Gly Gly Gly Cys Thr Gly Gly Thr Cys Cys Thr Gly Gly Ala
1 5 10 15

Thr Cys Thr Thr Cys Cys Thr Gly Thr Thr Cys Cys Thr Gly Cys Thr
20 25 30

Gly Thr Cys Thr Gly Ala Gly Ala Cys Thr Gly Cys Cys Gly Gly Cys
35 40 45

Gly Thr Gly Cys Thr Gly Ala Gly Thr Gly Ala Ala Gly Thr Thr Cys
50 55 60

Ala Gly Cys Thr Gly Cys Ala Gly Cys Ala Gly Thr Cys Thr Gly Gly
65 70 75 80

Cys Cys Cys Cys Gly Thr Gly Cys Thr Thr Gly Thr Gly Ala Ala Ala
85 90 95

Cys Cys Thr Gly Gly Cys Gly Cys Cys Thr Cys Thr Gly Thr Cys Ala
100 105 110

Gly Ala Ala Thr Gly Ala Gly Cys Thr Gly Cys Ala Ala Gly Gly Cys
115 120 125

Cys Ala Gly Cys Gly Gly Cys Thr Ala Cys Ala Cys Cys Thr Thr Cys
130 135 140

Ala Cys Cys Gly Ala Cys Thr Ala Cys Ala Ala Cys Ala Thr Cys Cys
145 150 155 160

Ala Cys Thr Gly Gly Gly Thr Cys Ala Ala Gly Cys Ala Gly Ala Gly
165 170 175

Cys Cys Ala Cys Gly Gly Cys Ala Gly Ala Thr Cys Cys Cys Thr Thr
180 185 190

Gly Ala Gly Thr Gly Gly Gly Thr Cys Gly Gly Ala Thr Ala Thr Ala
195 200 205

Thr Cys Ala Ala Cys Cys Cys Cys Thr Ala Cys Ala Ala Cys Gly Gly
210 215 220

Cys Cys Gly Gly Ala Cys Cys Gly Gly Cys Thr Ala Cys Ala Ala Cys
225 230 235 240

Cys Ala Gly Ala Ala Gly Thr Thr Cys Ala Ala Gly Gly Cys Cys Ala
245 250 255

Ala Gly Gly Cys Cys Ala Cys Ala Cys Thr Gly Ala Cys Cys Gly Thr
260 265 270

Gly Ala Ala Cys Ala Ala Gly Ala Gly Cys Ala Gly Cys Ala Gly Cys

```
        275                 280                 285

Ala Cys Cys Gly Cys Cys Thr Ala Cys Ala Thr Gly Gly Ala Cys Cys
    290                 295                 300

Thr Gly Ala Gly Ala Ala Gly Cys Cys Thr Gly Ala Cys Cys Ala Gly
305                 310                 315                 320

Cys Gly Ala Gly Gly Ala Cys Ala Gly Cys Gly Cys Cys Gly Thr Gly
                325                 330                 335

Thr Ala Cys Thr Ala Thr Thr Gly Cys Gly Cys Cys Ala Gly Ala Thr
            340                 345                 350

Gly Gly Gly Ala Thr Gly Gly Cys Ala Gly Cys Ala Gly Cys Thr Ala
        355                 360                 365

Cys Thr Thr Cys Gly Ala Thr Thr Ala Thr Thr Gly Gly Gly Gly Cys
    370                 375                 380

Cys Ala Gly Gly Gly Cys Ala Cys Ala Ala Cys Cys Cys Thr Gly Ala
385                 390                 395                 400

Cys Cys Gly Thr Thr Thr Cys Thr Thr Cys Thr Gly Gly Thr Gly Gly
                405                 410                 415

Cys Gly Gly Ala Gly Gly Ala Thr Cys Thr Gly Gly Cys Gly Gly Ala
            420                 425                 430

Gly Gly Thr Gly Gly Ala Ala Gly Cys Gly Gly Cys Gly Gly Ala Gly
        435                 440                 445

Gly Cys Gly Gly Ala Thr Cys Thr Ala Thr Gly Gly Ala Thr Thr Thr
    450                 455                 460

Cys Cys Gly Gly Gly Thr Gly Cys Ala Gly Ala Thr Cys Thr Thr Cys
465                 470                 475                 480

Ala Gly Cys Thr Thr Cys Cys Thr Gly Cys Thr Gly Ala Thr Cys Thr
                485                 490                 495

Cys Cys Gly Thr Gly Ala Cys Cys Gly Thr Gly Thr Cys Cys Ala Gly
            500                 505                 510

Ala Gly Gly Cys Gly Ala Gly Ala Thr Cys Gly Thr Gly Cys Thr Gly
        515                 520                 525

Ala Cys Ala Cys Ala Gly Ala Gly Cys Cys Cys Thr Gly Cys Cys Ala
    530                 535                 540

Thr Thr Ala Cys Ala Gly Cys Cys Gly Cys Thr Thr Cys Thr Cys Thr
545                 550                 555                 560

Gly Gly Gly Cys Cys Ala Gly Ala Ala Ala Gly Thr Gly Ala Cys Cys
                565                 570                 575

Ala Thr Cys Ala Cys Ala Thr Gly Cys Ala Gly Cys Gly Cys Cys Ala
            580                 585                 590

Gly Cys Ala Gly Cys Ala Gly Cys Gly Thr Gly Thr Cys Cys Thr Ala
        595                 600                 605

Cys Ala Thr Gly Cys Ala Cys Thr Gly Gly Thr Ala Thr Cys Ala Gly
    610                 615                 620

Cys Ala Gly Ala Ala Gly Thr Cys Cys Gly Gly Cys Ala Cys Ala Ala
625                 630                 635                 640

Gly Cys Cys Cys Cys Ala Ala Gly Cys Cys Thr Thr Gly Gly Ala Thr
                645                 650                 655

Cys Thr Ala Cys Gly Ala Gly Ala Thr Cys Thr Cys Cys Ala Ala Gly
            660                 665                 670

Cys Thr Gly Gly Cys Cys Thr Cys Thr Gly Gly Cys Gly Thr Gly Cys
        675                 680                 685

Cys Ala Gly Cys Cys Ala Gly Ala Thr Thr Thr Thr Cys Thr Gly Gly
    690                 695                 700
```

Cys Thr Cys Thr Gly Gly Cys Ala Gly Cys Gly Gly Cys Ala Cys Cys
705 710 715 720

Ala Gly Cys Thr Ala Cys Thr Cys Cys Cys Thr Gly Ala Cys Ala Ala
725 730 735

Thr Cys Ala Gly Cys Ala Gly Cys Ala Thr Gly Gly Ala Ala Gly Cys
740 745 750

Cys Gly Ala Gly Gly Ala Cys Gly Cys Cys Gly Cys Cys Ala Thr Cys
755 760 765

Thr Ala Cys Thr Ala Cys Thr Gly Cys Cys Ala Gly Cys Ala Gly Thr
770 775 780

Gly Gly Ala Ala Cys Thr Ala Cys Cys Cys Thr Cys Thr Gly Ala Thr
785 790 795 800

Cys Ala Cys Cys Thr Thr Thr Gly Gly Ala Gly Cys Cys Gly Gly Cys
805 810 815

Ala Cys Cys Ala Ala Gly Cys Thr Gly Gly Ala Ala Cys Thr Gly Ala
820 825 830

Ala Gly

<210> SEQ ID NO 44
<211> LENGTH: 834
<212> TYPE: PRT
<213> ORGANISM: Artificial Sequence
<220> FEATURE:
<223> OTHER INFORMATION: Vb5.1LH

<400> SEQUENCE: 44

Ala Thr Gly Gly Ala Cys Thr Thr Cys Cys Gly Gly Gly Thr Gly Cys
1 5 10 15

Ala Gly Ala Thr Cys Thr Thr Cys Ala Gly Cys Thr Thr Cys Cys Thr
20 25 30

Gly Cys Thr Gly Ala Thr Cys Thr Cys Cys Gly Thr Gly Ala Cys Cys
35 40 45

Gly Thr Gly Thr Cys Cys Ala Gly Ala Gly Gly Cys Gly Ala Gly Ala
50 55 60

Thr Cys Gly Thr Gly Cys Thr Gly Ala Cys Ala Cys Ala Gly Ala Gly
65 70 75 80

Cys Cys Cys Thr Gly Cys Cys Ala Thr Thr Ala Cys Ala Gly Cys Cys
85 90 95

Gly Cys Thr Thr Cys Thr Cys Thr Gly Gly Gly Cys Cys Ala Gly Ala
100 105 110

Ala Ala Gly Thr Gly Ala Cys Cys Ala Thr Cys Ala Cys Ala Thr Gly
115 120 125

Cys Ala Gly Cys Gly Cys Cys Ala Gly Cys Ala Gly Cys Ala Gly Cys
130 135 140

Gly Thr Gly Thr Cys Cys Thr Ala Cys Ala Thr Gly Cys Ala Cys Thr
145 150 155 160

Gly Gly Thr Ala Thr Cys Ala Gly Cys Ala Gly Ala Ala Gly Thr Cys
165 170 175

Cys Gly Gly Cys Ala Cys Ala Ala Gly Cys Cys Cys Cys Ala Ala Gly
180 185 190

Cys Cys Thr Thr Gly Gly Ala Thr Cys Thr Ala Cys Gly Ala Gly Ala
195 200 205

Thr Cys Thr Cys Cys Ala Ala Gly Cys Thr Gly Gly Cys Cys Thr Cys
210 215 220

-continued

```
Thr Gly Gly Cys Gly Thr Gly Cys Cys Ala Gly Cys Cys Ala Gly Ala
225                 230                 235                 240

Thr Thr Thr Thr Cys Thr Gly Gly Cys Thr Cys Thr Gly Gly Cys Ala
                245                 250                 255

Gly Cys Gly Gly Cys Ala Cys Cys Ala Gly Cys Thr Ala Cys Ala Gly
            260                 265                 270

Cys Cys Thr Gly Ala Cys Ala Ala Thr Cys Ala Gly Cys Ala Gly Cys
        275                 280                 285

Ala Thr Gly Gly Ala Ala Gly Cys Cys Gly Ala Gly Gly Ala Cys Gly
    290                 295                 300

Cys Cys Gly Cys Cys Ala Thr Cys Thr Ala Cys Thr Ala Cys Thr Gly
305                 310                 315                 320

Cys Cys Ala Gly Cys Ala Gly Thr Gly Gly Ala Ala Cys Thr Ala Cys
                325                 330                 335

Cys Cys Thr Cys Thr Gly Ala Thr Cys Ala Cys Cys Thr Thr Thr Gly
            340                 345                 350

Gly Ala Gly Cys Cys Gly Gly Cys Ala Cys Cys Ala Ala Gly Cys Thr
        355                 360                 365

Gly Gly Ala Ala Cys Thr Gly Ala Ala Ala Gly Gly Cys Gly Gly Cys
    370                 375                 380

Gly Gly Ala Gly Gly Ala Thr Cys Thr Gly Gly Cys Gly Gly Ala Gly
385                 390                 395                 400

Gly Thr Gly Gly Ala Ala Gly Cys Gly Gly Ala Gly Gly Cys Gly Gly
                405                 410                 415

Thr Gly Gly Ala Thr Cys Thr Ala Thr Gly Gly Gly Ala Thr Gly Gly
            420                 425                 430

Thr Cys Cys Thr Gly Gly Ala Thr Cys Thr Thr Cys Cys Thr Gly Thr
        435                 440                 445

Thr Cys Cys Thr Gly Cys Thr Gly Thr Cys Cys Gly Ala Ala Ala Cys
    450                 455                 460

Ala Gly Cys Cys Gly Gly Cys Gly Thr Gly Cys Thr Gly Thr Cys Thr
465                 470                 475                 480

Gly Ala Ala Gly Thr Thr Cys Ala Gly Cys Thr Gly Cys Ala Gly Cys
                485                 490                 495

Ala Gly Thr Cys Thr Gly Gly Cys Cys Cys Cys Gly Thr Gly Cys Thr
            500                 505                 510

Thr Gly Thr Gly Ala Ala Ala Cys Cys Thr Gly Gly Cys Gly Cys Cys
        515                 520                 525

Thr Cys Thr Gly Thr Cys Ala Gly Ala Ala Thr Gly Ala Gly Cys Thr
    530                 535                 540

Gly Cys Ala Ala Gly Gly Cys Cys Ala Gly Cys Gly Gly Cys Thr Ala
545                 550                 555                 560

Cys Ala Cys Cys Thr Thr Cys Ala Cys Cys Gly Ala Cys Thr Ala Cys
                565                 570                 575

Ala Ala Cys Ala Thr Cys Cys Ala Cys Thr Gly Gly Gly Thr Cys Ala
            580                 585                 590

Ala Gly Cys Ala Gly Ala Gly Cys Cys Ala Cys Gly Gly Cys Ala Gly
        595                 600                 605

Ala Thr Cys Cys Cys Thr Thr Gly Ala Gly Thr Gly Gly Gly Thr Cys
    610                 615                 620

Gly Gly Ala Thr Ala Thr Ala Thr Cys Ala Ala Cys Cys Cys Cys Thr
625                 630                 635                 640

Ala Cys Ala Ala Cys Gly Gly Cys Cys Gly Gly Ala Cys Cys Gly Gly
```

645 650 655

Cys Thr Ala Cys Ala Ala Cys Cys Ala Gly Ala Ala Gly Thr Thr Cys
660 665 670

Ala Ala Gly Gly Cys Cys Ala Ala Gly Gly Cys Cys Ala Cys Ala Cys
675 680 685

Thr Gly Ala Cys Cys Gly Thr Gly Ala Ala Cys Ala Ala Gly Ala Gly
690 695 700

Cys Ala Gly Cys Ala Gly Cys Ala Cys Cys Gly Cys Cys Thr Ala Cys
705 710 715 720

Ala Thr Gly Gly Ala Cys Cys Thr Gly Ala Gly Ala Ala Gly Cys Cys
725 730 735

Thr Gly Ala Cys Cys Ala Gly Cys Gly Ala Gly Gly Ala Cys Ala Gly
740 745 750

Cys Gly Cys Cys Gly Thr Gly Thr Ala Cys Thr Ala Thr Thr Gly Cys
755 760 765

Gly Cys Cys Ala Gly Ala Thr Gly Gly Gly Ala Thr Gly Gly Cys Ala
770 775 780

Gly Cys Ala Gly Cys Thr Ala Cys Thr Thr Cys Gly Ala Thr Thr Ala
785 790 795 800

Thr Thr Gly Gly Gly Gly Cys Cys Ala Gly Gly Gly Cys Ala Cys Ala
805 810 815

Ala Cys Cys Cys Thr Gly Ala Cys Ala Gly Thr Gly Thr Cys Cys Thr
820 825 830

Cys Thr

<210> SEQ ID NO 45
<211> LENGTH: 864
<212> TYPE: PRT
<213> ORGANISM: Artificial Sequence
<220> FEATURE:
<223> OTHER INFORMATION: Vb7.1HL

<400> SEQUENCE: 45

Ala Thr Gly Ala Ala Cys Thr Thr Cys Gly Gly Cys Cys Thr Gly Ala
1 5 10 15

Gly Cys Cys Thr Gly Ala Thr Cys Thr Thr Cys Cys Thr Gly Gly Thr
20 25 30

Gly Cys Thr Gly Thr Thr Cys Cys Thr Gly Ala Ala Gly Gly Gly Cys
35 40 45

Gly Thr Gly Cys Ala Gly Thr Gly Cys Gly Ala Ala Gly Thr Gly Cys
50 55 60

Ala Gly Cys Thr Gly Gly Thr Thr Gly Ala Ala Thr Cys Thr Gly Gly
65 70 75 80

Cys Gly Gly Cys Gly Gly Ala Cys Thr Gly Gly Thr Thr Ala Ala Gly
85 90 95

Cys Cys Thr Gly Gly Cys Gly Gly Ala Thr Cys Thr Cys Thr Gly Ala
100 105 110

Ala Gly Cys Thr Gly Ala Gly Cys Thr Gly Thr Gly Cys Cys Gly Cys
115 120 125

Cys Ala Gly Cys Gly Gly Cys Thr Thr Cys Ala Cys Cys Thr Thr Cys
130 135 140

Ala Gly Cys Gly Ala Cys Thr Ala Cys Thr Ala Cys Ala Thr Gly Thr
145 150 155 160

Ala Cys Thr Gly Gly Gly Thr Cys Cys Gly Ala Cys Ala Gly Ala Cys
165 170 175

```
Cys Cys Cys Thr Gly Ala Gly Ala Ala Gly Cys Gly Gly Cys Thr Gly
            180                 185                 190

Gly Ala Ala Thr Gly Gly Gly Thr Cys Gly Cys Cys Ala Cys Ala Ala
        195                 200                 205

Thr Thr Thr Cys Thr Gly Gly Cys Gly Gly Ala Gly Gly Cys Ala Gly
    210                 215                 220

Cys Thr Ala Cys Ala Cys Ala Thr Ala Cys Ala Gly Cys Cys Cys Cys
225                 230                 235                 240

Gly Ala Thr Thr Cys Thr Gly Thr Gly Ala Ala Gly Gly Gly Cys Ala
                245                 250                 255

Gly Ala Thr Thr Cys Ala Cys Cys Ala Thr Cys Ala Gly Cys Cys Gly
            260                 265                 270

Gly Gly Ala Cys Ala Ala Cys Gly Cys Cys Ala Ala Gly Ala Ala Cys
        275                 280                 285

Ala Ala Cys Cys Thr Gly Thr Ala Cys Cys Thr Gly Cys Ala Gly Ala
    290                 295                 300

Thr Gly Ala Gly Cys Ala Gly Cys Cys Thr Gly Cys Gly Gly Ala Gly
305                 310                 315                 320

Cys Gly Ala Gly Gly Ala Cys Ala Cys Cys Gly Cys Cys Ala Thr Gly
                325                 330                 335

Thr Ala Cys Thr Thr Thr Thr Gly Cys Gly Cys Cys Ala Gly Ala Gly
            340                 345                 350

Ala Gly Cys Gly Gly Gly Ala Cys Ala Thr Cys Thr Ala Cys Thr Ala
        355                 360                 365

Cys Gly Gly Cys Ala Ala Cys Thr Thr Cys Ala Ala Cys Gly Cys Cys
    370                 375                 380

Ala Thr Gly Gly Thr Gly Thr Ala Cys Thr Gly Gly Gly Gly Cys Ala
385                 390                 395                 400

Gly Ala Gly Gly Cys Ala Cys Cys Ala Gly Cys Gly Thr Gly Ala Cys
                405                 410                 415

Ala Gly Thr Thr Ala Gly Thr Ala Gly Cys Gly Gly Ala Gly Gly Cys
            420                 425                 430

Gly Gly Ala Gly Gly Ala Thr Cys Ala Gly Gly Thr Gly Gly Cys Gly
        435                 440                 445

Gly Thr Gly Gly Ala Ala Gly Thr Gly Gly Thr Gly Gly Thr Gly Gly
    450                 455                 460

Cys Gly Gly Cys Ala Gly Cys Ala Thr Gly Gly Ala Ala Ala Cys Cys
465                 470                 475                 480

Gly Ala Thr Ala Cys Ala Cys Thr Gly Cys Thr Gly Cys Thr Gly Thr
                485                 490                 495

Gly Gly Gly Thr Gly Cys Thr Gly Cys Thr Cys Cys Thr Thr Thr Gly
            500                 505                 510

Gly Gly Thr Gly Cys Cys Cys Gly Gly Ala Thr Cys Thr Ala Cys Ala
        515                 520                 525

Gly Gly Cys Gly Ala Cys Ala Thr Cys Gly Thr Gly Cys Thr Gly Ala
    530                 535                 540

Cys Ala Cys Ala Gly Ala Gly Cys Cys Cys Cys Gly Thr Gly Thr Cys
545                 550                 555                 560

Thr Cys Thr Gly Ala Cys Ala Gly Thr Gly Thr Cys Cys Cys Thr Gly
                565                 570                 575

Gly Gly Ala Cys Ala Gly Ala Gly Ala Gly Cys Cys Ala Cys Ala Ala
            580                 585                 590
```

Thr Cys Ala Gly Cys Thr Gly Cys Ala Gly Ala Gly Cys Cys Ala Gly
595 600 605

Cys Ala Ala Gly Ala Gly Cys Gly Thr Gly Thr Cys Cys Ala Cys Ala
610 615 620

Ala Gly Cys Gly Gly Cys Thr Ala Cys Ala Gly Cys Thr Ala Cys Ala
625 630 635 640

Thr Gly Cys Ala Cys Thr Gly Gly Thr Ala Thr Cys Ala Gly Cys Ala
645 650 655

Gly Ala Ala Gly Cys Cys Cys Gly Gly Cys Cys Ala Gly Cys Cys Thr
660 665 670

Cys Cys Thr Ala Ala Gly Cys Thr Gly Cys Thr Gly Ala Thr Cys Thr
675 680 685

Ala Cys Cys Thr Gly Gly Cys Cys Ala Gly Cys Ala Ala Cys Cys Thr
690 695 700

Gly Gly Ala Ala Ala Gly Cys Gly Gly Ala Gly Thr Gly Cys Cys Thr
705 710 715 720

Gly Cys Cys Ala Gly Ala Thr Thr Thr Thr Cys Thr Gly Gly Cys Ala
725 730 735

Gly Cys Gly Gly Cys Thr Cys Thr Gly Gly Cys Ala Cys Cys Gly Ala
740 745 750

Cys Thr Thr Cys Ala Cys Cys Cys Thr Gly Ala Ala Thr Ala Thr Cys
755 760 765

Cys Ala Thr Cys Cys Thr Gly Thr Gly Gly Ala Ala Gly Ala Ala Gly
770 775 780

Ala Gly Gly Ala Cys Gly Cys Cys Gly Cys Cys Ala Cys Cys Thr Ala
785 790 795 800

Cys Thr Ala Cys Thr Gly Thr Cys Ala Gly Cys Ala Cys Ala Gly Cys
805 810 815

Ala Gly Ala Gly Ala Thr Cys Thr Gly Cys Cys Cys Thr Gly Gly Ala
820 825 830

Cys Cys Thr Thr Thr Gly Gly Ala Gly Gly Cys Gly Gly Cys Ala Cys
835 840 845

Cys Ala Ala Gly Cys Thr Gly Gly Ala Ala Ala Thr Cys Ala Ala Gly
850 855 860

<210> SEQ ID NO 46
<211> LENGTH: 864
<212> TYPE: PRT
<213> ORGANISM: Artificial Sequence
<220> FEATURE:
<223> OTHER INFORMATION: Vb7.1LH scFv

<400> SEQUENCE: 46

Ala Thr Gly Gly Ala Ala Ala Cys Cys Gly Ala Cys Ala Cys Ala Cys
1 5 10 15

Thr Gly Cys Thr Gly Cys Thr Gly Thr Gly Gly Gly Thr Gly Cys Thr
20 25 30

Gly Cys Thr Thr Cys Thr Thr Thr Gly Gly Gly Thr Gly Cys Cys Cys
35 40 45

Gly Gly Ala Ala Gly Cys Ala Cys Ala Gly Gly Cys Gly Ala Cys Ala
50 55 60

Thr Cys Gly Thr Gly Cys Thr Thr Ala Cys Ala Cys Ala Gly Ala Gly
65 70 75 80

Cys Cys Cys Cys Gly Thr Gly Thr Cys Thr Cys Thr Gly Ala Cys Ala
85 90 95

```
Gly Thr Gly Thr Cys Cys Cys Thr Gly Gly Gly Ala Cys Ala Gly Ala
            100                 105                 110

Gly Ala Gly Cys Cys Ala Cys Cys Ala Thr Cys Ala Gly Cys Thr Gly
        115                 120                 125

Thr Ala Gly Ala Gly Cys Cys Ala Gly Cys Ala Ala Gly Ala Gly Cys
    130                 135                 140

Gly Thr Gly Thr Cys Cys Ala Cys Cys Ala Gly Cys Gly Gly Cys Thr
145                 150                 155                 160

Ala Cys Ala Gly Cys Thr Ala Cys Ala Thr Gly Cys Ala Cys Thr Gly
                165                 170                 175

Gly Thr Ala Thr Cys Ala Gly Cys Ala Gly Ala Ala Gly Cys Cys Cys
            180                 185                 190

Gly Gly Cys Cys Ala Gly Cys Cys Thr Cys Cys Thr Ala Ala Gly Cys
        195                 200                 205

Thr Gly Cys Thr Gly Ala Thr Cys Thr Ala Cys Cys Thr Gly Gly Cys
    210                 215                 220

Cys Ala Gly Cys Ala Ala Cys Cys Thr Gly Gly Ala Ala Ala Gly Cys
225                 230                 235                 240

Gly Gly Ala Gly Thr Gly Cys Cys Thr Gly Cys Cys Ala Gly Ala Thr
                245                 250                 255

Thr Thr Thr Cys Thr Gly Gly Cys Ala Gly Cys Gly Gly Cys Thr Cys
            260                 265                 270

Thr Gly Gly Cys Ala Cys Cys Gly Ala Cys Thr Thr Cys Ala Cys Cys
        275                 280                 285

Cys Thr Gly Ala Ala Thr Ala Thr Cys Cys Ala Thr Cys Cys Thr Gly
    290                 295                 300

Thr Gly Gly Ala Ala Gly Ala Ala Gly Ala Gly Gly Ala Cys Gly Cys
305                 310                 315                 320

Cys Gly Cys Cys Ala Cys Cys Thr Ala Cys Thr Ala Cys Thr Gly Thr
                325                 330                 335

Cys Ala Gly Cys Ala Cys Ala Gly Cys Ala Gly Ala Gly Ala Thr Cys
            340                 345                 350

Thr Gly Cys Cys Cys Thr Gly Gly Ala Cys Cys Thr Thr Thr Gly Gly
        355                 360                 365

Cys Gly Gly Cys Gly Gly Ala Ala Cys Ala Ala Ala Gly Cys Thr Gly
    370                 375                 380

Gly Ala Ala Ala Thr Cys Ala Ala Ala Gly Gly Cys Gly Gly Cys Gly
385                 390                 395                 400

Gly Ala Gly Gly Ala Thr Cys Thr Gly Gly Cys Gly Gly Ala Gly Gly
                405                 410                 415

Thr Gly Gly Ala Ala Gly Cys Gly Gly Ala Gly Gly Cys Gly Gly Thr
            420                 425                 430

Gly Gly Cys Thr Cys Thr Ala Thr Gly Ala Ala Thr Thr Thr Thr Gly
        435                 440                 445

Gly Cys Cys Thr Gly Ala Gly Cys Cys Thr Gly Ala Thr Cys Thr Thr
    450                 455                 460

Cys Cys Thr Gly Gly Thr Gly Cys Thr Gly Thr Thr Cys Cys Thr Gly
465                 470                 475                 480

Ala Ala Gly Gly Gly Cys Gly Thr Gly Cys Ala Gly Thr Gly Cys Gly
                485                 490                 495

Ala Ala Gly Thr Gly Cys Ala Gly Cys Thr Gly Gly Thr Thr Gly Ala
            500                 505                 510

Ala Ala Gly Thr Gly Gly Cys Gly Gly Ala Gly Gly Cys Cys Thr Gly
```

```
        515                 520                 525

Gly Thr Thr Ala Ala Gly Cys Cys Thr Gly Gly Cys Gly Gly Ala Thr
    530                 535                 540

Cys Thr Cys Thr Gly Ala Ala Gly Cys Thr Gly Ala Gly Cys Thr Gly
545                 550                 555                 560

Thr Gly Cys Cys Gly Cys Cys Ala Gly Cys Gly Gly Cys Thr Thr Cys
                565                 570                 575

Ala Cys Cys Thr Thr Cys Ala Gly Cys Gly Ala Cys Thr Ala Cys Thr
            580                 585                 590

Ala Cys Ala Thr Gly Thr Ala Cys Thr Gly Gly Gly Thr Cys Cys Gly
        595                 600                 605

Ala Cys Ala Gly Ala Cys Cys Cys Cys Thr Gly Ala Gly Ala Ala Gly
    610                 615                 620

Cys Gly Gly Cys Thr Gly Gly Ala Ala Thr Gly Gly Gly Thr Cys Gly
625                 630                 635                 640

Cys Cys Ala Cys Ala Ala Thr Thr Thr Cys Ala Gly Gly Cys Gly Gly
                645                 650                 655

Ala Gly Gly Cys Ala Gly Cys Thr Ala Cys Ala Cys Ala Thr Ala Cys
            660                 665                 670

Ala Gly Cys Cys Cys Cys Gly Ala Thr Thr Cys Thr Gly Thr Gly Ala
        675                 680                 685

Ala Gly Gly Gly Cys Cys Gly Cys Thr Thr Thr Ala Cys Cys Ala Thr
    690                 695                 700

Cys Ala Gly Cys Cys Gly Gly Gly Ala Cys Ala Ala Cys Gly Cys Cys
705                 710                 715                 720

Ala Ala Gly Ala Ala Cys Ala Ala Cys Cys Thr Gly Thr Ala Cys Cys
                725                 730                 735

Thr Gly Cys Ala Gly Ala Thr Gly Ala Gly Cys Ala Gly Cys Cys Thr
            740                 745                 750

Gly Cys Gly Gly Ala Gly Cys Gly Ala Gly Gly Ala Cys Ala Cys Cys
        755                 760                 765

Gly Cys Cys Ala Thr Gly Thr Ala Cys Thr Thr Thr Thr Gly Cys Gly
    770                 775                 780

Cys Cys Ala Gly Ala Gly Ala Gly Cys Gly Gly Gly Ala Cys Ala Thr
785                 790                 795                 800

Cys Thr Ala Cys Thr Ala Cys Gly Gly Cys Ala Ala Cys Thr Thr Cys
                805                 810                 815

Ala Ala Cys Gly Cys Cys Ala Thr Gly Gly Thr Gly Thr Ala Cys Thr
            820                 825                 830

Gly Gly Gly Gly Cys Ala Gly Ala Gly Gly Cys Ala Cys Cys Thr Cys
        835                 840                 845

Thr Gly Thr Gly Ala Cys Cys Gly Thr Thr Ala Gly Cys Thr Cys Thr
    850                 855                 860


<210> SEQ ID NO 47
<211> LENGTH: 834
<212> TYPE: PRT
<213> ORGANISM: Artificial Sequence
<220> FEATURE:
<223> OTHER INFORMATION: Vb7.2HL scFv

<400> SEQUENCE: 47

Ala Thr Gly Gly Ala Ala Cys Gly Gly Cys Ala Cys Thr Gly Gly Ala
1               5                   10                  15

Thr Cys Thr Thr Thr Cys Thr Gly Cys Thr Gly Cys Thr Gly Cys Thr
```

```
            20                  25                  30

Gly Ala Gly Cys Gly Thr Thr Ala Cys Ala Gly Cys Cys Gly Gly Cys
        35                  40                  45

Gly Cys Thr Cys Ala Cys Thr Cys Thr Cys Ala Ala Gly Thr Gly Cys
    50                  55                  60

Ala Thr Cys Thr Gly Cys Ala Gly Cys Ala Ala Thr Cys Thr Gly Gly
65                  70                  75                  80

Cys Gly Cys Cys Gly Ala Gly Cys Thr Thr Gly Cys Thr Ala Gly Ala
                85                  90                  95

Cys Cys Thr Gly Gly Cys Gly Cys Cys Thr Cys Thr Gly Thr Gly Ala
            100                 105                 110

Ala Gly Ala Thr Gly Ala Gly Cys Thr Gly Thr Ala Ala Ala Gly Cys
        115                 120                 125

Cys Ala Gly Cys Gly Gly Cys Thr Ala Cys Ala Thr Cys Thr Thr Cys
    130                 135                 140

Ala Cys Cys Gly Ala Cys Thr Ala Cys Ala Cys Cys Ala Thr Gly Cys
145                 150                 155                 160

Ala Cys Thr Gly Gly Gly Thr Cys Ala Ala Gly Cys Ala Gly Ala Gly
                165                 170                 175

Gly Cys Cys Thr Gly Gly Ala Cys Ala Gly Gly Gly Ala Cys Thr Cys
            180                 185                 190

Gly Ala Gly Thr Gly Gly Ala Thr Cys Gly Gly Cys Cys Ala Cys Ala
        195                 200                 205

Thr Cys Ala Ala Thr Cys Cys Thr Ala Gly Cys Thr Cys Cys Gly Gly
    210                 215                 220

Cys Thr Ala Cys Ala Gly Cys Ala Cys Cys Thr Ala Cys Ala Ala Cys
225                 230                 235                 240

Cys Ala Gly Ala Ala Gly Thr Thr Cys Ala Ala Gly Gly Ala Cys Ala
                245                 250                 255

Ala Gly Gly Cys Cys Ala Cys Ala Cys Thr Gly Ala Cys Cys Gly Cys
            260                 265                 270

Cys Gly Ala Cys Ala Ala Gly Ala Gly Cys Ala Gly Cys Thr Cys Thr
        275                 280                 285

Ala Cys Ala Gly Cys Cys Thr Ala Cys Ala Thr Gly Cys Ala Gly Cys
    290                 295                 300

Thr Gly Ala Gly Cys Ala Gly Cys Cys Thr Gly Ala Cys Cys Ala Gly
305                 310                 315                 320

Cys Gly Ala Ala Gly Ala Thr Ala Gly Cys Gly Cys Cys Gly Thr Gly
                325                 330                 335

Thr Ala Cys Thr Ala Cys Thr Gly Cys Gly Cys Cys Ala Gly Ala Ala
            340                 345                 350

Gly Cys Cys Thr Gly Cys Ala Gly Cys Thr Gly Gly Gly Cys Ala Gly
        355                 360                 365

Ala Gly Ala Thr Thr Ala Thr Thr Gly Gly Gly Gly Cys Cys Ala Gly
    370                 375                 380

Gly Gly Cys Ala Cys Ala Ala Cys Cys Cys Thr Gly Ala Cys Cys Gly
385                 390                 395                 400

Thr Thr Thr Cys Thr Thr Cys Thr Gly Gly Thr Gly Gly Cys Gly Gly
                405                 410                 415

Ala Gly Gly Ala Thr Cys Thr Gly Gly Cys Gly Gly Ala Gly Gly Thr
            420                 425                 430

Gly Gly Ala Ala Gly Cys Gly Gly Cys Gly Gly Ala Gly Gly Cys Gly
        435                 440                 445
```

```
Gly Ala Thr Cys Thr Ala Thr Gly Gly Ala Ala Thr Cys Thr Cys Ala
    450                 455                 460

Gly Ala Thr Cys Cys Ala Gly Gly Thr Gly Thr Thr Cys Gly Thr Gly
465                 470                 475                 480

Thr Thr Thr Gly Thr Gly Thr Thr Cys Cys Thr Gly Thr Gly Gly Cys
                485                 490                 495

Thr Gly Thr Cys Thr Gly Gly Cys Gly Thr Gly Gly Ala Cys Gly Gly
            500                 505                 510

Cys Gly Ala Thr Ala Thr Cys Gly Thr Gly Ala Thr Gly Ala Cys Cys
        515                 520                 525

Cys Ala Gly Ala Gly Cys Cys Ala Cys Ala Ala Gly Thr Thr Cys Ala
    530                 535                 540

Thr Gly Ala Gly Cys Ala Cys Cys Ala Gly Cys Gly Thr Gly Gly Gly
545                 550                 555                 560

Cys Gly Ala Cys Ala Gly Ala Gly Thr Gly Thr Cys Cys Ala Thr Cys
                565                 570                 575

Ala Cys Ala Thr Gly Cys Ala Ala Gly Gly Cys Cys Ala Gly Cys Cys
            580                 585                 590

Ala Gly Gly Ala Cys Gly Thr Gly Thr Ala Cys Ala Cys Ala Gly Cys
        595                 600                 605

Cys Gly Thr Gly Gly Cys Thr Thr Gly Gly Thr Ala Thr Cys Ala Gly
    610                 615                 620

Cys Ala Gly Ala Ala Gly Cys Cys Cys Gly Gly Cys Cys Ala Gly Thr
625                 630                 635                 640

Cys Thr Cys Cys Thr Ala Ala Gly Cys Thr Gly Cys Thr Gly Ala Thr
                645                 650                 655

Cys Thr Ala Cys Ala Gly Cys Gly Cys Cys Ala Gly Cys Ala Ala Cys
            660                 665                 670

Ala Gly Ala Thr Ala Cys Ala Cys Cys Gly Gly Cys Gly Thr Gly Cys
        675                 680                 685

Cys Cys Gly Ala Thr Ala Gly Ala Thr Thr Cys Ala Cys Ala Gly Gly
    690                 695                 700

Cys Thr Cys Thr Gly Gly Cys Ala Gly Cys Gly Gly Cys Ala Cys Cys
705                 710                 715                 720

Gly Ala Cys Thr Thr Cys Ala Cys Cys Thr Thr Thr Ala Cys Ala Ala
                725                 730                 735

Thr Cys Ala Gly Cys Ala Gly Cys Gly Thr Gly Cys Ala Gly Gly Cys
            740                 745                 750

Cys Gly Ala Gly Gly Ala Cys Cys Thr Gly Gly Cys Cys Gly Thr Gly
        755                 760                 765

Thr Ala Thr Thr Ala Thr Thr Gly Cys Cys Ala Gly Cys Ala Gly Cys
    770                 775                 780

Ala Cys Thr Ala Cys Ala Cys Cys Ala Cys Ala Cys Cys Thr Cys Gly
785                 790                 795                 800

Gly Ala Cys Cys Thr Thr Thr Gly Gly Cys Gly Gly Cys Gly Gly Ala
                805                 810                 815

Ala Cys Ala Ala Ala Gly Cys Thr Gly Gly Ala Ala Ala Thr Cys Ala
            820                 825                 830

Ala Gly
```

<210> SEQ ID NO 48
<211> LENGTH: 834
<212> TYPE: PRT

<213> ORGANISM: Artificial Sequence
<220> FEATURE:
<223> OTHER INFORMATION: Vb7.2LH scFv

<400> SEQUENCE: 48

Ala Thr Gly Gly Ala Ala Ala Gly Cys Cys Ala Gly Ala Thr Cys Cys
1 5 10 15

Ala Gly Gly Thr Gly Thr Thr Cys Gly Thr Gly Thr Thr Thr Gly Thr
20 25 30

Gly Thr Thr Cys Cys Thr Gly Thr Gly Gly Cys Thr Gly Thr Cys Thr
35 40 45

Gly Gly Cys Gly Thr Gly Gly Ala Cys Gly Gly Cys Gly Ala Thr Ala
50 55 60

Thr Cys Gly Thr Gly Ala Thr Gly Ala Cys Cys Cys Ala Gly Ala Gly
65 70 75 80

Cys Cys Ala Cys Ala Ala Gly Thr Thr Cys Ala Thr Gly Ala Gly Cys
85 90 95

Ala Cys Cys Ala Gly Cys Gly Thr Gly Gly Gly Cys Gly Ala Cys Ala
100 105 110

Gly Ala Gly Thr Gly Thr Cys Cys Ala Thr Cys Ala Cys Cys Thr Gly
115 120 125

Thr Ala Ala Ala Gly Cys Cys Ala Gly Cys Cys Ala Gly Gly Ala Cys
130 135 140

Gly Thr Gly Thr Ala Cys Ala Cys Ala Gly Cys Cys Gly Thr Gly Gly
145 150 155 160

Cys Cys Thr Gly Gly Thr Ala Thr Cys Ala Gly Cys Ala Gly Ala Ala
165 170 175

Gly Cys Cys Thr Gly Gly Cys Cys Ala Gly Thr Cys Thr Cys Cys Thr
180 185 190

Ala Ala Gly Cys Thr Gly Cys Thr Gly Ala Thr Cys Thr Ala Cys Ala
195 200 205

Gly Cys Gly Cys Cys Ala Gly Cys Ala Ala Cys Ala Gly Ala Thr Ala
210 215 220

Cys Ala Cys Cys Gly Gly Cys Gly Thr Gly Cys Cys Cys Gly Ala Thr
225 230 235 240

Ala Gly Ala Thr Thr Cys Ala Cys Ala Gly Gly Cys Thr Cys Thr Gly
245 250 255

Gly Cys Ala Gly Cys Gly Gly Cys Ala Cys Cys Gly Ala Cys Thr Thr
260 265 270

Cys Ala Cys Cys Thr Thr Thr Ala Cys Ala Ala Thr Cys Ala Gly Cys
275 280 285

Ala Gly Cys Gly Thr Gly Cys Ala Gly Gly Cys Cys Gly Ala Gly Gly
290 295 300

Ala Cys Cys Thr Gly Gly Cys Cys Gly Thr Gly Thr Ala Thr Thr Ala
305 310 315 320

Thr Thr Gly Cys Cys Ala Gly Cys Ala Gly Cys Ala Cys Thr Ala Cys
325 330 335

Ala Cys Cys Ala Cys Ala Cys Cys Thr Cys Gly Gly Ala Cys Cys Thr
340 345 350

Thr Thr Gly Gly Cys Gly Gly Cys Gly Gly Ala Ala Cys Ala Ala Ala
355 360 365

Gly Cys Thr Gly Gly Ala Ala Ala Thr Cys Ala Ala Ala Gly Gly Cys
370 375 380

Gly Gly Cys Gly Gly Ala Gly Gly Ala Thr Cys Thr Gly Gly Cys Gly

```
385                 390                 395                 400

Gly Ala Gly Gly Thr Gly Gly Ala Ala Gly Cys Gly Gly Ala Gly Gly
                405                 410                 415

Cys Gly Gly Thr Gly Gly Thr Thr Cys Thr Ala Thr Gly Gly Ala Ala
            420                 425                 430

Cys Gly Gly Cys Ala Cys Thr Gly Gly Ala Thr Cys Thr Thr Thr Cys
        435                 440                 445

Thr Gly Cys Thr Gly Cys Thr Gly Cys Thr Gly Ala Gly Cys Gly Thr
    450                 455                 460

Thr Ala Cys Ala Gly Cys Cys Gly Gly Cys Gly Cys Thr Cys Ala Cys
465                 470                 475                 480

Thr Cys Thr Cys Ala Ala Gly Thr Gly Cys Ala Thr Cys Thr Gly Cys
                485                 490                 495

Ala Gly Cys Ala Ala Thr Cys Thr Gly Gly Cys Gly Cys Cys Gly Ala
            500                 505                 510

Gly Cys Thr Thr Gly Cys Thr Ala Gly Ala Cys Cys Thr Gly Gly Cys
        515                 520                 525

Gly Cys Cys Thr Cys Thr Gly Thr Gly Ala Ala Gly Ala Thr Gly Ala
    530                 535                 540

Gly Cys Thr Gly Cys Ala Ala Gly Gly Cys Cys Ala Gly Cys Gly Gly
545                 550                 555                 560

Cys Thr Ala Cys Ala Thr Cys Thr Thr Cys Ala Cys Cys Gly Ala Cys
                565                 570                 575

Thr Ala Cys Ala Cys Cys Ala Thr Gly Cys Ala Cys Thr Gly Gly Gly
            580                 585                 590

Thr Cys Ala Ala Gly Cys Ala Gly Ala Gly Gly Cys Cys Thr Gly Gly
        595                 600                 605

Ala Cys Ala Gly Gly Gly Ala Cys Thr Cys Gly Ala Gly Thr Gly Gly
    610                 615                 620

Ala Thr Cys Gly Gly Cys Cys Ala Cys Ala Thr Cys Ala Ala Thr Cys
625                 630                 635                 640

Cys Thr Ala Gly Cys Thr Cys Cys Gly Gly Cys Thr Ala Cys Ala Gly
                645                 650                 655

Cys Ala Cys Cys Thr Ala Cys Ala Ala Cys Cys Ala Gly Ala Ala Gly
            660                 665                 670

Thr Thr Cys Ala Ala Gly Gly Ala Cys Ala Ala Gly Gly Cys Cys Ala
        675                 680                 685

Cys Ala Cys Thr Gly Ala Cys Cys Gly Cys Cys Gly Ala Cys Ala Ala
    690                 695                 700

Gly Ala Gly Cys Ala Gly Cys Thr Cys Thr Ala Cys Ala Gly Cys Cys
705                 710                 715                 720

Thr Ala Cys Ala Thr Gly Cys Ala Gly Cys Thr Gly Ala Gly Cys Ala
                725                 730                 735

Gly Cys Cys Thr Gly Ala Cys Cys Ala Gly Cys Gly Ala Ala Gly Ala
            740                 745                 750

Thr Ala Gly Cys Gly Cys Cys Gly Thr Gly Thr Ala Cys Thr Ala Cys
        755                 760                 765

Thr Gly Cys Gly Cys Thr Ala Gly Ala Ala Gly Cys Cys Thr Gly Cys
    770                 775                 780

Ala Gly Cys Thr Gly Gly Cys Ala Gly Ala Gly Ala Thr Thr Ala
785                 790                 795                 800

Thr Thr Gly Gly Gly Gly Cys Cys Ala Gly Gly Gly Cys Ala Cys Ala
                805                 810                 815
```

Ala Cys Cys Cys Thr Gly Ala Cys Cys Gly Thr Gly Thr Cys Ala Thr
820 825 830

Cys Thr

<210> SEQ ID NO 49
<211> LENGTH: 831
<212> TYPE: PRT
<213> ORGANISM: Artificial Sequence
<220> FEATURE:
<223> OTHER INFORMATION: Vb11HL scFv

<400> SEQUENCE: 49

Ala Thr Gly Gly Gly Cys Thr Gly Gly Thr Cys Cys Thr Gly Cys Ala
1 5 10 15

Thr Cys Ala Thr Cys Thr Thr Thr Thr Thr Thr Cys Thr Gly Gly Thr
20 25 30

Gly Gly Cys Cys Ala Cys Thr Gly Cys Cys Ala Cys Cys Gly Gly Cys
35 40 45

Gly Thr Gly Cys Ala Cys Thr Cys Thr Cys Ala Ala Gly Thr Thr Cys
50 55 60

Ala Gly Cys Thr Gly Cys Ala Gly Cys Ala Gly Thr Cys Thr Gly Gly
65 70 75 80

Cys Cys Cys Cys Gly Ala Ala Gly Thr Cys Gly Thr Thr Ala Gly Ala
85 90 95

Cys Cys Thr Gly Gly Cys Gly Thr Gly Thr Cys Cys Gly Thr Gly Ala
100 105 110

Ala Gly Ala Thr Cys Ala Gly Cys Thr Gly Cys Ala Ala Ala Gly Gly
115 120 125

Cys Ala Gly Cys Gly Gly Cys Thr Ala Cys Cys Gly Gly Thr Thr Cys
130 135 140

Ala Cys Cys Gly Ala Thr Thr Cys Thr Gly Cys Cys Ala Thr Gly Cys
145 150 155 160

Ala Cys Thr Gly Gly Gly Thr Cys Ala Ala Gly Cys Ala Gly Ala Gly
165 170 175

Cys Cys Ala Cys Gly Cys Cys Ala Ala Gly Ala Gly Cys Cys Thr Gly
180 185 190

Gly Ala Ala Thr Gly Gly Ala Thr Cys Gly Gly Cys Gly Thr Gly Ala
195 200 205

Thr Cys Ala Gly Cys Ala Gly Cys Thr Ala Cys Ala Ala Cys Gly Gly
210 215 220

Cys Ala Ala Cys Ala Cys Cys Ala Ala Cys Thr Ala Cys Ala Ala Cys
225 230 235 240

Cys Ala Gly Ala Ala Gly Thr Thr Cys Ala Ala Gly Gly Gly Cys Ala
245 250 255

Ala Ala Gly Cys Cys Ala Cys Cys Ala Thr Gly Ala Cys Cys Gly Thr
260 265 270

Gly Gly Ala Cys Ala Ala Gly Ala Gly Cys Ala Gly Cys Ala Gly Cys
275 280 285

Ala Cys Cys Gly Cys Cys Thr Ala Cys Ala Thr Gly Gly Ala Ala Cys
290 295 300

Thr Gly Gly Cys Cys Ala Gly Ala Ala Thr Gly Ala Cys Cys Ala Gly
305 310 315 320

Cys Gly Ala Gly Gly Ala Cys Ala Gly Cys Gly Cys Cys Ala Thr Cys
325 330 335

```
Thr Ala Cys Thr Ala Cys Thr Gly Cys Gly Cys Cys Ala Gly Ala Thr
            340                 345                 350

Cys Cys Ala Gly Ala Gly Ala Thr Gly Cys Cys Ala Thr Gly Gly Ala
        355                 360                 365

Cys Thr Ala Thr Thr Gly Gly Gly Gly Cys Cys Ala Gly Gly Gly Cys
    370                 375                 380

Ala Cys Cys Ala Gly Cys Gly Thr Gly Ala Cys Ala Gly Thr Thr Thr
385                 390                 395                 400

Cys Thr Thr Cys Thr Gly Gly Cys Gly Gly Cys Gly Gly Ala Gly Gly
                405                 410                 415

Ala Ala Gly Cys Gly Gly Ala Gly Gly Cys Gly Gly Ala Gly Gly Thr
            420                 425                 430

Thr Cys Thr Gly Gly Thr Gly Gly Thr Gly Gly Thr Gly Gly Cys Thr
        435                 440                 445

Cys Thr Ala Thr Gly Ala Gly Ala Ala Cys Cys Cys Cys Thr Gly Cys
    450                 455                 460

Thr Cys Ala Gly Thr Thr Cys Cys Thr Gly Gly Gly Cys Ala Thr Cys
465                 470                 475                 480

Cys Thr Gly Cys Thr Gly Cys Thr Thr Thr Gly Gly Thr Thr Cys Cys
                485                 490                 495

Cys Cys Gly Gly Cys Ala Thr Cys Ala Ala Gly Thr Gly Cys Gly Ala
            500                 505                 510

Cys Ala Thr Cys Ala Ala Gly Ala Thr Gly Ala Cys Ala Cys Ala Gly
        515                 520                 525

Ala Gly Cys Cys Cys Cys Ala Gly Cys Thr Cys Thr Ala Thr Gly Thr
    530                 535                 540

Ala Cys Gly Cys Cys Ala Gly Cys Cys Thr Gly Gly Gly Ala Gly Ala
545                 550                 555                 560

Gly Ala Gly Ala Gly Thr Gly Ala Cys Cys Ala Thr Thr Ala Cys Cys
                565                 570                 575

Thr Gly Cys Ala Ala Gly Gly Cys Cys Ala Gly Cys Cys Ala Gly Gly
            580                 585                 590

Ala Cys Ala Thr Cys Ala Ala Cys Ala Gly Cys Thr Ala Cys Cys Thr
        595                 600                 605

Gly Ala Gly Cys Thr Gly Gly Thr Thr Cys Cys Ala Gly Cys Ala Gly
    610                 615                 620

Ala Ala Gly Gly Cys Cys Gly Gly Cys Ala Ala Gly Ala Gly Cys Cys
625                 630                 635                 640

Cys Cys Ala Ala Gly Ala Cys Ala Cys Thr Gly Ala Thr Cys Thr Ala
                645                 650                 655

Cys Ala Gly Ala Gly Cys Cys Ala Ala Cys Ala Gly Ala Cys Thr Gly
            660                 665                 670

Gly Thr Gly Gly Ala Cys Gly Gly Cys Gly Thr Gly Cys Cys Cys Ala
        675                 680                 685

Gly Cys Ala Gly Ala Thr Thr Thr Thr Cys Thr Gly Gly Ala Ala Gly
    690                 695                 700

Cys Gly Gly Cys Ala Gly Cys Gly Gly Cys Cys Ala Gly Gly Ala Cys
705                 710                 715                 720

Thr Ala Cys Ala Gly Cys Cys Thr Gly Ala Cys Ala Ala Thr Cys Ala
                725                 730                 735

Gly Cys Thr Cys Cys Cys Thr Gly Gly Ala Ala Thr Ala Cys Gly Ala
            740                 745                 750

Gly Gly Ala Cys Ala Thr Gly Gly Gly Gly Ala Thr Cys Thr Ala Cys
```

```
        755                 760                 765

Thr Ala Thr Thr Gly Cys Cys Thr Gly Cys Ala Gly Thr Ala Cys Gly
    770                 775                 780

Ala Cys Gly Ala Gly Thr Thr Cys Cys Cys Ala Thr Thr Cys Ala Cys
785                 790                 795                 800

Cys Thr Thr Thr Gly Gly Cys Gly Gly Ala Gly Gly Cys Ala Cys Cys
                805                 810                 815

Cys Gly Gly Cys Thr Gly Gly Ala Ala Ala Thr Cys Ala Ala Ala
            820                 825                 830


<210> SEQ ID NO 50
<211> LENGTH: 831
<212> TYPE: PRT
<213> ORGANISM: Artificial Sequence
<220> FEATURE:
<223> OTHER INFORMATION: Vb11LH scFv

<400> SEQUENCE: 50

Ala Thr Gly Ala Gly Ala Ala Cys Cys Cys Cys Thr Gly Cys Thr Cys
1               5                   10                  15

Ala Gly Thr Thr Cys Cys Thr Gly Gly Gly Cys Ala Thr Cys Cys Thr
            20                  25                  30

Gly Cys Thr Gly Cys Thr Thr Thr Gly Gly Thr Thr Cys Cys Cys Cys
        35                  40                  45

Gly Gly Cys Ala Thr Cys Ala Ala Gly Thr Gly Cys Gly Ala Cys Ala
    50                  55                  60

Thr Cys Ala Ala Gly Ala Thr Gly Ala Cys Ala Cys Ala Gly Ala Gly
65                  70                  75                  80

Cys Cys Cys Cys Ala Gly Cys Thr Cys Thr Ala Thr Gly Thr Ala Cys
                85                  90                  95

Gly Cys Cys Ala Gly Cys Cys Thr Gly Gly Gly Ala Gly Ala Gly Ala
            100                 105                 110

Gly Ala Gly Thr Gly Ala Cys Cys Ala Thr Thr Ala Cys Cys Thr Gly
        115                 120                 125

Cys Ala Ala Gly Gly Cys Cys Ala Gly Cys Cys Ala Gly Gly Ala Cys
    130                 135                 140

Ala Thr Cys Ala Ala Cys Ala Gly Cys Thr Ala Cys Cys Thr Gly Ala
145                 150                 155                 160

Gly Cys Thr Gly Gly Thr Thr Cys Cys Ala Gly Cys Ala Gly Ala Ala
                165                 170                 175

Gly Gly Cys Cys Gly Gly Cys Ala Ala Gly Ala Gly Cys Cys Cys Cys
            180                 185                 190

Ala Ala Gly Ala Cys Ala Cys Thr Gly Ala Thr Cys Thr Ala Cys Ala
        195                 200                 205

Gly Ala Gly Cys Cys Ala Ala Cys Ala Gly Ala Cys Thr Gly Gly Thr
    210                 215                 220

Gly Gly Ala Cys Gly Gly Cys Gly Thr Gly Cys Cys Cys Ala Gly Cys
225                 230                 235                 240

Ala Gly Ala Thr Thr Thr Thr Cys Thr Gly Gly Cys Thr Cys Thr Gly
                245                 250                 255

Gly Ala Ala Gly Cys Gly Gly Cys Cys Ala Gly Gly Ala Cys Thr Ala
            260                 265                 270

Cys Ala Gly Cys Cys Thr Gly Ala Cys Ala Ala Thr Cys Ala Gly Cys
        275                 280                 285

Ala Gly Cys Cys Thr Gly Gly Ala Ala Thr Ala Cys Gly Ala Gly Gly
```

```
    290                 295                 300

Ala Cys Ala Thr Gly Gly Gly Cys Ala Thr Cys Thr Ala Cys Thr Ala
305                 310                 315                 320

Cys Thr Gly Cys Cys Thr Gly Cys Ala Gly Thr Ala Cys Gly Ala Cys
                325                 330                 335

Gly Ala Gly Thr Thr Cys Cys Cys Ala Thr Thr Cys Ala Cys Cys Thr
            340                 345                 350

Thr Thr Gly Gly Cys Gly Gly Cys Gly Gly Ala Ala Cys Cys Cys Gly
        355                 360                 365

Gly Cys Thr Gly Gly Ala Ala Ala Thr Cys Ala Ala Ala Gly Gly Thr
    370                 375                 380

Gly Gly Cys Gly Gly Ala Gly Gly Ala Thr Cys Thr Gly Gly Cys Gly
385                 390                 395                 400

Gly Ala Gly Gly Cys Gly Gly Ala Thr Cys Ala Gly Gly Cys Gly Gly
                405                 410                 415

Cys Gly Gly Thr Gly Gly Ala Thr Cys Thr Ala Thr Gly Gly Gly Cys
            420                 425                 430

Thr Gly Gly Thr Cys Cys Thr Gly Cys Ala Thr Cys Ala Thr Cys Thr
        435                 440                 445

Thr Thr Thr Thr Thr Cys Thr Gly Gly Thr Gly Gly Cys Cys Ala Cys
    450                 455                 460

Thr Gly Cys Cys Ala Cys Cys Gly Gly Cys Gly Thr Gly Cys Ala Cys
465                 470                 475                 480

Thr Cys Thr Cys Ala Ala Gly Thr Thr Cys Ala Gly Cys Thr Gly Cys
                485                 490                 495

Ala Gly Cys Ala Gly Thr Cys Thr Gly Gly Cys Cys Cys Cys Gly Ala
            500                 505                 510

Ala Gly Thr Cys Gly Thr Thr Ala Gly Ala Cys Cys Thr Gly Gly Cys
        515                 520                 525

Gly Thr Gly Thr Cys Cys Gly Thr Gly Ala Ala Gly Ala Thr Cys Ala
    530                 535                 540

Gly Cys Thr Gly Cys Ala Ala Ala Gly Gly Cys Ala Gly Cys Gly Gly
545                 550                 555                 560

Cys Thr Ala Cys Cys Gly Gly Thr Thr Cys Ala Cys Cys Gly Ala Thr
                565                 570                 575

Thr Cys Thr Gly Cys Cys Ala Thr Gly Cys Ala Cys Thr Gly Gly Gly
            580                 585                 590

Thr Cys Ala Ala Gly Cys Ala Gly Ala Gly Cys Cys Ala Cys Gly Cys
        595                 600                 605

Cys Ala Ala Gly Thr Cys Thr Cys Thr Gly Gly Ala Ala Thr Gly Gly
    610                 615                 620

Ala Thr Cys Gly Gly Cys Gly Thr Gly Ala Thr Cys Ala Gly Cys Ala
625                 630                 635                 640

Gly Cys Thr Ala Cys Ala Ala Cys Gly Gly Cys Ala Ala Cys Ala Cys
                645                 650                 655

Cys Ala Ala Cys Thr Ala Cys Ala Ala Cys Cys Ala Gly Ala Ala Gly
            660                 665                 670

Thr Thr Cys Ala Ala Gly Gly Gly Cys Ala Ala Ala Gly Cys Cys Ala
        675                 680                 685

Cys Cys Ala Thr Gly Ala Cys Cys Gly Thr Gly Gly Ala Cys Ala Ala
    690                 695                 700

Gly Ala Gly Cys Ala Gly Cys Ala Gly Cys Ala Cys Cys Gly Cys Cys
705                 710                 715                 720
```

```
Thr Ala Cys Ala Thr Gly Gly Ala Ala Cys Thr Gly Gly Cys Cys Ala
                725                 730                 735

Gly Ala Ala Thr Gly Ala Cys Cys Ala Gly Cys Gly Ala Gly Gly Ala
            740                 745                 750

Cys Ala Gly Cys Gly Cys Cys Ala Thr Cys Thr Ala Thr Thr Ala Cys
        755                 760                 765

Thr Gly Thr Gly Cys Cys Ala Gly Ala Thr Cys Cys Ala Gly Gly Gly
    770                 775                 780

Ala Cys Gly Cys Cys Ala Thr Gly Gly Ala Cys Thr Ala Thr Thr Gly
785                 790                 795                 800

Gly Gly Gly Cys Cys Ala Gly Gly Gly Ala Ala Cys Ala Ala Gly Cys
                805                 810                 815

Gly Thr Gly Ala Cys Cys Gly Thr Gly Thr Cys Cys Thr Cys Thr
            820                 825                 830
```

<210> SEQ ID NO 51
<211> LENGTH: 852
<212> TYPE: PRT
<213> ORGANISM: Artificial Sequence
<220> FEATURE:
<223> OTHER INFORMATION: Vb13.2HL scFv

<400> SEQUENCE: 51

```
Ala Thr Gly Gly Gly Cys Thr Gly Gly Thr Cys Cys Thr Gly Gly Ala
1               5                   10                  15

Thr Cys Thr Thr Cys Cys Thr Gly Thr Thr Thr Cys Thr Gly Cys Thr
            20                  25                  30

Gly Thr Cys Thr Gly Gly Cys Ala Cys Ala Gly Cys Cys Gly Gly Cys
        35                  40                  45

Gly Thr Gly Cys Ala Cys Thr Cys Thr Gly Ala Ala Gly Thr Thr Cys
    50                  55                  60

Ala Gly Cys Thr Gly Cys Ala Gly Cys Ala Gly Thr Cys Thr Gly Gly
65                  70                  75                  80

Cys Cys Cys Cys Gly Ala Gly Cys Thr Thr Gly Thr Gly Ala Ala Ala
                85                  90                  95

Cys Cys Thr Gly Gly Cys Gly Cys Cys Thr Cys Thr Gly Thr Gly Ala
            100                 105                 110

Ala Gly Ala Thr Gly Ala Gly Cys Thr Gly Cys Ala Ala Cys Gly Cys
        115                 120                 125

Cys Ala Gly Cys Gly Gly Cys Thr Ala Cys Ala Cys Cys Thr Thr Cys
    130                 135                 140

Ala Cys Cys Gly Ala Cys Thr Ala Cys Thr Ala Cys Ala Thr Cys Cys
145                 150                 155                 160

Ala Cys Thr Gly Gly Cys Thr Gly Ala Ala Gly Cys Ala Gly Cys Gly
                165                 170                 175

Gly Cys Ala Cys Gly Gly Cys Ala Ala Ala Gly Gly Cys Cys Thr Gly
            180                 185                 190

Gly Ala Ala Thr Gly Gly Ala Thr Cys Gly Gly Cys Ala Thr Cys Gly
        195                 200                 205

Thr Gly Ala Ala Cys Ala Cys Cys Ala Ala Cys Ala Ala Cys Gly Gly
    210                 215                 220

Cys Gly Ala Cys Ala Cys Cys Ala Ala Cys Thr Ala Cys Ala Ala Cys
225                 230                 235                 240

Cys Ala Gly Cys Gly Gly Thr Thr Cys Ala Ala Gly Gly Gly Cys Ala
                245                 250                 255
```

```
Ala Ala Gly Cys Cys Ala Gly Cys Cys Thr Gly Ala Cys Cys Gly Thr
            260                 265                 270

Gly Gly Ala Thr Ala Ala Gly Ala Gly Cys Ala Gly Cys Ala Gly Cys
        275                 280                 285

Ala Cys Cys Gly Cys Cys Thr Ala Cys Ala Thr Gly Gly Ala Ala Cys
    290                 295                 300

Thr Gly Ala Ala Cys Thr Cys Cys Cys Thr Gly Ala Cys Cys Ala Gly
305                 310                 315                 320

Cys Gly Ala Gly Gly Ala Cys Ala Gly Cys Gly Cys Cys Gly Thr Gly
                325                 330                 335

Thr Thr Cys Thr Ala Thr Thr Gly Thr Gly Cys Cys Ala Gly Gly Gly
            340                 345                 350

Cys Thr Cys Thr Gly Thr Ala Cys Ala Cys Cys Gly Gly Cys Ala Gly
        355                 360                 365

Cys Thr Ala Thr Thr Gly Gly Thr Thr Cys Gly Cys Cys Thr Ala Thr
    370                 375                 380

Thr Gly Gly Gly Gly Cys Cys Ala Gly Gly Gly Cys Ala Cys Cys Cys
385                 390                 395                 400

Thr Gly Gly Thr Thr Ala Cys Ala Gly Thr Thr Thr Cys Thr Gly Cys
                405                 410                 415

Ala Gly Gly Cys Gly Gly Cys Gly Gly Ala Gly Gly Ala Thr Cys Thr
            420                 425                 430

Gly Gly Cys Gly Gly Ala Gly Gly Thr Gly Gly Ala Ala Gly Cys Gly
        435                 440                 445

Gly Ala Gly Gly Cys Gly Gly Thr Gly Gly Cys Thr Cys Thr Ala Thr
    450                 455                 460

Gly Gly Ala Thr Thr Thr Cys Cys Ala Cys Gly Thr Gly Cys Ala Gly
465                 470                 475                 480

Ala Thr Cys Thr Thr Cys Ala Gly Cys Thr Thr Cys Ala Thr Gly Cys
                485                 490                 495

Thr Gly Ala Thr Cys Thr Cys Cys Gly Thr Gly Ala Cys Cys Gly Thr
            500                 505                 510

Gly Ala Thr Gly Cys Thr Gly Thr Cys Cys Ala Gly Cys Gly Gly Ala
        515                 520                 525

Gly Ala Gly Ala Thr Cys Gly Thr Gly Cys Thr Gly Ala Cys Ala Cys
    530                 535                 540

Ala Gly Thr Cys Thr Cys Cys Ala Gly Cys Cys Gly Thr Gly Ala Thr
545                 550                 555                 560

Gly Gly Cys Thr Gly Cys Thr Thr Cys Cys Cys Cys Thr Gly Gly Cys
                565                 570                 575

Gly Ala Gly Ala Ala Ala Gly Thr Gly Ala Cys Cys Ala Thr Cys Ala
            580                 585                 590

Cys Ala Thr Gly Thr Ala Gly Cys Gly Cys Cys Ala Gly Cys Ala Gly
        595                 600                 605

Cys Thr Cys Cys Ala Thr Cys Ala Gly Cys Thr Cys Cys Ala Cys Cys
    610                 615                 620

Ala Ala Cys Cys Thr Gly Cys Ala Cys Thr Gly Gly Thr Ala Thr Cys
625                 630                 635                 640

Ala Gly Cys Ala Gly Ala Ala Gly Thr Cys Cys Gly Ala Gly Ala Cys
                645                 650                 655

Ala Ala Gly Cys Cys Cys Cys Ala Ala Gly Cys Cys Thr Thr Gly Gly
            660                 665                 670
```

```
Ala Thr Cys Thr Ala Cys Gly Gly Cys Ala Cys Cys Ala Gly Cys Ala
        675                 680                 685

Ala Thr Cys Thr Gly Gly Cys Cys Ala Gly Cys Gly Gly Ala Gly Thr
    690                 695                 700

Gly Cys Cys Thr Gly Thr Cys Ala Gly Ala Thr Thr Thr Thr Cys Thr
705                 710                 715                 720

Gly Gly Cys Ala Gly Cys Gly Gly Cys Thr Cys Thr Gly Gly Cys Ala
                725                 730                 735

Cys Cys Ala Gly Cys Thr Ala Cys Ala Gly Cys Cys Thr Gly Ala Cys
            740                 745                 750

Ala Ala Thr Cys Ala Gly Cys Ala Gly Cys Ala Thr Cys Gly Ala Gly
        755                 760                 765

Gly Cys Cys Gly Ala Ala Gly Ala Thr Gly Cys Cys Gly Cys Cys Ala
    770                 775                 780

Cys Cys Thr Ala Cys Thr Ala Cys Thr Gly Cys Cys Ala Gly Cys Ala
785                 790                 795                 800

Gly Thr Gly Gly Thr Cys Cys Ala Gly Ala Thr Ala Thr Cys Cys Cys
                805                 810                 815

Cys Thr Gly Ala Cys Ala Thr Thr Thr Gly Gly Cys Thr Cys Cys Gly
            820                 825                 830

Gly Cys Ala Cys Cys Ala Ala Gly Cys Thr Gly Gly Ala Ala Ala Thr
        835                 840                 845

Cys Ala Thr Thr
    850
```

<210> SEQ ID NO 52
<211> LENGTH: 852
<212> TYPE: PRT
<213> ORGANISM: Artificial Sequence
<220> FEATURE:
<223> OTHER INFORMATION: Vb13.2LH scFv

<400> SEQUENCE: 52

```
Ala Thr Gly Gly Ala Cys Thr Thr Cys Cys Ala Cys Gly Thr Gly Cys
1               5                   10                  15

Ala Gly Ala Thr Cys Thr Thr Cys Ala Gly Cys Thr Thr Cys Ala Thr
            20                  25                  30

Gly Cys Thr Gly Ala Thr Cys Thr Cys Cys Gly Thr Gly Ala Cys Cys
        35                  40                  45

Gly Thr Gly Ala Thr Gly Cys Thr Gly Ala Gly Cys Ala Gly Cys Gly
    50                  55                  60

Gly Ala Gly Ala Gly Ala Thr Cys Gly Thr Gly Cys Thr Gly Ala Cys
65                  70                  75                  80

Ala Cys Ala Gly Thr Cys Thr Cys Cys Ala Gly Cys Cys Gly Thr Gly
                85                  90                  95

Ala Thr Gly Gly Cys Thr Gly Cys Thr Thr Cys Cys Cys Cys Thr Gly
            100                 105                 110

Gly Cys Gly Ala Gly Ala Ala Ala Gly Thr Gly Ala Cys Cys Ala Thr
        115                 120                 125

Cys Ala Cys Ala Thr Gly Thr Ala Gly Cys Gly Cys Cys Ala Gly Cys
    130                 135                 140

Ala Gly Cys Ala Gly Cys Ala Thr Cys Ala Gly Cys Ala Gly Cys Ala
145                 150                 155                 160

Cys Cys Ala Ala Cys Cys Thr Gly Cys Ala Cys Thr Gly Gly Thr Ala
                165                 170                 175
```

```
Thr Cys Ala Gly Cys Ala Gly Ala Ala Gly Thr Cys Cys Gly Ala Gly
            180                 185                 190

Ala Cys Ala Ala Gly Cys Cys Cys Cys Ala Ala Gly Cys Cys Thr Thr
        195                 200                 205

Gly Gly Ala Thr Cys Thr Ala Cys Gly Gly Cys Ala Cys Cys Ala Gly
    210                 215                 220

Cys Ala Ala Thr Cys Thr Gly Gly Cys Cys Ala Gly Cys Gly Gly Ala
225                 230                 235                 240

Gly Thr Gly Cys Cys Thr Gly Thr Cys Ala Gly Ala Thr Thr Thr Thr
                245                 250                 255

Cys Thr Gly Gly Cys Ala Gly Cys Gly Gly Cys Thr Cys Thr Gly Gly
            260                 265                 270

Cys Ala Cys Cys Ala Gly Cys Thr Ala Cys Ala Gly Cys Cys Thr Gly
        275                 280                 285

Ala Cys Ala Ala Thr Cys Ala Gly Cys Thr Cys Cys Ala Thr Cys Gly
    290                 295                 300

Ala Gly Gly Cys Cys Gly Ala Ala Gly Ala Thr Gly Cys Cys Gly Cys
305                 310                 315                 320

Cys Ala Cys Cys Thr Ala Cys Thr Ala Cys Thr Gly Cys Cys Ala Gly
                325                 330                 335

Cys Ala Gly Thr Gly Gly Thr Cys Cys Ala Gly Ala Thr Ala Thr Cys
            340                 345                 350

Cys Cys Cys Thr Gly Ala Cys Ala Thr Thr Cys Gly Gly Cys Ala Gly
        355                 360                 365

Cys Gly Gly Cys Ala Cys Cys Ala Ala Gly Cys Thr Gly Gly Ala Ala
    370                 375                 380

Ala Thr Cys Ala Thr Cys Gly Gly Ala Gly Gly Cys Gly Gly Ala Gly
385                 390                 395                 400

Gly Ala Thr Cys Thr Gly Gly Thr Gly Gly Cys Gly Gly Ala Gly Gly
                405                 410                 415

Ala Ala Gly Cys Gly Gly Thr Gly Gly Cys Gly Gly Cys Gly Gly Ala
            420                 425                 430

Thr Cys Thr Ala Thr Gly Gly Gly Ala Thr Gly Gly Thr Cys Cys Thr
        435                 440                 445

Gly Gly Ala Thr Cys Thr Thr Cys Cys Thr Gly Thr Thr Cys Cys Thr
    450                 455                 460

Gly Cys Thr Gly Thr Cys Thr Gly Gly Ala Ala Cys Ala Gly Cys Cys
465                 470                 475                 480

Gly Gly Cys Gly Thr Gly Cys Ala Cys Thr Cys Thr Gly Ala Ala Gly
                485                 490                 495

Thr Thr Cys Ala Gly Cys Thr Gly Cys Ala Gly Cys Ala Gly Thr Cys
            500                 505                 510

Thr Gly Gly Cys Cys Cys Cys Gly Ala Gly Cys Thr Thr Gly Thr Gly
        515                 520                 525

Ala Ala Ala Cys Cys Thr Gly Gly Cys Gly Cys Cys Thr Cys Thr Gly
    530                 535                 540

Thr Gly Ala Ala Gly Ala Thr Gly Ala Gly Cys Thr Gly Cys Ala Ala
545                 550                 555                 560

Cys Gly Cys Cys Ala Gly Cys Gly Gly Cys Thr Ala Cys Ala Cys Cys
                565                 570                 575

Thr Thr Cys Ala Cys Cys Gly Ala Cys Thr Ala Cys Thr Ala Cys Ala
            580                 585                 590

Thr Cys Cys Ala Cys Thr Gly Gly Cys Thr Gly Ala Ala Gly Cys Ala
```

```
        595                 600                 605

Gly Ala Gly Ala Cys Ala Cys Gly Gly Cys Ala Ala Ala Gly Gly Cys
    610                 615                 620

Cys Thr Gly Gly Ala Ala Thr Gly Gly Ala Thr Cys Gly Gly Cys Ala
625                 630                 635                 640

Thr Cys Gly Thr Gly Ala Ala Cys Ala Cys Cys Ala Ala Cys Ala Ala
                645                 650                 655

Cys Gly Gly Cys Gly Ala Cys Ala Cys Cys Ala Ala Cys Thr Ala Cys
            660                 665                 670

Ala Ala Cys Cys Ala Gly Cys Gly Gly Thr Thr Cys Ala Ala Gly Gly
        675                 680                 685

Gly Cys Ala Ala Ala Gly Cys Cys Ala Gly Cys Cys Thr Gly Ala Cys
    690                 695                 700

Cys Gly Thr Gly Gly Ala Thr Ala Ala Gly Ala Gly Cys Ala Gly Cys
705                 710                 715                 720

Thr Cys Cys Ala Cys Cys Gly Cys Cys Thr Ala Cys Ala Thr Gly Gly
                725                 730                 735

Ala Ala Cys Thr Gly Ala Ala Cys Thr Cys Cys Cys Thr Gly Ala Cys
            740                 745                 750

Cys Ala Gly Cys Gly Ala Gly Gly Ala Cys Ala Gly Cys Gly Cys Cys
        755                 760                 765

Gly Thr Gly Thr Thr Cys Thr Ala Thr Thr Gly Thr Gly Cys Cys Ala
    770                 775                 780

Gly Gly Gly Cys Thr Cys Thr Gly Thr Ala Cys Ala Cys Cys Gly Gly
785                 790                 795                 800

Cys Ala Gly Cys Thr Ala Thr Thr Gly Gly Thr Thr Cys Gly Cys Cys
                805                 810                 815

Thr Ala Thr Thr Gly Gly Gly Gly Cys Cys Ala Gly Gly Gly Cys Ala
            820                 825                 830

Cys Cys Cys Thr Gly Gly Thr Thr Ala Cys Ala Gly Thr Thr Thr Cys
        835                 840                 845

Thr Gly Cys Thr
    850
```

```
<210> SEQ ID NO 53
<211> LENGTH: 849
<212> TYPE: PRT
<213> ORGANISM: Artificial Sequence
<220> FEATURE:
<223> OTHER INFORMATION: Vb13.3HL scFv

<400> SEQUENCE: 53

Ala Thr Gly Gly Gly Cys Thr Gly Gly Thr Cys Cys Thr Gly Cys Ala
1               5                   10                  15

Thr Cys Ala Thr Cys Cys Thr Gly Ala Thr Thr Cys Thr Gly Gly Thr
            20                  25                  30

Gly Gly Cys Thr Gly Cys Cys Gly Cys Thr Ala Cys Ala Gly Gly Cys
        35                  40                  45

Gly Thr Gly Cys Ala Cys Thr Cys Thr Cys Ala Gly Gly Thr Thr Cys
    50                  55                  60

Ala Gly Cys Thr Thr Cys Ala Gly Cys Ala Gly Cys Cys Thr Gly Gly
65                  70                  75                  80

Cys Gly Cys Cys Gly Ala Gly Cys Thr Thr Gly Thr Gly Ala Ala Ala
                85                  90                  95

Cys Cys Thr Gly Gly Cys Gly Cys Cys Thr Cys Thr Gly Thr Gly Ala
```

```
            100                 105                 110

Ala Gly Ala Thr Gly Ala Gly Cys Thr Gly Cys Ala Ala Gly Gly Cys
        115                 120                 125

Cys Ala Gly Cys Gly Gly Cys Thr Ala Cys Ala Cys Cys Thr Thr Cys
    130                 135                 140

Ala Cys Cys Ala Gly Cys Thr Ala Cys Thr Gly Gly Ala Thr Cys Ala
145                 150                 155                 160

Cys Cys Thr Gly Gly Gly Thr Cys Ala Ala Gly Cys Ala Gly Ala Gly
                165                 170                 175

Gly Cys Cys Thr Gly Gly Ala Cys Ala Gly Gly Gly Ala Cys Thr Cys
            180                 185                 190

Gly Ala Gly Thr Gly Gly Ala Thr Cys Gly Gly Cys Gly Ala Thr Ala
        195                 200                 205

Thr Cys Thr Ala Thr Cys Cys Thr Gly Gly Cys Ala Gly Cys Gly Gly
    210                 215                 220

Cys Ala Gly Cys Ala Thr Cys Ala Ala Cys Thr Ala Cys Ala Ala Cys
225                 230                 235                 240

Gly Ala Gly Ala Ala Gly Thr Thr Cys Ala Ala Cys Ala Ala Cys Ala
                245                 250                 255

Ala Gly Gly Cys Cys Ala Cys Ala Cys Thr Gly Ala Cys Cys Gly Thr
            260                 265                 270

Gly Gly Ala Cys Ala Cys Cys Ala Gly Cys Ala Gly Cys Ala Gly Cys
        275                 280                 285

Ala Cys Ala Gly Cys Cys Thr Ala Cys Ala Thr Gly Cys Ala Gly Cys
    290                 295                 300

Thr Gly Ala Gly Cys Ala Gly Cys Cys Thr Gly Ala Cys Cys Ala Gly
305                 310                 315                 320

Cys Gly Ala Ala Gly Ala Thr Ala Gly Cys Gly Cys Cys Gly Thr Gly
                325                 330                 335

Thr Ala Cys Thr Ala Cys Thr Gly Cys Gly Cys Cys Ala Gly Ala Cys
            340                 345                 350

Gly Gly Gly Ala Cys Thr Ala Cys Thr Ala Cys Ala Gly Cys Cys Thr
        355                 360                 365

Gly Thr Ala Cys Thr Ala Cys Thr Ala Thr Gly Cys Cys Cys Thr Gly
    370                 375                 380

Gly Ala Cys Thr Ala Cys Thr Gly Gly Gly Gly Cys Cys Ala Gly Gly
385                 390                 395                 400

Gly Cys Ala Cys Ala Ala Gly Cys Gly Thr Gly Ala Cys Ala Gly Thr
                405                 410                 415

Thr Thr Cys Thr Thr Cys Thr Gly Gly Cys Gly Gly Cys Gly Gly Ala
            420                 425                 430

Gly Gly Ala Thr Cys Thr Gly Gly Cys Gly Gly Ala Gly Gly Thr Gly
        435                 440                 445

Gly Ala Ala Gly Cys Gly Gly Ala Gly Gly Cys Gly Gly Thr Gly Gly
    450                 455                 460

Ala Thr Cys Thr Ala Thr Gly Thr Cys Thr Gly Thr Gly Cys Cys Thr
465                 470                 475                 480

Ala Cys Ala Cys Ala Gly Gly Thr Gly Cys Thr Gly Gly Gly Cys Cys
                485                 490                 495

Thr Gly Cys Thr Gly Cys Thr Thr Cys Thr Gly Thr Gly Gly Thr Thr
            500                 505                 510

Gly Ala Cys Ala Gly Gly Cys Gly Cys Cys Ala Gly Ala Thr Gly Cys
        515                 520                 525
```

```
Gly Ala Cys Ala Thr Cys Cys Ala Gly Ala Thr Gly Ala Cys Ala Cys
    530                 535                 540

Ala Gly Ala Gly Cys Cys Cys Thr Gly Cys Cys Ala Gly Cys Cys Thr
545                 550                 555                 560

Gly Ala Gly Thr Gly Cys Cys Thr Cys Thr Gly Thr Gly Gly Gly Ala
                565                 570                 575

Gly Ala Gly Ala Cys Ala Gly Thr Gly Ala Cys Cys Ala Thr Gly Ala
            580                 585                 590

Cys Cys Thr Gly Thr Cys Gly Gly Gly Cys Cys Ala Gly Cys Gly Ala
        595                 600                 605

Gly Ala Ala Cys Ala Thr Cys Thr Ala Cys Ala Gly Cys Ala Ala Cys
    610                 615                 620

Cys Thr Gly Gly Cys Cys Thr Gly Gly Thr Ala Thr Cys Ala Gly Cys
625                 630                 635                 640

Ala Gly Ala Ala Gly Cys Ala Gly Gly Gly Cys Ala Ala Gly Thr Cys
                645                 650                 655

Thr Cys Cys Thr Cys Ala Gly Cys Thr Gly Cys Thr Gly Gly Thr Cys
            660                 665                 670

Thr Ala Cys Gly Cys Cys Gly Cys Cys Ala Cys Cys Ala Ala Thr Cys
        675                 680                 685

Thr Thr Gly Cys Thr Gly Ala Thr Gly Gly Cys Gly Thr Gly Cys Cys
    690                 695                 700

Cys Ala Gly Cys Ala Gly Ala Thr Thr Cys Ala Gly Cys Gly Thr Gly
705                 710                 715                 720

Thr Cys Cys Gly Gly Ala Thr Cys Thr Gly Gly Cys Ala Cys Cys Cys
                725                 730                 735

Ala Cys Thr Thr Cys Ala Gly Cys Cys Thr Gly Ala Ala Gly Ala Thr
            740                 745                 750

Cys Ala Ala Cys Ala Gly Cys Cys Thr Gly Cys Ala Gly Cys Cys Ala
        755                 760                 765

Gly Ala Gly Gly Ala Cys Thr Thr Cys Gly Gly Cys Ala Gly Cys Thr
    770                 775                 780

Ala Cys Thr Ala Cys Thr Gly Cys Cys Ala Gly Cys Ala Cys Thr Thr
785                 790                 795                 800

Cys Thr Ala Cys Gly Gly Cys Ala Cys Cys Cys Cys Thr Thr Ala Cys
                805                 810                 815

Ala Cys Cys Thr Thr Thr Gly Gly Cys Gly Gly Ala Gly Gly Cys Ala
            820                 825                 830

Cys Cys Ala Ala Gly Cys Thr Gly Gly Ala Ala Ala Thr Cys Ala Ala
        835                 840                 845

Gly
```

<210> SEQ ID NO 54
<211> LENGTH: 849
<212> TYPE: PRT
<213> ORGANISM: Artificial Sequence
<220> FEATURE:
<223> OTHER INFORMATION: Vb13.3LH scFv

<400> SEQUENCE: 54

```
Ala Thr Gly Ala Gly Cys Gly Thr Gly Cys Cys Ala Ala Cys Ala Cys
1               5                   10                  15

Ala Gly Gly Thr Thr Cys Thr Gly Gly Gly Ala Cys Thr Gly Cys Thr
            20                  25                  30
```

Gly Cys Thr Gly Cys Thr Gly Thr Gly Gly Cys Thr Gly Ala Cys Ala
35 40 45

Gly Gly Cys Gly Cys Cys Ala Gly Ala Thr Gly Cys Gly Ala Cys Ala
50 55 60

Thr Cys Cys Ala Gly Ala Thr Gly Ala Cys Ala Cys Ala Gly Ala Gly
65 70 75 80

Cys Cys Cys Thr Gly Cys Cys Ala Gly Cys Cys Thr Gly Thr Cys Thr
85 90 95

Gly Cys Cys Thr Cys Thr Gly Thr Gly Gly Gly Ala Gly Ala Gly Ala
100 105 110

Cys Ala Gly Thr Gly Ala Cys Cys Ala Thr Gly Ala Cys Cys Thr Gly
115 120 125

Thr Cys Gly Gly Gly Cys Cys Ala Gly Cys Gly Ala Gly Ala Ala Cys
130 135 140

Ala Thr Cys Thr Ala Cys Ala Gly Cys Ala Ala Cys Cys Thr Gly Gly
145 150 155 160

Cys Cys Thr Gly Gly Thr Ala Thr Cys Ala Gly Cys Ala Gly Ala Ala
165 170 175

Gly Cys Ala Gly Gly Gly Cys Ala Ala Gly Thr Cys Thr Cys Cys Thr
180 185 190

Cys Ala Gly Cys Thr Gly Cys Thr Gly Gly Thr Gly Thr Ala Cys Gly
195 200 205

Cys Cys Gly Cys Cys Ala Cys Cys Ala Ala Thr Cys Thr Thr Gly Cys
210 215 220

Thr Gly Ala Thr Gly Gly Cys Gly Thr Gly Cys Cys Cys Ala Gly Cys
225 230 235 240

Ala Gly Ala Thr Thr Cys Ala Gly Cys Gly Thr Gly Thr Cys Cys Gly
245 250 255

Gly Ala Thr Cys Thr Gly Gly Cys Ala Cys Cys Cys Ala Cys Thr Thr
260 265 270

Cys Ala Gly Cys Cys Thr Gly Ala Ala Gly Ala Thr Cys Ala Ala Cys
275 280 285

Ala Gly Cys Cys Thr Gly Cys Ala Gly Cys Cys Thr Gly Ala Gly Gly
290 295 300

Ala Cys Thr Thr Cys Gly Gly Cys Ala Gly Cys Thr Ala Cys Thr Ala
305 310 315 320

Cys Thr Gly Cys Cys Ala Gly Cys Ala Cys Thr Thr Cys Thr Ala Cys
325 330 335

Gly Gly Cys Ala Cys Cys Cys Cys Thr Thr Ala Cys Ala Cys Cys Thr
340 345 350

Thr Thr Gly Gly Cys Gly Gly Ala Gly Gly Cys Ala Cys Cys Ala Ala
355 360 365

Gly Cys Thr Gly Gly Ala Ala Ala Thr Cys Ala Ala Ala Gly Gly Cys
370 375 380

Gly Gly Cys Gly Gly Ala Gly Gly Ala Ala Gly Cys Gly Gly Ala Gly
385 390 395 400

Gly Cys Gly Gly Ala Gly Gly Ala Thr Cys Thr Gly Gly Thr Gly Gly
405 410 415

Thr Gly Gly Thr Gly Gly Ala Thr Cys Thr Ala Thr Gly Gly Gly Cys
420 425 430

Thr Gly Gly Thr Cys Cys Thr Gly Cys Ala Thr Cys Ala Thr Cys Cys
435 440 445

Thr Gly Ala Thr Cys Cys Thr Gly Gly Thr Gly Gly Cys Thr Gly Cys

```
    450                 455                 460

Thr Gly Cys Thr Ala Cys Ala Gly Gly Cys Gly Thr Gly Cys Ala Cys
465                 470                 475                 480

Thr Cys Thr Cys Ala Gly Gly Thr Thr Cys Ala Gly Cys Thr Gly Cys
                485                 490                 495

Ala Ala Cys Ala Gly Cys Cys Ala Gly Gly Cys Gly Cys Cys Gly Ala
            500                 505                 510

Gly Cys Thr Thr Gly Thr Gly Ala Ala Ala Cys Cys Thr Gly Gly Cys
        515                 520                 525

Gly Cys Cys Thr Cys Thr Gly Thr Gly Ala Ala Gly Ala Thr Gly Ala
    530                 535                 540

Gly Cys Thr Gly Cys Ala Ala Gly Gly Cys Cys Ala Gly Cys Gly Gly
545                 550                 555                 560

Cys Thr Ala Cys Ala Cys Cys Thr Thr Cys Ala Cys Cys Ala Gly Cys
                565                 570                 575

Thr Ala Cys Thr Gly Gly Ala Thr Cys Ala Cys Cys Thr Gly Gly Gly
            580                 585                 590

Thr Cys Ala Ala Gly Cys Ala Gly Ala Gly Gly Cys Cys Thr Gly Gly
        595                 600                 605

Ala Cys Ala Gly Gly Gly Ala Cys Thr Cys Gly Ala Gly Thr Gly Gly
    610                 615                 620

Ala Thr Cys Gly Gly Cys Gly Ala Thr Ala Thr Cys Thr Ala Thr Cys
625                 630                 635                 640

Cys Thr Gly Gly Cys Ala Gly Cys Gly Gly Cys Ala Gly Cys Ala Thr
                645                 650                 655

Cys Ala Ala Cys Thr Ala Cys Ala Ala Cys Gly Ala Gly Ala Ala Gly
            660                 665                 670

Thr Thr Cys Ala Ala Cys Ala Ala Cys Ala Ala Gly Gly Cys Cys Ala
        675                 680                 685

Cys Ala Cys Thr Gly Ala Cys Cys Gly Thr Gly Gly Ala Cys Ala Cys
    690                 695                 700

Cys Ala Gly Cys Thr Cys Thr Ala Gly Cys Ala Cys Ala Gly Cys Cys
705                 710                 715                 720

Thr Ala Cys Ala Thr Gly Cys Ala Gly Cys Thr Gly Ala Gly Cys Ala
                725                 730                 735

Gly Cys Cys Thr Gly Ala Cys Cys Ala Gly Cys Gly Ala Ala Gly Ala
            740                 745                 750

Thr Ala Gly Cys Gly Cys Cys Gly Thr Gly Thr Ala Cys Thr Ala Cys
        755                 760                 765

Thr Gly Cys Gly Cys Cys Ala Gly Ala Cys Gly Gly Gly Ala Cys Thr
    770                 775                 780

Ala Cys Thr Ala Cys Ala Gly Cys Cys Thr Gly Thr Ala Cys Thr Ala
785                 790                 795                 800

Cys Thr Ala Thr Gly Cys Cys Cys Thr Gly Gly Ala Cys Thr Ala Cys
                805                 810                 815

Thr Gly Gly Gly Gly Cys Cys Ala Gly Gly Gly Cys Ala Cys Ala Ala
            820                 825                 830

Gly Cys Gly Thr Gly Ala Cys Ala Gly Thr Cys Thr Cys Thr Thr Cys
        835                 840                 845

Thr

<210> SEQ ID NO 55
<211> LENGTH: 831
```

<212> TYPE: PRT
<213> ORGANISM: Artificial Sequence
<220> FEATURE:
<223> OTHER INFORMATION: Vb22HL scFv

<400> SEQUENCE: 55

```
Ala Thr Gly Gly Ala Cys Thr Thr Cys Gly Gly Cys Cys Thr Gly Ala
1               5                   10                  15

Thr Cys Thr Thr Cys Thr Thr Cys Ala Thr Cys Gly Thr Gly Gly Cys
            20                  25                  30

Cys Cys Thr Gly Cys Thr Gly Ala Ala Ala Gly Gly Cys Gly Thr Gly
        35                  40                  45

Cys Ala Gly Thr Gly Cys Gly Ala Ala Gly Thr Gly Ala Ala Gly Cys
    50                  55                  60

Thr Gly Cys Thr Gly Gly Ala Ala Thr Cys Thr Gly Gly Cys Gly Gly
65                  70                  75                  80

Ala Gly Gly Ala Cys Thr Gly Gly Thr Thr Cys Ala Gly Cys Cys Thr
                85                  90                  95

Gly Gly Cys Gly Gly Ala Thr Cys Thr Cys Thr Gly Ala Ala Gly Cys
            100                 105                 110

Thr Gly Thr Cys Thr Thr Gly Thr Gly Cys Cys Gly Cys Cys Ala Gly
        115                 120                 125

Cys Gly Gly Cys Thr Thr Cys Gly Ala Cys Thr Thr Cys Ala Gly Cys
    130                 135                 140

Cys Gly Gly Thr Ala Cys Thr Gly Gly Ala Thr Gly Ala Ala Cys Thr
145                 150                 155                 160

Gly Gly Gly Thr Cys Cys Gly Ala Cys Ala Gly Gly Cys Cys Cys Cys
                165                 170                 175

Thr Gly Gly Cys Ala Ala Ala Gly Gly Cys Cys Thr Gly Gly Ala Ala
            180                 185                 190

Thr Gly Gly Ala Thr Cys Gly Gly Cys Gly Ala Gly Ala Thr Cys Ala
        195                 200                 205

Ala Cys Ala Gly Cys Gly Ala Cys Ala Gly Cys Ala Ala Cys Ala Cys
    210                 215                 220

Cys Ala Thr Cys Ala Ala Cys Thr Ala Cys Ala Cys Cys Cys Cys Thr
225                 230                 235                 240

Ala Gly Cys Cys Thr Gly Ala Ala Gly Gly Ala Cys Ala Ala Gly Thr
                245                 250                 255

Thr Cys Ala Thr Cys Ala Thr Cys Ala Gly Cys Cys Gly Gly Gly Ala
            260                 265                 270

Cys Ala Ala Cys Gly Cys Cys Ala Ala Gly Ala Ala Cys Ala Cys Cys
        275                 280                 285

Cys Thr Gly Thr Ala Cys Cys Thr Gly Cys Ala Gly Ala Thr Gly Ala
    290                 295                 300

Ala Cys Ala Ala Ala Gly Thr Gly Cys Gly Gly Ala Gly Cys Gly Ala
305                 310                 315                 320

Gly Gly Ala Cys Ala Cys Ala Gly Cys Cys Cys Thr Gly Thr Ala Cys
                325                 330                 335

Thr Ala Cys Thr Gly Thr Gly Cys Thr Ala Gly Ala Gly Gly Cys Gly
            340                 345                 350

Gly Cys Cys Thr Gly Cys Thr Gly Ala Gly Ala Gly Ala Thr Gly Thr
        355                 360                 365

Gly Thr Gly Gly Gly Gly Ala Gly Cys Thr Gly Gly Ala Ala Cys Cys
    370                 375                 380
```

```
Ala Cys Cys Gly Thr Gly Ala Cys Ala Gly Thr Thr Thr Cys Thr Ala
385                 390                 395                 400

Gly Cys Gly Gly Ala Gly Gly Cys Gly Gly Ala Gly Gly Thr Thr Cys
                405                 410                 415

Thr Gly Gly Cys Gly Gly Cys Gly Gly Ala Gly Gly Ala Ala Gly Thr
            420                 425                 430

Gly Gly Thr Gly Gly Cys Gly Gly Ala Gly Gly Cys Thr Cys Thr Ala
        435                 440                 445

Thr Gly Gly Cys Thr Thr Gly Gly Ala Thr Cys Thr Cys Cys Cys Thr
    450                 455                 460

Gly Ala Thr Cys Cys Thr Gly Thr Cys Thr Cys Thr Gly Cys Thr Gly
465                 470                 475                 480

Gly Cys Cys Cys Thr Thr Ala Gly Cys Thr Cys Thr Gly Gly Cys Gly
                485                 490                 495

Cys Cys Ala Thr Thr Thr Cys Thr Cys Ala Gly Gly Cys Cys Gly Thr
            500                 505                 510

Gly Gly Thr Cys Ala Cys Ala Cys Ala Ala Gly Ala Gly Ala Gly Cys
        515                 520                 525

Gly Cys Cys Cys Thr Gly Ala Cys Ala Ala Cys Ala Ala Gly Cys Cys
    530                 535                 540

Cys Thr Gly Gly Cys Gly Ala Gly Ala Cys Ala Gly Thr Gly Ala Cys
545                 550                 555                 560

Cys Cys Thr Gly Ala Cys Cys Thr Gly Thr Ala Gly Ala Thr Cys Thr
                565                 570                 575

Thr Cys Thr Ala Cys Ala Gly Gly Cys Gly Cys Cys Gly Thr Gly Ala
            580                 585                 590

Cys Cys Ala Cys Cys Ala Gly Cys Ala Ala Cys Thr Ala Cys Gly Cys
        595                 600                 605

Cys Ala Ala Thr Thr Gly Gly Gly Thr Gly Cys Ala Ala Gly Ala Gly
    610                 615                 620

Ala Ala Gly Cys Cys Cys Gly Ala Cys Cys Ala Cys Cys Thr Gly Thr
625                 630                 635                 640

Thr Cys Ala Cys Ala Gly Gly Ala Cys Thr Gly Ala Thr Cys Gly Gly
                645                 650                 655

Cys Gly Gly Cys Ala Cys Cys Ala Ala Cys Ala Ala Thr Ala Gly Ala
            660                 665                 670

Gly Cys Ala Cys Cys Thr Gly Gly Cys Gly Thr Gly Cys Cys Ala Gly
        675                 680                 685

Cys Cys Ala Gly Ala Thr Thr Cys Ala Gly Cys Gly Gly Thr Thr Cys
    690                 695                 700

Thr Cys Thr Gly Ala Thr Cys Gly Gly Ala Gly Ala Cys Ala Gly Ala
705                 710                 715                 720

Gly Cys Cys Gly Cys Ala Cys Thr Gly Ala Cys Ala Ala Thr Cys Ala
                725                 730                 735

Cys Ala Gly Gly Cys Gly Cys Cys Cys Ala Gly Ala Cys Ala Gly Ala
            740                 745                 750

Gly Gly Ala Cys Gly Ala Gly Gly Cys Cys Ala Thr Cys Thr Ala Cys
        755                 760                 765

Thr Thr Thr Thr Gly Cys Gly Cys Cys Cys Thr Gly Thr Gly Gly Thr
    770                 775                 780

Ala Cys Ala Gly Cys Ala Ala Cys Cys Ala Cys Thr Gly Gly Gly Thr
785                 790                 795                 800

Thr Thr Thr Cys Gly Gly Cys Gly Gly Ala Gly Gly Cys Ala Cys Cys
```

805 810 815

Ala Ala Gly Cys Thr Gly Ala Cys Ala Gly Thr Thr Cys Thr Gly
820 825 830

<210> SEQ ID NO 56
<211> LENGTH: 831
<212> TYPE: PRT
<213> ORGANISM: Artificial Sequence
<220> FEATURE:
<223> OTHER INFORMATION: Vb22LH scFv

<400> SEQUENCE: 56

Ala Thr Gly Gly Cys Cys Thr Gly Gly Ala Thr Thr Ala Gly Cys Cys
1 5 10 15

Thr Gly Ala Thr Cys Cys Thr Gly Thr Cys Thr Cys Thr Gly Cys Thr
20 25 30

Gly Gly Cys Cys Cys Thr Gly Thr Cys Thr Ala Gly Cys Gly Gly Ala
35 40 45

Gly Cys Cys Ala Thr Thr Thr Cys Thr Cys Ala Gly Gly Cys Cys Gly
50 55 60

Thr Gly Gly Thr Cys Ala Cys Ala Cys Ala Ala Gly Ala Gly Ala Gly
65 70 75 80

Cys Gly Cys Cys Cys Thr Gly Ala Cys Ala Ala Cys Ala Ala Gly Cys
85 90 95

Cys Cys Thr Gly Gly Cys Gly Ala Gly Ala Cys Ala Gly Thr Gly Ala
100 105 110

Cys Cys Cys Thr Gly Ala Cys Cys Thr Gly Cys Ala Gly Ala Thr Cys
115 120 125

Thr Thr Cys Thr Ala Cys Ala Gly Gly Cys Gly Cys Cys Gly Thr Gly
130 135 140

Ala Cys Cys Ala Cys Cys Ala Gly Cys Ala Ala Cys Thr Ala Cys Gly
145 150 155 160

Cys Cys Ala Ala Thr Thr Gly Gly Gly Thr Gly Cys Ala Ala Gly Ala
165 170 175

Gly Ala Ala Gly Cys Cys Cys Gly Ala Cys Cys Ala Cys Cys Thr Gly
180 185 190

Thr Thr Cys Ala Cys Ala Gly Gly Ala Cys Thr Gly Ala Thr Cys Gly
195 200 205

Gly Cys Gly Gly Cys Ala Cys Cys Ala Ala Cys Ala Ala Thr Ala Gly
210 215 220

Ala Gly Cys Ala Cys Cys Thr Gly Gly Cys Gly Thr Gly Cys Cys Ala
225 230 235 240

Gly Cys Cys Ala Gly Ala Thr Thr Cys Ala Gly Cys Gly Gly Ala Thr
245 250 255

Cys Thr Cys Thr Gly Ala Thr Cys Gly Gly Ala Gly Ala Cys Ala Gly
260 265 270

Ala Gly Cys Cys Gly Cys Ala Cys Thr Gly Ala Cys Ala Ala Thr Cys
275 280 285

Ala Cys Ala Gly Gly Cys Gly Cys Cys Cys Ala Gly Ala Cys Ala Gly
290 295 300

Ala Gly Gly Ala Cys Gly Ala Gly Gly Cys Cys Ala Thr Cys Thr Ala
305 310 315 320

Cys Thr Thr Thr Thr Gly Cys Gly Cys Cys Cys Thr Gly Thr Gly Gly
325 330 335

Thr Ala Cys Ala Gly Cys Ala Ala Cys Cys Ala Cys Thr Gly Gly Gly

```
            340                 345                 350

Thr Thr Thr Thr Cys Gly Gly Cys Gly Gly Ala Gly Gly Cys Ala Cys
        355                 360                 365

Cys Ala Ala Gly Cys Thr Gly Ala Cys Ala Gly Thr Thr Cys Thr Thr
    370                 375                 380

Gly Gly Ala Gly Gly Cys Gly Gly Ala Gly Gly Ala Thr Cys Thr Gly
385                 390                 395                 400

Gly Cys Gly Gly Ala Gly Gly Thr Gly Gly Ala Ala Gly Thr Gly Gly
                405                 410                 415

Cys Gly Gly Ala Gly Gly Cys Gly Gly Cys Thr Cys Thr Ala Thr Gly
            420                 425                 430

Gly Ala Thr Thr Thr Cys Gly Gly Cys Cys Thr Gly Ala Thr Cys Thr
        435                 440                 445

Thr Cys Thr Thr Cys Ala Thr Cys Gly Thr Gly Gly Cys Cys Cys Thr
    450                 455                 460

Gly Cys Thr Gly Ala Ala Ala Gly Gly Cys Gly Thr Gly Cys Ala Gly
465                 470                 475                 480

Thr Gly Cys Gly Ala Ala Gly Thr Gly Ala Ala Gly Cys Thr Gly Cys
                485                 490                 495

Thr Gly Gly Ala Ala Thr Cys Thr Gly Gly Thr Gly Gly Cys Gly Gly
            500                 505                 510

Ala Cys Thr Gly Gly Thr Thr Cys Ala Gly Cys Cys Thr Gly Gly Cys
        515                 520                 525

Gly Gly Cys Thr Cys Thr Cys Thr Gly Ala Ala Ala Cys Thr Gly Thr
    530                 535                 540

Cys Thr Thr Gly Thr Gly Cys Cys Gly Cys Cys Ala Gly Cys Gly Gly
545                 550                 555                 560

Cys Thr Thr Cys Gly Ala Cys Thr Thr Cys Ala Gly Cys Cys Gly Gly
                565                 570                 575

Thr Ala Cys Thr Gly Gly Ala Thr Gly Ala Ala Cys Thr Gly Gly Gly
            580                 585                 590

Thr Cys Cys Gly Ala Cys Ala Gly Gly Cys Cys Cys Cys Thr Gly Gly
        595                 600                 605

Cys Ala Ala Ala Gly Gly Cys Cys Thr Gly Gly Ala Ala Thr Gly Gly
    610                 615                 620

Ala Thr Cys Gly Gly Cys Gly Ala Gly Ala Thr Cys Ala Ala Cys Ala
625                 630                 635                 640

Gly Cys Gly Ala Cys Ala Gly Cys Ala Ala Cys Ala Cys Cys Ala Thr
                645                 650                 655

Cys Ala Ala Cys Thr Ala Cys Ala Cys Cys Cys Cys Thr Ala Gly Cys
            660                 665                 670

Cys Thr Gly Ala Ala Gly Gly Ala Cys Ala Ala Gly Thr Thr Cys Ala
        675                 680                 685

Thr Cys Ala Thr Cys Ala Gly Cys Cys Gly Gly Gly Ala Cys Ala Ala
    690                 695                 700

Cys Gly Cys Cys Ala Ala Gly Ala Ala Cys Ala Cys Ala Cys Thr Gly
705                 710                 715                 720

Thr Ala Cys Cys Thr Cys Cys Ala Gly Ala Thr Gly Ala Ala Cys Ala
                725                 730                 735

Ala Ala Gly Thr Gly Cys Gly Gly Ala Gly Cys Gly Ala Gly Gly Ala
            740                 745                 750

Cys Ala Cys Ala Gly Cys Cys Cys Thr Gly Thr Ala Cys Thr Ala Cys
        755                 760                 765
```

Thr Gly Thr Gly Cys Thr Ala Gly Ala Gly Gly Cys Gly Gly Cys Cys
770 775 780

Thr Gly Cys Thr Gly Ala Gly Ala Gly Ala Thr Gly Thr Gly Thr Gly
785 790 795 800

Gly Gly Gly Ala Gly Cys Thr Gly Gly Ala Ala Cys Cys Ala Cys Cys
805 810 815

Gly Thr Gly Ala Cys Cys Gly Thr Thr Ala Gly Thr Thr Cys Thr
820 825 830

<210> SEQ ID NO 57
<211> LENGTH: 117
<212> TYPE: PRT
<213> ORGANISM: Artificial Sequence
<220> FEATURE:
<223> OTHER INFORMATION: Vb12 VH

<400> SEQUENCE: 57

Glu Val Met Leu Val Glu Ser Gly Gly Gly Leu Val Lys Pro Gly Gly
1 5 10 15

Ser Leu Lys Leu Ser Cys Ala Ala Ser Gly Phe Thr Phe Arg Ser Tyr
20 25 30

Ala Met Ser Trp Val Arg Gln Thr Pro Glu Lys Arg Leu Glu Trp Val
35 40 45

Ala Thr Ile Ser Ser Gly Gly Ser Tyr Thr Asn Tyr Pro Asp Ser Val
50 55 60

Lys Gly Arg Phe Thr Ile Ser Arg Asp Asn Ala Lys Asn Thr Leu Asn
65 70 75 80

Leu Gln Met Asn Ser Leu Arg Ser Glu Asp Thr Ala Met Tyr Tyr Cys
85 90 95

Ala Arg Gly Tyr His Gly Tyr Leu Asp Val Trp Gly Ala Gly Thr Thr
100 105 110

Val Thr Val Ser Ser
115

<210> SEQ ID NO 58
<211> LENGTH: 4
<212> TYPE: PRT
<213> ORGANISM: Artificial Sequence
<220> FEATURE:
<223> OTHER INFORMATION: Vb12 VH HCDR1

<400> SEQUENCE: 58

Ser Tyr Ala Met
1

<210> SEQ ID NO 59
<211> LENGTH: 17
<212> TYPE: PRT
<213> ORGANISM: Artificial Sequence
<220> FEATURE:
<223> OTHER INFORMATION: Vb12 VH HCDR2

<400> SEQUENCE: 59

Thr Ile Ser Ser Gly Gly Ser Tyr Thr Asn Tyr Pro Asp Ser Val Lys
1 5 10 15

Gly

<210> SEQ ID NO 60
<211> LENGTH: 8
<212> TYPE: PRT

<213> ORGANISM: Artificial Sequence
<220> FEATURE:
<223> OTHER INFORMATION: Vb12 VH HCDR3

<400> SEQUENCE: 60

Gly Tyr His Gly Tyr Leu Asp Val
1 5

<210> SEQ ID NO 61
<211> LENGTH: 107
<212> TYPE: PRT
<213> ORGANISM: Artificial Sequence
<220> FEATURE:
<223> OTHER INFORMATION: Vb12 VL

<400> SEQUENCE: 61

Asp Ile Leu Leu Thr Gln Ser Pro Ala Phe Leu Ser Val Ser Pro Gly
1 5 10 15

Glu Arg Val Ser Phe Ser Cys Arg Ala Ser Gln Ser Ile Gly Thr Ser
20 25 30

Ile His Trp Tyr Gln Gln Arg Thr Asn Gly Ser Pro Arg Leu Leu Ile
35 40 45

Lys Tyr Ala Ser Glu Ser Phe Ser Gly Ile Pro Ser Arg Phe Ser Gly
50 55 60

Ser Gly Ser Gly Thr Asp Phe Thr Leu Ser Ile Ser Ser Val Glu Ser
65 70 75 80

Glu Asp Ile Ala Asp Tyr Tyr Cys Gln Gln Ser Tyr Ser Trp Pro Tyr
85 90 95

Thr Phe Gly Gly Gly Thr Lys Leu Glu Ile Lys
100 105

<210> SEQ ID NO 62
<211> LENGTH: 11
<212> TYPE: PRT
<213> ORGANISM: Artificial Sequence
<220> FEATURE:
<223> OTHER INFORMATION: Vb12 VL LCDR1

<400> SEQUENCE: 62

Arg Ala Ser Gln Ser Ile Gly Thr Ser Ile His
1 5 10

<210> SEQ ID NO 63
<211> LENGTH: 6
<212> TYPE: PRT
<213> ORGANISM: Artificial Sequence
<220> FEATURE:
<223> OTHER INFORMATION: Vb12 VL LCDR2

<400> SEQUENCE: 63

Tyr Ala Ser Glu Ser Phe
1 5

<210> SEQ ID NO 64
<211> LENGTH: 9
<212> TYPE: PRT
<213> ORGANISM: Artificial Sequence
<220> FEATURE:
<223> OTHER INFORMATION: Vb12 VL LCDR3

<400> SEQUENCE: 64

Gln Gln Ser Tyr Ser Trp Pro Tyr Thr
1 5

<210> SEQ ID NO 65
<211> LENGTH: 137
<212> TYPE: PRT
<213> ORGANISM: Artificial Sequence
<220> FEATURE:
<223> OTHER INFORMATION: Vb9 VH

<400> SEQUENCE: 65

```
Met Lys Phe Ser Trp Val Ile Phe Phe Leu Met Ala Val Val Thr Gly
1               5                   10                  15

Val Asn Ser Glu Val Gln Leu Gln Gln Ser Val Ala Glu Leu Val Arg
            20                  25                  30

Pro Gly Ala Ser Val Lys Leu Ser Cys Thr Ala Ser Gly Phe Asn Ile
        35                  40                  45

Lys Asn Thr Phe Met His Trp Val Lys Gln Arg Pro Glu Gln Gly Leu
    50                  55                  60

Glu Trp Ile Gly Arg Ile Asp Pro Thr Asn Gly Tyr Thr Lys Phe Ala
65                  70                  75                  80

Pro Lys Phe Gln Gly Lys Ala Thr Leu Thr Ala Val Thr Ser Ser Asn
                85                  90                  95

Thr Val Tyr Leu Gln Leu Ser Ser Leu Thr Ser Glu Asp Thr Ala Ile
            100                 105                 110

Tyr Tyr Cys Ala His Asp Tyr Asp Ala Pro Trp Phe Ala Tyr Trp Gly
        115                 120                 125

Gln Gly Thr Leu Val Ile Val Ser Ala
    130                 135
```

<210> SEQ ID NO 66
<211> LENGTH: 5
<212> TYPE: PRT
<213> ORGANISM: Artificial Sequence
<220> FEATURE:
<223> OTHER INFORMATION: Vb9 VH HCDR1

<400> SEQUENCE: 66

```
Asn Thr Phe Met His
1               5
```

<210> SEQ ID NO 67
<211> LENGTH: 17
<212> TYPE: PRT
<213> ORGANISM: Artificial Sequence
<220> FEATURE:
<223> OTHER INFORMATION: Vb9 VH HCDR2

<400> SEQUENCE: 67

```
Arg Ile Asp Pro Thr Asn Gly Tyr Thr Lys Phe Ala Pro Lys Phe Gln
1               5                   10                  15

Gly
```

<210> SEQ ID NO 68
<211> LENGTH: 9
<212> TYPE: PRT
<213> ORGANISM: Artificial Sequence
<220> FEATURE:
<223> OTHER INFORMATION: Vb9 VH HCDR3

<400> SEQUENCE: 68

```
Asp Tyr Asp Ala Pro Trp Phe Ala Tyr
1               5
```

<210> SEQ ID NO 69
<211> LENGTH: 127
<212> TYPE: PRT
<213> ORGANISM: Artificial Sequence
<220> FEATURE:
<223> OTHER INFORMATION: Vb9 VL

<400> SEQUENCE: 69

Met Leu Ser Pro Ala Pro Leu Leu Ser Leu Leu Leu Leu Cys Val Ser
1               5                   10                  15

Asp Ser Arg Ala Glu Thr Thr Val Thr Gln Ser Pro Ala Ser Leu Ser
            20                  25                  30

Val Ala Thr Gly Glu Lys Val Thr Ile Arg Cys Ile Ser Ser Thr Asp
        35                  40                  45

Ile Asp Asp Asp Met Asn Trp Tyr Gln Gln Lys Ser Gly Glu Pro Pro
    50                  55                  60

Lys Leu Leu Ile Ser Glu Gly Asn Thr Leu Arg Pro Gly Val Pro Ser
65                  70                  75                  80

Arg Phe Ser Ser Ser Gly Tyr Gly Thr Asp Phe Val Phe Thr Ile Glu
                85                  90                  95

Asn Met Leu Ser Glu Asp Val Ala Asp Tyr Tyr Cys Leu Gln Ser Asp
            100                 105                 110

Asn Met Pro Leu Thr Phe Gly Ala Gly Thr Lys Leu Glu Leu Lys
        115                 120                 125

<210> SEQ ID NO 70
<211> LENGTH: 11
<212> TYPE: PRT
<213> ORGANISM: Artificial Sequence
<220> FEATURE:
<223> OTHER INFORMATION: Vb9 VL LCDR1

<400> SEQUENCE: 70

Ile Ser Ser Thr Asp Ile Asp Asp Asp Met Asn
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Vb9 VL LCDR2

<400> SEQUENCE: 71

Glu Gly Asn Thr Leu Arg Pro
1               5

<210> SEQ ID NO 72
<211> LENGTH: 9
<212> TYPE: PRT
<213> ORGANISM: Artificial Sequence
<220> FEATURE:
<223> OTHER INFORMATION: Vb9 VL LCDR3

<400> SEQUENCE: 72

Leu Gln Ser Asp Asn Met Pro Leu Thr
1               5

<210> SEQ ID NO 73
<211> LENGTH: 142
<212> TYPE: PRT
<213> ORGANISM: Artificial Sequence
<220> FEATURE:
<223> OTHER INFORMATION: Vb1 VH

<400> SEQUENCE: 73

Met Asp Trp Val Trp Asn Leu Leu Phe Leu Met Ala Val Ala Gln Thr
1               5                   10                  15

Gly Ala Gln Ala Gln Leu Gln Leu Val Gln Ser Gly Pro Glu Leu Arg
            20                  25                  30

Glu Pro Gly Glu Ser Val Lys Ile Ser Cys Lys Ala Ser Gly Tyr Thr
        35                  40                  45

Phe Thr Asp Tyr Ile Val His Trp Val Lys Gln Ala Pro Gly Lys Gly
    50                  55                  60

Leu Lys Trp Met Gly Trp Ile Asn Thr Tyr Thr Gly Thr Pro Thr Tyr
65                  70                  75                  80

Ala Asp Asp Phe Glu Gly Arg Phe Val Phe Ser Leu Glu Ala Ser Ala
                85                  90                  95

Ser Thr Ala Asn Leu Gln Ile Ser Asn Leu Lys Asn Glu Asp Thr Ala
            100                 105                 110

Thr Tyr Phe Cys Ala Arg Ser Trp Arg Arg Gly Ile Arg Gly Ile Gly
        115                 120                 125

Phe Asp Tyr Trp Gly Gln Gly Val Met Val Thr Val Ser Ser
    130                 135                 140

<210> SEQ ID NO 74
<211> LENGTH: 5
<212> TYPE: PRT
<213> ORGANISM: Artificial Sequence
<220> FEATURE:
<223> OTHER INFORMATION: Vb1 VH HCDR1

<400> SEQUENCE: 74

Asp Tyr Ile Val His
1               5

<210> SEQ ID NO 75
<211> LENGTH: 17
<212> TYPE: PRT
<213> ORGANISM: Artificial Sequence
<220> FEATURE:
<223> OTHER INFORMATION: Vb1 VH HCDR2

<400> SEQUENCE: 75

Trp Ile Asn Thr Tyr Thr Gly Thr Pro Thr Tyr Ala Asp Asp Phe Glu
1               5                   10                  15

Gly

<210> SEQ ID NO 76
<211> LENGTH: 13
<212> TYPE: PRT
<213> ORGANISM: Artificial Sequence
<220> FEATURE:
<223> OTHER INFORMATION: Vb1 VH HCDR3

<400> SEQUENCE: 76

Ser Trp Arg Arg Gly Ile Arg Gly Ile Gly Phe Asp Tyr
1               5                   10

<210> SEQ ID NO 77
<211> LENGTH: 127
<212> TYPE: PRT
<213> ORGANISM: Artificial Sequence
<220> FEATURE:
<223> OTHER INFORMATION: Vb1 VL

<400> SEQUENCE: 77

Met Arg Val Gln Ile Gln Phe Trp Gly Leu Leu Leu Leu Trp Thr Ser
1 5 10 15

Gly Ile Gln Cys Asp Val Gln Met Thr Gln Ser Pro Tyr Asn Leu Ala
20 25 30

Ala Ser Pro Gly Glu Ser Val Ser Ile Asn Cys Lys Ala Ser Lys Ser
35 40 45

Ile Asn Lys Tyr Leu Ala Trp Tyr Gln Gln Lys Pro Gly Lys Pro Asn
50 55 60

Lys Leu Leu Ile Tyr Asp Gly Ser Thr Leu Gln Ser Gly Ile Pro Ser
65 70 75 80

Arg Phe Ser Gly Ser Gly Ser Gly Thr Asp Phe Thr Leu Thr Ile Arg
85 90 95

Gly Leu Glu Pro Glu Asp Phe Gly Leu Tyr Tyr Cys Gln Gln His Asn
100 105 110

Glu Tyr Pro Pro Thr Phe Gly Ala Gly Thr Lys Leu Glu Leu Lys
115 120 125

<210> SEQ ID NO 78
<211> LENGTH: 11
<212> TYPE: PRT
<213> ORGANISM: Artificial Sequence
<220> FEATURE:
<223> OTHER INFORMATION: Vb1 VL LCDR1

<400> SEQUENCE: 78

Lys Ala Ser Lys Ser Ile Asn Lys Tyr Leu Ala
1 5 10

<210> SEQ ID NO 79
<211> LENGTH: 7
<212> TYPE: PRT
<213> ORGANISM: Artificial Sequence
<220> FEATURE:
<223> OTHER INFORMATION: Vb1 VL LCDR2

<400> SEQUENCE: 79

Asp Gly Ser Thr Leu Gln Ser
1 5

<210> SEQ ID NO 80
<211> LENGTH: 9
<212> TYPE: PRT
<213> ORGANISM: Artificial Sequence
<220> FEATURE:
<223> OTHER INFORMATION: Vb1 VL LCDR3

<400> SEQUENCE: 80

Gln Gln His Asn Glu Tyr Pro Pro Thr
1 5

<210> SEQ ID NO 81
<211> LENGTH: 138
<212> TYPE: PRT
<213> ORGANISM: Artificial Sequence
<220> FEATURE:
<223> OTHER INFORMATION: Vb2 VH

<400> SEQUENCE: 81

Met Lys Phe Ser Trp Val Ile Phe Phe Leu Met Ala Val Val Thr Gly
1 5 10 15

Val Asn Ser Glu Val Gln Leu Gln Gln Ser Val Ala Asp Leu Val Arg

```
            20                  25                  30

Pro Gly Ala Ser Leu Lys Leu Ser Cys Thr Ala Ser Gly Phe Asn Ile
        35                  40                  45

Lys Ser Ala Tyr Met His Trp Val Ile Gln Arg Pro Asp Gln Gly Pro
    50                  55                  60

Glu Cys Leu Gly Arg Ile Asp Pro Ala Thr Gly Lys Thr Lys Tyr Ala
65                  70                  75                  80

Pro Lys Phe Gln Ala Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Ile
            100                 105                 110

Tyr Tyr Cys Thr Arg Ser Leu Asn Trp Asp Tyr Gly Leu Asp Tyr Trp
        115                 120                 125

Gly Gln Gly Thr Ser Val Thr Val Ser Ser
    130                 135


<210> SEQ ID NO 82
<211> LENGTH: 4
<212> TYPE: PRT
<213> ORGANISM: Artificial Sequence
<220> FEATURE:
<223> OTHER INFORMATION: Vb2 VH HCDR1

<400> SEQUENCE: 82

Ala Tyr Met His
1


<210> SEQ ID NO 83
<211> LENGTH: 17
<212> TYPE: PRT
<213> ORGANISM: Artificial Sequence
<220> FEATURE:
<223> OTHER INFORMATION: Vb2 VH HCDR2

<400> SEQUENCE: 83

Arg Ile Asp Pro Ala Thr Gly Lys Thr Lys Tyr Ala Pro Lys Phe Gln
1               5                   10                  15

Ala


<210> SEQ ID NO 84
<211> LENGTH: 10
<212> TYPE: PRT
<213> ORGANISM: Artificial Sequence
<220> FEATURE:
<223> OTHER INFORMATION: Vb2 VH HCDR3

<400> SEQUENCE: 84

Ser Leu Asn Trp Asp Tyr Gly Leu Asp Tyr
1               5                   10


<210> SEQ ID NO 85
<211> LENGTH: 131
<212> TYPE: PRT
<213> ORGANISM: Artificial Sequence
<220> FEATURE:
<223> OTHER INFORMATION: Vb2 VL

<400> SEQUENCE: 85

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30
```

```
Val Ser Leu Gly Gln Arg Ala Thr Ile Ser Cys Arg Ala Ser Lys Ser
        35                  40                  45

Val Ser Ile Leu Gly Thr His Leu Ile His Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Val Pro Ala Arg Phe Ser Gly Ser Gly Ser Glu Thr Val Phe Thr
                85                  90                  95

Leu Asn Ile His Pro Val Glu Glu Glu Asp Ala Ala Thr Tyr Phe Cys
            100                 105                 110

Gln Gln Ser Ile Glu Asp Pro Trp Thr Phe Gly Gly Gly Thr Lys Leu
        115                 120                 125

Gly Ile Lys
    130


<210> SEQ ID NO 86
<211> LENGTH: 15
<212> TYPE: PRT
<213> ORGANISM: Artificial Sequence
<220> FEATURE:
<223> OTHER INFORMATION: Vb2 VL LCDR1

<400> SEQUENCE: 86

Arg Ala Ser Lys Ser Val Ser Ile Leu Gly Thr His Leu Ile His
1               5                   10                  15


<210> SEQ ID NO 87
<211> LENGTH: 7
<212> TYPE: PRT
<213> ORGANISM: Artificial Sequence
<220> FEATURE:
<223> OTHER INFORMATION: Vb2 VL LCDR2

<400> SEQUENCE: 87

Ala Ala Ser Asn Leu Glu Ser
1               5


<210> SEQ ID NO 88
<211> LENGTH: 9
<212> TYPE: PRT
<213> ORGANISM: Artificial Sequence
<220> FEATURE:
<223> OTHER INFORMATION: Vb2 VL LCDR3

<400> SEQUENCE: 88

Gln Gln Ser Ile Glu Asp Pro Trp Thr
1               5


<210> SEQ ID NO 89
<211> LENGTH: 139
<212> TYPE: PRT
<213> ORGANISM: Artificial Sequence
<220> FEATURE:
<223> OTHER INFORMATION: Vb4 VH

<400> SEQUENCE: 89

Met Glu Trp Ser Trp Ile Phe Leu Phe Leu Leu Ser Val Thr Ala Val
1               5                   10                  15

Val His Ser Gln Val Gln Leu Gln Gln Ser Gly Ala Glu Leu Ala Lys
            20                  25                  30

Pro Gly Thr Ser Val Lys Leu Ser Cys Lys Ala Ser Gly Tyr Thr Phe
        35                  40                  45
```

```
Thr Ser Tyr Tyr Ile Tyr Trp Val Lys Gln Arg Pro Gly Gln Gly Leu
    50                  55                  60

Glu Trp Leu Gly Tyr Ile Tyr Pro Gly Asn Gly Gly Thr Tyr Tyr Ser
65                  70                  75                  80

Glu Lys Phe Lys Gly Lys Ala Thr Phe Thr Ala Asp Thr Ser Ser Asn
                85                  90                  95

Thr Ala Tyr Met Leu Leu Gly Ser Leu Thr Pro Glu Asp Ser Ala Tyr
            100                 105                 110

Tyr Phe Cys Ala Arg Gly Ser Gly Asp Arg Tyr Asn Ser Leu Ala Tyr
        115                 120                 125

Trp Gly Gln Gly Thr Leu Val Thr Val Ser Ser
    130                 135


<210> SEQ ID NO 90
<211> LENGTH: 4
<212> TYPE: PRT
<213> ORGANISM: Artificial Sequence
<220> FEATURE:
<223> OTHER INFORMATION: Vb4 VH HCDR1

<400> SEQUENCE: 90

Tyr Tyr Ile Tyr
1


<210> SEQ ID NO 91
<211> LENGTH: 17
<212> TYPE: PRT
<213> ORGANISM: Artificial Sequence
<220> FEATURE:
<223> OTHER INFORMATION: Vb4 VH HCDR2

<400> SEQUENCE: 91

Tyr Ile Tyr Pro Gly Asn Gly Gly Thr Tyr Tyr Ser Glu Lys Phe Lys
1               5                   10                  15

Gly


<210> SEQ ID NO 92
<211> LENGTH: 11
<212> TYPE: PRT
<213> ORGANISM: Artificial Sequence
<220> FEATURE:
<223> OTHER INFORMATION: Vb4 VH HCDR3

<400> SEQUENCE: 92

Gly Ser Gly Asp Arg Tyr Asn Ser Leu Ala Tyr
1               5                   10


<210> SEQ ID NO 93
<211> LENGTH: 127
<212> TYPE: PRT
<213> ORGANISM: Artificial Sequence
<220> FEATURE:
<223> OTHER INFORMATION: Vb4 VL

<400> SEQUENCE: 93

Met Ala Ile Pro Thr Gln Leu Leu Gly Leu Leu Leu Leu Trp Ile Thr
1               5                   10                  15

Asp Ala Ile Cys Asp Ile Gln Met Thr Gln Ser Pro His Ser Leu Ser
            20                  25                  30

Ala Ser Leu Gly Glu Thr Val Ser Ile Glu Cys Leu Ala Ser Glu Gly
        35                  40                  45
```

```
Ile Ser Asn Phe Leu Ala Trp Tyr Gln Gln Lys Pro Gly Lys Ser Pro
    50                  55                  60

Gln Leu Leu Ile Tyr Tyr Thr Ser Ser Leu Gln Asp Gly Val Pro Ser
65                  70                  75                  80

Arg Phe Ser Gly Ser Gly Ser Gly Thr Gln Tyr Ser Leu Lys Ile Ser
                85                  90                  95

Asn Met Gln Pro Glu Asp Glu Gly Val Tyr Tyr Cys Gln Gln Gly Tyr
            100                 105                 110

Lys Phe Pro Arg Thr Phe Gly Gly Gly Thr Lys Leu Glu Leu Lys
        115                 120                 125


<210> SEQ ID NO 94
<211> LENGTH: 11
<212> TYPE: PRT
<213> ORGANISM: Artificial Sequence
<220> FEATURE:
<223> OTHER INFORMATION: Vb4 VL LCDR1

<400> SEQUENCE: 94

Leu Ala Ser Glu Gly Ile Ser Asn Phe Leu Ala
1               5                   10


<210> SEQ ID NO 95
<211> LENGTH: 7
<212> TYPE: PRT
<213> ORGANISM: Artificial Sequence
<220> FEATURE:
<223> OTHER INFORMATION: Vb4 VL LCDR2

<400> SEQUENCE: 95

Tyr Thr Ser Ser Leu Gln Asp
1               5


<210> SEQ ID NO 96
<211> LENGTH: 9
<212> TYPE: PRT
<213> ORGANISM: Artificial Sequence
<220> FEATURE:
<223> OTHER INFORMATION: Vb4 VL LCDR3

<400> SEQUENCE: 96

Gln Gln Gly Tyr Lys Phe Pro Arg Thr
1               5


<210> SEQ ID NO 97
<211> LENGTH: 137
<212> TYPE: PRT
<213> ORGANISM: Artificial Sequence
<220> FEATURE:
<223> OTHER INFORMATION: Vb5.1 VH

<400> SEQUENCE: 97

Met Gly Trp Ser Trp Ile Phe Leu Phe Leu Leu Ser Glu Thr Ala Gly
1               5                   10                  15

Val Leu Ser Glu Val Gln Leu Gln Gln Ser Gly Pro Val Leu Val Lys
            20                  25                  30

Pro Gly Ala Ser Val Arg Met Ser Cys Lys Ala Ser Gly Tyr Thr Phe
        35                  40                  45

Thr Asp Tyr Asn Ile His Trp Val Lys Gln Ser His Gly Arg Ser Leu
    50                  55                  60

Glu Trp Val Gly Tyr Ile Asn Pro Tyr Asn Gly Arg Thr Gly Tyr Asn
65                  70                  75                  80
```

```
Gln Lys Phe Lys Ala Lys Ala Thr Leu Thr Val Asn Lys Ser Ser Ser
                85                  90                  95

Thr Ala Tyr Met Asp Leu Arg Ser Leu Thr Ser Glu Asp Ser Ala Val
            100                 105                 110

Tyr Tyr Cys Ala Arg Trp Asp Gly Ser Ser Tyr Phe Asp Tyr Trp Gly
        115                 120                 125

Gln Gly Thr Thr Leu Thr Val Ser Ser
    130                 135


<210> SEQ ID NO 98
<211> LENGTH: 5
<212> TYPE: PRT
<213> ORGANISM: Artificial Sequence
<220> FEATURE:
<223> OTHER INFORMATION: Vb5.1 VH HCDR1

<400> SEQUENCE: 98

Asp Tyr Asn Ile His
1               5


<210> SEQ ID NO 99
<211> LENGTH: 17
<212> TYPE: PRT
<213> ORGANISM: Artificial Sequence
<220> FEATURE:
<223> OTHER INFORMATION: Vb5.1 VH HCDR2

<400> SEQUENCE: 99

Tyr Ile Asn Pro Tyr Asn Gly Arg Thr Gly Tyr Asn Gln Lys Phe Lys
1               5                   10                  15

Ala


<210> SEQ ID NO 100
<211> LENGTH: 9
<212> TYPE: PRT
<213> ORGANISM: Artificial Sequence
<220> FEATURE:
<223> OTHER INFORMATION: Vb5.1 VH HCDR3

<400> SEQUENCE: 100

Trp Asp Gly Ser Ser Tyr Phe Asp Tyr
1               5


<210> SEQ ID NO 101
<211> LENGTH: 126
<212> TYPE: PRT
<213> ORGANISM: Artificial Sequence
<220> FEATURE:
<223> OTHER INFORMATION: Vb5.1 VL

<400> SEQUENCE: 101

Met Asp Phe Arg Val Gln Ile Phe Ser Phe Leu Leu Ile Ser Val Thr
1               5                   10                  15

Val Ser Arg Gly Glu Ile Val Leu Thr Gln Ser Pro Ala Ile Thr Ala
            20                  25                  30

Ala Ser Leu Gly Gln Lys Val Thr Ile Thr Cys Ser Ala Ser Ser Ser
        35                  40                  45

Val Ser Tyr Met His Trp Tyr Gln Gln Lys Ser Gly Thr Ser Pro Lys
    50                  55                  60

Pro Trp Ile Tyr Glu Ile Ser Lys Leu Ala Ser Gly Val Pro Ala Arg
65                  70                  75                  80

Phe Ser Gly Ser Gly Ser Gly Thr Ser Tyr Ser Leu Thr Ile Ser Ser
```

```
                85                  90                  95

Met Glu Ala Glu Asp Ala Ala Ile Tyr Tyr Cys Gln Gln Trp Asn Tyr
            100                 105                 110

Pro Leu Ile Thr Phe Gly Ala Gly Thr Lys Leu Glu Leu Lys
        115                 120                 125


<210> SEQ ID NO 102
<211> LENGTH: 10
<212> TYPE: PRT
<213> ORGANISM: Artificial Sequence
<220> FEATURE:
<223> OTHER INFORMATION: Vb5.1 VL LCDR1

<400> SEQUENCE: 102

Ser Ala Ser Ser Ser Val Ser Tyr Met His
1               5                   10


<210> SEQ ID NO 103
<211> LENGTH: 7
<212> TYPE: PRT
<213> ORGANISM: Artificial Sequence
<220> FEATURE:
<223> OTHER INFORMATION: Vb5.1 VL LCDR2

<400> SEQUENCE: 103

Glu Ile Ser Lys Leu Ala Ser
1               5


<210> SEQ ID NO 104
<211> LENGTH: 9
<212> TYPE: PRT
<213> ORGANISM: Artificial Sequence
<220> FEATURE:
<223> OTHER INFORMATION: Vb5.1 VL LCDR3

<400> SEQUENCE: 104

Gln Gln Trp Asn Tyr Pro Leu Ile Thr
1               5


<210> SEQ ID NO 105
<211> LENGTH: 142
<212> TYPE: PRT
<213> ORGANISM: Artificial Sequence
<220> FEATURE:
<223> OTHER INFORMATION: Vb7.1 VH

<400> SEQUENCE: 105

Met Asn Phe Gly Leu Ser Leu Ile Phe Leu Val Leu Phe Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Thr Ile Ser Gly Gly Gly Ser Tyr Thr Tyr Ser Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Ser Ser Leu Arg Ser Glu Asp Thr Ala Met
            100                 105                 110

Tyr Phe Cys Ala Arg Glu Arg Asp Ile Tyr Tyr Gly Asn Phe Asn Ala
```

```
        115                 120                 125

Met Val Tyr Trp Gly Arg Gly Thr Ser Val Thr Val Ser Ser
    130                 135                 140


<210> SEQ ID NO 106
<211> LENGTH: 5
<212> TYPE: PRT
<213> ORGANISM: Artificial Sequence
<220> FEATURE:
<223> OTHER INFORMATION: Vb7.1 VH HCDR1

<400> SEQUENCE: 106

Asp Tyr Tyr Met Tyr
1               5


<210> SEQ ID NO 107
<211> LENGTH: 17
<212> TYPE: PRT
<213> ORGANISM: Artificial Sequence
<220> FEATURE:
<223> OTHER INFORMATION: Vb7.1 VH HCDR2

<400> SEQUENCE: 107

Thr Ile Ser Gly Gly Gly Ser Tyr Thr Tyr Ser Pro Asp Ser Val Lys
1               5                   10                  15

Gly


<210> SEQ ID NO 108
<211> LENGTH: 14
<212> TYPE: PRT
<213> ORGANISM: Artificial Sequence
<220> FEATURE:
<223> OTHER INFORMATION: Vb7.1 VH HCDR3

<400> SEQUENCE: 108

Glu Arg Asp Ile Tyr Tyr Gly Asn Phe Asn Ala Met Val Tyr
1               5                   10


<210> SEQ ID NO 109
<211> LENGTH: 131
<212> TYPE: PRT
<213> ORGANISM: Artificial Sequence
<220> FEATURE:
<223> OTHER INFORMATION: Vb7.1 VL

<400> SEQUENCE: 109

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Val Ser Leu Thr
            20                  25                  30

Val Ser Leu Gly Gln Arg Ala Thr Ile Ser Cys Arg Ala Ser Lys Ser
        35                  40                  45

Val Ser Thr Ser Gly Tyr Ser Tyr Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ser Arg Asp Leu Pro Trp Thr Phe Gly Gly Gly Thr Lys Leu
        115                 120                 125
```

Glu Ile Lys
130

<210> SEQ ID NO 110
<211> LENGTH: 15
<212> TYPE: PRT
<213> ORGANISM: Artificial Sequence
<220> FEATURE:
<223> OTHER INFORMATION: Vb7.1 VL LCDR1

<400> SEQUENCE: 110

Arg Ala Ser Lys Ser Val Ser Thr Ser Gly Tyr Ser Tyr Met His
1 5 10 15

<210> SEQ ID NO 111
<211> LENGTH: 7
<212> TYPE: PRT
<213> ORGANISM: Artificial Sequence
<220> FEATURE:
<223> OTHER INFORMATION: Vb7.1 VL LCDR2

<400> SEQUENCE: 111

Leu Ala Ser Asn Leu Glu Ser
1 5

<210> SEQ ID NO 112
<211> LENGTH: 9
<212> TYPE: PRT
<213> ORGANISM: Artificial Sequence
<220> FEATURE:
<223> OTHER INFORMATION: Vb7.1 VL LCDR3

<400> SEQUENCE: 112

Gln His Ser Arg Asp Leu Pro Trp Thr
1 5

<210> SEQ ID NO 113
<211> LENGTH: 136
<212> TYPE: PRT
<213> ORGANISM: Artificial Sequence
<220> FEATURE:
<223> OTHER INFORMATION: Vb7.2 VH

<400> SEQUENCE: 113

Met Glu Arg His Trp Ile Phe Leu Leu Leu Leu Ser Val Thr Ala Gly
1 5 10 15

Ala His Ser Gln Val His Leu Gln Gln Ser Gly Ala Glu Leu Ala Arg
20 25 30

Pro Gly Ala Ser Val Lys Met Ser Cys Lys Ala Ser Gly Tyr Ile Phe
35 40 45

Thr Asp Tyr Thr Met His Trp Val Lys Gln Arg Pro Gly Gln Gly Leu
50 55 60

Glu Trp Ile Gly His Ile Asn Pro Ser Ser Gly Tyr Ser Thr Tyr Asn
65 70 75 80

Gln Lys Phe Lys Asp Lys Ala Thr Leu Thr Ala Asp Lys Ser Ser Ser
85 90 95

Thr Ala Tyr Met Gln Leu Ser Ser Leu Thr Ser Glu Asp Ser Ala Val
100 105 110

Tyr Tyr Cys Ala Arg Ser Leu Gln Leu Gly Arg Asp Tyr Trp Gly Gln
115 120 125

Gly Thr Thr Leu Thr Val Ser Ser
130 135

<210> SEQ ID NO 114
<211> LENGTH: 5
<212> TYPE: PRT
<213> ORGANISM: Artificial Sequence
<220> FEATURE:
<223> OTHER INFORMATION: Vb7.2 VH HCDR1

<400> SEQUENCE: 114

Asp Tyr Thr Met His
1               5

<210> SEQ ID NO 115
<211> LENGTH: 17
<212> TYPE: PRT
<213> ORGANISM: Artificial Sequence
<220> FEATURE:
<223> OTHER INFORMATION: Vb7.2 VH HCDR2

<400> SEQUENCE: 115

His Ile Asn Pro Ser Ser Gly Tyr Ser Thr Tyr Asn Gln Lys Phe Lys
1               5                   10                  15

Asp

<210> SEQ ID NO 116
<211> LENGTH: 7
<212> TYPE: PRT
<213> ORGANISM: Artificial Sequence
<220> FEATURE:
<223> OTHER INFORMATION: Vb7.2 VH HCDR3

<400> SEQUENCE: 116

Leu Gln Leu Gly Arg Asp Tyr
1               5

<210> SEQ ID NO 117
<211> LENGTH: 127
<212> TYPE: PRT
<213> ORGANISM: Artificial Sequence
<220> FEATURE:
<223> OTHER INFORMATION: Vb7.2 VL

<400> SEQUENCE: 117

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Tyr Thr Ala Val Ala Trp Tyr Gln Gln Lys Pro Gly Gln Ser Pro
    50                  55                  60

Lys Leu Leu Ile Tyr Ser Ala Ser Asn Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Gln Gln His Tyr
            100                 105                 110

Thr Thr Pro Arg Thr Phe Gly Gly Gly Thr Lys Leu Glu Ile Lys
        115                 120                 125

<210> SEQ ID NO 118
<211> LENGTH: 11

<212> TYPE: PRT
<213> ORGANISM: Artificial Sequence
<220> FEATURE:
<223> OTHER INFORMATION: Vb7.2 VL LCDR1

<400> SEQUENCE: 118

Lys Ala Ser Gln Asp Val Tyr Thr Ala Val Ala
1 5 10

<210> SEQ ID NO 119
<211> LENGTH: 6
<212> TYPE: PRT
<213> ORGANISM: Artificial Sequence
<220> FEATURE:
<223> OTHER INFORMATION: Vb7.2 VL LCDR2

<400> SEQUENCE: 119

Ala Ser Asn Arg Tyr Thr
1 5

<210> SEQ ID NO 120
<211> LENGTH: 9
<212> TYPE: PRT
<213> ORGANISM: Artificial Sequence
<220> FEATURE:
<223> OTHER INFORMATION: Vb7.2 VL LCDR3

<400> SEQUENCE: 120

Gln Gln His Tyr Thr Thr Pro Arg Thr
1 5

<210> SEQ ID NO 121
<211> LENGTH: 135
<212> TYPE: PRT
<213> ORGANISM: Artificial Sequence
<220> FEATURE:
<223> OTHER INFORMATION: Vb11 VH

<400> SEQUENCE: 121

Met Gly Trp Ser Cys Ile Ile Phe Phe Leu Val Ala Thr Ala Thr Gly
1 5 10 15

Val His Ser Gln Val Gln Leu Gln Gln Ser Gly Pro Glu Val Val Arg
20 25 30

Pro Gly Val Ser Val Lys Ile Ser Cys Lys Gly Ser Gly Tyr Arg Phe
35 40 45

Thr Asp Ser Ala Met His Trp Val Lys Gln Ser His Ala Lys Ser Leu
50 55 60

Glu Trp Ile Gly Val Ile Ser Ser Tyr Asn Gly Asn Thr Asn Tyr Asn
65 70 75 80

Gln Lys Phe Lys Gly Lys Ala Thr Met Thr Val Asp Lys Ser Ser Ser
85 90 95

Thr Ala Tyr Met Glu Leu Ala Arg Met Thr Ser Glu Asp Ser Ala Ile
100 105 110

Tyr Tyr Cys Ala Arg Ser Arg Asp Ala Met Asp Tyr Trp Gly Gln Gly
115 120 125

Thr Ser Val Thr Val Ser Ser
130 135

<210> SEQ ID NO 122
<211> LENGTH: 5
<212> TYPE: PRT
<213> ORGANISM: Artificial Sequence
<220> FEATURE:

<223> OTHER INFORMATION: Vb11 VH HCDR1

<400> SEQUENCE: 122

Asp Ser Ala Met His
1 5

<210> SEQ ID NO 123
<211> LENGTH: 17
<212> TYPE: PRT
<213> ORGANISM: Artificial Sequence
<220> FEATURE:
<223> OTHER INFORMATION: Vb11 VH HCDR2

<400> SEQUENCE: 123

Val Ile Ser Ser Tyr Asn Gly Asn Thr Asn Tyr Asn Gln Lys Phe Lys
1 5 10 15

Gly

<210> SEQ ID NO 124
<211> LENGTH: 6
<212> TYPE: PRT
<213> ORGANISM: Artificial Sequence
<220> FEATURE:
<223> OTHER INFORMATION: Vb11 VH HCDR3

<400> SEQUENCE: 124

Arg Asp Ala Met Asp Tyr
1 5

<210> SEQ ID NO 125
<211> LENGTH: 127
<212> TYPE: PRT
<213> ORGANISM: Artificial Sequence
<220> FEATURE:
<223> OTHER INFORMATION: Vb11 VL

<400> SEQUENCE: 125

Met Arg Thr Pro Ala Gln Phe Leu Gly Ile Leu Leu Leu Trp Phe Pro
1 5 10 15

Gly Ile Lys Cys Asp Ile Lys Met Thr Gln Ser Pro Ser Ser Met Tyr
20 25 30

Ala Ser Leu Gly Glu Arg Val Thr Ile Thr Cys Lys Ala Ser Gln Asp
35 40 45

Ile Asn Ser Tyr Leu Ser Trp Phe Gln Gln Lys Ala Gly Lys Ser Pro
50 55 60

Lys Thr Leu Ile Tyr Arg Ala Asn Arg Leu Val Asp Gly Val Pro Ser
65 70 75 80

Arg Phe Ser Gly Ser Gly Ser Gly Gln Asp Tyr Ser Leu Thr Ile Ser
85 90 95

Ser Leu Glu Tyr Glu Asp Met Gly Ile Tyr Tyr Cys Leu Gln Tyr Asp
100 105 110

Glu Phe Pro Phe Thr Phe Gly Gly Gly Thr Arg Leu Glu Ile Lys
115 120 125

<210> SEQ ID NO 126
<211> LENGTH: 10
<212> TYPE: PRT
<213> ORGANISM: Artificial Sequence
<220> FEATURE:
<223> OTHER INFORMATION: Vb11 VL LCDR1

<400> SEQUENCE: 126

```
Lys Ala Ser Gln Asp Ile Asn Ser Tyr Leu
1               5                   10


<210> SEQ ID NO 127
<211> LENGTH: 7
<212> TYPE: PRT
<213> ORGANISM: Artificial Sequence
<220> FEATURE:
<223> OTHER INFORMATION: Vb11 VL LCDR2

<400> SEQUENCE: 127

Arg Ala Asn Arg Leu Val Asp
1               5


<210> SEQ ID NO 128
<211> LENGTH: 9
<212> TYPE: PRT
<213> ORGANISM: Artificial Sequence
<220> FEATURE:
<223> OTHER INFORMATION: Vb11 VL LCDR3

<400> SEQUENCE: 128

Leu Gln Tyr Asp Glu Phe Pro Phe Thr
1               5


<210> SEQ ID NO 129
<211> LENGTH: 139
<212> TYPE: PRT
<213> ORGANISM: Artificial Sequence
<220> FEATURE:
<223> OTHER INFORMATION: Vb13.2 VH

<400> SEQUENCE: 129

Met Gly Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Asn Ala Ser Gly Tyr Thr Phe
        35                  40                  45

Thr Asp Tyr Tyr Ile His Trp Leu Lys Gln Arg His Gly Lys Gly Leu
    50                  55                  60

Glu Trp Ile Gly Ile Val Asn Thr Asn Asn Gly Asp Thr Asn Tyr Asn
65                  70                  75                  80

Gln Arg Phe Lys Gly Lys Ala Ser Leu Thr Val Asp Lys Ser Ser Ser
                85                  90                  95

Thr Ala Tyr Met Glu Leu Asn Ser Leu Thr Ser Glu Asp Ser Ala Val
            100                 105                 110

Phe Tyr Cys Ala Arg Ala Leu Tyr Thr Gly Ser Tyr Trp Phe Ala Tyr
        115                 120                 125

Trp Gly Gln Gly Thr Leu Val Thr Val Ser Ala
    130                 135


<210> SEQ ID NO 130
<211> LENGTH: 5
<212> TYPE: PRT
<213> ORGANISM: Artificial Sequence
<220> FEATURE:
<223> OTHER INFORMATION: Vb13.2 VH HCDR1

<400> SEQUENCE: 130

Asp Tyr Tyr Ile His
1               5
```

<210> SEQ ID NO 131
<211> LENGTH: 17
<212> TYPE: PRT
<213> ORGANISM: Artificial Sequence
<220> FEATURE:
<223> OTHER INFORMATION: Vb13.2 VH HCDR2

<400> SEQUENCE: 131

Ile Val Asn Thr Asn Asn Gly Asp Thr Asn Tyr Asn Gln Arg Phe Lys
1 5 10 15

Gly

<210> SEQ ID NO 132
<211> LENGTH: 11
<212> TYPE: PRT
<213> ORGANISM: Artificial Sequence
<220> FEATURE:
<223> OTHER INFORMATION: Vb13.2 VH HCDR3

<400> SEQUENCE: 132

Ala Leu Tyr Thr Gly Ser Tyr Trp Phe Ala Tyr
1 5 10

<210> SEQ ID NO 133
<211> LENGTH: 130
<212> TYPE: PRT
<213> ORGANISM: Artificial Sequence
<220> FEATURE:
<223> OTHER INFORMATION: Vb13.2 VL

<400> SEQUENCE: 133

Met Asp Phe His Val Gln Ile Phe Ser Phe Met Leu Ile Ser Val Thr
1 5 10 15

Val Met Leu Ser Ser Gly Glu Ile Val Leu Thr Gln Ser Pro Ala Val
20 25 30

Met Ala Ala Ser Pro Gly Glu Lys Val Thr Ile Thr Cys Ser Ala Ser
35 40 45

Ser Ser Ile Ser Ser Thr Asn Leu His Trp Tyr Gln Gln Lys Ser Glu
50 55 60

Thr Ser Pro Lys Pro Trp Ile Tyr Gly Thr Ser Asn Leu Ala Ser Gly
65 70 75 80

Val Pro Val Arg Phe Ser Gly Ser Gly Ser Gly Thr Ser Tyr Ser Leu
85 90 95

Thr Ile Ser Ser Ile Glu Ala Glu Asp Ala Ala Thr Tyr Tyr Cys Gln
100 105 110

Gln Trp Ser Arg Tyr Pro Leu Thr Phe Gly Ser Gly Thr Lys Leu Glu
115 120 125

Ile Ile
130

<210> SEQ ID NO 134
<211> LENGTH: 12
<212> TYPE: PRT
<213> ORGANISM: Artificial Sequence
<220> FEATURE:
<223> OTHER INFORMATION: Vb13.2 VL LCDR1

<400> SEQUENCE: 134

Ser Ala Ser Ser Ser Ile Ser Ser Thr Asn Leu His
1 5 10

<210> SEQ ID NO 135
<211> LENGTH: 7
<212> TYPE: PRT
<213> ORGANISM: Artificial Sequence
<220> FEATURE:
<223> OTHER INFORMATION: Vb13.2 VL LCDR2

<400> SEQUENCE: 135

Gly Thr Ser Asn Leu Ala Ser
1 5

<210> SEQ ID NO 136
<211> LENGTH: 9
<212> TYPE: PRT
<213> ORGANISM: Artificial Sequence
<220> FEATURE:
<223> OTHER INFORMATION: Vb13.2 VL LCDR3

<400> SEQUENCE: 136

Gln Gln Trp Ser Arg Tyr Pro Leu Thr
1 5

<210> SEQ ID NO 137
<211> LENGTH: 141
<212> TYPE: PRT
<213> ORGANISM: Artificial Sequence
<220> FEATURE:
<223> OTHER INFORMATION: Vb13.3 VH

<400> SEQUENCE: 137

Met Gly Trp Ser Cys Ile Ile Leu Ile Leu Val Ala Ala Ala Thr Gly
1 5 10 15

Val His Ser Gln Val Gln Leu Gln Gln Pro Gly Ala Glu Leu Val Lys
20 25 30

Pro Gly Ala Ser Val Lys Met Ser Cys Lys Ala Ser Gly Tyr Thr Phe
35 40 45

Thr Ser Tyr Trp Ile Thr Trp Val Lys Gln Arg Pro Gly Gln Gly Leu
50 55 60

Glu Trp Ile Gly Asp Ile Tyr Pro Gly Ser Gly Ser Ile Asn Tyr Asn
65 70 75 80

Glu Lys Phe Asn Asn Lys Ala Thr Leu Thr Val Asp Thr Ser Ser Ser
85 90 95

Thr Ala Tyr Met Gln Leu Ser Ser Leu Thr Ser Glu Asp Ser Ala Val
100 105 110

Tyr Tyr Cys Ala Arg Arg Asp Tyr Tyr Ser Leu Tyr Tyr Tyr Ala Leu
115 120 125

Asp Tyr Trp Gly Gln Gly Thr Ser Val Thr Val Ser Ser
130 135 140

<210> SEQ ID NO 138
<211> LENGTH: 5
<212> TYPE: PRT
<213> ORGANISM: Artificial Sequence
<220> FEATURE:
<223> OTHER INFORMATION: Vb13.3 VH HCDR1

<400> SEQUENCE: 138

Ser Tyr Trp Ile Thr
1 5

<210> SEQ ID NO 139
<211> LENGTH: 17
<212> TYPE: PRT

<213> ORGANISM: Artificial Sequence
<220> FEATURE:
<223> OTHER INFORMATION: Vb13.3 VH HCDR2

<400> SEQUENCE: 139

Asp Ile Tyr Pro Gly Ser Gly Ser Ile Asn Tyr Asn Glu Lys Phe Asn
1 5 10 15

Asn

<210> SEQ ID NO 140
<211> LENGTH: 13
<212> TYPE: PRT
<213> ORGANISM: Artificial Sequence
<220> FEATURE:
<223> OTHER INFORMATION: Vb13.3 VH HCDR3

<400> SEQUENCE: 140

Arg Asp Tyr Tyr Ser Leu Tyr Tyr Tyr Ala Leu Asp Tyr
1 5 10

<210> SEQ ID NO 141
<211> LENGTH: 127
<212> TYPE: PRT
<213> ORGANISM: Artificial Sequence
<220> FEATURE:
<223> OTHER INFORMATION: Vb13.3 VL

<400> SEQUENCE: 141

Met Ser Val Pro Thr Gln Val Leu Gly Leu Leu Leu Leu Trp Leu Thr
1 5 10 15

Gly Ala Arg Cys Asp Ile Gln Met Thr Gln Ser Pro Ala Ser Leu Ser
20 25 30

Ala Ser Val Gly Glu Thr Val Thr Met Thr Cys Arg Ala Ser Glu Asn
35 40 45

Ile Tyr Ser Asn Leu Ala Trp Tyr Gln Gln Lys Gln Gly Lys Ser Pro
50 55 60

Gln Leu Leu Val Tyr Ala Ala Thr Asn Leu Ala Asp Gly Val Pro Ser
65 70 75 80

Arg Phe Ser Val Ser Gly Ser Gly Thr His Phe Ser Leu Lys Ile Asn
85 90 95

Ser Leu Gln Pro Glu Asp Phe Gly Ser Tyr Tyr Cys Gln His Phe Tyr
100 105 110

Gly Thr Pro Tyr Thr Phe Gly Gly Gly Thr Lys Leu Glu Ile Lys
115 120 125

<210> SEQ ID NO 142
<211> LENGTH: 11
<212> TYPE: PRT
<213> ORGANISM: Artificial Sequence
<220> FEATURE:
<223> OTHER INFORMATION: Vb13.3 VL LCDR1

<400> SEQUENCE: 142

Arg Ala Ser Glu Asn Ile Tyr Ser Asn Leu Ala
1 5 10

<210> SEQ ID NO 143
<211> LENGTH: 7
<212> TYPE: PRT
<213> ORGANISM: Artificial Sequence
<220> FEATURE:
<223> OTHER INFORMATION: Vb13.3 VL LCDR2

<400> SEQUENCE: 143

Ala Ala Thr Asn Leu Ala Asp
1 5

<210> SEQ ID NO 144
<211> LENGTH: 9
<212> TYPE: PRT
<213> ORGANISM: Artificial Sequence
<220> FEATURE:
<223> OTHER INFORMATION: Vb13.3 VL LCDR3

<400> SEQUENCE: 144

Gln His Phe Tyr Gly Thr Pro Tyr Thr
1 5

<210> SEQ ID NO 145
<211> LENGTH: 134
<212> TYPE: PRT
<213> ORGANISM: Artificial Sequence
<220> FEATURE:
<223> OTHER INFORMATION: Vb22 VH

<400> SEQUENCE: 145

Met Asp Phe Gly Leu Ile Phe Phe Ile Val Ala Leu Leu Lys Gly Val
1 5 10 15

Gln Cys Glu Val Lys Leu Leu Glu Ser Gly Gly Gly Leu Val Gln Pro
20 25 30

Gly Gly Ser Leu Lys Leu Ser Cys Ala Ala Ser Gly Phe Asp Phe Ser
35 40 45

Arg Tyr Trp Met Asn Trp Val Arg Gln Ala Pro Gly Lys Gly Leu Glu
50 55 60

Trp Ile Gly Glu Ile Asn Ser Asp Ser Asn Thr Ile Asn Tyr Thr Pro
65 70 75 80

Ser Leu Lys Asp Lys Phe Ile Ile Ser Arg Asp Asn Ala Lys Asn Thr
85 90 95

Leu Tyr Leu Gln Met Asn Lys Val Arg Ser Glu Asp Thr Ala Leu Tyr
100 105 110

Tyr Cys Ala Arg Gly Gly Leu Leu Arg Asp Val Trp Gly Ala Gly Thr
115 120 125

Thr Val Thr Val Ser Ser
130

<210> SEQ ID NO 146
<211> LENGTH: 5
<212> TYPE: PRT
<213> ORGANISM: Artificial Sequence
<220> FEATURE:
<223> OTHER INFORMATION: Vb22 VH HCDR1

<400> SEQUENCE: 146

Arg Tyr Trp Met Asn
1 5

<210> SEQ ID NO 147
<211> LENGTH: 17
<212> TYPE: PRT
<213> ORGANISM: Artificial Sequence
<220> FEATURE:
<223> OTHER INFORMATION: Vb22 VH HCDR2

<400> SEQUENCE: 147

Glu Ile Asn Ser Asp Ser Asn Thr Ile Asn Tyr Thr Pro Ser Leu Lys 1 5 10 15

Asp

<210> SEQ ID NO 148
<211> LENGTH: 7
<212> TYPE: PRT
<213> ORGANISM: Artificial Sequence
<220> FEATURE:
<223> OTHER INFORMATION: Vb22 VH HCDR3

<400> SEQUENCE: 148

Gly Gly Leu Leu Arg Asp Val
1 5

<210> SEQ ID NO 149
<211> LENGTH: 128
<212> TYPE: PRT
<213> ORGANISM: Artificial Sequence
<220> FEATURE:
<223> OTHER INFORMATION: Vb22 VL

<400> SEQUENCE: 149

Met Ala Trp Ile Ser Leu Ile Leu Ser Leu Leu Ala Leu Ser Ser Gly
1 5 10 15

Ala Ile Ser Gln Ala Val Val Thr Gln Glu Ser Ala Leu Thr Thr Ser
20 25 30

Pro Gly Glu Thr Val Thr Leu Thr Cys Arg Ser Ser Thr Gly Ala Val
35 40 45

Thr Thr Ser Asn Tyr Ala Asn Trp Val Gln Glu Lys Pro Asp His Leu
50 55 60

Phe Thr Gly Leu Ile Gly Gly Thr Asn Asn Arg Ala Pro Gly Val Pro
65 70 75 80

Ala Arg Phe Ser Gly Ser Leu Ile Gly Asp Arg Ala Ala Leu Thr Ile
85 90 95

Thr Gly Ala Gln Thr Glu Asp Glu Ala Ile Tyr Phe Cys Ala Leu Trp
100 105 110

Tyr Ser Asn His Trp Val Phe Gly Gly Gly Thr Lys Leu Thr Val Leu
115 120 125

<210> SEQ ID NO 150
<211> LENGTH: 14
<212> TYPE: PRT
<213> ORGANISM: Artificial Sequence
<220> FEATURE:
<223> OTHER INFORMATION: Vb22 VL LCDR1

<400> SEQUENCE: 150

Arg Ser Ser Thr Gly Ala Val Thr Thr Ser Asn Tyr Ala Asn
1 5 10

<210> SEQ ID NO 151
<211> LENGTH: 7
<212> TYPE: PRT
<213> ORGANISM: Artificial Sequence
<220> FEATURE:
<223> OTHER INFORMATION: Vb22 VL LCDR2

<400> SEQUENCE: 151

Gly Thr Asn Asn Arg Ala Pro
1 5

<210> SEQ ID NO 152

<211> LENGTH: 9
<212> TYPE: PRT
<213> ORGANISM: Artificial Sequence
<220> FEATURE:
<223> OTHER INFORMATION: Vb22 VL LCDR3

<400> SEQUENCE: 152

Ala Leu Trp Tyr Ser Asn His Trp Val
1 5

<210> SEQ ID NO 153
<211> LENGTH: 468
<212> TYPE: PRT
<213> ORGANISM: Artificial Sequence
<220> FEATURE:
<223> OTHER INFORMATION: Vb12HL-28z

<400> SEQUENCE: 153

Glu Val Met Leu Val Glu Ser Gly Gly Gly Leu Val Lys Pro Gly Gly
1 5 10 15

Ser Leu Lys Leu Ser Cys Ala Ala Ser Gly Phe Thr Phe Arg Ser Tyr
20 25 30

Ala Met Ser Trp Val Arg Gln Thr Pro Glu Lys Arg Leu Glu Trp Val
35 40 45

Ala Thr Ile Ser Ser Gly Gly Ser Tyr Thr Asn Tyr Pro Asp Ser Val
50 55 60

Lys Gly Arg Phe Thr Ile Ser Arg Asp Asn Ala Lys Asn Thr Leu Asn
65 70 75 80

Leu Gln Met Asn Ser Leu Arg Ser Glu Asp Thr Ala Met Tyr Tyr Cys
85 90 95

Ala Arg Gly Tyr His Gly Tyr Leu Asp Val Trp Gly Ala Gly Thr Thr
100 105 110

Val Thr Val Ser Ser Gly Gly Gly Gly Ser Gly Gly Gly Gly Ser Gly
115 120 125

Gly Gly Gly Ser Asp Ile Leu Leu Thr Gln Ser Pro Ala Phe Leu Ser
130 135 140

Val Ser Pro Gly Glu Arg Val Ser Phe Ser Cys Arg Ala Ser Gln Ser
145 150 155 160

Ile Gly Thr Ser Ile His Trp Tyr Gln Gln Arg Thr Asn Gly Ser Pro
165 170 175

Arg Leu Leu Ile Lys Tyr Ala Ser Glu Ser Phe Ser Gly Ile Pro Ser
180 185 190

Arg Phe Ser Gly Ser Gly Ser Gly Thr Asp Phe Thr Leu Ser Ile Ser
195 200 205

Ser Val Glu Ser Glu Asp Ile Ala Asp Tyr Tyr Cys Gln Gln Ser Tyr
210 215 220

Ser Trp Pro Tyr Thr Phe Gly Gly Gly Thr Lys Leu Glu Ile Lys Ala
225 230 235 240

Ser Thr Thr Thr Pro Ala Pro Arg Pro Pro Thr Pro Ala Pro Thr Ile
245 250 255

Ala Ser Gln Pro Leu Ser Leu Arg Pro Glu Ala Cys Arg Pro Ala Ala
260 265 270

Gly Gly Ala Val His Thr Arg Gly Leu Asp Phe Ala Cys Asp Phe Trp
275 280 285

Val Leu Val Val Val Gly Gly Val Leu Ala Cys Tyr Ser Leu Leu Val
290 295 300

Thr Val Ala Phe Ile Ile Phe Trp Val Arg Ser Lys Arg Ser Arg Leu 305 310 315 320

Leu His Ser Asp Tyr Met Asn Met Thr Pro Arg Arg Pro Gly Pro Thr
325 330 335

Arg Lys His Tyr Gln Pro Tyr Ala Pro Pro Arg Asp Phe Ala Ala Tyr
340 345 350

Arg Ser Ile Asp Arg Val Lys Phe Ser Arg Ser Ala Asp Ala Pro Ala
355 360 365

Tyr Gln Gln Gly Gln Asn Gln Leu Tyr Asn Glu Leu Asn Leu Gly Arg
370 375 380

Arg Glu Glu Tyr Asp Val Leu Asp Lys Arg Arg Gly Arg Asp Pro Glu
385 390 395 400

Met Gly Gly Lys Pro Arg Arg Lys Asn Pro Gln Glu Gly Leu Tyr Asn
405 410 415

Glu Leu Gln Lys Asp Lys Met Ala Glu Ala Tyr Ser Glu Ile Gly Met
420 425 430

Lys Gly Glu Arg Arg Arg Gly Lys Gly His Asp Gly Leu Tyr Gln Gly
435 440 445

Leu Ser Thr Ala Thr Lys Asp Thr Tyr Asp Ala Leu His Met Gln Ala
450 455 460

Leu Pro Pro Arg
465

<210> SEQ ID NO 154
<211> LENGTH: 464
<212> TYPE: PRT
<213> ORGANISM: Artificial Sequence
<220> FEATURE:
<223> OTHER INFORMATION: Vb12HL-BBz

<400> SEQUENCE: 154

Glu Val Met Leu Val Glu Ser Gly Gly Gly Leu Val Lys Pro Gly Gly
1 5 10 15

Ser Leu Lys Leu Ser Cys Ala Ala Ser Gly Phe Thr Phe Arg Ser Tyr
20 25 30

Ala Met Ser Trp Val Arg Gln Thr Pro Glu Lys Arg Leu Glu Trp Val
35 40 45

Ala Thr Ile Ser Ser Gly Gly Ser Tyr Thr Asn Tyr Pro Asp Ser Val
50 55 60

Lys Gly Arg Phe Thr Ile Ser Arg Asp Asn Ala Lys Asn Thr Leu Asn
65 70 75 80

Leu Gln Met Asn Ser Leu Arg Ser Glu Asp Thr Ala Met Tyr Tyr Cys
85 90 95

Ala Arg Gly Tyr His Gly Tyr Leu Asp Val Trp Gly Ala Gly Thr Thr
100 105 110

Val Thr Val Ser Ser Gly Gly Gly Gly Ser Gly Gly Gly Gly Ser Gly
115 120 125

Gly Gly Gly Ser Asp Ile Leu Leu Thr Gln Ser Pro Ala Phe Leu Ser
130 135 140

Val Ser Pro Gly Glu Arg Val Ser Phe Ser Cys Arg Ala Ser Gln Ser
145 150 155 160

Ile Gly Thr Ser Ile His Trp Tyr Gln Gln Arg Thr Asn Gly Ser Pro
165 170 175

Arg Leu Leu Ile Lys Tyr Ala Ser Glu Ser Phe Ser Gly Ile Pro Ser
180 185 190

Arg Phe Ser Gly Ser Gly Ser Gly Thr Asp Phe Thr Leu Ser Ile Ser

```
        195                 200                 205

Ser Val Glu Ser Glu Asp Ile Ala Asp Tyr Tyr Cys Gln Gln Ser Tyr
    210                 215                 220

Ser Trp Pro Tyr Thr Phe Gly Gly Gly Thr Lys Leu Glu Ile Lys Ala
225                 230                 235                 240

Ser Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Ile Tyr
        275                 280                 285

Ile Trp Ala Pro Leu Ala Gly Thr Cys Gly Val Leu Leu Leu Ser Leu
    290                 295                 300

Val Ile Thr Leu Tyr Cys Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Lys Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460


<210> SEQ ID NO 155
<211> LENGTH: 318
<212> TYPE: PRT
<213> ORGANISM: Artificial Sequence
<220> FEATURE:
<223> OTHER INFORMATION: Vb12HL-Dz

<400> SEQUENCE: 155

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Arg Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Asn Tyr Pro Asp Ser Val
    50                  55                  60

Lys Gly Arg Phe Thr Ile Ser Arg Asp Asn Ala Lys Asn Thr Leu Asn
65                  70                  75                  80

Leu Gln Met Asn Ser Leu Arg Ser Glu Asp Thr Ala Met Tyr Tyr Cys
                85                  90                  95

Ala Arg Gly Tyr His Gly Tyr Leu Asp Val Trp Gly Ala Gly Thr Thr
```

```
            100                 105                 110

Val Thr Val Ser Ser Gly Gly Gly Gly Ser Gly Gly Gly Gly Ser Gly
        115                 120                 125

Gly Gly Gly Ser Asp Ile Leu Leu Thr Gln Ser Pro Ala Phe Leu Ser
    130                 135                 140

Val Ser Pro Gly Glu Arg Val Ser Phe Ser Cys Arg Ala Ser Gln Ser
145                 150                 155                 160

Ile Gly Thr Ser Ile His Trp Tyr Gln Gln Arg Thr Asn Gly Ser Pro
                165                 170                 175

Arg Leu Leu Ile Lys Tyr Ala Ser Glu Ser Phe Ser Gly Ile Pro Ser
            180                 185                 190

Arg Phe Ser Gly Ser Gly Ser Gly Thr Asp Phe Thr Leu Ser Ile Ser
        195                 200                 205

Ser Val Glu Ser Glu Asp Ile Ala Asp Tyr Tyr Cys Gln Gln Ser Tyr
    210                 215                 220

Ser Trp Pro Tyr Thr Phe Gly Gly Gly Thr Lys Leu Glu Ile Lys Ala
225                 230                 235                 240

Ser Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser
305                 310                 315


<210> SEQ ID NO 156
<211> LENGTH: 468
<212> TYPE: PRT
<213> ORGANISM: Artificial Sequence
<220> FEATURE:
<223> OTHER INFORMATION: Vb12LH-28z

<400> SEQUENCE: 156

Asp Ile Leu Leu Thr Gln Ser Pro Ala Phe Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Phe Ser Gly Ile Pro Ser Arg Phe Ser Gly
    50                  55                  60

Ser Gly Ser Gly Thr Asp Phe Thr Leu Ser Ile Ser Ser Val Glu Ser
65                  70                  75                  80

Glu Asp Ile Ala Asp Tyr Tyr Cys Gln Gln Ser Tyr Ser Trp Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Gly Ser Glu Val Met Leu Val Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Arg Ser Tyr Ala Met Ser Trp Val Arg
```

```
145                 150                 155                 160

Gln Thr Pro Glu Lys Arg Leu Glu Trp Val Ala Thr Ile Ser Ser Gly
                165                 170                 175

Gly Ser Tyr Thr Asn Tyr Pro Asp Ser Val Lys Gly Arg Phe Thr Ile
            180                 185                 190

Ser Arg Asp Asn Ala Lys Asn Thr Leu Asn Leu Gln Met Asn Ser Leu
        195                 200                 205

Arg Ser Glu Asp Thr Ala Met Tyr Tyr Cys Ala Arg Gly Tyr His Gly
    210                 215                 220

Tyr Leu Asp Val Trp Gly Ala Gly Thr Thr Val Thr Val Ser Ser Ala
225                 230                 235                 240

Ser Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Ile Asp Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg
465


<210> SEQ ID NO 157
<211> LENGTH: 464
<212> TYPE: PRT
<213> ORGANISM: Artificial Sequence
<220> FEATURE:
<223> OTHER INFORMATION: Vb12LH-BBz

<400> SEQUENCE: 157

Asp Ile Leu Leu Thr Gln Ser Pro Ala Phe Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
```

```
        35                  40                  45

Lys Tyr Ala Ser Glu Ser Phe Ser Gly Ile Pro Ser Arg Phe Ser Gly
    50                  55                  60

Ser Gly Ser Gly Thr Asp Phe Thr Leu Ser Ile Ser Ser Val Glu Ser
65                  70                  75                  80

Glu Asp Ile Ala Asp Tyr Tyr Cys Gln Gln Ser Tyr Ser Trp Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Gly Ser Glu Val Met Leu Val Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Arg Ser Tyr Ala Met Ser Trp Val Arg
145                 150                 155                 160

Gln Thr Pro Glu Lys Arg Leu Glu Trp Val Ala Thr Ile Ser Ser Gly
                165                 170                 175

Gly Ser Tyr Thr Asn Tyr Pro Asp Ser Val Lys Gly Arg Phe Thr Ile
            180                 185                 190

Ser Arg Asp Asn Ala Lys Asn Thr Leu Asn Leu Gln Met Asn Ser Leu
        195                 200                 205

Arg Ser Glu Asp Thr Ala Met Tyr Tyr Cys Ala Arg Gly Tyr His Gly
    210                 215                 220

Tyr Leu Asp Val Trp Gly Ala Gly Thr Thr Val Thr Val Ser Ser Ala
225                 230                 235                 240

Ser Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Ile Tyr
        275                 280                 285

Ile Trp Ala Pro Leu Ala Gly Thr Cys Gly Val Leu Leu Leu Ser Leu
    290                 295                 300

Val Ile Thr Leu Tyr Cys Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Lys Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460
```

<210> SEQ ID NO 158
<211> LENGTH: 318
<212> TYPE: PRT
<213> ORGANISM: Artificial Sequence
<220> FEATURE:
<223> OTHER INFORMATION: Vb12LH-Dz

<400> SEQUENCE: 158

Asp Ile Leu Leu Thr Gln Ser Pro Ala Phe Leu Ser Val Ser Pro Gly
1 5 10 15

Glu Arg Val Ser Phe Ser Cys Arg Ala Ser Gln Ser Ile Gly Thr Ser
20 25 30

Ile His Trp Tyr Gln Gln Arg Thr Asn Gly Ser Pro Arg Leu Leu Ile
35 40 45

Lys Tyr Ala Ser Glu Ser Phe Ser Gly Ile Pro Ser Arg Phe Ser Gly
50 55 60

Ser Gly Ser Gly Thr Asp Phe Thr Leu Ser Ile Ser Ser Val Glu Ser
65 70 75 80

Glu Asp Ile Ala Asp Tyr Tyr Cys Gln Gln Ser Tyr Ser Trp Pro Tyr
85 90 95

Thr Phe Gly Gly Gly Thr Lys Leu Glu Ile Lys Gly Gly Gly Gly Ser
100 105 110

Gly Gly Gly Gly Ser Gly Gly Gly Gly Ser Glu Val Met Leu Val Glu
115 120 125

Ser Gly Gly Gly Leu Val Lys Pro Gly Gly Ser Leu Lys Leu Ser Cys
130 135 140

Ala Ala Ser Gly Phe Thr Phe Arg Ser Tyr Ala Met Ser Trp Val Arg
145 150 155 160

Gln Thr Pro Glu Lys Arg Leu Glu Trp Val Ala Thr Ile Ser Ser Gly
165 170 175

Gly Ser Tyr Thr Asn Tyr Pro Asp Ser Val Lys Gly Arg Phe Thr Ile
180 185 190

Ser Arg Asp Asn Ala Lys Asn Thr Leu Asn Leu Gln Met Asn Ser Leu
195 200 205

Arg Ser Glu Asp Thr Ala Met Tyr Tyr Cys Ala Arg Gly Tyr His Gly
210 215 220

Tyr Leu Asp Val Trp Gly Ala Gly Thr Thr Val Thr Val Ser Ser Ala
225 230 235 240

Ser Thr Thr Thr Pro Ala Pro Arg Pro Pro Thr Pro Ala Pro Thr Ile
245 250 255

Ala Ser Gln Pro Leu Ser Leu Arg Pro Glu Ala Cys Arg Pro Ala Ala
260 265 270

Gly Gly Ala Val His Thr Arg Gly Leu Asp Phe Ala Cys Asp Phe Trp
275 280 285

Val Leu Val Val Val Gly Gly Val Leu Ala Cys Tyr Ser Leu Leu Val
290 295 300

Thr Val Ala Phe Ile Ile Phe Trp Val Arg Ser Lys Arg Ser
305 310 315

<210> SEQ ID NO 159
<211> LENGTH: 508
<212> TYPE: PRT
<213> ORGANISM: Artificial Sequence
<220> FEATURE:
<223> OTHER INFORMATION: Vb9HL-28z

<400> SEQUENCE: 159

```
Met Lys Phe Ser Trp Val Ile Phe Phe Leu Met Ala Val Val Thr Gly
1               5                   10                  15

Val Asn Ser Glu Val Gln Leu Gln Gln Ser Val Ala Glu Leu Val Arg
            20                  25                  30

Pro Gly Ala Ser Val Lys Leu Ser Cys Thr Ala Ser Gly Phe Asn Ile
        35                  40                  45

Lys Asn Thr Phe Met His Trp Val Lys Gln Arg Pro Glu Gln Gly Leu
    50                  55                  60

Glu Trp Ile Gly Arg Ile Asp Pro Thr Asn Gly Tyr Thr Lys Phe Ala
65                  70                  75                  80

Pro Lys Phe Gln Gly Lys Ala Thr Leu Thr Ala Val Thr Ser Ser Asn
                85                  90                  95

Thr Val Tyr Leu Gln Leu Ser Ser Leu Thr Ser Glu Asp Thr Ala Ile
            100                 105                 110

Tyr Tyr Cys Ala His Asp Tyr Asp Ala Pro Trp Phe Ala Tyr Trp Gly
        115                 120                 125

Gln Gly Thr Leu Val Ile Val Ser Ala Gly Gly Gly Gly Ser Gly Gly
    130                 135                 140

Gly Gly Ser Gly Gly Gly Gly Ser Met Leu Ser Pro Ala Pro Leu Leu
145                 150                 155                 160

Ser Leu Leu Leu Leu Cys Val Ser Asp Ser Arg Ala Glu Thr Thr Val
                165                 170                 175

Thr Gln Ser Pro Ala Ser Leu Ser Val Ala Thr Gly Glu Lys Val Thr
            180                 185                 190

Ile Arg Cys Ile Ser Ser Thr Asp Ile Asp Asp Asp Met Asn Trp Tyr
        195                 200                 205

Gln Gln Lys Ser Gly Glu Pro Pro Lys Leu Leu Ile Ser Glu Gly Asn
    210                 215                 220

Thr Leu Arg Pro Gly Val Pro Ser Arg Phe Ser Ser Ser Gly Tyr Gly
225                 230                 235                 240

Thr Asp Phe Val Phe Thr Ile Glu Asn Met Leu Ser Glu Asp Val Ala
                245                 250                 255

Asp Tyr Tyr Cys Leu Gln Ser Asp Asn Met Pro Leu Thr Phe Gly Ala
            260                 265                 270

Gly Thr Lys Leu Glu Leu Lys Ala Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Ile Asp Arg Val Lys Phe
385                 390                 395                 400

Ser Arg Ser Ala Asp Ala Pro Ala Tyr Gln Gln Gly Gln Asn Gln Leu
                405                 410                 415
```

```
Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505


<210> SEQ ID NO 160
<211> LENGTH: 504
<212> TYPE: PRT
<213> ORGANISM: Artificial Sequence
<220> FEATURE:
<223> OTHER INFORMATION: Vb9HL-BBz

<400> SEQUENCE: 160

Met Lys Phe Ser Trp Val Ile Phe Phe Leu Met Ala Val Val Thr Gly
1               5                   10                  15

Val Asn Ser Glu Val Gln Leu Gln Gln Ser Val Ala Glu Leu Val Arg
            20                  25                  30

Pro Gly Ala Ser Val Lys Leu Ser Cys Thr Ala Ser Gly Phe Asn Ile
        35                  40                  45

Lys Asn Thr Phe Met His Trp Val Lys Gln Arg Pro Glu Gln Gly Leu
    50                  55                  60

Glu Trp Ile Gly Arg Ile Asp Pro Thr Asn Gly Tyr Thr Lys Phe Ala
65                  70                  75                  80

Pro Lys Phe Gln Gly Lys Ala Thr Leu Thr Ala Val Thr Ser Ser Asn
                85                  90                  95

Thr Val Tyr Leu Gln Leu Ser Ser Leu Thr Ser Glu Asp Thr Ala Ile
            100                 105                 110

Tyr Tyr Cys Ala His Asp Tyr Asp Ala Pro Trp Phe Ala Tyr Trp Gly
        115                 120                 125

Gln Gly Thr Leu Val Ile Val Ser Ala Gly Gly Gly Gly Ser Gly Gly
    130                 135                 140

Gly Gly Ser Gly Gly Gly Gly Ser Met Leu Ser Pro Ala Pro Leu Leu
145                 150                 155                 160

Ser Leu Leu Leu Leu Cys Val Ser Asp Ser Arg Ala Glu Thr Thr Val
                165                 170                 175

Thr Gln Ser Pro Ala Ser Leu Ser Val Ala Thr Gly Glu Lys Val Thr
            180                 185                 190

Ile Arg Cys Ile Ser Ser Thr Asp Ile Asp Asp Asp Met Asn Trp Tyr
        195                 200                 205

Gln Gln Lys Ser Gly Glu Pro Pro Lys Leu Leu Ile Ser Glu Gly Asn
    210                 215                 220

Thr Leu Arg Pro Gly Val Pro Ser Arg Phe Ser Ser Ser Gly Tyr Gly
225                 230                 235                 240

Thr Asp Phe Val Phe Thr Ile Glu Asn Met Leu Ser Glu Asp Val Ala
                245                 250                 255

Asp Tyr Tyr Cys Leu Gln Ser Asp Asn Met Pro Leu Thr Phe Gly Ala
            260                 265                 270
```

```
Gly Thr Lys Leu Glu Leu Lys Ala Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Lys Arg
            340                 345                 350

Gly Arg Lys Lys Leu Leu Tyr Ile Phe Lys Gln Pro Phe Met Arg Pro
        355                 360                 365

Val Gln Thr Thr Gln Glu Glu Asp Gly Cys Ser Cys Arg Phe Pro Glu
    370                 375                 380

Glu Glu Glu Gly Gly Cys Glu Leu Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500
```

<210> SEQ ID NO 161
<211> LENGTH: 468
<212> TYPE: PRT
<213> ORGANISM: Artificial Sequence
<220> FEATURE:
<223> OTHER INFORMATION: VB9HL-Dz

<400> SEQUENCE: 161

```
Asp Ile Leu Leu Thr Gln Ser Pro Ala Phe Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Phe Ser Gly Ile Pro Ser Arg Phe Ser Gly
    50                  55                  60

Ser Gly Ser Gly Thr Asp Phe Thr Leu Ser Ile Ser Ser Val Glu Ser
65                  70                  75                  80

Glu Asp Ile Ala Asp Tyr Tyr Cys Gln Gln Ser Tyr Ser Trp Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Gly Ser Glu Val Met Leu Val Glu
        115                 120                 125
```

Ser Gly Gly Gly Leu Val Lys Pro Gly Gly Ser Leu Lys Leu Ser Cys
    130                 135                 140

Ala Ala Ser Gly Phe Thr Phe Arg Ser Tyr Ala Met Ser Trp Val Arg
145                 150                 155                 160

Gln Thr Pro Glu Lys Arg Leu Glu Trp Val Ala Thr Ile Ser Ser Gly
                165                 170                 175

Gly Ser Tyr Thr Asn Tyr Pro Asp Ser Val Lys Gly Arg Phe Thr Ile
            180                 185                 190

Ser Arg Asp Asn Ala Lys Asn Thr Leu Asn Leu Gln Met Asn Ser Leu
        195                 200                 205

Arg Ser Glu Asp Thr Ala Met Tyr Tyr Cys Ala Arg Gly Tyr His Gly
    210                 215                 220

Tyr Leu Asp Val Trp Gly Ala Gly Thr Thr Val Thr Val Ser Ser Ala
225                 230                 235                 240

Ser Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Ile Asp Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 162
<211> LENGTH: 508
<212> TYPE: PRT
<213> ORGANISM: Artificial Sequence
<220> FEATURE:
<223> OTHER INFORMATION: Vb9LH-28z

<400> SEQUENCE: 162

Met Leu Ser Pro Ala Pro Leu Leu Ser Leu Leu Leu Leu Cys Val Ser
1               5                   10                  15

```
Asp Ser Arg Ala Glu Thr Thr Val Thr Gln Ser Pro Ala Ser Leu Ser
            20                  25                  30

Val Ala Thr Gly Glu Lys Val Thr Ile Arg Cys Ile Ser Ser Thr Asp
        35                  40                  45

Ile Asp Asp Asp Met Asn Trp Tyr Gln Gln Lys Ser Gly Glu Pro Pro
    50                  55                  60

Lys Leu Leu Ile Ser Glu Gly Asn Thr Leu Arg Pro Gly Val Pro Ser
65                  70                  75                  80

Arg Phe Ser Ser Ser Gly Tyr Gly Thr Asp Phe Val Phe Thr Ile Glu
                85                  90                  95

Asn Met Leu Ser Glu Asp Val Ala Asp Tyr Tyr Cys Leu Gln Ser Asp
            100                 105                 110

Asn Met Pro Leu Thr Phe Gly Ala Gly Thr Lys Leu Glu Leu Lys Gly
        115                 120                 125

Gly Gly Gly Ser Gly Gly Gly Gly Ser Gly Gly Gly Gly Ser Met Lys
    130                 135                 140

Phe Ser Trp Val Ile Phe Phe Leu Met Ala Val Val Thr Gly Val Asn
145                 150                 155                 160

Ser Glu Val Gln Leu Gln Gln Ser Val Ala Glu Leu Val Arg Pro Gly
                165                 170                 175

Ala Ser Val Lys Leu Ser Cys Thr Ala Ser Gly Phe Asn Ile Lys Asn
            180                 185                 190

Thr Phe Met His Trp Val Lys Gln Arg Pro Glu Gln Gly Leu Glu Trp
        195                 200                 205

Ile Gly Arg Ile Asp Pro Thr Asn Gly Tyr Thr Lys Phe Ala Pro Lys
    210                 215                 220

Phe Gln Gly Lys Ala Thr Leu Thr Ala Val Thr Ser Ser Asn Thr Val
225                 230                 235                 240

Tyr Leu Gln Leu Ser Ser Leu Thr Ser Glu Asp Thr Ala Ile Tyr Tyr
                245                 250                 255

Cys Ala His Asp Tyr Asp Ala Pro Trp Phe Ala Tyr Trp Gly Gln Gly
            260                 265                 270

Thr Leu Val Ile Val Ser Ala Ala Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Ile Asp Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430
```

```
Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505


<210> SEQ ID NO 163
<211> LENGTH: 504
<212> TYPE: PRT
<213> ORGANISM: Artificial Sequence
<220> FEATURE:
<223> OTHER INFORMATION: Vb9LH-BBz

<400> SEQUENCE: 163

Met Leu Ser Pro Ala Pro Leu Leu Ser Leu Leu Leu Leu Cys Val Ser
1               5                   10                  15

Asp Ser Arg Ala Glu Thr Thr Val Thr Gln Ser Pro Ala Ser Leu Ser
            20                  25                  30

Val Ala Thr Gly Glu Lys Val Thr Ile Arg Cys Ile Ser Ser Thr Asp
        35                  40                  45

Ile Asp Asp Asp Met Asn Trp Tyr Gln Gln Lys Ser Gly Glu Pro Pro
    50                  55                  60

Lys Leu Leu Ile Ser Glu Gly Asn Thr Leu Arg Pro Gly Val Pro Ser
65                  70                  75                  80

Arg Phe Ser Ser Ser Gly Tyr Gly Thr Asp Phe Val Phe Thr Ile Glu
                85                  90                  95

Asn Met Leu Ser Glu Asp Val Ala Asp Tyr Tyr Cys Leu Gln Ser Asp
            100                 105                 110

Asn Met Pro Leu Thr Phe Gly Ala Gly Thr Lys Leu Glu Leu Lys Gly
        115                 120                 125

Gly Gly Gly Ser Gly Gly Gly Gly Ser Gly Gly Gly Gly Ser Met Lys
    130                 135                 140

Phe Ser Trp Val Ile Phe Phe Leu Met Ala Val Val Thr Gly Val Asn
145                 150                 155                 160

Ser Glu Val Gln Leu Gln Gln Ser Val Ala Glu Leu Val Arg Pro Gly
                165                 170                 175

Ala Ser Val Lys Leu Ser Cys Thr Ala Ser Gly Phe Asn Ile Lys Asn
            180                 185                 190

Thr Phe Met His Trp Val Lys Gln Arg Pro Glu Gln Gly Leu Glu Trp
        195                 200                 205

Ile Gly Arg Ile Asp Pro Thr Asn Gly Tyr Thr Lys Phe Ala Pro Lys
    210                 215                 220

Phe Gln Gly Lys Ala Thr Leu Thr Ala Val Thr Ser Ser Asn Thr Val
225                 230                 235                 240

Tyr Leu Gln Leu Ser Ser Leu Thr Ser Glu Asp Thr Ala Ile Tyr Tyr
                245                 250                 255

Cys Ala His Asp Tyr Asp Ala Pro Trp Phe Ala Tyr Trp Gly Gln Gly
            260                 265                 270

Thr Leu Val Ile Val Ser Ala Ala Ser Thr Thr Thr Pro Ala Pro Arg
        275                 280                 285
```

```
Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Lys Arg
            340                 345                 350

Gly Arg Lys Lys Leu Leu Tyr Ile Phe Lys Gln Pro Phe Met Arg Pro
        355                 360                 365

Val Gln Thr Thr Gln Glu Glu Asp Gly Cys Ser Cys Arg Phe Pro Glu
    370                 375                 380

Glu Glu Glu Gly Gly Cys Glu Leu Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500
```

<210> SEQ ID NO 164
<211> LENGTH: 358
<212> TYPE: PRT
<213> ORGANISM: Artificial Sequence
<220> FEATURE:
<223> OTHER INFORMATION: Vb9LH-Dz

<400> SEQUENCE: 164

```
Met Leu Ser Pro Ala Pro Leu Leu Ser Leu Leu Leu Leu Cys Val Ser
1               5                   10                  15

Asp Ser Arg Ala Glu Thr Thr Val Thr Gln Ser Pro Ala Ser Leu Ser
            20                  25                  30

Val Ala Thr Gly Glu Lys Val Thr Ile Arg Cys Ile Ser Ser Thr Asp
        35                  40                  45

Ile Asp Asp Asp Met Asn Trp Tyr Gln Gln Lys Ser Gly Glu Pro Pro
    50                  55                  60

Lys Leu Leu Ile Ser Glu Gly Asn Thr Leu Arg Pro Gly Val Pro Ser
65                  70                  75                  80

Arg Phe Ser Ser Ser Gly Tyr Gly Thr Asp Phe Val Phe Thr Ile Glu
                85                  90                  95

Asn Met Leu Ser Glu Asp Val Ala Asp Tyr Tyr Cys Leu Gln Ser Asp
            100                 105                 110

Asn Met Pro Leu Thr Phe Gly Ala Gly Thr Lys Leu Glu Leu Lys Gly
        115                 120                 125

Gly Gly Gly Ser Gly Gly Gly Gly Ser Gly Gly Gly Gly Ser Met Lys
    130                 135                 140
```

Phe Ser Trp Val Ile Phe Phe Leu Met Ala Val Val Thr Gly Val Asn
145 150 155 160

Ser Glu Val Gln Leu Gln Gln Ser Val Ala Glu Leu Val Arg Pro Gly
165 170 175

Ala Ser Val Lys Leu Ser Cys Thr Ala Ser Gly Phe Asn Ile Lys Asn
180 185 190

Thr Phe Met His Trp Val Lys Gln Arg Pro Glu Gln Gly Leu Glu Trp
195 200 205

Ile Gly Arg Ile Asp Pro Thr Asn Gly Tyr Thr Lys Phe Ala Pro Lys
210 215 220

Phe Gln Gly Lys Ala Thr Leu Thr Ala Val Thr Ser Ser Asn Thr Val
225 230 235 240

Tyr Leu Gln Leu Ser Ser Leu Thr Ser Glu Asp Thr Ala Ile Tyr Tyr
245 250 255

Cys Ala His Asp Tyr Asp Ala Pro Trp Phe Ala Tyr Trp Gly Gln Gly
260 265 270

Thr Leu Val Ile Val Ser Ala Ala Ser Thr Thr Thr Pro Ala Pro Arg
275 280 285

Pro Pro Thr Pro Ala Pro Thr Ile Ala Ser Gln Pro Leu Ser Leu Arg
290 295 300

Pro Glu Ala Cys Arg Pro Ala Ala Gly Gly Ala Val His Thr Arg Gly
305 310 315 320

Leu Asp Phe Ala Cys Asp Phe Trp Val Leu Val Val Val Gly Gly Val
325 330 335

Leu Ala Cys Tyr Ser Leu Leu Val Thr Val Ala Phe Ile Ile Phe Trp
340 345 350

Val Arg Ser Lys Arg Ser
355

<210> SEQ ID NO 165
<211> LENGTH: 509
<212> TYPE: PRT
<213> ORGANISM: Artificial Sequence
<220> FEATURE:
<223> OTHER INFORMATION: Vb1HL-BBz

<400> SEQUENCE: 165

Met Asp Trp Val Trp Asn Leu Leu Phe Leu Met Ala Val Ala Gln Thr
1 5 10 15

Gly Ala Gln Ala Gln Leu Gln Leu Val Gln Ser Gly Pro Glu Leu Arg
20 25 30

Glu Pro Gly Glu Ser Val Lys Ile Ser Cys Lys Ala Ser Gly Tyr Thr
35 40 45

Phe Thr Asp Tyr Ile Val His Trp Val Lys Gln Ala Pro Gly Lys Gly
50 55 60

Leu Lys Trp Met Gly Trp Ile Asn Thr Tyr Thr Gly Thr Pro Thr Tyr
65 70 75 80

Ala Asp Asp Phe Glu Gly Arg Phe Val Phe Ser Leu Glu Ala Ser Ala
85 90 95

Ser Thr Ala Asn Leu Gln Ile Ser Asn Leu Lys Asn Glu Asp Thr Ala
100 105 110

Thr Tyr Phe Cys Ala Arg Ser Trp Arg Arg Gly Ile Arg Gly Ile Gly
115 120 125

Phe Asp Tyr Trp Gly Gln Gly Val Met Val Thr Val Ser Ser Gly Gly
130 135 140

```
Gly Gly Ser Gly Gly Gly Gly Ser Gly Gly Gly Gly Ser Met Arg Val
145                 150                 155                 160

Gln Ile Gln Phe Trp Gly Leu Leu Leu Leu Trp Thr Ser Gly Ile Gln
                165                 170                 175

Cys Asp Val Gln Met Thr Gln Ser Pro Tyr Asn Leu Ala Ala Ser Pro
            180                 185                 190

Gly Glu Ser Val Ser Ile Asn Cys Lys Ala Ser Lys Ser Ile Asn Lys
        195                 200                 205

Tyr Leu Ala Trp Tyr Gln Gln Lys Pro Gly Lys Pro Asn Lys Leu Leu
    210                 215                 220

Ile Tyr Asp Gly Ser Thr Leu Gln Ser Gly Ile Pro Ser Arg Phe Ser
225                 230                 235                 240

Gly Ser Gly Ser Gly Thr Asp Phe Thr Leu Thr Ile Arg Gly Leu Glu
                245                 250                 255

Pro Glu Asp Phe Gly Leu Tyr Tyr Cys Gln Gln His Asn Glu Tyr Pro
            260                 265                 270

Pro Thr Phe Gly Ala Gly Thr Lys Leu Glu Leu Lys Ala Ser Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505
```

<210> SEQ ID NO 166
<211> LENGTH: 509
<212> TYPE: PRT
<213> ORGANISM: Artificial Sequence
<220> FEATURE:
<223> OTHER INFORMATION: Vb1LH-BBz

<400> SEQUENCE: 166

```
Met Arg Val Gln Ile Gln Phe Trp Gly Leu Leu Leu Leu Trp Thr Ser
1               5                   10                  15

Gly Ile Gln Cys Asp Val Gln Met Thr Gln Ser Pro Tyr Asn Leu Ala
            20                  25                  30

Ala Ser Pro Gly Glu Ser Val Ser Ile Asn Cys Lys Ala Ser Lys Ser
        35                  40                  45

Ile Asn Lys Tyr Leu Ala Trp Tyr Gln Gln Lys Pro Gly Lys Pro Asn
    50                  55                  60

Lys Leu Leu Ile Tyr Asp Gly Ser Thr Leu Gln Ser Gly Ile Pro Ser
65                  70                  75                  80

Arg Phe Ser Gly Ser Gly Ser Gly Thr Asp Phe Thr Leu Thr Ile Arg
                85                  90                  95

Gly Leu Glu Pro Glu Asp Phe Gly Leu Tyr Tyr Cys Gln Gln His Asn
            100                 105                 110

Glu Tyr Pro Pro Thr Phe Gly Ala Gly Thr Lys Leu Glu Leu Lys Gly
        115                 120                 125

Gly Gly Gly Ser Gly Gly Gly Gly Ser Gly Gly Gly Gly Ser Met Asp
    130                 135                 140

Trp Val Trp Asn Leu Leu Phe Leu Met Ala Val Ala Gln Thr Gly Ala
145                 150                 155                 160

Gln Ala Gln Leu Gln Leu Val Gln Ser Gly Pro Glu Leu Arg Glu Pro
                165                 170                 175

Gly Glu Ser Val Lys Ile Ser Cys Lys Ala Ser Gly Tyr Thr Phe Thr
            180                 185                 190

Asp Tyr Ile Val His Trp Val Lys Gln Ala Pro Gly Lys Gly Leu Lys
        195                 200                 205

Trp Met Gly Trp Ile Asn Thr Tyr Thr Gly Thr Pro Thr Tyr Ala Asp
    210                 215                 220

Asp Phe Glu Gly Arg Phe Val Phe Ser Leu Glu Ala Ser Ala Ser Thr
225                 230                 235                 240

Ala Asn Leu Gln Ile Ser Asn Leu Lys Asn Glu Asp Thr Ala Thr Tyr
                245                 250                 255

Phe Cys Ala Arg Ser Trp Arg Arg Gly Ile Arg Gly Ile Gly Phe Asp
            260                 265                 270

Tyr Trp Gly Gln Gly Val Met Val Thr Val Ser Ser Ala Ser Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
```

```
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505


<210> SEQ ID NO 167
<211> LENGTH: 509
<212> TYPE: PRT
<213> ORGANISM: Artificial Sequence
<220> FEATURE:
<223> OTHER INFORMATION: Vb2HL-BBz

<400> SEQUENCE: 167

Met Lys Phe Ser Trp Val Ile Phe Phe Leu Met Ala Val Val Thr Gly
1               5                   10                  15

Val Asn Ser Glu Val Gln Leu Gln Gln Ser Val Ala Asp Leu Val Arg
            20                  25                  30

Pro Gly Ala Ser Leu Lys Leu Ser Cys Thr Ala Ser Gly Phe Asn Ile
        35                  40                  45

Lys Ser Ala Tyr Met His Trp Val Ile Gln Arg Pro Asp Gln Gly Pro
    50                  55                  60

Glu Cys Leu Gly Arg Ile Asp Pro Ala Thr Gly Lys Thr Lys Tyr Ala
65                  70                  75                  80

Pro Lys Phe Gln Ala Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Ile
            100                 105                 110

Tyr Tyr Cys Thr Arg Ser Leu Asn Trp Asp Tyr Gly Leu Asp Tyr Trp
        115                 120                 125

Gly Gln Gly Thr Ser Val Thr Val Ser Ser Gly Gly Gly Gly Ser Gly
    130                 135                 140

Gly Gly Gly Ser Gly Gly Gly Gly Ser Met Glu Thr Asp Thr Leu Leu
145                 150                 155                 160

Leu Trp Val Leu Leu Leu Trp Val Pro Gly Ser Thr Gly Asp Ile Val
                165                 170                 175

Leu Thr Gln Ser Pro Ala Ser Leu Ala Val Ser Leu Gly Gln Arg Ala
            180                 185                 190

Thr Ile Ser Cys Arg Ala Ser Lys Ser Val Ser Ile Leu Gly Thr His
        195                 200                 205

Leu Ile His Trp Tyr Gln Gln Lys Pro Gly Gln Pro Pro Lys Leu Leu
    210                 215                 220

Ile Tyr Ala Ala Ser Asn Leu Glu Ser Gly Val Pro Ala Arg Phe Ser
225                 230                 235                 240

Gly Ser Gly Ser Glu Thr Val Phe Thr Leu Asn Ile His Pro Val Glu
                245                 250                 255

Glu Glu Asp Ala Ala Thr Tyr Phe Cys Gln Gln Ser Ile Glu Asp Pro
            260                 265                 270

Trp Thr Phe Gly Gly Gly Thr Lys Leu Gly Ile Lys Ala Ser Thr Thr
```

```
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505


<210> SEQ ID NO 168
<211> LENGTH: 509
<212> TYPE: PRT
<213> ORGANISM: Artificial Sequence
<220> FEATURE:
<223> OTHER INFORMATION: Vb2LH-BBz

<400> SEQUENCE: 168

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Ile Leu Gly Thr His Leu Ile His Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Val Pro Ala Arg Phe Ser Gly Ser Gly Ser Glu Thr Val Phe Thr
                85                  90                  95

Leu Asn Ile His Pro Val Glu Glu Glu Asp Ala Ala Thr Tyr Phe Cys
            100                 105                 110

Gln Gln Ser Ile Glu Asp Pro Trp Thr Phe Gly Gly Gly Thr Lys Leu
        115                 120                 125

Gly Ile Lys Gly Gly Gly Gly Ser Gly Gly Gly Gly Ser Gly Gly Gly
```

```
    130                 135                 140

Gly Ser Met Lys Phe Ser Trp Val Ile Phe Phe Leu Met Ala Val Val
145                 150                 155                 160

Thr Gly Val Asn Ser Glu Val Gln Leu Gln Gln Ser Val Ala Asp Leu
                165                 170                 175

Val Arg Pro Gly Ala Ser Leu Lys Leu Ser Cys Thr Ala Ser Gly Phe
            180                 185                 190

Asn Ile Lys Ser Ala Tyr Met His Trp Val Ile Gln Arg Pro Asp Gln
        195                 200                 205

Gly Pro Glu Cys Leu Gly Arg Ile Asp Pro Ala Thr Gly Lys Thr Lys
    210                 215                 220

Tyr Ala Pro Lys Phe Gln Ala Lys Ala Thr Ile Thr Ala Asp Thr Ser
225                 230                 235                 240

Ser Asn Thr Ala Tyr Leu Gln Leu Ser Ser Leu Thr Ser Glu Asp Thr
                245                 250                 255

Ala Ile Tyr Tyr Cys Thr Arg Ser Leu Asn Trp Asp Tyr Gly Leu Asp
            260                 265                 270

Tyr Trp Gly Gln Gly Thr Ser Val Thr Val Ser Ser Ala Ser Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505
```

<210> SEQ ID NO 169
<211> LENGTH: 506
<212> TYPE: PRT
<213> ORGANISM: Artificial Sequence
<220> FEATURE:
<223> OTHER INFORMATION: Vb4HL-BBz

<400> SEQUENCE: 169

Met Glu Trp Ser Trp Ile Phe Leu Phe Leu Leu Ser Val Thr Ala Val
1               5                   10                  15

Val His Ser Gln Val Gln Leu Gln Gln Ser Gly Ala Glu Leu Ala Lys
            20                  25                  30

Pro Gly Thr Ser Val Lys Leu Ser Cys Lys Ala Ser Gly Tyr Thr Phe
        35                  40                  45

Thr Ser Tyr Tyr Ile Tyr Trp Val Lys Gln Arg Pro Gly Gln Gly Leu
    50                  55                  60

Glu Trp Leu Gly Tyr Ile Tyr Pro Gly Asn Gly Gly Thr Tyr Tyr Ser
65                  70                  75                  80

Glu Lys Phe Lys Gly Lys Ala Thr Phe Thr Ala Asp Thr Ser Ser Asn
                85                  90                  95

Thr Ala Tyr Met Leu Leu Gly Ser Leu Thr Pro Glu Asp Ser Ala Tyr
            100                 105                 110

Tyr Phe Cys Ala Arg Gly Ser Gly Asp Arg Tyr Asn Ser Leu Ala Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Met Ala Ile Pro Thr Gln
145                 150                 155                 160

Leu Leu Gly Leu Leu Leu Leu Trp Ile Thr Asp Ala Ile Cys Asp Ile
                165                 170                 175

Gln Met Thr Gln Ser Pro His Ser Leu Ser Ala Ser Leu Gly Glu Thr
            180                 185                 190

Val Ser Ile Glu Cys Leu Ala Ser Glu Gly Ile Ser Asn Phe Leu Ala
        195                 200                 205

Trp Tyr Gln Gln Lys Pro Gly Lys Ser Pro Gln Leu Leu Ile Tyr Tyr
    210                 215                 220

Thr Ser Ser Leu Gln Asp Gly Val Pro Ser Arg Phe Ser Gly Ser Gly
225                 230                 235                 240

Ser Gly Thr Gln Tyr Ser Leu Lys Ile Ser Asn Met Gln Pro Glu Asp
                245                 250                 255

Glu Gly Val Tyr Tyr Cys Gln Gln Gly Tyr Lys Phe Pro Arg Thr Phe
            260                 265                 270

Gly Gly Gly Thr Lys Leu Glu Leu Lys Ala Ser Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
            340                 345                 350

Lys Arg Gly Arg Lys Lys Leu Leu Tyr Ile Phe Lys Gln Pro Phe Met
        355                 360                 365

Arg Pro Val Gln Thr Thr Gln Glu Glu Asp Gly Cys Ser Cys Arg Phe
    370                 375                 380

Pro Glu Glu Glu Glu Gly Gly Cys Glu Leu Arg Val Lys Phe Ser Arg
385                 390                 395                 400

Ser Ala Asp Ala Pro Ala Tyr Gln Gln Gly Gln Asn Gln Leu Tyr Asn
                405                 410                 415

```
Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
        435                 440                 445

Gln Glu Gly Leu Tyr Asn Glu Leu Gln Lys Asp Lys Met Ala Glu Ala
    450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
            500                 505


<210> SEQ ID NO 170
<211> LENGTH: 506
<212> TYPE: PRT
<213> ORGANISM: Artificial Sequence
<220> FEATURE:
<223> OTHER INFORMATION: Vb4LH-BBz

<400> SEQUENCE: 170

Met Ala Ile Pro Thr Gln Leu Leu Gly Leu Leu Leu Leu Trp Ile Thr
1               5                   10                  15

Asp Ala Ile Cys Asp Ile Gln Met Thr Gln Ser Pro His Ser Leu Ser
            20                  25                  30

Ala Ser Leu Gly Glu Thr Val Ser Ile Glu Cys Leu Ala Ser Glu Gly
        35                  40                  45

Ile Ser Asn Phe Leu Ala Trp Tyr Gln Gln Lys Pro Gly Lys Ser Pro
    50                  55                  60

Gln Leu Leu Ile Tyr Tyr Thr Ser Ser Leu Gln Asp Gly Val Pro Ser
65                  70                  75                  80

Arg Phe Ser Gly Ser Gly Ser Gly Thr Gln Tyr Ser Leu Lys Ile Ser
                85                  90                  95

Asn Met Gln Pro Glu Asp Glu Gly Val Tyr Tyr Cys Gln Gln Gly Tyr
            100                 105                 110

Lys Phe Pro Arg Thr Phe Gly Gly Gly Thr Lys Leu Glu Leu Lys Gly
        115                 120                 125

Gly Gly Gly Ser Gly Gly Gly Gly Ser Gly Gly Gly Gly Ser Met Glu
    130                 135                 140

Trp Ser Trp Ile Phe Leu Phe Leu Leu Ser Val Thr Ala Val Val His
145                 150                 155                 160

Ser Gln Val Gln Leu Gln Gln Ser Gly Ala Glu Leu Ala Lys Pro Gly
                165                 170                 175

Thr Ser Val Lys Leu Ser Cys Lys Ala Ser Gly Tyr Thr Phe Thr Ser
            180                 185                 190

Tyr Tyr Ile Tyr Trp Val Lys Gln Arg Pro Gly Gln Gly Leu Glu Trp
        195                 200                 205

Leu Gly Tyr Ile Tyr Pro Gly Asn Gly Gly Thr Tyr Tyr Ser Glu Lys
    210                 215                 220

Phe Lys Gly Lys Ala Thr Phe Thr Ala Asp Thr Ser Ser Asn Thr Ala
225                 230                 235                 240

Tyr Met Leu Leu Gly Ser Leu Thr Pro Glu Asp Ser Ala Tyr Tyr Phe
                245                 250                 255

Cys Ala Arg Gly Ser Gly Asp Arg Tyr Asn Ser Leu Ala Tyr Trp Gly
            260                 265                 270
```

```
Gln Gly Thr Leu Val Thr Val Ser Ser Ala Ser Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
            340                 345                 350

Lys Arg Gly Arg Lys Lys Leu Leu Tyr Ile Phe Lys Gln Pro Phe Met
        355                 360                 365

Arg Pro Val Gln Thr Thr Gln Glu Glu Asp Gly Cys Ser Cys Arg Phe
    370                 375                 380

Pro Glu Glu Glu Glu Gly Gly Cys Glu Leu Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
        435                 440                 445

Gln Glu Gly Leu Tyr Asn Glu Leu Gln Lys Asp Lys Met Ala Glu Ala
    450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
            500                 505
```

<210> SEQ ID NO 171
<211> LENGTH: 503
<212> TYPE: PRT
<213> ORGANISM: Artificial Sequence
<220> FEATURE:
<223> OTHER INFORMATION: Vb5.1HL-BBz

<400> SEQUENCE: 171

```
Met Gly Trp Ser Trp Ile Phe Leu Phe Leu Leu Ser Glu Thr Ala Gly
1               5                   10                  15

Val Leu Ser Glu Val Gln Leu Gln Gln Ser Gly Pro Val Leu Val Lys
            20                  25                  30

Pro Gly Ala Ser Val Arg Met Ser Cys Lys Ala Ser Gly Tyr Thr Phe
        35                  40                  45

Thr Asp Tyr Asn Ile His Trp Val Lys Gln Ser His Gly Arg Ser Leu
    50                  55                  60

Glu Trp Val Gly Tyr Ile Asn Pro Tyr Asn Gly Arg Thr Gly Tyr Asn
65                  70                  75                  80

Gln Lys Phe Lys Ala Lys Ala Thr Leu Thr Val Asn Lys Ser Ser Ser
                85                  90                  95

Thr Ala Tyr Met Asp Leu Arg Ser Leu Thr Ser Glu Asp Ser Ala Val
            100                 105                 110

Tyr Tyr Cys Ala Arg Trp Asp Gly Ser Ser Tyr Phe Asp Tyr Trp Gly
        115                 120                 125
```

```
Gln Gly Thr Thr Leu Thr Val Ser Ser Gly Gly Gly Gly Ser Gly Gly
    130                 135                 140

Gly Gly Ser Gly Gly Gly Gly Ser Met Asp Phe Arg Val Gln Ile Phe
145                 150                 155                 160

Ser Phe Leu Leu Ile Ser Val Thr Val Ser Arg Gly Glu Ile Val Leu
                165                 170                 175

Thr Gln Ser Pro Ala Ile Thr Ala Ala Ser Leu Gly Gln Lys Val Thr
            180                 185                 190

Ile Thr Cys Ser Ala Ser Ser Ser Val Ser Tyr Met His Trp Tyr Gln
        195                 200                 205

Gln Lys Ser Gly Thr Ser Pro Lys Pro Trp Ile Tyr Glu Ile Ser Lys
    210                 215                 220

Leu Ala Ser Gly Val Pro Ala Arg Phe Ser Gly Ser Gly Ser Gly Thr
225                 230                 235                 240

Ser Tyr Ser Leu Thr Ile Ser Ser Met Glu Ala Glu Asp Ala Ala Ile
                245                 250                 255

Tyr Tyr Cys Gln Gln Trp Asn Tyr Pro Leu Ile Thr Phe Gly Ala Gly
            260                 265                 270

Thr Lys Leu Glu Leu Lys Ala Ser Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Lys Arg Gly
            340                 345                 350

Arg Lys Lys Leu Leu Tyr Ile Phe Lys Gln Pro Phe Met Arg Pro Val
        355                 360                 365

Gln Thr Thr Gln Glu Glu Asp Gly Cys Ser Cys Arg Phe Pro Glu Glu
    370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
            500
```

<210> SEQ ID NO 172
<211> LENGTH: 503
<212> TYPE: PRT
<213> ORGANISM: Artificial Sequence
<220> FEATURE:

<223> OTHER INFORMATION: Vb5.1LH-BBz

<400> SEQUENCE: 172

```
Met Asp Phe Arg Val Gln Ile Phe Ser Phe Leu Leu Ile Ser Val Thr
1               5                   10                  15

Val Ser Arg Gly Glu Ile Val Leu Thr Gln Ser Pro Ala Ile Thr Ala
            20                  25                  30

Ala Ser Leu Gly Gln Lys Val Thr Ile Thr Cys Ser Ala Ser Ser Ser
        35                  40                  45

Val Ser Tyr Met His Trp Tyr Gln Gln Lys Ser Gly Thr Ser Pro Lys
    50                  55                  60

Pro Trp Ile Tyr Glu Ile Ser Lys Leu Ala Ser Gly Val Pro Ala Arg
65                  70                  75                  80

Phe Ser Gly Ser Gly Ser Gly Thr Ser Tyr Ser Leu Thr Ile Ser Ser
                85                  90                  95

Met Glu Ala Glu Asp Ala Ala Ile Tyr Tyr Cys Gln Gln Trp Asn Tyr
            100                 105                 110

Pro Leu Ile Thr Phe Gly Ala Gly Thr Lys Leu Glu Leu Lys Gly Gly
        115                 120                 125

Gly Gly Ser Gly Gly Gly Gly Ser Gly Gly Gly Gly Ser Met Gly Trp
    130                 135                 140

Ser Trp Ile Phe Leu Phe Leu Leu Ser Glu Thr Ala Gly Val Leu Ser
145                 150                 155                 160

Glu Val Gln Leu Gln Gln Ser Gly Pro Val Leu Val Lys Pro Gly Ala
                165                 170                 175

Ser Val Arg Met Ser Cys Lys Ala Ser Gly Tyr Thr Phe Thr Asp Tyr
            180                 185                 190

Asn Ile His Trp Val Lys Gln Ser His Gly Arg Ser Leu Glu Trp Val
        195                 200                 205

Gly Tyr Ile Asn Pro Tyr Asn Gly Arg Thr Gly Tyr Asn Gln Lys Phe
    210                 215                 220

Lys Ala Lys Ala Thr Leu Thr Val Asn Lys Ser Ser Ser Thr Ala Tyr
225                 230                 235                 240

Met Asp Leu Arg Ser Leu Thr Ser Glu Asp Ser Ala Val Tyr Tyr Cys
                245                 250                 255

Ala Arg Trp Asp Gly Ser Ser Tyr Phe Asp Tyr Trp Gly Gln Gly Thr
            260                 265                 270

Thr Leu Thr Val Ser Ser Ala Ser Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Lys Arg Gly
            340                 345                 350

Arg Lys Lys Leu Leu Tyr Ile Phe Lys Gln Pro Phe Met Arg Pro Val
        355                 360                 365

Gln Thr Thr Gln Glu Glu Asp Gly Cys Ser Cys Arg Phe Pro Glu Glu
    370                 375                 380

Glu Glu Gly Gly Cys Glu Leu Arg Val Lys Phe Ser Arg Ser Ala Asp
385                 390                 395                 400
```

```
Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
            500


<210> SEQ ID NO 173
<211> LENGTH: 513
<212> TYPE: PRT
<213> ORGANISM: Artificial Sequence
<220> FEATURE:
<223> OTHER INFORMATION: Vb7.1HL-BBz

<400> SEQUENCE: 173

Met Asn Phe Gly Leu Ser Leu Ile Phe Leu Val Leu Phe Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Thr Ile Ser Gly Gly Gly Ser Tyr Thr Tyr Ser Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Ser Ser Leu Arg Ser Glu Asp Thr Ala Met
            100                 105                 110

Tyr Phe Cys Ala Arg Glu Arg Asp Ile Tyr Tyr Gly Asn Phe Asn Ala
        115                 120                 125

Met Val Tyr Trp Gly Arg Gly Thr Ser Val Thr Val Ser Ser Gly Gly
    130                 135                 140

Gly Gly Ser Gly Gly Gly Gly Ser Gly Gly Gly Gly Ser Met Glu Thr
145                 150                 155                 160

Asp Thr Leu Leu Leu Trp Val Leu Leu Leu Trp Val Pro Gly Ser Thr
                165                 170                 175

Gly Asp Ile Val Leu Thr Gln Ser Pro Val Ser Leu Thr Val Ser Leu
            180                 185                 190

Gly Gln Arg Ala Thr Ile Ser Cys Arg Ala Ser Lys Ser Val Ser Thr
        195                 200                 205

Ser Gly Tyr Ser Tyr Met His Trp Tyr Gln Gln Lys Pro Gly Gln Pro
    210                 215                 220

Pro Lys Leu Leu Ile Tyr Leu Ala Ser Asn Leu Glu Ser Gly Val Pro
225                 230                 235                 240

Ala Arg Phe Ser Gly Ser Gly Ser Gly Thr Asp Phe Thr Leu Asn Ile
                245                 250                 255
```

His Pro Val Glu Glu Glu Asp Ala Ala Thr Tyr Tyr Cys Gln His Ser
260 265 270

Arg Asp Leu Pro Trp Thr Phe Gly Gly Gly Thr Lys Leu Glu Ile Lys
275 280 285

Ala Ser Thr Thr Thr Pro Ala Pro Arg Pro Pro Thr Pro Ala Pro Thr
290 295 300

Ile Ala Ser Gln Pro Leu Ser Leu Arg Pro Glu Ala Cys Arg Pro Ala
305 310 315 320

Ala Gly Gly Ala Val His Thr Arg Gly Leu Asp Phe Ala Cys Asp Ile
325 330 335

Tyr Ile Trp Ala Pro Leu Ala Gly Thr Cys Gly Val Leu Leu Leu Ser
340 345 350

Leu Val Ile Thr Leu Tyr Cys Lys Arg Gly Arg Lys Lys Leu Leu Tyr
355 360 365

Ile Phe Lys Gln Pro Phe Met Arg Pro Val Gln Thr Thr Gln Glu Glu
370 375 380

Asp Gly Cys Ser Cys Arg Phe Pro Glu Glu Glu Glu Gly Gly Cys Glu
385 390 395 400

Leu Arg Val Lys Phe Ser Arg Ser Ala Asp Ala Pro Ala Tyr Gln Gln
405 410 415

Gly Gln Asn Gln Leu Tyr Asn Glu Leu Asn Leu Gly Arg Arg Glu Glu
420 425 430

Tyr Asp Val Leu Asp Lys Arg Arg Gly Arg Asp Pro Glu Met Gly Gly
435 440 445

Lys Pro Arg Arg Lys Asn Pro Gln Glu Gly Leu Tyr Asn Glu Leu Gln
450 455 460

Lys Asp Lys Met Ala Glu Ala Tyr Ser Glu Ile Gly Met Lys Gly Glu
465 470 475 480

Arg Arg Arg Gly Lys Gly His Asp Gly Leu Tyr Gln Gly Leu Ser Thr
485 490 495

Ala Thr Lys Asp Thr Tyr Asp Ala Leu His Met Gln Ala Leu Pro Pro
500 505 510

Arg

<210> SEQ ID NO 174
<211> LENGTH: 513
<212> TYPE: PRT
<213> ORGANISM: Artificial Sequence
<220> FEATURE:
<223> OTHER INFORMATION: Vb7.1LH-BBz

<400> SEQUENCE: 174

Met Glu Thr Asp Thr Leu Leu Leu Trp Val Leu Leu Leu Trp Val Pro
1 5 10 15

Gly Ser Thr Gly Asp Ile Val Leu Thr Gln Ser Pro Val Ser Leu Thr
20 25 30

Val Ser Leu Gly Gln Arg Ala Thr Ile Ser Cys Arg Ala Ser Lys Ser
35 40 45

Val Ser Thr Ser Gly Tyr Ser Tyr Met His Trp Tyr Gln Gln Lys Pro
50 55 60

Gly Gln Pro Pro Lys Leu Leu Ile Tyr Leu Ala Ser Asn Leu Glu Ser
65 70 75 80

Gly Val Pro Ala Arg Phe Ser Gly Ser Gly Ser Gly Thr Asp Phe Thr
85 90 95

Leu Asn Ile His Pro Val Glu Glu Glu Asp Ala Ala Thr Tyr Tyr Cys

```
            100                 105                 110

Gln His Ser Arg Asp Leu Pro Trp Thr Phe Gly Gly Gly Thr Lys Leu
        115                 120                 125

Glu Ile Lys Gly Gly Gly Gly Ser Gly Gly Gly Gly Ser Gly Gly Gly
    130                 135                 140

Gly Ser Met Asn Phe Gly Leu Ser Leu Ile Phe Leu Val Leu Phe Leu
145                 150                 155                 160

Lys Gly Val Gln Cys Glu Val Gln Leu Val Glu Ser Gly Gly Gly Leu
                165                 170                 175

Val Lys Pro Gly Gly Ser Leu Lys Leu Ser Cys Ala Ala Ser Gly Phe
            180                 185                 190

Thr Phe Ser Asp Tyr Tyr Met Tyr Trp Val Arg Gln Thr Pro Glu Lys
        195                 200                 205

Arg Leu Glu Trp Val Ala Thr Ile Ser Gly Gly Gly Ser Tyr Thr Tyr
    210                 215                 220

Ser Pro Asp Ser Val Lys Gly Arg Phe Thr Ile Ser Arg Asp Asn Ala
225                 230                 235                 240

Lys Asn Asn Leu Tyr Leu Gln Met Ser Ser Leu Arg Ser Glu Asp Thr
                245                 250                 255

Ala Met Tyr Phe Cys Ala Arg Glu Arg Asp Ile Tyr Tyr Gly Asn Phe
            260                 265                 270

Asn Ala Met Val Tyr Trp Gly Arg Gly Thr Ser Val Thr Val Ser Ser
        275                 280                 285

Ala Ser Thr Thr Thr Pro Ala Pro Arg Pro Pro Thr Pro Ala Pro Thr
    290                 295                 300

Ile Ala Ser Gln Pro Leu Ser Leu Arg Pro Glu Ala Cys Arg Pro Ala
305                 310                 315                 320

Ala Gly Gly Ala Val His Thr Arg Gly Leu Asp Phe Ala Cys Asp Ile
                325                 330                 335

Tyr Ile Trp Ala Pro Leu Ala Gly Thr Cys Gly Val Leu Leu Leu Ser
            340                 345                 350

Leu Val Ile Thr Leu Tyr Cys Lys Arg Gly Arg Lys Lys Leu Leu Tyr
        355                 360                 365

Ile Phe Lys Gln Pro Phe Met Arg Pro Val Gln Thr Thr Gln Glu Glu
    370                 375                 380

Asp Gly Cys Ser Cys Arg Phe Pro Glu Glu Glu Glu Gly Gly Cys Glu
385                 390                 395                 400

Leu Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
            420                 425                 430

Tyr Asp Val Leu Asp Lys Arg Arg Gly Arg Asp Pro Glu Met Gly Gly
        435                 440                 445

Lys Pro Arg Arg Lys Asn Pro Gln Glu Gly Leu Tyr Asn Glu Leu Gln
    450                 455                 460

Lys Asp Lys Met Ala Glu Ala Tyr Ser Glu Ile Gly Met Lys Gly Glu
465                 470                 475                 480

Arg Arg Arg Gly Lys Gly His Asp Gly Leu Tyr Gln Gly Leu Ser Thr
                485                 490                 495

Ala Thr Lys Asp Thr Tyr Asp Ala Leu His Met Gln Ala Leu Pro Pro
            500                 505                 510

Arg
```

<210> SEQ ID NO 175
<211> LENGTH: 503
<212> TYPE: PRT
<213> ORGANISM: Artificial Sequence
<220> FEATURE:
<223> OTHER INFORMATION: Vb7.2HL-BBz

<400> SEQUENCE: 175

Met Glu Arg His Trp Ile Phe Leu Leu Leu Leu Ser Val Thr Ala Gly
1 5 10 15

Ala His Ser Gln Val His Leu Gln Gln Ser Gly Ala Glu Leu Ala Arg
20 25 30

Pro Gly Ala Ser Val Lys Met Ser Cys Lys Ala Ser Gly Tyr Ile Phe
35 40 45

Thr Asp Tyr Thr Met His Trp Val Lys Gln Arg Pro Gly Gln Gly Leu
50 55 60

Glu Trp Ile Gly His Ile Asn Pro Ser Ser Gly Tyr Ser Thr Tyr Asn
65 70 75 80

Gln Lys Phe Lys Asp Lys Ala Thr Leu Thr Ala Asp Lys Ser Ser Ser
85 90 95

Thr Ala Tyr Met Gln Leu Ser Ser Leu Thr Ser Glu Asp Ser Ala Val
100 105 110

Tyr Tyr Cys Ala Arg Ser Leu Gln Leu Gly Arg Asp Tyr Trp Gly Gln
115 120 125

Gly Thr Thr Leu Thr Val Ser Ser Gly Gly Gly Gly Ser Gly Gly Gly
130 135 140

Gly Ser Gly Gly Gly Gly Ser Met Glu Ser Gln Ile Gln Val Phe Val
145 150 155 160

Phe Val Phe Leu Trp Leu Ser Gly Val Asp Gly Asp Ile Val Met Thr
165 170 175

Gln Ser His Lys Phe Met Ser Thr Ser Val Gly Asp Arg Val Ser Ile
180 185 190

Thr Cys Lys Ala Ser Gln Asp Val Tyr Thr Ala Val Ala Trp Tyr Gln
195 200 205

Gln Lys Pro Gly Gln Ser Pro Lys Leu Leu Ile Tyr Ser Ala Ser Asn
210 215 220

Arg Tyr Thr Gly Val Pro Asp Arg Phe Thr Gly Ser Gly Ser Gly Thr
225 230 235 240

Asp Phe Thr Phe Thr Ile Ser Ser Val Gln Ala Glu Asp Leu Ala Val
245 250 255

Tyr Tyr Cys Gln Gln His Tyr Thr Thr Pro Arg Thr Phe Gly Gly Gly
260 265 270

Thr Lys Leu Glu Ile Lys Ala Ser Thr Thr Thr Pro Ala Pro Arg Pro
275 280 285

Pro Thr Pro Ala Pro Thr Ile Ala Ser Gln Pro Leu Ser Leu Arg Pro
290 295 300

Glu Ala Cys Arg Pro Ala Ala Gly Gly Ala Val His Thr Arg Gly Leu
305 310 315 320

Asp Phe Ala Cys Asp Ile Tyr Ile Trp Ala Pro Leu Ala Gly Thr Cys
325 330 335

Gly Val Leu Leu Leu Ser Leu Val Ile Thr Leu Tyr Cys Lys Arg Gly
340 345 350

Arg Lys Lys Leu Leu Tyr Ile Phe Lys Gln Pro Phe Met Arg Pro Val
355 360 365

```
Gln Thr Thr Gln Glu Glu Asp Gly Cys Ser Cys Arg Phe Pro Glu Glu
    370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
            500


<210> SEQ ID NO 176
<211> LENGTH: 503
<212> TYPE: PRT
<213> ORGANISM: Artificial Sequence
<220> FEATURE:
<223> OTHER INFORMATION: Vb7.2LH-BBz

<400> SEQUENCE: 176

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Tyr Thr Ala Val Ala Trp Tyr Gln Gln Lys Pro Gly Gln Ser Pro
    50                  55                  60

Lys Leu Leu Ile Tyr Ser Ala Ser Asn Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Gln Gln His Tyr
            100                 105                 110

Thr Thr Pro Arg Thr Phe Gly Gly Gly Thr Lys Leu Glu Ile Lys Gly
        115                 120                 125

Gly Gly Gly Ser Gly Gly Gly Gly Ser Gly Gly Gly Gly Ser Met Glu
    130                 135                 140

Arg His Trp Ile Phe Leu Leu Leu Leu Ser Val Thr Ala Gly Ala His
145                 150                 155                 160

Ser Gln Val His Leu Gln Gln Ser Gly Ala Glu Leu Ala Arg Pro Gly
                165                 170                 175

Ala Ser Val Lys Met Ser Cys Lys Ala Ser Gly Tyr Ile Phe Thr Asp
            180                 185                 190

Tyr Thr Met His Trp Val Lys Gln Arg Pro Gly Gln Gly Leu Glu Trp
        195                 200                 205

Ile Gly His Ile Asn Pro Ser Ser Gly Tyr Ser Thr Tyr Asn Gln Lys
    210                 215                 220
```

Phe Lys Asp Lys Ala Thr Leu Thr Ala Asp Lys Ser Ser Ser Thr Ala
225 230 235 240

Tyr Met Gln Leu Ser Ser Leu Thr Ser Glu Asp Ser Ala Val Tyr Tyr
245 250 255

Cys Ala Arg Ser Leu Gln Leu Gly Arg Asp Tyr Trp Gly Gln Gly Thr
260 265 270

Thr Leu Thr Val Ser Ser Ala Ser Thr Thr Thr Pro Ala Pro Arg Pro
275 280 285

Pro Thr Pro Ala Pro Thr Ile Ala Ser Gln Pro Leu Ser Leu Arg Pro
290 295 300

Glu Ala Cys Arg Pro Ala Ala Gly Gly Ala Val His Thr Arg Gly Leu
305 310 315 320

Asp Phe Ala Cys Asp Ile Tyr Ile Trp Ala Pro Leu Ala Gly Thr Cys
325 330 335

Gly Val Leu Leu Leu Ser Leu Val Ile Thr Leu Tyr Cys Lys Arg Gly
340 345 350

Arg Lys Lys Leu Leu Tyr Ile Phe Lys Gln Pro Phe Met Arg Pro Val
355 360 365

Gln Thr Thr Gln Glu Glu Asp Gly Cys Ser Cys Arg Phe Pro Glu Glu
370 375 380

Glu Glu Gly Gly Cys Glu Leu Arg Val Lys Phe Ser Arg Ser Ala Asp
385 390 395 400

Ala Pro Ala Tyr Gln Gln Gly Gln Asn Gln Leu Tyr Asn Glu Leu Asn
405 410 415

Leu Gly Arg Arg Glu Glu Tyr Asp Val Leu Asp Lys Arg Arg Gly Arg
420 425 430

Asp Pro Glu Met Gly Gly Lys Pro Arg Arg Lys Asn Pro Gln Glu Gly
435 440 445

Leu Tyr Asn Glu Leu Gln Lys Asp Lys Met Ala Glu Ala Tyr Ser Glu
450 455 460

Ile Gly Met Lys Gly Glu Arg Arg Arg Gly Lys Gly His Asp Gly Leu
465 470 475 480

Tyr Gln Gly Leu Ser Thr Ala Thr Lys Asp Thr Tyr Asp Ala Leu His
485 490 495

Met Gln Ala Leu Pro Pro Arg
500

<210> SEQ ID NO 177
<211> LENGTH: 502
<212> TYPE: PRT
<213> ORGANISM: Artificial Sequence
<220> FEATURE:
<223> OTHER INFORMATION: Vb11HL-BBz

<400> SEQUENCE: 177

Met Gly Trp Ser Cys Ile Ile Phe Phe Leu Val Ala Thr Ala Thr Gly
1 5 10 15

Val His Ser Gln Val Gln Leu Gln Gln Ser Gly Pro Glu Val Val Arg
20 25 30

Pro Gly Val Ser Val Lys Ile Ser Cys Lys Gly Ser Gly Tyr Arg Phe
35 40 45

Thr Asp Ser Ala Met His Trp Val Lys Gln Ser His Ala Lys Ser Leu
50 55 60

Glu Trp Ile Gly Val Ile Ser Ser Tyr Asn Gly Asn Thr Asn Tyr Asn
65 70 75 80

```
Gln Lys Phe Lys Gly Lys Ala Thr Met Thr Val Asp Lys Ser Ser Ser
                85                  90                  95

Thr Ala Tyr Met Glu Leu Ala Arg Met Thr Ser Glu Asp Ser Ala Ile
            100                 105                 110

Tyr Tyr Cys Ala Arg Ser Arg Asp Ala Met Asp Tyr Trp Gly Gln Gly
        115                 120                 125

Thr Ser Val Thr Val Ser Ser Gly Gly Gly Gly Ser Gly Gly Gly Gly
    130                 135                 140

Ser Gly Gly Gly Gly Ser Met Arg Thr Pro Ala Gln Phe Leu Gly Ile
145                 150                 155                 160

Leu Leu Leu Trp Phe Pro Gly Ile Lys Cys Asp Ile Lys Met Thr Gln
                165                 170                 175

Ser Pro Ser Ser Met Tyr Ala Ser Leu Gly Glu Arg Val Thr Ile Thr
            180                 185                 190

Cys Lys Ala Ser Gln Asp Ile Asn Ser Tyr Leu Ser Trp Phe Gln Gln
        195                 200                 205

Lys Ala Gly Lys Ser Pro Lys Thr Leu Ile Tyr Arg Ala Asn Arg Leu
    210                 215                 220

Val Asp Gly Val Pro Ser Arg Phe Ser Gly Ser Gly Ser Gly Gln Asp
225                 230                 235                 240

Tyr Ser Leu Thr Ile Ser Ser Leu Glu Tyr Glu Asp Met Gly Ile Tyr
                245                 250                 255

Tyr Cys Leu Gln Tyr Asp Glu Phe Pro Phe Thr Phe Gly Gly Gly Thr
            260                 265                 270

Arg Leu Glu Ile Lys Ala Ser Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
```

500

<210> SEQ ID NO 178
<211> LENGTH: 502
<212> TYPE: PRT
<213> ORGANISM: Artificial Sequence
<220> FEATURE:
<223> OTHER INFORMATION: Vb11LH-BBz

<400> SEQUENCE: 178

Met Arg Thr Pro Ala Gln Phe Leu Gly Ile Leu Leu Leu Trp Phe Pro
1 5 10 15

Gly Ile Lys Cys Asp Ile Lys Met Thr Gln Ser Pro Ser Ser Met Tyr
20 25 30

Ala Ser Leu Gly Glu Arg Val Thr Ile Thr Cys Lys Ala Ser Gln Asp
35 40 45

Ile Asn Ser Tyr Leu Ser Trp Phe Gln Gln Lys Ala Gly Lys Ser Pro
50 55 60

Lys Thr Leu Ile Tyr Arg Ala Asn Arg Leu Val Asp Gly Val Pro Ser
65 70 75 80

Arg Phe Ser Gly Ser Gly Ser Gly Gln Asp Tyr Ser Leu Thr Ile Ser
85 90 95

Ser Leu Glu Tyr Glu Asp Met Gly Ile Tyr Tyr Cys Leu Gln Tyr Asp
100 105 110

Glu Phe Pro Phe Thr Phe Gly Gly Gly Thr Arg Leu Glu Ile Lys Gly
115 120 125

Gly Gly Gly Ser Gly Gly Gly Gly Ser Gly Gly Gly Gly Ser Met Gly
130 135 140

Trp Ser Cys Ile Ile Phe Phe Leu Val Ala Thr Ala Thr Gly Val His
145 150 155 160

Ser Gln Val Gln Leu Gln Gln Ser Gly Pro Glu Val Val Arg Pro Gly
165 170 175

Val Ser Val Lys Ile Ser Cys Lys Gly Ser Gly Tyr Arg Phe Thr Asp
180 185 190

Ser Ala Met His Trp Val Lys Gln Ser His Ala Lys Ser Leu Glu Trp
195 200 205

Ile Gly Val Ile Ser Ser Tyr Asn Gly Asn Thr Asn Tyr Asn Gln Lys
210 215 220

Phe Lys Gly Lys Ala Thr Met Thr Val Asp Lys Ser Ser Ser Thr Ala
225 230 235 240

Tyr Met Glu Leu Ala Arg Met Thr Ser Glu Asp Ser Ala Ile Tyr Tyr
245 250 255

Cys Ala Arg Ser Arg Asp Ala Met Asp Tyr Trp Gly Gln Gly Thr Ser
260 265 270

Val Thr Val Ser Ser Ala Ser Thr Thr Thr Pro Ala Pro Arg Pro Pro
275 280 285

Thr Pro Ala Pro Thr Ile Ala Ser Gln Pro Leu Ser Leu Arg Pro Glu
290 295 300

Ala Cys Arg Pro Ala Ala Gly Gly Ala Val His Thr Arg Gly Leu Asp
305 310 315 320

Phe Ala Cys Asp Ile Tyr Ile Trp Ala Pro Leu Ala Gly Thr Cys Gly
325 330 335

Val Leu Leu Leu Ser Leu Val Ile Thr Leu Tyr Cys Lys Arg Gly Arg
340 345 350

Lys Lys Leu Leu Tyr Ile Phe Lys Gln Pro Phe Met Arg Pro Val Gln

```
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500
```

<210> SEQ ID NO 179
<211> LENGTH: 509
<212> TYPE: PRT
<213> ORGANISM: Artificial Sequence
<220> FEATURE:
<223> OTHER INFORMATION: Vb13.2HL-BBz

<400> SEQUENCE: 179

```
Met Gly Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Asn Ala Ser Gly Tyr Thr Phe
        35                  40                  45

Thr Asp Tyr Tyr Ile His Trp Leu Lys Gln Arg His Gly Lys Gly Leu
    50                  55                  60

Glu Trp Ile Gly Ile Val Asn Thr Asn Asn Gly Asp Thr Asn Tyr Asn
65                  70                  75                  80

Gln Arg Phe Lys Gly Lys Ala Ser Leu Thr Val Asp Lys Ser Ser Ser
                85                  90                  95

Thr Ala Tyr Met Glu Leu Asn Ser Leu Thr Ser Glu Asp Ser Ala Val
            100                 105                 110

Phe Tyr Cys Ala Arg Ala Leu Tyr Thr Gly Ser Tyr Trp Phe Ala Tyr
        115                 120                 125

Trp Gly Gln Gly Thr Leu Val Thr Val Ser Ala Gly Gly Gly Gly Ser
    130                 135                 140

Gly Gly Gly Gly Ser Gly Gly Gly Gly Ser Met Asp Phe His Val Gln
145                 150                 155                 160

Ile Phe Ser Phe Met Leu Ile Ser Val Thr Val Met Leu Ser Ser Gly
                165                 170                 175

Glu Ile Val Leu Thr Gln Ser Pro Ala Val Met Ala Ala Ser Pro Gly
            180                 185                 190

Glu Lys Val Thr Ile Thr Cys Ser Ala Ser Ser Ser Ile Ser Ser Thr
        195                 200                 205

Asn Leu His Trp Tyr Gln Gln Lys Ser Glu Thr Ser Pro Lys Pro Trp
```

```
    210                 215                 220

Ile Tyr Gly Thr Ser Asn Leu Ala Ser Gly Val Pro Val Arg Phe Ser
225                 230                 235                 240

Gly Ser Gly Ser Gly Thr Ser Tyr Ser Leu Thr Ile Ser Ser Ile Glu
                245                 250                 255

Ala Glu Asp Ala Ala Thr Tyr Tyr Cys Gln Gln Trp Ser Arg Tyr Pro
            260                 265                 270

Leu Thr Phe Gly Ser Gly Thr Lys Leu Glu Ile Ile Ala Ser Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505
```

<210> SEQ ID NO 180
<211> LENGTH: 509
<212> TYPE: PRT
<213> ORGANISM: Artificial Sequence
<220> FEATURE:
<223> OTHER INFORMATION: Vb13.2LH-BBz

<400> SEQUENCE: 180

```
Met Asp Phe His Val Gln Ile Phe Ser Phe Met Leu Ile Ser Val Thr
1               5                   10                  15

Val Met Leu Ser Ser Gly Glu Ile Val Leu Thr Gln Ser Pro Ala Val
            20                  25                  30

Met Ala Ala Ser Pro Gly Glu Lys Val Thr Ile Thr Cys Ser Ala Ser
        35                  40                  45

Ser Ser Ile Ser Ser Thr Asn Leu His Trp Tyr Gln Gln Lys Ser Glu
    50                  55                  60

Thr Ser Pro Lys Pro Trp Ile Tyr Gly Thr Ser Asn Leu Ala Ser Gly
```

```
65                  70                  75                  80

Val Pro Val Arg Phe Ser Gly Ser Gly Ser Gly Thr Ser Tyr Ser Leu
                85                  90                  95

Thr Ile Ser Ser Ile Glu Ala Glu Asp Ala Ala Thr Tyr Tyr Cys Gln
            100                 105                 110

Gln Trp Ser Arg Tyr Pro Leu Thr Phe Gly Ser Gly Thr Lys Leu Glu
        115                 120                 125

Ile Ile Gly Gly Gly Gly Ser Gly Gly Gly Gly Ser Gly Gly Gly Gly
    130                 135                 140

Ser Met Gly Trp Ser Trp Ile Phe Leu Phe Leu Leu Ser Gly Thr Ala
145                 150                 155                 160

Gly Val His Ser Glu Val Gln Leu Gln Gln Ser Gly Pro Glu Leu Val
                165                 170                 175

Lys Pro Gly Ala Ser Val Lys Met Ser Cys Asn Ala Ser Gly Tyr Thr
            180                 185                 190

Phe Thr Asp Tyr Tyr Ile His Trp Leu Lys Gln Arg His Gly Lys Gly
        195                 200                 205

Leu Glu Trp Ile Gly Ile Val Asn Thr Asn Asn Gly Asp Thr Asn Tyr
    210                 215                 220

Asn Gln Arg Phe Lys Gly Lys Ala Ser Leu Thr Val Asp Lys Ser Ser
225                 230                 235                 240

Ser Thr Ala Tyr Met Glu Leu Asn Ser Leu Thr Ser Glu Asp Ser Ala
                245                 250                 255

Val Phe Tyr Cys Ala Arg Ala Leu Tyr Thr Gly Ser Tyr Trp Phe Ala
            260                 265                 270

Tyr Trp Gly Gln Gly Thr Leu Val Thr Val Ser Ala Ala Ser Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495
```

```
Thr Tyr Asp Ala Leu His Met Gln Ala Leu Pro Pro Arg
            500                 505


<210> SEQ ID NO 181
<211> LENGTH: 508
<212> TYPE: PRT
<213> ORGANISM: Artificial Sequence
<220> FEATURE:
<223> OTHER INFORMATION: Vb13.3HL-BBz

<400> SEQUENCE: 181

Met Gly Trp Ser Cys Ile Ile Leu Ile Leu Val Ala Ala Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Trp Ile Thr Trp Val Lys Gln Arg Pro Gly Gln Gly Leu
    50                  55                  60

Glu Trp Ile Gly Asp Ile Tyr Pro Gly Ser Gly Ser Ile Asn Tyr Asn
65                  70                  75                  80

Glu Lys Phe Asn Asn Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Tyr Tyr Ser Leu Tyr Tyr Tyr Ala Leu
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Met Ser Val Pro
145                 150                 155                 160

Thr Gln Val Leu Gly Leu Leu Leu Leu Trp Leu Thr Gly Ala Arg Cys
                165                 170                 175

Asp Ile Gln Met Thr Gln Ser Pro Ala Ser Leu Ser Ala Ser Val Gly
            180                 185                 190

Glu Thr Val Thr Met Thr Cys Arg Ala Ser Glu Asn Ile Tyr Ser Asn
        195                 200                 205

Leu Ala Trp Tyr Gln Gln Lys Gln Gly Lys Ser Pro Gln Leu Leu Val
    210                 215                 220

Tyr Ala Ala Thr Asn Leu Ala Asp Gly Val Pro Ser Arg Phe Ser Val
225                 230                 235                 240

Ser Gly Ser Gly Thr His Phe Ser Leu Lys Ile Asn Ser Leu Gln Pro
                245                 250                 255

Glu Asp Phe Gly Ser Tyr Tyr Cys Gln His Phe Tyr Gly Thr Pro Tyr
            260                 265                 270

Thr Phe Gly Gly Gly Thr Lys Leu Glu Ile Lys Ala Ser Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350
```

```
Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505
```

<210> SEQ ID NO 182
<211> LENGTH: 508
<212> TYPE: PRT
<213> ORGANISM: Artificial Sequence
<220> FEATURE:
<223> OTHER INFORMATION: Vb13.3LH-BBz

<400> SEQUENCE: 182

```
Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Met Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Ala Ala Thr Asn Leu Ala Asp Gly Val Pro Ser
65                  70                  75                  80

Arg Phe Ser Val Ser Gly Ser Gly Thr His Phe Ser Leu Lys Ile Asn
                85                  90                  95

Ser Leu Gln Pro Glu Asp Phe Gly Ser Tyr Tyr Cys Gln His Phe Tyr
            100                 105                 110

Gly Thr Pro Tyr Thr Phe Gly Gly Gly Thr Lys Leu Glu Ile Lys Gly
        115                 120                 125

Gly Gly Gly Ser Gly Gly Gly Gly Ser Gly Gly Gly Gly Ser Met Gly
    130                 135                 140

Trp Ser Cys Ile Ile Leu Ile Leu Val Ala Ala Ala Thr Gly Val His
145                 150                 155                 160

Ser Gln Val Gln Leu Gln Gln Pro Gly Ala Glu Leu Val Lys Pro Gly
                165                 170                 175

Ala Ser Val Lys Met Ser Cys Lys Ala Ser Gly Tyr Thr Phe Thr Ser
            180                 185                 190

Tyr Trp Ile Thr Trp Val Lys Gln Arg Pro Gly Gln Gly Leu Glu Trp
        195                 200                 205
```

```
Ile Gly Asp Ile Tyr Pro Gly Ser Gly Ser Ile Asn Tyr Asn Glu Lys
    210                 215                 220

Phe Asn Asn Lys Ala Thr Leu Thr Val Asp Thr Ser Ser Ser Thr Ala
225                 230                 235                 240

Tyr Met Gln Leu Ser Ser Leu Thr Ser Glu Asp Ser Ala Val Tyr Tyr
                245                 250                 255

Cys Ala Arg Arg Asp Tyr Tyr Ser Leu Tyr Tyr Tyr Ala Leu Asp Tyr
            260                 265                 270

Trp Gly Gln Gly Thr Ser Val Thr Val Ser Ser Ala Ser Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505


<210> SEQ ID NO 183
<211> LENGTH: 502
<212> TYPE: PRT
<213> ORGANISM: Artificial Sequence
<220> FEATURE:
<223> OTHER INFORMATION: Vb22HL-BBz

<400> SEQUENCE: 183

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Asn Trp Val Arg Gln Ala Pro Gly Lys Gly Leu Glu
    50                  55                  60
```

```
Trp Ile Gly Glu Ile Asn Ser Asp Ser Asn Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Met Asn Lys Val Arg Ser Glu Asp Thr Ala Leu Tyr
            100                 105                 110

Tyr Cys Ala Arg Gly Gly Leu Leu Arg Asp Val Trp Gly Ala Gly Thr
        115                 120                 125

Thr Val Thr Val Ser Ser Gly Gly Gly Gly Ser Gly Gly Gly Gly Ser
    130                 135                 140

Gly Gly Gly Gly Ser Met Ala Trp Ile Ser Leu Ile Leu Ser Leu Leu
145                 150                 155                 160

Ala Leu Ser Ser Gly Ala Ile Ser Gln Ala Val Val Thr Gln Glu Ser
                165                 170                 175

Ala Leu Thr Thr Ser Pro Gly Glu Thr Val Thr Leu Thr Cys Arg Ser
            180                 185                 190

Ser Thr Gly Ala Val Thr Thr Ser Asn Tyr Ala Asn Trp Val Gln Glu
        195                 200                 205

Lys Pro Asp His Leu Phe Thr Gly Leu Ile Gly Gly Thr Asn Asn Arg
    210                 215                 220

Ala Pro Gly Val Pro Ala Arg Phe Ser Gly Ser Leu Ile Gly Asp Arg
225                 230                 235                 240

Ala Ala Leu Thr Ile Thr Gly Ala Gln Thr Glu Asp Glu Ala Ile Tyr
                245                 250                 255

Phe Cys Ala Leu Trp Tyr Ser Asn His Trp Val Phe Gly Gly Gly Thr
            260                 265                 270

Lys Leu Thr Val Leu Ala Ser Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480
```

Gln Gly Leu Ser Thr Ala Thr Lys Asp Thr Tyr Asp Ala Leu His Met
485 490 495

Gln Ala Leu Pro Pro Arg
500

<210> SEQ ID NO 184
<211> LENGTH: 502
<212> TYPE: PRT
<213> ORGANISM: Artificial Sequence
<220> FEATURE:
<223> OTHER INFORMATION: Vb22LH-BBz

<400> SEQUENCE: 184

Met Ala Trp Ile Ser Leu Ile Leu Ser Leu Leu Ala Leu Ser Ser Gly
1 5 10 15

Ala Ile Ser Gln Ala Val Val Thr Gln Glu Ser Ala Leu Thr Thr Ser
20 25 30

Pro Gly Glu Thr Val Thr Leu Thr Cys Arg Ser Ser Thr Gly Ala Val
35 40 45

Thr Thr Ser Asn Tyr Ala Asn Trp Val Gln Glu Lys Pro Asp His Leu
50 55 60

Phe Thr Gly Leu Ile Gly Gly Thr Asn Asn Arg Ala Pro Gly Val Pro
65 70 75 80

Ala Arg Phe Ser Gly Ser Leu Ile Gly Asp Arg Ala Ala Leu Thr Ile
85 90 95

Thr Gly Ala Gln Thr Glu Asp Glu Ala Ile Tyr Phe Cys Ala Leu Trp
100 105 110

Tyr Ser Asn His Trp Val Phe Gly Gly Gly Thr Lys Leu Thr Val Leu
115 120 125

Gly Gly Gly Gly Ser Gly Gly Gly Gly Ser Gly Gly Gly Gly Ser Met
130 135 140

Asp Phe Gly Leu Ile Phe Phe Ile Val Ala Leu Leu Lys Gly Val Gln
145 150 155 160

Cys Glu Val Lys Leu Leu Glu Ser Gly Gly Gly Leu Val Gln Pro Gly
165 170 175

Gly Ser Leu Lys Leu Ser Cys Ala Ala Ser Gly Phe Asp Phe Ser Arg
180 185 190

Tyr Trp Met Asn Trp Val Arg Gln Ala Pro Gly Lys Gly Leu Glu Trp
195 200 205

Ile Gly Glu Ile Asn Ser Asp Ser Asn Thr Ile Asn Tyr Thr Pro Ser
210 215 220

Leu Lys Asp Lys Phe Ile Ile Ser Arg Asp Asn Ala Lys Asn Thr Leu
225 230 235 240

Tyr Leu Gln Met Asn Lys Val Arg Ser Glu Asp Thr Ala Leu Tyr Tyr
245 250 255

Cys Ala Arg Gly Gly Leu Leu Arg Asp Val Trp Gly Ala Gly Thr Thr
260 265 270

Val Thr Val Ser Ser Ala Ser Thr Thr Thr Pro Ala Pro Arg Pro Pro
275 280 285

Thr Pro Ala Pro Thr Ile Ala Ser Gln Pro Leu Ser Leu Arg Pro Glu
290 295 300

Ala Cys Arg Pro Ala Ala Gly Gly Ala Val His Thr Arg Gly Leu Asp
305 310 315 320

Phe Ala Cys Asp Ile Tyr Ile Trp Ala Pro Leu Ala Gly Thr Cys Gly
325 330 335

-continued

```
Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500
```